US009539243B2

(12) United States Patent
Burlison et al.

(10) Patent No.: US 9,539,243 B2
(45) Date of Patent: *Jan. 10, 2017

(54) TRIAZOLE COMPOUNDS THAT MODULATE HSP90 ACTIVITY

(71) Applicant: Synta Pharmaceuticals Corp., Lexington, MA (US)

(72) Inventors: Joseph Burlison, Louisville, KY (US); Shijie Zhang, Nashua, NH (US); Weiwen Ying, Lexington, MA (US); Dinesh U. Chimmanamada, Arlington, MA (US); Minghu Song, Chester Springs, PA (US); Junghyun Chae, Youngdengpo-Yu (KR); Stefan M. Schweizer, Memphis, TN (US)

(73) Assignee: Synta Pharmaceuticals Corp., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/591,092

(22) Filed: Jan. 7, 2015

(65) Prior Publication Data

US 2015/0126499 A1 May 7, 2015

Related U.S. Application Data

(63) Continuation of application No. 13/941,081, filed on Jul. 12, 2013, now Pat. No. 8,937,094, which is a (Continued)

(51) Int. Cl.
| | |
|---|---|
| *C07D 249/10* | (2006.01) |
| *A61K 31/4196* | (2006.01) |
| *C07D 249/08* | (2006.01) |
| *C07D 249/12* | (2006.01) |
| *C07D 249/14* | (2006.01) |
| *C07D 401/04* | (2006.01) |
| *C07D 401/10* | (2006.01) |
| *C07D 401/14* | (2006.01) |
| *C07D 403/08* | (2006.01) |
| *C07D 403/10* | (2006.01) |
| *C07D 403/12* | (2006.01) |
| *C07D 403/14* | (2006.01) |
| *C07D 405/04* | (2006.01) |
| *C07D 405/10* | (2006.01) |
| *C07D 409/04* | (2006.01) |
| *C07D 409/12* | (2006.01) |
| *A61K 31/4439* | (2006.01) |
| *A61K 31/454* | (2006.01) |
| *A61K 31/496* | (2006.01) |
| *A61K 31/5377* | (2006.01) |
| *A61K 31/541* | (2006.01) |
| *A61K 31/635* | (2006.01) |
| *A61K 45/06* | (2006.01) |
| *C07D 401/12* | (2006.01) |
| *C07D 403/04* | (2006.01) |
| *C07D 405/06* | (2006.01) |

(52) U.S. Cl.
CPC ....... *A61K 31/4196* (2013.01); *A61K 31/4439* (2013.01); *A61K 31/454* (2013.01); *A61K 31/496* (2013.01); *A61K 31/5377* (2013.01); *A61K 31/541* (2013.01); *A61K 31/635* (2013.01); *A61K 45/06* (2013.01); *C07D 249/08* (2013.01); *C07D 249/10* (2013.01); *C07D 249/12* (2013.01); *C07D 249/14* (2013.01); *C07D 401/04* (2013.01); *C07D 401/10* (2013.01); *C07D 401/12* (2013.01); *C07D 401/14* (2013.01); *C07D 403/04* (2013.01); *C07D 403/08* (2013.01); *C07D 403/10* (2013.01); *C07D 403/12* (2013.01); *C07D 403/14* (2013.01); *C07D 405/04* (2013.01); *C07D 405/06* (2013.01); *C07D 405/10* (2013.01); *C07D 409/04* (2013.01); *C07D 409/12* (2013.01)

(58) Field of Classification Search
CPC .................................................... C07D 249/10
See application file for complete search history.

(56) References Cited

U.S. PATENT DOCUMENTS

| | | | |
|---|---|---|---|
| 6,602,867 B1 | 8/2003 | Starck et al. | |
| 7,608,635 B2 | 10/2009 | Ying et al. | |

(Continued)

FOREIGN PATENT DOCUMENTS

| | | |
|---|---|---|
| EP | 1 857 446 A1 | 11/2007 |
| WO | 2005/000300 A1 | 1/2005 |
| WO | 2006/055760 A1 | 5/2006 |
| WO | 2006/087077 A2 | 8/2006 |
| WO | 2008097640 A2 | 8/2008 |
| WO | 2009/023211 A1 | 2/2009 |
| WO | 2009148599 A1 | 12/2009 |
| WO | 2010017545 A2 | 2/2010 |

OTHER PUBLICATIONS

Jhaveri, 2012, Biochimica et Biophysica Acta, vol. 1823, pp. 742-755.*

(Continued)

*Primary Examiner* — Michael Barker
*Assistant Examiner* — Karen Cheng
(74) *Attorney, Agent, or Firm* — McCarter & English, LLP; Steven G. Davis; Mei Bai

(57) ABSTRACT

The present invention relates to substituted triazole compounds and compositions comprising substituted triazole compounds. The invention further relates to methods of inhibiting the activity of Hsp90 in a subject in need thereof and methods for treating hyperproliferative disorders, such as cancer, in a subject in need thereof comprising administering to the subject a substituted triazole compound of the invention, or a pharmaceutical composition comprising such a compound.

7 Claims, No Drawings

Related U.S. Application Data continuation of application No. 13/333,191, filed on Dec. 21, 2011, now Pat. No. 8,486,932, which is a continuation of application No. 12/538,751, filed on Aug. 10, 2009, now Pat. No. 8,106,083.

(60) Provisional application No. 61/188,543, filed on Aug. 8, 2008.

(56) References Cited

U.S. PATENT DOCUMENTS

| | | |
|---|---|---|
| 7,662,813 B2 | 2/2010 | Ying et al. |
| 7,825,148 B2 | 11/2010 | Ying et al. |
| 8,034,834 B2 | 10/2011 | Du et al. |
| 8,053,456 B2 | 11/2011 | Sun et al. |
| 8,063,083 B2 | 11/2011 | Foley |
| 8,106,083 B2 | 1/2012 | Burlison et al. |
| 8,183,384 B2 | 5/2012 | Chimmanamada et al. |
| 8,188,075 B2 | 5/2012 | Ying et al. |
| 8,299,107 B2 | 10/2012 | Chimmanamada et al. |
| 8,318,790 B2 | 11/2012 | Ying et al. |
| 8,329,736 B2 | 12/2012 | Chimmanamada et al. |
| 8,329,899 B2 | 12/2012 | Ying et al. |
| 8,362,055 B2 | 1/2013 | Ying et al. |
| 8,415,377 B2 | 4/2013 | Sun et al. |
| 8,450,500 B2 | 5/2013 | Chimmanamada et al. |
| 8,486,932 B2 | 7/2013 | Burlison et al. |
| 8,524,712 B2 | 9/2013 | Lee et al. |
| 8,628,752 B2 | 1/2014 | Zhou et al. |
| 8,629,285 B2 | 1/2014 | Ying et al. |
| 8,648,071 B2 | 2/2014 | Burlison et al. |
| 8,648,104 B2 | 2/2014 | Du et al. |
| 8,742,133 B2 | 6/2014 | Ying et al. |
| 8,748,424 B2 | 6/2014 | Chimmanamada et al. |
| 8,785,658 B2 | 7/2014 | Chimmanamada et al. |
| 8,835,464 B2 | 9/2014 | Sun et al. |
| 8,901,308 B2 | 12/2014 | Ying et al. |
| 8,906,885 B2 | 12/2014 | El-Hariry et al. |
| 8,921,407 B2 | 12/2014 | Ying et al. |
| 8,927,548 B2 | 1/2015 | Ying et al. |
| 8,937,094 B2 | 1/2015 | Burlison et al. |
| 8,969,396 B2 | 3/2015 | Du et al. |
| 8,993,608 B2 | 3/2015 | Du et al. |
| 9,006,277 B2 | 4/2015 | Sun et al. |
| 9,067,884 B2 | 6/2015 | Chimmanamada et al. |
| 9,090,569 B2 | 7/2015 | Ying et al. |
| 9,101,614 B2 | 8/2015 | Foley |
| 9,108,933 B2 | 8/2015 | Du et al. |
| 9,120,745 B2 | 9/2015 | Ying et al. |
| 9,126,953 B2 | 9/2015 | Ying et al. |
| 9,156,794 B2 | 10/2015 | Ying et al. |
| 9,156,836 B2 | 10/2015 | Burlison et al. |
| 9,205,086 B2 | 12/2015 | Blackman et al. |
| 9,206,162 B2 | 12/2015 | Sun et al. |
| 2006/0167070 A1 | 7/2006 | Ying et al. |
| 2007/0087998 A1 | 4/2007 | Ying et al. |
| 2008/0004277 A1 | 1/2008 | Chimmanamada et al. |
| 2008/0027047 A1 | 1/2008 | Ying |
| 2008/0090887 A1 | 4/2008 | Ying et al. |
| 2008/0125587 A1 | 5/2008 | Chimmanamada et al. |
| 2008/0176840 A1 | 7/2008 | Sun et al. |
| 2010/0069442 A1 | 3/2010 | Ying et al. |
| 2010/0081635 A1 | 4/2010 | Chen et al. |
| 2010/0093717 A1 | 4/2010 | Ying et al. |
| 2010/0249185 A1 | 9/2010 | Du et al. |
| 2010/0273846 A1 | 10/2010 | Du et al. |
| 2010/0280032 A1 | 11/2010 | Zhou et al. |
| 2010/0298331 A1 | 11/2010 | Lee et al. |
| 2011/0009397 A1 | 1/2011 | Ying et al. |
| 2011/0046125 A1 | 2/2011 | Ying |
| 2011/0105483 A1 | 5/2011 | Chimmanamada et al. |
| 2011/0152310 A1 | 6/2011 | Burlison et al. |
| 2011/0195094 A1 | 8/2011 | Ying et al. |
| 2011/0224206 A1 | 9/2011 | Ying et al. |
| 2011/0319404 A1 | 12/2011 | Foley |
| 2012/0046288 A1 | 2/2012 | Burlison et al. |
| 2012/0064175 A1 | 3/2012 | Vukovic et al. |
| 2012/0122869 A1 | 5/2012 | Ying et al. |
| 2012/0128665 A1 | 5/2012 | Blackman et al. |
| 2012/0245186 A1 | 9/2012 | Blackman et al. |
| 2012/0330009 A1 | 12/2012 | Ying et al. |
| 2013/0072461 A1 | 3/2013 | Chimmanamada et al. |
| 2013/0072489 A1 | 3/2013 | Chimmanamada et al. |
| 2013/0072536 A1 | 3/2013 | Ying et al. |
| 2013/0109045 A1 | 5/2013 | Zhou et al. |
| 2013/0150385 A1 | 6/2013 | Blackman et al. |
| 2013/0156755 A1 | 6/2013 | Blackman et al. |
| 2013/0171105 A1 | 7/2013 | Blackman et al. |
| 2013/0172333 A1 | 7/2013 | Jain et al. |
| 2013/0225870 A1 | 8/2013 | Lee et al. |
| 2013/0331357 A1 | 12/2013 | Proia et al. |
| 2013/0338155 A1 | 12/2013 | Ying |
| 2013/0345219 A1 | 12/2013 | Lee et al. |
| 2014/0005145 A1 | 1/2014 | Proia |
| 2014/0024030 A1 | 1/2014 | Blackman et al. |
| 2014/0045908 A1 | 2/2014 | Blackman et al. |
| 2014/0051664 A1 | 2/2014 | Foley et al. |
| 2014/0051665 A1 | 2/2014 | Proia et al. |
| 2014/0079636 A1 | 3/2014 | Chimmanamada et al. |
| 2014/0094436 A1 | 4/2014 | Ying et al. |
| 2014/0127740 A1 | 5/2014 | Zhou et al. |
| 2014/0135370 A1 | 5/2014 | Vukovic |
| 2014/0141511 A1 | 5/2014 | Zhou et al. |
| 2014/0178366 A1 | 6/2014 | Blackman et al. |
| 2014/0194388 A1 | 7/2014 | Proia et al. |
| 2014/0221375 A1 | 8/2014 | Du et al. |
| 2014/0228418 A1 | 8/2014 | Proia et al. |
| 2014/0255348 A1 | 9/2014 | Proia |
| 2014/0256680 A1 | 9/2014 | Proia et al. |
| 2014/0286902 A1 | 9/2014 | Proia |
| 2014/0288301 A1 | 9/2014 | Chimmanamada et al. |
| 2014/0296176 A1 | 10/2014 | Proia et al. |
| 2014/0296186 A1 | 10/2014 | Ying et al. |
| 2014/0315943 A1 | 10/2014 | Proia et al. |
| 2014/0363830 A1 | 12/2014 | Ying |
| 2015/0005299 A1 | 1/2015 | Chimmanamada et al. |
| 2015/0051203 A1 | 2/2015 | Chimmanamada et al. |
| 2015/0094349 A1 | 4/2015 | Du et al. |
| 2015/0099721 A1 | 4/2015 | Acquaviva et al. |
| 2015/0119395 A1 | 4/2015 | Chimmanamada et al. |
| 2015/0139905 A1 | 5/2015 | Chimmanamada et al. |
| 2015/0150850 A1 | 6/2015 | El-Hariry et al. |
| 2015/0150851 A1 | 6/2015 | Jain et al. |
| 2015/0174134 A1 | 6/2015 | Du et al. |
| 2015/0183771 A1 | 7/2015 | Ying et al. |
| 2015/0253330 A1 | 9/2015 | Vukovic et al. |
| 2015/0266858 A1 | 9/2015 | Sun et al. |
| 2015/0283147 A1 | 10/2015 | Proia et al. |
| 2015/0366885 A1 | 12/2015 | Ying et al. |
| 2015/0374672 A1 | 12/2015 | Vukovic et al. |
| 2016/0000756 A1 | 1/2016 | Ying et al. |
| 2016/0009724 A1 | 1/2016 | Burlison et al. |
| 2016/0120848 A1 | 5/2016 | Vukovic |
| 2016/0120849 A1 | 5/2016 | Blackman et al. |

OTHER PUBLICATIONS

Golub, 1999, Science, vol. 286, pp. 531-537.*
Target Cancer Therapies, http://www.cancer.gov/cancertopics/factsheet/therapy/targeted, accessed Jan. 12, 2011.*
Cancer Prevention Overview, http://www.cancer.gov/cancertopics/pdq/prevention/overview/patient, accessed Apr. 9, 2010.*
PCT International Search Report—(PCT/US2009/053272) Date of Mailing Jan. 28, 2010.
Patani, et al., Chem. Rev., 1996, 96, pp. 3147-3176.

* cited by examiner

TRIAZOLE COMPOUNDS THAT MODULATE HSP90 ACTIVITY

RELATED APPLICATIONS

This application is a continuation of U.S. patent application Ser. No. 13/941,081 filed Jul. 12, 2013, which is a continuation of U.S. patent application Ser. No. 13/333,191, filed Dec. 21, 2011, now U.S. Pat. No. 8,486,932, which is a continuation of U.S. patent application Ser. No. 12/538,751, filed Aug. 10, 2009, now U.S. Pat. No. 8,106,083, which claims the benefit of U.S. Provisional Application No. 61/188,543 filed Aug. 8, 2008. This application is related to U.S. Provisional Application No. 60/900,225, filed Feb. 8, 2007, U.S. Provisional Application No. 60/993,709, filed Sep. 13, 2007, and PCT Application No. PCT/US2008/01693, filed Feb. 8, 2008. The entire teachings of all of these applications are incorporated herein by reference.

BACKGROUND OF THE INVENTION

Although tremendous advances have been made in elucidating the genomic abnormalities that cause malignant cancer cells, currently available chemotherapy remains unsatisfactory, and the prognosis for the majority of patients diagnosed with cancer remains dismal. Most chemotherapeutic agents act on a specific molecular target thought to be involved in the development of the malignant phenotype. However, a complex network of signaling pathways regulate cell proliferation and the majority of malignant cancers are facilitated by multiple genetic abnormalities in these pathways. Therefore, it is unlikely that a therapeutic agent that acts on one molecular target will be fully effective in curing a patient who has cancer.

Heat shock proteins (HSPs) are a class of chaperone proteins that are up-regulated in response to elevated temperature and other environmental stresses, such as ultraviolet light, nutrient deprivation and oxygen deprivation. HSPs act as chaperones to other cellular proteins (called client proteins), facilitate their proper folding and repair and aid in the refolding of misfolded client proteins. There are several known families of HSPs, each having its own set of client proteins. The Hsp90 family is one of the most abundant HSP families accounting for about 1-2% of proteins in a cell that is not under stress and increasing to about 4-6% in a cell under stress. Inhibition of Hsp90 results in the degradation of its client proteins via the ubiquitin proteasome pathway. Unlike other chaperone proteins, the client proteins of Hsp90 are mostly protein kinases or transcription factors involved in signal transduction, and a number of its client proteins have been shown to be involved in the progression of cancer. Examples of Hsp90 client proteins that have been implicated in the progression of cancer are described below.

Her2 is a transmembrane tyrosine kinase cell surface growth factor receptor that is expressed in normal epithelial cells. Her2 has an extracellular domain that interacts with extracellular growth factors and an internal tyrosine kinase portion that transmits the external growth signal to the nucleus of the cell. Her2 is overexpressed in a significant proportion of malignancies, such as breast cancer, ovarian cancer, prostate cancer and gastric cancers, and is typically associated with a poor prognosis.

Akt kinase is a serine/threonine kinase which is a downstream effector molecule of phosphoinositide 3-kinase and is involved in protecting a cell from apoptosis. Akt kinase is thought to be involved in the progression of cancer because it stimulates cell proliferation and suppresses apoptosis.

Cdk4/cyclin D complexes are involved in phosphorylation of the retinoblastoma protein, which is an essential step in progression of a cell through the G1 phase of the cell cycle. Disruption of Hsp90 activity has been shown to decrease the half life of newly synthesized Cdk4.

Raf-1 is a MAP 3-kinase (MAP3K) which, when activated, can phosphorylate and activate the serine/threonine specific protein kinases ERK1 and ERK2. Activated ERKs play an important role in the control of gene expression involved in the cell division cycle, apoptosis, cell differentiation and cell migration.

The transforming protein of the Rous sarcoma virus, v-src, is a prototype of an oncogene family that induces cellular transformation (i.e., tumorogenesis) by non-regulated kinase activity. Hsp90 has been shown to complex with v-scr and inhibit its degradation.

Hsp90 is required to maintain steroid hormone receptors in conformations capable of binding hormones with high affinity. Inhibition of the action of Hsp90 therefore is expected to be useful in treating hormone-associated malignancies such as breast cancer.

p53 is a tumor suppressor protein that causes cell cycle arrest and apoptosis. Mutation of the p53 gene is found in about half of all human cancers, making it one of the most common genetic alterations found in cancerous cells. In addition, the p53 mutation is associated with a poor prognosis. Wild-type p53 has been shown to interact with Hsp90, but mutated p53 forms a more stable association with Hsp90 than wild-type p53 as a result of its misfolded conformation. A stronger interaction with Hsp90 protects the mutated protein from normal proteolytic degradation and prolongs its half-life. In a cell that is heterozygous for mutated and wild-type p53, inhibition of the stabilizing effect of Hsp90 causes mutant p53 to be degraded and restores the normal transcriptional activity of wild-type p53.

Hif-1α is a hypoxia-inducible transcription factor that is up-regulated under low oxygen conditions. Under normal oxygen conditions, Hif-1α associates with the Von Hippel-Lindau (VHL) tumor suppressor protein and is degraded. Low oxygen conditions inhibit this association and allows Hif-1α to accumulate and complex with Hif-1β to form an active transcription complex. The activated complex associates with hypoxia-response elements to trigger the transcription of vascular endothelial growth factor (VEGF). Increased Hif-1α is associated with increased metastasis and a poor prognosis.

There are two classes of protein kinases (PKs): protein tyrosine kinases (PTKs), which catalyze the phosphorylation of tyrosine kinase residues, and the serine-threonine kinases (STK5), which catalyze the phosphorylation of serine or threonine residues. Growth factor receptors with PTK activity are known as receptor tyrosine kinases. Receptor tyrosine kinases are a family of tightly regulated enzymes, and the aberrant activation of various members of the family is one of the hallmarks of cancer. The receptor tyrosine kinase family can be divided into subgroups that have similar structural organization and sequence similarity within the kinase domain.

Epidermal Growth Factor Receptor (EGFR) is a member of the type 1 subgroup of receptor tyrosine kinase family of growth factor receptors which play critical roles in cellular growth, differentiation and survival. Activation of these receptors typically occurs via specific ligand binding which results in hetero- or homodimerization between receptor family members, with subsequent autophosphorylation of the tyrosine kinase domain. Specific ligands which bind to EGFR include epidermal growth factor (EGF), transforming growth factor α (TGFα), amphiregulin and some viral growth factors. Activation of EGFR triggers a cascade of intracellular signaling pathways involved in both cellular proliferation (the ras/raf/MAP kinase pathway) and survival (the PI3 kinase/Akt pathway). Members of this family, including EGFR and HER2, have been directly implicated in cellular transformation.

A number of human malignancies are associated with aberrant or overexpression of EGFR and/or overexpression of its specific ligands. Gullick, *Br. Med. Bull.* (1991), 47:87-98; Modijtahedi & Dean, *Int. J. Oncol.* (1994), 4:277-96; Salomon, et al., *Crit. Rev. Oncol. Hematol.* (1995), 19:183-232. Aberrant or overexpression of EGFR has been associated with an adverse prognosis in a number of human cancers, including head and neck, breast, colon, prostate, lung (e.g., NSCLC, adenocarcinoma and squamous lung cancer), ovarian, gastrointestinal cancers (gastric, colon, pancreatic), renal cell cancer, bladder cancer, glioma, gynecological carcinomas and prostate cancer. In some instances, overexpression of tumor EGFR has been correlated with both chemoresistance and a poor prognosis. Lei, et al., *Anti-cancer Res.* (1999), 19:221-28; Veale, et al., *Br. J. Cancer* (1993); 68:162-65.

Gefitinib, a chemotherapeutic agent that inhibits the activity of EGFR, has been found to be highly efficacious in a subset of lung cancer patients that have mutations in the tyrosine kinase domain of EGFR. In the presence of EGF, these mutants displayed two to three times higher activity than wild type EGFR. In addition, wild type EGFR was internalized by the cells and down-regulated after 15 minutes, whereas mutant EGFR was internalized more slowly and continued to be activated for up to three hours. Lynch, et al., *New Eng. J. Med.* (2006), 350:2129-2139.

Gliomas are another type of cancer that is characterized by the amplification and/or mutation of the EGFR gene. One of the most common mutations in the EGFR gene is a deletion of exons 2-7 which results in a truncated form of EGFR in which amino acids 6-273 of the extracellular domain are replaced with a single glycine residue. This mutation is called EGFRvIII and is expressed in about half of all glioblastomas. EGFRvIII is unable to bind EGF and TGFα and has constitutive, ligand-independent tyrosine kinase activity. Hsp90 co-purifies with EGFRvIII, indicating that Hsp90 complexes with EGFRvIII. Moreover, the Hsp90 inhibitor geldanamycin, a benzoquinone ansamycin antibiotic, is able to decrease the expression of EGFRvIII, indicating that interaction with Hsp90 is essential to maintain high expression levels of EGFRvIII. Lavictoire, et al., *J. Biological Chem.* (2003), 278(7):5292-5299. These results demonstrate that inhibiting the activity of Hsp90 is an effective strategy for treating cancers that are associated with inappropriate EGFR activity.

The members of the type III group of receptor tyrosine kinases include platelet-derived growth factor receptors (PDGF receptors alpha and beta), colony-stimulating factor receptor (CSF-1R, c-Fms), Fms-like tyrosine kinase (FLT3), and stem cell factor receptor (c-Kit). FLT3 is primarily expressed on immature hematopoietic progenitors and regulates their proliferation and survival.

Hematologic cancers, also known as hematologic or hematopoietic malignancies, are cancers of the blood or bone marrow, including leukemia and lymphoma. Acute myelogenous leukemia (AML) is a clonal hematopoietic stem cell leukemia that represents about 90% of all acute leukemias in adults with an incidence of 3.9 per 100,000. See e.g., Lowenberg, et al., *N. Eng. J. Med.* (1999), 341: 1051-62; Menezes, et al., *Clin. Cancer Res.* (2005), 11(14): 5281-5291. While chemotherapy can result in complete remissions, the long term disease-free survival rate for AML is about 14%, with about 7,400 deaths from AML each year in the United States. Approximately 70% of AML blasts express wild type FLT3 and about 25% to about 35% express FLT3 kinase receptor mutations which result in constitutively active FLT3. Two types of activating mutations have been identified in AML patients: internal tandem duplications (ITDs) and point mutation in the activating loop of the kinase domain. FLT3-ITD mutations in AML patients are indicative of a poor prognosis for survival. In patients who are in remission, FLT3-ITD mutations are the most significant factor adversely affecting relapse rate with 64% of patients having the mutation relapsing within 5 years. See Advani, *Current Pharmaceutical Design* (2005), 11:3449-3457. The prognostic significance of FLT3 mutations in clinical studies suggests that FLT3 plays a driving role in AML and may be necessary for the development and maintenance of the disease.

Mixed Lineage Leukemia (MLL) involves translocations of chromosome 11 band q23 (11q23) and occurs in approximately 80% of infant hematological malignancies and 10% of adult acute leukemias. Although certain 11q23 translocations have been shown to be essential to immortalization of hematopoietic progenitors in vitro, a secondary genotoxic event is required to develop leukemia. There is a strong concordance between FLT3 and MLL fusion gene expression, and the most consistently overexpressed gene in MLL is FLT3. Moreover, it has been shown that activated FLT3 together with MLL fusion gene expression induces acute leukemia with a short latency period. See Ono, et al., *J. Clinical Investigation* (2005), 115:919-929. Therefore, it is believed that FLT3 signaling is involved in the development and maintenance of MLL. Armstrong, et al., *Cancer Cell* (2003), 3:173-183.

The FLT3-ITD mutation is also present in about 3% of cases of adult myelodysplastic syndrome and some cases of acute lymphocytic leukemia (ALL). Advani, *Current Pharmaceutical Design* (2005), 11:3449-3457.

FLT3 has been shown to be a client protein of Hsp90, and 17AAG, a benzoquinone ansamycin antibiotic that inhibits Hsp90 activity, has been shown to disrupt the association of FLT3 with Hsp90. The growth of leukemia cells that express either wild type FLT3 or FLT3-ITD mutations was found to be inhibited by treatment with 17AAG. Yao, et al., *Clinical Cancer Research* (2003), 9:4483-4493.

c-Kit is a membrane type III receptor protein tyrosine kinase which binds Stem Cell Factor (SCF) to its extraellular domain. c-Kit has tyrosine kinase activity and is required for normal hematopoiesis. However, mutations in c-Kit can result in ligand-independent tyrosine kinase activity, autophosphorylation and uncontrolled cell proliferation. Aberrant expression and/or activation of c-Kit has been implicated in a variety of pathologic states. For example, there is evidence of a contribution of c-Kit to neoplastic pathology, including its association with leukemias and mast cell tumors, small cell lung cancer, testicular cancer and some cancers of the gastrointestinal tract and central nervous system. In addition, c-Kit has been implicated in carcinogenesis of the female genital tract, sarcomas of neuroectodermal origin, and Schwann cell neoplasia associated with neurofibromatosis. Yang et al., *J Clin Invest.* (2003), 112: 1851-1861; Viskochil, *J Clin Invest.* (2003), 112:1791-1793. c-Kit has been shown to be a client protein of Hsp90, and Hsp90 inhibitor 17AAG has been shown to induce apoptosis in Kasumi-1 cells, an acute myeloid leukemia cell line that harbors a mutation in c-Kit.

c-Met is a receptor tyrosine kinase that is encoded by the Met protooncogene and transduces the biological effects of hepatocyte growth factor (HGF), which is also referred to as scatter factor (SF). Jiang, et al., *Crit. Rev. Oncol. Hemtol.* (1999), 29: 209-248. c-Met and HGF are expressed in numerous tissues, although their expression is normally predominantly confined to cells of epithelial and mesenchymal origin, respectively. c-Met and HGF are required for normal mammalian development and have been shown to be important in cell migration, cell proliferation, cell survival, morphogenic differentiation and the organization of 3-dimensional tubular structures (e.g., renal tubular cells, gland formation, etc.). The c-Met receptor has been shown to be expressed in a number of human cancers. c-Met and its ligand, HGF, have also been shown to be co-expressed at elevated levels in a variety of human cancers, particularly sarcomas. However, because the receptor and ligand are usually expressed by different cell types, c-Met signaling is most commonly regulated by tumor-stroma (tumor-host) interactions. Furthermore, c-Met gene amplification, mutation and rearrangement have been observed in a subset of human cancers. Families with germine mutations that activate c-Met kinase are prone to multiple kidney tumors, as well as tumors in other tissues. Numerous studies have correlated the expression of c-Met and/or HGF/SF with the state of disease progression of different types of cancer, including lung, colon, breast, prostate, liver, pancreas, brain, kidney, ovarian, stomach, skin and bone cancers. Furthermore, the overexpression of c-Met or HGF have been shown to correlate with poor prognosis and disease outcome in a number of major human cancers including lung, liver, gastric and breast.

BCR-ABL is an oncoprotein with tyrosine kinase activity that has been associated with chronic myelogenous leukemia (CML), acute lymphocytic leukemia (ALL) in a subset of patients and acute myelogenous leukemia (AML) in a subset of patients. In fact, the BCR-ABL oncogene has been found in at least 90-95% of patients with CML, about 20% of adults with ALL, about 5% of children with ALL and in about 2% of adults with AML. The BCR-ABL oncoprotein is generated by the translocation of gene sequences from the c-ABL protein tyrosine kinase on chromosome 9 into the BCR sequences on chromosome 22, producing the Philadelphia chromosome. The BCR-ABL gene has been shown to produce at least three alternative chimeric proteins, p230 BCR-ABL, p210 BCR-ABL and p190 BCR-ABL, which have unregulated tyrosine kinase activity. The p210 BCR-ABL fusion protein is most often associated with CML, while the p190 BCR-ABL fusion protein is most often associated with ALL. BCR-ABL has also been associated with a variety of additional hematological malignancies including granulocytic hyperplasia, myelomonocytic leukemia, lymphomas and erythroid leukemia.

Studies have shown that lowering the expression or activity of BCR-ABL is effective in treating BCR-ABL-positive leukemias. For example, agents such as $As_2O_3$ which lower BCR-ABL expression have been shown to be highly effective against BCR-ABL leukemias. In addition, inhibition of BCR-ABL tyrosine kinase activity by Imatinib (also known as STI571 and GLEEVEC) induces differentiation and apoptosis and causes eradication of BCR-ABL positive leukemia cells both in vivo and in vitro. In patients with CML in the chronic phase, as well as in a blast crisis, treatment with Imatinib typically will induce remission. However, in many cases, particularly in those patients who were in a blast crisis before remission, the remission is not durable because the BCR-ABL fusion protein develops mutations that cause it to be resistance to Imatinib. Nimmanapalli, et al., *Cancer Research* (2001), 61:1799-1804; Gone, et al., *Blood* (2002), 100:3041-3044.

BCR-ABL fusion proteins exist as complexes with Hsp90 and are rapidly degraded when the action of Hsp90 is inhibited. It has been shown that geldanamycin, a benzoquinone ansamycin antibiotic that disrupts the association of BCR-ABL with Hsp90, results in proteasomal degradation of BCR-ABL and induces apoptosis in BCR-ABL leukemia cells.

Hsp90 has been shown by mutational analysis to be necessary for the survival of normal eukaryotic cells. However, Hsp90 is over expressed in many tumor types indicating that it may play a significant role in the survival of cancer cells, and that cancer cells may be more sensitive to inhibition of Hsp90 than normal cells. For example, cancer cells typically have a large number of mutated and overexpressed oncoproteins that are dependent on Hsp90 for folding. In addition, because the environment of a tumor is typically hostile due to hypoxia, nutrient deprivation, acidosis, etc., tumor cells may be especially dependent on Hsp90 for survival. Moreover, inhibition of Hsp90 causes the simultaneous inhibition of a number of oncoproteins, hormone receptors and transcription factors, thus making it an attractive target for an anti-cancer agent. In fact, benzoquinone ansamycins, a family of natural products that inhibit Hsp90, have shown evidence of therapeutic activity in clinical trials.

Although promising, benzoquinone ansamycins, and their derivatives, suffer from a number of limitations. For example, they have low oral bioavailability and their limited solubility makes them difficult to formulate. In addition, they are metabolized by polymorphic cytochrome P450 CYP3A4 and are a substrate for the P-glycoprotein export pump involved in the development of multidrug resistance. Therefore, a need exists for new therapeutics that improve the prognosis of cancer patients and that reduce or overcome the limitations of currently used anti-cancer agents.

HSPs are highly conserved from microorganisms to mammals. When a pathogen invades a host, both the pathogen and the host increase HSP production. HSPs appear to play various roles in the infection process. For instance, Hsp90 has been shown to play a role in the pathways involved in the uptake and/or killing of bacteria in phagocytic cells. Yan, L., et al., *Eukaryotic Cell* (2004), 3(3):567-578. Hsp90 has also been shown to be essential for the uptake of binary actin ADP-ribosylating toxins into eukaryotic cells. Haug, G., *Infection and Immunity* (2004), 12:3066-3068. Additionally, Hsp90 has been identified as playing a role in viral proliferation in a number of viruses including influenza virus, vaccinia virus, herpes simplex virus type I and HIV-1 virus. Momose, F., et al., *J. Biol. Chem.* (2002), 277(47):45306-45314; Hung, J., et al., *J. Virology* (2002), 76(3)1379-1390; Li, Y., et al., *Antimicrobial Agents and Chemotherapy* (2004), 48(3):867-872; O'Keefe, B., et al., *J. Biol. Chem.* (2000), 275(1):279-287.

Opportunistic fungal infections that are resistant to antifungal drugs have become an increasing problem, particularly in immunocompromised patients. Hsp90 has been shown to play a role in the evolution of drug resistance in fungi. Cowen, L., et al., *Eukaryotic Cell* (2006), 5(12):2184-2188; Cowen, L., et al., *Science* (2005), 309:2185-2189.

SUMMARY OF THE INVENTION

The invention provides in one aspect, HSP90 inhibitors according to Formulae (I)-(V), and Table 1. These compounds are suitable for the treatment of hyperproliferative diseases such as cancer, infections, immune disorders and inflammation.

In one embodiment, the present invention provides compounds represented by structural Formula (I) or Table 1, or a pharmaceutically acceptable salt thereof:

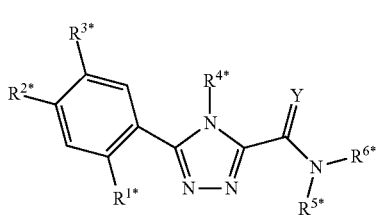

(I)

$R^{1*}$ is H, $C_1$-$C_6$ alkyl, $C_3$-$C_7$ cycloalkyl, $-OR^{12}$ or $-SR^{12}$.

$R^{2*}$ and $R^{3*}$ are individually H, halo, nitro, cyano, azido, $C_1$-$C_6$ alkyl, $C_2$-$C_6$ alkenyl, $C_2$-$C_6$ alkynyl, $C_3$-$C_7$ cycloalkyl, $-OR^{10}$, $-N(R^{10})_2$, $-C(O)R^{11}$, $-C(O)OR^{10}$, $-C(S)R^{11}$, $-C(O)SR^{10}$, $-C(O)N(R^{10})_2$, $-N(R^{10})C(O)N(R^{10})_2$, $-N(R^{10})C(O)R^{11}$, $-C(S)N(R^{10})_2$, $-C(NR^{10})OR^{10}$, $-C(NR^{10})R^{11}$, $-C(NR^{10})N(R^{10})_2$, $-S(O)_pR^{10}$ or $-S(O)_pN(R^{10})_2$, wherein each alkyl, alkenyl, alkynyl and cycloalkyl represented by $R^{2*}$ and $R^{3*}$ is independently and optionally substituted with one or more $R^{20*}$.

$R^{4*}$ is $Z^*R^{**}$, $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, wherein each substituent represented by $R^{4*}$ may be optionally substituted with one or more $R^{20*}$.

$R^{5*}$ and $R^{6*}$ are independently H, $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, $-OR^{10*}$, $-N(R^{10*})_2$, $-C(O)R^{11*}$, $-C(O)OR^{10*}$, $-C(S)R^{11*}$, $-C(O)SR^{10*}$, $-C(O)N(R^{10*})_2$, $-C(S)N(R^{10*})_2$, $-C(NR^{10*})OR^{10*}$, $-C(NR^{10*})R^{11*}$, $-C(NR^{10*})N(R^{10*})_2$, $-C(NR^{10*})SR^{10*}$, $-S(O)_pR^{10*}$, $-S(O)_pOR^{10*}$ or $-S(O)_pN(R^{10*})_2$, wherein each alkyl, alkenyl, alkynyl, cycloalkyl, aryl, heterocyclyl and heteroaryl represented by $R^{5*}$ or $R^{6*}$ is optionally and independently substituted with one or more $R^{20*}$; or $R^{5*}$ and $R^{6*}$, together with nitrogen atom to which they are attached form a 5 to 7 membered heterocyclic or heteroaromatic ring, which is optionally substituted with one or more $R^{20*}$.

Each $R^{10*}$ is independently selected from H, $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, $-OR^{12*}$, $-N(R^{12*})_2$, $-C(O)R^{12*}$, $-C(O)OR^{12*}$, $-C(S)R^{12*}$, $-C(O)SR^{12*}$, $-C(O)N(R^{12*})_2$, $-C(S)N(R^{12*})_2$, $-C(NR^{12*})OR^{12*}$, $-C(NR^{12*})R^{12*}$, $-C(NR^{12*})N(R^{12*})_2$, $-C(NR^{12*})SR^{12*}$, $-S(O)_pR^{12*}$, $-S(O)_pOR^{12*}$ or $-S(O)_pN(R^{12*})_2$, wherein the alkyl, alkenyl, alkynyl, cycloalkyl, heterocyclyl, aryl and heteroaryl represented by $R^{10*}$ are independently and optionally substituted by one or more $R^{20*}$; or two $R^{10*}$ moieties attached to the same nitrogen atom are taken together to form a 5-14 membered heterocyclyl or a 5-14 membered heteroaryl, each of which are optionally and independently substituted with one or more $R^{20*}$.

Each $R^{11*}$ is independently selected from H, $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, halo, cyano, $-OR^{12*}$, $-C(O)R^{12*}$, $-C(O)OR^{12*}$, $-C(S)R^{12*}$, $-C(O)SR^{12*}$, $-C(O)N(R^{12*})_2$, $-C(S)N(R^{12*})_2$, $-C(NR^{12*})OR^{12*}$, $-C(NR^{12*})R^{12*}$, $-C(NR^{12*})N(R^{12*})_2$, $-C(NR^{12*})SR^{12*}$, $-OC(O)N(R^{12*})_2$, $-OC(O)R^{12*}$, $-OC(O)OR^{12*}$, $-OC(S)OR^{12*}$, $-OC(NR^{12*})OR^{12*}$, $-SC(O)R^{12*}$, $-SC(O)OR^{12*}$, $-SC(NR^{12*})OR^{12*}$, $-OC(S)R^{12*}$, $-OC(O)N(R^{12*})_2$, $-OC(S)N(R^{12*})_2$, $-OC(NR^{12*})N(R^{12*})_2$, $-SC(O)N(R^{12*})_2$, $-NR^{12*}C(O)R^{12*}$, $-NR^{12*}C(S)R^{12*}$, $-NR^{12*}C(S)OR^{12*}$, $-NR^{12*}C(NR^{12*})R^{12*}$, $-NR^{12*}C(O)OR^{12*}$, $-NR^{12*}C(NR^{12*})OR^{12*}$, $-NR^{12*}C(O)N(R^{12*})_2$, $-NR^{12*}C(S)N(R^{12*})_2$, $-NR^{12*}C(NR^{12*})N(R^{12*})_2$, $-S(O)_pR^{12*}$, $-OS(O)_pR^{12*}$, $-OS(O)_pOR^{12*}$, $-OS(O)_pN(R^{12*})_2$, $-S(O)_pOR^{12*}$, $-NR^{12*}S(O)_pR^{12*}$, $-NR^{12*}S(O)_pN(R^{12*})_2$, $-NR^{12*}$, $-S(O)_pN(R^{12*})_2$ or $-OP(O)(OR^{12*})_2$, wherein the alkyl, alkenyl, alkynyl, cycloalkyl, heterocyclyl, aryl and heteroaryl represented by $R^{11*}$ are each independently and optionally substituted by one or more $R^{20*}$; or two $R^{11*}$ moieties attached to the same carbon atom together form an oxo (=O), thioxo (=S) or imino (=$NR^{12*}$).

Each $R^{12*}$ is independently H, $C_1$-$C_3$ alkyl, $C_2$-$C_3$ alkenyl, $C_1$-$C_3$ haloalkyl, $C_1$-$C_3$ alkoxy, $C_1$-$C_3$ haloalkoxy, $C_3$-$C_7$ cycloalkyl, phenyl, or benzyl, wherein each $R^{12}$ with at least one hydrogen atom is optionally substituted with one or more $R^{20*}$; or two $R^{12*}$ substituents that are attached to the same atom or adjacent atoms, taken together with the atom(s) to which they are attached, form a 5-7 membered heterocyclyl or $C_3$-$C_7$ cycloalkyl which are each optionally and independently substituted with one or more $R^{20*}$.

Each $R^{20*}$ is independently selected from the group consisting of $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, $C_3$-$C_7$ cycloalkyl-($C_1$-$C_3$)alkyl, 5-14 membered heterocyclyl-($C_1$-$C_3$)alkyl, $C_6$-$C_{20}$ aryl-($C_1$-$C_3$)alkyl, 5-14 membered heteroaryl-($C_1$-$C_3$)alkyl, halo, cyano, nitro, azido, $-N(R^{12*})_2$, $-OR^{12*}$, $-C(O)R^{12*}$, $-C(O)OR^{12*}$, $-C(S)R^{12*}$, $-C(O)SR^{12*}$, $-C(S)SR^{12*}$, $-C(S)OR^{12*}$, $-C(O)N(R^{12*})_2$, $-C(S)N(R^{12*})_2$, $-C(NR^{12*})OR^{12*}$, $-C(NR^{12*})R^{12*}$, $-C(NR^{12*})N(R^{12*})_2$, $-C(NR^{12*})SR^{12*}$, $-OC(O)N(R^{12*})_2$, $-OC(O)R^{12*}$, $-OC(O)OR^{12*}$, $-OC(S)OR^{12*}$, $-OC(NR^{12*})OR^{12*}$, $-SC(O)R^{12*}$, $-SC(O)OR^{12*}$, $-SC(NR^{12*})OR^{12*}$, $-OC(S)R^{12*}$, $-SC(S)R^{12*}$, $-SC(S)OR^{12*}$, $-OC(O)N(R^{12*})_2$, $-OC(S)N(R^{12*})_2$, $-OC(NR^{12*})N(R^{12*})_2$, $-SC(O)N(R^{12*})_2$, $-SC(NR^{12*})N(R^{12*})_2$, $-SC(S)N(R^{12*})_2$, $-OC(NR^{12*})R^{12*}$, $-SC(NR^{12*})R^{12*}$, $-NR^{12*}C(O)R^{12*}$, $-NR^{12*}C(S)R^{12*}$, $-NR^{12*}C(S)OR^{12*}$, $-NR^{12*}C(NR^{12*})R^{12*}$, $-NR^{12*}C(O)OR^{12*}$, $-NR^{12*}C(NR^{12*})OR^{12*}$, $-NR^{12}C(O)N(R^{12})_2$, $-NR^{12*}C(S)N(R^{12*})_2$, $-NR^{12*}C(NR^{12*})N(R^{12*})_2$, $-S(O)_pR^{12*}$, $-OS(O)_pR^{12*}$, $-OS(O)_pOR^{12*}$, $-OS(O)_pN(R^{12*})_2$, $-S(O)_pOR^{12*}$, $-NR^{12*}S(O)_pR^{12*}$, $-NR^{12*}S(O)_pN(R^{12*})_2$, $-NR^{12*}S(O)_pOR^{12*}$, $-S(O)_pN(R^{12*})_2$, $-SS(O)_pR^{12*}$, $-SS(O)_pOR^{12*}$, $-SS(O)_pN(R^{12*})_2$, $-OP(O)(OR^{12*})_2$, or $-SP(O)(OR^{12*})_2$, wherein the alkyl, alkenyl, alkynyl, cycloalkyl, heterocyclyl, aryl, heteroaryl, aralkyl, and heteroaralkyl represented by $R^{20}$ are each optionally and independently substituted with one to three groups from halo, $C_1$-$C_3$ alkyl, phenyl, benzyl, $C_1$-$C_3$ haloalkyl, $C_1$-$C_3$ alkoxy, $C_1$-$C_3$ haloalkoxy, nitro, cyano, azido, amino and $C_1$-$C_5$ carbamoyl; or two $R^{20}$ moieties attached to the same atom form an oxo (=O), thioxo (=S) or imino (=$NR^{12*}$).

$R^{**}$ is $C_6$-$C_{20}$ aryl or 5-14 membered heteroaryl, each of which is optionally substituted with one or more $R^{20*}$. $Z^*$ is $NR^{10*}$, C(O), C(S), C(=$NR^{10*}$), $NR^{10*}S(O)_p$, $S(O)_p$ or $S(O)_pNR^{10*}$. The variable p is 0, 1 or 2.

Provided that no more than one of $R^{1*}$, $R^{2*}$ and $R^{3*}$ is hydrogen.

In one embodiment, the present invention provides compounds represented by structural Formula (II), or a pharmaceutically acceptable salt thereof:

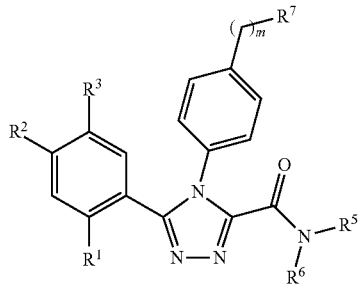

(II)

$R^1$ is H, $OR^{12}$ or $C_1$-$C_3$ alkyl. $R^2$ is $OR^{12}$ or halo. $R^3$ is H, $C_1$-$C_6$ alkyl or $C_3$-$C_6$ cycloalkyl. The variable m is 0 or 1. $R^7$ is phenyl, $S(O)_pR^{10}$, $OR^{10}$, $N(R^{10})_2$ or $=NN(R^{10})_2$.

$R^5$ and $R^6$ are individually hydrogen, $C_1$-$C_6$ alkyl, $C_2$-$C_6$ alkenyl, $C_2$-$C_6$ alkynyl, $C_3$-$C_7$ cycloalkyl, 5-7 membered heterocyclyl, phenyl, benzyl, 5-7 membered heteroaryl, $-N(R^{12})_2$, $-C(O)R^{12}$, $-C(O)OR^{12}$, $-S(O)_pR^{12}$, or $-S(O)_pN(R^{12})_2$, wherein each $R^5$ and $R^6$ that is not hydrogen is optionally and independently substituted with one or more $R^{20}$; or $R^5$ and $R^6$, taken together with the nitrogen to which they are attached, form a 5-7 membered heterocyclyl which is optionally substituted with one or more $R^{20}$.

Each $R^{10}$ is independently selected from H, $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, $-OR^{12}$, $-N(R^{12})_2$, $-C(O)R^{12}$, $-C(O)OR^{12}$, $-C(S)R^{12}$, $-C(O)SR^{12}$, $-C(O)N(R^{12})_2$, $-C(S)N(R^{12})_2$, $-C(NR^{12})OR^{12}$, $-C(NR^{12})R^{12}$, $-C(NR^{12})N(R^{12})_2$, $-C(NR^{12})SR^{12}$, $-S(O)_pR^{12}$, $-S(O)_pOR^{12}$ or $-S(O)_pN(R^{12})_2$, wherein the alkyl, alkenyl, alkynyl, cycloalkyl, heterocyclyl, aryl and heteroaryl represented by $R^{10}$ are independently and optionally substituted by one or more $R^{20}$; or two $R^{10}$ moieties attached to the same nitrogen atom are taken together to form a 5-14 membered heterocyclyl or a 5-14 membered heteroaryl, each of which are optionally and independently substituted with one or more $R^{20}$.

Each $R^{12}$ is independently H, $C_1$-$C_3$ alkyl, $C_2$-$C_3$ alkenyl, $C_1$-$C_3$ haloalkyl, $C_1$-$C_3$ alkoxy, $C_1$-$C_3$ haloalkoxy, $C_3$-$C_7$ cycloalkyl, phenyl, or benzyl, wherein each $R^{12}$ with at least one hydrogen atom is optionally substituted with one or more $R^{20}$; or two $R^{12}$ substituents that are attached to the same atom or adjacent atoms, taken together with the atom(s) to which they are attached, form a 5-7 membered heterocyclyl or $C_3$-$C_7$ cycloalkyl which are each optionally and independently substituted with one or more $R^{20}$.

Each $R^{20}$ is independently selected from the group consisting of $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, $C_3$-$C_7$ cycloalkyl-($C_1$-$C_3$)alkyl, 5-14 membered heterocyclyl-($C_1$-$C_3$)alkyl, $C_6$-$C_{20}$ aryl-($C_1$-$C_3$) alkyl, 5-14 membered heteroaryl-($C_1$-$C_3$)alkyl, halo, cyano, nitro, azido, $-N(R^{12})_2$, $-OR^{12}$, $-C(O)R^{12}$, $-C(O)OR^{12}$, $-C(S)R^{12}$, $-C(O)SR^{12}$, $-C(S)SR^{12}$, $-C(S)OR^{12}$, $-C(O)N(R^{12})_2$, $-C(S)N(R^{12})_2$, $-C(NR^{12})OR^{12}$, $-C(NR^{12})R^{12}$, $-C(NR^{12})N(R^{12})_2$, $-C(NR^{12})SR^{12}$, $-OC(O)N(R^{12})_2$, $-OC(O)R^{12}$, $-OC(O)OR^{12}$, $-OC(S)R^{12}$, $-OC(NR^{12})OR^{12}$, $-SC(O)R^{12}$, $-SC(O)OR^{12}$, $-SC(NR^{12})OR_{12}$, $-OC(S)R^{12}$, $-SC(S)R^{12}$, $-SC(S)OR^{12}$, $-OC(O)N(R^{12})_2$, $-OC(S)N(R^{12})_2$, $-OC(NR^{12})N(R^{12})_2$, $-SC(O)N(R^{12})_2$, $-SC(NR^{12})N(R^{12})_2$, $-SC(S)N(R^{12})_2$, $-OC(NR^{12})R^{12}$, $-SC(NR^{12})R^{12}$, $-NR^{12}C(O)R^{12}$, $-NR^{12}C(S)R^{12}$, $-NR^{12}C(S)OR^{12}$, $-NR^{12}C(NR^{12})R^{12}$, $-NR^{12}C(O)OR^{12}$, $-NR^{12}C(NR^{12})OR^{12}$, $-NR^{12}C(O)N(R^{12})_2$, $-NR^{12}C(S)N(R^{12})_2$, $-NR^{12}C(NR^{12})N(R^{12})_2$, $-S(O)_pR^{12}$, $-OS(O)_pR^{12}$, $-OS(O)_pR^{12}$, $-OS(O)_pOR^{12}$, $-OS(O)_pN(R^{12})_2$, $-S(O)_pOR^{12}$, $-NR^{12}S(O)_pR^{12}$, $-NR^{12}S(O)_pN(R^{12})_2$, $-NR^{12}S(O)_pOR^{12}$, $-S(O)_pN(R^{12})_2$, $-SS(O)_pR^{12}$, $-SS(O)_pOR^{12}$, $-SS(O)_pN(R^{12})_2$, $-OP(O)(OR^{12})_2$, or $-SP(O)(OR^{12})_2$, wherein the alkyl, alkenyl, alkynyl, cycloalkyl, heterocyclyl, aryl, heteroaryl, aralkyl, and heteroaralkyl represented by $R^{20}$ are each optionally and independently substituted with one to three groups from halo, $C_1$-$C_3$ alkyl, phenyl, benzyl, $C_1$-$C_3$haloalkyl, $C_1$-$C_3$ alkoxy, $C_1$-$C_3$ haloalkoxy, nitro, cyano, azido, amino and $C_1$-$C_5$ carbamoyl; or two $R^{20}$ moieties attached to the same atom form an oxo ($=O$), thioxo ($=S$) or imino ($=NR^{12}$).

Provided that one of $R^1$ and $R^3$ is hydrogen.

In one embodiment, the present invention provides compounds represented by structural Formula (III), or a pharmaceutically acceptable salt thereof:

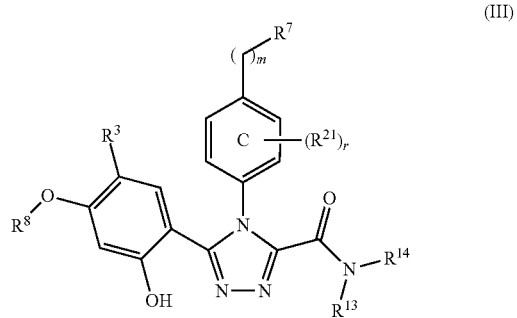

(III)

The variable m is 0 or 1. The variable r is 0, 1 or 2. $R^8$ is $C_1$-$C_3$ alkyl or $C_1$-$C_3$ haloalkyl. $R^3$ is H, $C_1$-$C_4$ alkyl or $C_3$-$C_6$ cycloalkyl. $R^7$ is phenyl, $S(O)_pR^{31}$, $OR^{31}$, $N(R^{31})_2$ or $=NN(R^{31})_2$.

$R^{13}$ and $R^{14}$ are individually hydrogen, $C_1$-$C_6$ alkyl, $C_2$-$C_6$ alkenyl, $C_2$-$C_6$ alkynyl, $C_3$-$C_7$ cycloalkyl, 5-7 membered heterocyclyl, phenyl, benzyl, 5-7 membered heteroaryl, $-N(R^{32})_2$, $-C(O)R^{32}$, $-C(O)OR^{32}$, $-S(O)_pR^{32}$, or $-S(O)_pN(R^{32})_2$, wherein each $R^{13}$ and $R^{14}$ that is not hydrogen is optionally and independently substituted with one or more $R^{21}$; or $R^{13}$ and $R^{14}$, taken together with the nitrogen to which they are attached, form a 5-7 membered heterocyclyl which is optionally substituted with one or more $R^{21}$.

Each $R^{31}$ is independently selected from H, $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, $-OR^{32}$, $-N(R^{32})_2$, $-C(O)R^{32}$, $-C(O)OR^{32}$, $-C(S)R^{32}$, $-C(O)SR^{32}$, $-C(O)N(R^{32})_2$, $-C(S)N(R^{32})_2$, $-C(NR^{32})OR^{32}$, $-C(NR^{32})R^{32}$, $-C(NR^{32})N(R^{32})_2$, $-C(NR^{32})SR^{32}$, $-S(O)_pR^{32}$, $-S(O)_pOR^{32}$ or $-S(O)_pN(R^{32})_2$, wherein the alkyl, alkenyl, alkynyl, cycloalkyl, heterocyclyl, aryl and heteroaryl represented by $R^{31}$ are independently and optionally substituted by one or more $R^{21}$; or two $R^{31}$ moieties attached to the same nitrogen atom are taken together to form a 5-14 membered heterocyclyl or a 5-14 membered heteroaryl, each of which are optionally and independently substituted with one or more $R^{21}$.

Each $R^{12}$ is independently H, $C_1$-$C_3$ alkyl, $C_2$-$C_3$ alkenyl, $C_1$-$C_3$ haloalkyl, $C_1$-$C_3$ alkoxy, $C_1$-$C_3$ haloalkoxy, $C_3$-$C_7$ cycloalkyl, phenyl, or benzyl, wherein each $R^{12}$ with at least one hydrogen atom is optionally substituted with one or more $R^{21}$; or two $R^{12}$ substituents that are attached to the same atom or adjacent atoms, taken together with the atom(s) to which they are attached, form a 5-7 membered heterocyclyl or $C_3$-$C_7$ cycloalkyl which are each optionally and independently substituted with one or more $R^{21}$.

Each $R^{21}$ is independently selected from the group consisting of $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, $C_3$-$C_7$ cycloalkyl-($C_1$-$C_3$)alkyl, 5-14 membered heterocyclyl-($C_1$-$C_3$)alkyl, $C_6$-$C_{20}$ aryl-($C_1$-$C_3$) alkyl, 5-14 membered heteroaryl-($C_1$-$C_3$)alkyl, halo, cyano, nitro, azido, —N($R^{32}$)$_2$, —O$R^{32}$, —C(O)$R^{32}$, —C(O)O$R^{32}$, —C(S)$R^{32}$, —C(O)S$R^{32}$, —C(S)S$R^{32}$, —C(S)O$R^{32}$, —C(O)N($R^{32}$)$_2$, —C(S)N($R^{32}$)$_2$, —C(N$R^{32}$)O$R^{32}$, —C(N$R^{12}$)$R^{32}$, —C(N$R^{32}$)N($R^{32}$)$_2$, —C(N$R^{32}$)S$R^{32}$, —OC(O)N($R^{32}$)$_2$, —OC(O)$R^{32}$, —OC(O)O$R^{32}$, —OC(S)O$R^{32}$, —OC(N$R^{32}$)O$R^{32}$, —SC(O)$R^{32}$, —SC(O)O$R^{32}$, —SC(N$R^{32}$)O$R^{32}$, —OC(S)$R^{32}$, —SC(S)$R^{32}$, —SC(S)O$R^{32}$, —OC(O)N($R^{32}$)$_2$, —OC(S)N($R^{32}$)$_2$, —OC(N$R^{32}$)N($R^{32}$)$_2$, —SC(O)N($R^{32}$)$_2$, —SC(N$R^{32}$)N($R^{32}$)$_2$, —SC(S)N($R^{32}$)$_2$, —OC(N$R^{32}$)$R^{32}$, —SC(N$R^{32}$)$R^{32}$, —N$R^{32}$C(O)$R^{32}$, —N$R^{32}$C(S)$R^{32}$, —N$R^{32}$C(S)O$R^{32}$, —N$R^{32}$C(N$R^{32}$)$R^{32}$, —N$R^{32}$C(O)O$R^{32}$, —N$R^{32}$C(N$R^{32}$)O$R^{32}$, —N$R^{32}$C(O)N($R^{32}$)$_2$, —N$R^{32}$C(S)N($R^{32}$)$_2$, —N$R^{32}$C(N$R^{32}$)N($R^{32}$)$_2$, —S(O)$_p R^{32}$, —OS(O)$_p R^{32}$, —OS(O)$_p$O$R^{32}$, —OS(O)$_p$N($R^{32}$)$_2$, —S(O)$_p$O$R^{32}$, —N$R^{32}$S(O)$_p R^{32}$, —N$R^{32}$S(O)$_p$N($R^{32}$)$_2$, —N$R^{32}$S(O)$_p$O$R^{32}$, —S(O)$_p$N($R^{32}$)$_2$, —SS(O)$_p R^{32}$, —SS(O)$_p$O$R^{32}$, —SS(O)$_p$N($R^{32}$)$_2$, —OP(O)(O$R^{32}$)$_2$, or —SP(O)(O$R^{32}$)$_2$, wherein the alkyl, alkenyl, alkynyl, cycloalkyl, heterocyclyl, aryl, heteroaryl, aralkyl, and heteroaralkyl represented by $R^{21}$ are each optionally and independently substituted with one to three groups from halo, $C_1$-$C_3$ alkyl, phenyl, benzyl, $C_1$-$C_3$ haloalkyl, $C_1$-$C_3$ alkoxy, $C_1$-$C_3$ haloalkoxy, nitro, cyano, azido, amino and $C_1$-$C_5$ carbamoyl; or two $R^{21}$ moieties attached to the same atom form an oxo (=O), thioxo (=S) or imino (=N$R^{32}$).

In one embodiment, the present invention provides compounds represented by structural Formula (IV), or a pharmaceutically acceptable salt thereof:

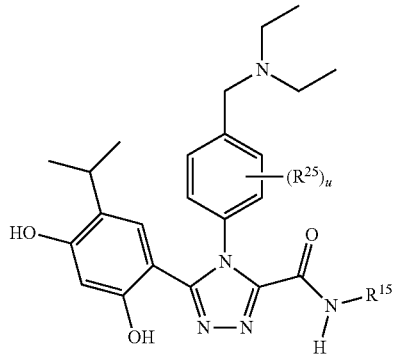

(IV)

$R^{15}$ is $C_1$-$C_6$ alkyl, $C_2$-$C_6$ alkenyl, $C_3$-$C_7$ cycloalkyl, phenyl, benzyl, —C(O)$R^{42}$, —N($R^{42}$)$_2$, —C(N$R^{42}$)$R^{42}$, —C(N$R^{42}$)N($R^{42}$)$_2$, —S(O)$_p R^{42}$ or —S(O)$_p$N($R^{42}$)$_2$, wherein each alkyl, alkenyl, cycloalkyl, phenyl and benzyl, represented by $R^{15}$ is optionally substituted with one or more $R^{22}$.

Each $R^{42}$ is independently H or $C_1$-$C_4$ alkyl; or two $R^{42}$ moieties attached to the same nitrogen atom are taken together to form a 5-7 membered heterocyclyl.

Each $R^{22}$ is independently halo, $C_1$-$C_3$ alkyl, $C_1$-$C_3$ haloalkyl, $C_1$-$C_3$ alkoxy, $C_1$-$C_3$ haloalkoxyl, $C_3$-$C_6$ cycloalkyl, 5-7 membered heterocycle, —C(O)$R^{42}$, —C(O)O$R^{42}$, —C(O)N($R^{42}$)$_2$, —N($R^{42}$)$_2$, or —N$R^{42}$C(O)$R^{42}$; or two $R^{21}$ moieties attached to the same atom, taken together, form an oxo (=O), thiooxo (=S), or imino (=N).

Each $R^{25}$ is independently halo, $C_1$-$C_3$ alkyl, $C_1$-$C_3$ haloalkyl, $C_1$-$C_3$ alkoxy, $C_1$-$C_3$ haloalkoxyl, $C_3$-$C_6$ cycloalkyl, 5-7 membered heterocycle, —C(O)$R^{42}$, —C(O)O$R^{42}$, —C(O)N($R^{42}$)$_2$, —N($R^{42}$)$_2$, or —N$R^{42}$C(O)$R^{42}$; or two $R^{25}$ moieties attached to the same atom, taken together, form an oxo (=O), thiooxo (=S), or imino (=N). The variable u is 0, 1 or 2.

Provided that $R^{15}$ is other than isopropyl or —(CH$_2$)$_2$N(CH$_3$)$_2$.

In one embodiment, the present invention provides compounds represented by structural Formula (V), or a pharmaceutically acceptable salt thereof:

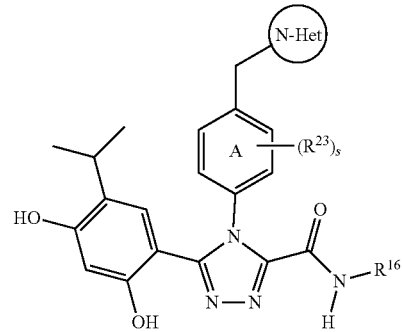

(V)

N-Het is piperidine, piperazine, morpholine, pyrrolidine, imidazolidine, hexahydropyrimidine or pyrazolidine, each optionally and independently substituted with one or two $R^{23}$.

$R^{16}$ is H, $C_1$-$C_6$ alkyl, $C_2$-$C_6$ alkenyl, $C_3$-$C_7$ cycloalkyl, phenyl, benzyl, —C(O)$R^{52}$, —N($R^{52}$)$_2$, —C(N$R^{52}$)$R^{52}$, —C(N$R^{52}$)N($R^{52}$)$_2$, —S(O)$_p R^{52}$ or —S(O)$_p$N($R^{52}$)$_2$, wherein each alkyl, alkenyl, cycloalkyl, phenyl and benzyl, represented by $R^{16}$ is optionally substituted with one or more $R^{23}$.

Each $R^{52}$ is independently H or $C_1$-$C_4$ alkyl; or two $R^{52}$ moieties attached to the same nitrogen atom are taken together to form a 5-7 membered heterocyclyl.

Each $R^{23}$ is independently halo, $C_1$-$C_3$ alkyl, $C_1$-$C_3$ haloalkyl, $C_1$-$C_3$ alkoxy, $C_1$-$C_3$ haloalkoxyl, $C_3$-$C_6$ cycloalkyl, 5-7 membered heterocycle, —C(O)$R^{52}$, —C(O)O$R^{52}$, —C(O)N($R^{52}$)$_2$, —N($R^{52}$)$_2$, or —N$R^{52}$C(O)$R^{52}$; or two $R^{23}$ moieties attached to the same atom, taken together, form an oxo (=O), thiooxo (=S), or imino (=N).

The variable s is 0, 1 or 2.

Provided that when N-Het is morpholine and s is 0, then $R^{16}$ is other than H, ethyl, isopropyl, isobutyl, propyl, cyclohexyl, or an ethylene substituted with hydroxyl, methoxy, dimethylamine, diethylamine, pyrrolidine, 4-methylpiperazine or morpholine; when N-Het is 4-methylpiperidinyl and s is 0, then $R^{16}$ is other than H; when N-Het is pyrrolidinyl and s is 0, then $R^{16}$ is other than an ethylene substituted with a pyrrolidine, morpholine, or 4-methyl-piperazine; and when N-Het is 4-methylpiperazinyl or 4-ethylpiperazinyl and s is 0, then $R^{16}$ is other than isopropyl.

In one embodiment, the present invention provides compounds represented by structural Formula (VI), or a pharmaceutically acceptable salt thereof:

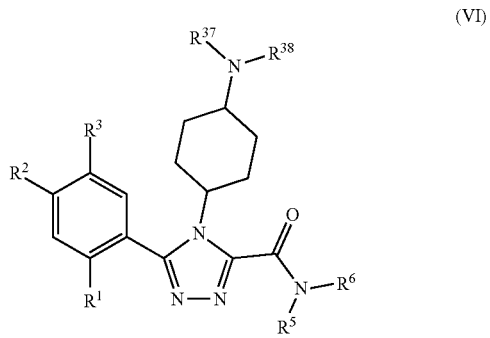

(VI)

$R^1$ is H, $OR^{12}$ or $C_1$-$C_3$ alkyl. $R^2$ is $OR^{12}$ or halo. $R^3$ is H, $C_1$-$C_6$ alkyl or $C_3$-$C_6$ cycloalkyl.

$R^5$ and $R^6$ are individually hydrogen, $C_1$-$C_6$ alkyl, $C_2$-$C_6$ alkenyl, $C_2$-$C_6$ alkynyl, $C_3$-$C_7$ cycloalkyl, 5-7 membered heterocyclyl, phenyl, benzyl, 5-7 membered heteroaryl, —N($R^{12}$)$_2$, —C(O)$R^{12}$, —C(O)O$R^{12}$, —S(O)$_p$$R^{12}$, or —S(O)$_p$N($R^{12}$)$_2$, wherein each $R^5$ and $R^6$ that is not hydrogen is optionally and independently substituted with one or more $R^{20}$; or $R^5$ and $R^6$, taken together with the nitrogen to which they are attached, form a 5-7 membered heterocyclyl which is optionally substituted with one or more $R^{20}$.

Each $R^{12}$ is independently H, $C_1$-$C_3$ alkyl, $C_2$-$C_3$ alkenyl, $C_1$-$C_3$ haloalkyl, $C_1$-$C_3$ alkoxy, $C_1$-$C_3$ haloalkoxy, $C_3$-$C_7$ cycloalkyl, phenyl, or benzyl, wherein each $R^{12}$ with at least one hydrogen atom is optionally substituted with one or more $R^{20}$; or two $R^{12}$ substituents that are attached to the same atom or adjacent atoms, taken together with the atom(s) to which they are attached, form a 5-7 membered heterocyclyl or $C_3$-$C_7$ cycloalkyl which are each optionally and independently substituted with one or more $R^{20}$.

Each $R^{20}$ is independently selected from the group consisting of $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, $C_3$-$C_7$ cycloalkyl-($C_1$-$C_3$)alkyl, 5-14 membered heterocyclyl-($C_1$-$C_3$)alkyl, $C_6$-$C_{20}$ aryl-($C_1$-$C_3$) alkyl, 5-14 membered heteroaryl-($C_1$-$C_3$)alkyl, halo, cyano, nitro, azido, —N($R^{12}$)$_2$, —O$R^{12}$, —C(O)$R^{12}$, —C(O)O$R^{12}$, —C(S)$R^{12}$, —C(O)S$R^{12}$, —C(S)S$R^{12}$, —C(S)O$R^{12}$, —C(O)N($R^{12}$)$_2$, —C(S)N($R^{12}$)$_2$, —C(N$R^{12}$)O$R^{12}$, —C(N$R^{12}$)$R^{12}$, —C(N$R^{12}$)N($R^{12}$)$_2$, —C(N$R^{12}$)S$R^{12}$, —OC(O)N($R^{12}$)$_2$, —OC(O)$R^{12}$, —OC(O)O$R^{12}$, —OC(S)O$R^{12}$, —OC(N$R^{12}$)O$R^{12}$, —SC(O)$R^{12}$, —SC(O)O$R^{12}$, —SC(N$R^{12}$)O$R_{12}$, —OC(S)$R^{12}$, —SC(S)$R^{12}$, —SC(S)O$R^{12}$, —OC(O)N($R^{12}$)$_2$, —OC(S)N($R^{12}$)$_2$, —OC(N$R^{12}$)N($R^{12}$)$_2$, —SC(O)N($R^{12}$)$_2$, —SC(N$R^{12}$)N($R^{12}$)$_2$, —SC(S)N($R^{12}$)$_2$, —OC(N$R^{12}$)$R^{12}$, —SC(N$R^{12}$)$R^{12}$, —N$R^{12}$C(O)$R^{12}$, —N$R^{12}$C(S)$R^{12}$, —N$R^{12}$C(S)O$R^{12}$, —N$R^{12}$C(N$R^{12}$)$R^{12}$, —N$R^{12}$C(O)O$R^{12}$, —N$R^{12}$C(N$R^{12}$)O$R^{12}$, —N$R^{12}$C(O)N($R^{12}$)$_2$, —N$R^{12}$C(S)N($R^{12}$)$_2$, N$R^{12}$C(N$R^{12}$)N($R^{12}$)$_2$, —S(O)$_p$ $R^{12}$, —OS(O)$_p$$R^{12}$, —OS(O)$_p$O$R^{12}$, —OS(O)$_p$N($R^{12}$)$_2$, —S(O)$_p$O$R^{12}$, —N$R^{12}$S(O)$_p$$R^{12}$, —N$R^{12}$S(O)$_p$N($R^{12}$)$_2$, —N$R^{12}$S(O)$_p$O$R^{12}$, —S(O)$_p$N($R^{12}$)$_2$, —SS(O)$_p$$R^{12}$, —SS(O)$_p$O$R^{12}$, —SS(O)$_p$N($R^{12}$)$_2$, —OP(O)(O$R^{12}$)$_2$, or —SP(O)(O$R^{12}$)$_2$, wherein the alkyl, alkenyl, alkynyl, cycloalkyl, heterocyclyl, aryl, heteroaryl, aralkyl, and heteroaralkyl represented by $R^{20}$ are each optionally and independently substituted with one to three groups from halo, $C_1$-$C_3$ alkyl, phenyl, benzyl, $C_1$-$C_3$ haloalkyl, $C_1$-$C_3$ alkoxy, $C_1$-$C_3$ haloalkoxy, nitro, cyano, azido, amino and $C_1$-$C_5$ carbamoyl; or two $R^{20}$ moieties attached to the same atom form an oxo (=O), thioxo (=S) or imino (=N$R^{12}$).

$R^{37}$ and $R^{38}$ are individually hydrogen, $C_1$-$C_6$ alkyl, $C_2$-$C_6$ alkenyl, $C_2$-$C_6$ alkynyl, $C_3$-$C_7$ cycloalkyl, 5-7 membered heterocyclyl, phenyl, benzyl, 5-7 membered heteroaryl, —N($R^{12}$)$_2$, —C(O)$R^{12}$, —C(O)O$R^{12}$, —S(O)$_p$$R^{12}$, or —S(O)$_p$N($R^{12}$)$_2$, wherein each $R^{37}$ and $R^{38}$ that is not hydrogen is optionally and independently substituted with one or more $R^{20}$; or $R^{37}$ and $R^{38}$, taken together with the nitrogen to which they are attached, form a 5-7 membered heterocyclyl which is optionally substituted with one or more $R^{20}$.

The present invention provides a method of inhibiting HSP90 in a cell, comprising administering to the cell an effective amount of a compound of Formulae (I)-(VI) or Table 1. The invention also provides a method of treating a proliferative disorder in a subject in need thereof, comprising administering to the subject an effective amount of a compound of Formulae (I)-(VI) or Table 1. Additionally, the invention provides a method of treating cancer in a subject in need thereof, comprising administering to the subject an effective amount of a compound of Formulae (I)-(VI) or Table 1.

The present invention provides a method of inducing degradation of c-Kit proteins in a cell, comprising administering to the cell an effective amount of a compound of Formulae (I)-(VI) or Table 1. The invention encompasses a method of treating a c-Kit associated cancer in a subject in need thereof, comprising administering to the subject an effective amount of a compound of Formulae (I)-(VI) or Table 1.

The present invention provides a method of inducing degradation of BCR-ABL proteins in a cell, comprising administering to the cell an effective amount of a compound of Formulae (I)-(VI) or Table 1. The invention encompasses a method of treating a BCR-ABL associated cancer in a subject in need thereof, comprising administering to the subject an effective amount of a compound of Formulae (I)-(VI) or Table 1.

The present invention provides a method of inducing degradation of FLT3 proteins in a cell, comprising administering to the cell an effective amount of a compound of Formulae (I)-(VI) or Table 1. The invention encompasses a method of treating a FLT3 associated cancer in a subject in need thereof, comprising administering to the subject an effective amount of a compound of Formulae (I)-(VI) or Table 1.

The present invention provides a method of inducing degradation of EGFR proteins in a cell, comprising administering to the cell an effective amount of a compound of Formulae (I)-(VI) or Table 1. The invention encompasses a method of treating a EGFR associated cancer in a subject in need thereof, comprising administering to the subject an effective amount of a compound of Formulae (I)-(VI) or Table 1.

The present invention also provides a method of treating an infection in a subject in need thereof, comprising administering to the subject an effective amount of a compound of Formulae (I)-(VI) or Table 1. The present invention includes a method of treating a fungal infection in a subject in need thereof, comprising administering to the subject an effective amount of a compound of Formulae (I)-(VI) or Table 1. The present invention includes a method of treating a viral infection in a subject in need thereof, comprising administering to the subject an effective amount of a compound of Formulae (I)-(VI) or Table 1. The present invention includes a method of treating a bacterial infection in a subject in need thereof, comprising administering to the subject an effective amount of a compound of Formulae (I)-(VI or Table 1. The present invention includes a method of treating a parasitic infection in a subject in need thereof, comprising administering to the subject an effective amount of a compound of Formulae (I)-(VI) or Table 1.

The present invention also provides a method of inhibiting angiogenesis in a subject in need thereof, comprising administering to the subject an effective amount of a compound of Formulae (I)-(VI) or Table 1. The invention also includes a method of occluding, blocking, or otherwise disrupting the blood flow in neovasculature, comprising contacting the neovasculature with an effective amount of a compound of Formulae (I)-(VI) or Table 1.

The present invention provides a method for treating a non-Hodgkin's lymphoma in a subject in need thereof, comprising administering to the subject an effective amount of a compound of Formulae (I)-(VI) or Table 1. The invention includes a method of treating B-cell and/or T-cell non-Hodgkin's lymphoma.

The present invention also provides method of inhibiting the activity of topoisomerase II in a cell, comprising administering to a cell an effective amount of a compound of Formulae (I)-(VI) or Table 1.

The present invention also provides method of modulating the activity of glucocorticoid receptors in a cell, comprising administering to a cell an effective amount of a compound of Formulae (I)-(VI) or Table 1.

The present invention additionally includes a method of treating an inflammatory disorder in a subject in need thereof, comprising administering to the subject an effective amount of a compound of Formulae (I)-(VI) or Table 1.

The present invention additionally includes a method of treating an immune disorder in a subject in need thereof, comprising administering to the subject an effective amount of a compound of Formulae (I)-(VI) or Table 1. The invention provides a method of suppressing the immune system of a subject in need thereof, comprising administering to the subject an effective amount of a compound of Formulae (I)-(VI) or Table 1.

The present invention further provides a pharmaceutical composition of a compound of Formulae (I)-(VI) or Table 1, comprising said compound and a pharmaceutically acceptable carrier. An additional embodiment of the invention includes a pharmaceutical composition comprising a compound of Formulae (I)-(VI) or Table 1 and an additional therapeutic agent.

The compounds shown in Table 1 or compounds of any formula herein, or pharmaceutically acceptable salts thereof, inhibit the activity of Hsp90 and, thereby facilitates the degradation of Hsp90 client proteins. Hsp90 is necessary for the survival of normal eukaryotic cells. However, Hsp90 is over expressed in many tumor types indicating that it may play a significant role in the survival of cancer cells and that cancer cells may be more sensitive to inhibition of Hsp90 than normal cells. Thus, the compounds shown in Table 1 or compounds of any formula herein, or pharmaceutically acceptable salts thereof, are useful treating proliferative disorders such as cancer.

Although traditional chemotherapeutic agents may initially cause tumor regression, most agents that are currently used to treat cancer target only one pathway to tumor progression. Therefore, in many instances, after treatment with one or more chemotherapeutic agents, a tumor develops multidrug resistance and no longer responses positively to treatment. One of the advantages of inhibiting Hsp90 activity is that several of its client proteins, which are mostly protein kinases or transcription factors involved in signal transduction, have been shown to be involved in the progression of cancer. Thus, inhibition of Hsp90 provides a method of simultaneously short circuiting multiple pathways for tumor progression. Therefore, treatment of tumors with an Hsp90 inhibitor of the invention either alone, or in combination with other chemotherapeutic agents, is more likely to result in regression or elimination of the tumor, and less likely to result in the development of more aggressive multidrug resistant tumors than other currently available therapies.

DETAILED DESCRIPTION OF THE INVENTION

The invention provides, in a first aspect, novel compounds according to Formulae (I)-(VI) or Table 1 that inhibit HSP90, as well as the pharmaceutically acceptable salts thereof, that are useful for the treatment of hyperproliferative disorders such as cancer, infections, immune disorders and inflammation.

In Formula (II):

$R^1$ is H, $OR^{12}$ or $C_1$-$C_3$ alkyl. More specifically, $R^1$ is H, OH or methoxy.

$R^2$ is $OR^{12}$ or halo. Particularly, $R^2$ is methyl, F, OH, methoxy, ethoxy, propoxy, or isopropoxy.

$R^3$ is H, $C_1$-$C_6$ alkyl or $C_3$-$C_6$ cycloalkyl. More particularly, $R^3$ is H, methyl, ethyl, propyl, i-propyl, butyl, i-butyl, s-butyl, t-butyl or $C_5$-$C_6$ cycloalkyl.

The variable m is 0 or 1. More particularly, m is 1. Alternatively, m is 0.

$R^7$ is phenyl, $S(O)_pR^{10}$, $OR^{10}$, $N(R^{10})_2$ or $=NN(R^{10})_2$. More specifically, $R^7$ is $OR^{10}$. More particularly, $R^7$ is $N(R^{10})_2$.

$R^5$ and $R^6$ are individually hydrogen, $C_1$-$C_6$ alkyl, $C_2$-$C_6$ alkenyl, $C_2$-$C_6$ alkynyl, $C_3$-$C_7$ cycloalkyl, 5-7 membered heterocyclyl, phenyl, benzyl, 5-7 membered heteroaryl, —$N(R^{12})_2$, —$C(O)R^{12}$, —$C(O)OR^{12}$, —$S(O)_pR^{12}$, or —$S(O)_pN(R^{12})_2$, wherein each $R^5$ and $R^6$ that is not hydrogen is optionally and independently substituted with one or more $R^{20}$; or $R^5$ and $R^6$, taken together with the nitrogen to which they are attached, form a 5-7 membered heterocyclyl which is optionally substituted with one or more $R^{20}$. Particularly, $R^5$ and $R^6$ are independently H, $C_1$-$C_6$ alkyl, $C_2$-$C_6$ alkenyl, $C_3$-$C_7$ cycloalkyl, phenyl, benzyl, —$C(O)R^{12}$, —$C(NR^{12})R^{12}$, —$C(NR^{12})N(R^{12})_2$, —$S(O)_pR^{12}$ or —$S(O)_pN(R^{12})_2$, wherein each alkyl, alkenyl, cycloalkyl, phenyl and benzyl, represented by $R^5$ or $R^6$ is optionally and independently substituted with one or more $R^{20}$; or $R^5$ and $R^6$, together with nitrogen atom to which they are attached form a 5 to 7 membered heterocyclic or heteroaryl ring which is optionally substituted with one or more $R^{20}$. More particularly, $R^5$ and $R^6$ are independently H, $C_1$-$C_6$ alkyl, cyclopropyl, cyclopentyl, cyclohexyl or phenyl, wherein each alkyl, cycloalkyl or phenyl is optionally substituted with one, two or three $R^{20}$; or $R^5$ and $R^6$ taken together with the nitrogen atom to which they are attached, form a 5-6 membered heterocycle, optionally substituted with one or two $R^{20}$. Specifically, at least one of $R^5$ or $R^6$ is H. More specifically, one of $R^5$ and $R^6$ is H and the other is methyl, ethyl, cyclopropyl, n-propyl, isopropyl, or 2,2,2-trifluoroethyl. More specifically, $R^5$ and $R^6$ are both H.

Each $R^{10}$ is independently selected from H, $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, —$OR^{12}$, —$N(R^{12})_2$, —$C(O)R^{12}$, —$C(O)OR^{12}$, —$C(S)R^{12}$, —$C(O)SR^{12}$, —$C(O)N(R^{12})_2$, —$C(S)N(R^{12})_2$, —$C(NR^{12})OR^{12}$, —$C(NR^{12})R^{12}$, —$C(NR^{12})N(R^{12})_2$, —$C(NR^{12})SR^{12}$, —$S(O)_pR^{12}$, —$S(O)_pOR^{12}$ or —$S(O)_pN(R^{12})_2$, wherein the alkyl, alkenyl, alkynyl, cycloalkyl, heterocyclyl, aryl and heteroaryl represented by $R^{10}$ are independently and optionally substituted by one or more $R^{20}$; or two $R^{10}$ moieties attached to the same nitrogen atom are taken together to form a 5-14 membered heterocyclyl or a 5-14 membered heteroaryl, each of which are optionally and independently substituted with one or more $R^{20}$. Particularly, $R^{10}$ is H or $C_1$-$C_4$ alkyl which is optionally substituted with one or two $R^{20}$; each $R^{20}$ is independently $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, F, Cl, Br, cyano, $COR^{12}$, $CO_2R^{12}$, $N(R^{12})_2$, $CONR^{12}$ or $NR^{12}COR^{12}$. In some instances, each $R^{10}$ is independently H, $C_1$-$C_4$ alkyl which is optionally substituted with one to three $R^{20}$; or two $R^{10}$ moieties are taken together with the nitrogen to which they are attached to form a 5-7 membered heterocyclyl containing up to three additional heteroatoms selected from N, O and S, wherein said heterocyclyl is optionally substituted with one to three $R^{20}$. Particularly, each $R^{10}$ is H, methyl, ethyl, isopropyl or propyl. Otherwise, both $R^{10}$ moieties, taken together with the N atom to which they are attached form a heterocycle selected from the group consisting of: piperidine, piperazine, morpholine, thiomorpholine, 4,4-dioxo-thiomorpholine, pyrrolidine, imidizolidine, oxazolidine, thiazolidine, pyrazolidine, hexahydropyrimidine, wherein each heterocycle is optionally substituted with one to three $R^{20}$. More specifically, a heterocycle formed by two $R^{10}$ moieties is a piperazine substituted with methyl, ethyl propyl or isopropyl; morpholine; thiomorpholine; 4,4-dioxothiomorpholine; or pyrrolidine.

Each $R^{12}$ is independently H, $C_1$-$C_3$ alkyl, $C_2$-$C_3$ alkenyl, $C_1$-$C_3$ haloalkyl, $C_1$-$C_3$ alkoxy, $C_1$-$C_3$ haloalkoxy, $C_3$-$C_7$ cycloalkyl, phenyl, or benzyl, wherein each $R^{12}$ with at least one hydrogen atom is optionally substituted with one or more $R^{20}$; or two $R^{12}$ substituents that are attached to the same atom or adjacent atoms, taken together with the atom(s) to which they are attached, form a 5-7 membered heterocyclyl or $C_3$-$C_7$ cycloalkyl which are each optionally and independently substituted with one or more $R^{20}$. More particularly, each $R^{12}$ is independently H or $C_1$-$C_3$ alkyl.

Each $R^{20}$ is independently selected from the group consisting of $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, $C_3$-$C_7$ cycloalkyl-($C_1$-$C_3$)alkyl, 5-14 membered heterocyclyl-($C_1$-$C_3$)alkyl, $C_6$-$C_{20}$ aryl-($C_1$-$C_3$) alkyl, 5-14 membered heteroaryl-($C_1$-$C_3$)alkyl, halo, cyano, nitro, azido, —$N(R^{12})_2$, —$OR^{12}$, —$C(O)R^{12}$, —$C(O)OR^{12}$, —$C(S)R^{12}$, —$C(O)SR^{12}$, —$C(S)SR^{12}$, —$C(S)OR^{12}$, —$C(O)N(R^{12})_2$, —$C(S)N(R^{12})_2$, —$C(NR^{12})OR^{12}$, —$C(NR^{12})R^{12}$, —$C(NR^{12})N(R^{12})_2$, —$C(NR^{12})SR^{12}$, —$OC(O)N(R^{12})_2$, —$OC(O)R^{12}$, —$OC(O)OR^{12}$, —$OC(S)OR^{12}$, —$OC(NR^{12})OR^{12}$, —$SC(O)R^{12}$, —$SC(O)OR^{12}$, —$SC(NR^{12})OR_{12}$, —$OC(S)R^{12}$, —$SC(S)R^{12}$, —$SC(S)OR^{12}$, —$OC(O)N(R^{12})_2$, —$OC(S)N(R^{12})_2$, —$OC(NR^{12})N(R^{12})_2$, —$SC(O)N(R^{12})_2$, —$SC(NR^{12})N(R^{12})_2$, —$SC(S)N(R^{12})_2$, —$OC(NR^{12})R^{12}$, —$SC(NR^{12})R^{12}$, —$NR^{12}C(O)R^{12}$, —$NR^{12}C(S)R^{12}$, —$NR^{12}C(S)OR^{12}$, —$NR^{12}C(NR^{12})R^{12}$, —$NR^{12}C(O)OR^{12}$, —$NR^{12}C(NR^{12})OR^{12}$, —$NR^{12}C(O)N(R^{12})_2$, —$NR^{12}C(S)N(R^{12})_2$, —$NR^{12}C(NR^{12})N(R^{12})_2$, —$S(O)_pR^{12}$, —$OS(O)_pR^{12}$, —$OS(O)_pOR^{12}$, —$OS(O)_pN(R^{12})_2$, —$S(O)_pOR^{12}$, —$NR^{12}S(O)_pR^{12}$, —$NR^{12}S(O)_pN(R^{12})_2$, —$NR^{12}S(O)_pOR^{12}$, —$S(O)_pN(R^{12})_2$, —$SS(O)_pR^{12}$, —$SS(O)_pOR^{12}$, —$SS(O)_pN(R^{12})_2$, —$OP(O)(OR^{12})_2$, or —$SP(O)(OR^{12})_2$, wherein the alkyl, alkenyl, alkynyl, cycloalkyl, heterocyclyl, aryl, heteroaryl, aralkyl, and heteroaralkyl represented by $R^{20}$ are each optionally and independently substituted with one to three groups from halo, $C_1$-$C_3$ alkyl, phenyl, benzyl, $C_1$-$C_3$ haloalkyl, $C_1$-$C_3$ alkoxy, $C_1$-$C_3$ haloalkoxy, nitro, cyano, azido, amino and $C_1$-$C_5$ carbamoyl; or two $R^{20}$ moieties attached to the same atom form an oxo (=O), thioxo (=S) or imino (=$NR^{12}$). More particularly, each $R^{20}$ is independently $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, F, Cl, Br, cyano, $COR^{12}$, $CO_2R^{12}$, $N(R^{12})_2$, $CONR^{12}$ or $NR^{12}COR^{12}$. Other particular aspects are when each $R^{20}$ is independently F, Cl, Br, $C_1$-$C_3$ alkyl, $C_1$-$C_3$ haloalkyl or $N(R^{12})_2$. More particularly, $R^{20}$ is methyl, ethyl propyl or isopropyl.

For Formula (III):

The variable m is 0 or 1. In some instances m is 0. In other instances, m is 1.

The variable r is 0, 1 or 2. Particularly, r is 0. Otherwise, r is 1.

$R^8$ is $C_1$-$C_3$ alkyl or $C_1$-$C_3$ haloalkyl. Particularly, $R^8$ is methyl or ethyl. More particularly, $R^8$ is methyl.

$R^3$ is H, $C_1$-$C_4$ alkyl or $C_3$-$C_6$ cycloalkyl. Particularly, $R^3$ is H, cyclopentyl, cyclopropyl, methyl, ethyl, propyl, i-propyl, t-butyl, i-butyl, n-butyl or s-butyl. More particularly, $R^3$ is i-propyl or ethyl.

$R^7$ isphenyl, $S(O)_pR^{31}$, $OR^{31}$, $N(R^{31})_2$ or =$NN(R^{31})_2$. Particularly, $R^7$ is $OR^{31}$ or $N(R^{31})_2$. Sometimes, $R^7$ is $OR^{31}$. Other times, $R^7$ is $N(R^{31})_2$.

$R^{13}$ and $R^{14}$ are individually hydrogen, $C_1$-$C_6$ alkyl, $C_2$-$C_6$ alkenyl, $C_2$-$C_6$ alkynyl, $C_3$-$C_7$ cycloalkyl, 5-7 membered heterocyclyl, phenyl, benzyl, 5-7 membered heteroaryl, —$N(R^{32})_2$, —$C(O)R^{32}$, —$C(O)OR^{32}$, —$S(O)_pR^{32}$, or —$S(O)_pN(R^{32})_2$, wherein each $R^{13}$ and $R^{14}$ that is not hydrogen is optionally and independently substituted with one or more $R^{21}$; or $R^{13}$ and $R^{14}$, taken together with the nitrogen to which they are attached, form a 5-7 membered heterocyclyl which is optionally substituted with one or more $R^{21}$. Particularly, $R^{13}$ and $R^{14}$ are independently H, $C_1$-$C_6$ alkyl, $C_2$-$C_6$ alkenyl, $C_3$-$C_7$ cycloalkyl, phenyl, benzyl, —$C(O)R^{32}$, —$C(NR^{32})R^{32}$, —$C(NR^{32})N(R^{32})_2$, —$S(O)_pR^{32}$ or —$S(O)_pN(R^{32})_2$, wherein each alkyl, alkenyl, cycloalkyl, phenyl and benzyl, represented by $R^{13}$ or $R^{14}$ is optionally and independently substituted with one or more $R^{21}$; or $R^{13}$ and $R^{14}$, together with nitrogen atom to which they are attached form a 5 to 7 membered heterocyclic or heteroaryl ring which is optionally substituted with one or more $R^{21}$. More particularly, $R^{13}$ and $R^{14}$ are independently H, $C_1$-$C_6$ alkyl, cyclopropyl, cyclopentyl, cyclohexyl or phenyl, wherein each alkyl, cycloalkyl or phenyl is optionally substituted with one or two $R^{21}$; or $R^{13}$ and $R^{14}$ taken together with the nitrogen atom to which they are attached, form a 5-6 membered heterocycle, optionally substituted with one or two $R^{21}$. Even more particularly, $R^{13}$ or $R^{14}$ is a $C_1$-$C_4$ alkyl or $C_3$-$C_6$ cycloalkyl, optionally substituted with one to three $R^{21}$. More specifically, one of $R^{13}$ and $R^{14}$ is H and the other is methyl, ethyl, cyclopropyl, n-propyl, isopropyl, or 2,2,2-trifluoroethyl. Sometimes, at least one of $R^{13}$ or $R^{14}$ is H.

Each $R^{31}$ is independently selected from H, $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, —$OR^{32}$, —$N(R^{32})_2$, —$C(O)R^{32}$, —$C(O)OR^{32}$, —$C(S)R^{32}$, —$C(O)SR^{32}$, —$C(O)N(R^{32})_2$, —$C(S)N(R^{32})_2$, —$C(NR^{32})OR^{32}$, —$C(NR^{32})R^{32}$, —$C(NR^{32})N(R^{32})_2$, —$C(NR^{32})SR^{32}$, —S(O)$_p$R$^{32}$, —S(O)$_p$OR$^{32}$ or —S(O)$_p$N(R$^{32}$)$_2$, wherein the alkyl, alkenyl, alkynyl, cycloalkyl, heterocyclyl, aryl and heteroaryl represented by R$^{31}$ are independently and optionally substituted by one or more R$^{21}$; or two R$^{31}$ moieties attached to the same nitrogen atom are taken together to form a 5-14 membered heterocyclyl or a 5-14 membered heteroaryl, each of which are optionally and independently substituted with one or more R$^{21}$. Particularly, each R$^{31}$ is independently selected from H, C$_1$-C$_6$ alkyl, C$_2$-C$_6$ alkenyl, C$_3$-C$_6$ cycloalkyl, 5-7 membered heterocyclyl, phenyl, naphthyl, 5-7 membered heteroaryl, —C(O)R$^{32}$, —C(O) OR$^{32}$, —C(S)R$^{32}$, —C(O)SR$^{32}$, —C(O)N(R$^{32}$)$_2$, wherein the alkyl, alkenyl, cycloalkyl, heterocyclyl, phenyl, naphthyl and heteroaryl represented by R$^{31}$ are each independently and optionally substituted by one or more R$^{21}$; or two R$^{31}$ moieties attached to the same nitrogen atom are taken together to form a 5-14 membered heterocyclyl or a 5-14 membered heteroaryl, each of which are optionally and independently substituted with one or more R$^{21}$. More particularly, R$^{31}$ is H or C$_1$-C$_4$ alkyl which is optionally substituted with one or two R$^{21}$. In another instance, each R$^{31}$ is independently H, C$_1$-C$_4$ alkyl which is optionally substituted with one to three R$^{21}$; or two R$^{31}$ moieties are taken together with the nitrogen to which they are attached to form a 5-7 membered heterocyclyl containing up to three additional heteroatoms selected from N, O and S, wherein said heterocyclyl is optionally substituted with one to three R$^{21}$. Optionally, each R$^{31}$ is H, methyl, ethyl, isopropyl or propyl. Alternatively, two R$^{31}$ moieties, taken together with the N atom to which they are attached form a heterocycle selected from the group consisting of: piperidine, piperazine, morpholine, thiomorpholine, 4,4-dioxo-thiomorpholine, pyrrolidine, imidizolidine, oxazolidine, thiazolidine, pyrazolidine, hexahydropyrimidine, wherein each heterocycle is optionally substituted with one to three R$^{21}$. More particularly, the above heterocycle is a piperazine substituted with methyl, ethyl propyl or isopropyl; morpholine; thiomorpholine; piperidin-1yl; N-methyl-piperidin-4-yl; 4,4-dioxothiomorpholine; or pyrrolidine.

Each R$^{32}$ is independently H, C$_1$-C$_3$ alkyl, C$_2$-C$_3$ alkenyl, C$_1$-C$_3$ haloalkyl, C$_1$-C$_3$ alkoxy, C$_1$-C$_3$ haloalkoxy, C$_3$-C$_7$ cycloalkyl, phenyl, or benzyl, wherein each R$^{32}$ with at least one hydrogen atom is optionally substituted with one or more R$^{21}$; or two R$^{32}$ substituents that are attached to the same atom or adjacent atoms, taken together with the atom(s) to which they are attached, form a 5-7 membered heterocyclyl or C$_3$-C$_7$ cycloalkyl which are each optionally and independently substituted with one or more R$^{21}$. Particularly, each R$^{32}$ is independently H or C$_1$-C$_3$ alkyl.

Each R$^{21}$ is independently selected from the group consisting of C$_1$-C$_6$ alkyl, C$_2$-C$_6$ alkenyl, C$_2$-C$_6$ alkynyl, C$_3$-C$_7$ cycloalkyl, 5-14 membered heterocyclyl, C$_6$-C$_{20}$ aryl, 5-14 membered heteroaryl, C$_3$-C$_7$ cycloalkyl-(C$_1$-C$_3$)alkyl, 5-14 membered heterocyclyl-(C$_1$-C$_3$)alkyl, C$_6$-C$_{20}$ aryl-(C$_1$-C$_3$) alkyl, 5-14 membered heteroaryl-(C$_1$-C$_3$)alkyl, halo, cyano, nitro, azido, —N(R$^{32}$)$_2$, —OR$^{32}$, —C(O)R$^{32}$, —C(O)OR$^{32}$, —C(S)R$^{32}$, —C(O)SR$^{32}$, —C(S)SR$^{32}$, —C(S)OR$^{32}$, —C(O)N(R$^{32}$)$_2$, —C(S)N(R$^{32}$)$_2$, —C(NR$^{32}$)OR$^{32}$, —C(NR$^{32}$)R$^{32}$, —C(NR$^{32}$)N(R$^{32}$)$_2$, —C(NR$^{32}$)SR$^{32}$, —OC(O)N(R$^{32}$)$_2$, —OC(O)R$^{32}$, —OC(O)OR$^{32}$, —OC(S)OR$^{32}$, —OC(NR$^{32}$)OR$^{32}$, —SC(O)R$^{32}$, —SC(O)OR$^{32}$, —SC(NR$^{32}$)OR$^{32}$, —OC(S)R$^{32}$, —SC(S)R$^{32}$, —SC(S)OR$^{32}$, —OC(O)N(R$^{32}$)$_2$, —OC(S)N(R$^{32}$)$_2$, —OC(NR$^{32}$)N(R$^{32}$)$_2$, —SC(O)N(R$^{32}$)$_2$, —SC(NR$^{32}$)N(R$^{32}$)$_2$, —SC(S)N(R$^{32}$)$_2$, —OC(NR$^{32}$)R$^{32}$, —SC(NR$^{32}$)R$^{32}$, —NR$^{32}$C(O)R$^{32}$, —NR$^{32}$C(S)R$^{32}$, —NR$^{32}$C(S)OR$^{32}$, —NR$^{32}$C(NR$^{32}$)R$^{32}$, —NR$^{32}$C(O)OR$^{32}$, —NR$^{32}$C(NR$^{32}$)OR$^{32}$, —NR$^{32}$C(O)N (R$^{32}$)$_2$, —NR(R$^{32}$C(S)N(R$^{32}$)$_2$, —NR$^{32}$C(NR$^{32}$)N(R$^{32}$)$_2$, —S(O)$_p$R$^{32}$, —OS(O)$_p$R$^{32}$, —OS(O)$_p$R$^{32}$, —OS(O)$_p$OR$^{32}$, —OS(O)$_p$N(R$^{32}$)$_2$, —S(O)$_p$OR$^{32}$, —NR$^{32}$S(O)$_p$R$^{32}$, —NR$^{32}$S(O)$_p$N(R$^{32}$)$_2$, —NR$^{32}$S(O)$_p$OR$^{32}$, —S(O)$_p$N(R$^{32}$)$_2$, —SS(O)$_p$R$^{32}$, —SS(O)$_p$OR$^{32}$, —SS(O)$_p$N(R$^{32}$)$_2$, —OP(O)(OR$^{32}$)$_2$, or —SP(O)(OR$^{32}$)$_2$, wherein the alkyl, alkenyl, alkynyl, cycloalkyl, heterocyclyl, aryl, heteroaryl, aralkyl, and heteroaralkyl represented by R$^{21}$ are each optionally and independently substituted with one to three groups from halo, C$_1$-C$_3$ alkyl, phenyl, benzyl, C$_1$-C$_3$ haloalkyl, C$_1$-C$_3$ alkoxy, C$_1$-C$_3$ haloalkoxy, nitro, cyano, azido, amino and C$_1$-C$_5$ carbamoyl; or two R$^{21}$ moieties attached to the same atom form an oxo (=O), thioxo (=S) or imino (=NR$^{32}$). Particularly, each R$^{21}$ is independently C$_1$-C$_3$ alkyl, C$_1$-C$_3$ haloalkyl, C$_3$-C$_6$ cycloalkyl, C$_1$-C$_3$ alkoxy, C$_1$-C$_3$ haloalkoxy, F, Cl, Br, cyano, COR$^{32}$, CO$_2$R$^{32}$, N(R$^{32}$)$_2$, CONR$^{32}$ or NR$^{32}$COR$^{32}$. In other instances, each R$^{21}$ is independently F, Cl, Br, C$_1$-C$_3$ alkyl, C$_1$-C$_3$ haloalkyl or N(R$^{32}$)$_2$. More particularly, each R$^{21}$ is independently COR$^{32}$, CO$_2$R$^{32}$, N(R$^{32}$)$_2$ or CONR$^{32}$. More particularly, R$^{21}$ is F.

For Formula (IV):

R$^{15}$ is C$_1$-C$_6$ alkyl, C$_2$-C$_6$ alkenyl, C$_3$-C$_7$ cycloalkyl, phenyl, benzyl, —C(O)R$^{42}$, —N(R$^{42}$)$_2$, C(NR$^{42}$)R$^{42}$, —C(NR$^{42}$)N(R$^{42}$)$_2$, —S(O)$_p$R$^{42}$ or —S(O)$_p$N(R$^{42}$)$_2$, wherein each alkyl, alkenyl, cycloalkyl, phenyl and benzyl, represented by R$^{15}$ is optionally substituted with one or more R$^{22}$, provided that R$^{15}$ is other than isopropyl or —(CH$_2$)$_2$N(CH$_3$)$_2$. Particularly, R$^{15}$ is a C$_1$-C$_4$ alkyl substituted with one or more R$^{22}$. More specifically, R$^{15}$ is methyl, ethyl, cyclopropyl, n-propyl, isopropyl, or 2,2,2-trifluoroethyl. More particularly, R$^{15}$ is a C$_2$-C$_3$ alkyl substituted with one R$^{22}$.

Each R$^{42}$ is independently H or C$_1$-C$_4$ alkyl; or two R$^{42}$ moieties attached to the same nitrogen atom are taken together to form a 5-7 membered heterocyclyl.

Each R$^{22}$ is independently halo, C$_1$-C$_3$ alkyl, C$_1$-C$_3$ haloalkyl, C$_1$-C$_3$ alkoxy, C$_1$-C$_3$ haloalkoxyl, C$_3$-C$_6$ cycloalkyl, 5-7 membered heterocycle, —C(O)R$^{42}$, —C(O) OR$^{42}$, —C(O)N(R$^{42}$)$_2$, —N(R$^{42}$)$_2$, or —NR$^{42}$C(O)R$^{12}$; or two R$^{21}$ moieties attached to the same atom, taken together, form an oxo (=O), thiooxo (=S), or imino (=NR$^{42}$). Particularly, each R$^{22}$ is independently halo or a 5-7 membered heterocycle. More particularly, R$^{22}$ is morpholinyl, N-methylpiperidin-4-yl, 4-methylpiperazinyl, 4-ethylpiperazinyl, or pyrrolidinyl.

Each R$^{25}$ is independently halo, C$_1$-C$_3$ alkyl, C$_1$-C$_3$ haloalkyl, C$_1$-C$_3$ alkoxy, C$_1$-C$_3$ haloalkoxyl, C$_3$-C$_6$ cycloalkyl, 5-7 membered heterocycle, —C(O)R$^{42}$, —C(O) OR$^{42}$, —C(O)N(R$^{42}$)$_2$, —N(R$^{42}$)$_2$, or —NR$^{42}$C(O)R$^{12}$; or two R$^{25}$ moieties attached to the same atom, taken together, form an oxo (=O), thiooxo (=S), or imino (=NR$^{42}$). Particularly, each R$^{25}$ is independently halo, C$_1$-C$_3$ alkyl, C$_1$-C$_3$ haloalkyl, C$_1$-C$_3$ alkoxy, or C$_1$-C$_3$ haloalkoxyl. More particularly, each R$^{25}$ is F, Cl, methoxy or ethoxy.

The variable u is 0, 1 or 2. Particularly, u is 0. Alternatively u is 1. More particularly, u is 2.

For Formula (V):

N-Het is piperidine, piperazine, morpholine, pyrrolidine, imidazolidine, hexahydropyrimidine or pyrazolidine, each optionally and independently substituted with one or two R$^{23}$. Particularly, N-Het is piperidinyl, piperazinyl, morpholinyl or pyrrolidinyl, each optionally and independently substituted with one R$^{23}$. More particularly, N-Het is morpholinyl. More particularly, N-Het is 4-methyl-piperazinyl or 4-ethyl-piperazinyl.

$R^{16}$ is H, $C_1$-$C_6$ alkyl, $C_2$-$C_6$ alkenyl, $C_3$-$C_7$ cycloalkyl, phenyl, benzyl, —C(O)$R^{52}$, —N($R^{52}$)$_2$, —C(N$R^{52}$)$R^{52}$, —C(N$R^{52}$)N($R^{52}$)$_2$, —S(O)$_p$$R^{52}$ or —S(O)$_p$N($R^{52}$)$_2$, wherein each alkyl, alkenyl, cycloalkyl, phenyl and benzyl, represented by $R^{16}$ is optionally substituted with one or more $R^{23}$. Particularly, $R^{16}$ is H, $C_1$-$C_6$ alkyl, $C_2$-$C_6$ alkenyl, $C_3$-$C_7$ cycloalkyl, —N($R^{52}$)$_2$, —C(O)$R^{52}$, —C(O)N($R^{52}$)$_2$, —S(O)$_p$$R^{52}$ or —S(O)$_p$N($R^{52}$)$_2$, wherein each alkyl, alkenyl and cycloalkyl represented by $R^{16}$ is optionally substituted with one or more $R^{23}$. More particularly, $R^{16}$ is N($R^{52}$)$_2$ or an $C_2$-$C_3$ alkyl substituted with a 5-7 membered heterocyclyl. More particularly, $R^{16}$ is H, $C_1$-$C_6$ alkyl, $C_3$-$C_7$ cycloalkyl or —N($R^{52}$)$_2$, wherein each alkyl and cycloalkyl represented by $R^{16}$ is optionally substituted with one or more $R^{23}$. More specifically, $R^{16}$ is methyl, ethyl, cyclopropyl, n-propyl, isopropyl, or 2,2,2-trifluoroethyl.

Each $R^{52}$ is independently H or $C_1$-$C_4$ alkyl; or two $R^{52}$ moieties attached to the same nitrogen atom are taken together to form a 5-7 membered heterocyclyl.

Each $R^{23}$ is independently halo, $C_1$-$C_3$ alkyl, $C_1$-$C_3$ haloalkyl, $C_1$-$C_3$ alkoxy, $C_1$-$C_3$ haloalkoxyl, $C_3$-$C_6$ cycloalkyl, 5-7 membered heterocycle, —C(O)$R^{52}$, —C(O)O$R^{52}$, —C(O)N($R^{52}$)$_2$, —N($R^{52}$)$_2$, or —N$R^{52}$C(O)$R^{52}$; or two $R^{23}$ moieties attached to the same atom, taken together, form an oxo (=O), thiooxo (=S), or imino (=N). In some instances, each $R^{23}$ is halo, $C_1$-$C_3$ alkyl, $C_3$-$C_6$ cycloalkyl, 5-7 membered heterocycle, —N($R^{52}$)$_2$ or —C(O)O$R^{52}$. Particularly, each $R^{23}$ is halo, $C_1$-$C_3$ alkyl, $C_3$-$C_6$ cycloalkyl, 5-7 membered heterocycle or —C(O)O$R^{52}$. More particularly, $R^{23}$ is a 5-7 membered heterocyclyl. More particularly, $R^{23}$ is F.

The variable s is 0, 1 or 2. Particularly, s is 0 or 1. More particularly, s is 0. More particularly, is 1. Alternatively, s is 2.

In one embodiment, for a compound of Formula (II), $R^7$ is O$R^{10}$; m is 0; $R^{10}$ is H or $C_1$-$C_4$ alkyl which is optionally substituted with one or two $R^{20}$; each $R^{20}$ is independently $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, F, Cl, Br, cyano, CO$R^{12}$, CO$_2$$R^{12}$, N($R^{12}$)$_2$, CON$R^{12}$ or N$R^{12}$CO$R^{12}$; and/or each $R^{12}$ is independently H or $C_1$-$C_3$ alkyl.

In another embodiment, $R^7$ is N($R^{10}$)$_2$; each $R^{10}$ is independently H, $C_1$-$C_4$ alkyl which is optionally substituted with one to three $R^{20}$; or two $R^{10}$ moieties are taken together with the nitrogen to which they are attached to form a 5-7 membered heterocyclyl containing up to three additional heteroatoms selected from N, O and S, wherein said heterocyclyl is optionally substituted with one to three $R^{20}$; each $R^{20}$ is independently $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, F, Cl, Br, cyano, CO$R^{12}$, CO$_2$$R^{12}$, N($R^{12}$)$_2$, CON$R^{12}$ or N$R^{12}$CO$R^{12}$; and/or each $R^{12}$ is independently H or $C_1$-$C_3$ alkyl. In this embodiment, each $R^{10}$ is H, methyl, ethyl, isopropyl or propyl or both $R^{10}$ moieties, taken together with the N atom to which they are attached form a heterocycle selected from the group consisting of: piperidine, piperazine, morpholine, thiomorpholine, 4,4-dioxo-thiomorpholine, pyrrolidine, imidizolidine, oxazolidine, thiazolidine, pyrazolidine, hexahydropyrimidine, wherein each heterocycle is optionally substituted with one to three $R^{20}$ and each $R^{20}$ is independently F, Cl, Br, $C_1$-$C_3$ alkyl, $C_1$-$C_3$ haloalkyl or N($R^{12}$)$_2$. In a further aspect of this embodiment, the heterocycle is a piperazine substituted with methyl, ethyl propyl or isopropyl, morpholine, thiomorpholine, 4,4-dioxothiomorpholine, or pyrrolidine.

In either one of the two above embodiments, $R^5$ and $R^6$ are independently H, $C_1$-$C_6$ alkyl, $C_2$-$C_6$ alkenyl, $C_3$-$C_7$ cycloalkyl, phenyl, benzyl, —C(O)$R^{12}$, —C(N$R^{12}$)$R^{12}$, —C(N$R^{12}$)N($R^{12}$)$_2$, —S(O)$_p$$R^{12}$ or —S(O)$_p$N($R^{12}$)$_2$, wherein each alkyl, alkenyl, cycloalkyl, phenyl and benzyl, represented by $R^6$ or $R^7$ is optionally and independently substituted with one or more $R^{20}$; or $R^5$ and $R^6$, together with nitrogen atom to which they are attached form a 5 to 7 membered heterocyclic or heteroaryl ring which is optionally substituted with one or more $R^{20}$; $R^2$ is methyl, F, OH, methoxy, ethoxy, propoxy, or isopropoxy; $R^1$ is H, OH or methoxy; and/or $R^3$ is H, $C_1$-$C_4$ alkyl or $C_5$-$C_6$ cycloalkyl.

Alternatively, for any of the above embodiments for Formula (II), $R^5$ and $R^6$ are independently H, $C_1$-$C_6$ alkyl, cyclopropyl, cyclopentyl, cyclohexyl or phenyl, wherein each alkyl, cycloalkyl or phenyl is optionally substituted with one or two $R^{20}$; or $R^5$ and $R^6$ taken together with the nitrogen atom to which they are attached, form a 5-6 membered heterocycle, optionally substituted with one or two $R^{20}$. In one embodiment, one of $R^5$ and $R^6$ is hydrogen. In another embodiment, both $R^5$ and $R^6$ are hydrogen.

In one embodiment of the invention, for Formula (III), $R^8$ is methyl or ethyl; $R^3$ is H, cyclopentyl, cyclopropyl, methyl, ethyl, propyl, i-propyl, t-butyl, i-butyl, n-butyl or s-butyl; r is 0; $R^7$ is N($R^{31}$)$_2$ or O$R^{31}$; m is 0; $R^{31}$ is H or $C_1$-$C_4$ alkyl which is optionally substituted with one or two $R^{21}$; each $R^{21}$ is independently $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, F, Cl, Br, cyano, CO$R^{32}$, CO$_2$$R^{32}$, N($R^{32}$)$_2$, CON$R^{32}$ or N$R^{32}$CO$R^{32}$; and/or each $R^{32}$ is independently H or $C_1$-$C_3$ alkyl. In this embodiment, $R^{21}$ can also independently be CO$R^{32}$, CO$_2$$R^{32}$, N($R^{32}$)$_2$ or CON$R^{32}$.

In another embodiment, $R^3$ is i-propyl or ethyl; $R^8$ is methyl; r is 1; the $R^{21}$ on ring C is F; $R^7$ is O$R^{31}$; m is 0; $R^{31}$ is H or $C_1$-$C_4$ alkyl which is optionally substituted with one or two $R^{21}$; each $R^{21}$ is independently $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, F, Cl, Br, cyano, CO$R^{32}$, CO$_2$$R^{32}$, N($R^{32}$)$_2$, CON$R^{32}$ or N$R^{32}$CO$R^{32}$; and/or each $R^{32}$ is independently H or $C_1$-$C_3$ alkyl. In this embodiment, $R^{21}$ can also independently be CO$R^{32}$, CO$_2$$R^{32}$, N($R^{32}$)$_2$ or CON$R^{32}$.

In another embodiment, $R^3$ is i-propyl or ethyl; $R^8$ is methyl; r is 1; the $R^{21}$ on ring C is F; $R^7$ is N($R^{31}$)$_2$; m is 0; each $R^{31}$ is independently H, $C_1$-$C_4$ alkyl which is optionally substituted with one to three $R^{21}$; or two $R^{31}$ moieties are taken together with the nitrogen to which they are attached to form a 5-7 membered heterocyclyl containing up to three additional heteroatoms selected from N, O and S, wherein said heterocyclyl is optionally substituted with one to three $R^{21}$; $R^{13}$ and $R^{14}$ are independently H, $C_1$-$C_6$ alkyl, cyclopropyl, cyclopentyl, cyclohexyl or phenyl, wherein each alkyl, cycloalkyl or phenyl is optionally substituted with one or two $R^{21}$; or $R^{13}$ and $R^{14}$ taken together with the nitrogen atom to which they are attached, form a 5-6 membered heterocycle, optionally substituted with one or two $R^{21}$; each $R^{21}$ is independently $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, F, Cl, Br, cyano, CO$R^{32}$, CO$_2$$R^{32}$, N($R^{32}$)$_2$, CON$R^{32}$ or N$R^{32}$CO$R^{32}$; and/or each $R^{32}$ is independently H or $C_1$-$C_3$ alkyl.

In the above embodiment, each $R^{31}$ can alternatively be H, methyl, ethyl, isopropyl or propyl or two $R^{31}$ moieties can be taken together with the N atom to which they are attached form a heterocycle selected from the group consisting of: piperidine, piperazine, morpholine, thiomorpholine, 4,4-dioxo-thiomorpholine, pyrrolidine, imidizolidine, oxazolidine, thiazolidine, pyrazolidine, hexahydropyrimidine, wherein each heterocycle is optionally substituted with one to three $R^{21}$; at least one of $R^{13}$ or $R^{14}$ is a $C_1$-$C_4$ alkyl or $C_3$-$C_6$ cycloalkyl, optionally substituted with one to three $R^{21}$; and/or each $R^{21}$ is independently F, Cl, Br, $C_1$-$C_3$ alkyl, $C_1$-$C_3$ haloalkyl or $N(R^{32})_2$. In some embodiments, at least one of $R^{13}$ and $R^{14}$ are hydrogen.

In any of the above embodiments for Formula (III), when at lest one of $R^{13}$ or $R^{14}$ is $C_1$-$C_4$ alkyl, it may be substituted with a 5-7 membered heterocyclyl or one or more F atoms.

In any of the above embodiments for Formula (III), when two $R^{31}$ moieties are taken together to form a 5-7 membered heterocycle, the heterocycle is a piperazine substituted with methyl, ethyl propyl or isopropyl; morpholine; thiomorpholine; piperidin-1yl; N-methyl-piperidin-4-yl; 4,4-dioxothiomorpholine; or pyrrolidine.

In one embodiment, for Formula (IV), $R^{15}$ is $C_1$-$C_6$ alkyl, $C_2$-$C_6$ alkenyl, $C_3$-$C_7$ cycloalkyl, phenyl, benzyl, —C(O)$R^{42}$, —N($R^{42}$)$_2$, —C(N$R^{42}$)$R^{42}$, —C(N$R^{42}$)N($R^{42}$)$_2$, —S(O)$_p$$R^{42}$ or —S(O)$_p$N($R^{42}$)$_2$, wherein each alkyl, alkenyl, cycloalkyl, phenyl and benzyl, represented by $R^{15}$ is optionally substituted with one or more $R^{22}$; each $R^{42}$ is independently H or $C_1$-$C_4$ alkyl; or two $R^{42}$ moieties attached to the same nitrogen atom are taken together to form a 5-7 membered heterocyclyl; and/or each $R^{22}$ is independently halo, $C_1$-$C_3$ alkyl, $C_1$-$C_3$ haloalkyl, $C_1$-$C_3$ alkoxy, $C_1$-$C_3$ haloalkoxyl, $C_3$-$C_6$ cycloalkyl, 5-7 membered heterocycle, —C(O)$R^{42}$, —C(O)O$R^{42}$, —C(O)N($R^{42}$)$_2$, —N($R^{42}$)$_2$, or —N$R^{42}$C(O)$R^{42}$; or two $R^{21}$ moieties attached to the same atom, taken together, form an oxo (=O), thiooxo (=S), or imino (=N); provided that $R^{15}$ is other than isopropyl or —(CH$_2$)$_2$N(CH$_3$)$_2$.

In a further embodiment, $R^{15}$ is a $C_1$-$C_4$ alkyl substituted with one or more $R^{22}$; and each $R^{22}$ is independently halo or a 5-7 membered heterocycle. In another embodiment, $R^{15}$ is a $C_2$-$C_3$ alkyl substituted with one $R^{22}$; and $R^{22}$ is morpholinyl, N-methylpiperidin-4-yl, 4-methylpiperazinyl, 4-ethylpiperazinyl, or pyrrolidinyl.

In one embodiment of the invention, for Formula (V), N-Het is piperidine, piperazine, morpholine, pyrrolidine, imidazolidine, hexahydropyrimidine or pyrazolidine, each optionally and independently substituted with one or two $R^{23}$; $R^{16}$ is H, $C_1$-$C_6$ alkyl, $C_2$-$C_6$ alkenyl, $C_3$-$C_7$ cycloalkyl, phenyl, benzyl, —C(O)$R^{52}$, —N($R^{52}$)$_2$, —C(N$R^{52}$)$R^{52}$, —C(N$R^{52}$)N($R^{52}$)$_2$, —S(O)$_p$$R^{52}$ or —S(O)$_p$N($R^{52}$)$_2$, wherein each alkyl, alkenyl, cycloalkyl, phenyl and benzyl, represented by $R^{16}$ is optionally substituted with one or more $R^{23}$; each $R^{52}$ is independently H or $C_1$-$C_4$ alkyl; or two $R^{52}$ moieties attached to the same nitrogen atom are taken together to form a 5-7 membered heterocyclyl; s is 0, 1 or 2; and/or each $R^{23}$ is independently halo, $C_1$-$C_3$ alkyl, $C_1$-$C_3$ haloalkyl, $C_1$-$C_3$ alkoxy, $C_1$-$C_3$ haloalkoxyl, $C_3$-$C_6$ cycloalkyl, 5-7 membered heterocycle, —C(O)$R^{52}$, —C(O)O$R^{52}$, —C(O)N($R^{52}$)$_2$, —N($R^{52}$)$_2$, or —N$R^{52}$C(O)$R^{52}$; or two $R^{23}$ moieties attached to the same atom, taken together, form an oxo (=O), thiooxo (=S), or imino (=N); provided that when N-Het is morpholine and s is 0, then $R^{16}$ is other than H, ethyl, isopropyl, isobutyl, propyl, cyclohexyl, or an ethylene substituted with hydroxyl, methoxy, dimethylamine, diethylamine, pyrrolidine, 4-methylpiperazine or morpholine; when N-Het is 4-methylpiperidinyl and s is 0, then $R^{16}$ is other than H; when N-Het is pyrrolidinyl and s is 0, then $R^{16}$ is other than an ethylene substituted with a pyrrolidine, morpholine, or 4-methyl-piperazine; and when N-Het is 4-methylpiperazinyl or 4-ethylpiperazinyl and s is 0, then $R^{16}$ is other than isopropyl.

In a further embodiment, N-Het is piperidinyl, piperazinyl, morpholinyl or pyrrolidinyl, each optionally and independently substituted with one $R^{23}$; $R^{16}$ is H, $C_1$-$C_6$ alkyl, $C_2$-$C_6$ alkenyl, $C_3$-$C_7$ cycloalkyl, —N($R^{52}$)$_2$, —C(O)$R^{52}$, —C(O)N($R^{52}$)$_2$, —S(O)$_p$$R^{52}$ or —S(O)$_p$N($R^{52}$)$_2$, wherein each alkyl, alkenyl and cycloalkyl represented by $R^{16}$ is optionally substituted with one or more $R^{23}$; and/or each $R^{23}$ is halo, $C_1$-$C_3$ alkyl, $C_3$-$C_6$ cycloalkyl, 5-7 membered heterocycle or —C(O)O$R^{52}$. Optionally, in this embodiment, s is 1; and $R^{23}$ on ring A is F. Alternatively, s is 0.

In another embodiment, N-Het is morpholinyl and $R^{16}$ is $N(R^{52})_2$ or an $C_2$-$C_3$ alkyl substituted with a 5-7 membered heterocyclyl. Optionally, in this embodiment, s is 1; and $R^{23}$ on ring A is F. Alternatively, s is 0.

In an additional embodiment, N-Het is 4-methyl-piperazinyl or 4-ethyl-piperazinyl; $R^{16}$ is H, $C_1$-$C_6$ alkyl, $C_3$-$C_7$ cycloalkyl or —N($R^{52}$)$_2$, wherein each alkyl, alkenyl and cycloalkyl represented by $R^{16}$ is optionally substituted with one or more $R^{23}$; and/or each $R^{23}$ is halo, $C_1$-$C_3$ alkyl, $C_3$-$C_6$ cycloalkyl, 5-7 membered heterocycle, —N($R^{52}$)$_2$ or —C(O)O$R^{52}$.

In Formula (VI)

$R^1$ is H, O$R^{12}$ or $C_1$-$C_3$ alkyl. More specifically, $R^1$ is H, OH or methoxy.

$R^2$ is O$R^{12}$ or halo. Particularly, $R^2$ is methyl, F, OH, methoxy, ethoxy, propoxy, or isopropoxy.

$R^3$ is H, $C_1$-$C_6$ alkyl or $C_3$-$C_6$ cycloalkyl. More particularly, $R^3$ is H, methyl, ethyl, propyl, i-propyl, butyl, i-butyl, s-butyl, t-butyl or $C_5$-$C_6$ cycloalkyl.

$R^5$ and $R^6$ are individually hydrogen, $C_1$-$C_6$ alkyl, $C_2$-$C_6$ alkenyl, $C_2$-$C_6$ alkynyl, $C_3$-$C_7$ cycloalkyl, 5-7 membered heterocyclyl, phenyl, benzyl, 5-7 membered heteroaryl, —N($R^{12}$)$_2$, —C(O)$R^{12}$, —C(O)O$R^{12}$, —S(O)$_p$$R^{12}$, or —S(O)$_p$N($R^{12}$)$_2$, wherein each $R^5$ and $R^6$ that is not hydrogen is optionally and independently substituted with one or more $R^{20}$; or $R^5$ and $R^6$, taken together with the nitrogen to which they are attached, form a 5-7 membered heterocyclyl which is optionally substituted with one or more $R^{20}$. Particularly, $R^5$ and $R^6$ are independently H, $C_1$-$C_6$ alkyl, $C_2$-$C_6$ alkenyl, $C_3$-$C_7$ cycloalkyl, phenyl, benzyl, —C(O)$R^{12}$, —C(N$R^{12}$)$R^{12}$, —C(N$R^{12}$)N($R^{12}$)$_2$, —S(O)$_p$$R^{12}$ or —S(O)$_p$N($R^{12}$)$_2$, wherein each alkyl, alkenyl, cycloalkyl, phenyl and benzyl, represented by $R^5$ or $R^6$ is optionally and independently substituted with one or more $R^{20}$; or $R^5$ and $R^6$, together with nitrogen atom to which they are attached form a 5 to 7 membered heterocyclic or heteroaryl ring which is optionally substituted with one or more $R^{20}$. More particularly, $R^5$ and $R^6$ are independently H, $C_1$-$C_6$ alkyl, cyclopropyl, cyclopentyl, cyclohexyl or phenyl, wherein each alkyl, cycloalkyl or phenyl is optionally substituted with one, two or three $R^{20}$; or $R^5$ and $R^6$ taken together with the nitrogen atom to which they are attached, form a 5-6 membered heterocycle, optionally substituted with one or two $R^{20}$. Specifically, at least one of $R^5$ or $R^6$ is H. More specifically, one of $R^5$ and $R^6$ is H and the other is methyl, ethyl, cyclopropyl, n-propyl, isopropyl, or 2,2,2-trifluoroethyl. More specifically, $R^5$ and $R^6$ are both H.

Each $R^{12}$ is independently H, $C_1$-$C_3$ alkyl, $C_2$-$C_3$ alkenyl, $C_1$-$C_3$ haloalkyl, $C_1$-$C_3$ alkoxy, $C_1$-$C_3$ haloalkoxy, $C_3$-$C_7$ cycloalkyl, phenyl, or benzyl, wherein each $R^{12}$ with at least one hydrogen atom is optionally substituted with one or more $R^{20}$; or two $R^{12}$ substituents that are attached to the same atom or adjacent atoms, taken together with the atom(s) to which they are attached, form a 5-7 membered heterocyclyl or $C_3$-$C_7$ cycloalkyl which are each optionally and independently substituted with one or more $R^{20}$. More particularly, each $R^{12}$ is independently H or $C_1$-$C_3$ alkyl.

Each $R^{20}$ is independently selected from the group consisting of $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, $C_3$-$C_7$ cycloalkyl-($C_1$-$C_3$)alkyl, 5-14 membered heterocyclyl-($C_1$-$C_3$)alkyl, $C_6$-$C_{20}$ aryl-($C_1$-$C_3$)

alkyl, 5-14 membered heteroaryl-($C_1$-$C_3$)alkyl, halo, cyano, nitro, azido, —N($R^{12}$)$_2$, —O$R^{12}$, —C(O)$R^{12}$, —C(O)O$R^{12}$, —C(S)$R^{12}$, —C(O)S$R^{12}$, —C(S)S$R^{12}$, —C(S)O$R^{12}$, —C(O)N($R^{12}$)$_2$, —C(S)N($R^{12}$)$_2$, —C(N$R^{12}$)O$R^{12}$, —C(N$R^{12}$)$R^{12}$, —C(N$R^{12}$)N($R^{12}$)$_2$, —C(N$R^{12}$)S$R^{12}$, —OC(O)N($R^{12}$)$_2$, —OC(O)$R^{12}$, —OC(O)O$R^{12}$, —OC(S)O$R^{12}$, —OC(N$R^{12}$)O$R^{12}$, —SC(O)$R^{12}$, —SC(O)O$R^{12}$, —SC(N$R^{12}$)O$R_{12}$, —OC(S)$R^{12}$, —SC(S)$R^{12}$, —SC(S)O$R^{12}$, —OC(O)N($R^{12}$)$_2$, —OC(S)N($R^{12}$)$_2$, —OC(N$R^{12}$)N($R^{12}$)$_2$, —SC(O)N($R^{12}$)$_2$, —SC(N$R^{12}$)N($R^{12}$)$_2$, —SC(S)N($R^{12}$)$_2$, —OC(N$R^{12}$)$R^{12}$, —SC(N$R^{12}$)$R^{12}$, —N$R^{12}$C(O)$R^{12}$, —N$R^{12}$C(S)$R^{12}$, —N$R^{12}$C(S)O$R^{12}$, —N$R^{12}$C(N$R^{12}$)$R^{12}$, —N$R^{12}$C(O)O$R^{12}$, —N$R^{12}$C(N$R^{12}$)O$R^{12}$, —N$R^{12}$C(O)N($R^{12}$)$_2$, —N$R^{12}$C(S)N($R^{12}$)$_2$, —N$R^{12}$C(N$R^{12}$)N($R^{12}$)$_2$, —S(O)$_p$$R^{12}$, —OS(O)$_p$$R^{12}$, —OS(O)$_p$O$R^{12}$, —OS(O)$_p$N($R^{12}$)$_2$, —S(O)$_p$O$R^{12}$, —N$R^{12}$S(O)$_p$$R^{12}$, —N$R^{12}$S(O)$_p$N($R^{12}$)$_2$, —N$R^{12}$S(O)$_p$O$R^{12}$, —S(O)$_p$N($R^{12}$)$_2$, —SS(O)$_p$$R^{12}$, —SS(O)$_p$O$R^{12}$, —SS(O)$_p$N($R^{12}$)$_2$, —OP(O)(O$R^{12}$)$_2$, or —SP(O)(O$R^{12}$)$_2$, wherein the alkyl, alkenyl, alkynyl, cycloalkyl, heterocyclyl, aryl, heteroaryl, aralkyl, and heteroaralkyl represented by $R^{20}$ are each optionally and independently substituted with one to three groups from halo, $C_1$-$C_3$ alkyl, phenyl, benzyl, $C_1$-$C_3$ haloalkyl, $C_1$-$C_3$ alkoxy, $C_1$-$C_3$ haloalkoxy, nitro, cyano, azido, amino and $C_1$-$C_5$ carbamoyl; or two $R^{20}$ moieties attached to the same atom form an oxo (=O), thioxo (=S) or imino (=N$R^{12}$). More particularly, each $R^{20}$ is independently $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, F, Cl, Br, cyano, CO$R^{12}$, CO$_2$$R^{12}$, N($R^{12}$)$_2$, CON$R^{12}$ or N$R^{12}$CO$R^{12}$. Other particular aspects are when each $R^{20}$ is independently F, Cl, Br, $C_1$-$C_3$ alkyl, $C_1$-$C_3$ haloalkyl or N($R^{12}$)$_2$. More particularly, $R^{20}$ is methyl, ethyl propyl or isopropyl.

$R^{37}$ and $R^{38}$ are individually hydrogen, $C_1$-$C_6$ alkyl, $C_2$-$C_6$ alkenyl, $C_2$-$C_6$ alkynyl, $C_3$-$C_7$ cycloalkyl, 5-7 membered heterocyclyl, phenyl, benzyl, 5-7 membered heteroaryl, —N($R^{12}$)$_2$, —C(O)$R^{12}$, —C(O)O$R^{12}$, —S(O)$_p$$R^{12}$, or —S(O)$_p$N($R^{12}$)$_2$, wherein each $R^{37}$ and $R^{38}$ that is not hydrogen is optionally and independently substituted with one or more $R^{20}$; or $R^{37}$ and $R^{38}$, taken together with the nitrogen to which they are attached, form a 5-7 membered heterocyclyl which is optionally substituted with one or more $R^{20}$. Particularly, $R^{37}$ and $R^{38}$ are individually $C_1$-$C_4$ alkyl optionally substituted with one or more $R^{20}$; or are taken together with the N atom to which they are attached to form a 5- or 6-membered heterocyclyl which is optionally substituted with one or more $R^{20}$. More particularly, $R^{37}$ and $R^{38}$ are independently and individually methyl, ethyl. More particularly, $R^{37}$ and $R^{38}$ are taken together with the N atom to which they are attached to form a pyrrole, piperidine, piperizine, or morpholine.

One embodiment of the invention is a compound selected from the group consisting of:

5-(2,4-dihydroxy-5-isopropylphenyl)-4-(4-((4-ethylpiperazin-1-yl)methyl)phenyl)-4H-1,2,4-triazole-3-carboxamide;

5-(2,4-dihydroxy-5-isopropylphenyl)-4-(4-((4-ethylpiperazin-1-yl)methyl)phenyl)-N-methyl-4H-1,2,4-triazole-3-carboxamide;

5-(2,4-dihydroxy-5-isopropylphenyl)-N-ethyl-4-(4-((4-ethylpiperazin-1-yl)methyl)phenyl)-4H-1,2,4-triazole-3-carboxamide;

5-(2,4-dihydroxy-5-isopropylphenyl)-N-methyl-4-(4-((4-methylpiperazin-1-yl)methyl)phenyl)-4H-1,2,4-triazole-3-carboxamide;

5-(2,4-dihydroxy-5-isopropylphenyl)-4-(4-((4-ethylpiperazin-1-yl)methyl)phenyl)-N-(2-morpholinoethyl)-4H-1,2,4-triazole-3-carboxamide;

5-(2,4-dihydroxy-5-isopropylphenyl)-4-(6-morpholinopyridin-3-yl)-N-(3-(4,4-dioxo-thiomorpholinopropyl))-4H-1,2,4-triazole-3-carboxamide;

5-(2,4-dihydroxy-5-isopropylphenyl)-4-(4-((4-ethylpiperazin-1-yl)methyl)phenyl)-N-propyl-4H-1,2,4-triazole-3-carboxamide;

5-(2,4-dihydroxy-5-isopropylphenyl)-4-(4-((4-methylpiperazin-1-yl)methyl)phenyl)-N-propyl-4H-1,2,4-triazole-3-carboxamide;

4-(benzo[d][1,3]dioxol-5-yl)-N-ethyl-5-(2-hydroxy-5-isopropyl-4-methoxyphenyl)-4H-1,2,4-triazole-3-carboxamide;

5-(2,4-dihydroxy-5-isopropylphenyl)-N-ethyl-4-(4-((4-methylpiperazin-1-yl)methyl)phenyl)-4H-1,2,4-triazole-3-carboxamide;

N-(3-(diethylamino)propyl)-5-(2,4-dihydroxy-5-isopropylphenyl)-4-(4-(morpholinomethyl)phenyl)-4H-1,2,4-triazole-3-carboxamide;

N-(2-(diethylamino)ethyl)-5-(2,4-dihydroxy-5-isopropylphenyl)-4-(4-(pyrrolidin-1-ylmethyl)phenyl)-4H-1,2,4-triazole-3-carboxamide;

5-(2,4-dihydroxy-5-isopropylphenyl)-4-(4-(morpholinomethyl)phenyl)-N-(2-(pyrrolidin-1-yl)ethyl)-4H-1,2,4-triazole-3-carboxamide;

5-(2,4-dihydroxy-5-isopropylphenyl)-N-(2-morpholinoethyl)-4-(4-(pyrrolidin-1-ylmethyl)phenyl)-4H-1,2,4-triazole-3-carboxamide;

5-(2,4-dihydroxy-5-isopropylphenyl)-N-(2-morpholinoethyl)-4-(4-(morpholinomethyl)phenyl)-4H-1,2,4-triazole-3-carboxamide;

5-(2,4-dihydroxy-5-isopropylphenyl)-N-(2-(4-methylpiperazin-1-yl)ethyl)-4-(4-(morpholinomethyl)phenyl)-4H-1,2,4-triazole-3-carboxamide;

5-(2-hydroxy-5-isopropyl-4-methoxyphenyl)-N-isopropyl-4-(4-morpholinophenyl)-4H-1,2,4-triazole-3-carboxamide;

4-(4-(diethylamino)phenyl)-5-(2-hydroxy-5-isopropyl-4-methoxyphenyl)-N-isopropyl-4H-1,2,4-triazole-3-carboxamide;

5-(4-ethoxy-2-hydroxy-5-isopropylphenyl)-N-isopropyl-4-(4-(pyrrolidin-1-ylmethyl)phenyl)-4H-1,2,4-triazole-3-carboxamide;

N-(2-(diethylamino)ethyl)-5-(2,4-dihydroxy-5-isopropylphenyl)-4-(4-((4-methylpiperazin-1-yl)methyl)phenyl)-4H-1,2,4-triazole-3-carboxamide;

5-(2,4-dihydroxy-5-isopropylphenyl)-N-(2-(4-ethylpiperazin-1-yl)ethyl)-4-(4-(morpholinomethyl)phenyl)-4H-1,2,4-triazole-3-carboxamide;

5-(2,4-dihydroxy-5-isopropylphenyl)-4-(4-(morpholinomethyl)phenyl)-N-(3-morpholinopropyl)-4H-1,2,4-triazole-3-carboxamide;

5-(2,4-dihydroxy-5-isopropylphenyl)-4-(4-(morpholinomethyl)phenyl)-N-(3-(pyrrolidin-1-yl)propyl)-4H-1,2,4-triazole-3-carboxamide;

5-(2,4-dihydroxy-5-isopropylphenyl)-4-(4-((4-methylpiperazin-1-yl)methyl)phenyl)-N-(2-morpholinoethyl)-4H-1,2,4-triazole-3-carboxamide;

5-(4-ethoxy-2-hydroxy-5-isopropylphenyl)-N-ethyl-4-(4-(morpholinomethyl)-phenyl)-4H-1,2,4-triazole-3-carboxamide;

4-(4-((diethylamino)methyl)-phenyl)-5-(2,4-dihydroxy-5-isopropylphenyl)-N-(2-morpholinoethyl)-4H-1,2,4-triazole-3-carboxamide;

5-(2,4-dihydroxy-5-isopropylphenyl)-N-(3-morpholinopropyl)-4-(4-(pyrrolidin-1-ylmethyl)phenyl)-4H-1,2,4-triazole-3-carboxamide;

N-ethyl-5-(2-hydroxy-5-isopropyl-4-methoxyphenyl)-4-(4-(morpholinomethyl)phenyl)-4H-1,2,4-triazole-3-carboxamide;

5-(4-ethoxy-2-hydroxyphenyl)-4-(4-(morpholinomethyl)phenyl)-4H-1,2,4-triazole-3-carboxamide;

5-(2-hydroxy-4-methoxyphenyl)-4-(4-(morpholinomethyl)phenyl)-4H-1,2,4-triazole-3-carboxamide;

5-(2,4-dihydroxy-5-isopropylphenyl)-N-ethyl-4-(4-(4,4-dioxo-thiomorpholinophenyl))-4H-1,2,4-triazole-3-carboxamide;

5-(2-hydroxy-5-isopropyl-4-methoxyphenyl)-4-(4-(pyrrolidin-1-ylmethyl)phenyl)-4H-1,2,4-triazole-3-carboxamide;

5-(2,4-dihydroxy-5-isopropylphenyl)-N-(2-(4-ethylpiperazin-1-yl)ethyl)-4-(4-((4-methylpiperazin-1-yl)methyl)phenyl)-4H-1,2,4-triazole-3-carboxamide;

5-(2,4-dihydroxy-5-isopropylphenyl)-N-(2-(4-methylpiperazin-1-yl)ethyl)-4-(4-((4-methylpiperazin-1-yl)methyl)phenyl)-4H-1,2,4-triazole-3-carboxamide;

4-(4-((diethylamino)methyl)-phenyl)-5-(2,4-dihydroxy-5-isopropylphenyl)-N-(2-(4-ethylpiperazin-1-yl)ethyl)-4H-1,2,4-triazole-3-carboxamide;

5-(2,4-dihydroxy-5-isopropylphenyl)-N-(1-methylpiperidin-4-yl)-4-(4-(morpholinomethyl)phenyl)-4H-1,2,4-triazole-3-carboxamide;

4-(4-((diethylamino)methyl)-phenyl)-5-(2,4-dihydroxy-5-isopropylphenyl)-N-(2-(4-methylpiperazin-1-yl)ethyl)-4H-1,2,4-triazole-3-carboxamide;

4-(4-((diethylamino)methyl)-phenyl)-5-(2,4-dihydroxy-5-isopropylphenyl)-N-(3-morpholinopropyl)-4H-1,2,4-triazole-3-carboxamide;

4-(4-((diethylamino)methyl)-phenyl)-5-(2,4-dihydroxy-5-isopropylphenyl)-N-(2-(pyrrolidin-1-yl)ethyl)-4H-1,2,4-triazole-3-carboxamide;

5-(2-hydroxy-5-isopropyl-4-methoxyphenyl)-4-(1-methyl-1H-indol-5-yl)-4H-1,2,4-triazole-3-carboxamide;

N-ethyl-5-(2-hydroxy-5-isopropyl-4-propoxyphenyl)-4-(4-(morpholinomethyl)-phenyl)-4H-1,2,4-triazole-3-carboxamide;

N-ethyl-5-(2-hydroxy-4-isopropoxy-5-isopropylphenyl)-4-(4-(morpholinomethyl)phenyl)-4H-1,2,4-triazole-3-carboxamide;

5-(2,4-dihydroxy-5-isopropylphenyl)-4-(4-(morpholinomethyl)phenyl)-4H-1,2,4-triazole-3-carboxamide;

4-(4-((diethylamino)methyl)-phenyl)-5-(2,4-dihydroxy-5-isopropylphenyl)-N-(3-(pyrrolidin-1-yl)propyl)-4H-1,2,4-triazole-3-carboxamide;

4-(4-((diethylamino)methyl)-phenyl)-5-(2,4-dihydroxy-5-isopropylphenyl)-N-(1-methylpiperidin-4-yl)-4H-1,2,4-triazole-3-carboxamide;

ethyl 2-(4-(3-(2,4-dihydroxy-5-isopropylphenyl)-5-(ethylcarbamoyl)-4H-1,2,4-triazol-4-yl)phenoxy)acetate;

2-(4-(3-(2,4-dihydroxy-5-isopropylphenyl)-5-(ethylcarbamoyl)-4H-1,2,4-triazol-4-yl)phenoxy)acetic acid;

5-(2-hydroxy-5-isopropyl-4-methylphenyl)-4-(4-methoxyphenyl)-4H-1,2,4-triazole-3-carboxamide;

5-(4-(difluoromethoxy)-2-hydroxy-5-isopropylphenyl)-4-(1-methyl-1H-indol-5-yl)-4H-1,2,4-triazole-3-carboxamide;

4-(benzo[d][1,3]dioxol-5-ylmethyl)-5-(2-hydroxy-5-isopropyl-4-methoxyphenyl)-4H-1,2,4-triazole-3-carboxamide;

5-(2-hydroxy-4-propoxyphenyl)-4-(4-(morpholinomethyl)phenyl)-4H-1,2,4-triazole-3-carboxamide;

5-(2-hydroxy-4-isopropoxyphenyl)-4-(4-(morpholinomethyl)phenyl)-4H-1,2,4-triazole-3-carboxamide;

5-(5-tert-butyl-2,4-dihydroxyphenyl)-4-(4-(morpholinomethyl)phenyl)-4H-1,2,4-triazole-3-carboxamide;

4-cyclohexyl-5-(2,4-dihydroxy-5-isopropylphenyl)-4H-1,2,4-triazole-3-carboxamide 5-(2,4-dihydroxy-5-isopropylphenyl)-4-(4-(morpholinomethyl)phenyl)-N'-(2,2,2-trifluoroethyl)-4H-1,2,4-triazole-3-carbohydrazide;

5-(2,4-dihydroxy-5-isopropylphenyl)-4-(4-((4-ethylpiperazin-1-yl)methyl)phenyl)-N-(2-(4-methylpiperazin-1-yl)ethyl)-4H-1,2,4-triazole-3-carboxamide;

5-(2,4-dihydroxy-5-isopropylphenyl)-N-(2-(4-ethylpiperazin-1-yl)ethyl)-4-(4-((4-ethylpiperazin-1-yl)methyl)phenyl)-4H-1,2,4-triazole-3-carboxamide;

5-(5-ethyl-2-hydroxy-4-methoxyphenyl)-4-(4-(morpholinomethyl)phenyl)-4H-1,2,4-triazole-3-carboxamide;

5-(2,4-dimethoxyphenyl)-4-(4-(morpholinomethyl)-phenyl)-4H-1,2,4-triazole-3-carboxamide;

5-(2,4-dihydroxy-5-isopropylphenyl)-N',N'-dimethyl-4-(4-(morpholinomethyl)phenyl)-4H-1,2,4-triazole-3-carbohydrazide;

5-(2,4-dihydroxy-5-isopropylphenyl)-4-(4-((4-ethylpiperazin-1-yl)methyl)phenyl)-N-(2-(pyrrolidin-1-yl)ethyl)-4H-1,2,4-triazole-3-carboxamide;

5-(5-ethyl-2,4-dihydroxyphenyl)-4-(4-(morpholinomethyl)phenyl)-4H-1,2,4-triazole-3-carboxamide;

5-(2,4-dihydroxy-5-methylphenyl)-4-(4-(morpholinomethyl)phenyl)-4H-1,2,4-triazole-3-carboxamide;

5-(4-ethoxy-5-ethyl-2-hydroxyphenyl)-4-(4-(morpholinomethyl)phenyl)-4H-1,2,4-triazole-3-carboxamide;

5-(2,4-dihydroxy-5-isopropylphenyl)-4-(2-morpholinoethyl)-4H-1,2,4-triazole-3-carboxamide;

5-(2-hydroxy-4-methoxy-5-methylphenyl)-4-(4-(morpholinomethyl)phenyl)-4H-1,2,4-triazole-3-carboxamide;

5-(2,4-dihydroxy-5-isopropylphenyl)-4-(4-methoxyphenyl)-4H-1,2,4-triazole-3-carboxamide;

ethyl 1-(4-(3-(2,4-dihydroxy-5-isopropylphenyl)-5-(ethylcarbamoyl)-4H-1,2,4-triazol-4-yl)benzyl)piperidine-4-carboxylate;

1-(4-(3-(2,4-dihydroxy-5-isopropylphenyl)-5-(ethylcarbamoyl)-4H-1,2,4-triazol-4-yl)benzyl)piperidine-4-carboxylic acid;

5-(2-hydroxy-4-isopropylphenyl)-4-(4-methoxyphenyl)-4H-1,2,4-triazole-3-carboxamide;

5-(2-hydroxy-4-methylphenyl)-4-(4-methoxyphenyl)-4H-1,2,4-triazole-3-carboxamide;

N-cyclopentyl-5-(2-hydroxy-5-isopropyl-4-methoxyphenyl)-4-(4-(morpholinomethyl)phenyl)-4H-1,2,4-triazole-3-carboxamide;

5-(2,4-dihydroxy-5-isopropylphenyl)-4-(4-(methylsulfonyl)phenyl)-4H-1,2,4-triazole-3-carboxamide;

5-(2-hydroxy-5-isopropyl-4-methoxyphenyl)-N-isopropyl-4-(4-((4-methylpiperazin-1-yl)methyl)phenyl)-4H-1,2,4-triazole-3-carboxamide;

5-(2-hydroxy-5-isopropyl-4-methoxyphenyl)-N-methyl-4-(4-((4-methylpiperazin-1-yl)methyl)phenyl)-4H-1,2,4-triazole-3-carboxamide;

5-(4-ethoxy-2-hydroxy-5-methylphenyl)-4-(4-(morpholinomethyl)phenyl)-4H-1,2,4-triazole-3-carboxamide;

5-(2-hydroxy-5-isopropyl-4-methoxyphenyl)-N-methyl-4-(4-(morpholinomethyl)-phenyl)-4H-1,2,4-triazole-3-carboxamide;

N-cyclopentyl-5-(2-hydroxy-5-isopropyl-4-methoxyphenyl)-4-(4-((4-methylpiperazin-1-yl)methyl)phenyl)-4H-1,2,4-triazole-3-carboxamide;

5-(2-hydroxy-5-isopropyl-4-methoxyphenyl)-N-isopropyl-4-(4-(morpholinomethyl)phenyl)-4H-1,2,4-triazole-3-carboxamide;
5-(2,4-dihydroxy-5-isopropylphenyl)-4-(4-(morpholinomethyl)phenyl)-N-(piperidin-1-yl)-4H-1,2,4-triazole-3-carboxamide;
5-(2,4-dihydroxy-5-isopropylphenyl)-N-morpholino-4-(4-(morpholinomethyl)phenyl)-4H-1,2,4-triazole-3-carboxamide;
5-(4-hydroxy-3-isopropylphenyl)-4-(4-methoxyphenyl)-4H-1,2,4-triazole-3-carboxamide;
5-(4-hydroxy-5-isopropyl-2-methylphenyl)-4-(4-methoxyphenyl)-4H-1,2,4-triazole-3-carboxamide;
5-(4-hydroxy-2,6-dimethylphenyl)-4-(4-methoxyphenyl)-4H-1,2,4-triazole-3-carboxamide;
5-(2-hydroxy-5-isopropyl-4-methoxyphenyl)-N-isopropyl-4-(4-(piperidin-1-ylmethyl)phenyl)-4H-1,2,4-triazole-3-carboxamide;
5-(2,4-dihydroxy-5-isopropylphenyl)-4-(4-(morpholinomethyl)phenyl)-N-(2,2,2-trifluoroethyl)-4H-1,2,4-triazole-3-carboxamide;
4-(4-((4-ethylpiperazin-1-yl)methyl)phenyl)-5-(2-hydroxy-5-isopropyl-4-methoxyphenyl)-N-methyl-4H-1,2,4-triazole-3-carboxamide;
5-(2,4-dihydroxy-5-isopropylphenyl)-4-(4-((4-methylpiperazin-1-yl)methyl)phenyl)-N-(2,2,2-trifluoroethyl)-4H-1,2,4-triazole-3-carboxamide;
4-(4-((4-ethylpiperazin-1-yl)methyl)phenyl)-5-(2-hydroxy-5-isopropyl-4-methoxyphenyl)-N-isopropyl-4H-1,2,4-triazole-3-carboxamide;
N-cyclopentyl-4-(4-((4-ethylpiperazin-1-yl)methyl)phenyl)-5-(2-hydroxy-5-isopropyl-4-methoxyphenyl)-4H-1,2,4-triazole-3-carboxamide;
4-(1-benzylpiperidin-4-yl)-5-(2,4-dihydroxy-5-isopropylphenyl)-4H-1,2,4-triazole-3-carboxamide;
5-(2,4-dihydroxy-5-isopropylphenyl)-4-(4-(morpholinomethyl)phenyl)-N-(1,1-dioxo-tetrahydrothiophen-3-yl)-4H-1,2,4-triazole-3-carboxamide;
5-(3-tert-butyl-4-hydroxyphenyl)-4-(4-methoxyphenyl)-4H-1,2,4-triazole-3-carboxamide;
5-(4-hydroxy-2,5-dimethylphenyl)-4-(4-methoxyphenyl)-4H-1,2,4-triazole-3-carboxamide;
5-(2-hydroxy-5-isopropyl-4-methoxyphenyl)-4-(4-((4-methylpiperazin-1-yl)methyl)phenyl)-N-(2,2,2-trifluoroethyl)-4H-1,2,4-triazole-3-carboxamide;
5-(2,4-dihydroxy-5-isopropylphenyl)-N-isopropyl-4-(4-(pyrrolidin-1-ylmethyl)phenyl)-4H-1,2,4-triazole-3-carboxamide;
5-(4-hydroxy-3-propylphenyl)-4-(4-methoxyphenyl)-4H-1,2,4-triazole-3-carboxamide;
5-(3-cyclopentyl-4-hydroxyphenyl)-4-(4-methoxyphenyl)-4H-1,2,4-triazole-3-carboxamide;
5-(2-hydroxy-5-isopropyl-4-methoxyphenyl)-N-isopropyl-4-(4-(pyrrolidin-1-ylmethyl)phenyl)-4H-1,2,4-triazole-3-carboxamide;
5-(2-hydroxy-5-isopropyl-4-methoxyphenyl)-N-isopropyl-4-(4-((4-isopropylpiperazin-1-yl)methyl)phenyl)-4H-1,2,4-triazole-3-carboxamide;
5-(2-hydroxy-5-isopropyl-4-methoxyphenyl)-N-isopropyl-4-(4-((4-methylpiperidin-1-yl)methyl)phenyl)-4H-1,2,4-triazole-3-carboxamide;
5-(2,4-dihydroxy-5-isopropylphenyl)-4-(piperidin-4-yl)-4H-1,2,4-triazole-3-carboxamide;
5-(4-fluoro-2-hydroxy-5-isopropylphenyl)-4-(4-methoxyphenyl)-4H-1,2,4-triazole-3-carboxamide;
5-(3-ethyl-4-hydroxyphenyl)-4-(4-methoxyphenyl)-4H-1,2,4-triazole-3-carboxamide;
5-(3-sec-butyl-4-hydroxyphenyl)-4-(4-methoxyphenyl)-4H-1,2,4-triazole-3-carboxamide;
5-(2-hydroxy-5-isopropyl-4-methoxyphenyl)-4-(4-((4-methylpiperidin-1-yl)methyl)phenyl)-N-(2,2,2-trifluoroethyl)-4H-1,2,4-triazole-3-carboxamide;
N-(2-(diethylamino)ethyl)-5-(2-hydroxy-5-isopropyl-4-methoxyphenyl)-4-(4-(morpholinomethyl)phenyl)-4H-1,2,4-triazole-3-carboxamide;
N-ethyl-5-(2-hydroxy-5-isopropyl-4-methoxyphenyl)-4-(4-((4-methylpiperidin-1-yl)methyl)phenyl)-4H-1,2,4-triazole-3-carboxamide;
5-(2-hydroxy-5-isopropyl-4-methoxyphenyl)-N-(1-methylpiperidin-4-yl)-4-(4-(pyrrolidin-1-yl)phenyl)-4H-1,2,4-triazole-3-carboxamide;
(E)-5-(2-hydroxy-5-isopropyl-4-methoxyphenyl)-N-isopropyl-4-(4-((4-methylpiperazin-1-ylimino)methyl)phenyl)-4H-1,2,4-triazole-3-carboxamide;
5-(2-hydroxy-5-isopropyl-4-methoxyphenyl)-4-(4-(morpholinomethyl)phenyl)-N-(2,2,2-trifluoroethyl)-4H-1,2,4-triazole-3-carboxamide;
5-(2-hydroxy-5-isopropyl-4-methoxyphenyl)-4-(4-((4-isopropylpiperazin-1-yl)methyl)phenyl)-N-(2,2,2-trifluoroethyl)-4H-1,2,4-triazole-3-carboxamide;
5-(2,4-dihydroxy-5-isopropylphenyl)-N-isopropyl-4-(4-((4-isopropylpiperazin-1-yl)methyl)phenyl)-4H-1,2,4-triazole-3-carboxamide;
5-(2,4-dihydroxy-5-isopropylphenyl)-N-isopropyl-4-(4-((4-methylpiperidin-1-yl)methyl)phenyl)-4H-1,2,4-triazole-3-carboxamide;
4-(4-((4-ethylpiperazin-1-yl)methyl)phenyl)-5-(2-hydroxy-5-isopropyl-4-methoxyphenyl)-N-(2,2,2-trifluoroethyl)-4H-1,2,4-triazole-3-carboxamide;
5-(2-hydroxy-5-isopropyl-4-methoxyphenyl)-N-isopropyl-4-(4-(4-methylpiperazin-1-yl)phenyl)-4H-1,2,4-triazole-3-carboxamide;
5-(2-hydroxy-5-isopropyl-4-methoxyphenyl)-4-(4-(piperidin-1-ylmethyl)phenyl)-N-(2,2,2-trifluoroethyl)-4H-1,2,4-triazole-3-carboxamide
N-cyclopropyl-5-(2-hydroxy-5-isopropyl-4-methoxyphenyl)-4-(4-(morpholinomethyl)phenyl)-4H-1,2,4-triazole-3-carboxamide;
4-(3-fluoro-4-((4-methylpiperazin-1-yl)methyl)phenyl)-5-(2-hydroxy-5-isopropyl-4-methoxyphenyl)-N-(2,2,2-trifluoroethyl)-4H-1,2,4-triazole-3-carboxamide;
N-cyclopentyl-5-(2-hydroxy-5-isopropyl-4-methoxyphenyl)-4-(4-(4-methylpiperazin-1-yl)phenyl)-4H-1,2,4-triazole-3-carboxamide;
N-cyclopentyl-5-(2-hydroxy-5-isopropyl-4-methoxyphenyl)-4-(4-((4-isopropylpiperazin-1-yl)methyl)phenyl)-4H-1,2,4-triazole-3-carboxamide;
5-(4-(difluoromethoxy)-2-hydroxy-5-isopropylphenyl)-4-(1-methyl-1H-indol-5-yl)-4H-1,2,4-triazol-3-ol;
5-(2,4-dihydroxy-5-isopropylphenyl)-4-(4-(morpholinomethyl)phenyl)-4H-1,2,4-triazole-3-carboxylic acid;
5-(3-cyclohexyl-4-hydroxyphenyl)-4-(4-methoxyphenyl)-4H-1,2,4-triazole-3-carboxamide;
N-(2-(5-(3-(2,4-dihydroxy-5-isopropylphenyl)-5-hydroxy-4H-1,2,4-triazol-4-yl)-1H-indol-1-yl)ethyl)-4-(2,5-dioxopyrrolidin-1-yl)butanamide;
N-(2-(5-(3-(2,4-dihydroxy-5-isopropylphenyl)-5-mercapto-4H-1,2,4-triazol-4-yl)-1H-indol-1-yl)ethyl)-4-(2,5-dioxopyrrolidin-1-yl)butanamide;
N-(2-(5-(3-(2,4-dihydroxy-5-isopropylphenyl)-5-hydroxy-4H-1,2,4-triazol-4-yl)-1H-indol-1-yl)ethyl)-4-(2,5-dioxo-2,5-dihydro-1H-pyrrol-1-yl)-N-methylbutanamide;

N-(2-(5-(3-(2,4-dihydroxy-5-isopropylphenyl)-5-hydroxy-4H-1,2,4-triazol-4-yl)-1H-indol-1-yl)ethyl)-4-(2,5-dioxo-2,5-dihydro-1H-pyrrol-1-yl)butanamide;

4-(5-amino-4-(4-(morpholinomethyl)phenyl)-4H-1,2,4-triazol-3-yl)-6-isopropylbenzene-1,3-diol;

N-cyclopentyl-5-(2-hydroxy-5-isopropyl-4-methoxyphenyl)-4-(4-((4-methylpiperidin-1-yl)methyl)phenyl)-4H-1,2,4-triazole-3-carboxamide;

N-(2-(diethylamino)ethyl)-5-(2,4-dihydroxy-5-isopropylphenyl)-4-(3-fluoro-4-(morpholinomethyl)-phenyl)-4H-1,2,4-triazole-3-carboxamide;

N-ethyl-5-(2-hydroxy-5-isopropyl-4-methoxyphenyl)-4-(4-((4-methylpiperazin-1-yl)methyl)phenyl)-4H-1,2,4-triazole-3-carboxamide;

N-ethyl-5-(2-hydroxy-5-isopropyl-4-methoxyphenyl)-4-(4-(piperidin-1-ylmethyl)phenyl)-4H-1,2,4-triazole-3-carboxamide;

N-cyclopentyl-5-(2-hydroxy-5-isopropyl-4-methoxyphenyl)-4-(4-(piperidin-1-ylmethyl)phenyl)-4H-1,2,4-triazole-3-carboxamide;

(E)-5-(2-hydroxy-5-isopropyl-4-methoxyphenyl)-N-isopropyl-4-(4-((morpholinoimino)methyl)-phenyl)-4H-1,2,4-triazole-3-carboxamide;

N,N'-(undecane-1,11-diyl)bis(5-(2,4-dihydroxy-5-isopropylphenyl)-4-(4-(morpholinomethyl)phenyl)-4H-1,2,4-triazole-3-carboxamide);

N-cyclopentyl-4-(3-fluoro-4-((4-methylpiperazin-1-yl)methyl)phenyl)-5-(2-hydroxy-5-isopropyl-4-methoxyphenyl)-4H-1,2,4-triazole-3-carboxamide;

N-cyclopropyl-5-(2-hydroxy-5-isopropyl-4-methoxyphenyl)-4-(4-(piperidin-1-ylmethyl)phenyl)-4H-1,2,4-triazole-3-carboxamide;

5-(2-hydroxy-5-isopropyl-4-methoxyphenyl)-4-(4-(4-methylpiperazin-1-yl)phenyl)-N-(2,2,2-trifluoroethyl)-4H-1,2,4-triazole-3-carboxamide;

N-ethyl-5-(2-hydroxy-5-isopropyl-4-methoxyphenyl)-4-(4-(4-methylpiperazin-1-yl)phenyl)-4H-1,2,4-triazole-3-carboxamide;

N-cyclopentyl-4-(4-((diethylamino)methyl)phenyl)-5-(2-hydroxy-5-isopropyl-4-methoxyphenyl)-4H-1,2,4-triazole-3-carboxamide;

N-cyclopropyl-5-(2-hydroxy-5-isopropyl-4-methoxyphenyl)-4-(4-((4-methylpiperidin-1-yl)methyl)phenyl)-4H-1,2,4-triazole-3-carboxamide;

3-(2,4-dihydroxy-5-isopropylphenyl)-1-methyl-4-(1-methyl-1H-indol-5-yl)-1H-1,2,4-triazol-5(4H)-one;

3-(4-hydroxy-5-isopropyl-2-methoxyphenyl)-4-(1-methyl-1H-indol-5-yl)-1H-1,2,4-triazol-5(4H)-one;

3-(2-hydroxy-5-isopropyl-4-methoxyphenyl)-4-(1-methyl-1H-indol-5-yl)-1H-1,2,4-triazol-5(4H)-one;

5-(5-hydroxy-4-(1-methyl-1H-indol-5-yl)-4H-1,2,4-triazol-3-yl)benzene-1,3-diol; and 5-(2,4-dihydroxy-5-isopropylphenyl)-4-(4-((4-methylpiperazin-1-yl)methyl)phenyl)-4H-1,2,4-triazole-3-carboxamide;

5-(2,4-dihydroxy-5-isopropylphenyl)-4-(4-(4-ethyl-3-fluoropiperazin-1-yl)phenyl)-N-(2,2,2-trifluoroethyl)-4H-1,2,4-triazole-3-carboxamide;

5-(2,4-dihydroxy-5-isopropylphenyl)-N-ethyl-4-(4-(piperidin-1-ylsulfonyl)phenyl)-4H-1,2,4-triazole-3-carboxamide;

4-(4-(N,N-diethylsulfamoyl)phenyl)-N-ethyl-5-(2-hydroxy-5-isopropyl-4-methoxyphenyl)-4H-1,2,4-triazole-3-carboxamide;

N-ethyl-5-(2-hydroxy-5-isopropyl-4-methoxyphenyl)-4-(4-(piperidin-1-ylsulfonyl)phenyl)-4H-1,2,4-triazole-3-carboxamide;

N-ethyl-5-(2-hydroxy-5-isopropyl-4-methoxyphenyl)-4-(4-(morpholinosulfonyl)phenyl)-4H-1,2,4-triazole-3-carboxamide;

N-ethyl-5-(2-hydroxy-5-isopropyl-4-methoxyphenyl)-4-(4-(4-methylpiperazin-1-ylsulfonyl)phenyl)-4H-1,2,4-triazole-3-carboxamide;

5-(2,4-dihydroxy-5-isopropylphenyl)-N-isopropyl-4-(4-(4-methylpiperazin-1-ylsulfonyl)phenyl)-4H-1,2,4-triazole-3-carboxamide;

5-(2-hydroxy-5-isopropyl-4-methoxyphenyl)-N-isopropyl-4-(4-(morpholinosulfonyl)phenyl)-4H-1,2,4-triazole-3-carboxamide;

N-cyclopropyl-5-(2-hydroxy-5-isopropyl-4-methoxyphenyl)-4-(4-(4-methylpiperazin-1-ylsulfonyl)phenyl)-4H-1,2,4-triazole-3-carboxamide;

5-(2,4-dihydroxy-5-isopropylphenyl)-4-(4-(4-methylpiperazin-1-ylsulfonyl)phenyl)-N-(2,2,2-trifluoroethyl)-4H-1,2,4-triazole-3-carboxamide;

5-(2-hydroxy-5-isopropyl-4-methoxyphenyl)-4-(4-(4-methylpiperazin-1-ylsulfonyl)phenyl)-N-(2,2,2-trifluoroethyl)-4H-1,2,4-triazole-3-carboxamide;

N-ethyl-4-(4-(4-ethylpiperazine-1-carbonyl)phenyl)-5-(2-hydroxy-5-isopropyl-4-methoxyphenyl)-4H-1,2,4-triazole-3-carboxamide;

N-cyclopropyl-4-(4-(4-ethylpiperazine-1-carbonyl)phenyl)-5-(2-hydroxy-5-isopropyl-4-methoxyphenyl)-4H-1,2,4-triazole-3-carboxamide;

N-cyclopropyl-5-(2-hydroxy-5-isopropyl-4-methoxyphenyl)-4-(4-(morpholinosulfonyl)phenyl)-4H-1,2,4-triazole-3-carboxamide;

4-(4-(4-ethylpiperazine-1-carbonyl)phenyl)-5-(2-hydroxy-5-isopropyl-4-methoxyphenyl)-N-isopropyl-4H-1,2,4-triazole-3-carboxamide;

4-(3-chloro-4-fluorophenyl)-5-(2,4-dihydroxy-5-isopropylphenyl)-4H-1,2,4-triazole-3-carboxamide;

5-(2,4-dihydroxy-5-isopropylphenyl)-4-(5-fluoropyridin-3-yl)-N-(2-morpholinoethyl)-4H-1,2,4-triazole-3-carboxamide;

5-(4,6-dihydroxy-4'-(propylcarbamoyl)biphenyl-3-yl)-4-(4-methoxyphenyl)-4H-1,2,4-triazole-3-carboxamide;

N-cyclopropyl-5-(2,4-dihydroxy-5-isopropylphenyl)-4-(2-(pyrrolidin-1-yl)-2,3-dihydro-1H-inden-5-yl)-4H-1,2,4-triazole-3-carboxamide;

5-(4'-(diethylcarbamoyl)-4,6-dihydroxybiphenyl-3-yl)-4-(4-methoxyphenyl)-4H-1,2,4-triazole-3-carboxamide;

5-(5-bromo-2,4-dihydroxyphenyl)-4-(2-methoxyethyl)-4H-1,2,4-triazole-3-carboxamide;

5-(5-(benzo[d][1,3]dioxol-5-yl)-2,4-dihydroxyphenyl)-4-(2-methoxyethyl)-4H-1,2,4-triazole-3-carboxamide;

5-(4,6-dihydroxy-5'-isopropyl-2'-methoxybiphenyl-3-yl)-4-(4-ethylphenyl)-4H-1,2,4-triazole-3-carboxamide;

N-(2-(benzyloxy)ethyl)-5-(2,4-dihydroxy-5-isopropylphenyl)-4-(4-morpholinophenyl)-4H-1,2,4-triazole-3-carboxamide;

5-(2,4-dihydroxy-5-isopropylphenyl)-N-(2-hydroxyethyl)-4-(4-morpholinophenyl)-4H-1,2,4-triazole-3-carboxamide;

5-(5-(2-(biphenyl-4-yl)ethyl)-2,4-dihydroxyphenyl)-4-(4-methoxyphenyl)-4H-1,2,4-triazole-3-carboxamide;

N-cyclopropyl-5-(2,4-dihydroxy-5-isopropylphenyl)-4-(4-(4-ethylpiperazine-1-carbonyl)phenyl)-4H-1,2,4-triazole-3-carboxamide;

5-(2,4-dihydroxy-5-isopropylphenyl)-N-ethyl-4-(4-(4-methylpiperazine-1-carbonyl)phenyl)-4H-1,2,4-triazole-3-carboxamide;

N-cyclopropyl-5-(2-hydroxy-5-isopropyl-4-methoxyphenyl)-4-(4-(4-methylpiperazine-1-carbonyl)phenyl)-4H-1,2,4-triazole-3-carboxamide;

5-(2,4-dihydroxy-5-isopropylphenyl)-N-ethyl-4-(4-(4-methylpiperazin-1-ylsulfonyl)phenyl)-4H-1,2,4-triazole-3-carboxamide;

4-(2,6-difluoro-4-morpholinophenyl)-5-(2,4-dihydroxy-5-isopropylphenyl)-N-ethyl-4H-1,2,4-triazole-3-carboxamide;

4-(2,6-difluoro-4-morpholinophenyl)-5-(2,4-dihydroxy-5-isopropylphenyl)-N-isopropyl-4H-1,2,4-triazole-3-carboxamide;

5-(2,4-dihydroxy-5-isopropylphenyl)-4-(4-(4-ethylpiperazin-1-yl)-2,6-difluorophenyl)-N-isopropyl-4H-1,2,4-triazole-3-carboxamide;

5-(2,4-dihydroxy-5-isopropylphenyl)-4-(4-(4-ethylpiperazin-1-yl)-2,6-difluorophenyl)-N-(2,2,2-trifluoroethyl)-4H-1,2,4-triazole-3-carboxamide;

5-(2,4-dihydroxy-5-isopropylphenyl)-N-ethyl-4-(4-(4-ethylpiperazin-1-yl)-2,6-difluorophenyl)-4H-1,2,4-triazole-3-carboxamide;

5-(2,4-dihydroxy-5-isopropylphenyl)-4-(4-(4-ethylpiperazin-1-yl)-2,6-difluorophenyl)-N-methyl-4H-1,2,4-triazole-3-carboxamide;

4-(2,6-difluoro-4-(4-methylpiperazin-1-yl)phenyl)-5-(2,4-dihydroxy-5-isopropylphenyl)-N-methyl-4H-1,2,4-triazole-3-carboxamide;

4-(2,6-difluoro-4-(4-methylpiperazin-1-yl)phenyl)-5-(2,4-dihydroxy-5-isopropylphenyl)-N-isopropyl-4H-1,2,4-triazole-3-carboxamide;

4-(2,6-difluoro-4-(4-methylpiperazin-1-yl)phenyl)-5-(2,4-dihydroxy-5-isopropylphenyl)-N-ethyl-4H-1,2,4-triazole-3-carboxamide;

4-(2,6-difluoro-4-(4-methylpiperazin-1-yl)phenyl)-5-(2,4-dihydroxy-5-isopropylphenyl)-N-(2,2,2-trifluoroethyl)-4H-1,2,4-triazole-3-carboxamide;

4-(2-chloro-4-(morpholinomethyl)phenyl)-5-(2,4-dihydroxy-5-isopropylphenyl)-N-isopropyl-4H-1,2,4-triazole-3-carboxamide;

4-(2-chloro-4-((4-methylpiperazin-1-yl)methyl)phenyl)-5-(2,4-dihydroxy-5-isopropylphenyl)-N-ethyl-4H-1,2,4-triazole-3-carboxamide;

4-(2-chloro-4-((4-methylpiperazin-1-yl)methyl)phenyl)-5-(2,4-dihydroxy-5-isopropylphenyl)-N-(2,2,2-trifluoroethyl)-4H-1,2,4-triazole-3-carboxamide;

4-(2-chloro-4-((4-ethylpiperazin-1-yl)methyl)phenyl)-N-cyclopropyl-5-(2,4-dihydroxy-5-isopropylphenyl)-4H-1,2,4-triazole-3-carboxamide;

4-(2-chloro-4-((4-methylpiperazin-1-yl)methyl)phenyl)-N-cyclopropyl-5-(2,4-dihydroxy-5-isopropylphenyl)-4H-1,2,4-triazole-3-carboxamide;

4-(2-chloro-4-(morpholinomethyl)phenyl)-5-(2,4-dihydroxy-5-isopropylphenyl)-N-ethyl-4H-1,2,4-triazole-3-carboxamide;

4-(2-chloro-4-(morpholinomethyl)phenyl)-5-(2,4-dihydroxy-5-isopropylphenyl)-N-(2,2,2-trifluoroethyl)-4H-1,2,4-triazole-3-carboxamide;

4-(2-chloro-4-(morpholinomethyl)phenyl)-N-cyclopropyl-5-(2,4-dihydroxy-5-isopropylphenyl)-4H-1,2,4-triazole-3-carboxamide;

4-(2-chloro-4-((4-methylpiperazin-1-yl)methyl)phenyl)-5-(2,4-dihydroxy-5-isopropylphenyl)-N-isopropyl-4H-1,2,4-triazole-3-carboxamide;

4-(2-chloro-4-((4-ethylpiperazin-1-yl)methyl)phenyl)-5-(2,4-dihydroxy-5-isopropylphenyl)-N-ethyl-4H-1,2,4-triazole-3-carboxamide;

4-(2-chloro-4-((4-ethylpiperazin-1-yl)methyl)phenyl)-5-(2,4-dihydroxy-5-isopropylphenyl)-N-isopropyl-4H-1,2,4-triazole-3-carboxamide;

4-(2-chloro-4-((4-methylpiperazin-1-yl)methyl)phenyl)-5-(2-hydroxy-5-isopropyl-4-methoxyphenyl)-N-isopropyl-4H-1,2,4-triazole-3-carboxamide;

4-(2-chloro-4-((4-methylpiperazin-1-yl)methyl)phenyl)-N-cyclopropyl-5-(2-hydroxy-5-isopropyl-4-methoxyphenyl)-4H-1,2,4-triazole-3-carboxamide;

4-(2-chloro-4-((4-methylpiperazin-1-yl)methyl)phenyl)-N-ethyl-5-(2-hydroxy-5-isopropyl-4-methoxyphenyl)-4H-1,2,4-triazole-3-carboxamide;

4-(2-chloro-4-((4-methylpiperazin-1-yl)methyl)phenyl)-5-(2-hydroxy-5-isopropyl-4-methoxyphenyl)-N-(2,2,2-trifluoroethyl)-4H-1,2,4-triazole-3-carboxamide;

4-(2-chloro-4-((4-ethylpiperazin-1-yl)methyl)phenyl)-5-(2-hydroxy-5-isopropyl-4-methoxyphenyl)-N-isopropyl-4H-1,2,4-triazole-3-carboxamide;

4-(2-chloro-4-(morpholinomethyl)phenyl)-N-cyclopropyl-5-(2-hydroxy-5-isopropyl-4-methoxyphenyl)-4H-1,2,4-triazole-3-carboxamide;

4-(2-chloro-4-(morpholinomethyl)phenyl)-N-ethyl-5-(2-hydroxy-5-isopropyl-4-methoxyphenyl)-4H-1,2,4-triazole-3-carboxamide;

4-(2-chloro-4-(morpholinomethyl)phenyl)-5-(2-hydroxy-5-isopropyl-4-methoxyphenyl)-N-isopropyl-4H-1,2,4-triazole-3-carboxamide;

4-(2-chloro-4-(morpholinomethyl)phenyl)-5-(2-hydroxy-5-isopropyl-4-methoxyphenyl)-N-(2,2,2-trifluoroethyl)-4H-1,2,4-triazole-3-carboxamide;

4-(2-chloro-4-((4-ethylpiperazin-1-yl)methyl)phenyl)-N-cyclopropyl-5-(2-hydroxy-5-isopropyl-4-methoxyphenyl)-4H-1,2,4-triazole-3-carboxamide;

4-(2-chloro-4-((4-ethylpiperazin-1-yl)methyl)phenyl)-N-ethyl-5-(2-hydroxy-5-isopropyl-4-methoxyphenyl)-4H-1,2,4-triazole-3-carboxamide;

5-(2,4-dihydroxy-5-isopropylphenyl)-N-ethyl-4-(2-fluoro-4-(morpholino-methyl)phenyl)-4H-1,2,4-triazole-3-carboxamide;

5-(2,4-dihydroxy-5-isopropylphenyl)-4-(2-fluoro-4-(morpholinomethyl)-phenyl)-N-isopropyl-4H-1,2,4-triazole-3-carboxamide;

N-cyclopropyl-5-(2,4-dihydroxy-5-isopropylphenyl)-4-(2-fluoro-4-(morpholinomethyl)-phenyl)-4H-1,2,4-triazole-3-carboxamide;

5-(2,4-dihydroxy-5-isopropylphenyl)-4-(2-fluoro-4-(morpholinomethyl)-phenyl)-N-(2,2,2-trifluoroethyl)-4H-1,2,4-triazole-3-carboxamide;

5-(2,4-dihydroxy-5-isopropylphenyl)-4-(2-fluoro-4-((4-methylpiperazin-1-yl)methyl)phenyl)-N-(2,2,2-trifluoroethyl)-4H-1,2,4-triazole-3-carboxamide;

5-(2,4-dihydroxy-5-isopropylphenyl)-4-(2-fluoro-4-((4-methylpiperazin-1-yl)methyl)phenyl)-N-isopropyl-4H-1,2,4-triazole-3-carboxamide;

5-(2,4-dihydroxy-5-isopropylphenyl)-N-ethyl-4-(2-fluoro-4-((4-methylpiperazin-1-yl)methyl)phenyl)-4H-1,2,4-triazole-3-carboxamide;

N-cyclopropyl-5-(2,4-dihydroxy-5-isopropylphenyl)-4-(2-fluoro-4-((4-methylpiperazin-1-yl)methyl)phenyl)-4H-1,2,4-triazole-3-carboxamide;

5-(2,4-dihydroxy-5-isopropylphenyl)-N-ethyl-4-(4-(4-ethylpiperazin-1-yl)-2-fluorophenyl)-4H-1,2,4-triazole-3-carboxamide;

5-(2,4-dihydroxy-5-isopropylphenyl)-4-(4-(4-ethylpiperazin-1-yl)-2-fluorophenyl)-N-isopropyl-4H-1,2,4-triazole-3-carboxamide;

5-(2,4-dihydroxy-5-isopropylphenyl)-4-(4-(4-ethylpiperazin-1-yl)-2-fluorophenyl)-N-methyl-4H-1,2,4-triazole-3-carboxamide;

5-(2,4-dihydroxy-5-isopropylphenyl)-N-ethyl-4-(4-((4-ethylpiperazin-1-yl)methyl)-2-fluorophenyl)-4H-1,2,4-triazole-3-carboxamide;

5-(2,4-dihydroxy-5-isopropylphenyl)-4-(2-fluoro-4-(4-methylpiperazin-1-yl)phenyl)-N-methyl-4H-1,2,4-triazole-3-carboxamide;

5-(2,4-dihydroxy-5-isopropylphenyl)-4-(4-((4-ethylpiperazin-1-yl)methyl)-2-fluorophenyl)-N-isopropyl-4H-1,2,4-triazole-3-carboxamide;

N-cyclopropyl-5-(2,4-dihydroxy-5-isopropylphenyl)-4-(4-((4-ethylpiperazin-1-yl)methyl)-2-fluorophenyl)-4H-1,2,4-triazole-3-carboxamide;

5-(2,4-dihydroxy-5-isopropylphenyl)-4-(4-(4-ethylpiperazin-1-yl)-2-fluorophenyl)-N-(2,2,2-trifluoroethyl)-4H-1,2,4-triazole-3-carboxamide;

N-cyclopropyl-5-(2,4-dihydroxy-5-isopropylphenyl)-4-(4-(4-ethylpiperazin-1-yl)-2-fluorophenyl)-4H-1,2,4-triazole-3-carboxamide;

N-cyclopropyl-5-(2,4-dihydroxy-5-isopropylphenyl)-4-(2-fluoro-4-(4-methylpiperazin-1-yl)phenyl)-4H-1,2,4-triazole-3-carboxamide;

5-(2,4-dihydroxy-5-isopropylphenyl)-4-(2-fluoro-4-(4-methylpiperazin-1-yl)phenyl)-N-isopropyl-4H-1,2,4-triazole-3-carboxamide;

4-(2-fluoro-4-((4-methylpiperazin-1-yl)methyl)phenyl)-5-(2-hydroxy-5-isopropyl-4-methoxyphenyl)-N-(2,2,2-trifluoroethyl)-4H-1,2,4-triazole-3-carboxamide;

4-(2-fluoro-4-((4-methylpiperazin-1-yl)methyl)phenyl)-5-(2-hydroxy-5-isopropyl-4-methoxyphenyl)-N-isopropyl-4H-1,2,4-triazole-3-carboxamide;

N-ethyl-4-(2-fluoro-4-((4-methylpiperazin-1-yl)methyl)phenyl)-5-(2-hydroxy-5-isopropyl-4-methoxyphenyl)-4H-1,2,4-triazole-3-carboxamide;

N-cyclopropyl-4-(2-fluoro-4-((4-methylpiperazin-1-yl)methyl)phenyl)-5-(2-hydroxy-5-isopropyl-4-methoxyphenyl)-4H-1,2,4-triazole-3-carboxamide;

N-ethyl-4-(2-fluoro-4-(morpholinomethyl)phenyl)-5-(2-hydroxy-5-isopropyl-4-methoxyphenyl)-4H-1,2,4-triazole-3-carboxamide;

N-cyclopropyl-4-(2-fluoro-4-(morpholinomethyl)phenyl)-5-(2-hydroxy-5-isopropyl-4-methoxyphenyl)-4H-1,2,4-triazole-3-carboxamide;

N-cyclopropyl-4-(4-((4-ethylpiperazin-1-yl)methyl)-2-fluorophenyl)-5-(2-hydroxy-5-isopropyl-4-methoxyphenyl)-4H-1,2,4-triazole-3-carboxamide;

4-(4-((4-ethylpiperazin-1-yl)methyl)-2-fluorophenyl)-5-(2-hydroxy-5-isopropyl-4-methoxyphenyl)-N-isopropyl-4H-1,2,4-triazole-3-carboxamide;

N-ethyl-4-(4-((4-ethylpiperazin-1-yl)methyl)-2-fluorophenyl)-5-(2-hydroxy-5-isopropyl-4-methoxyphenyl)-4H-1,2,4-triazole-3-carboxamide;

N-cyclopropyl-4-(3,5-difluoro-4-((4-methylpiperazin-1-yl)methyl)phenyl)-5-(2,4-dihydroxy-5-isopropylphenyl)-4H-1,2,4-triazole-3-carboxamide;

4-(3,5-difluoro-4-((4-methylpiperazin-1-yl)methyl)phenyl)-5-(2,4-dihydroxy-5-isopropylphenyl)-N-ethyl-4H-1,2,4-triazole-3-carboxamide;

4-(3,5-difluoro-4-((4-methylpiperazin-1-yl)methyl)phenyl)-5-(2,4-dihydroxy-5-isopropylphenyl)-N-isopropyl-4H-1,2,4-triazole-3-carboxamide;

4-(3-chloro-4-((4-methylpiperazin-1-yl)methyl)phenyl)-N-cyclopropyl-5-(2,4-dihydroxy-5-isopropylphenyl)-4H-1,2,4-triazole-3-carboxamide;

4-(3-chloro-4-((4-ethylpiperazin-1-yl)methyl)phenyl)-5-(2,4-dihydroxy-5-isopropylphenyl)-N-isopropyl-4H-1,2,4-triazole-3-carboxamide;

4-(3-chloro-4-((4-methylpiperazin-1-yl)methyl)phenyl)-5-(2,4-dihydroxy-5-isopropylphenyl)-N-(2,2,2-trifluoroethyl)-4H-1,2,4-triazole-3-carboxamide;

4-(3-chloro-4-(morpholinomethyl)phenyl)-5-(2,4-dihydroxy-5-isopropylphenyl)-N-(2,2,2-trifluoroethyl)-4H-1,2,4-triazole-3-carboxamide;

4-(3-chloro-4-(morpholinomethyl)phenyl)-5-(2,4-dihydroxy-5-isopropylphenyl)-N-isopropyl-4H-1,2,4-triazole-3-carboxamide;

4-(3-chloro-4-(morpholinomethyl)phenyl)-5-(2,4-dihydroxy-5-isopropylphenyl)-N-ethyl-4H-1,2,4-triazole-3-carboxamide;

4-(3-chloro-4-(morpholinomethyl)phenyl)-N-cyclopropyl-5-(2,4-dihydroxy-5-isopropylphenyl)-4H-1,2,4-triazole-3-carboxamide;

4-(3-chloro-4-((4-methylpiperazin-1-yl)methyl)phenyl)-5-(2,4-dihydroxy-5-isopropylphenyl)-N-isopropyl-4H-1,2,4-triazole-3-carboxamide;

4-(3-chloro-4-((4-methylpiperazin-1-yl)methyl)phenyl)-5-(2,4-dihydroxy-5-isopropylphenyl)-N-ethyl-4H-1,2,4-triazole-3-carboxamide;

4-(3-chloro-4-((4-ethylpiperazin-1-yl)methyl)phenyl)-N-cyclopropyl-5-(2,4-dihydroxy-5-isopropylphenyl)-4H-1,2,4-triazole-3-carboxamide;

4-(3-chloro-4-((4-methylpiperazin-1-yl)methyl)phenyl)-N-ethyl-5-(2-hydroxy-5-isopropyl-4-methoxyphenyl)-4H-1,2,4-triazole-3-carboxamide;

4-(3-chloro-4-((4-methylpiperazin-1-yl)methyl)phenyl)-5-(2-hydroxy-5-isopropyl-4-methoxyphenyl)-N-(2,2,2-trifluoroethyl)-4H-1,2,4-triazole-3-carboxamide;

4-(3-chloro-4-((4-methylpiperazin-1-yl)methyl)phenyl)-N-cyclopropyl-5-(2-hydroxy-5-isopropyl-4-methoxyphenyl)-4H-1,2,4-triazole-3-carboxamide;

4-(3-chloro-4-((4-ethylpiperazin-1-yl)methyl)phenyl)-N-cyclopropyl-5-(2-hydroxy-5-isopropyl-4-methoxyphenyl)-4H-1,2,4-triazole-3-carboxamide;

4-(3-chloro-4-(morpholinomethyl)phenyl)-5-(2-hydroxy-5-isopropyl-4-methoxyphenyl)-N-isopropyl-4H-1,2,4-triazole-3-carboxamide;

4-(3-chloro-4-(morpholinomethyl)phenyl)-5-(2-hydroxy-5-isopropyl-4-methoxyphenyl)-N-(2,2,2-trifluoroethyl)-4H-1,2,4-triazole-3-carboxamide;

4-(3-chloro-4-(morpholinomethyl)phenyl)-N-ethyl-5-(2-hydroxy-5-isopropyl-4-methoxyphenyl)-4H-1,2,4-triazole-3-carboxamide;

4-(3-chloro-4-(morpholinomethyl)phenyl)-N-cyclopropyl-5-(2-hydroxy-5-isopropyl-4-methoxyphenyl)-4H-1,2,4-triazole-3-carboxamide;

4-(3-chloro-4-((4-ethylpiperazin-1-yl)methyl)phenyl)-5-(2-hydroxy-5-isopropyl-4-methoxyphenyl)-N-isopropyl-4H-1,2,4-triazole-3-carboxamide;

4-(3-chloro-4-((4-ethylpiperazin-1-yl)methyl)phenyl)-N-ethyl-5-(2-hydroxy-5-isopropyl-4-methoxyphenyl)-4H-1,2,4-triazole-3-carboxamide;

5-(2,4-dihydroxy-5-isopropylphenyl)-4-(3-fluoro-4-((4-methylpiperazin-1-yl)methyl)phenyl)-N-isopropyl-4H-1,2,4-triazole-3-carboxamide;

5-(2,4-dihydroxy-5-isopropylphenyl)-N-ethyl-4-(3-fluoro-4-((4-methylpiperazin-1-yl)methyl)phenyl)-4H-1,2,4-triazole-3-carboxamide;

5-(2,4-dihydroxy-5-isopropylphenyl)-4-(4-((4-ethylpiperazin-1-yl)methyl)-3-fluorophenyl)-N-isopropyl-4H-1,2,4-triazole-3-carboxamide;

N-cyclopropyl-5-(2,4-dihydroxy-5-isopropylphenyl)-4-(4-((4-ethylpiperazin-1-yl)methyl)-3-fluorophenyl)-4H-1,2,4-triazole-3-carboxamide;

N-cyclopropyl-5-(2,4-dihydroxy-5-isopropylphenyl)-4-(3-fluoro-4-((4-methylpiperazin-1-yl)methyl)phenyl)-4H-1,2,4-triazole-3-carboxamide;

5-(2,4-dihydroxy-5-isopropylphenyl)-N-ethyl-4-(4-((4-ethylpiperazin-1-yl)methyl)-3-fluorophenyl)-4H-1,2,4-triazole-3-carboxamide;

5-(2,4-dihydroxy-5-isopropylphenyl)-4-(3-fluoro-4-(morpholinomethyl)phenyl)-N-(2,2,2-trifluoroethyl)-4H-1,2,4-triazole-3-carboxamide;

5-(2,4-dihydroxy-5-isopropylphenyl)-4-(3-fluoro-4-((4-methylpiperazin-1-yl)methyl)phenyl)-N-(2,2,2-trifluoroethyl)-4H-1,2,4-triazole-3-carboxamide;

5-(2,4-dihydroxy-5-isopropylphenyl)-4-(3-fluoro-4-((4-isopropylpiperazin-1-yl)methyl)phenyl)-N-(2,2,2-trifluoroethyl)-4H-1,2,4-triazole-3-carboxamide;

5-(2,4-dihydroxy-5-isopropylphenyl)-4-(3-fluoro-4-(4-methylpiperazin-1-yl)phenyl)-N-(2,2,2-trifluoroethyl)-4H-1,2,4-triazole-3-carboxamide;

5-(2,4-dihydroxy-5-isopropylphenyl)-4-(3-fluoro-4-(4-methylpiperazin-1-yl)phenyl)-N-methyl-4H-1,2,4-triazole-3-carboxamide;

5-(2,4-dihydroxy-5-isopropylphenyl)-N-ethyl-4-(3-fluoro-4-(4-methylpiperazin-1-yl)phenyl)-4H-1,2,4-triazole-3-carboxamide;

5-(2,4-dihydroxy-5-isopropylphenyl)-4-(4-(4-ethylpiperazin-1-yl)-3-fluorophenyl)-N-methyl-4H-1,2,4-triazole-3-carboxamide;

5-(2,4-dihydroxy-5-isopropylphenyl)-4-(4-(4-ethylpiperazin-1-yl)-3-fluorophenyl)-N-isopropyl-4H-1,2,4-triazole-3-carboxamide;

5-(2,4-dihydroxy-5-isopropylphenyl)-4-(3-fluoro-4-(4-methylpiperazin-1-yl)phenyl)-N-isopropyl-4H-1,2,4-triazole-3-carboxamide;

N-cyclopropyl-5-(2,4-dihydroxy-5-isopropylphenyl)-4-(3-fluoro-4-(4-methylpiperazin-1-yl)phenyl)-4H-1,2,4-triazole-3-carboxamide;

5-(2,4-dihydroxy-5-isopropylphenyl)-N-ethyl-4-(4-(4-ethylpiperazin-1-yl)-3-fluorophenyl)-4H-1,2,4-triazole-3-carboxamide;

N-cyclopropyl-5-(2,4-dihydroxy-5-isopropylphenyl)-4-(4-(4-ethylpiperazin-1-yl)-3-fluorophenyl)-4H-1,2,4-triazole-3-carboxamide;

N-ethyl-4-(3-fluoro-4-((4-methylpiperazin-1-yl)methyl)phenyl)-5-(2-hydroxy-5-isopropyl-4-methoxyphenyl)-4H-1,2,4-triazole-3-carboxamide;

4-(4-((1H-imidazol-1-yl)methyl)-3-fluorophenyl)-N-ethyl-5-(2-hydroxy-5-isopropyl-4-methoxyphenyl)-4H-1,2,4-triazole-3-carboxamide;

4-(4-((1H-imidazol-1-yl)methyl)-3-fluorophenyl)-5-(2-hydroxy-5-isopropyl-4-methoxyphenyl)-N-isopropyl-4H-1,2,4-triazole-3-carboxamide;

4-(4-((1H-imidazol-1-yl)methyl)-3-fluorophenyl)-5-(2-hydroxy-5-isopropyl-4-methoxyphenyl)-N-(2,2,2-trifluoroethyl)-4H-1,2,4-triazole-3-carboxamide;

N-ethyl-4-(4-((4-ethylpiperazin-1-yl)methyl)-3-fluorophenyl)-5-(2-hydroxy-5-isopropyl-4-methoxyphenyl)-4H-1,2,4-triazole-3-carboxamide;

4-(3-fluoro-4-(morpholinomethyl)phenyl)-5-(2-hydroxy-5-isopropyl-4-methoxyphenyl)-N-isopropyl-4H-1,2,4-triazole-3-carboxamide;

N-ethyl-4-(3-fluoro-4-(morpholinomethyl)phenyl)-5-(2-hydroxy-5-isopropyl-4-methoxyphenyl)-4H-1,2,4-triazole-3-carboxamide;

4-(4-((4-ethylpiperazin-1-yl)methyl)-3-fluorophenyl)-5-(2-hydroxy-5-isopropyl-4-methoxyphenyl)-N-isopropyl-4H-1,2,4-triazole-3-carboxamide;

4-(3-fluoro-4-((4-methylpiperazin-1-yl)methyl)phenyl)-5-(2-hydroxy-5-isopropyl-4-methoxyphenyl)-N-isopropyl-4H-1,2,4-triazole-3-carboxamide;

4-(4-((4-ethylpiperazin-1-yl)methyl)-3-fluorophenyl)-5-(2-hydroxy-5-isopropyl-4-methoxyphenyl)-N-(2,2,2-trifluoroethyl)-4H-1,2,4-triazole-3-carboxamide;

4-(3-fluoro-4-(morpholinomethyl)phenyl)-5-(2-hydroxy-5-isopropyl-4-methoxyphenyl)-N-(2,2,2-trifluoroethyl)-4H-1,2,4-triazole-3-carboxamide;

5-(2,4-dihydroxy-5-(N-phenethylsulfamoyl)phenyl)-4-p-tolyl-4H-1,2,4-triazole-3-carboxamide;

5-(2,4-dihydroxy-5-(N-(2-hydroxyphenethyl)sulfamoyl)phenyl)-4-p-tolyl-4H-1,2,4-triazole-3-carboxamide;

5-(2,4-dihydroxy-5-(N-(3-hydroxyphenethyl)sulfamoyl)phenyl)-4-p-tolyl-4H-1,2,4-triazole-3-carboxamide;

5-(5-(N-(cyclohexylmethyl)sulfamoyl)-2,4-dihydroxyphenyl)-4-p-tolyl-4H-1,2,4-triazole-3-carboxamide;

5-(2,4-dihydroxy-5-(N-(2-(pyridin-2-yl)ethyl)sulfamoyl)phenyl)-4-p-tolyl-4H-1,2,4-triazole-3-carboxamide;

5-(2,4-dihydroxy-5-(N-(4-hydroxyphenethyl)sulfamoyl)phenyl)-4-p-tolyl-4H-1,2,4-triazole-3-carboxamide;

5-(5-(N-(2-(cyclohexyl(methyl)amino)ethyl)sulfamoyl)-2,4-dihydroxyphenyl)-4-p-tolyl-4H-1,2,4-triazole-3-carboxamide;

5-(2,4-dihydroxy-5-(N-(1-(3-methylbenzyl)piperidin-4-yl)sulfamoyl)phenyl)-4-p-tolyl-4H-1,2,4-triazole-3-carboxamide;

5-(5-(N-(4-(diethylamino)butyl)sulfamoyl)-2,4-dihydroxyphenyl)-4-p-tolyl-4H-1,2,4-triazole-3-carboxamide;

5-(2,4-dihydroxy-5-(N-(1-(thiophen-2-ylmethyl)piperidin-4-yl)sulfamoyl)phenyl)-4-p-tolyl-4H-1,2,4-triazole-3-carboxamide;

5-(2,4-dihydroxy-5-isopropylphenyl)-N-isopropyl-4-(4-(pyrrolidin-1-yl)cyclohexyl)-4H-1,2,4-triazole-3-carboxamide;

4-(4-(diethylamino)cyclohexyl)-5-(2,4-dihydroxy-5-isopropylphenyl)-N-isopropyl-4H-1,2,4-triazole-3-carboxamide;

5-(2,4-dihydroxy-5-isopropylphenyl)-N-isopropyl-4-(4-(piperidin-1-yl)cyclohexyl)-4H-1,2,4-triazole-3-carboxamide;

5-(2,4-dihydroxy-5-isopropylphenyl)-N-isopropyl-4-(4-morpholinocyclohexyl)-4H-1,2,4-triazole-3-carboxamide;

5-(2-hydroxy-5-isopropyl-4-methoxyphenyl)-4-(4-hydroxycyclohexyl)-N-isopropyl-4H-1,2,4-triazole-3-carboxamide;

5-(2,4-dihydroxy-5-isopropylphenyl)-N-isopropyl-4-(4-(4-methylpiperazin-1-yl)cyclohexyl)-4H-1,2,4-triazole-3-carboxamide;

5-(2,4-dihydroxy-5-isopropylphenyl)-4-(4-morpholinocyclohexyl)-N-(2,2,2-trifluoroethyl)-4H-1,2,4-triazole-3-carboxamide;

5-(2,4-dihydroxy-5-isopropylphenyl)-4-(4-(piperidin-1-yl)cyclohexyl)-N-(2,2,2-trifluoroethyl)-4H-1,2,4-triazole-3-carboxamide;

5-(2,4-dihydroxy-5-isopropylphenyl)-4-(4-(4-methylpiperazin-1-yl)cyclohexyl)-N-(2,2,2-trifluoroethyl)-4H-1,2,4-triazole-3-carboxamide;

5-(2,4-dihydroxy-5-isopropylphenyl)-4-(4-(4-ethylpiperazin-1-yl)cyclohexyl;

5-(2,4-dihydroxy-5-isopropylphenyl)-4-(4-(pyrrolidin-1-yl)cyclohexyl)-N-(2,2,2-trifluoroethyl)-4H-1,2,4-triazole-3-carboxamide;

N-cyclopropyl-5-(2,4-dihydroxy-5-isopropylphenyl)-4-(4-(pyrrolidin-1-yl)cyclohexyl)-4H-1,2,4-triazole-3-carboxamide;

N-cyclopropyl-5-(2,4-dihydroxy-5-isopropylphenyl)-4-(4-morpholinocyclohexyl)-4H-1,2,4-triazole-3-carboxamide;

N-cyclopropyl-5-(2,4-dihydroxy-5-isopropylphenyl)-4-(4-(4-methylpiperazin-1-yl)cyclohexyl)-4H-1,2,4-triazole-3-carboxamide;

N-cyclopropyl-5-(2,4-dihydroxy-5-isopropylphenyl)-4-(4-(4-ethylpiperazin-1-yl)cyclohexyl)-4H-1,2,4-triazole-3-carboxamide;

N-cyclopropyl-5-(2,4-dihydroxy-5-isopropylphenyl)-4-(4-(piperidin-1-yl)cyclohexyl)-4H-1,2,4-triazole-3-carboxamide;

5-(2,4-dihydroxy-5-isopropylphenyl)-N-ethyl-4-(4-(pyrrolidin-1-yl)cyclohexyl)-4H-1,2,4-triazole-3-carboxamide;

5-(2,4-dihydroxy-5-isopropylphenyl)-4-(4-(4-ethylpiperazin-1-yl)cyclohexyl)-N-isopropyl-4H-1,2,4-triazole-3-carboxamide;

4-(4-(diethylamino)cyclohexyl)-5-(2,4-dihydroxy-5-isopropylphenyl)-N-(2,2,2-trifluoroethyl)-4H-1,2,4-triazole-3-carboxamide;

5-(2,4-dihydroxy-5-isopropylphenyl)-N-ethyl-4-(4-(4-methylpiperazin-1-yl)cyclohexyl)-4H-1,2,4-triazole-3-carboxamide;

5-(2,4-dihydroxy-5-isopropylphenyl)-N-ethyl-4-(4-(piperidin-1-yl)cyclohexyl)-4H-1,2,4-triazole-3-carboxamide;

5-(2,4-dihydroxy-5-isopropylphenyl)-N-ethyl-4-(4-morpholinocyclohexyl)-4H-1,2,4-triazole-3-carboxamide;

5-(2,4-dihydroxy-5-isopropylphenyl)-N-ethyl-4-(4-(4-ethylpiperazin-1-yl)cyclohexyl)-4H-1,2,4-triazole-3-carboxamide;

5-(2,4-dihydroxy-5-isopropylphenyl)-4-(1-(ethylsulfonyl)piperidin-4-yl)-N-isopropyl-4H-1,2,4-triazole-3-carboxamide;

N-cyclopropyl-4-(4-(diethylamino)cyclohexyl)-5-(2,4-dihydroxy-5-isopropylphenyl)-4H-1,2,4-triazole-3-carboxamide;

4-(4-(diethylamino)cyclohexyl)-5-(2,4-dihydroxy-5-isopropylphenyl)-N-ethyl-4H-1,2,4-triazole-3-carboxamide;

5-(2,4-dihydroxy-5-isopropylphenyl)-4-(tetrahydro-2H-thiopyran-4-yl)-N-(2,2,2-trifluoroethyl)-4H-1,2,4-triazole-3-carboxamide;

5-(2,4-dihydroxy-5-isopropylphenyl)-4-(4-(4-ethylpiperazin-1-yl)phenyl)-N-(2,2,2-trifluoroethyl)-4H-1,2,4-triazole-3-carboxamide;

4-(4-(1H-imidazol-1-yl)phenyl)-5-(2-hydroxy-5-isopropyl-4-methoxyphenyl)-N-isopropyl-4H-1,2,4-triazole-3-carboxamide;

4-(4-(1H-imidazol-1-yl)phenyl)-5-(2-hydroxy-5-isopropyl-4-methoxyphenyl)-N-(2,2,2-trifluoroethyl)-4H-1,2,4-triazole-3-carboxamide;

N-ethyl-4-(4-(4-ethylpiperazin-1-yl)phenyl)-5-(2-hydroxy-5-isopropyl-4-methoxyphenyl)-4H-1,2,4-triazole-3-carboxamide;

4-(4-(4-ethylpiperazin-1-yl)phenyl)-5-(2-hydroxy-5-isopropyl-4-methoxyphenyl)-N-propyl-4H-1,2,4-triazole-3-carboxamide;

4-(4-(4-ethylpiperazin-1-yl)phenyl)-5-(2-hydroxy-5-isopropyl-4-methoxyphenyl)-N-methyl-4H-1,2,4-triazole-3-carboxamide;

N-cyclopentyl-4-(4-(4-ethylpiperazin-1-yl)phenyl)-5-(2-hydroxy-5-isopropyl-4-methoxyphenyl)-4H-1,2,4-triazole-3-carboxamide;

5-(2-hydroxy-5-isopropyl-4-methoxyphenyl)-4-(4-(4-methylpiperazin-1-yl)phenyl)-N-propyl-4H-1,2,4-triazole-3-carboxamide;

5-(2-hydroxy-5-isopropyl-4-methoxyphenyl)-N-methyl-4-(4-(4-methylpiperazin-1-yl)phenyl)-4H-1,2,4-triazole-3-carboxamide;

N-cyclopropyl-4-(4-(4-ethylpiperazin-1-yl)phenyl)-5-(2-hydroxy-5-isopropyl-4-methoxyphenyl)-4H-1,2,4-triazole-3-carboxamide;

4-(4-(4-ethylpiperazin-1-yl)phenyl)-5-(2-hydroxy-5-isopropyl-4-methoxyphenyl)-N-isopropyl-4H-1,2,4-triazole-3-carboxamide;

4-(4-(4-ethylpiperazin-1-yl)phenyl)-5-(2-hydroxy-5-isopropyl-4-methoxyphenyl)-N-(2,2,2-trifluoroethyl)-4H-1,2,4-triazole-3-carboxamide;

4-(4-(1H-imidazol-1-yl)phenyl)-5-(2,4-dihydroxy-5-isopropylphenyl)-4H-1,2,4-triazole-3-carboxamide;

5-(2,4-dihydroxy-5-isopropylphenyl)-N-isopropyl-4-(4-(4-methylpiperazin-1-yl)phenyl)-4H-1,2,4-triazole-3-carboxamide;

5-(2,4-dihydroxy-5-isopropylphenyl)-4-(4-(4-methylpiperazin-1-yl)phenyl)-N-(2,2,2-trifluoroethyl)-4H-1,2,4-triazole-3-carboxamide;

5-(2,4-dihydroxy-5-isopropylphenyl)-N-methyl-4-(4-(4-methylpiperazin-1-yl)phenyl)-4H-1,2,4-triazole-3-carboxamide;

N-cyclopropyl-5-(2,4-dihydroxy-5-isopropylphenyl)-4-(4-(4-methylpiperazin-1-yl)phenyl)-4H-1,2,4-triazole-3-carboxamide;

5-(2,4-dihydroxy-5-isopropylphenyl)-N-ethyl-4-(4-(4-methylpiperazin-1-yl)phenyl)-4H-1,2,4-triazole-3-carboxamide;

5-(2,4-dihydroxy-5-isopropylphenyl)-N-isopropyl-4-(4-(4-methylpiperazine-1-carbonyl)phenyl)-4H-1,2,4-triazole-3-carboxamide;

5-(2,4-dihydroxy-5-isopropylphenyl)-4-(4-(4-methylpiperazine-1-carbonyl)phenyl)-N-(2,2,2-trifluoroethyl)-4H-1,2,4-triazole-3-carboxamide;

5-(2-hydroxy-5-isopropyl-4-methoxyphenyl)-4-(4-(4-methylpiperazine-1-carbonyl)phenyl)-N-(2,2,2-trifluoroethyl)-4H-1,2,4-triazole-3-carboxamide;

5-(2,4-dihydroxy-5-isopropylphenyl)-4-(4-(4-ethylpiperazine-1-carbonyl)phenyl)-N-(2,2,2-trifluoroethyl)-4H-1,2,4-triazole-3-carboxamide;

5-(2,4-dihydroxy-5-isopropylphenyl)-4-(4-(4-ethylpiperazine-1-carbonyl)phenyl)-N-isopropyl-4H-1,2,4-triazole-3-carboxamide;

5-(2,4-dihydroxy-5-isopropylphenyl)-N-isopropyl-4-(2-(2-morpholinoethoxy)phenyl)-4H-1,2,4-triazole-3-carboxamide;

N-ethyl-5-(2-hydroxy-5-isopropyl-4-methoxyphenyl)-4-(4-(2-(4-methylpiperazin-1-yl)ethoxy)phenyl)-4H-1,2,4-triazole-3-carboxamide;

5-(2,4-dihydroxy-5-isopropylphenyl)-4-(2-hydroxyphenyl)-4H-1,2,4-triazole-3-carboxamide;

N-ethyl-5-(2-hydroxy-5-isopropyl-4-methoxyphenyl)-4-(4-(2-morpholinoethoxy)phenyl)-4H-1,2,4-triazole-3-carboxamide;

5-(2,4-dihydroxy-5-isopropylphenyl)-N-ethyl-4-(4-(2-(4-methylpiperazin-1-yl)ethoxy)phenyl)-4H-1,2,4-triazole-3-carboxamide;

4-(2-chlorophenyl)-5-(2,4-dihydroxy-5-isopropylphenyl)-4H-1,2,4-triazole-3-carboxamide;

5-(2,4-dihydroxy-5-isopropylphenyl)-4-(2-methoxyphenyl)-4H-1,2,4-triazole-3-carboxamide;

5-(2-hydroxy-5-isopropyl-4-methoxyphenyl)-N-isopropyl-4-(3-(2-morpholinoethyl)phenyl)-4H-1,2,4-triazole-3-carboxamide;
5-(2,4-dihydroxy-5-isopropylphenyl)-4-(2-fluorophenyl)-4H-1,2,4-triazole-3-carboxamide;
5-(2,4-dihydroxy-5-isopropylphenyl)-N-ethyl-4-(4-(2-morpholinoethoxy)-phenyl)-4H-1,2,4-triazole-3-carboxamide;
5-(2,4-dihydroxy-5-isopropylphenyl)-N-isopropyl-4-(4-(2-morpholinoethyl)phenyl)-4H-1,2,4-triazole-3-carboxamide;
4-(2,4-dimethoxyphenyl)-5-(2-hydroxy-5-isopropyl-4-methoxyphenyl)-4H-1,2,4-triazole-3-carboxamide;
5-(2,4-dihydroxy-5-isopropylphenyl)-4-(2,4-dimethoxyphenyl)-4H-1,2,4-triazole-3-carboxamide;
5-(2,4-dihydroxy-5-isopropylphenyl)-N-isopropyl-4-(2-(2-(4-methylpiperazin-1-yl)ethoxy)phenyl)-4H-1,2,4-triazole-3-carboxamide;
5-(2,4-dihydroxy-5-isopropylphenyl)-N-(2-(4-methylpiperazin-1-yl)ethyl)-4-(pyridin-3-yl)-4H-1,2,4-triazole-3-carboxamide;
5-(2,4-dihydroxy-5-isopropylphenyl)-N-isopropyl-4-(pyridin-3-yl)-4H-1,2,4-triazole-3-carboxamide;
5-(2,4-dihydroxy-5-isopropylphenyl)-4-(pyridin-3-yl)-N-(2,2,2-trifluoroethyl)-4H-1,2,4-triazole-3-carboxamide;
N-cyclopropyl-5-(2,4-dihydroxy-5-isopropylphenyl)-4-(pyridin-3-yl)-4H-1,2,4-triazole-3-carboxamide;
5-(2,4-dihydroxy-5-isopropylphenyl)-N-ethyl-4-(pyridin-3-yl)-4H-1,2,4-triazole-3-carboxamide;
5-(2,4-dihydroxy-5-isopropylphenyl)-N-ethyl-4-(pyridin-4-yl)-4H-1,2,4-triazole-3-carboxamide;
5-(2-hydroxy-5-isopropyl-4-methoxyphenyl)-N-isopropyl-4-(pyridin-3-yl)-4H-1,2,4-triazole-3-carboxamide;
N-cyclopropyl-5-(2-hydroxy-5-isopropyl-4-methoxyphenyl)-4-(pyridin-3-yl)-4H-1,2,4-triazole-3-carboxamide;
5-(2-hydroxy-5-isopropyl-4-methoxyphenyl)-4-(pyridin-3-yl)-N-(2,2,2-trifluoroethyl)-4H-1,2,4-triazole-3-carboxamide;
N-ethyl-5-(2-hydroxy-5-isopropyl-4-methoxyphenyl)-4-(pyridin-3-yl)-4H-1,2,4-triazole-3-carboxamide;
N-cyclopropyl-5-(2-hydroxy-5-isopropyl-4-methoxyphenyl)-4-(4-((4-methylpiperazin-1-yl)methyl)phenyl)-4H-1,2,4-triazole-3-carboxamide;
1-(4-(3-(ethylcarbamoyl)-5-(2-hydroxy-5-isopropyl-4-methoxyphenyl)-4H-1,2,4-triazol-4-yl)benzyl)piperidine-4-carboxylic acid;
5-(2-hydroxy-5-isopropyl-4-methoxyphenyl)-N-methyl-4-(4-(pyrrolidin-1-ylmethyl)phenyl)-4H-1,2,4-triazole-3-carboxamide;
1-(4-(3-(2-hydroxy-5-isopropyl-4-methoxyphenyl)-5-(2,2,2-trifluoroethyl-carbamoyl)-4H-1,2,4-triazol-4-yl)benzyl)piperidine-4-carboxylic acid;
1-(4-(3-(2-hydroxy-5-isopropyl-4-methoxyphenyl)-5-(isopropylcarbamoyl)-4H-1,2,4-triazol-4-yl)benzyl)pyrrolidine-2-carboxylic acid;
methyl 1-(4-(3-(2-hydroxy-5-isopropyl-4-methoxyphenyl)-5-(isopropylcarbamoyl)-4H-1,2,4-triazol-4-yl)benzyl)pyrrolidine-2-carboxylate;
(S)-2-((4-(3-(2-hydroxy-5-isopropyl-4-methoxyphenyl)-5-(isopropylcarbamoyl)-4H-1,2,4-triazol-4-yl)benzyl)(methyl)-amino)propanoic acid;
N-cyclopropyl-5-(2-hydroxy-5-isopropyl-4-methoxyphenyl)-4-(4-((pyrrolidin-1-ylmethyl)phenyl)-4H-1,2,4-triazole-3-carboxamide;
5-(2-hydroxy-5-isopropyl-4-methoxyphenyl)-4-(4-(pyrrolidin-1-ylmethyl)phenyl)-N-(2,2,2-trifluoroethyl)-4H-1,2,4-triazole-3-carboxamide;
1-(4-(3-(2,4-dihydroxy-5-isopropylphenyl)-5-(2,2,2-trifluoroethylcarbamoyl)-4H-1,2,4-triazol-4-yl)benzyl)piperidine-4-carboxylic acid;
4-(4-((1H-imidazol-1-yl)methyl)phenyl)-5-(2-hydroxy-5-isopropyl-4-methoxyphenyl)-N-(2,2,2-trifluoroethyl)-4H-1,2,4-triazole-3-carboxamide;
(S)-methyl 2-((4-(3-(2-hydroxy-5-isopropyl-4-methoxyphenyl)-5-(isopropylcarbamoyl)-4H-1,2,4-triazol-4-yl)benzyl)(methyl)amino)-3-methylbutanoate;
5-(2-hydroxy-5-isopropyl-4-methoxyphenyl)-N-propyl-4-(4-(pyrrolidin-1-ylmethyl)phenyl)-4H-1,2,4-triazole-3-carboxamide;
ethyl 1-(4-(3-(2-hydroxy-5-isopropyl-4-methoxyphenyl)-5-(isopropylcarbamoyl)-4H-1,2,4-triazol-4-yl)benzyl)piperidine-4-carboxylate;
1-(4-(3-(2-hydroxy-5-isopropyl-4-methoxyphenyl)-5-(isopropylcarbamoyl)-4H-1,2,4-triazol-4-yl)benzyl)piperidine-4-carboxylic acid;
methyl 2-((4-(3-(2-hydroxy-5-isopropyl-4-methoxyphenyl)-5-(isopropylcarbamoyl)-4H-1,2,4-triazol-4-yl)benzyl)-(methyl)amino)-propanoate;
5-(2,4-dihydroxy-5-isopropylphenyl)-N-isopropyl-4-(2-methoxy-4-((4-methylpiperazin-1-yl)methyl)phenyl)-4H-1,2,4-triazole-3-carboxamide;
2-((4-(3-(2-hydroxy-5-isopropyl-4-methoxyphenyl)-5-(isopropylcarbamoyl)-4H-1,2,4-triazol-4-yl)benzyl)-(methyl)amino)acetic acid;
N-ethyl-4-(4-((4-ethylpiperazin-1-yl)methyl)phenyl)-5-(2-hydroxy-5-isopropyl-4-methoxyphenyl)-4H-1,2,4-triazole-3-carboxamide;
5-(2-hydroxy-5-isopropyl-4-methoxyphenyl)-N-isopropyl-4-(4-((4-(2,2,2-trifluoroethyl)piperazin-1-yl)methyl)phenyl)-4H-1,2,4-triazole-3-carboxamide;
ethyl 2-((4-(3-(2-hydroxy-5-isopropyl-4-methoxyphenyl)-5-(isopropylcarbamoyl)-4H-1,2,4-triazol-4-yl)benzyl)-(methyl)amino)acetate;
N-ethyl-5-(2-hydroxy-5-isopropyl-4-methoxyphenyl)-4-(4-((4-isopropylpiperazin-1-yl)methyl)phenyl)-4H-1,2,4-triazole-3-carboxamide;
4-(4-((1H-imidazol-1-yl)methyl)phenyl)-5-(2-hydroxy-5-isopropyl-4-methoxyphenyl)-N-isopropyl-4H-1,2,4-triazole-3-carboxamide;
4-(4-((1H-imidazol-1-yl)methyl)phenyl)-N-ethyl-5-(2-hydroxy-5-isopropyl-4-methoxyphenyl)-4H-1,2,4-triazole-3-carboxamide;
5-(2-hydroxy-5-isopropyl-4-methoxyphenyl)-N-isopropyl-4-(4-((4-methylpiperazin-1-yl)methyl)phenyl)-4H-1,2,4-triazole-3-carboxamide;
5-(2-hydroxy-5-isopropyl-4-methoxyphenyl)-N-methyl-4-(4-((4-methylpiperidin-1-yl)methyl)phenyl)-4H-1,2,4-triazole-3-carboxamide;
N-cyclopentyl-4-(4-((4-ethylpiperazin-1-yl)methyl)phenyl)-5-(2-hydroxy-5-isopropyl-4-methoxyphenyl)-4H-1,2,4-triazole-3-carboxamide;
N-cyclopropyl-5-(2-hydroxy-5-isopropyl-4-methoxyphenyl)-4-(4-((4-isopropylpiperazin-1-yl)methyl)phenyl)-4H-1,2,4-triazole-3-carboxamide;
4-(4-((diethylamino)-methyl)phenyl)-N-ethyl-5-(2-hydroxy-5-isopropyl-4-methoxyphenyl)-4H-1,2,4-triazole-3-carboxamide;
4-(4-((diethylamino)-methyl)phenyl)-5-(2-hydroxy-5-isopropyl-4-methoxyphenyl)-N-propyl-4H-1,2,4-triazole-3-carboxamide;
4-(4-((4-ethylpiperazin-1-yl)methyl)phenyl)-5-(2-hydroxy-5-isopropyl-4-methoxyphenyl)-N-isopropyl-4H-1,2,4-triazole-3-carboxamide;

N-cyclopropyl-4-(4-((4-ethylpiperazin-1-yl)methyl)phenyl)-5-(2-hydroxy-5-isopropyl-4-methoxyphenyl)-4H-1,2,4-triazole-3-carboxamide;

5-(2-hydroxy-5-isopropyl-4-methoxyphenyl)-4-(4-((4-methylpiperidin-1-yl)methyl)phenyl)-N-propyl-4H-1,2,4-triazole-3-carboxamide;

5-(2-hydroxy-5-isopropyl-4-methoxyphenyl)-4-(4-((4-isopropylpiperazin-1-yl)methyl)phenyl)-N-propyl-4H-1,2,4-triazole-3-carboxamide;

5-(2-hydroxy-5-isopropyl-4-methoxyphenyl)-4-(4-((4-isopropylpiperazin-1-yl)methyl)phenyl)-N-methyl-4H-1,2,4-triazole-3-carboxamide;

5-(2-hydroxy-5-isopropyl-4-methoxyphenyl)-4-(4-(morpholinomethyl)phenyl)-N-propyl-4H-1,2,4-triazole-3-carboxamide;

5-(2-hydroxy-5-isopropyl-4-methoxyphenyl)-N-methyl-4-(4-(piperidin-1-ylmethyl)phenyl)-4H-1,2,4-triazole-3-carboxamide;

5-(2-hydroxy-5-isopropyl-4-methoxyphenyl)-4-(4-(piperidin-1-ylmethyl)phenyl)-N-propyl-4H-1,2,4-triazole-3-carboxamide;

5-(2-hydroxy-5-isopropyl-4-methoxyphenyl)-4-(4-((4-methylpiperazin-1-yl)methyl)phenyl)-N-(2,2,2-trifluoroethyl)-4H-1,2,4-triazole-3-carboxamide;

4-(4-((4-ethylpiperazin-1-yl)methyl)phenyl)-5-(2-hydroxy-5-isopropyl-4-methoxyphenyl)-N-propyl-4H-1,2,4-triazole-3-carboxamide;

4-(4-((diethylamino)-methyl)phenyl)-5-(2-hydroxy-5-isopropyl-4-methoxy-phenyl)-N-methyl-4H-1,2,4-triazole-3-carboxamide;

N-cyclopropyl-4-(4-((diethylamino)methyl)phenyl)-5-(2-hydroxy-5-isopropyl-4-methoxyphenyl)-4H-1,2,4-triazole-3-carboxamide;

5-(2,4-dihydroxy-5-isopropylphenyl)-N-ethyl-4-(4-((4-methylpiperazin-1-yl)methyl)-3-(trifluoromethyl)phenyl)-4H-1,2,4-triazole-3-carboxamide;

5-(2-hydroxy-5-isopropyl-4-methoxyphenyl)-N-isopropyl-4-(2-methoxy-4-((4-methylpiperazin-1-yl)methyl)phenyl)-4H-1,2,4-triazole-3-carboxamide;

N-cyclopentyl-5-(2-hydroxy-5-isopropyl-4-methoxyphenyl)-4-(4-(pyrrolidin-1-ylmethyl)phenyl)-4H-1,2,4-triazole-3-carboxamide;

5-(2,4-dihydroxy-5-isopropylphenyl)-N-isopropyl-4-(4-(pyrrolidin-1-ylsulfonyl)phenyl)-4H-1,2,4-triazole-3-carboxamide;

5-(2,4-dihydroxy-5-isopropylphenyl)-N-isopropyl-4-(4-(morpholino-sulfonyl)phenyl)-4H-1,2,4-triazole-3-carboxamide;

4-(4-(N,N-diethylsulfamoyl)phenyl)-5-(2,4-dihydroxy-5-isopropylphenyl)-N-isopropyl-4H-1,2,4-triazole-3-carboxamide;

5-(2,4-dihydroxy-5-isopropylphenyl)-N-isopropyl-4-(4-(piperidin-1-ylsulfonyl)phenyl)-4H-1,2,4-triazole-3-carboxamide;

5-(2,4-dihydroxy-5-isopropylphenyl)-N-ethyl-4-(4-(morpholino-sulfonyl)phenyl)-4H-1,2,4-triazole-3-carboxamide;

5-(2,4-dihydroxy-5-isopropylphenyl)-4-(4-(piperidin-1-ylsulfonyl)phenyl)-N-(2,2,2-trifluoroethyl)-4H-1,2,4-triazole-3-carboxamide;

4-(4-(N,N-diethylsulfamoyl)phenyl)-5-(2,4-dihydroxy-5-isopropylphenyl)-N-(2,2,2-trifluoroethyl)-4H-1,2,4-triazole-3-carboxamide;

5-(2,4-dihydroxy-5-isopropylphenyl)-4-(4-(morpholinosulfonyl)phenyl)-N-(2,2,2-trifluoroethyl)-4H-1,2,4-triazole-3-carboxamide;

N-cyclopropyl-5-(2,4-dihydroxy-5-isopropylphenyl)-4-(4-(piperidin-1-ylsulfonyl)phenyl)-4H-1,2,4-triazole-3-carboxamide;

4-(4-(N,N-diethylsulfamoyl)phenyl)-5-(2-hydroxy-5-isopropyl-4-methoxyphenyl)-N-(2,2,2-trifluoroethyl)-4H-1,2,4-triazole-3-carboxamide;

4-(4-(N,N-diethylsulfamoyl)phenyl)-5-(2-hydroxy-5-isopropyl-4-methoxyphenyl)-N-isopropyl-4H-1,2,4-triazole-3-carboxamide;

N-cyclopropyl-4-(4-(N,N-diethylsulfamoyl)phenyl)-5-(2,4-dihydroxy-5-isopropylphenyl)-4H-1,2,4-triazole-3-carboxamide;

4-(4-(N,N-diethylsulfamoyl)phenyl)-5-(2,4-dihydroxy-5-isopropylphenyl)-N-ethyl-4H-1,2,4-triazole-3-carboxamide;

5-(2-hydroxy-5-isopropyl-4-methylphenyl)-4-(4-methoxyphenyl)-N-(2-morpholinoethyl)-4H-1,2,4-triazole-3-carboxamide;

5-(2-hydroxy-5-isopropyl-4-methylphenyl)-4-(4-methoxyphenyl)-4H-1,2,4-triazole-3-carboxylic acid;

5-(2-hydroxy-5-isopropyl-4-methylphenyl)-N-isopropyl-4-(4-methoxyphenyl)-4H-1,2,4-triazole-3-carboxamide;

4-isopropyl-2-(4-(4-methoxyphenyl)-4H-1,2,4-triazol-3-yl)-5-methylphenol;

5-(2,4-Dihydroxyphenyl)-4-p-tolyl-4H-1,2,4-triazole-3-carboxamide;

5-(5-(N,N-Diethylsulfamoyl)-2,4-dihydroxyphenyl)-4-p-tolyl-4H-1,2,4-triazole-3-carboxamide;

5-(2,4-Dihydroxy-5-(pyrrolidin-1-ylsulfonyl)phenyl)-4-p-tolyl-4H-1,2,4-triazole-3-carboxamide;

5-(2,4-Dihydroxy-5-(morpholinosulfonyl)phenyl)-4-p-tolyl-4H-1,2,4-triazole-3-carboxamide;

5-(2,4-Dihydroxy-5-(N-isopropylsulfamoyl)phenyl)-4-p-tolyl-4H-1,2,4-triazole-3-carboxamide;

5-(2,4-Dihydroxy-5-(N-isobutylsulfamoyl)phenyl)-4-p-tolyl-4H-1,2,4-triazole-3-carboxamide;

5-(2,4-Dihydroxy-5-(N-(2-morpholinoethyl)sulfamoyl)phenyl)-4-p-tolyl-4H-1,2,4-triazole-3-carboxamide;

5-(5-(N-Benzylsulfamoyl)-2,4-dihydroxyphenyl)-4-p-tolyl-4H-1,2,4-triazole-3-carboxamide;

5-(2,4-Dihydroxy-5-(N-(3-morpholinopropyl)sulfamoyl)phenyl)-4-p-tolyl-4H-1,2,4-triazole-3-carboxamide;

5-(5-(N-(2-(Diethylamino)-ethyl)sulfamoyl)-2,4-dihydroxyphenyl)-4-p-tolyl-4H-1,2,4-triazole-3-carboxamide;

5-(5-bromo-2,4-dihydroxyphenyl)-4-(4-methoxyphenyl)-4H-1,2,4-triazole-3-carboxamide;

5-(2,4-Dihydroxy-5-phenethylphenyl)-4-(4-methoxyphenyl)-4H-1,2,4-triazole-3-carboxamide;

5-(2,4-Dihydroxy-5-(4-methoxyphenethyl)phenyl)-4-(4-methoxyphenyl)-4H-1,2,4-triazole-3-carboxamide;

5-(5-(4-Fluorophenethyl)-2,4-dihydroxyphenyl)-4-(4-methoxyphenyl)-4H-1,2,4-triazole-3-carboxamide;

5-(5-(3,4-Dimethoxyphenethyl)-2,4-dihydroxyphenyl)-4-(4-methoxyphenyl)-4H-1,2,4-triazole-3-carboxamide;

5-(2,4-Dihydroxy-5-(2-methoxyphenethyl)phenyl)-4-(4-methoxyphenyl)-4H-1,2,4-triazole-3-carboxamide;

5-(5-(2-Fluorophenethyl)-2,4-dihydroxyphenyl)-4-(4-methoxyphenyl)-4H-1,2,4-triazole-3-carboxamide;

5-(2,4-Dihydroxy-5-(4-methylphenethyl)phenyl)-4-(4-methoxyphenyl)-4H-1,2,4-triazole-3-carboxamide;

5-(2,4-Dihydroxy-5-(4-(trifluoromethyl)phenethyl)phenyl)-4-(4-methoxy-phenyl)-4H-1,2,4-triazole-3-carboxamide;

Methyl 4-(5-(5-carbamoyl-4-(4-methoxyphenyl)-4H-1,2,4-triazol-3-yl)-2,4-di-hydroxyphenethyl)benzoate;

5-(2,4-Dihydroxy-5-(3-methylphenethyl)phenyl)-4-(4-methoxyphenyl)-4H-1,2,4-triazole-3-carboxamide;

5-(2,4-Dihydroxy-5-(3-(trifluoromethyl)phenethyl)phenyl)-4-(4-methoxy-phenyl)-4H-1,2,4-triazole-3-carboxamide;
5-(2,4-Dihydroxy-5-(2-(naphthalen-1-yl)ethyl)phenyl)-4-(4-methoxyphenyl)-4H-1,2,4-triazole-3-carboxamide;
5-(5-(2,6-Difluorophenethyl)-2,4-dihydroxyphenyl)-4-(4-methoxyphenyl)-4H-1,2,4-triazole-3-carboxamide;
5-(2,4-Dihydroxy-5-(3-phenylpropyl)phenyl)-4-(4-methoxyphenyl)-4H-1,2,4-triazole-3-carboxamide;
5-(4,6-Dihydroxybiphenyl-3-yl)-4-(4-methoxyphenyl)-4H-1,2,4-triazole-3-carboxamide;
5-(5-(2-Cyclohexylethyl)-2,4-dihydroxyphenyl)-4-(4-methoxyphenyl)-4H-1,2,4-triazole-3-carboxamide;
5-(5-Hexyl-2,4-dihydroxyphenyl)-4-(4-methoxyphenyl)-4H-1,2,4-triazole-3-carboxamide;
5-(2,4-Dihydroxy-5-(4-hydroxybutyl)phenyl)-4-(4-methoxyphenyl)-4H-1,2,4-triazole-3-carboxamide;
5-(4,6-Dihydroxy-4'-methoxybiphenyl-3-yl)-4-(4-methoxyphenyl)-4H-1,2,4-triazole-3-carboxamide;
5-(4'-Fluoro-4,6-dihydroxybiphenyl-3-yl)-4-(4-methoxyphenyl)-4H-1,2,4-triazole-3-carboxamide;
5-(5-(Benzo[d][1,3]dioxol-5-yl)-2,4-dihydroxyphenyl)-4-(4-methoxyphenyl)-4H-1,2,4-triazole-3-carboxamide;
5-(2,4-Dihydroxy-5-(1H-indol-5-yl)phenyl)-4-(4-methoxyphenyl)-4H-1,2,4-triazole-3-carboxamide;
5-(5-(2,3-Dihydrobenzofuran-5-yl)-2,4-dihydroxyphenyl)-4-(4-methoxy-phenyl)-4H-1,2,4-triazole-3-carboxamide;
5-(2,4-Dihydroxy-5-(pyridin-4-yl)phenyl)-4-(4-methoxyphenyl)-4H-1,2,4-triazole-3-carboxamide;
5-(3'-Cyano-4,6-dihydroxybiphenyl-3-yl)-4-(4-methoxyphenyl)-4H-1,2,4-triazole-3-carboxamide;
Methyl 5'-(5-carbamoyl-4-(4-methoxyphenyl)-4H-1,2,4-triazol-3-yl)-2',4'-di-hydroxybiphenyl-4-carboxylate;
5-(4,6-Dihydroxy-3',4',5'-trimethoxybiphenyl-3-yl)-4-(4-methoxyphenyl)-4H-1,2,4-triazole-3-carboxamide;
Methyl 5'-(5-carbamoyl-4-(4-methoxyphenyl)-4H-1,2,4-triazol-3-yl)-2',4'-di-hydroxybiphenyl-3-carboxylate;
5-(5-(Biphenyl-4-yl)-2,4-dihydroxyphenyl)-4-(4-methoxyphenyl)-4H-1,2,4-triazole-3-carboxamide;
5-(5-(2-(Biphenyl-4-yl)ethyl)-2,4-dihydroxyphenyl)-4-(4-methoxyphenyl)-4H-1,2,4-triazole-3-carboxamide;
or pharmaceutically acceptable salts thereof.

In one embodiment, the invention includes use of a compound represented by Formulae (I)-(VI) or Table 1 for the manufacture of a medicament for treating a subject with a proliferative disorder. In one embodiment, said proliferative disorder is cancer. More particularly, the invention includes use of a compound represented by Formulae (I)-(VI) or Table 1 for the treatment of a c-Kit associated cancer, a BCR-ABL associated cancer, a FLT3 associated cancer, an EGFR associated cancer, or a Non-Hodgkin's lymphoma. In another embodiment, said non-Hodgkin's lymphoma is either a B-cell or a T-cell non-Hodgkin's lymphoma. More particularly, the B-cell non-Hodgkin's lymphoma is selected from the group consisting of Burkitt's lymphoma, follicular lymphoma, diffuse large B-cell lymphoma, nodal marginal zone B-cell lymphoma, plasma cell neoplasms, small lymphocytic lymphoma/chronic lymphocytic leukemia, mantle cell lymphoma, and lymphoplamacytic lymphoma/Waldenstrom macroglobulinemia. In another embodiment, the T-cell non-Hodgkin's lymphoma is selected from the group consisting of anaplastic large-cell lymphoma, precursor-T-cell lymphoblastic leukemia/lymphoma, unspecified peripheral T-cell lymphoma, and angioimmunoblastic T-cell lymphoma.

In another embodiment, the invention encompasses use of a compound represented by Formulae (I)-(VI) or Table 1 for the manufacture of a medicament for inhibiting HSP90 in a cell; treating or inhibiting angiogensis; blocking, occluding or otherwise disrupting blood flow in neovasculature; inhibiting topoisomerase II; or modulating the activity of glucocorticoid receptors.

In another embodiment, the invention encompasses use of a compound represented by Formulae (I)-(VI) or Table 1 for the manufacture of a medicament for inducing the degredation of a BCR-ABL protein; inducing the degradation of a c-Kit protein; inducing the degradation of a FLT3 protein; or inducing the degradation of an EGFR protein.

In another embodiment, the invention encompasses use of a compound represented by Formulae (I)-(VI) or Table 1 for the manufacture of a medicament for treating an infection; an inflammatory disorder; an immune disorder; or surpressing the immune system. More particularly, the infection is selected from a fungal infection, bacterial infection, viral infection and parasitic infection.

In a further embodiment, the invention includes use of a compound represented by Formulae (I)-(VI) or Table 1 in combination with an additional therapeutic agent(s) for treating the above enumerated conditions.

In another embodiment, the invention includes a compound represented by Formulae (I)-(VI) or Table 1 for use in therapy. Additionally, the invention includes a compound represented by Formulae (I)-(VI) or Table 1 in combination with an additional agent(s) for use in therapy.

A. Definitions

Unless otherwise specified, the below terms used herein are defined as follows:

As used herein, the term "alkyl" means a saturated, straight chain or branched, non-cyclic hydrocarbon having from 1 to 10 carbon atoms. Representative straight chain alkyls include methyl, ethyl, n-propyl, n-butyl, n-pentyl, n-hexyl, n-heptyl, n-octyl, n-nonyl and n-decyl; while representative branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl, and the like. The term "$(C_1$-$C_6)$alkyl" means a saturated, straight chain or branched, non-cyclic hydrocarbon having from 1 to 6 carbon atoms. Alkyl groups included in compounds of this invention may be optionally substituted with one or more substituents.

As used herein, the term "alkenyl" means a straight chain or branched, non-cyclic hydrocarbon having from 2 to 10 carbon atoms and having at least one carbon-carbon double bond. Representative straight chain and branched $(C_2$-$C_{10})$ alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl, and the like. Alkenyl groups included in compounds of the invention may be optionally substituted with one or more substituents.

As used herein, the term "alkynyl" means a straight chain or branched, non-cyclic hydrocarbon having from 2 to 10 carbon atoms and having at least one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl, and the like. Alkynyl groups included in compounds of the invention may be optionally substituted with one or more substituents.

As used herein, the term "cycloalkyl" means a saturated, mono- or polycyclic, non-aromatic hydrocarbon having from 3 to 20 carbon atoms. Representative cycloalkyls include cyclopropyl, 1-methylcyclopropyl, cyclobutyl, cyclopentyl, cyclohexyl, cycloheptyl, cyclooctyl, cyclononyl, cyclodecyl, octahydropentalenyl, and the like. Cycloalkyl groups included in compounds of the invention may be optionally substituted with one or more substituents.

As used herein, the term "cycloalkenyl" means a mono- or polycyclic, non-aromatic hydrocarbon having at least one carbon-carbon double bond in the cyclic system and having from 3 to 20 carbon atoms. Representative cycloalkenyls include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl, 1,2,3,4,5,8-hexahydronaphthalenyl, and the like. Cycloalkenyl groups included in compounds of the invention may be optionally substituted with one or more substituents.

As used herein, the term "alkylene" refers to an alkyl group that has two points of attachment. The term "$(C_1-C_6)$alkylene" refers to an alkylene group that has from one to six carbon atoms. Straight chain $(C_1-C_6)$alkylene groups are preferred. Non-limiting examples of alkylene groups include methylene (—$CH_2$—), ethylene (—$CH_2CH_2$—), n-propylene (—$CH_2CH_2CH_2$—), isopropylene (—$CH_2CH(CH_3)$—), and the like. Alkylene groups included in compounds of this invention may be optionally substituted with one or more substituents.

As used herein, the term "lower" refers to a group having up to four atoms. For example, a "lower alkyl" refers to an alkyl radical having from 1 to 4 carbon atoms, "lower alkoxy" refers to "—O—$(C_1-C_4)$alkyl and a "lower alkenyl" or "lower alkynyl" refers to an alkenyl or alkynyl radical having from 2 to 4 carbon atoms.

As used herein, the term "haloalkyl" means an alkyl group, in which one or more, including all, the hydrogen radicals are replaced by a halo group(s), wherein each halo group is independently selected from —F, —Cl, —Br, and —I. For example, the term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

As used herein, an "alkoxy" is an alkyl group which is attached to another moiety via an oxygen linker Alkoxy groups included in compounds of this invention may be optionally substituted with one or more substituents.

As used herein, a "haloalkoxy" is a haloalkyl group which is attached to another moiety via an oxygen linker.

As used herein, the term an "aromatic ring" or "aryl" means a mono- or polycyclic hydrocarbon, containing from 6 to 15 carbon atoms, in which at least one ring is aromatic. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Aryl groups included in compounds of this invention may be optionally substituted with one or more substituents. In one embodiment, the aryl group is a monocyclic ring, wherein the ring comprises 6 carbon atoms, referred to herein as "$(C_6)$aryl."

As used herein, the term "aralkyl" means an aryl group that is attached to another group by a $(C_1-C_6)$alkylene group. Representative aralkyl groups include benzyl, 2-phenylethyl, naphth-3-yl-methyl and the like. Aralkyl groups included in compounds of this invention may be optionally substituted with one or more substituents.

As used herein, the term "heterocyclyl" means a monocyclic or a polycyclic, saturated or unsaturated, non-aromatic ring or ring system which typically contains 5- to 20-members and at least one heteroatom. A heterocyclic ring system can contain saturated ring(s) or unsaturated non-aromatic ring(s), or a mixture thereof. A 3- to 10-membered heterocycle can contain up to 5 heteroatoms, and a 7- to 20-membered heterocycle can contain up to 7 heteroatoms. Typically, a heterocycle has at least one carbon atom ring member. Each heteroatom is independently selected from nitrogen, which can be oxidized (e.g., N(O)) or quaternized, oxygen and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, a nitrogen atom may be substituted with a tert-butoxycarbonyl group. Furthermore, the heterocyclyl included in compounds of this invention may be optionally substituted with one or more substituents. Only stable isomers of such substituted heterocyclic groups are contemplated in this definition.

As used herein, the term "heteroaromatic", "heteroaryl", or like terms, means a monocyclic or a polycyclic, unsaturated radical containing at least one heteroatom, in which at least one ring is aromatic. Polycyclic heteroaryl rings must contain at least one heteroatom, but not all rings of a polycyclic heteroaryl moiety must contain heteroatoms. Each heteroatom is independently selected from nitrogen, which can be oxidized (e.g., N(O)) or quaternized, oxygen and sulfur, including sulfoxide and sulfone. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, a isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzothienyl. In one embodiment, the heteroaromatic ring is selected from 5-8 membered monocyclic heteroaryl rings. The point of attachment of a heteroaromatic or heteroaryl ring may be at either a carbon atom or a heteroatom. Heteroaryl groups included in compounds of this invention may be optionally substituted with one or more substituents. As used herein, the term "$(C_5)$heteroaryl" means an heteroaromatic ring of 5 members, wherein at least one carbon atom of the ring is replaced with a heteroatom, such as, for example, oxygen, sulfur or nitrogen. Representative $(C_5)$ heteroaryls include furanyl, thienyl, pyrrolyl, oxazolyl, imidazolyl, thiazolyl, isoxazolyl, pyrazolyl, isothiazolyl, pyrazinyl, triazolyl, thiadiazolyl, and the like. As used herein, the term "($C_6$)heteroaryl" means an aromatic heterocyclic ring of 6 members, wherein at least one carbon atom of the ring is replaced with a heteroatom such as, for example, oxygen, nitrogen or sulfur. Representative ($C_6$) heteroaryls include pyridyl, pyridazinyl, pyrazinyl, triazinyl, tetrazinyl, and the like.

As used herein, the term "heteroaralkyl" means a heteroaryl group that is attached to another group by a ($C_1$-$C_6$) alkylene. Representative heteroaralkyls include 2-(pyridin-4-yl)-propyl, 2-(thien-3-yl)-ethyl, imidazol-4-yl-methyl, and the like. Heteroaralkyl groups included in compounds of this invention may be optionally substituted with one or more substituents.

As used herein, the term "halogen" or "halo" means —F, —Cl, —Br or —I.

As used herein the term "heteroalkyl" means a straight or branched alkyl group wherein one or more of the internal carbon atoms in the chain is replaced by a heteroatom. For example, a heteroalkyl is represented by the formula —[$CH_2$]$_x$—Z—[$CH_2$]$_y$[$CH_3$], wherein x is a positive integer and y is zero or a positive integer, Z is O, NR, S, S(O), or $S(O)_2$, and wherein replacement of the carbon atom does not result in a unstable compound. Heteroalkyl groups included in compounds of this invention may be optionally substituted with one or more substituents.

Suitable substituents for an alkyl, alkylene, alkenyl, alkynyl, cycloalkyl, cycloalkenyl, heterocyclyl, aryl, aralkyl, heteroaryl, and heteroaralkyl groups include are those substituents which form a stable compound of the invention without significantly adversely affecting the reactivity or biological activity of the compound of the invention. Examples of substituents for an alkyl, alkylene, alkenyl, alkynyl, cycloalkyl, cycloalkenyl, heterocyclyl, aryl, aralkyl, heteroaryl, and heteroaralkyl include an alkyl, alkenyl, alkynyl, cycloalkyl, cycloalkenyl, heterocyclyl, aryl, heteroaryl, aralkyl, heteraralkyl, heteroalkyl, alkoxy, (each of which can be optionally and independently substituted), —C(O)NR$^{28}$R$^{29}$, —C(S)NR$^{28}$R$^{29}$, —C(NR$^{32}$)NR$^{28}$R$^{29}$, —NR$^{33}$C(O)R$^{31}$, —NR$^{33}$C(S)R$^{31}$, —NR$^{33}$C(NR$^{32}$)R$^{31}$, halo, —OR$^{33}$, cyano, nitro, —C(O)R$^{33}$, —C(S)R$^{33}$, —C(NR$^{32}$)R$^{33}$, —NR$^{28}$R$^{29}$, —C(O)OR$^{33}$, —C(S)OR$^{33}$, —C(NR$^{32}$)OR$^{33}$, —OC(O)R$^{33}$, —OC(S)R$^{33}$, —OC(NR$^{32}$)R$^{33}$, —NR$^{30}$C(O)NR$^{28}$R$^{29}$, —NR$^{33}$C(S)NR$^{28}$R$^{29}$, —NR$^{33}$C(NR$^{32}$)NR$^{28}$R$^{29}$, —OC(O)NR$^{28}$R$^{29}$, —OC(S)NR$^{28}$R$^{29}$, —OC(NR$^{32}$)NR$^{28}$R$^{29}$, —NR$^{33}$C(O)OR$^{31}$, —NR$^{33}$C(S)OR$^{31}$, —NR$^{33}$C(NR$^{32}$)OR$^{31}$, —S(O)$_p$R$^{33}$, —OS(O)$_p$R$^{33}$, —NR$^{33}$S(O)$_p$R$^{33}$, —S(O)$_p$NR$^{28}$R$^{29}$, —OS(O)$_p$NR$^{28}$R$^{29}$, —NR$^{33}$S(O)$_p$NR$^{28}$R$^{29}$, guanadino, —C(O)SR$^{31}$, —C(S)SR$^{31}$, —C(NR$^{32}$)SR$^{31}$, —OC(O)OR$^{31}$, —OC(S)OR$^{31}$, —OC(NR$^{32}$)OR$^{31}$, —SC(O)R$^{33}$, —SC(O)OR$^{31}$, —SC(NR$^{32}$)OR$^{31}$, —SC(S)R$^{33}$, —SC(S)OR$^{31}$, —SC(O)NR$^{28}$R$^{29}$, —SC(NR$^{32}$)NR$^{28}$R$^{29}$, —SC(S)NR$^{28}$R$^{29}$, —SC(NR$^{32}$)R$^{33}$, —OS(O)$_p$OR$^{31}$, —S(O)$_p$OR$^{31}$, —NR$^{30}$S(O)$_p$OR$^{31}$, —SS(O)$_p$R$^{33}$, —SS(O)$_p$OR$^{31}$, —SS(O)$_p$NR$^{28}$R$^{29}$, —OP(O)(OR$^{31}$)$_2$, or —SP(O)(OR$^{31}$)$_2$. In addition, any saturated portion of an alkyl, cycloalkyl, alkylene, heterocyclyl, alkenyl, cycloalkenyl, alkynyl, aralkyl and heteroaralkyl groups, may also be substituted with =O, =S, or =N—R$^{32}$.

Each R$^{28}$ and R$^{29}$ is independently H, alkyl, alkenyl, alkynyl, cycloalkyl, cycloalkenyl, heterocyclyl, aryl, heteroaryl, aralkyl, or heteroalkyl, wherein each alkyl, alkenyl, alkynyl, cycloalkyl, cycloalkenyl, heterocyclyl, aryl, heteroaryl, aralkyl, or heteroalkyl represented by R$^{28}$ or R$^{29}$ is optionally and independently substituted.

Each R$^{31}$ and R$^{33}$ is independently H, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl represented by R$^{31}$ or R$^{33}$ is optionally and independently unsubstituted.

Each R$^{32}$ is independently H, alkyl, alkenyl, alkynyl, cycloalkyl, cycloalkenyl, heterocyclyl, aryl, heteroaryl, aralkyl, heteraralkyl, —C(O)R$^{33}$, —C(O)NR$^{28}$R$^{29}$, —S(O)$_p$R$^{33}$, or —S(O)$_p$NR$^{28}$R$^{29}$, wherein each alkyl, alkenyl, alkynyl, cycloalkyl, cycloalkenyl, heterocyclyl, aryl, heteroaryl, aralkyl and heteraralkyl represented by R$^{32}$ is optionally and independently substituted.

The variable p is 0, 1 or 2.

When a heterocyclyl, heteroaryl or heteroaralkyl group contains a nitrogen atom, it may be substituted or unsubstituted. When a nitrogen atom in the aromatic ring of a heteroaryl group has a substituent, the nitrogen may be oxidized or a quaternary nitrogen.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In a preferred embodiment, the subject is a human.

Unless indicated otherwise, the compounds of the invention containing reactive functional groups, such as, for example, carboxy, hydroxy, thiol and amino moieties, also include corresponding protected derivatives thereof. "Protected derivatives" are those compounds in which a reactive site or sites are blocked with one or more protecting groups. Examples of suitable protecting groups for hydroxyl groups include benzyl, methoxymethyl, allyl, trimethylsilyl, tert-butyldimethylsilyl, acetate, and the like. Examples of suitable amine protecting groups include benzyloxycarbonyl, tert-butoxycarbonyl, tert-butyl, benzyl and fluorenylmethyloxy-carbonyl (Fmoc). Examples of suitable thiol protecting groups include benzyl, tert-butyl, acetyl, methoxymethyl and the like. Other suitable protecting groups are well known to those of ordinary skill in the art and include those found in T. W. GREENE, PROTECTING GROUPS IN ORGANIC SYNTHESIS, (John Wiley & Sons, Inc., 1981).

As used herein, the term "compound(s) of this invention" and similar terms refers to a compound of Formulae (I)-(VI) or Table 1, or a pharmaceutically acceptable salt thereof. Also included in the scope of the present invention are a solvate, clathrate, hydrate, polymorph or prodrug, or protected derivative of a compound of Formulae (I)-(VI) or Table 1.

The compounds of the invention may contain one or more chiral centers and/or double bonds and, therefore, exist as stereoisomers, such as double-bond isomers (i.e., geometric isomers), enantiomers or diastereomers. According to this invention, the chemical structures depicted herein, including the compounds of this invention, encompass all of the corresponding compounds' enantiomers, diastereomers and geometric isomers, that is, both the stereochemically pure form (e.g., geometrically pure, enantiomerically pure, or diastereomerically pure) and isomeric mixtures (e.g., enantiomeric, diastereomeric and geometric isomeric mixtures). In some cases, one enantiomer, diastereomer or geometric isomer will possess superior activity or an improved toxicity or kinetic profile compared to other isomers. In those cases, such enantiomers, diastereomers and geometric isomers of compounds of this invention are preferred.

When a disclosed compound is named or depicted by structure, it is to be understood that solvates (e.g., hydrates) of the compound or a pharmaceutically acceptable salt thereof is also included. "Solvates" refer to crystalline forms wherein solvent molecules are incorporated into the crystal lattice during crystallization. Solvates may include water or nonaqueous solvents such as ethanol, isopropanol, DMSO, acetic acid, ethanolamine and ethyl acetate. When water is the solvent molecule incorporated into the crystal lattice of a solvate, it is typically referred to as a "hydrate". Hydrates include stoichiometric hydrates as well as compositions containing variable amounts of water.

When a disclosed compound is named or depicted by structure, it is to be understood that the compound, including solvates thereof, may exist in crystalline forms, non-crystalline forms or a mixture thereof. The compounds or solvates may also exhibit polymorphism (i.e., the capacity to occur in different crystalline forms). These different crystalline forms are typically known as "polymorphs." It is to be understood that when named or depicted by structure, the disclosed compounds and solvates (e.g., hydrates) also include all polymorphs thereof. Polymorphs have the same chemical composition but differ in packing, geometrical arrangement and other descriptive properties of the crystalline solid state. Polymorphs, therefore, may have different physical properties such as shape, density, hardness, deformability, stability and dissolution properties. Polymorphs typically exhibit different melting points, IR spectra and X-ray powder diffraction patterns, which may be used for identification. One of ordinary skill in the art will appreciate that different polymorphs may be produced, for example, by changing or adjusting the conditions used in crystallizing the compound. For example, changes in temperature, pressure or solvent may result in different polymorphs. In addition, one polymorph may spontaneously convert to another polymorph under certain conditions.

When a disclosed compound is named or depicted by structure, it is to be understood that clathrates ("inclusion compounds") of the compound or its pharmaceutically acceptable salt, solvate or polymorph, are also included. "Clathrate" means a compound of the present invention, or a salt thereof, in the form of a crystal lattice that contains spaces (e.g., channels) that have a guest molecule trapped within (e.g., a solvent or water).

As used herein, and unless otherwise indicated, the term "prodrug" means a derivative of a compound that can hydrolyze, oxidize, or otherwise react under biological conditions (in vitro or in vivo) to provide a compound of this invention. Prodrugs may become active upon such reaction under biological conditions, or they may have activity in their unreacted forms. Examples of prodrugs contemplated in this invention include, but are not limited to, analogs or derivatives of compounds of Formulae (I)-(VI) or Table 1 that comprise biohydrolyzable moieties such as biohydrolyzable amides, biohydrolyzable esters, biohydrolyzable carbamates, biohydrolyzable carbonates, biohydrolyzable ureides and biohydrolyzable phosphate analogues. Other examples of prodrugs include derivatives of compounds of Formulae (I)-(VI) or Table 1 that comprise —NO, —NO$_2$, —ONO, or —ONO$_2$ moieties. Prodrugs can typically be prepared using well-known methods, such as those described by 1 BURGER'S MEDICINAL CHEMISTRY AND DRUG DISCOVERY, (Manfred E. Wolff Ed., 5$^{th}$ ed. (1995)) 172-178, 949-982.

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide or phosphate analogue, respectively, that either: 1) does not destroy the biological activity of the compound and confers upon that compound advantageous properties in vivo, such as improved water solubility, improved circulating half-life in the blood (e.g., because of reduced metabolism of the prodrug), improved uptake, improved duration of action, or improved onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, "Hsp90" includes each member of the family of heat shock proteins having a mass of about 90-kiloDaltons. For example, in humans the highly conserved Hsp90 family includes the cytosolic Hsp90α and Hsp90β isoforms, as well as GRP94, which is found in the endoplasmic reticulum, and HSP75/TRAP1, which is found in the mitochondrial matrix.

The term "c-Kit" or "c-Kit kinase" refers to a membrane receptor protein tyrosine kinase which is preferably activated upon binding Stem Cell Factor (SCF) to its extracellular domain. Yarden, et al., *Embo. J.*, (1987)11:3341-3351; Qiu, et al., *Embo. J.*, (1988) 7:1003-1011. The full length amino acid sequence of a c-Kit kinase preferably is as set forth in Yarden, et al.; and Qiu, et al., which are incorporated by reference herein in their entirety, including any drawings. Mutant versions of c-Kit kinase are encompassed by the term "c-Kit" or "c-Kit kinase" and include those that fall into two classes: (1) having a single amino acid substitution at codon 816 of the human c-Kit kinase, or its equivalent position in other species (Ma, et al., *J. Invest Dermatol.*, (1999) 112:165-170), and (2) those which have mutations involving the putative juxtamembrane z-helix of the protein (Ma, et al., *J. Biol. Chem.*, (1999) 274:13399-13402). Both of these publications are incorporated by reference herein in their entirety, including any drawings.

As used herein, "BCR-ABL" is a fusion protein that results from the translocation of gene sequences from c-ABL protein tyrosine kinase on chromosome 9 into BCR sequences on chromosome 22 producing the Philadelphia chromosome. A schematic representation of human BCR, ABL and BCR-ABL can be seen in FIG. 1 of U.S. patent application Ser. No. 10/193,651, filed on Jul. 9, 2002, the entire teachings of which are incorporated herein by reference. Depending on the breaking point in the BCR gene, BCR-ABL fusion proteins can vary in size from 185-230 kDa but they must contain at least the OLI domain from BCR and the TK domain from ABL for transforming activity. The most common BCR-ABL gene products found in humans are P230 BCR-ABL, P210 BCR-ABL and P190 BCR-ABL. P210 BCR-ABL is characteristic of CML and P190 BCR-ABL is characteristic of ALL.

FLT3 kinase is a tyrosine kinase receptor involved in the regulation and stimulation of cellular proliferation. Gilliland, et al., *Blood* (2002), 100:1532-42. The FLT3 kinase has five immunoglobulin-like domains in its extracellular region, as well as an insert region of 75-100 amino acids in the middle of its cytoplasmic domain. FLT3 kinase is activated upon the binding of the FLT3 ligand which causes receptor dimerization. Dimerization of the FLT3 kinase by FLT3 ligand activates the intracellular kinase activity as well as a cascade of downstream substrates including Stat5, Ras, phosphatidylinositol-3-kinase (PI3K), Erk2, Akt, MAPK, SHC, SHP2 and SHIP. Rosnet, et al., *Acta Haematol.* (1996), 95:218; Hayakawa, et al., *Oncogene* (2000), 19:624; Mizuki, et al., *Blood* (2000), 96:3907; Gilliland, et al., *Curr. Opin. Hematol.* (2002), 9: 274-81. Both membrane-bound and soluble FLT3 ligand bind, dimerize, and subsequently activate the FLT3 kinase.

Normal cells that express FLT3 kinase include immature hematopoietic cells, typically CD34+ cells, placenta, gonads and brain. Rosnet, et al., *Blood* (1993), 82:1110-19; Small, et al., *Proc. Natl. Acad. Sci. U.S.A.* (1994), 91:459-63; Rosnet, et al., *Leukemia* (1996), 10:238-48. However, efficient stimulation of proliferation via FLT3 kinase typically requires other hematopoietic growth factors or interleukins FLT3 kinase also plays a critical role in immune function through its regulation of dendritic cell proliferation and differentiation. McKenna, et al., *Blood* (2000), 95:3489-497.

Numerous hematologic malignancies express FLT3 kinase, the most prominent of which is AML. Yokota, et al., *Leukemia* (1997), 11:1605-09. Other FLT3 expressing malignancies include B-precursor cell acute lymphoblastic leukemias, myelodysplastic leukemias, T-cell acute lymphoblastic leukemias, and chronic myelogenous leukemias. Rasko, et al., *Leukemia* (1995), 9:2058-66.

FLT3 kinase mutations associated with hematologic malignancies are activating mutations. In other words, the FLT3 kinase is constitutively activated without the need for binding and dimerization by FLT3 ligand, and therefore stimulates the cell to grow continuously. Two types of activating mutations have been identified: internal tandem duplications (ITDs) and point mutation in the activating loop of the kinase domain. As used herein, the term "FLT3 kinase" refers to both wild type FLT3 kinase and mutant FLT3 kinases, such as FLT3 kinases that have activating mutations.

Compounds provided herein are useful in treating conditions characterized by inappropriate FLT3 activity, such as proliferative disorders. Inappropriate FLT3 activity includes, but is not limited to, enhanced FLT3 activity resulting from increased or de novo expression of FLT3 in cells, increased FLT3 expression or activity and FLT3 mutations resulting in constitutive activation. The existence of inappropriate or abnormal FLT3 ligand and FLT3 levels or activity can be determined using well known methods in the art. For example, abnormally high FLT3 levels can be determined using commercially available ELISA kits. FLT3 levels can also be determined using flow cytometric analysis, immunohistochemical analysis and in situ hybridization techniques.

"Epidermal growth factor receptor" or "EGFR", as used herein, means any epidermal growth factor receptor (EGFR) protein, peptide, or polypeptide having EGFR or EGFR family activity (e.g., Her1, Her2, Her3 and/or Her4), such as encoded by EGFR Genbank Accession Nos. shown in Table I of U.S. patent application Ser. No. 10/923,354, filed on Aug. 20, 2004, or any other EGFR transcript derived from a EGFR gene and/or generated by EGFR translocation. The term "EGFR" is also meant to include other EGFR protein, peptide, or polypeptide derived from EGFR isoforms (e.g., Her1, Her2, Her3 and/or Her4), mutant EGFR genes, splice variants of EGFR genes, and EGFR gene polymorphisms.

As used herein, a "proliferative disorder" or a "hyperproliferative disorder," and other equivalent terms, means a disease or medical condition involving pathological growth of cells. Proliferative disorders include cancer, smooth muscle cell proliferation, systemic sclerosis, cirrhosis of the liver, adult respiratory distress syndrome, idiopathic cardiomyopathy, lupus erythematosus, retinopathy, (e.g., diabetic retinopathy or other retinopathies), cardiac hyperplasia, reproductive system associated disorders such as benign prostatic hyperplasia and ovarian cysts, pulmonary fibrosis, endometriosis, fibromatosis, harmatomas, lymphangiomatosis, sarcoidosis and desmoid tumors. Non-cancerous proliferative disorders also include hyperproliferation of cells in the skin such as psoriasis and its varied clinical forms, Reiter's syndrome, pityriasis rubra pilaris, hyperproliferative variants of disorders of keratinization (e.g., actinic keratosis, senile keratosis), scleroderma, and the like.

Smooth muscle cell proliferation includes hyperproliferation of cells in the vasculature, for example, intimal smooth muscle cell hyperplasia, restenosis and vascular occlusion, particularly stenosis following biologically- or mechanically-mediated vascular injury, e.g., vascular injury associated with angioplasty. Moreover, intimal smooth muscle cell hyperplasia can include hyperplasia in smooth muscle other than the vasculature, e.g., bile duct blockage, bronchial airways of the lung in patients with asthma, in the kidneys of patients with renal interstitial fibrosis, and the like.

In a preferred embodiment, the proliferative disorder is cancer. Cancers that can be treated by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia and heavy chain disease.

Other examples of leukemias include acute and/or chronic leukemias, e.g., lymphocytic leukemia, e.g., as exemplified by the p388 (murine) cell line, large granular lymphocytic leukemia, and lymphoblastic leukemia; T-cell leukemias, e.g., T-cell leukemia, as exemplified by the CEM, Jurkat, and HSB-2 (acute), YAC-1 (murine) cell lines, T-lymphocytic leukemia, and T-lymphoblastic leukemia; B-cell leukemia, e.g., as exemplified by the SB (acute) cell line, and B-lymphocytic leukemia; mixed cell leukemias, e.g., B- and T-cell leukemia and B- and T-lymphocytic leukemia; myeloid leukemias, e.g., granulocytic leukemia, myelocytic leukemia, e.g., as exemplified by the HL-60 (promyelocyte) cell line, and myelogenous leukemia, e.g., as exemplified by the K562(chronic) cell line; neutrophilic leukemia; eosinophilic leukemia; monocytic leukemia, e.g., as exemplified by the THP-1(acute) cell line; myelomonocytic leukemia; Naegeli-type myeloid leukemia; and nonlymphocytic leukemia. Other examples of leukemias are described in Chapter 60 of THE CHEMOTHERAPY SOURCEBOOK (Michael C. Perry Ed., Williams & Williams (1992)) and Section 36 of HOLLAND FRIE CANCER MEDICINE (Bast et al. Eds., 5th ed., B. C. Decker Inc. (2000)).

In one embodiment, the disclosed method is believed to be particularly effective in treating a subject with non-solid tumors such as multiple myeloma. In another embodiment, the disclosed method is believed to be particularly effective against T-cell leukemia, e.g., as exemplified by Jurkat and CEM cell lines; B-cell leukemia, e.g., as exemplified by the SB cell line; promyelocytes, e.g., as exemplified by the HL-60 cell line; uterine sarcoma, e.g., as exemplified by the MES-SA cell line; monocytic leukemia, e.g., as exemplified by the THP-1(acute) cell line; and lymphoma, e.g., as exemplified by the U937 cell line.

In one embodiment, the disclosed method is believed to be particularly effective in treating a subject with non-Hodgkin's lymphoma (NHL). Lymphomas are generally classified as either Hodgkin's disease (HD) or non-Hodgkin's lymphomas. NHL differs from HD by the absence of Reed-Sternberg cells. The course of NHL is less predictable than HD and is more likely to spread to areas beyond the lymph nodes. NHL can be further divided into B-cell NHL and T-cell NHL, each of which can be further categorized into a variety of different subtypes. For example, B-cell NHL includes Burkitt's lymphoma, follicular lymphoma, diffuse large B-cell lymphoma, nodal marginal zone B-cell lymphoma, plasma cell neoplasms, small lymphocytic lymphoma/chronic lymphocytic leukemia, mantle cell lymphoma, extranodal marginal zone B-cell lymphoma and lymphoplamacytic lymphoma/Waldenstrom macroglobulinemia. T-cell NHL includes anaplastic large-cell lymphoma, precursor-T-cell lymphoblastic leukemia/lymphoma, unspecified peripheral T-cell lymphoma, acute lymphoblastic leukemia/lymphoma, angioimmunoblastic T-cell lymphoma and mycosis fungoides.

Without wishing to be bound by any theory, it is believed that the compounds of the invention are useful for treating NHLs, including B-cell and T-cell NHLs, because Hsp90 is upregulated in many NHLs. In particular, in a survey of 412 cases of NHL in B-cell NHL, Hsp90 was found to be moderately to strongly over expressed in all cases of Burkitt's lymphoma (5/5, 100%), and in a subset of follicular lymphoma (17/28, 61%), diffuse large B-cell lymphoma (27/46, 59%), nodal marginal zone B-cell lymphoma (6/16, 38%), plasma cell neoplasms (14/39, 36%), small lymphocytic lymphoma/chronic lymphocytic leukemia (3/9, 33%), mantle cell lymphoma (12/38, 32%) and lymphoplamacytic lymphoma/Waldenstrom macroglobulinemia (3/10, 30%). In addition, in T-cell NHL, Hsp90 was found to be moderately to strongly over expressed in a subset of anaplastic large-cell lymphoma (14/24, 58%), precursor-T-cell lymphoblastic leukemia/lymphoma (20/65, 31%), unspecified peripheral T-cell lymphoma (8/43, 23%) and angioimmunoblastic T-cell lymphoma (2/17, 12%). Valbuena, et al., *Modern Pathology* (2005), 18:1343-1349.

Some of the disclosed methods can be particularly effective at treating subjects whose cancer has become "drug resistant" or "multi-drug resistant". A cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. "Drug resistant" tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

As used herein, the term "c-Kit associated cancer" refers to a cancer which has aberrant expression and/or activation of c-Kit. c-Kit associated cancers include leukemias, mast cell tumors, small cell lung cancer, testicular cancer, some cancers of the gastrointestinal tract and some cancers of the central nervous system. In addition, c-Kit has been implicated in playing a role in carcinogenesis of the female genital tract (Inoue, et al., *Cancer Res.*, (1994) 54(11):3049-3053), sarcomas of neuroectodermal origin (Ricotti, et al., *Blood*, (1998) 91:2397-2405), and Schwann cell neoplasia associated with neurofibromatosis (Ryan, et al., *J. Neuro. Res.*, (1994) 37:415-432).

Other anti-proliferative or anti-cancer therapies may be combined with the compounds of this invention to treat proliferative diseases and cancer. Other therapies or anti-cancer agents that may be used in combination with the inventive anti-cancer agents of the present invention include surgery, radiotherapy (including, but not limited to, gamma-radiation, neutron beam radiotherapy, electron beam radiotherapy, proton therapy, brachytherapy, and systemic radioactive isotopes), endocrine therapy, biologic response modifiers (including, but not limited to, interferons, interleukins, and tumor necrosis factor (TNF)), hyperthermia and cryotherapy, agents to attenuate any adverse effects (e.g., antiemetics), and other approved chemotherapeutic drugs.

In one embodiment, compounds of the invention are vascular targeting agents. In one aspect, compounds of the invention are effective for blocking, occluding, or otherwise disrupting blood flow in "neovasculature." In one aspect, the invention provides a novel treatment for diseases involving the growth of new blood vessels ("neovasculature"), including, but not limited to: cancer; infectious diseases; autoimmune disorders; benign tumors, e.g. hemangiomas, acoustic neuromas, neurofibromas, trachomas, and pyogenic granulomas; arteroscleric plaques; ocular angiogenic diseases, e.g., diabetic retinopathy, retinopathy of prematurity, macular degeneration, corneal graft rejection, neovascular glaucoma, retrolental fibroplasia, rubeosis, retinoblastoma, persistent hyperplastic vitreous syndrome, choroidal neovascularization, uvietis and Pterygia (abnormal blood vessel growth) of the eye; rheumatoid arthritis; psoriasis; warts; allergic dermatitis; blistering disease; Karposi sarcoma; delayed wound healing; endometriosis; uterine bleeding; ovarian cysts; ovarian hyperstimulation; vasculogenesis; granulations; hypertrophic scars (keloids); nonunion fractures; scleroderma; trachoma; vascular adhesions; vascular malformations; DiGeorge syndrome; hereditary hemorrhagic telangiectasia (HHT or Osler-Webber Syndrome); transplant arteriopathy; restinosis; obesity; myocardial angiogenesis; coronary collaterals; cerebral collaterals; arteriovenous malformations; ischemic limb angiogenesis; primary pulmonary hypertension; asthma; nasal polyps; inflammatory bowel disease; periodontal disease; ascites; peritoneal adhesions; plaque neovascularization; telangiectasia; hemophiliac joints; synovitis; osteomyelitis; osteophyte formation; angiofibroma; fibromuscular dysplasia; wound granulation; Crohn's disease; and atherosclerosis. Vascular targeting can be demonstrated by any method known to those skilled in the art, such as the method described herein in Example 8.

As used herein, the term "angiogenesis" refers to a fundamental process of generating new blood vessels in tissues or organs. Angiogenesis is involved with or associated with many diseases or conditions, including, but not limited to: cancer; ocular neovascular disease; age-related macular degeneration; diabetic retinopathy, retinopathy of prematurity; corneal graft rejection; neovascular glaucoma; retrolental fibroplasias; epidemic keratoconjunctivitis; Vitamin A deficiency; contact lens overwear; atopic keratitis; superior limbic keratitis; pterygium keratitis sicca; sjogrens; acne rosacea; warts; eczema; phylectenulosis; syphilis; Mycobacteria infections; lipid degeneration; chemical burns; bacterial ulcers; fungal ulcers; Herpes simplex infections; Herpes zoster infections; protozoan infections; Kaposi's sarcoma; Mooren's ulcer; Terrien's marginal degeneration; mariginal keratolysis; rheumatoid arthritis; systemic lupus; polyarteritis; trauma; Wegener's sarcoidosis; scleritis; Stevens-Johnson disease; pemphigoid; radial keratotomy; corneal graph rejection; sickle cell anemia; sarcoid; syphilis; pseudoxanthoma elasticum; Paget's disease; vein occlusion; artery occlusion; carotid obstructive disease; chronic uveitis/vitritis; mycobacterial infections; Lyme's disease; systemic lupus erythematosis; Eales' disease; Behcet's disease; infections causing a retinitis or choroiditis; presumed ocular histoplasmosis; Best's disease; myopia; optic pits; Stargardt's disease; pars planitis; chronic retinal detachment; hyperviscosity syndromes; toxoplasmosis; trauma and post-laser complications; diseases associated with rubeosis (neovasculariation of the angle); diseases caused by the abnormal proliferation of fibrovascular or fibrous tissue including all forms of proliferative vitreoretinopathy; rheumatoid arthritis; osteoarthritis; ulcerative colitis; Crohn's disease; Bartonellosis; atherosclerosis; Osler-Weber-Rendu disease (also known as hereditary hemorrhagic telangiectasia or HHT); pulmonary hemangiomatosis; pre-eclampsia; endometriosis; fibrosis of the liver and of the kidney; developmental abnormalities (organogenesis); skin discolorations (e.g., hemangioma, nevus flammeus or nevus simplex); wound healing; hypertrophic scars, i.e., keloids; wound granulation; vascular adhesions; cat scratch disease (Rochele ninalia quintosa); ulcers (Helicobacter pylori); keratoconjunctivitis; gingivitis; periodontal disease; epulis; hepatitis; tonsillitis; obesity; rhinitis; laryngitis; tracheitis; bronchitis; bronchiolitis; pneumonia; interstitial pulmonary fibrosis; neurodermitis; thyroiditis; thyroid enlargement; endometriosis; glomerulonephritis; gastritis; inflammatory bone and cartilage destruction; thromboembolic disease; and Buerger's disease.

The term "infection" is used herein in its broadest sense and refers to any infection, e.g., a viral infection or one caused by a microorganism, such as a bacterial infection, fungal infection or parasitic infection (e.g. protozoal, amoebic, or helminth). Examples of such infections may be found in a number of well known texts such as GREENWOOD, D., ET AL., MEDICAL MICROBIOLOGY (Churchill Livingstone Press, 2002); Mims, C., et al., Mims' Pathogenesis of Infectious Disease" (Academic Press, 2000); FIELDS, B. N., ET AL., FIELDS VIROLOGY (Lippincott Williams and Wilkins, 2001); SANFORD, J. P., ET AL., THE SANFORD GUIDE TO ANTIMICROBIAL THERAPY, (Antimicrobial Therapy, Inc., 26th ed. 1996).

"Bacterial infections" include, but are not limited to, infections caused by Gram positive acteria including *Bacillus cereus, Bacillus anthracia, Clostridium botulinum, Clostridium difficile, Clostridium tetani, Clostridium perfringens, Corynebacteria diphtheriae, Enterococcus* (*Streptococcus* D), *Listeria monocytogenes, Pneumoccoccal* infections (*Streptococcus pneumoniae*), *Staphylococcal* infections and *Streptococcal* infections; Gram negative bacteria including *Bacteroides, Bordetella pertussis, Brucella, Campylobacter* infections, enterohaemorrhagic *Escherichia coli* (EHEC/*E. coli* 0157: H7), enteroinvasive *Escherichia coli* (EIEC), enterotoxigenic *Escherichia coli* (ETEC), *Haemophilus influenzae, Helicobacter pylori, Klebsiella pneumoniae, Legionella* spp., *Moraxella catarrhalis, Neisseria gonnorrhoeae, Neisseria meningitidis, Proteus* spp., *Pseudomonas aeruginosa, Salmonella* spp., *Shigella* spp., *Vibrio cholera* and *Yersinia*; acid fast bacteria including *Mycobacterium tuberculosis, Mycobacterium avium-intracellulare, Myobacterium johnei, Mycobacterium leprae*, atypical bacteria, *Chlamydia, Mycoplasma, Rickettsia, Spirochetes, Treponema pallidum, Borrelia recurrentis, Borrelia burgdorfii* and *Leptospira icterohemorrhagiae*; or other miscellaneous bacteria, including *Actinomyces* and *Nocardia*.

The term "fungus" or "fungal" refers to a distinct group of eukaryotic, spore-forming organisms with absorptive nutrition and lacking chlorophyll. It includes mushrooms, molds, and yeasts. "Fungal infections" include, but are not limited to, infections caused by *Alternaria alternata, Aspergillus flavus, Aspergillus fumigatus, Aspergillus nidulans, Aspergillus niger, Aspergillus versicolor, Blastomyces dermatiditis, Candida albicans, Candida dubliensis, Candida krusei, Candida parapsilosis, Candida tropicalis, Candida glabrata, Coccidioides immitis, Cryptococcus neoformans, Epidermophyton floccosum, Histoplasma capsulatum, Malassezia furfur, Microsporum canis, Mucor* spp., *Paracoccidioides brasiliensis, Penicillium marneffei, Pityrosporum ovale, Pneumocystis carinii, Sporothrix schenkii, Trichophyton rubrum, Trichophyton interdigitale, Trichosporon beigelii, Rhodotorula* spp., *Brettanomyces clausenii, Brettanomyces custerii, Brettanomyces anomalous, Brettanomyces naardenensis, Candida himilis, Candida intermedia, Candida saki, Candida solani, Candida versatilis, Candida bechii, Candida famata, Candida lipolytica, Candida stellata, Candida vini, Debaromyces hansenii, Dekkera intermedia, Dekkera bruxellensis, Geotrichium sandidum, Hansenula fabiani, Hanseniaspora uvarum, Hansenula anomala, Hanseniaspora guillermondii, Hanseniaspora vinae, Kluyveromyces lactis, Kloekera apiculata, Kluveromyces marxianus, Kluyveromyces fragilis, Metschikowia pulcherrima, Pichia guilliermodii, Pichia orientalis, Pichia fermentans, Pichia memranefaciens, Rhodotorula Saccharomyces bayanus, Saccharomyces cerevisiae, Saccharomyces dairiensis, Saccharomyces exigus, Saccharomyces uinsporus, Saccharomyces uvarum, Saccharomyces oleaginosus, Saccharomyces boulardii, Saccharomycodies ludwigii, Schizosaccharomyces pombe, Torulaspora delbruekii, Torulopsis stellata, Zygoaccharomyces bailli* and *Zygosaccharomyces rouxii*.

Drug resistance in fungi is characterized by the failure of an antifungal therapy to control a fungal infection. "Antifungal resistance", as used herein, refers to both intrinsic or primary resistance, which is present before exposure to antifungal agents and secondary or acquired resistance, which develops after exposure to antifungal therapies. Hsp90 has been shown to play a role in the evolution of drug resistance in fungi. Cowen, L., et al., *Eukaryotic Cell*, (2006) 5(12):2184-2188; Cowen, L. et al., *Science*, (2005) 309: 2185-2189. It has been shown that the key mediator of Hsp90 dependent azole resistance is calcineurin, a client protein of Hsp90. Calcineurin is required for tolerating the membrane stress exerted by azole drugs. Hsp90 keeps calcineurin stable and poised for activation. In addition, it has been shown that Hsp90 is required for the emergence of drug resistance and continued drug resistance to azoles and echinocandins.

"Parasitic infections" include, but are not limited to, infections caused by *Leishmania, Toxoplasma, Plasmodia, Theileria, Acanthamoeba, Anaplasma, Giardia, Trichomonas, Trypanosoma, Coccidia* and *Babesia*. For example, parasitic infections include those caused by *Trypanosoma cruzi, Eimeria tenella, Plasmodium falciparum, Plasmodium vivax, Plasmodium ovale, Cryptosporidium parvum, Naegleria fowleri, Entamoeba histolytica, Balamuthia mandrillaris, Entameoba histolytica, Schistostoma mansoni, Plasmodium falciparum, P. vivax, P. ovale, P. malariae, P. berghei, Leishmania donovani, L. infantum, L. chagasi, L. mexicana, L. amazonensis, L. venezuelensis, L. tropics, L. major, L. minor, L. aethiopica, L. Biana braziliensis, L.* (V.) *guyanensis, L.* (V.) *panamensis, L.* (V.) *peruviana, Trypanosoma brucei rhodesiense, T. brucei gambiense, Giardia intestinalis, G. lambda, Toxoplasma gondii, Trichomonas vaginalis, Pneumocystis carinii, Acanthamoeba castellani, A. culbertsoni, A. polyphaga, A. healyi,* (*A. astronyxis*), *A. hatchetti, A. rhysodes*, and *Trichinella spiralis*.

As used herein, the term "viral infection" refers to any stage of a viral infection, including incubation phase, latent or dormant phase, acute phase, and development and maintenance of immunity towards a virus. Viral infections include, but are not limited to those caused by Adenovirus, Lassa fever virus (Arenavirus), Astrovirus, Hantavirus, Rift Valley Fever virus (Phlebovirus), Calicivirus, Ebola virus, Marburg Virus, Japanese encephalitis virus, Dengue virus, Yellow fever virus, Hepatitis A virus, Hepatitis C virus, Hepatitis G virus, Hepatitis B virus, Hepatitis D virus, Herpes simplex virus 1, Herpes simplex virus 2, Cytomegalovirus, Epstein Barr virus, Varicella Zoster virus, Human Herpesvirus 7, Human Herpesvirus 8, Influenza virus, Parainfluenza virus, Rubella virus, Mumps virus, Morbillivirus, Measles virus, Respiratory Syncytial virus, Papillomaviruses, JC virus (Polyomavirus), BK virus (Polyomavirus), Parvovirus, Coxsackie virus (A and B), Polioviruses, Rhinoviruses, Reovirus, Rabies Virus (Lyssavirus), Human Immunodeficiency virus 1 and 2, and Human T-cell Leukemia virus. Examples of viral infections include Adenovirus acute respiratory disease, Lassa fever, Astrovirus enteritis, Hantavirus pulmonary syndrome, Rift valley fever, Ebola hemorrhagic fever, Marburg hemorrhagic fever, Japanese encephalitis, Dengue fever, Yellow fever, Hepatitis C, Hepatitis G, Hepatitis B, Hepatitis D, Hepatitis E, cold sores, genital sores, Cytomegalovirus infection, Mononucleosis, Chicken Pox, Shingles, Human Herpesvirus infection 7, Kaposi Sarcoma, Influenza, Brochiolitis, German measles (rubeola), Mumps, Measles, Brochiolitis, Papillomas (Warts), cervical cancer, progressive multifocal leukoencephalopathy, kidney disease, Erythema infectiosum, viral myocarditis, meningitis, entertitis, Hepatitis, Poliomyelitis, the common cold, diarrhoea, Rabies, AIDS and Leukemia.

DNA topoisomerases are enzymes present in all cells that catalyze topological changes in DNA. Topoisomerase II ("topo II") plays important roles in DNA replication, chromosome segregation and the maintenance of the nuclear scaffold in eukaryotic cells. The enzyme acts by creating breaks in DNA, thereby allowing the DNA strands to unravel and separate. Due to the important roles of the enzyme in dividing cells, the enzyme is a highly attractive target for chemotherapeutic agents, especially in human cancers. The inhibition of topo II can be determined by any method known in the art. See, e.g., Gadelle, D., et al., *Biochemical Pharmacology*, (2006), 72(10):1207-1216.

The glucocorticoid receptor is a member of the steroid hormone nuclear receptor family which includes glucocorticoid receptors (GR), androgen receptors (AR), mineralocorticoid receptors (MR), estrogen receptors (ER) and progesterone receptors (PR). Glucocorticoid receptors bind glucocorticoids such as cortisol, corticosterone and cortisone.

"Immunosuppression" refers to the impairment of any component of the immune system resulting in decreased immune function. This impairment may be measured by any conventional means including whole blood assays of lymphocyte function, detection of lymphocyte proliferation and assessment of the expression of T cell surface antigens. The antisheep red blood cell (SRBC) primary (IgM) antibody response assay (usually referred to as the plaque assay) is one specific method. This and other methods are described in Luster, M. I, et al., *Fundam. Appl. Toxicol.* (1992), 18: 200-210. Measuring the immune response to a T-cell dependent immunogen is another particularly useful assay. Dean, J. H., et al., *Immunotoxicology: Effects of and Responses to, Drugs and Chemicals, In* PRINCIPLES AND METHODS OF TOXICOLOGY: FOURTH EDITION (A. W. Hayes, Ed.) (Taylor & Francis, Philadelphia, Pa.) (2001) 1415-1450. In one embodiment, a decrease in the expression of glucocorticoid receptors in PBMCs indicates impairment of immune function. A patient in need of immunosuppression can be determined by a physician, and can include patients with immune or inflammatory disorders. For example, patients that have undergone or will be undergoing an organ, tissue, bone marrow or stem cell transplantation are in need of immunosuppression to prevent inflammation and/or rejection of the transplanted organ or tissue. One embodiment of the invention provides treatment of a patient in need of immunosuppression, comprising administering an effective amount of a compound of the invention to the patient.

The compounds of this invention can be used to treat subjects with immune disorders. As used herein, the term "immune disorder", and like terms, means a disease, disorder or condition caused by the immune system of a subject, including autoimmune disorders. Immune disorders include those diseases, disorders or conditions that have an immune component and those that are substantially or entirely immune system-mediated. Autoimmune disorders are those wherein the subject's own immune system mistakenly attacks itself, thereby targeting the cells, tissues and/or organs of the subject's own body. For example, the autoimmune reaction is directed against the nervous system in multiple sclerosis and the gut in Crohn's disease. In other autoimmune disorders, such as systemic lupus erythematosus (lupus), affected tissues and organs may vary among subjects with the same disease. One subject with lupus may have affected skin and joints, whereas another may have affected skin, kidney and lungs. Ultimately, damage to certain tissues by the immune system may be permanent, as with destruction of insulin-producing cells of the pancreas in Type 1 diabetes mellitus. Specific autoimmune disorders that may be ameliorated using the compounds and methods of this invention include without limitation, autoimmune disorders of the nervous system (e.g., multiple sclerosis, myasthenia gravis, autoimmune neuropathies, such as Guillain-Barré, and autoimmune uveitis); autoimmune disorders of the blood (e.g., autoimmune hemolytic anemia, pernicious anemia and autoimmune thrombocytopenia); autoimmune disorders of the blood vessels (e.g., temporal arteritis, anti-phospholipid syndrome, vasculitides such as Wegener's granulomatosis and Behcet's disease); autoimmune disorders of the skin (e.g., psoriasis, dermatitis herpetiformis, pemphigus vulgaris and vitiligo); autoimmune disorders of the gastrointestinal system (e.g., Crohn's disease, ulcerative colitis, primary biliary cirrhosis and autoimmune hepatitis); autoimmune disorders of the endocrine glands (e.g., Type 1 or immune-mediated diabetes mellitus, Grave's disease. Hashimoto's thyroiditis, autoimmune oophoritis and orchitis, and autoimmune disorder of the adrenal gland); and autoimmune disorders of multiple organs including connective tissue and musculoskeletal system diseases (e.g., rheumatoid arthritis, systemic lupus erythematosus, scleroderma, polymyositis, dermatomyositis, spondyloarthropathies such as ankylosing spondylitis and Sjogren's syndrome). In addition, other immune system mediated diseases, such as graft-versus-host disease and allergic disorders, are also included in the definition of immune disorders herein. Because a number of immune disorders are caused by inflammation, there is some overlap between disorders that are considered immune disorders and inflammatory disorders. For the purpose of this invention, in the case of such an overlapping disorder, it may be considered either an immune disorder or an inflammatory disorder.

As used herein, the term "allergic disorder" means a disease, condition or disorder associated with an allergic response against normally innocuous substances. These substances may be found in the environment, such as indoor air pollutants and aeroallergens, or they may be non-environmental, such as those causing dermatological or food allergies. Allergens can enter the body through a number of routes, including by inhalation, ingestion, contact with the skin or injection (including by insect sting). Many allergic disorders are linked to atopy, a predisposition to generate the allergic antibody IgE. Because IgE is able to sensitize mast cells anywhere in the body, atopic individuals often express disease in more than one organ. For the purpose of this invention, allergic disorders include any hypersensitivity that occurs upon re-exposure to the sensitizing allergen, which in turn causes the release of inflammatory mediators. Allergic disorders include without limitation, allergic rhinitis (e.g., hay fever), sinusitis, rhinosinusitis, chronic or recurrent otitis media, drug reactions, insect sting reactions, latex reactions, conjunctivitis, urticaria, anaphylaxis and anaphylactoid reactions, atopic dermatitis, asthma and food allergies.

As used herein, the term "asthma" means a pulmonary disease, disorder or condition characterized by reversible airway obstruction, airway inflammation, and increased airway responsiveness to a variety of stimuli.

Compounds represented by any of the formulas disclosed herein can be used to treat subjects with inflammatory disorders. As used herein, an "inflammatory disorder" means a disease, disorder or condition characterized by inflammation of body tissue or having an inflammatory component. These include local inflammatory responses and systemic inflammation. Examples of such inflammatory disorders include: transplant rejection, including skin graft rejection; chronic inflammatory disorders of the joints, including arthritis, rheumatoid arthritis, osteoarthritis and bone diseases associated with increased bone resorption; inflammatory bowel diseases such as ileitis, ulcerative colitis, Barrett's syndrome and Crohn's disease; inflammatory lung disorders such as asthma, adult respiratory distress syndrome and chronic obstructive airway disease; inflammatory disorders of the eye including corneal dystrophy, trachoma, onchocerciasis, uveitis, sympathetic ophthalmitis and endophthalmitis; chronic inflammatory disorders of the gums, including gingivitis and periodontitis; tuberculosis; leprosy; inflammatory diseases of the kidney including uremic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune disorders, immune-complex vasculitis, systemic lupus erythematosus (SLE); and inflammatory diseases of the heart such as cardiomyopathy, ischemic heart disease hypercholesterolemia, atherosclerosis; as well as various other diseases with significant inflammatory components, including preeclampsia; chronic liver failure, brain and spinal cord trauma. There may also be a systemic inflammation of the body, exemplified by Gram positive or Gram negative shock, hemorrhagic or anaphylactic shock, or shock induced by cancer chemotherapy in response to pro-inflammatory cytokines, e.g., shock associated with pro-inflammatory cytokines. Such shock can be induced, for example, by a chemotherapeutic agent used in cancer chemotherapy.

As used herein, the term "pharmaceutically acceptable salt" refers to a salt prepared from a compound of Formulae (I)-(VI) or Table 1 having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of Formulae (I)-(V) or Table 1 having a basic functional group, such as an amine functional group, and a pharmaceutically acceptable inorganic or organic acid. Suitable acids include, but are not limited to, hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, isonicotinic acid, oleic acid, tannic acid, pantothenic acid, saccharic acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, pamoic acid and p-toluenesulfonic acid.

As used herein, the term "pharmaceutically acceptable solvate," is a solvate formed from the association of one or more pharmaceutically acceptable solvent molecules to one of the compounds of Formulae (I)-(VI) or Table 1. The term solvate includes hydrates, e.g., hemihydrate, monohydrate, dihydrate, trihydrate, tetrahydrate, and the like.

A pharmaceutically acceptable carrier may contain inert ingredients which do not unduly inhibit the biological activity of the compound(s). The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed, such as those described in REMINGTON, J. P., REMINGTON'S PHARMACEUTICAL SCIENCES (Mack Pub. Co., 17$^{th}$ ed., 1985). Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate, and the like. Methods for encapsulating compositions, such as in a coating of hard gelatin or cyclodextran, are known in the art. See BAKER, ET AL., CONTROLLED RELEASE OF BIOLOGICAL ACTIVE AGENTS, (John Wiley and Sons, 1986).

As used herein, the term "effective amount" refers to an amount of a compound of this invention which is sufficient to reduce or ameliorate the severity, duration, progression, or onset of a disease or disorder, delay onset of a disease or disorder, retard or halt the advancement of a disease or disorder, cause the regression of a disease or disorder, prevent or delay the recurrence, development, onset or progression of a symptom associated with a disease or disorder, or enhance or improve the therapeutic effect(s) of another therapy. In one embodiment of the invention, the disease or disorder is a proliferative disorder. The precise amount of compound administered to a subject will depend on the mode of administration, the type and severity of the disease or condition and on the characteristics of the subject, such as general health, age, sex, body weight and tolerance to drugs. For example, for a proliferative disease or disorder, determination of an effective amount will also depend on the degree, severity and type of cell proliferation. The skilled artisan will be able to determine appropriate dosages depending on these and other factors. When co-administered with other therapeutic agents, e.g., when co-administered with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the invention being used. In cases where no amount is expressly noted, an effective amount should be assumed. Non-limiting examples of an effective amount of a compound of the invention are provided herein below. In a specific embodiment, the invention provides a method of treating, managing, or ameliorating a disease or disorder, e.g. a proliferative disorder, or one or more symptoms thereof, said method comprising administering to a subject in need thereof a dose of at least 150 µg/kg, at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds of the invention once every day, once every 2 days, once every 3 days, once every 4 days, once every 5 days, once every 6 days, once every 7 days, once every 8 days, once every 10 days, once every two weeks, once every three weeks, or once a month.

The dosage of a therapeutic agent other than a compound of the invention, which has been or is currently being used to treat, manage, or ameliorate a disease or disorder, e.g., a proliferative disorder, or one or more symptoms thereof, can be used in the combination therapies of the invention. Preferably, the dosage of each individual therapeutic agent used in said combination therapy is lower than the dose of an individual therapeutic agent when given independently to treat, manage, or ameliorate a disease or disorder, or one or more symptoms thereof. In one embodiment of the invention, the disease or disorder being treated with a combination therapy is a proliferative disorder. In one embodiment, the proliferative disorder is cancer. The recommended dosages of therapeutic agents currently used for the treatment, management, or amelioration of a disease or disorder, or one or more symptoms thereof, can obtained from any reference in the art. See, e.g., GOODMAN & GILMAN'S THE PHARMACOLOGICAL BASIS OF BASIS OF THERAPEUTICS 9$^{TH}$ ED, (Hardman, et al., Eds., NY:Mc-Graw-Hill (1996)); PHYSICIAN'S DESK REFERENCE 57$^{TH}$ ED. (Medical Economics Co., Inc., Montvale, N.J. (2003)).

As used herein, the terms "treat", "treatment" and "treating" refer to the reduction or amelioration of the progression, severity and/or duration of a disease or disorder, delay of the onset of a disease or disorder, or the amelioration of one or more symptoms (preferably, one or more discernible symptoms) of a disease or disorder, resulting from the administration of one or more therapies (e.g., one or more therapeutic agents such as a compound of the invention). The terms "treat", "treatment" and "treating" also encompass the reduction of the risk of developing a disease or disorder, and the delay or inhibition of the recurrence of a disease or disorder. In one embodiment, the disease or disorder being treated is a proliferative disorder such as cancer. In specific embodiments, the terms "treat", "treatment" and "treating" refer to the amelioration of at least one measurable physical parameter of a disease or disorder, such as growth of a tumor, not necessarily discernible by the patient. In other embodiments the terms "treat", "treatment" and "treating" refer to the inhibition of the progression of a disease or disorder, e.g., a proliferative disorder, either physically by the stabilization of a discernible symptom, physiologically by the stabilization of a physical parameter, or both. In another embodiment, the terms "treat", "treatment" and "treating" of a proliferative disease or disorder refers to the reduction or stabilization of tumor size or cancerous cell count, and/or delay of tumor formation. In another embodiment, the terms "treat", "treating" and "treatment" also encompass the administration of a compound of the invention as a prophylactic measure to patients with a predisposition (genetic or environmental) to any disease or disorder described herein.

"Treatment of a viral infection" is meant to include aspects of generating or restoring immunity of the patient's immune system, as well as aspects of suppressing or inhibiting viral replication.

"Treatment of an immune disorder" herein refers to administering a compound represented by any of the formulas disclosed herein to a subject, who has an immune disorder, a symptom of such a disease or a predisposition towards such a disease, with the purpose to cure, relieve, alter, affect, or prevent the autoimmune disorder, the symptom of it, or the predisposition towards it.

"Treatment of an inflammatory disorder" herein refers to administering a compound or a composition of the invention to a subject who has an inflammatory disorder, a symptom of such a disorder or a predisposition towards such a disorder, with the purpose to cure, relieve, alter, affect, or prevent the inflammatory disorder, the symptom of it, or the predisposition towards it.

As used herein, the terms "therapeutic agent" and "therapeutic agents" refer to any agent(s) that can be used in the treatment of a disease or disorder, e.g. a proliferative disorder, or one or more symptoms thereof. In certain embodiments, the term "therapeutic agent" refers to a compound of the invention. In certain other embodiments, the term "therapeutic agent" does not refer to a compound of the invention. Preferably, a therapeutic agent is an agent that is known to be useful for, or has been or is currently being used for the treatment of a disease or disorder, e.g., a proliferative disorder, or one or more symptoms thereof.

As used herein, the term "synergistic" refers to a combination of a compound of the invention and another therapeutic agent, which, when taken together, is more effective than the additive effects of the individual therapies. A synergistic effect of a combination of therapies (e.g., a combination of therapeutic agents) permits the use of lower dosages of one or more of the therapeutic agent(s) and/or less frequent administration of said agent(s) to a subject with a disease or disorder, e.g., a proliferative disorder. The ability to utilize lower the dosage of one or more therapeutic agent and/or to administer said therapeutic agent less frequently reduces the toxicity associated with the administration of said agent to a subject without reducing the efficacy of said therapy in the treatment of a disease or disorder. In addition, a synergistic effect can result in improved efficacy of agents in the prevention, management or treatment of a disease or disorder, e.g. a proliferative disorder. Finally, a synergistic effect of a combination of therapies may avoid or reduce adverse or unwanted side effects associated with the use of either therapeutic agent alone.

As used herein, the phrase "side effects" encompasses unwanted and adverse effects of a therapeutic agent. Side effects are always unwanted, but unwanted effects are not necessarily adverse. An adverse effect from a therapeutic agent might be harmful or uncomfortable or risky to a subject. Side effects include, but are not limited to, fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

As used herein, the term "in combination" refers to the use of more than one therapeutic agent. The use of the term "in combination" does not restrict the order in which said therapeutic agents are administered to a subject with a disease or disorder, e.g., a proliferative disorder. A first therapeutic agent, such as a compound of the invention, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent, such as an anti-cancer agent, to a subject with a disease or disorder, e.g. a proliferative disorder, such as cancer.

As used herein, the terms "therapies" and "therapy" can refer to any protocol(s), method(s), and/or agent(s) that can be used in the prevention, treatment, management, or amelioration of a disease or disorder, e.g., a proliferative disorder, or one or more symptoms thereof.

A used herein, a "protocol" includes dosing schedules and dosing regimens. The protocols herein are methods of use and include therapeutic protocols.

As used herein, a composition that "substantially" comprises a compound means that the composition contains more than about 80% by weight, more preferably more than about 90% by weight, even more preferably more than about 95% by weight, and most preferably more than about 97% by weight of the compound.

As used herein, a reaction that is "substantially complete" means that the reaction contains more than about 80% by weight of the desired product, more preferably more than about 90% by weight of the desired product, even more preferably more than about 95% by weight of the desired product, and most preferably more than about 97% by weight of the desired product.

As used herein, a racemic mixture means about 50% of one enantiomer and about 50% of is corresponding enantiomer relative to a chiral center in the molecule. The invention encompasses all enantiomerically-pure, enantiomerically-enriched, diastereomerically pure, diastereomerically enriched, and racemic mixtures of the compounds of the invention.

Enantiomeric and diastereomeric mixtures can be resolved into their component enantiomers or diastereomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

The compounds of the invention are defined herein by their chemical structures and/or chemical names. Where a compound is referred to by both a chemical structure and a chemical name, and the chemical structure and chemical name conflict, the chemical structure is determinative of the compound's identity.

When administered to a subject (e.g., a non-human animal for veterinary use or for improvement of livestock or to a human for clinical use), the compounds of the invention are administered in an isolated form, or as the isolated form in a pharmaceutical composition. As used herein, "isolated" means that the compounds of the invention are separated from other components of either: (a) a natural source, such as a plant or cell, preferably bacterial culture, or (b) a synthetic organic chemical reaction mixture. Preferably, the compounds of the invention are purified via conventional techniques. As used herein, "purified" means that when isolated, the isolate contains at least 95%, preferably at least 98%, of a compound of the invention by weight of the isolate either as a mixture of stereoisomers, or as a diastereomeric or enantiomeric pure isolate.

As used herein, a composition that is "substantially free" of a compound means that the composition contains less than about 20% by weight, more preferably less than about 10% by weight, even more preferably less than about 5% by weight, and most preferably less than about 3% by weight of the compound.

Only those choices and combinations of substituents that result in a stable structure are contemplated. Such choices and combinations will be apparent to those of ordinary skill in the art and may be determined without undue experimentation.

The invention can be understood more fully by reference to the following detailed description and illustrative examples, which are intended to exemplify non-limiting embodiments of the invention.

B. The Compounds of the Invention

The present invention encompasses compounds having Formulae (I), (II), (III), (IV) and (V), those set forth in Table 1, tautomers, clathrates, solvate, prodrugs and pharmaceutically acceptable salts thereof.

Compounds of Formulae (I)-(V) and Table 1 inhibit the activity of Hsp90 and are particularly useful for treating or preventing proliferative disorders, such as cancer. In addition, compounds of Formulae (I)-(V) and Table 1 are particularly useful in treating cancer when given in combination with another anti-cancer agent.

In one embodiment, the invention provides compounds as set forth below:

TABLE 1

| No. | Structure | Name |
|---|---|---|
| 1 | 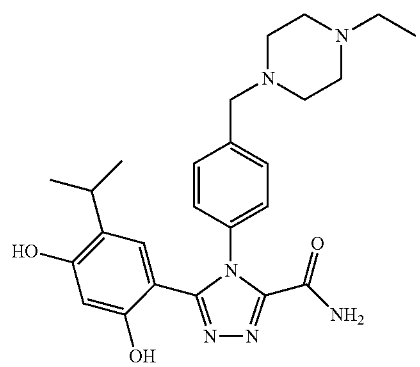 | 5-(2,4-dihydroxy-5-isopropylphenyl)-4-(4-((4-ethylpiperazin-1-yl)methyl)phenyl)-4H-1,2,4-triazole-3-carboxamide |
| 2 | 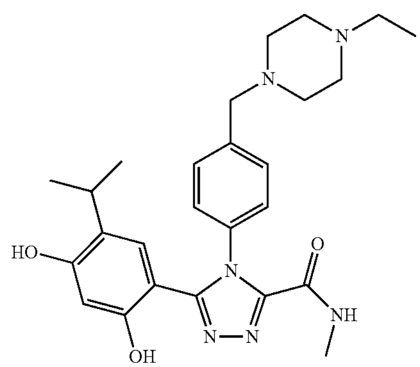 [SMILES: CCN1CCN(Cc2ccc(-n3c(C(=O)NC)nnc3-c3cc(C(C)C)c(O)cc3O)cc2)CC1] | 5-(2,4-dihydroxy-5-isopropylphenyl)-4-(4-((4-ethylpiperazin-1-yl)methyl)phenyl)-N-methyl-4H-1,2,4-triazole-3-carboxamide |
| 3 | 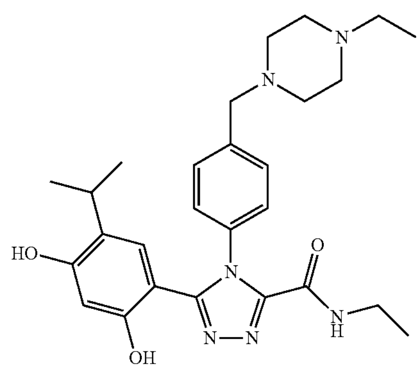 [SMILES: CCNC(=O)c1nnc(-c2cc(C(C)C)c(O)cc2O)n1-c1ccc(CN2CCN(CC)CC2)cc1] | 5-(2,4-dihydroxy-5-isopropylphenyl)-N-ethyl-4-(4-((4-ethylpiperazin-1-yl)methyl)phenyl)-4H-1,2,4-triazole-3-carboxamide |

TABLE 1-continued

| No. | Structure | Name |
|---|---|---|
| 4 | 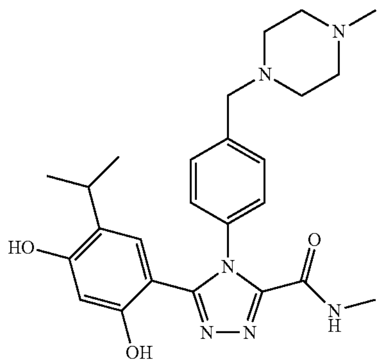 [SMILES: CNC(=O)c1nnc(-c2cc(C(C)C)c(O)cc2O)n1-c1ccc(CN2CCN(C)CC2)cc1] | 5-(2,4-dihydroxy-5-isopropylphenyl)-N-methyl-4-(4-((4-methylpiperazin-1-yl)methyl)phenyl)-4H-1,2,4-triazole-3-carboxamide |
| 5 | 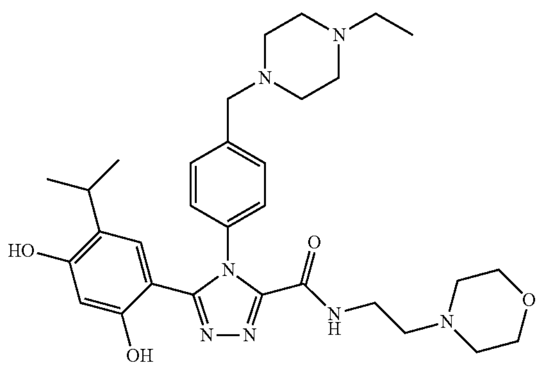 [SMILES: CCN1CCN(Cc2ccc(-n3c(C(=O)NCCN4CCOCC4)nnc3-c3cc(C(C)C)c(O)cc3O)cc2)CC1] | 5-(2,4-dihydroxy-5-isopropylphenyl)-4-(4-((4-ethylpiperazin-1-yl)methyl)phenyl)-N-(2-morpholinoethyl)-4H-1,2,4-triazole-3-carboxamide |
| 6 | 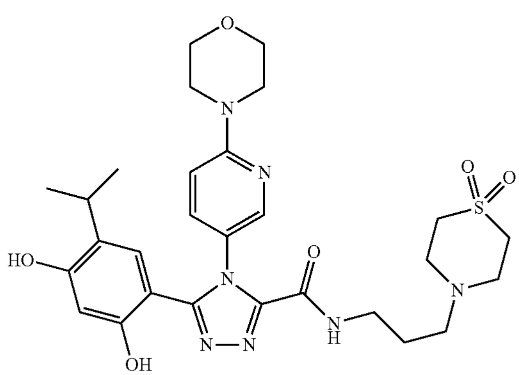 [SMILES: CC(C)c1cc(-c2nnc(C(=O)NCCCN3CCS(=O)(=O)CC3)n2-c2ccc(N3CCOCC3)nc2)c(O)cc1O] | 5-(2,4-dihydroxy-5-isopropylphenyl)-4-(6-morpholinopyridin-3-yl)-N-(3-(4,4-dioxo-thiomorpholinopropyl))-4H-1,2,4-triazole-3-carboxamide |
| 7 | 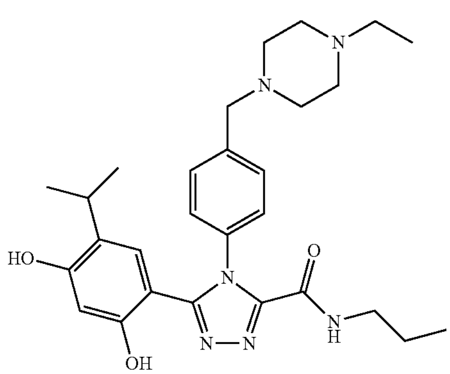 [SMILES: CCCNC(=O)c1nnc(-c2cc(C(C)C)c(O)cc2O)n1-c1ccc(CN2CCN(CC)CC2)cc1] | 5-(2,4-dihydroxy-5-isopropylphenyl)-4-(4-((4-ethylpiperazin-1-yl)methyl)phenyl)-N-propyl-4H-1,2,4-triazole-3-carboxamide |

TABLE 1-continued

| No. | Structure | Name |
|---|---|---|
| 8 | 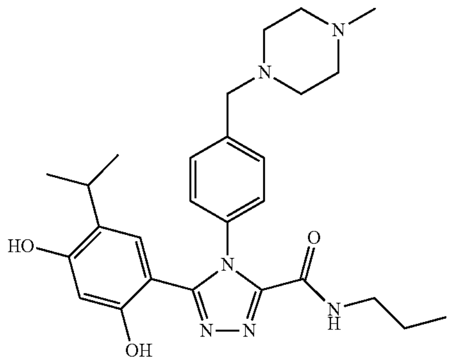 [SMILES: CCCNC(=O)c1nnc(-c2cc(C(C)C)c(O)cc2O)n1-c1ccc(CN2CCN(C)CC2)cc1] | 5-(2,4-dihydroxy-5-isopropylphenyl)-4-(4-((4-methylpiperazin-1-yl)methyl)phenyl)-N-propyl-4H-1,2,4-triazole-3-carboxamide |
| 9 | 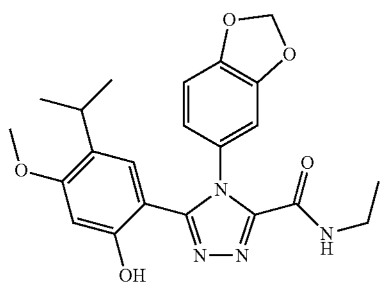 [SMILES: CCNC(=O)c1nnc(-c2cc(C(C)C)c(OC)cc2O)n1-c1ccc2c(c1)OCO2] | 4-(benzo[d][1,3]dioxol-5-yl)-N-ethyl-5-(2-hydroxy-5-isopropyl-4-methoxyphenyl)-4H-1,2,4-triazole-3-carboxamide |
| 10 | 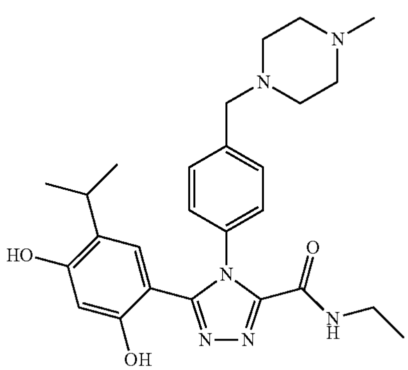 [SMILES: CCNC(=O)c1nnc(-c2cc(C(C)C)c(O)cc2O)n1-c1ccc(CN2CCN(C)CC2)cc1] | 5-(2,4-dihydroxy-5-isopropylphenyl)-N-ethyl-4-(4-((4-methylpiperazin-1-yl)methyl)phenyl)-4H-1,2,4-triazole-3-carboxamide |
| 11 | 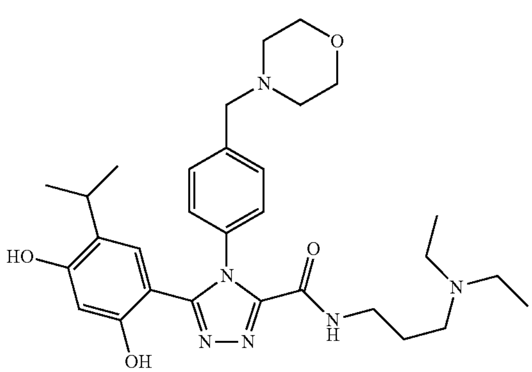 [SMILES: CCN(CC)CCCNC(=O)c1nnc(-c2cc(C(C)C)c(O)cc2O)n1-c1ccc(CN2CCOCC2)cc1] | N-(3-(diethylamino)propyl)-5-(2,4-dihydroxy-5-isopropylphenyl)-4-(4-(morpholinomethyl)phenyl)-4H-1,2,4-triazole-3-carboxamide |

TABLE 1-continued

| No. | Structure | Name |
|---|---|---|
| 12 | 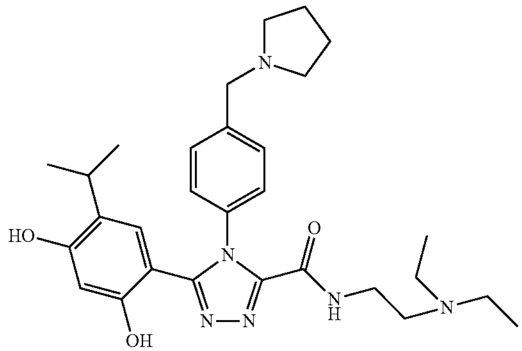 [SMILES: CCN(CC)CCNC(=O)c1nnc(-c2cc(C(C)C)c(O)cc2O)n1-c1ccc(CN2CCCC2)cc1] | N-(2-(diethylamino)ethyl)-5-(2,4-dihydroxy-5-isopropylphenyl)-4-(4-(pyrrolidin-1-ylmethyl)phenyl)-4H-1,2,4-triazole-3-carboxamide |
| 13 | 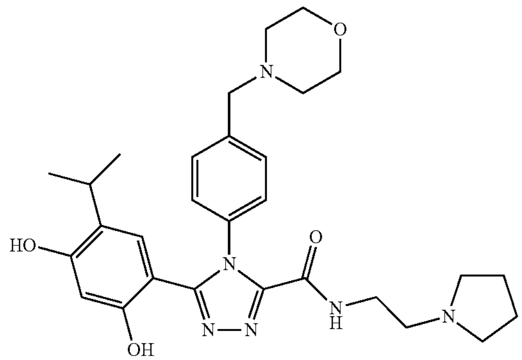 [SMILES: CC(C)c1cc(-c2nnc(C(=O)NCCN3CCCC3)n2-c2ccc(CN3CCOCC3)cc2)c(O)cc1O] | 5-(2,4-dihydroxy-5-isopropylphenyl)-4-(4-(morpholinomethyl)phenyl)-N-(2-(pyrrolidin-1-yl)ethyl)-4H-1,2,4-triazole-3-carboxamide |
| 14 | 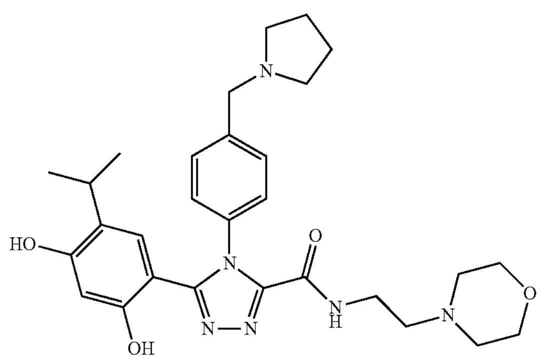 [SMILES: CC(C)c1cc(-c2nnc(C(=O)NCCN3CCOCC3)n2-c2ccc(CN3CCCC3)cc2)c(O)cc1O] | 5-(2,4-dihydroxy-5-isopropylphenyl)-N-(2-morpholinoethyl)-4-(4-(pyrrolidin-1-ylmethyl)phenyl)-4H-1,2,4-triazole-3-carboxamide |
| 15 | 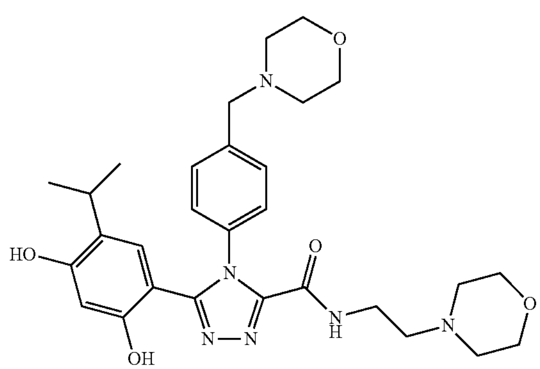 [SMILES: CC(C)c1cc(-c2nnc(C(=O)NCCN3CCOCC3)n2-c2ccc(CN3CCOCC3)cc2)c(O)cc1O] | 5-(2,4-dihydroxy-5-isopropylphenyl)-N-(2-morpholinoethyl)-4-(4-(morpholinomethyl)phenyl)-4H-1,2,4-triazole-3-carboxamide |

TABLE 1-continued

| No. | Structure | Name |
|---|---|---|
| 16 | 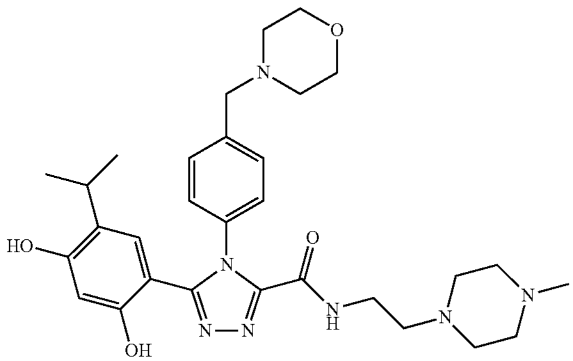 [SMILES: CC(C)c1cc(-c2nnc(C(=O)NCCN3CCN(C)CC3)n2-c2ccc(CN3CCOCC3)cc2)c(O)cc1O] | 5-(2,4-dihydroxy-5-isopropylphenyl)-N-(2-(4-methylpiperazin-1-yl)ethyl)-4-(4-(morpholinomethyl)phenyl)-4H-1,2,4-triazole-3-carboxamide |
| 17 | 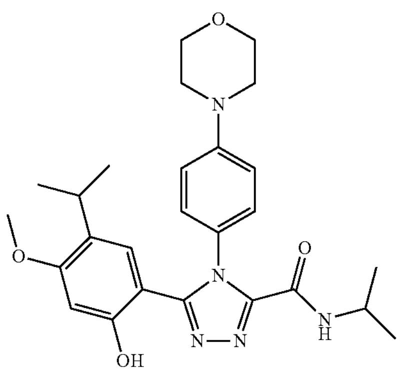 [SMILES: COc1cc(O)c(-c2nnc(C(=O)NC(C)C)n2-c2ccc(N3CCOCC3)cc2)cc1C(C)C] | 5-(2-hydroxy-5-isopropyl-4-methoxyphenyl)-N-isopropyl-4-(4-morpholinophenyl)-4H-1,2,4-triazole-3-carboxamide |
| 18 | 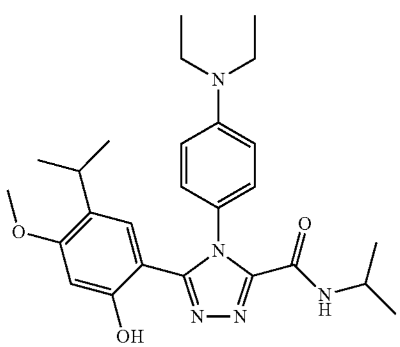 [SMILES: CCN(CC)c1ccc(-n2c(C(=O)NC(C)C)nnc2-c2cc(C(C)C)c(OC)cc2O)cc1] | 4-(4-(diethylamino)phenyl)-5-(2-hydroxy-5-isopropyl-4-methoxyphenyl)-N-isopropyl-4H-1,2,4-triazole-3-carboxamide |
| 19 | 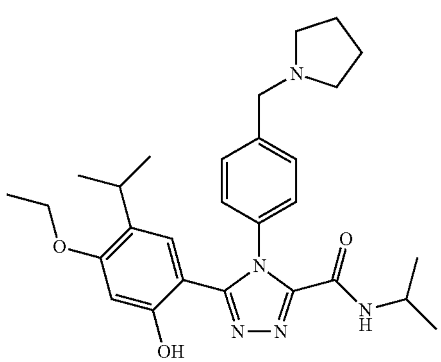 [SMILES: CCOc1cc(O)c(-c2nnc(C(=O)NC(C)C)n2-c2ccc(CN3CCCC3)cc2)cc1C(C)C] | 5-(4-ethoxy-2-hydroxy-5-isopropylphenyl)-N-isopropyl-4-(4-(pyrrolidin-1-ylmethyl)phenyl)-4H-1,2,4-triazole-3-carboxamide |

TABLE 1-continued

| No. | Structure | Name |
|---|---|---|
| 20 | 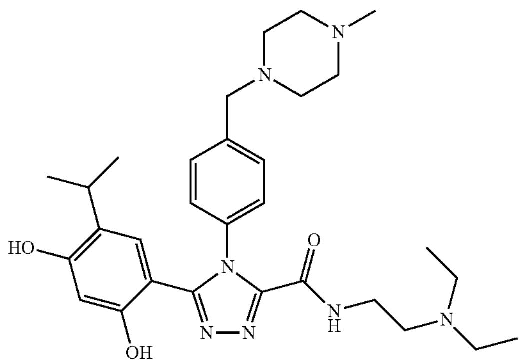 [SMILES: CCN(CC)CCNC(=O)c1nnc(-c2cc(C(C)C)c(O)cc2O)n1-c1ccc(CN2CCN(C)CC2)cc1] | N-(2-(diethylamino)ethyl)-5-(2,4-dihydroxy-5-isopropylphenyl)-4-(4-((4-methylpiperazin-1-yl)methyl)phenyl)-4H-1,2,4-triazole-3-carboxamide |
| 21 | 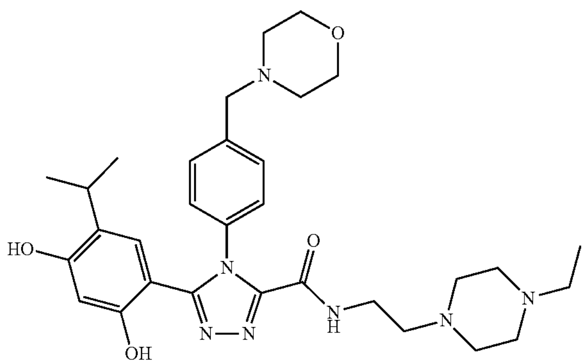 [SMILES: CCN1CCN(CCNC(=O)c2nnc(-c3cc(C(C)C)c(O)cc3O)n2-c2ccc(CN3CCOCC3)cc2)CC1] | 5-(2,4-dihydroxy-5-isopropylphenyl)-N-(2-(4-ethylpiperazin-1-yl)ethyl)-4-(4-(morpholinomethyl)phenyl)-4H-1,2,4-triazole-3-carboxamide |
| 22 | 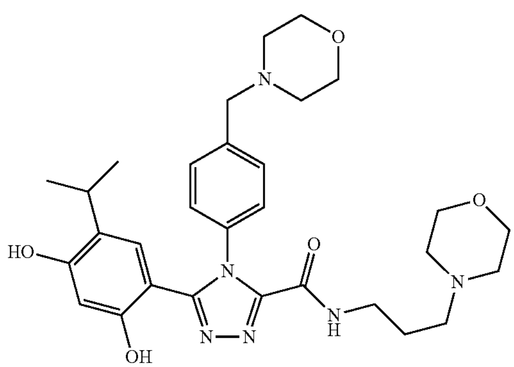 [SMILES: CC(C)c1cc(-c2nnc(C(=O)NCCCN3CCOCC3)n2-c2ccc(CN3CCOCC3)cc2)c(O)cc1O] | 5-(2,4-dihydroxy-5-isopropylphenyl)-4-(4-(morpholinomethyl)phenyl)-N-(3-morpholinopropyl)-4H-1,2,4-triazole-3-carboxamide |
| 23 | 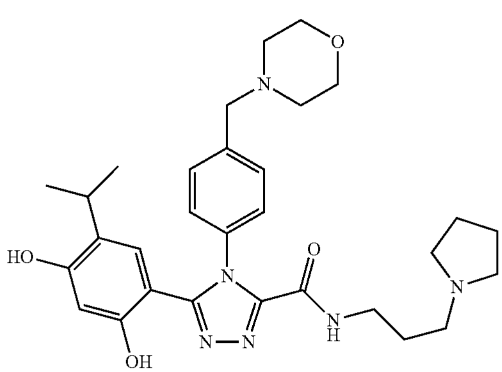 [SMILES: CC(C)c1cc(-c2nnc(C(=O)NCCCN3CCCC3)n2-c2ccc(CN3CCOCC3)cc2)c(O)cc1O] | 5-(2,4-dihydroxy-5-isopropylphenyl)-4-(4-(morpholinomethyl)phenyl)-N-(3-(pyrrolidin-1-yl)propyl)-4H-1,2,4-triazole-3-carboxamide |

TABLE 1-continued

| No. | Structure | Name |
|---|---|---|
| 24 | 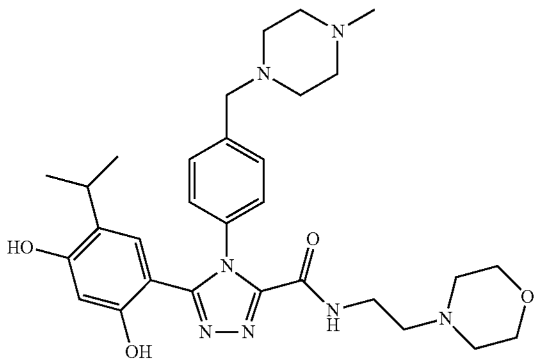 [SMILES: CC(C)c1cc(-c2nnc(C(=O)NCCN3CCOCC3)n2-c2ccc(CN3CCN(C)CC3)cc2)c(O)cc1O] | 5-(2,4-dihydroxy-5-isopropylphenyl)-4-(4-((4-methylpiperazin-1-yl)methyl)phenyl)-N-(2-morpholinoethyl)-4H-1,2,4-triazole-3-carboxamide |
| 25 | 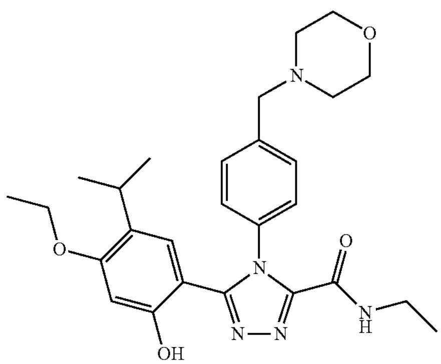 [SMILES: CCNC(=O)c1nnc(-c2cc(C(C)C)c(OCC)cc2O)n1-c1ccc(CN2CCOCC2)cc1] | 5-(4-ethoxy-2-hydroxy-5-isopropylphenyl)-N-ethyl-4-(4-(morpholinomethyl)-phenyl)-4H-1,2,4-triazole-3-carboxamide |
| 26 | 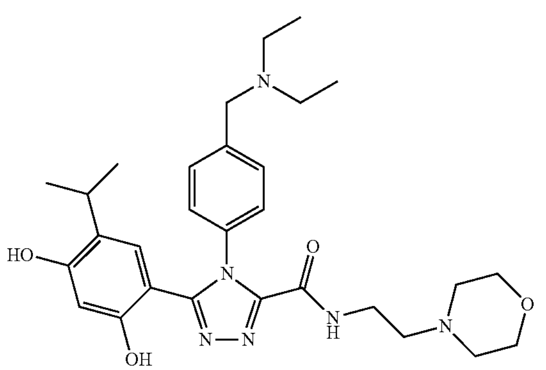 [SMILES: CCN(CC)Cc1ccc(-n2c(C(=O)NCCN3CCOCC3)nnc2-c2cc(C(C)C)c(O)cc2O)cc1] | 4-(4-((diethylamino)methyl)-phenyl)-5-(2,4-dihydroxy-5-isopropylphenyl)-N-(2-morpholinoethyl)-4H-1,2,4-triazole-3-carboxamide |
| 27 | 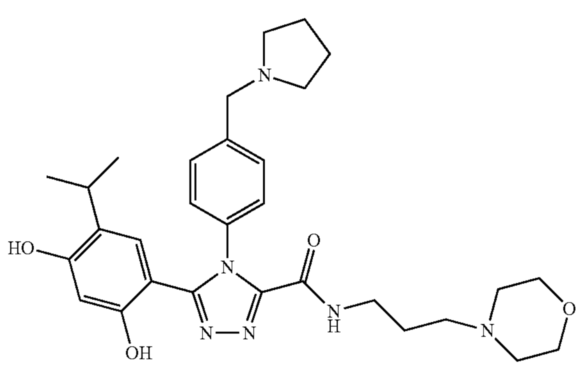 [SMILES: CC(C)c1cc(-c2nnc(C(=O)NCCCN3CCOCC3)n2-c2ccc(CN3CCCC3)cc2)c(O)cc1O] | 5-(2,4-dihydroxy-5-isopropylphenyl)-N-(3-morpholinopropyl)-4-(4-(pyrrolidin-1-ylmethyl)phenyl)-4H-1,2,4-triazole-3-carboxamide |

TABLE 1-continued

| No. | Structure | Name |
|---|---|---|
| 28 | 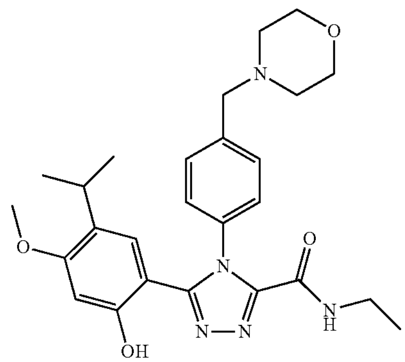 [SMILES: CCNC(=O)c1nnc(-c2cc(C(C)C)c(OC)cc2O)n1-c1ccc(CN2CCOCC2)cc1] | N-ethyl-5-(2-hydroxy-5-isopropyl-4-methoxyphenyl)-4-(4-(morpholinomethyl)phenyl)-4H-1,2,4-triazole-3-carboxamide |
| 29 | 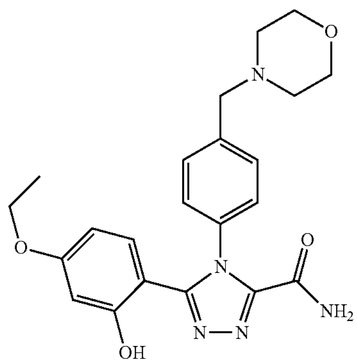 [SMILES: CCOc1ccc(-c2nnc(C(N)=O)n2-c2ccc(CN3CCOCC3)cc2)c(O)c1] | 5-(4-ethoxy-2-hydroxyphenyl)-4-(4-morpholinomethyl)phenyl)-4H-1,2,4-triazole-3-carboxamide |
| 30 | 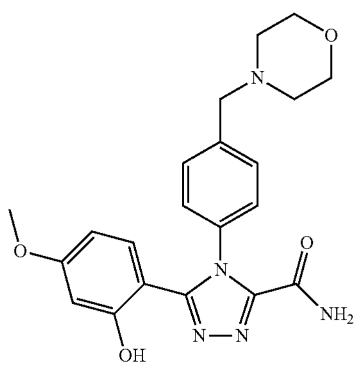 [SMILES: COc1ccc(-c2nnc(C(N)=O)n2-c2ccc(CN3CCOCC3)cc2)c(O)c1] | 5-(2-hydroxy-4-methoxyphenyl)-4-(4-(morpholinomethyl)phenyl)-4H-1,2,4-triazole-3-carboxamide |
| 31 | 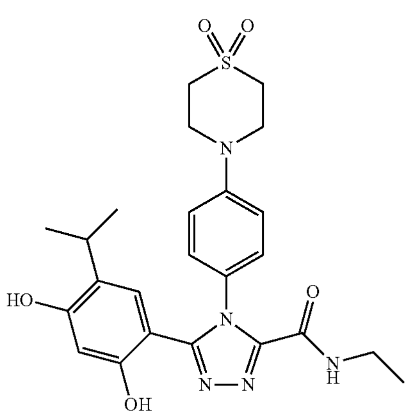 [SMILES: CCNC(=O)c1nnc(-c2cc(C(C)C)c(O)cc2O)n1-c1ccc(N2CCS(=O)(=O)CC2)cc1] | 5-(2,4-dihydroxy-5-isopropylphenyl)-N-ethyl-4-(4-(4,4-dioxo-thiomorpholinophenyl))-4H-1,2,4-triazole-3-carboxamide |

TABLE 1-continued

| No. | Structure | Name |
|---|---|---|
| 32 | 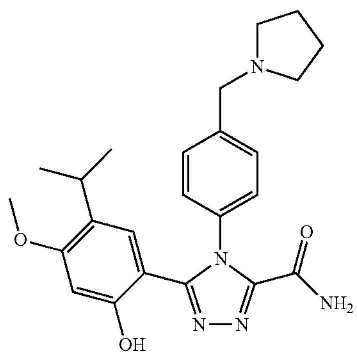 [SMILES: COc1cc(O)c(-c2nnc(C(N)=O)n2-c2ccc(CN3CCCC3)cc2)cc1C(C)C] | 5-(2-hydroxy-5-isopropyl-4-methoxyphenyl)-4-(4-(pyrrolidin-1-ylmethyl)phenyl)-4H-1,2,4-triazole-3-carboxamide |
| 33 | 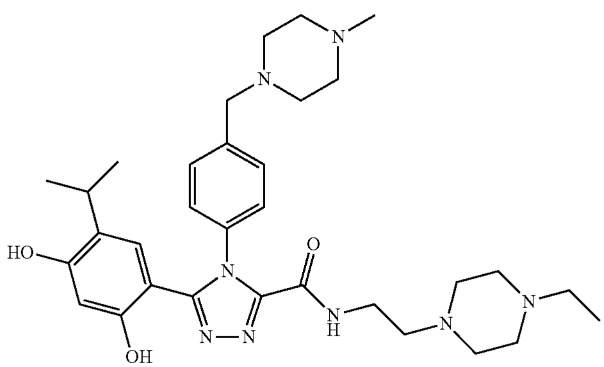 [SMILES: CCN1CCN(CCNC(=O)c2nnc(-c3cc(C(C)C)c(O)cc3O)n2-c2ccc(CN3CCN(C)CC3)cc2)CC1] | 5-(2,4-dihydroxy-5-isopropylphenyl)-N-(2-(4-ethylpiperazin-1-yl)ethyl)-4-(4-((4-methylpiperazin-1-yl)methyl)phenyl)-4H-1,2,4-triazole-3-carboxamide |
| 34 | 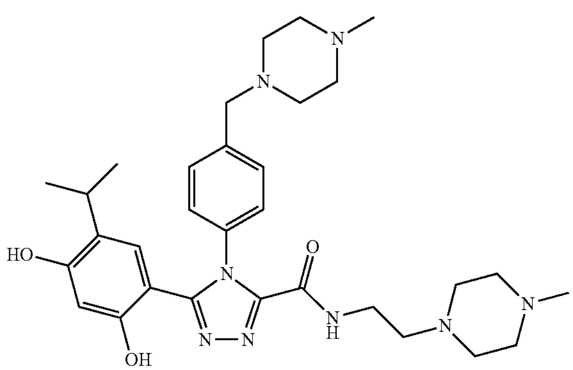 [SMILES: CC(C)c1cc(-c2nnc(C(=O)NCCN3CCN(C)CC3)n2-c2ccc(CN3CCN(C)CC3)cc2)c(O)cc1O] | 5-(2,4-dihydroxy-5-isopropylphenyl)-N-(2-(4-methylpiperazin-1-yl)ethyl)-4-(4-((4-methylpiperazin-1-yl)methyl)phenyl)-4H-1,2,4-triazole-3-carboxamide |
| 35 | 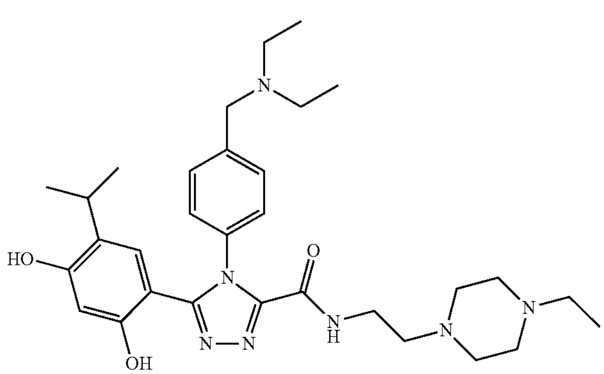 [SMILES: CCN1CCN(CCNC(=O)c2nnc(-c3cc(C(C)C)c(O)cc3O)n2-c2ccc(CN(CC)CC)cc2)CC1] | 4-(4-((diethylamino)methyl)phenyl)-5-(2,4-dihydroxy-5-isopropylphenyl)-N-(2-(4-ethylpiperazin-1-yl)ethyl)-4H-1,2,4-triazole-3-carboxamide |

TABLE 1-continued

| No. | Structure | Name |
|---|---|---|
| 36 | 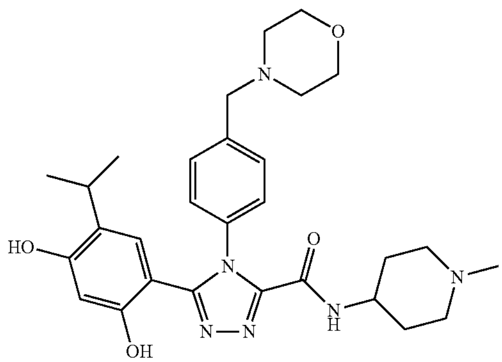 [SMILES: CC(C)c1cc(-c2nnc(C(=O)NC3CCN(C)CC3)n2-c2ccc(CN3CCOCC3)cc2)c(O)cc1O] | 5-(2,4-dihydroxy-5-isopropylphenyl)-N-(1-methylpiperidin-4-yl)-4-(4-(morpholinomethyl)phenyl)-4H-1,2,4-triazole-3-carboxamide |
| 37 | 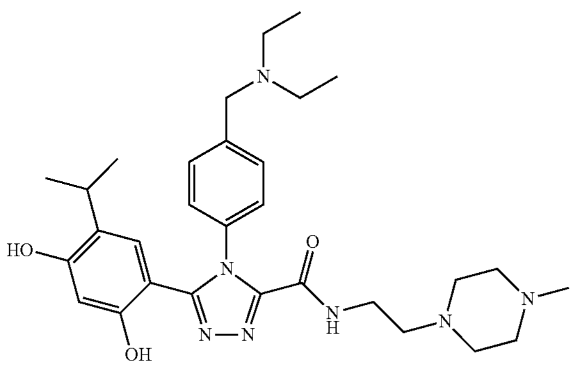 [SMILES: CCN(CC)Cc1ccc(-n2c(C(=O)NCCN3CCN(C)CC3)nnc2-c2cc(C(C)C)c(O)cc2O)cc1] | 4-(4-((diethylamino)methyl)phenyl)-5-(2,4-dihydroxy-5-isopropylphenyl)-N-(2-(4-methylpiperazin-1-yl)ethyl)-4H-1,2,4-triazole-3-carboxamide |
| 38 | 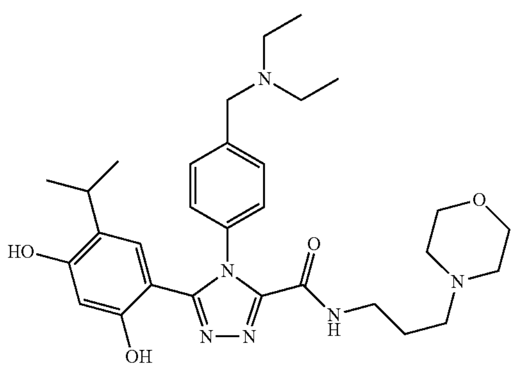 [SMILES: CCN(CC)Cc1ccc(-n2c(C(=O)NCCCN3CCOCC3)nnc2-c2cc(C(C)C)c(O)cc2O)cc1] | 4-(4-((diethylamino)methyl)phenyl)-5-(2,4-dihydroxy-5-isopropylphenyl)-N-(3-morpholinopropyl)-4H-1,2,4-triazole-3-carboxamide |
| 39 | 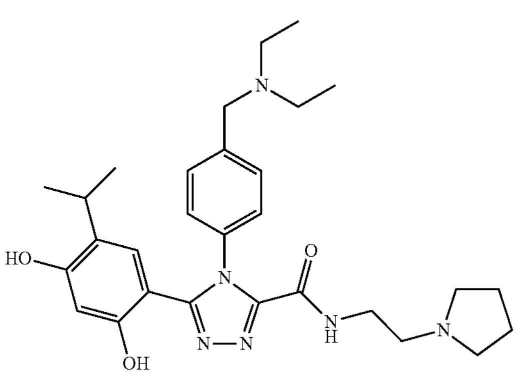 [SMILES: CCN(CC)Cc1ccc(-n2c(C(=O)NCCN3CCCC3)nnc2-c2cc(C(C)C)c(O)cc2O)cc1] | 4-(4-((diethylamino)methyl)phenyl)-5-(2,4-dihydroxy-5-isopropylphenyl)-N-(2-(pyrrolidin-1-yl)ethyl)-4H-1,2,4-triazole-3-carboxamide |

TABLE 1-continued

| No. | Structure | Name |
|---|---|---|
| 40 | 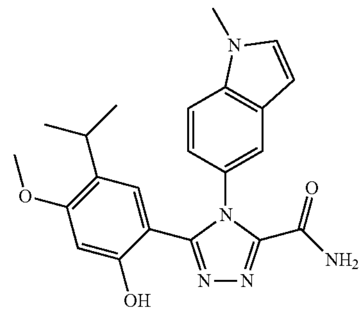 [SMILES: COc1cc(O)c(-c2nnc(C(N)=O)n2-c2ccc3c(ccn3C)c2)cc1C(C)C] | 5-(2-hydroxy-5-isopropyl-4-methoxyphenyl)-4-(1-methyl-1H-indol-5-yl)-4H-1,2,4-triazole-3-carboxamide |
| 41 | 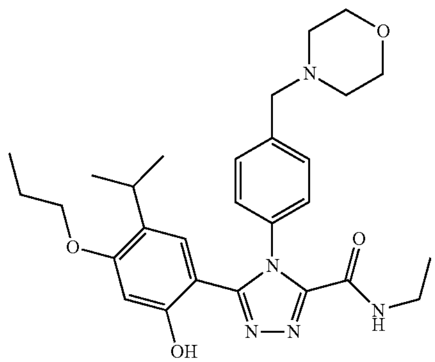 [SMILES: CCCOc1cc(O)c(-c2nnc(C(=O)NCC)n2-c2ccc(CN3CCOCC3)cc2)cc1C(C)C] | N-ethyl-5-(2-hydroxy-5-isopropyl-4-propoxyphenyl)-4-(4-(morpholinomethyl)-phenyl)-4H-1,2,4-triazole-3-carboxamide |
| 42 | 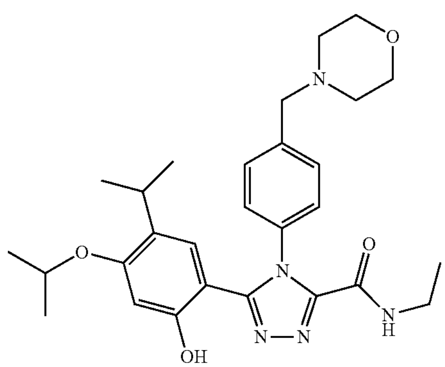 [SMILES: CCNC(=O)c1nnc(-c2cc(C(C)C)c(OC(C)C)cc2O)n1-c1ccc(CN2CCOCC2)cc1] | N-ethyl-5-(2-hydroxy-4-isopropoxy-5-isopropylphenyl)-4-(4-(morpholinomethyl)phenyl)-4H-1,2,4-triazole-3-carboxamide |
| 43 | 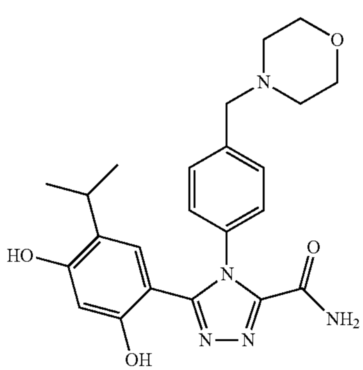 [SMILES: CC(C)c1cc(-c2nnc(C(N)=O)n2-c2ccc(CN3CCOCC3)cc2)c(O)cc1O] | 5-(2,4-dihydroxy-5-isopropylphenyl)-4-(4-(morpholinomethyl)phenyl)-4H-1,2,4-triazole-3-carboxamide |

TABLE 1-continued

| No. | Structure | Name |
|---|---|---|
| 44 | 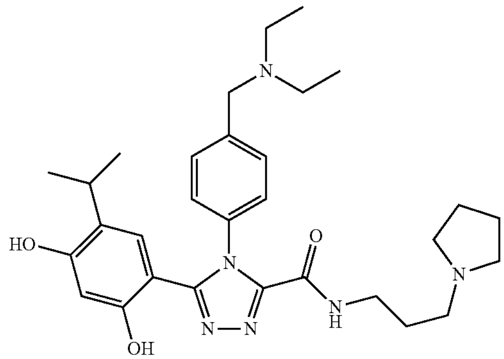 [SMILES: CCN(CC)Cc1ccc(-n2c(C(=O)NCCCN3CCCC3)nnc2-c2cc(C(C)C)c(O)cc2O)cc1] | 4-(4-((diethylamino)methyl)-phenyl)-5-(2,4-dihydroxy-5-isopropylphenyl)-N-(3-(pyrrolidin-1-yl)propyl)-4H-1,2,4-triazole-3-carboxamide |
| 45 | 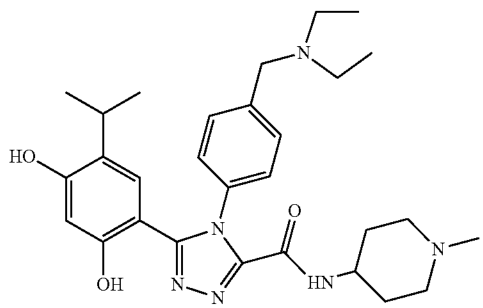 [SMILES: CCN(CC)Cc1ccc(-n2c(C(=O)NC3CCN(C)CC3)nnc2-c2cc(C(C)C)c(O)cc2O)cc1] | 4-(4-((diethylamino)methyl)-phenyl)-5-(2,4-dihydroxy-5-isopropylphenyl)-N-(1-methylpiperidin-4-yl)-4H-1,2,4-triazole-3-carboxamide |
| 46 | 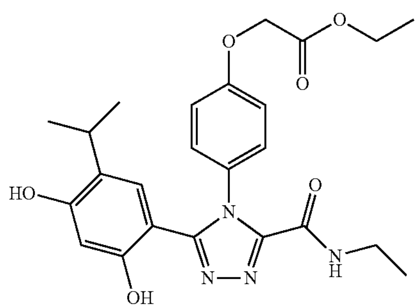 [SMILES: CCNC(=O)c1nnc(-c2cc(C(C)C)c(O)cc2O)n1-c1ccc(OCC(=O)OCC)cc1] | ethyl 2-(4-(3-(2,4-dihydroxy-5-isopropylphenyl)-5-(ethylcarbamoyl)-4H-1,2,4-triazol-4-yl)phenoxy)acetate |
| 47 | 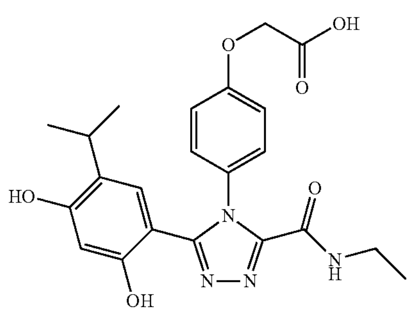 [SMILES: CCNC(=O)c1nnc(-c2cc(C(C)C)c(O)cc2O)n1-c1ccc(OCC(=O)O)cc1] | 2-(4-(3-(2,4-dihydroxy-5-isopropylphenyl)-5-(ethylcarbamoyl)-4H-1,2,4-triazol-4-yl)phenoxy)acetic acid |
| 48 | 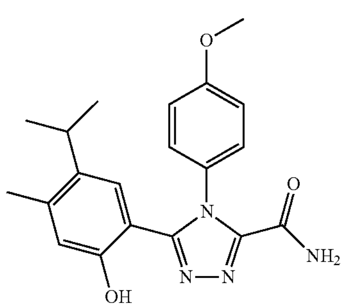 [SMILES: COc1ccc(-n2c(C(N)=O)nnc2-c2cc(C(C)C)c(C)cc2O)cc1] | 5-(2-hydroxy-5-isopropyl-4-methylphenyl)-4-(4-methoxyphenyl)-4H-1,2,4-triazole-3-carboxamide |

TABLE 1-continued

| No. | Structure | Name |
|---|---|---|
| 49 | 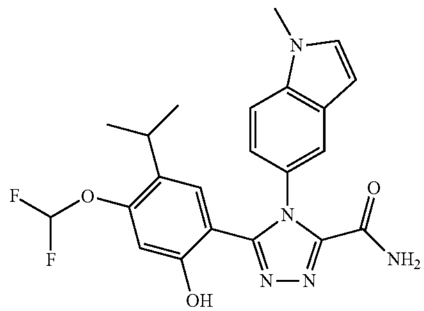 [SMILES: CC(C)c1cc(-c2nnc(C(N)=O)n2-c2ccc3c(ccn3C)c2)c(O)cc1OC(F)F] | 5-(4-(difluoromethoxy)-2-hydroxy-5-isopropylphenyl)-4-(1-methyl-1H-indol-5-yl)-4H-1,2,4-triazole-3-carboxamide |
| 50 | 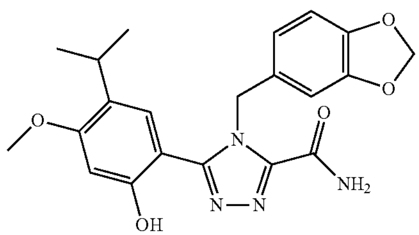 [SMILES: COc1cc(O)c(-c2nnc(C(N)=O)n2Cc2ccc3c(c2)OCO3)cc1C(C)C] | 4-(benzo[d][1,3]dioxol-5-ylmethyl)-5-(2-hydroxy-5-isopropyl-4-methoxyphenyl)-4H-1,2,4-triazole-3-carboxamide |
| 51 | 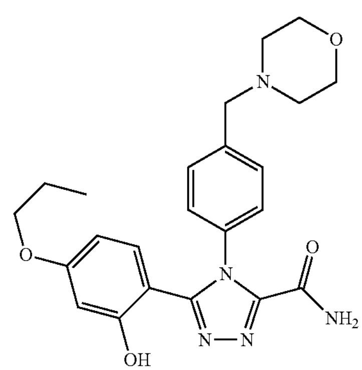 [SMILES: CCCOc1ccc(-c2nnc(C(N)=O)n2-c2ccc(CN3CCOCC3)cc2)c(O)c1] | 5-(2-hydroxy-4-propoxyphenyl)-4-(4-(morpholinomethyl)phenyl)-4H-1,2,4-triazole-3-carboxamide |
| 52 | 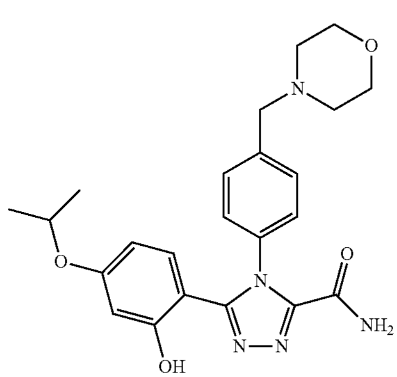 [SMILES: CC(C)Oc1ccc(-c2nnc(C(N)=O)n2-c2ccc(CN3CCOCC3)cc2)c(O)c1] | 5-(2-hydroxy-4-isopropoxyphenyl)-4-(4-(morpholinomethyl)phenyl)-4H-1,2,4-triazole-3-carboxamide |

TABLE 1-continued

| No. | Structure | Name |
|---|---|---|
| 53 | 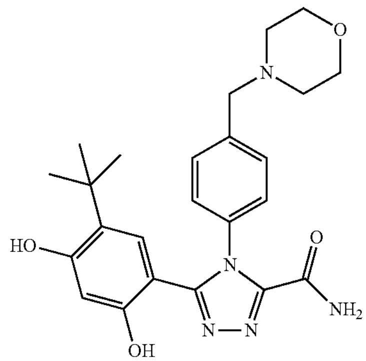 [SMILES: CC(C)(C)c1cc(-c2nnc(C(N)=O)n2-c2ccc(CN3CCOCC3)cc2)c(O)cc1O] | 5-(5-tert-butyl-2,4-dihydroxyphenyl)-4-(4-(morpholinomethyl)phenyl)-4H-1,2,4-triazole-3-carboxamide |
| 54 | 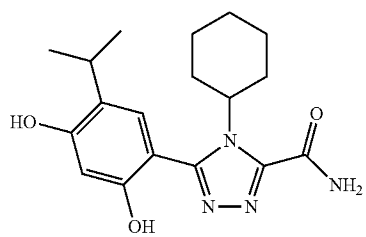 [SMILES: CC(C)c1cc(-c2nnc(C(N)=O)n2C2CCCCC2)c(O)cc1O] | 4-cyclohexyl-5-(2,4-dihydroxy-5-isopropylphenyl)-4H-1,2,4-triazole-3-carboxamide |
| 55 | 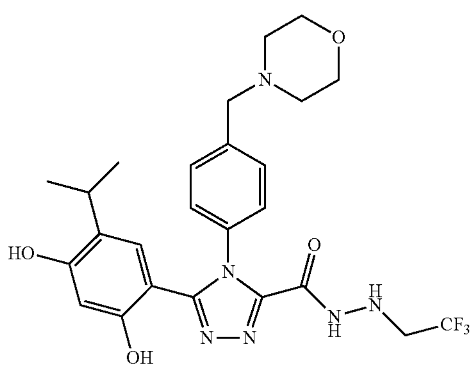 [SMILES: CC(C)c1cc(-c2nnc(C(=O)NNCC(F)(F)F)n2-c2ccc(CN3CCOCC3)cc2)c(O)cc1O] | 5-(2,4-dihydroxy-5-isopropylphenyl)-4-(4-(morpholinomethyl)phenyl)-N'-(2,2,2-trifluoroethyl)-4H-1,2,4-triazole-3-carbohydrazide |
| 56 | 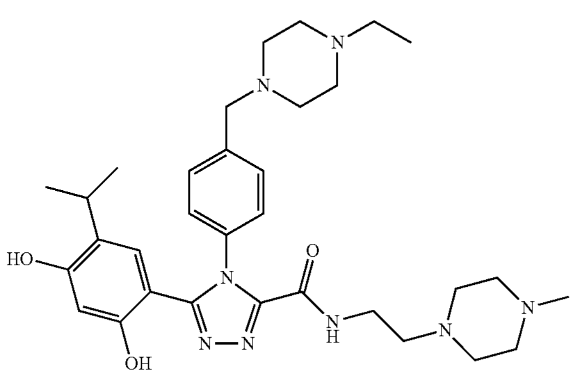 [SMILES: CCN1CCN(Cc2ccc(-n3c(C(=O)NCCN4CCN(C)CC4)nnc3-c3cc(C(C)C)c(O)cc3O)cc2)CC1] | 5-(2,4-dihydroxy-5-isopropylphenyl)-4-(4-((4-ethylpiperazin-1-yl)methyl)phenyl)-N-(2-(4-methylpiperazin-1-yl)ethyl)-4H-1,2,4-triazole-3-carboxamide |

TABLE 1-continued

| No. | Structure | Name |
|---|---|---|
| 57 | 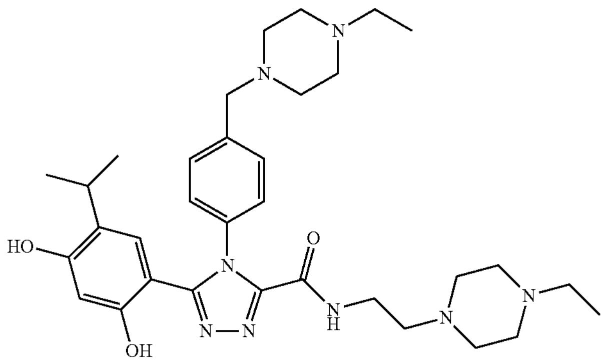 [SMILES: CCN1CCN(CCNC(=O)c2nnc(-c3cc(C(C)C)c(O)cc3O)n2-c2ccc(CN3CCN(CC)CC3)cc2)CC1] | 5-(2,4-dihydroxy-5-isopropylphenyl)-N-(2-(4-ethylpiperazin-1-yl)ethyl)-4-(4-((4-ethylpiperazin-1-yl)methyl)phenyl)-4H-1,2,4-triazole-3-carboxamide |
| 58 | 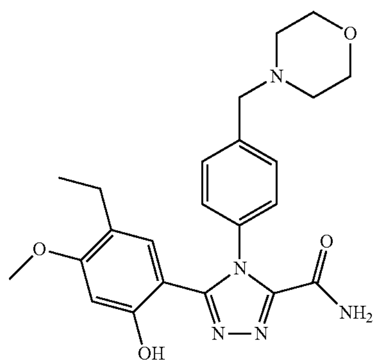 [SMILES: CCc1cc(-c2nnc(C(N)=O)n2-c2ccc(CN3CCOCC3)cc2)c(O)cc1OC] | 5-(5-ethyl-2-hydroxy-4-methoxyphenyl)-4-(4-(morpholinomethyl)phenyl)-4H-1,2,4-triazole-3-carboxamide |
| 59 | 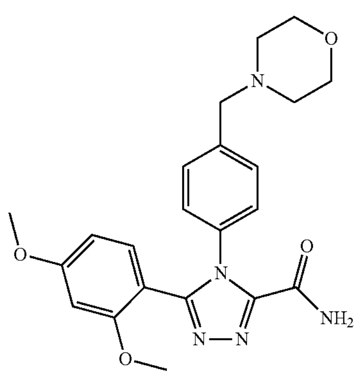 [SMILES: COc1ccc(-c2nnc(C(N)=O)n2-c2ccc(CN3CCOCC3)cc2)c(OC)c1] | 5-(2,4-dimethoxyphenyl)-4-(4-(morpholinomethyl)-phenyl)-4H-1,2,4-triazole-3-carboxamide |
| 60 | 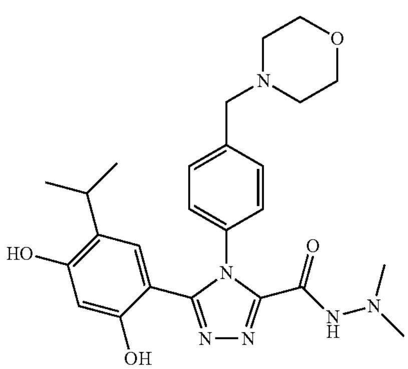 [SMILES: CC(C)c1cc(-c2nnc(C(=O)NN(C)C)n2-c2ccc(CN3CCOCC3)cc2)c(O)cc1O] | 5-(2,4-dihydroxy-5-isopropylphenyl)-N',N'-dimethyl-4-(4-(morpholinomethyl)phenyl)-4H-1,2,4-triazole-3-carbohydrazide |

| No. | Structure | Name |
|---|---|---|
| 61 | 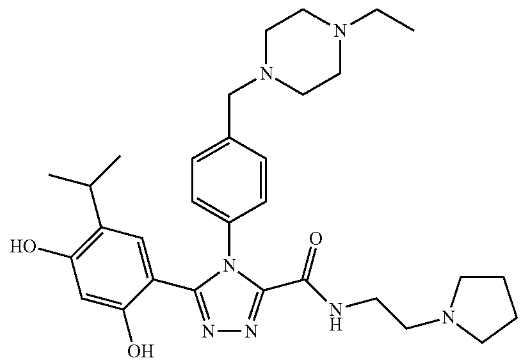 [SMILES: CCN1CCN(Cc2ccc(-n3c(C(=O)NCCN4CCCC4)nnc3-c3cc(C(C)C)c(O)cc3O)cc2)CC1] | 5-(2,4-dihydroxy-5-isopropylphenyl)-4-(4-((4-ethylpiperazin-1-yl)methyl)phenyl)-N-(2-(pyrrolidin-1-yl)ethyl)-4H-1,2,4-triazole-3-carboxamide |
| 62 | 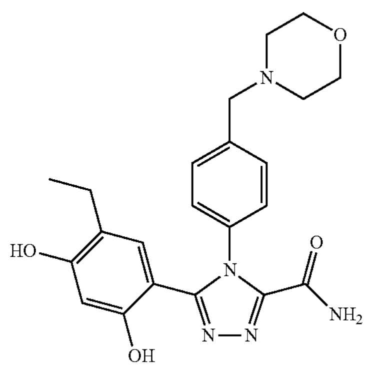 [SMILES: CCc1cc(-c2nnc(C(N)=O)n2-c2ccc(CN3CCOCC3)cc2)c(O)cc1O] | 5-(5-ethyl-2,4-dihydroxyphenyl)-4-(4-(morpholinomethyl)phenyl)-4H-1,2,4-triazole-3-carboxamide |
| 63 | 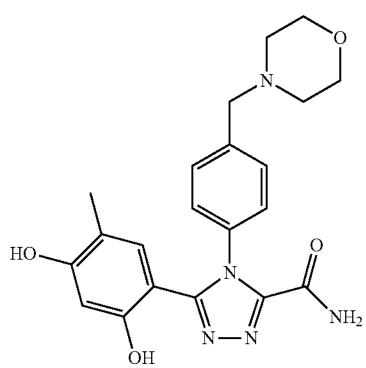 [SMILES: Cc1cc(-c2nnc(C(N)=O)n2-c2ccc(CN3CCOCC3)cc2)c(O)cc1O] | 5-(2,4-dihydroxy-5-methylphenyl)-4-(4-(morpholinomethyl)phenyl)-4H-1,2,4-triazole-3-carboxamide |
| 64 | 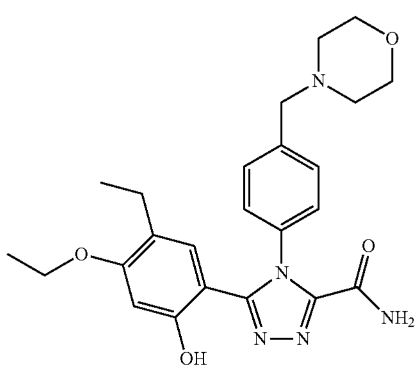 [SMILES: CCOc1cc(O)c(-c2nnc(C(N)=O)n2-c2ccc(CN3CCOCC3)cc2)cc1CC] | 5-(4-ethoxy-5-ethyl-2-hydroxyphenyl)-4-(4-(morpholinomethyl)phenyl)-4H-1,2,4-triazole-3-carboxamide |

TABLE 1-continued

| No. | Structure | Name |
|---|---|---|
| 65 | 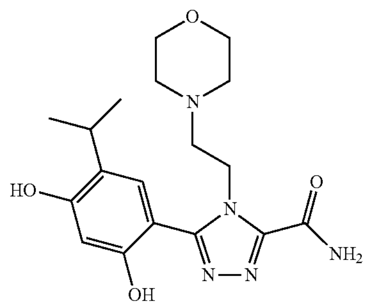 [SMILES: CC(C)c1cc(-c2nnc(C(N)=O)n2CCN2CCOCC2)c(O)cc1O] | 5-(2,4-dihydroxy-5-isopropylphenyl)-4-(2-morpholinoethyl)-4H-1,2,4-triazole-3-carboxamide |
| 66 | 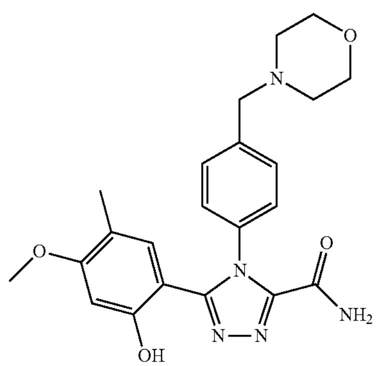 [SMILES: COc1cc(O)c(-c2nnc(C(N)=O)n2-c2ccc(CN3CCOCC3)cc2)cc1C] | 5-(2-hydroxy-4-methoxy-5-methylphenyl)-4-(4-(morpholinomethyl)phenyl)-4H-1,2,4-triazole-3-carboxamide |
| 67 | 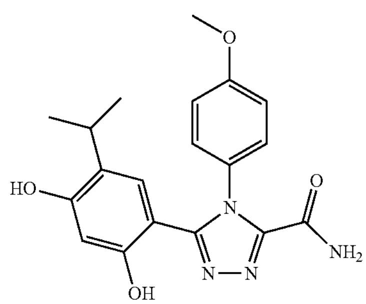 [SMILES: COc1ccc(-n2c(C(N)=O)nnc2-c2cc(C(C)C)c(O)cc2O)cc1] | 5-(2,4-dihydroxy-5-isopropylphenyl)-4-(4-methoxyphenyl)-4H-1,2,4-triazole-3-carboxamide |
| 68 | 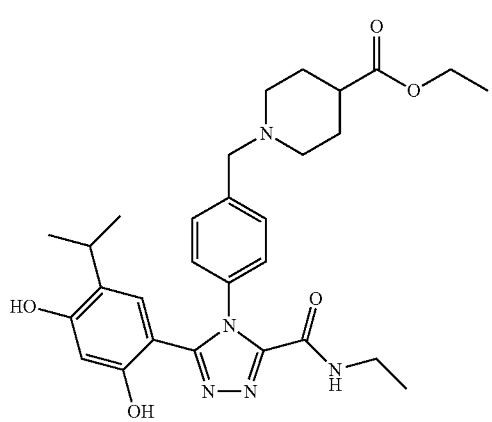 [SMILES: CCNC(=O)c1nnc(-c2cc(C(C)C)c(O)cc2O)n1-c1ccc(CN2CCC(C(=O)OCC)CC2)cc1] | ethyl 1-(4-(3-(2,4-dihydroxy-5-isopropylphenyl)-5-(ethylcarbamoyl)-4H-1,2,4-triazol-4-yl)benzyl)piperidine-4-carboxylate |

TABLE 1-continued

| No. | Structure | Name |
|---|---|---|
| 69 | 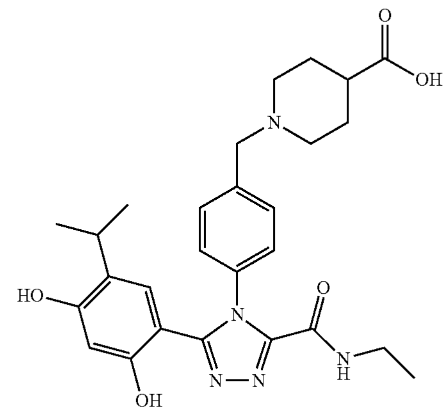 [SMILES: CCNC(=O)c1nnc(-c2cc(C(C)C)c(O)cc2O)n1-c1ccc(CN2CCC(C(=O)O)CC2)cc1] | 1-(4-(3-(2,4-dihydroxy-5-isopropylphenyl)-5-(ethylcarbamoyl)-4H-1,2,4-triazol-4-yl)benzyl)piperidine-4-carboxylic acid |
| 70 | 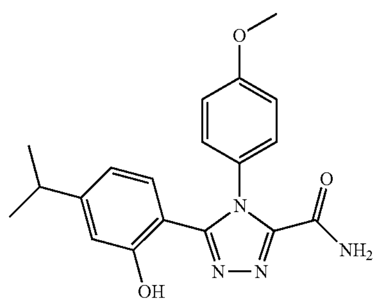 [SMILES: COc1ccc(-n2c(C(N)=O)nnc2-c2ccc(C(C)C)cc2O)cc1] | 5-(2-hydroxy-4-isopropylphenyl)-4-(4-methoxyphenyl)-4H-1,2,4-triazole-3-carboxamide |
| 71 | 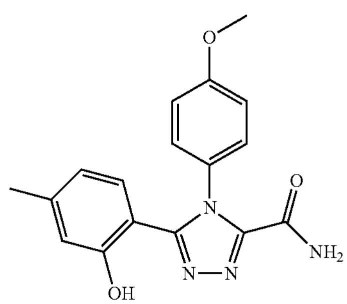 [SMILES: COc1ccc(-n2c(C(N)=O)nnc2-c2ccc(C)cc2O)cc1] | 5-(2-hydroxy-4-methylphenyl)-4-(4-methoxyphenyl)-4H-1,2,4-triazole-3-carboxamide |
| 72 | 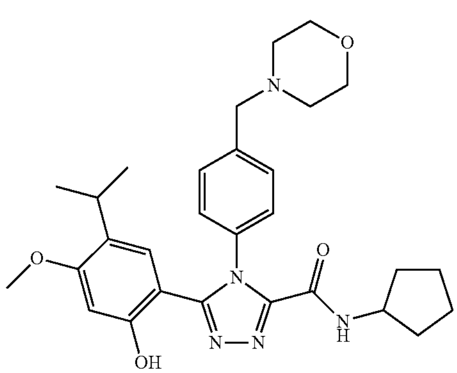 [SMILES: COc1cc(O)c(-c2nnc(C(=O)NC3CCCC3)n2-c2ccc(CN3CCOCC3)cc2)cc1C(C)C] | N-cyclopentyl-5-(2-hydroxy-5-isopropyl-4-methoxyphenyl)-4-(4-(morpholinomethyl)phenyl)-4H-1,2,4-triazole-3-carboxamide |

TABLE 1-continued

| No. | Structure | Name |
|---|---|---|
| 73 | 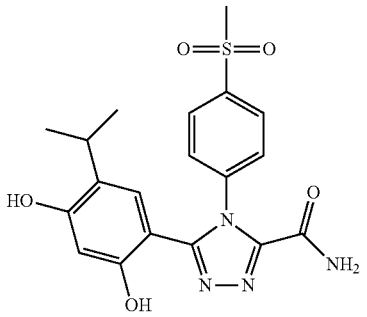 [SMILES: CC(C)c1cc(-c2nnc(C(N)=O)n2-c2ccc(S(C)(=O)=O)cc2)c(O)cc1O] | 5-(2,4-dihydroxy-5-isopropylphenyl)-4-(4-(methylsulfonyl)phenyl)-4H-1,2,4-triazole-3-carboxamide |
| 74 | 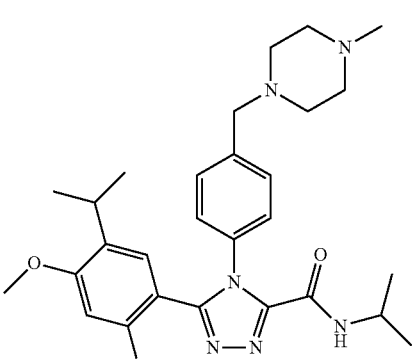 | 5-(2-hydroxy-5-isopropyl-4-niethoxyphenyl)-N-isopropyl-4-(4-((4-methylpiperazin-1-yl)methyl)phenyl)-4H-1,2,4-triazole-3-carboxamide |
| 75 | 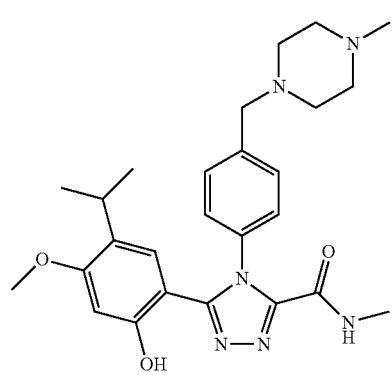 | 5-(2-hydroxy-5-isopropyl-4-methoxyphenyl)-N-methyl-4-(4-((4-methylpiperazin-1-yl)methyl)phenyl)-4H-1,2,4-triazole-3-carboxamide |
| 76 | 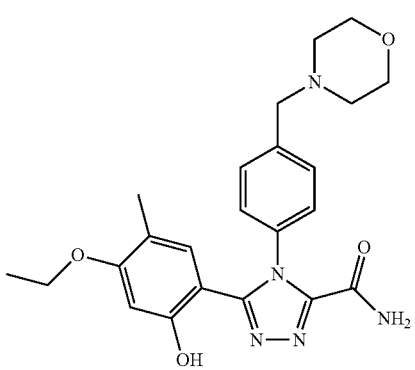 [SMILES: CCOc1cc(O)c(-c2nnc(C(N)=O)n2-c2ccc(CN3CCOCC3)cc2)cc1C] | 5-(4-ethoxy-2-hydroxy-5-methylphenyl)-4-(4-(morpholinomethyl)phenyl)-4H-1,2,4-triazole-3-carboxamide |

TABLE 1-continued

| No. | Structure | Name |
|---|---|---|
| 77 | 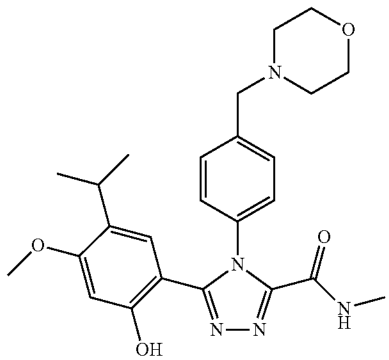 | 5-(2-hydroxy-5-isopropyl-4-methoxyphenyl)-N-methyl-4-(4-(morpholinomethyl)-phenyl)-4H-1,2,4-triazole-3-carboxamide |
| 78 | 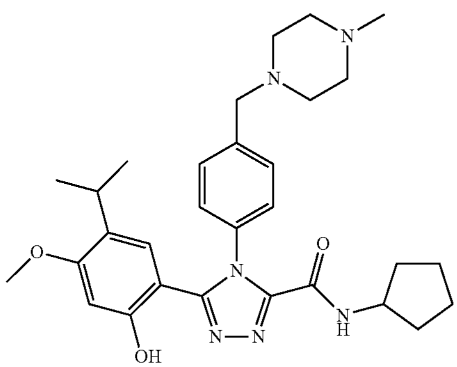 [SMILES: COc1cc(O)c(-c2nnc(C(=O)NC3CCCC3)n2-c2ccc(CN3CCN(C)CC3)cc2)cc1C(C)C] | N-cyclopentyl-5-(2-hydroxy-5-isopropyl-4-methoxyphenyl)-4-(4-((4-methylpiperazin-1-yl)methyl)phenyl)-4H-1,2,4-triazole-3-carboxamide |
| 79 | 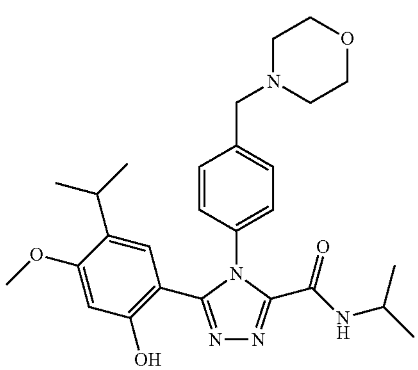 | 5-(2-hydroxy-5-isopropyl-4-methoxyphenyl)-N-isopropyl-4-(4-(morpholinomethyl)phenyl)-4H-1,2,4-triazole-3-carboxamide |
| 80 | 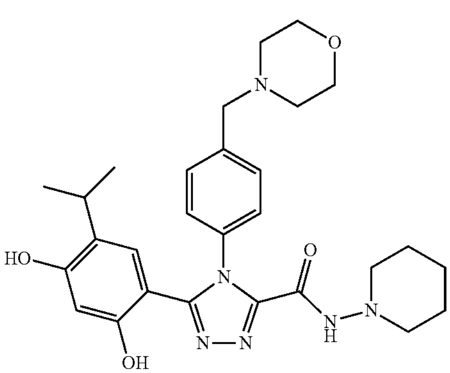 [SMILES: CC(C)c1cc(-c2nnc(C(=O)NN3CCCCC3)n2-c2ccc(CN3CCOCC3)cc2)c(O)cc1O] | 5-(2,4-dihydroxy-5-isopropylphenyl)-4-(4-(morpholinomethyl)phenyl)-N-(piperidin-1-yl)-4H-1,2,4-triazole-3-carboxamide |

TABLE 1-continued

| No. | Structure | Name |
|---|---|---|
| 81 | 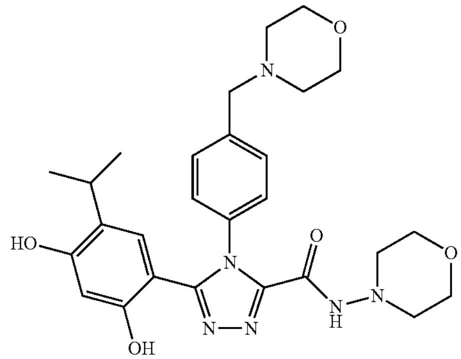 [SMILES: CC(C)c1cc(-c2nnc(C(=O)NN3CCOCC3)n2-c2ccc(CN3CCOCC3)cc2)c(O)cc1O] | 5-(2,4-dihydroxy-5-isopropylphenyl)-N-morpholino-4-(4-(morpholinomethyl)phenyl)-4H-1,2,4-triazole-3-carboxamide |
| 82 | 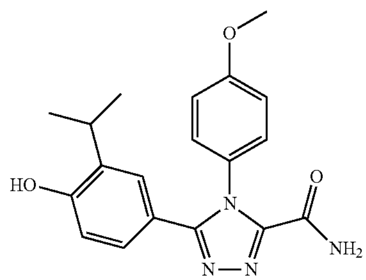 [SMILES: COc1ccc(-n2c(C(N)=O)nnc2-c2ccc(O)c(C(C)C)c2)cc1] | 5-(4-hydroxy-3-isopropylphenyl)-4-(4-methoxyphenyl)-4H-1,2,4-triazole-3-carboxamide |
| 83 | 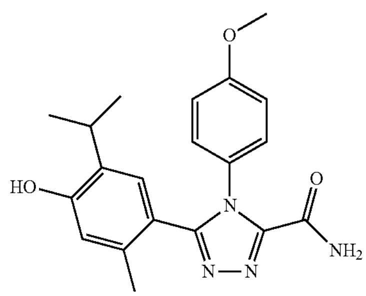 [SMILES: COc1ccc(-n2c(C(N)=O)nnc2-c2cc(C(C)C)c(O)cc2C)cc1] | 5-(4-hydroxy-5-isopropyl-2-methylphenyl)-4-(4-methoxyphenyl)-4H-1,2,4-triazole-3-carboxamide |
| 84 | 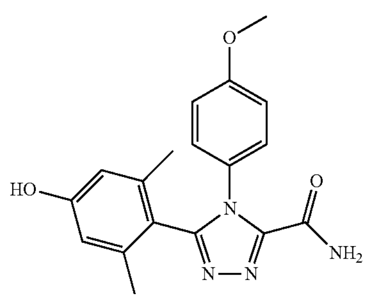 [SMILES: COc1ccc(-n2c(C(N)=O)nnc2-c2c(C)cc(O)cc2C)cc1] | 5-(4-hydroxy-2,6-dimethylphenyl)-4-(4-methoxyphenyl)-4H-1,2,4-triazole-3-carboxamide |
| 85 | 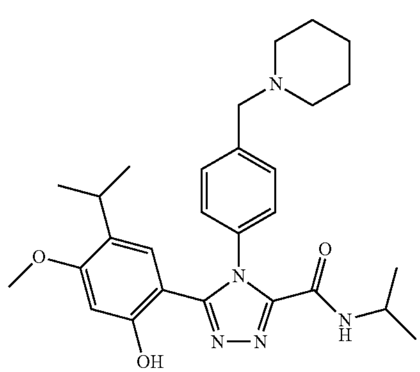 [SMILES: COc1cc(O)c(-c2nnc(C(=O)NC(C)C)n2-c2ccc(CN3CCCCC3)cc2)cc1C(C)C] | 5-(2-hydroxy-5-isopropyl-4-methoxyphenyl)-N-isopropyl-4-(4-(piperidin-1-ylmethyl)phenyl)-4H-1,2,4-triazole-3-carboxamide |

TABLE 1-continued

| No. | Structure | Name |
|---|---|---|
| 86 | 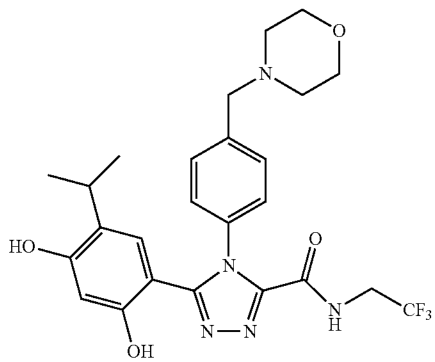 [SMILES: CC(C)c1cc(-c2nnc(C(=O)NCC(F)(F)F)n2-c2ccc(CN3CCOCC3)cc2)c(O)cc1O] | 5-(2,4-dihydroxy-5-isopropylphenyl)-4-(4-(morpholinomethyl)phenyl)-N-(2,2,2-trifluoroethyl)-4H-1,2,4-triazole-3-carboxamide |
| 87 | 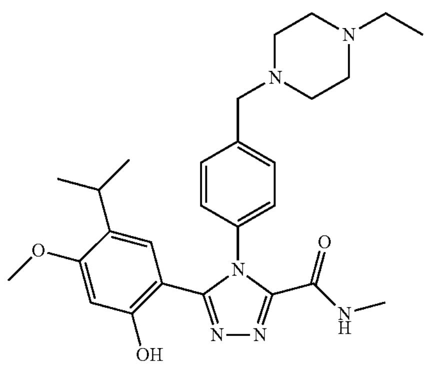 [SMILES: CCN1CCN(Cc2ccc(-n3c(C(=O)NC)nnc3-c3cc(C(C)C)c(OC)cc3O)cc2)CC1] | 4-(4-((4-ethylpiperazin-1-yl)methyl)phenyl)-5-(2-hydroxy-5-isopropyl-4-methoxyphenyl)-N-methyl-4H-1,2,4-triazole-3-carboxamide |
| 88 | 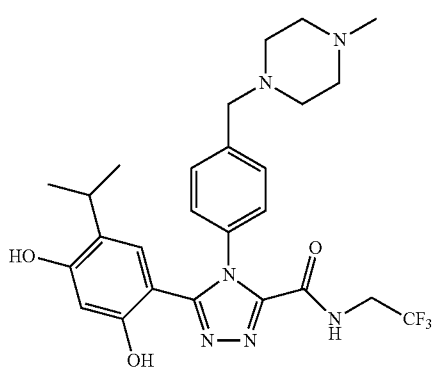 [SMILES: CC(C)c1cc(-c2nnc(C(=O)NCC(F)(F)F)n2-c2ccc(CN3CCN(C)CC3)cc2)c(O)cc1O] | 5-(2,4-dihydroxy-5-isopropylphenyl)-4-(4-((4-methylpiperazin-1-yl)methyl)phenyl)-N-(2,2,2-trifluoroethyl)-4H-1,2,4-triazole-3-carboxamide |
| 89 | 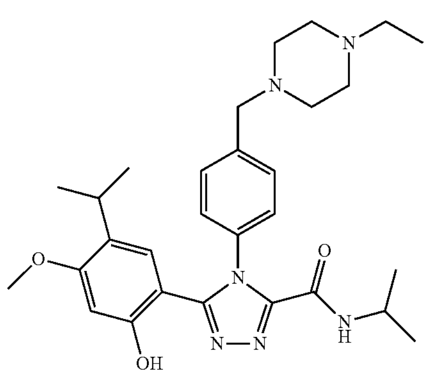 [SMILES: CCN1CCN(Cc2ccc(-n3c(C(=O)NC(C)C)nnc3-c3cc(C(C)C)c(OC)cc3O)cc2)CC1] | 4-(4-((4-ethylpiperazin-1-yl)methyl)phenyl)-5-(2-hydroxy-5-isopropyl-4-methoxyphenyl)-N-isopropyl-4H-1,2,4-triazole-3-carboxamide |

TABLE 1-continued

| No. | Structure | Name |
|---|---|---|
| 90 | 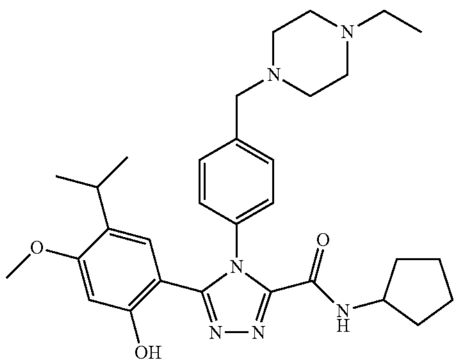 [SMILES: CCN1CCN(Cc2ccc(-n3c(C(=O)NC4CCCC4)nnc3-c3cc(C(C)C)c(OC)cc3O)cc2)CC1] | N-cyclopentyl-4-(4-((4-ethylpiperazin-1-yl)methyl)phenyl)-5-(2-hydroxy-5-isopropyl-4-methoxyphenyl)-4H-1,2,4-triazole-3-carboxamide |
| 91 | 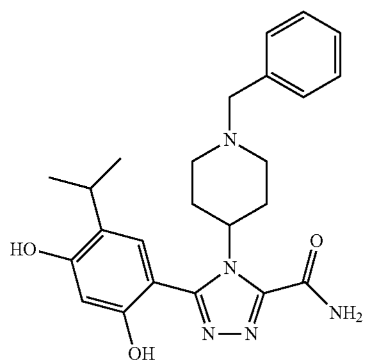 [SMILES: CC(C)c1cc(-c2nnc(C(N)=O)n2C2CCN(Cc3ccccc3)CC2)c(O)cc1O] | 4-(1-benzylpiperidin-4-yl)-5-(2,4-dihydroxy-5-isopropylphenyl)-4H-1,2,4-triazole-3-carboxamide |
| 92 | 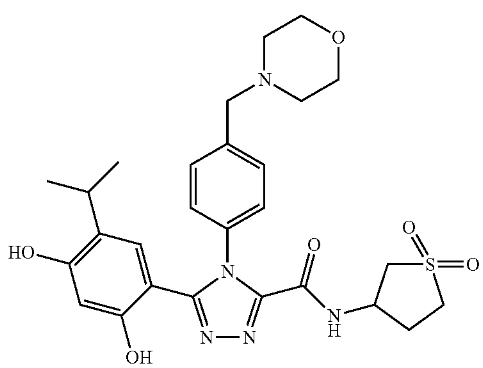 [SMILES: CC(C)c1cc(-c2nnc(C(=O)NC3CCS(=O)(=O)C3)n2-c2ccc(CN3CCOCC3)cc2)c(O)cc1O] | 5-(2,4-dihydroxy-5-isopropylphenyl)-4-(4-(morpholinomelhyl)phenyl)-N-(1,1-dioxo-tetrahydrothiophen-3-yl)-4H-1,2,4-triazole-3-carboxamide |
| 93 | 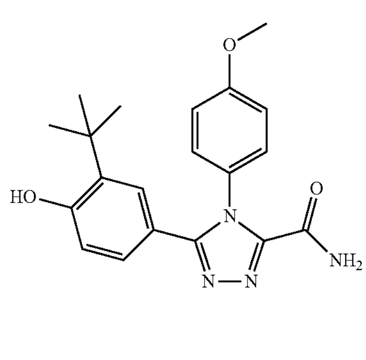 [SMILES: COc1ccc(-n2c(C(N)=O)nnc2-c2ccc(O)c(C(C)(C)C)c2)cc1] | 5-(3-tert-butyl-4-hydroxyphenyl)-4-(4-methoxyphenyl)-4H-1,2,4-triazole-3-carboxamide |

TABLE 1-continued

| No. | Structure | Name |
|---|---|---|
| 94 | 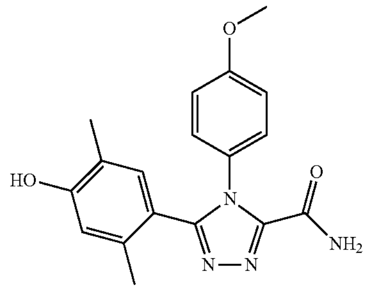 [SMILES: COc1ccc(-n2c(C(N)=O)nnc2-c2cc(C)c(O)cc2C)cc1] | 5-(4-hydroxy-2,5-dimethylphenyl)-4-(4-methoxyphenyl)-4H-1,2,4-triazole-3-carboxamide |
| 95 | 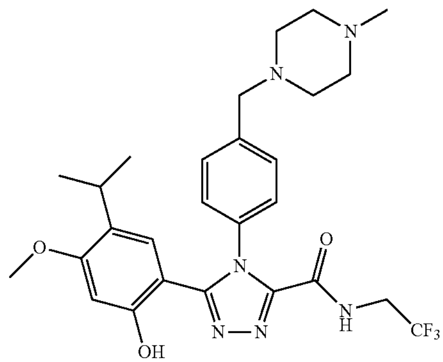 [SMILES: COc1cc(O)c(-c2nnc(C(=O)NCC(F)(F)F)n2-c2ccc(CN3CCN(C)CC3)cc2)cc1C(C)C] | 5-(2-hydroxy-5-isopropyl-4-methoxyphenyl)-4-(4-((4-methylpiperazin-1-yl)methyl)phenyl)-N-(2,2,2-trifluoroethyl)-4H-1,2,4-triazole-3-carboxamide |
| 96 | 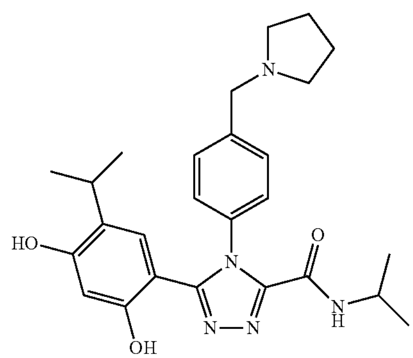 [SMILES: CC(C)NC(=O)c1nnc(-c2cc(C(C)C)c(O)cc2O)n1-c1ccc(CN2CCCC2)cc1] | 5-(2,4-dihydroxy-5-isopropylphenyl)-N-isopropyl-4-(4-(pyrrolidin-1-ylmethyl)phenyl)-4H-1,2,4-triazole-3-carboxamide |
| 97 | 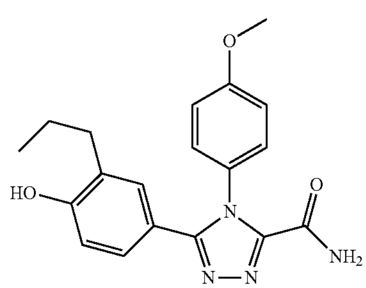 [SMILES: CCCc1cc(-c2nnc(C(N)=O)n2-c2ccc(OC)cc2)ccc1O] | 5-(4-hydroxy-3-propylphenyl)-4-(4-methoxyphenyl)-4H-1,2,4-triazole-3-carboxamide |
| 98 | 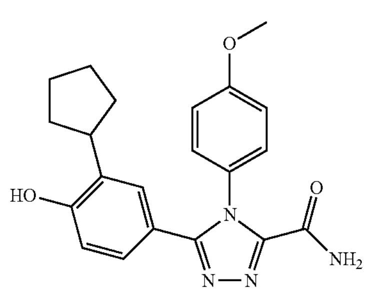 [SMILES: COc1ccc(-n2c(C(N)=O)nnc2-c2ccc(O)c(C3CCCC3)c2)cc1] | 5-(3-cyclopentyl-4-hydroxyphenyl)-4-(4-methoxyphenyl)-4H-1,2,4-triazole-3-carboxamide |

TABLE 1-continued

| No. | Structure | Name |
|---|---|---|
| 99 | 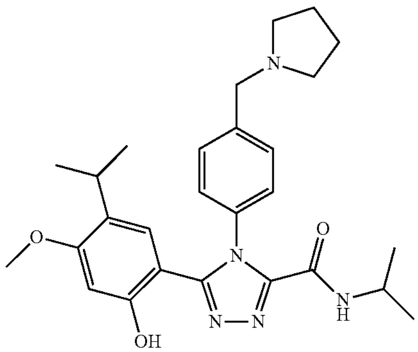 [SMILES: COc1cc(O)c(-c2nnc(C(=O)NC(C)C)n2-c2ccc(CN3CCCC3)cc2)cc1C(C)C] | 5-(2-hydroxy-5-isopropyl-4-methoxyphenyl)-N-isopropyl-4-(4-(pyrrolidin-1-ylmethyl)phenyl)-4H-1,2,4-triazole-3-carboxamide |
| 100 | 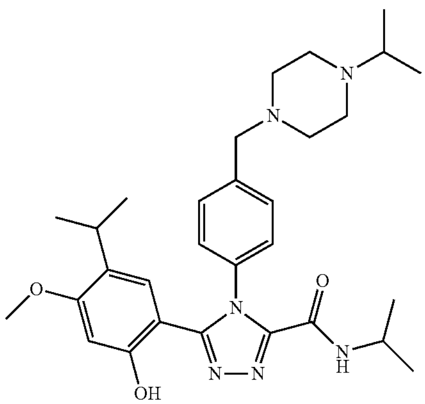 [SMILES: COc1cc(O)c(-c2nnc(C(=O)NC(C)C)n2-c2ccc(CN3CCN(C(C)C)CC3)cc2)cc1C(C)C] | 5-(2-hydroxy-5-isopropyl-4-methoxyphenyl)-N-isopropyl-4-(4-((4-isopropylpiperazin-1-yl)methyl)phenyl)-4H-1,2,4-triazole-3-carboxamide |
| 101 | 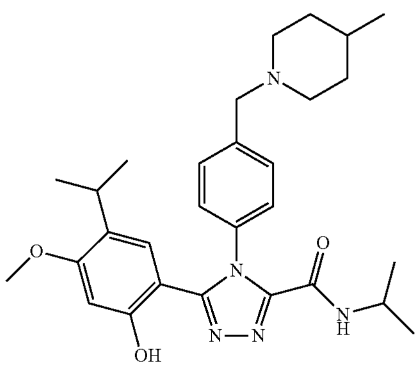 [SMILES: COc1cc(O)c(-c2nnc(C(=O)NC(C)C)n2-c2ccc(CN3CCC(C)CC3)cc2)cc1C(C)C] | 5-(2-hydroxy-5-isopropyl-4-methoxyphenyl)-N-isopropyl-4-(4-((4-methylpiperidin-1-yl)methyl)phenyl)-4H-1,2,4-triazole-3-carboxamide |
| 102 | 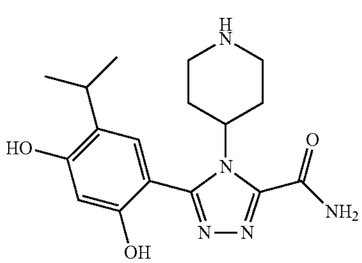 [SMILES: CC(C)c1cc(-c2nnc(C(N)=O)n2C2CCNCC2)c(O)cc1O] | 5-(2,4-dihydroxy-5-isopropylphenyl)-4-(piperidinyl)-4H-1,2,4-triazole-3-carboxamide |

TABLE 1-continued

| No. | Structure | Name |
|---|---|---|
| 103 | 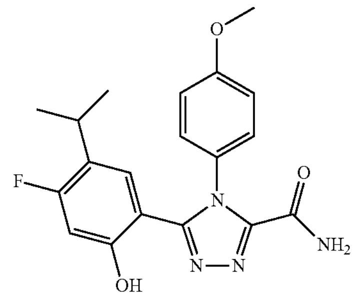 [SMILES: COc1ccc(-n2c(C(N)=O)nnc2-c2cc(C(C)C)c(F)cc2O)cc1] | 5-(4-fluoro-2-hydroxy-5-isopropylphenyl)-4-(4-methoxyphenyl)-4H-1,2,4-triazole-3-carboxamide |
| 104 | 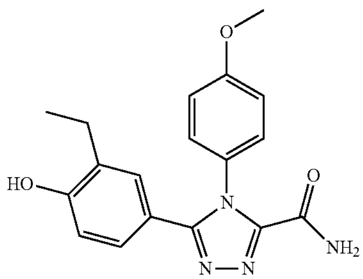 [SMILES: CCc1cc(-c2nnc(C(N)=O)n2-c2ccc(OC)cc2)ccc1O] | 5-(3-ethyl-4-hydroxyphenyl)-4-(4-methoxyphenyl)-4H-1,2,4-triazole-3-carboxamide |
| 105 | 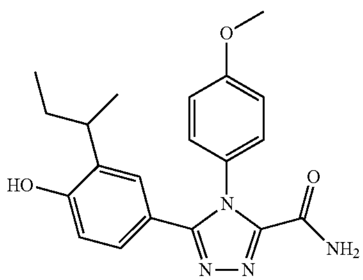 [SMILES: CCC(C)c1cc(-c2nnc(C(N)=O)n2-c2ccc(OC)cc2)ccc1O] | 5-(3-sec-butyl-4-hydroxyphenyl)-4-(4-methoxyphenyl)-4H-1,2,4-triazole-3-carboxamide |
| 106 | 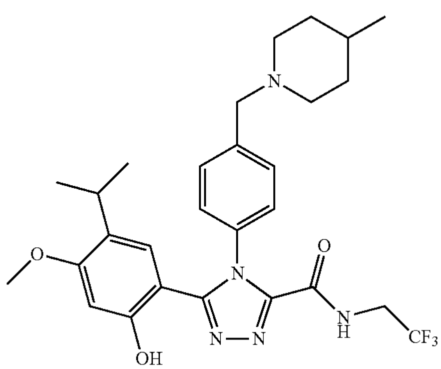 [SMILES: COc1cc(O)c(-c2nnc(C(=O)NCC(F)(F)F)n2-c2ccc(CN3CCC(C)CC3)cc2)cc1C(C)C] | 5-(2-hydroxy-5-isopropyl-4-methoxyphenyl)-4-(4-((4-methylpiperidin-1-yl)methyl)phenyl)-N-(2,2,2-trifluoroethyl)-4H-1,2,4-triazole-3-carboxamide |
| 107 | 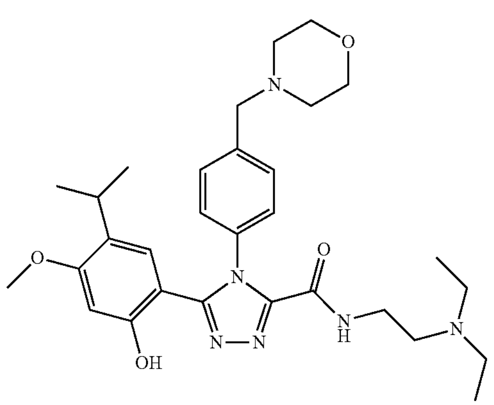 [SMILES: CCN(CC)CCNC(=O)c1nnc(-c2cc(C(C)C)c(OC)cc2O)n1-c1ccc(CN2CCOCC2)cc1] | N-(2-(diethylamino)ethyl)-5-(2-hydroxy-5-isopropyl-4-methoxyphenyl)-4-(4-(morpholinomethyl)phenyl)-4H-1,2,4-triazole-3-carboxamide |

TABLE 1-continued

| No. | Structure | Name |
|---|---|---|
| 108 | 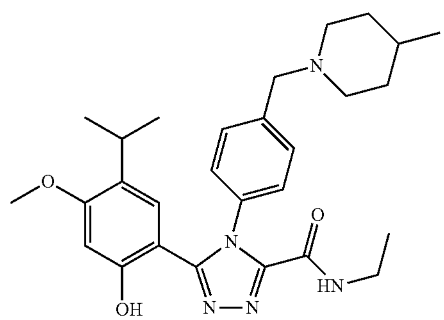 | N-ethyl-5-(2-hydroxy-5-isopropyl-4-methoxyphenyl)-4-(4-((4-methylpiperidin-1-yl)methyl)phenyl)-4H-1,2,4-triazole-3-carboxamide |
| 109 | 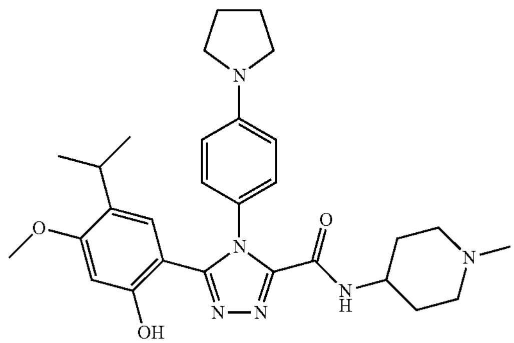 | 5-(2-hydroxy-5-isopropyl-4-methoxyphenyl)-N-(1-methylpiperidin-4-yl)-4-(4-(pyrrolidin-1-yl)phenyl)-4H-1,2,4-triazole-3-carboxamide |
| 110 | 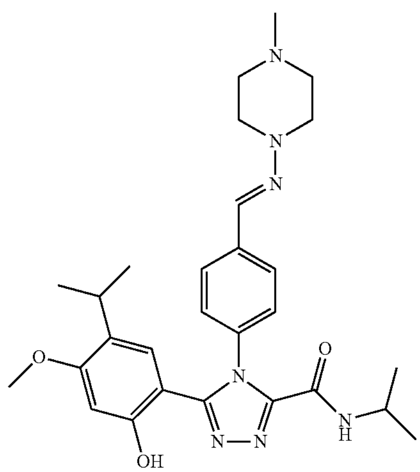 [SMILES: COc1cc(O)c(-c2nnc(C(=O)NC(C)C)n2-c2ccc(/C=N/N3CCN(C)CC3)cc2)cc1C(C)C] | (E)-5-(2-hydroxy-5-isopropyl-4-methoxyphenyl)-N-isopropyl-4-(4-((4-methylpiperazin-1-ylimino)methyl)phenyl)-4H-1,2,4-triazole-3-carboxamide |
| 111 | 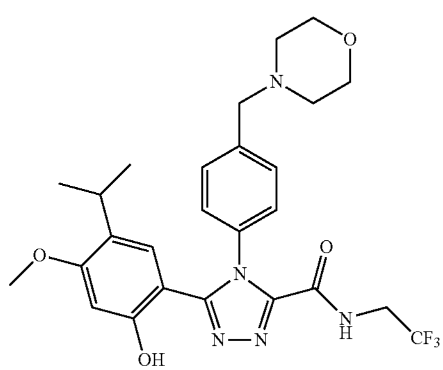 [SMILES: COc1cc(O)c(-c2nnc(C(=O)NCC(F)(F)F)n2-c2ccc(CN3CCOCC3)cc2)cc1C(C)C] | 5-(2-hydroxy-5-isopropyl-4-methoxyphenyl)-4-(4-(morpholinomethyl)phenyl)-N-(2,2,2-trifluoroethyl)-4H-1,2,4-triazole-3-carboxamide |

TABLE 1-continued

| No. | Structure | Name |
|---|---|---|
| 112 | 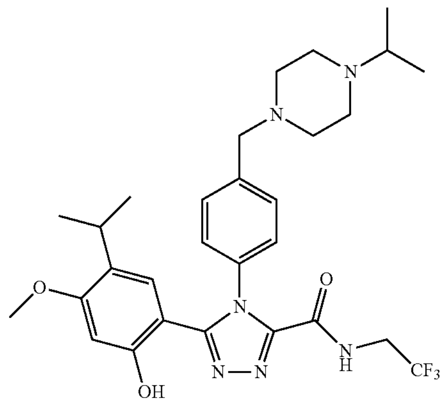 [SMILES: COc1cc(O)c(-c2nnc(C(=O)NCC(F)(F)F)n2-c2ccc(CN3CCN(C(C)C)CC3)cc2)cc1C(C)C] | 5-(2-hydroxy-5-isopropyl-4-methoxyphenyl)-4-(4-((4-isopropylpiperazin-1-yl)methyl)phenyl)-N-(2,2,2-trifluoroethyl)-4H-1,2,4-triazole-3-carboxamide |
| 113 | 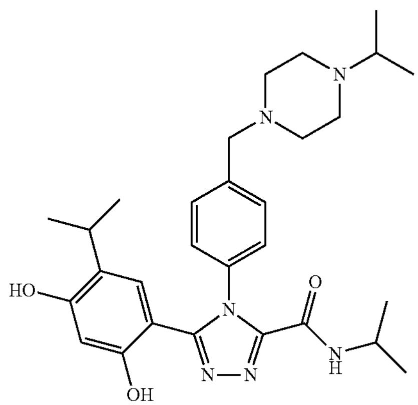 [SMILES: CC(C)NC(=O)c1nnc(-c2cc(C(C)C)c(O)cc2O)n1-c1ccc(CN2CCN(C(C)C)CC2)cc1] | 5-(2,4-dihydroxy-5-isopropylphenyl)-N-isopropyl-4-(4-((4-isopropylpiperazin-1-yl)methyl)phenyl)-4H-1,2,4-triazole-3-carboxamide |
| 114 | 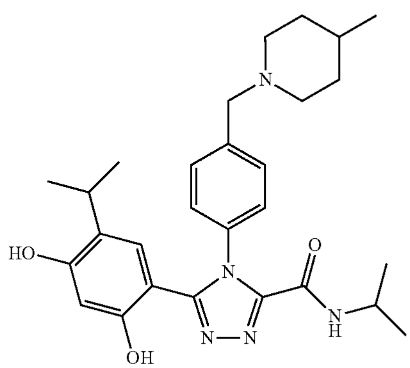 [SMILES: CC1CCN(Cc2ccc(-n3c(C(=O)NC(C)C)nnc3-c3cc(C(C)C)c(O)cc3O)cc2)CC1] | 5-(2,4-dihydroxy-5-isopropylphenyl)-N-isopropyl-4-(4-((4-methylpiperidin-1-yl)methyl)phenyl)-4H-1,2,4-triazole-3-carboxamide |
| 115 | 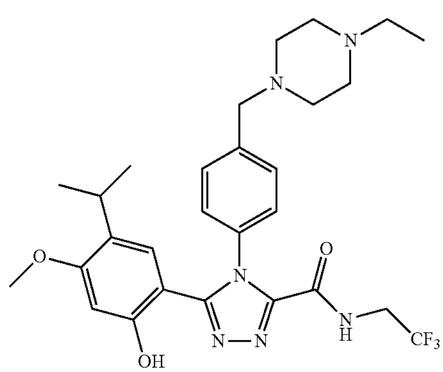 [SMILES: CCN1CCN(Cc2ccc(-n3c(C(=O)NCC(F)(F)F)nnc3-c3cc(C(C)C)c(OC)cc3O)cc2)CC1] | 4-(4-((4-ethylpiperazin-1-yl)methyl)phenyl)-5-(2-hydroxy-5-isopropyl-4-methoxyphenyl)-N-(2,2,2-trifluoroethyl)-4H-1,2,4-triazole-3-carboxamide |

TABLE 1-continued

| No. | Structure | Name |
|---|---|---|
| 116 | 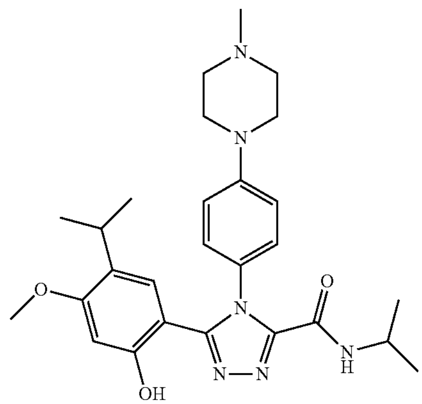 [SMILES: COc1cc(O)c(-c2nnc(C(=O)NC(C)C)n2-c2ccc(N3CCN(C)CC3)cc2)cc1C(C)C] | 5-(2-hydroxy-5-isopropyl-4-methoxyphenyl)-N-isopropyl-4-(4-(4-methylpiperazin-1-yl)phenyl)-4H-1,2,4-triazole-3-carboxamide |
| 117 | 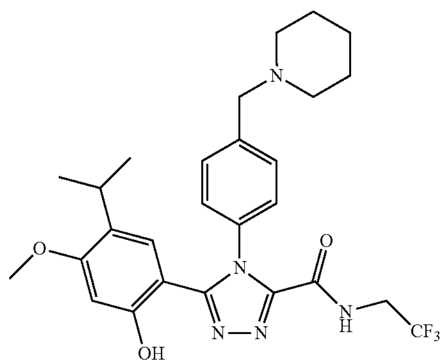 [SMILES: COc1cc(O)c(-c2nnc(C(=O)NCC(F)(F)F)n2-c2ccc(CN3CCCCC3)cc2)cc1C(C)C] | 5-(2-hydroxy-5-isopropyl-4-methoxyphenyl)-4-(4-(piperidin-1-ylmethyl)phenyl)-N-(2,2,2-trifluoroethyl)-4H-1,2,4-triazole-3-carboxamide |
| 118 | 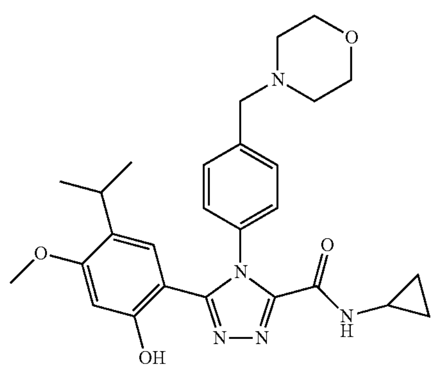 [SMILES: COc1cc(O)c(-c2nnc(C(=O)NC3CC3)n2-c2ccc(CN3CCOCC3)cc2)cc1C(C)C] | N-cyclopropyl-5-(2-hydroxy-5-isopropyl-4-methoxyphenyl)-4-(4-(morpholinomethyl)phenyl)-4H-1,2,4-triazole-3-carboxamide |
| 119 | 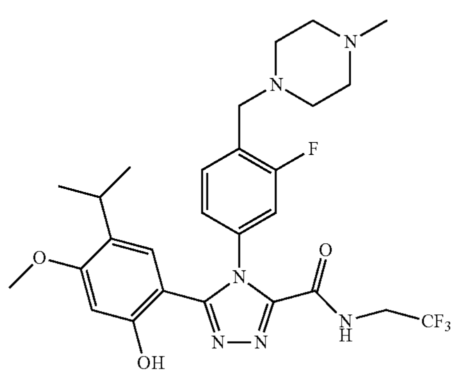 [SMILES: COc1cc(O)c(-c2nnc(C(=O)NCC(F)(F)F)n2-c2ccc(CN3CCN(C)CC3)c(F)c2)cc1C(C)C] | 4-(3-fluoro-4-((4-methylpiperazin-1-yl)methyl)phenyl)-5-(2-hydroxy-5-isopropyl-4-methoxyphenyl)-N-(2,2,2-trifluoroethyl)-4H-1,2,4-triazole-3-carboxamide |

TABLE 1-continued

| No. | Structure | Name |
|---|---|---|
| 120 | 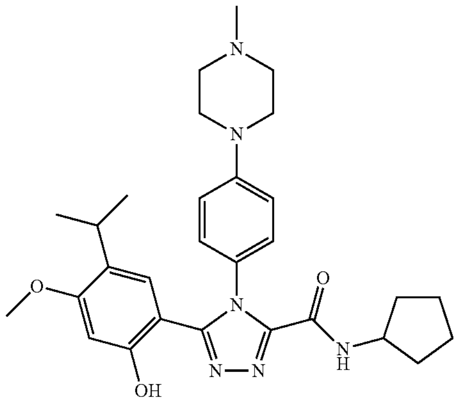 [SMILES: COc1cc(O)c(-c2nnc(C(=O)NC3CCCC3)n2-c2ccc(N3CCN(C)CC3)cc2)cc1C(C)C] | N-cyclopentyl-5-(2-hydroxy-5-isopropyl-4-methoxyphenyl)-4-(4-(4-methylpiperazin-1-yl)phenyl)-4H-1,2,4-triazole-3-carboxamide |
| 121 | 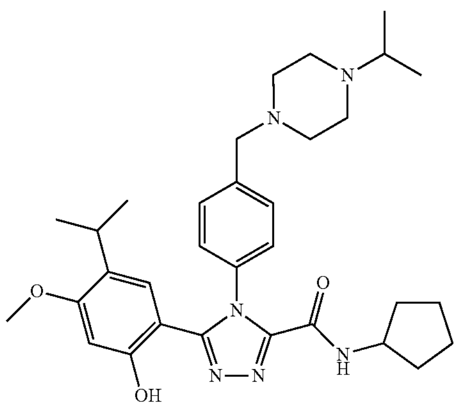 [SMILES: COc1cc(O)c(-c2nnc(C(=O)NC3CCCC3)n2-c2ccc(CN3CCN(C(C)C)CC3)cc2)cc1C(C)C] | N-cyclopentyl-5-(2-hydroxy-5-isopropyl-4-methoxyphenyl)-4-(4-((4-isopropylpiperazin-1-yl)methyl)phenyl)-4H-1,2,4-triazole-3-carboxamide |
| 122 | 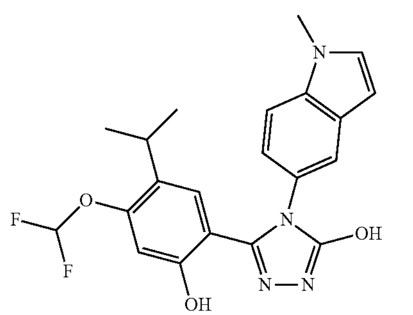 [SMILES: CC(C)c1cc(-c2nnc(O)n2-c2ccc3c(ccn3C)c2)c(O)cc1OC(F)F] | 5-(4-(difluoromethoxy)-2-hydroxy-5-isopropylphenyl)-4-(1-methyl-1H-indol-5-yl)-4H-1,2,4-triazol-3-ol |
| 123 | 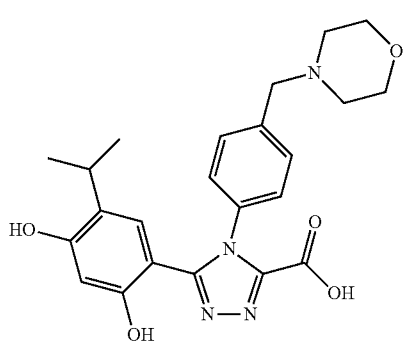 [SMILES: CC(C)c1cc(-c2nnc(C(=O)O)n2-c2ccc(CN3CCOCC3)cc2)c(O)cc1O] | 5-(2,4-dihydroxy-5-isopropylphenyl)-4-(4-(morpholinomethyl)phenyl)-4H-1,2,4-triazole-3-carboxylic acid |

| No. | Structure | Name |
|---|---|---|
| 124 | 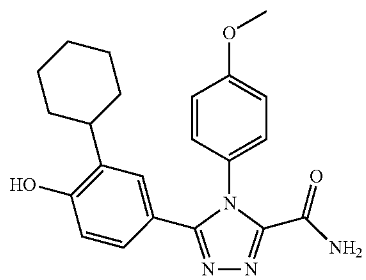 [SMILES: COc1ccc(-n2c(C(N)=O)nnc2-c2ccc(O)c(C3CCCCC3)c2)cc1] | 5-(3-cyclohexyl-4-hydroxyphenyl)-4-(4-methoxyphenyl)-4H-1,2,4-triazole-3-carboxamide |
| 125 | 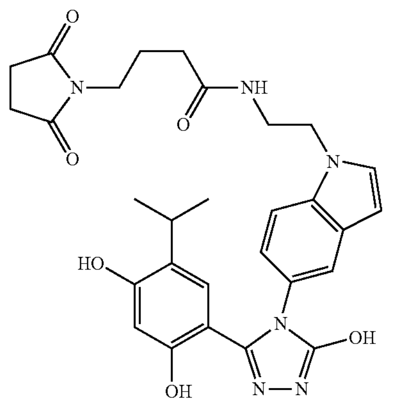 [SMILES: CC(C)c1cc(-c2nnc(O)n2-c2ccc3c(ccn3CCNC(=O)CCCN3C(=O)CCC3=O)c2)c(O)cc1O] | N-(2-(5-(3-(2,4-dihydroxy-5-isopropylphenyl)-5-hydroxy-4H-1,2,4-triazol-4-yl)-1H-indol-1-yl)ethyl)-4-(2,5-dioxopyrrolidin-1-yl)butanamide |
| 126 | 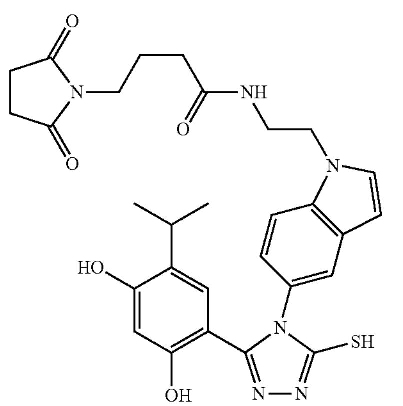 [SMILES: CC(C)c1cc(-c2nnc(S)n2-c2ccc3c(ccn3CCNC(=O)CCCN3C(=O)CCC3=O)c2)c(O)cc1O] | N-(2-(5-(3-(2,4-dihydroxy-5-isopropylphenyl)-5-mercapto-4H-1,2,4-triazol-4-yl)-1H-indol-1-yl)ethyl)-4-(2,5-dioxopyrrolidin-1-yl)butanamide |
| 127 | 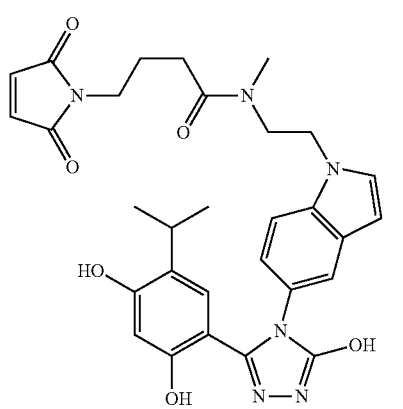 [SMILES: CC(C)c1cc(-c2nnc(O)n2-c2ccc3c(ccn3CCN(C)C(=O)CCCN3C(=O)C=CC3=O)c2)c(O)cc1O] | N-(2-(5-(3-(2,4-dihydroxy-5-isopropylphenyl)-5-hydroxy-4H-1,2,4-triazol-4-yl)-1H-indol-1-yl)ethyl)-4-(2,5-dioxo-2,5-dihydro-1H-pyrrol-1-yl)-N-methylbutanamide |

TABLE 1-continued

| No. | Structure | Name |
|---|---|---|
| 128 | 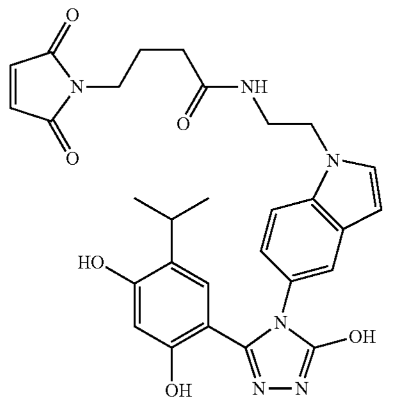 [SMILES: CC(C)c1cc(-c2nnc(O)n2-c2ccc3c(ccn3CCNC(=O)CCCN3C(=O)C=CC3=O)c2)c(O)cc1O] | N-(2-(5-(3-(2,4-dihydroxy-5-isopropylphenyl)-5-hydroxy-4H-1,2,4-triazol-4-yl)-1H-indol-1-yl)ethyl)-4-(2,5-dioxo-2,5-dihydro-1H-pyrrol-1-yl)butanamide |
| 129 | 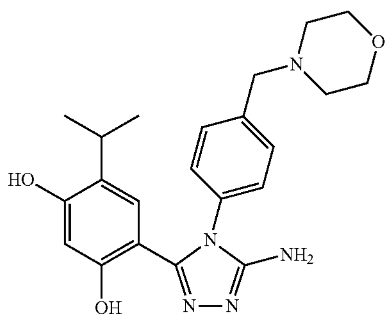 [SMILES: CC(C)c1cc(-c2nnc(N)n2-c2ccc(CN3CCOCC3)cc2)c(O)cc1O] | 4-(5-amino-4-(4-(morpholinomethyl)phenyl)-4H-1,2,4-triazol-3-yl)-6-isopropylbenzene-1,3-diol |
| 130 | 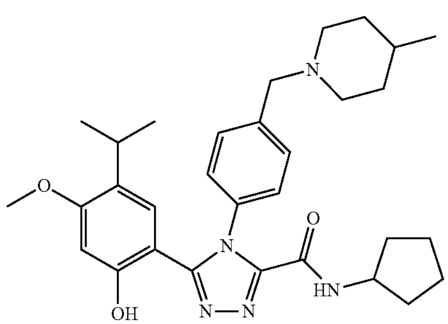 [SMILES: COc1cc(O)c(-c2nnc(C(=O)NC3CCCC3)n2-c2ccc(CN3CCC(C)CC3)cc2)cc1C(C)C] | N-cyclopentyl-5-(2-hydroxy-5-isopropyl-4-methoxyphenyl)-4-(4-((4-methylpiperidin-1-yl)methyl)phenyl)-4H-1,2,4-triazole-3-carboxamide |
| 131 | 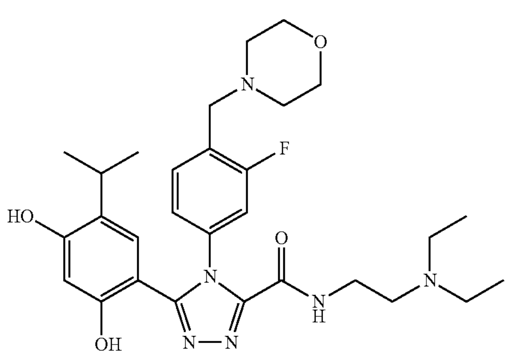 [SMILES: CCN(CC)CCNC(=O)c1nnc(-c2cc(C(C)C)c(O)cc2O)n1-c1ccc(CN2CCOCC2)c(F)c1] | N-(2-(diethylamino)ethyl)-5-(2,4-dihydroxy-5-isopropylphenyl)-4-(3-fluoro-4-(morpholinomethyl)-phenyl)-4H-1,2,4-triazole-3-carboxamide |

| No. | Structure | Name |
|---|---|---|
| 132 | 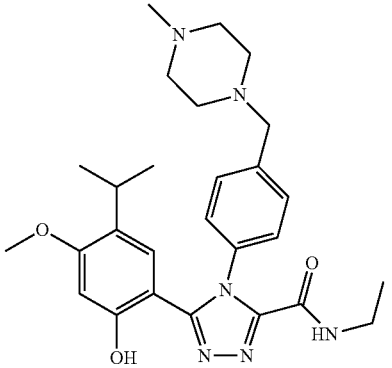 [SMILES: CCNC(=O)c1nnc(-c2cc(C(C)C)c(OC)cc2O)n1-c1ccc(CN2CCN(C)CC2)cc1] | N-ethyl-5-(2-hydroxy-5-isopropyl-4-methoxyphenyl)-4-(4-((4-methylpiperazin-1-yl)methyl)phenyl)-4H-1,2,4-triazole-3-carboxamide |
| 133 | 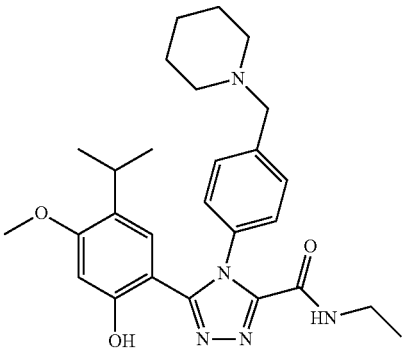 [SMILES: CCNC(=O)c1nnc(-c2cc(C(C)C)c(OC)cc2O)n1-c1ccc(CN2CCCCC2)cc1] | N-ethyl-5-(2-hydroxy-5-isopropyl-4-methoxyphenyl)-4-(4-(piperidin-1-ylmethyl)phenyl)-4H-1,2,4-triazole-3-carboxamide |
| 134 | 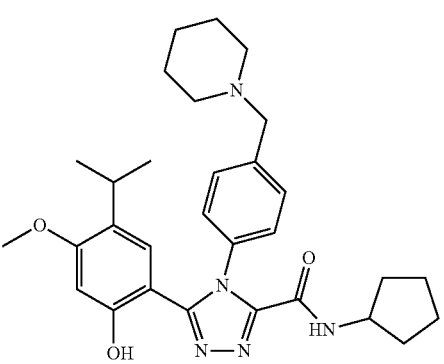 [SMILES: COc1cc(O)c(-c2nnc(C(=O)NC3CCCC3)n2-c2ccc(CN3CCCCC3)cc2)cc1C(C)C] | N-cyclopentyl-5-(2-hydroxy-5-isopropyl-4-methoxyphenyl)-4-(4-(piperidin-1-ylmethyl)phenyl)-4H-1,2,4-triazole-3-carboxamide |
| 135 | 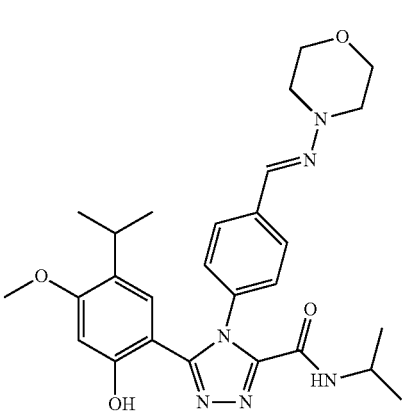 [SMILES: COc1cc(O)c(-c2nnc(C(=O)NC(C)C)n2-c2ccc(/C=N/N3CCOCC3)cc2)cc1C(C)C] | (E)-5-(2-hydroxy-5-isopropyl-4-methoxyphenyl)-N-isopropyl-4-(4-((morpholinoimino)methyl)phenyl)-4H-1,2,4-triazole-3-carboxamide |

| No. | Structure | Name |
|---|---|---|
| 136 | 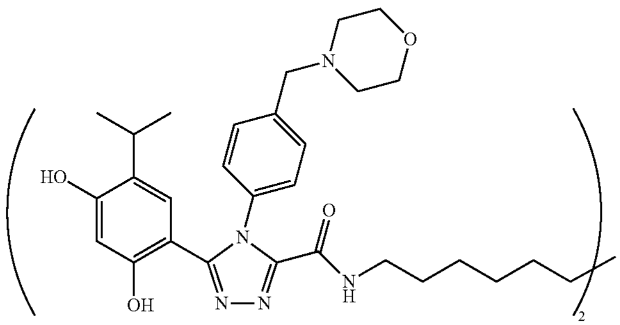 | N,N'-(undecane-1,11-diyl)bis(5-(2,4-dihydroxy-5-isopropylphenyl)-4-(4-(morpholinomethyl)phenyl)-4H-1,2,4-triazole-3-carboxamide) |
| 137 | 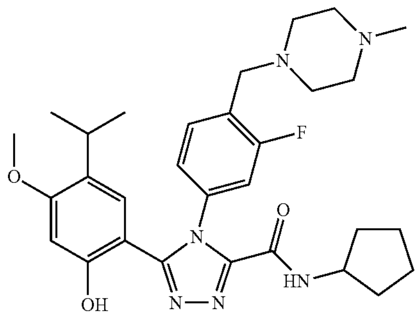 [SMILES: COc1cc(O)c(-c2nnc(C(=O)NC3CCCC3)n2-c2ccc(CN3CCN(C)CC3)c(F)c2)cc1C(C)C] | N-cyclopentyl-4-(3-fluoro-4-((4-methylpiperazin-1-yl)methyl)phenyl)-5-(2-hydroxy-5-isopropyl-4-methoxyphenyl)-4H-1,2,4-triazole-3-carboxamide |
| 138 | 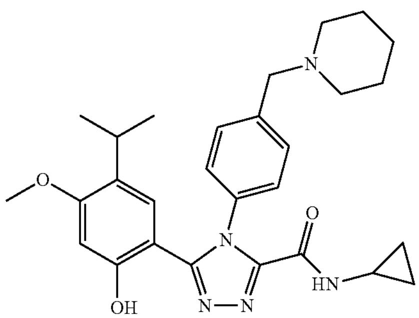 [SMILES: COc1cc(O)c(-c2nnc(C(=O)NC3CC3)n2-c2ccc(CN3CCCCC3)cc2)cc1C(C)C] | N-cyclopropyl-5-(2-hydroxy-5-isopropyl-4-methoxyphenyl)-4-(4-(piperidin-1-ylmethyl)phenyl)-4H-1,2,4-triazole-3-carboxamide |
| 139 | 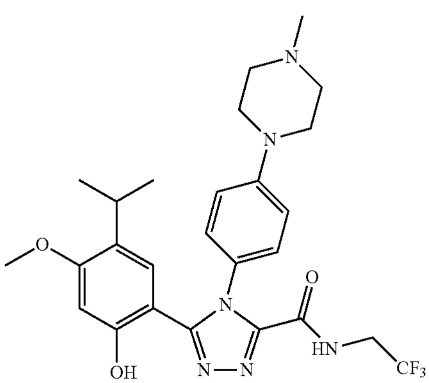 [SMILES: COc1cc(O)c(-c2nnc(C(=O)NCC(F)(F)F)n2-c2ccc(N3CCN(C)CC3)cc2)cc1C(C)C] | 5-(2-hydroxy-5-isopropyl-4-methoxyphenyl)-4-(4-(4-methylpiperazin-1-yl)phenyl)-N-(2,2,2-trifluoroethyl)-4H-1,2,4-triazole-3-carboxamide |

TABLE 1-continued

| No. | Structure | Name |
|---|---|---|
| 140 | 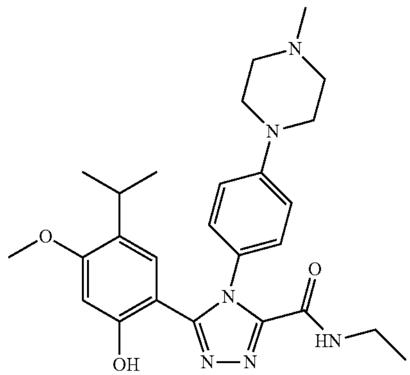 [SMILES: CCNC(=O)c1nnc(-c2cc(C(C)C)c(OC)cc2O)n1-c1ccc(N2CCN(C)CC2)cc1] | N-ethyl-5-(2-hydroxy-5-isopropyl-4-methoxyphenyl)-4-(4-(4-methylpiperazin-1-yl)phenyl)-4H-1,2,4-triazole-3-carboxamide |
| 141 | 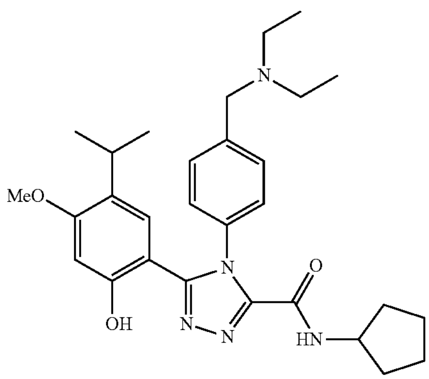 [SMILES: CCN(CC)Cc1ccc(-n2c(C(=O)NC3CCCC3)nnc2-c2cc(C(C)C)c(OC)cc2O)cc1] | N-cyclopentyl-4-(4-((diethylamino)methyl)phenyl)-5-(2-hydroxy-5-isopropyl-4-methoxyphenyl)-4H-1,2,4-triazole-3-carboxamide |
| 142 | 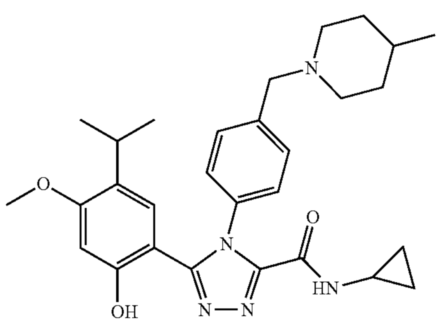 | N-cyclopropyl-5-(2-hydroxy-5-isopropyl-4-methoxyphenyl)-4-(4-((4-methylpiperidin-1-yl)methyl)phenyl)-4H-1,2,4-triazole-3-carboxamide |
| 143 | 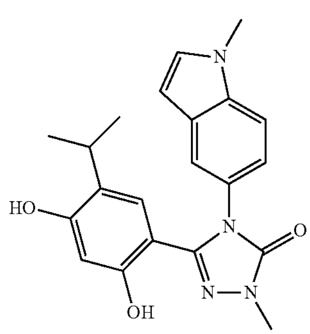 [SMILES: CC(C)c1cc(-c2nn(C)c(=O)n2-c2ccc3c(ccn3C)c2)c(O)cc1O] | 3-(2,4-dihydroxy-5-isopropylphenyl)-1-methyl-4-(1-methyl-1H-indol-5-yl)-1H-1,2,4-triazol-5(4H)-one |

TABLE 1-continued

| No. | Structure | Name |
|---|---|---|
| 144 | 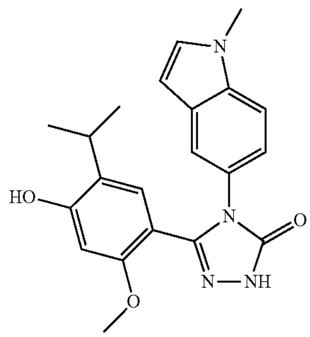 [SMILES: COc1cc(O)c(C(C)C)cc1-c1n[nH]c(=O)n1-c1ccc2c(ccn2C)c1] | 3-(4-hydroxy-5-isopropyl-2-methoxyphenyl)-4-(1-methyl-1H-indol-5-yl)-1H-1,2,4-triazol-5(4H)-one |
| 145 | 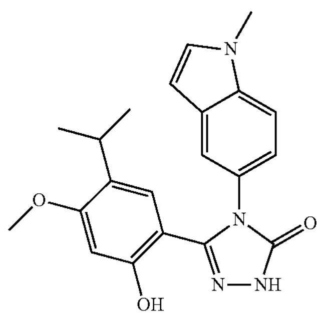 [SMILES: COc1cc(O)c(-c2n[nH]c(=O)n2-c2ccc3c(ccn3C)c2)cc1C(C)C] | 3-(2-hydroxy-5-isopropyl-4-methoxyphenyl)-4-(1-methyl-1H-indol-5-yl)-1H-1,2,4-triazol-5(4H)-one |
| 146 | 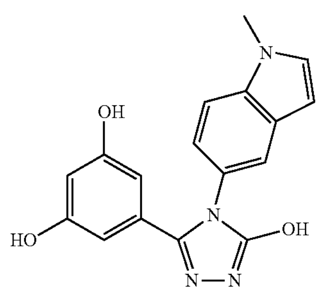 [SMILES: Cn1ccc2cc(-n3c(O)nnc3-c3cc(O)cc(O)c3)ccc21] | 5-(5-hydroxy-4-(1-methyl-1H-indol-5-yl)-4H-1,2,4-triazol-3-yl)benzene-1,3-diol |
| 147 | 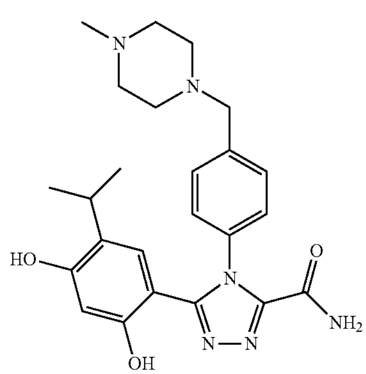 [SMILES: CC(C)c1cc(-c2nnc(C(N)=O)n2-c2ccc(CN3CCN(C)CC3)cc2)c(O)cc1O] | 5-(2,4-dihydroxy-5-isopropylphenyl)-4-(4-((4-methylpiperazin-1-yl)methyl)phenyl)-4H-1,2,4-triazole-3-carboxamide |

US 9,539,243 B2
TABLE 1-continued
| No. | Structure | Name |
|---|---|---|
| 148 | 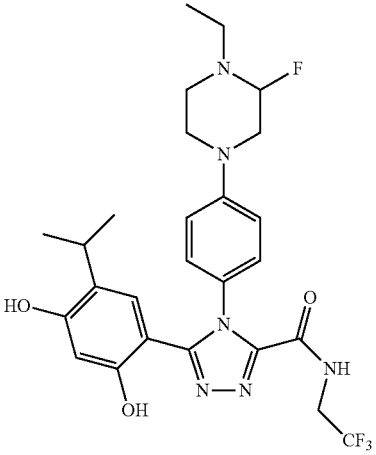 [SMILES: CCN1CCN(c2ccc(-n3c(C(=O)NCC(F)(F)F)nnc3-c3cc(C(C)C)c(O)cc3O)cc2)CC1F] | 5-(2,4-dihydroxy-5-isopropylphenyl)-4-(4-(4-ethyl-3-fluoropiperazin-1-yl)phenyl)-N-(2,2,2-trifluoroethyl)-4H-1,2,4-triazole-3-carboxamide |
| 149 | 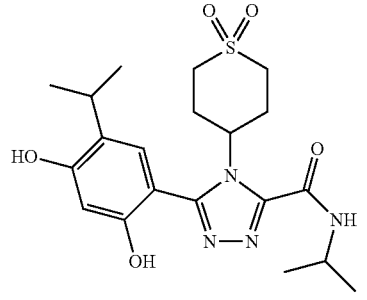 [SMILES: CC(C)NC(=O)c1nnc(-c2cc(C(C)C)c(O)cc2O)n1C1CCS(=O)(=O)CC1] | |
| 150 | 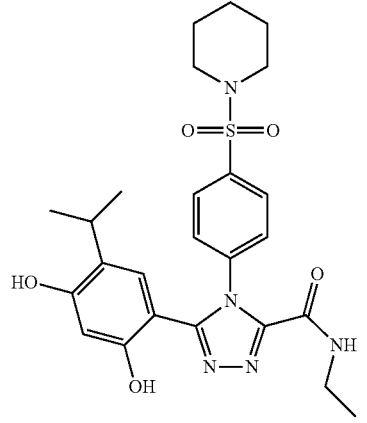 [SMILES: CCNC(=O)c1nnc(-c2cc(C(C)C)c(O)cc2O)n1-c1ccc(S(=O)(=O)N2CCCCC2)cc1] | 5-(2,4-dihydroxy-5-isopropylphenyl)-N-ethyl-4-(4-(piperidin-1-ylsulfonyl)phenyl)-4H-1,2,4-triazole-3-carboxamide |
| 151 | 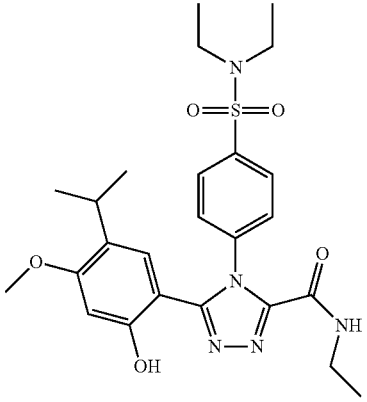 [SMILES: CCNC(=O)c1nnc(-c2cc(C(C)C)c(OC)cc2O)n1-c1ccc(S(=O)(=O)N(CC)CC)cc1] | 4-(4-(N,N-diethylsulfamoyl)phenyl)-N-ethyl-5-(2-hydroxy-5-isopropyl-4-methoxyphenyl)-4H-1,2,4-triazole-3-carboxamide |

| No. | Structure | Name |
| --- | --- | --- |
| 152 | 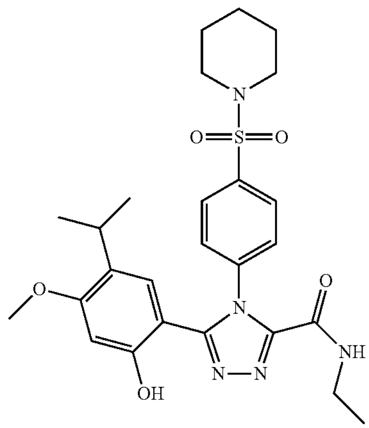 [SMILES: CCNC(=O)c1nnc(-c2cc(C(C)C)c(OC)cc2O)n1-c1ccc(S(=O)(=O)N2CCCCC2)cc1] | N-ethyl-5-(2-hydroxy-5-isopropyl-4-methoxyphenyl)-4-(4-(piperidin-1-ylsulfonyl)phenyl)-4H-1,2,4-triazole-3-carboxamide |
| 153 | 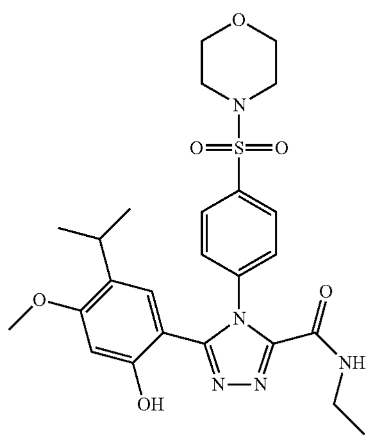 [SMILES: CCNC(=O)c1nnc(-c2cc(C(C)C)c(OC)cc2O)n1-c1ccc(S(=O)(=O)N2CCOCC2)cc1] | N-ethyl-5-(2-hydroxy-5-isopropyl-4-methoxyphenyl)-4-(4-(morpholinosulfonyl)phenyl)-4H-1,2,4-triazole-3-carboxamide |
| 154 | 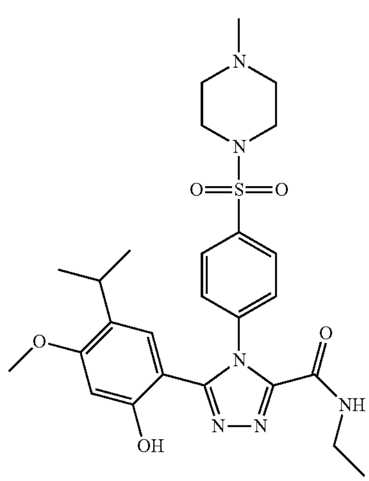 [SMILES: CCNC(=O)c1nnc(-c2cc(C(C)C)c(OC)cc2O)n1-c1ccc(S(=O)(=O)N2CCN(C)CC2)cc1] | N-ethyl-5-(2-hydroxy-5-isopropyl-4-methoxyphenyl)-4-(4-(4-methylpiperazin-1-ylsulfonyl)phenyl)-4H-1,2,4-triazole-3-carboxamide |

TABLE 1-continued

| No. | Structure | Name |
|---|---|---|
| 155 | 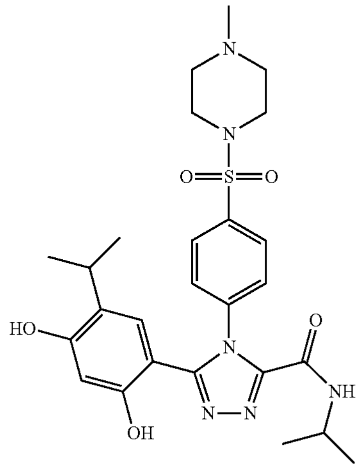 [SMILES: CC(C)NC(=O)c1nnc(-c2cc(C(C)C)c(O)cc2O)n1-c1ccc(S(=O)(=O)N2CCN(C)CC2)cc1] | 5-(2,4-dihydroxy-5-isopropylphenyl)-N-isopropyl-4-(4-(4-methylpiperazin-1-ylsulfonyl)phenyl)-4H-1,2,4-triazole-3-carboxamide |
| 156 | 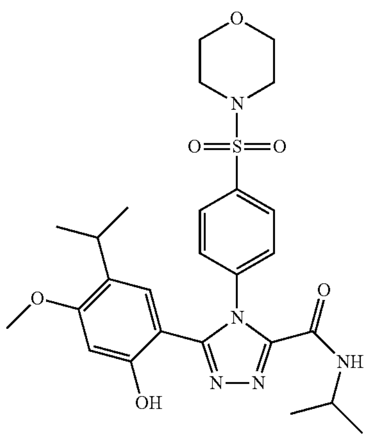 [SMILES: COc1cc(O)c(-c2nnc(C(=O)NC(C)C)n2-c2ccc(S(=O)(=O)N3CCOCC3)cc2)cc1C(C)C] | 5-(2-hydroxy-5-isopropyl-4-methoxyphenyl)-N-isopropyl-4-(4-(morpholinosulfonyl)phenyl)-4H-1,2,4-triazole-3-carboxamide |
| 157 | 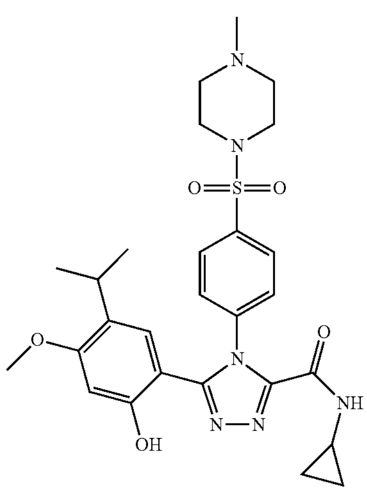 [SMILES: COc1cc(O)c(-c2nnc(C(=O)NC3CC3)n2-c2ccc(S(=O)(=O)N3CCN(C)CC3)cc2)cc1C(C)C] | N-cyclopropyl-5-(2-hydroxy-5-isopropyl-4-methoxyphenyl)-4-(4-(4-methylpiperazin-1-ylsulfonyl)phenyl)-4H-1,2,4-triazole-3-carboxamide |

TABLE 1-continued
| No. | Structure | Name |
|---|---|---|
| 158 | 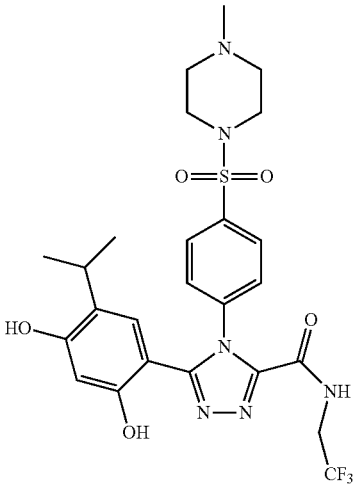 [SMILES: CC(C)c1cc(-c2nnc(C(=O)NCC(F)(F)F)n2-c2ccc(S(=O)(=O)N3CCN(C)CC3)cc2)c(O)cc1O] | 5-(2,4-dihydroxy-5-isopropylphenyl)-4-(4-(4-methylpiperazin-1-ylsulfonyl)phenyl)-N-(2,2,2-trifluoroethyl)-4H-1,2,4-triazole-3-carboxamide |
| 159 | 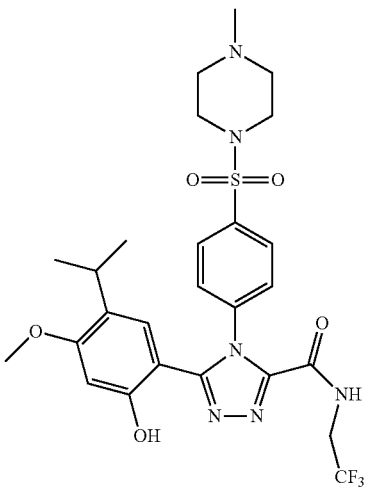 [SMILES: COc1cc(O)c(-c2nnc(C(=O)NCC(F)(F)F)n2-c2ccc(S(=O)(=O)N3CCN(C)CC3)cc2)cc1C(C)C] | 5-(2-hydroxy-5-isopropyl-4-methoxyphenyl)-4-(4-(4-methylpiperazin-1-ylsulfonyl)phenyl)-N-(2,2,2-trifluoroethyl)-4H-1,2,4-triazole-3-carboxamide |
| 160 | 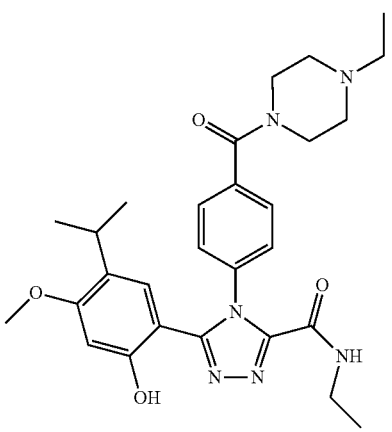 [SMILES: CCNC(=O)c1nnc(-c2cc(C(C)C)c(OC)cc2O)n1-c1ccc(C(=O)N2CCN(CC)CC2)cc1] | N-ethyl-4-(4-(4-ethylpiperazine-1-carbonyl)phenyl)-5-(2-hydroxy-5-isopropyl-4-methoxyphenyl)-4H-1,2,4-triazole-3-carboxamide |

TABLE 1-continued

| No. | Structure | Name |
|---|---|---|
| 161 | 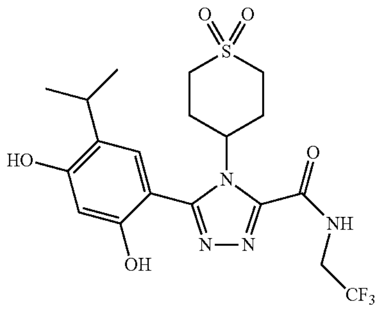 [SMILES: CC(C)c1cc(-c2nnc(C(=O)NCC(F)(F)F)n2C2CCS(=O)(=O)CC2)c(O)cc1O] | |
| 162 | 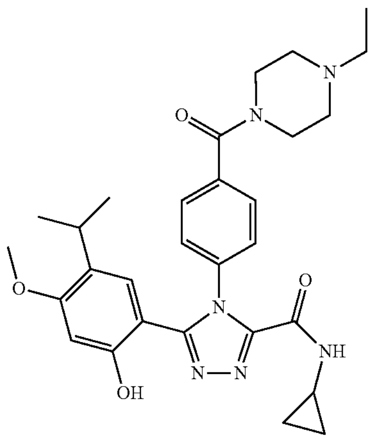 [SMILES: CCN1CCN(C(=O)c2ccc(-n3c(C(=O)NC4CC4)nnc3-c3cc(C(C)C)c(OC)cc3O)cc2)CC1] | N-cyclopropyl-4-(4-(4-ethylpiperazine-1-carbonyl)phenyl)-5-(2-hydroxy-5-isopropyl-4-methoxyphenyl)-4H-1,2,4-triazole-3-carboxamide |
| 163 | 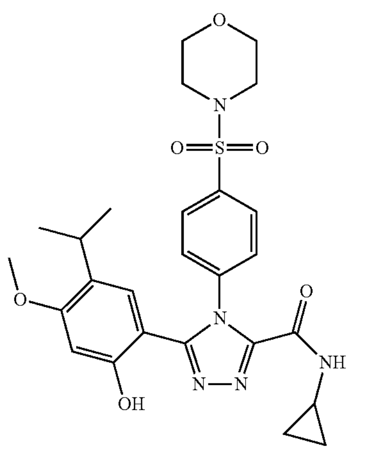 [SMILES: COc1cc(O)c(-c2nnc(C(=O)NC3CC3)n2-c2ccc(S(=O)(=O)N3CCOCC3)cc2)cc1C(C)C] | N-cyclopropyl-5-(2-hydroxy-5-isopropyl-4-methoxyphenyl)-4-(4-(morpholinosulfonyl)phenyl)-4H-1,2,4-triazole-3-carboxamide |
| 164 | 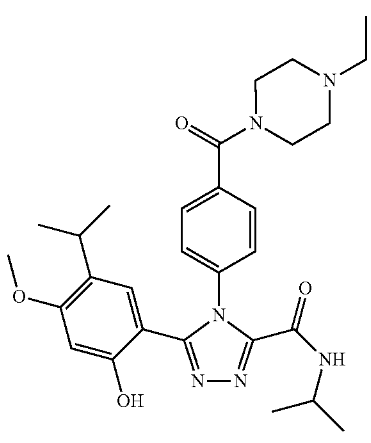 [SMILES: CCN1CCN(C(=O)c2ccc(-n3c(C(=O)NC(C)C)nnc3-c3cc(C(C)C)c(OC)cc3O)cc2)CC1] | 4-(4-(4-ethylpiperazine-1-carbonyl)phenyl)-5-(2-hydroxy isopropyl-4-methoxyphenyl)-N-isopropyl-4H-1,2,4-triazole-3-carboxamide |

TABLE 1-continued

| No. | Structure | Name |
|---|---|---|
| 165 | 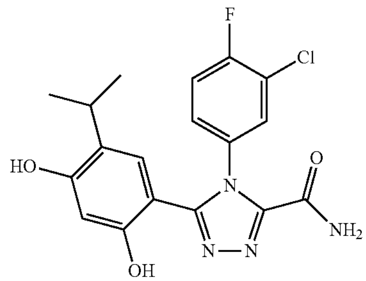 [SMILES: CC(C)c1cc(-c2nnc(C(N)=O)n2-c2ccc(F)c(Cl)c2)c(O)cc1O] | 4-(3-chloro-4-fluorophenyl)-5-(2,4-dihydroxy-5-isopropylphenyl)-4H-1,2,4-triazole-3-carboxamide |
| 166 | 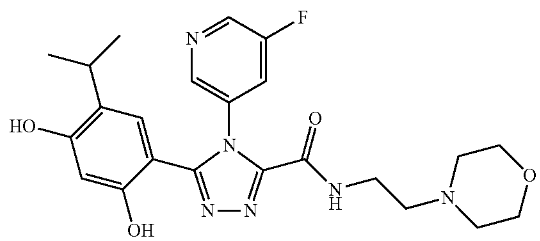 [SMILES: CC(C)c1cc(-c2nnc(C(=O)NCCN3CCOCC3)n2-c2cncc(F)c2)c(O)cc1O] | 5-(2,4-dihydroxy-5-isopropylphenyl)-4-(5-fluoropyridin-3-yl)-N-(2-morpholinoethyl)-4H-1,2,4-triazole-3-carboxamide |
| 167 | 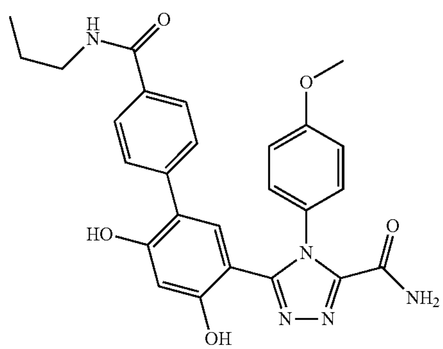 [SMILES: CCCNC(=O)c1ccc(-c2cc(-c3nnc(C(N)=O)n3-c3ccc(OC)cc3)c(O)cc2O)cc1] | 5-(4,6-dihydroxy-4'-(propylcarbamoyl)biphenyl-3-yl)-4-(4-methoxyphenyl)-4H-1,2,4-triazole-3-carboxamide |
| 168 | 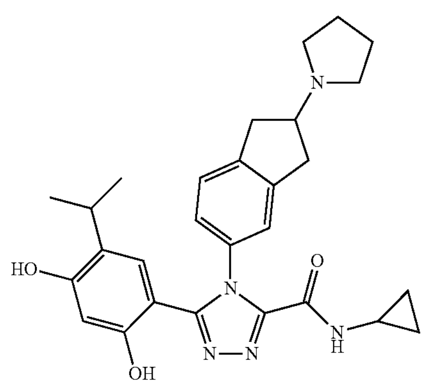 [SMILES: CC(C)c1cc(-c2nnc(C(=O)NC3CC3)n2-c2ccc3c(c2)CC(N2CCCC2)C3)c(O)cc1O] | N-cyclopropyl-5-(2,4-dihydroxy-5-isopropylphenyl)-4-(2-(pyrrolidin-1-yl)-2,3-dihydro-1H-inden-5-yl)-4H-1,2,4-triazole-3-carboxamide |

TABLE 1-continued

| No. | Structure | Name |
|---|---|---|
| 169 | 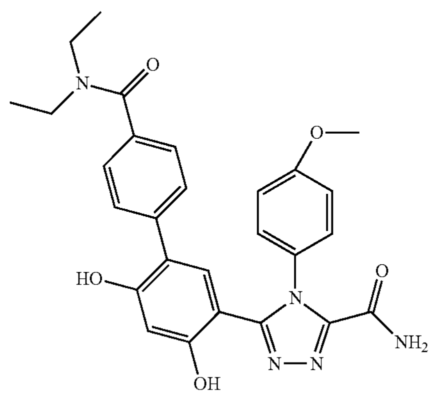 [SMILES: CCN(CC)C(=O)c1ccc(-c2cc(-c3nnc(C(N)=O)n3-c3ccc(OC)cc3)c(O)cc2O)cc1] | 5-(4'-(diethylcarbamoyl)-4,6-dihydroxybiphenyl-3-yl)-4-(4-methoxyphenyl)-4H-1,2,4-triazole-3-carboxamide |
| 170 | 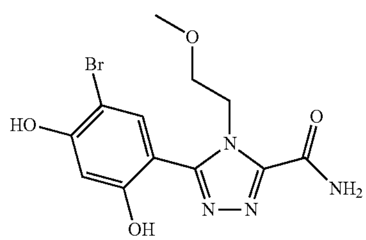 [SMILES: COCCn1c(C(N)=O)nnc1-c1cc(Br)c(O)cc1O] | 5-(5-bromo-2,4-dihydroxyphenyl)-4-(2-methoxyethyl)-4H-1,2,4-triazole-3-carboxamide |
| 171 | 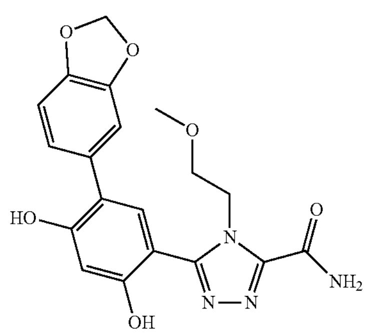 [SMILES: COCCn1c(C(N)=O)nnc1-c1cc(-c2ccc3c(c2)OCO3)c(O)cc1O] | 5-(5-(benzo[d][1,3]dioxol-5-yl)-2,4-dihydroxyphenyl)-4-(2-methoxyethyl)-4H-1,2,4-triazole-3-carboxamide |
| 172 | 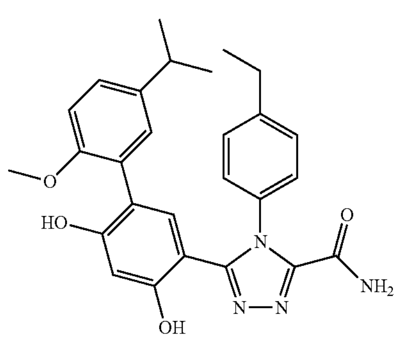 [SMILES: CCc1ccc(-n2c(C(N)=O)nnc2-c2cc(-c3cc(C(C)C)ccc3OC)c(O)cc2O)cc1] | 5-(4,6-dihydroxy-5'-isopropyl-2'-methoxybiphenyl-3-yl)-4-(4-ethylphenyl)-4H-1,2,4-triazole-3-carboxamide |

| No. | Structure | Name |
|---|---|---|
| 173 | 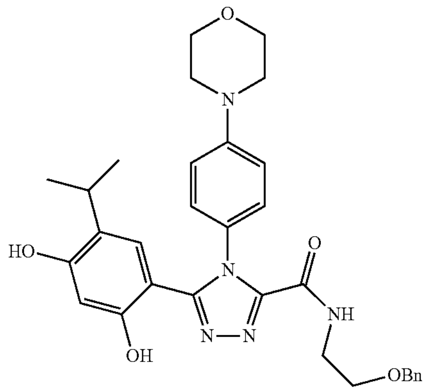 [SMILES: CC(C)c1cc(-c2nnc(C(=O)NCCOCc3ccccc3)n2-c2ccc(N3CCOCC3)cc2)c(O)cc1O] | N-(2-(benzyloxy)ethyl)-5-(2,4-dihydroxy-5-isopropylphenyl)-4-(4-morpholinophenyl)-4H-1,2,4-triazole-3-carboxamide |
| 174 | 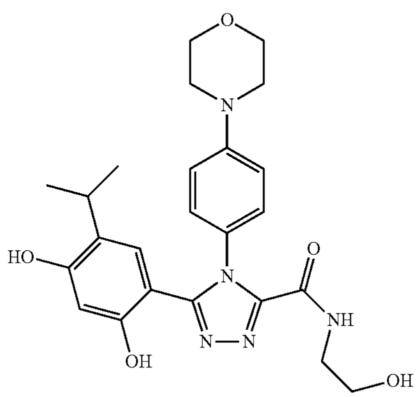 [SMILES: CC(C)c1cc(-c2nnc(C(=O)NCCO)n2-c2ccc(N3CCOCC3)cc2)c(O)cc1O] | 5-(2,4-dihydroxy-5-isopropylphenyl)-N-(2-hydroxyethyl)-4-(4-morpholinophenyl)-4H-1,2,4-triazole-3-carboxamide |
| 175 | 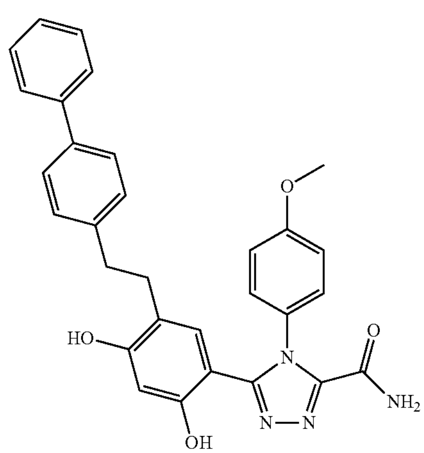 [SMILES: COc1ccc(-n2c(C(N)=O)nnc2-c2cc(CCc3ccc(-c4ccccc4)cc3)c(O)cc2O)cc1] | 5-(5-(2-([1,1'-biphenyl]-4-yl)ethyl)-2,4-dihydroxyphenyl)-4-(4-methoxyphenyl)-4H-1,2,4-triazole-3-carboxamide |

TABLE 1-continued
| No. | Structure | Name |
|---|---|---|
| 176 | 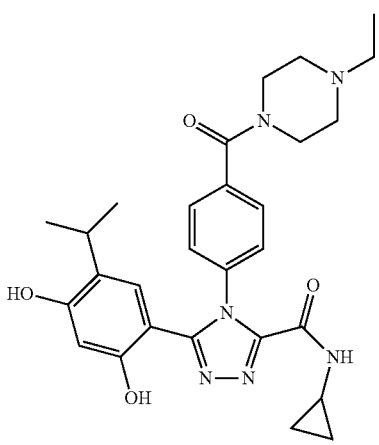 [SMILES: CCN1CCN(C(=O)c2ccc(-n3c(C(=O)NC4CC4)nnc3-c3cc(C(C)C)c(O)cc3O)cc2)CC1] | N-cyclopropyl-5-(2,4-dihydroxy-5-isopropylphenyl)-4-(4-(4-ethylpiperazine-1-carbonyl)phenyl)-4H-1,2,4-triazole-3-carboxamide |
| 177 | 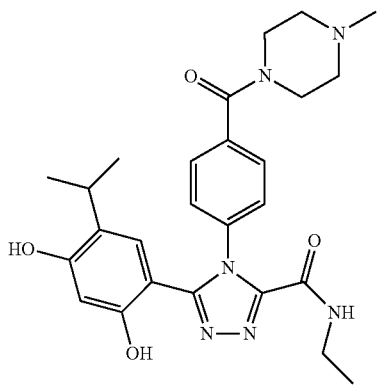 [SMILES: CCNC(=O)c1nnc(-c2cc(C(C)C)c(O)cc2O)n1-c1ccc(C(=O)N2CCN(C)CC2)cc1] | 5-(2,4-dihydroxy-5-isopropylphenyl)-N-ethyl-4-(4-(4-methylpiperazine-1-carbonyl)phenyl)-4H-1,2,4-triazole-3-carboxamide |
| 178 | 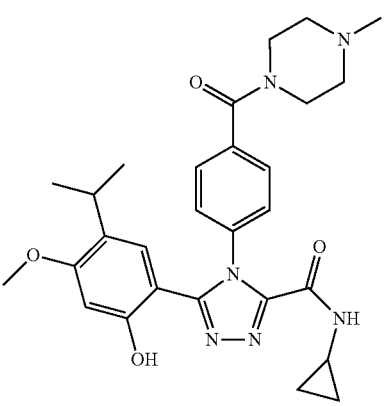 | N-cyclopropyl-5-(2-hydroxy-5-isopropyl-4-methoxyphenyl)-4-(4-(4-methylpiperazine-1-carbonyl)phenyl)-4H-1,2,4-triazole-3-carboxamide |

TABLE 1-continued

| No. | Structure | Name |
|---|---|---|
| 179 | 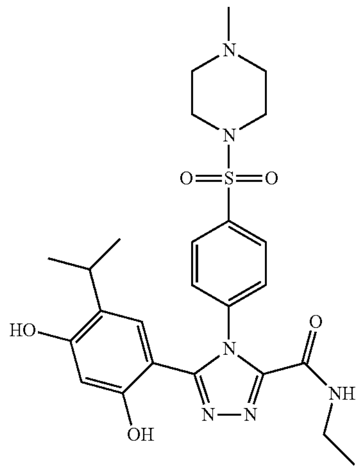 [SMILES: CCNC(=O)c1nnc(-c2cc(C(C)C)c(O)cc2O)n1-c1ccc(S(=O)(=O)N2CCN(C)CC2)cc1] | 5-(2,4-dihydroxy-5-isopropylphenyl)-N-ethyl-4-(4-(4-methylpiperazin-1-ylsulfonyl)phenyl)-4H-1,2,4-triazole-3-carboxamide |
| 180 | 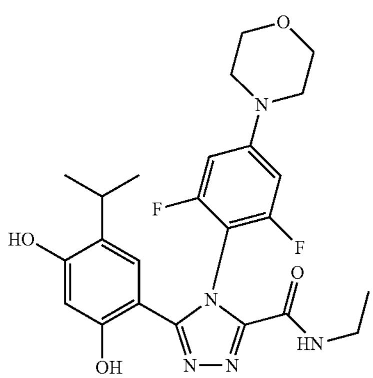 [SMILES: CCNC(=O)c1nnc(-c2cc(C(C)C)c(O)cc2O)n1-c1c(F)cc(N2CCOCC2)cc1F] | 4-(2,6-difluoro-4-morpholinophenyl)-5-(2,4-dihydroxy-5-isopropylphenyl)-N-ethyl-4H-1,2,4-triazole-3-carboxamide |
| 181 | 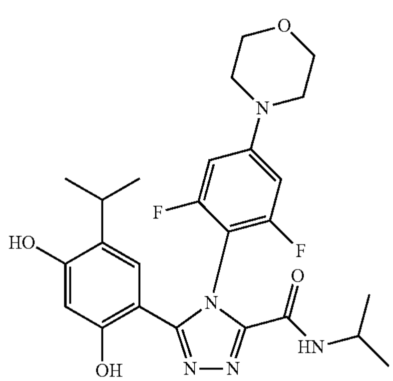 [SMILES: CC(C)NC(=O)c1nnc(-c2cc(C(C)C)c(O)cc2O)n1-c1c(F)cc(N2CCOCC2)cc1F] | 4-(2,6-difluoro-4-morpholinophenyl)-5-(2,4-dihydroxy-5-isopropylphenyl)-N-isopropyl-4H-1,2,4-triazole-3-carboxamide |

TABLE 1-continued

| No. | Structure | Name |
|---|---|---|
| 182 | 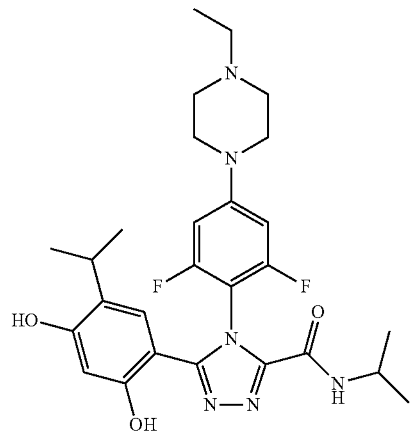 [SMILES: CCN1CCN(c2cc(F)c(-n3c(C(=O)NC(C)C)nnc3-c3cc(C(C)C)c(O)cc3O)c(F)c2)CC1] | 5-(2,4-dihydroxy-5-isopropylphenyl)-4-(4-(4-ethylpiperazin-1-yl)-2,6-difluorophenyl)-N-isopropyl-4H-1,2,4-triazole-3-carboxamide |
| 183 | 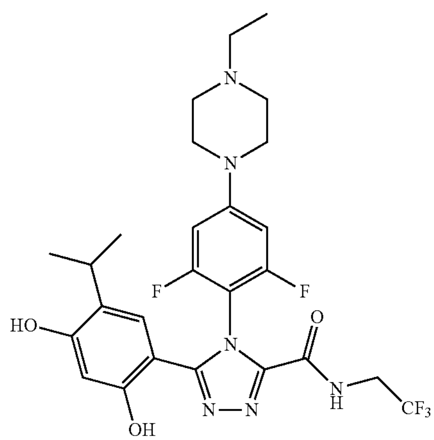 [SMILES: CCN1CCN(c2cc(F)c(-n3c(C(=O)NCC(F)(F)F)nnc3-c3cc(C(C)C)c(O)cc3O)c(F)c2)CC1] | 5-(2,4-dihydroxy-5-isopropylphenyl)-4-(4-(4-ethylpiperazin-1-yl)-2,6-difluorophenyl)-N-(2,2,2-trifluoroethyl)-4H-1,2,4-triazole-3-carboxamide |
| 184 | 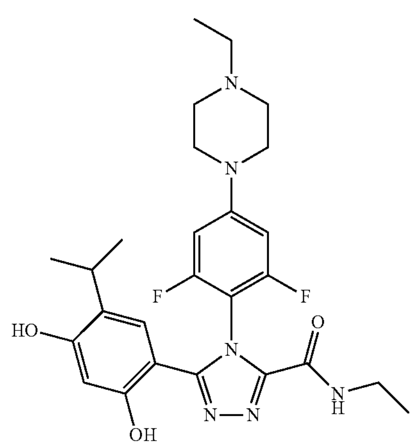 [SMILES: CCNC(=O)c1nnc(-c2cc(C(C)C)c(O)cc2O)n1-c1c(F)cc(N2CCN(CC)CC2)cc1F] | 5-(2,4-dihydroxy-5-isopropylphenyl)-N-ethyl-4-(4-(4-ethylpiperazin-1-yl)-2,6-difluorophenyl)-4H-1,2,4-triazole-3-carboxamide |

TABLE 1-continued

| No. | Structure | Name |
|---|---|---|
| 185 | 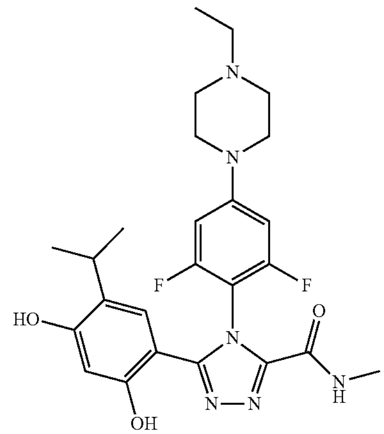 [SMILES: CCN1CCN(c2cc(F)c(-n3c(C(=O)NC)nnc3-c3cc(C(C)C)c(O)cc3O)c(F)c2)CC1] | 5-(2,4-dihydroxy-5-isopropylphenyl)-4-(4-(4-ethylpiperazin-1-yl)-2,6-difluorophenyl)-N-methyl-4H-1,2,4-triazole-3-carboxamide |
| 186 | 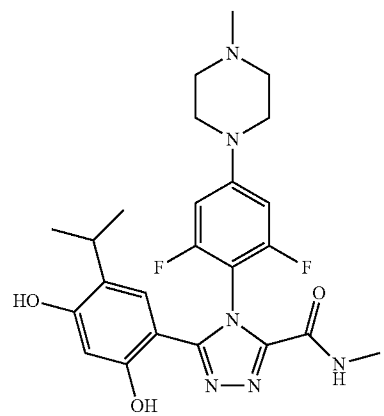 [SMILES: CNC(=O)c1nnc(-c2cc(C(C)C)c(O)cc2O)n1-c1c(F)cc(N2CCN(C)CC2)cc1F] | 4-(2,6-difluoro-4-(4-methylpiperazin-1-yl)phenyl)-5-(2,4-dihydroxy-5-isopropylphenyl)-N-methyl-4H-1,2,4-triazole-3-carboxamide |
| 187 | 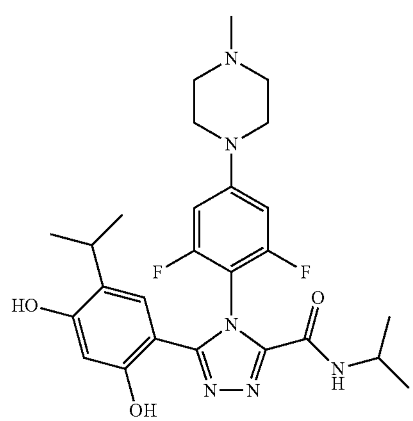 [SMILES: CC(C)NC(=O)c1nnc(-c2cc(C(C)C)c(O)cc2O)n1-c1c(F)cc(N2CCN(C)CC2)cc1F] | 4-(2,6-difluoro-4-(4-methylpiperazin-1-yl)phenyl)-5-(2,4-dihydroxy-5-isopropylphenyl)-N-isopropyl-4H-1,2,4-triazole-3-carboxamide |

TABLE 1-continued

| No. | Structure | Name |
|---|---|---|
| 188 | 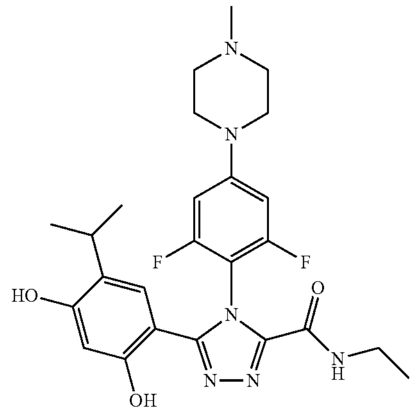 [SMILES: CCNC(=O)c1nnc(-c2cc(C(C)C)c(O)cc2O)n1-c1c(F)cc(N2CCN(C)CC2)cc1F] | 4-(2,6-difluoro-4-(4-methylpiperazin-1-yl)phenyl)-5-(2,4-dihydroxy-5-isopropylphenyl)-N-ethyl-4H-1,2,4-triazole-3-carboxamide |
| 189 | 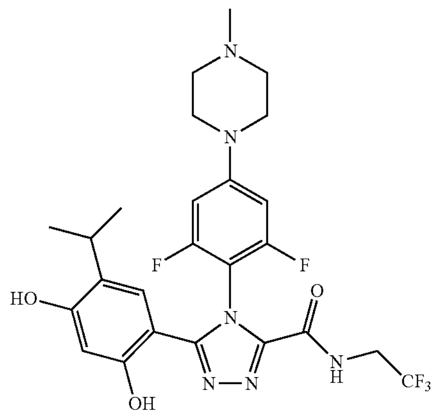 [SMILES: CC(C)c1cc(-c2nnc(C(=O)NCC(F)(F)F)n2-c2c(F)cc(N3CCN(C)CC3)cc2F)c(O)cc1O] | 4-(2,6-difluoro-4-(4-methylpiperazin-1-yl)phenyl)-5-(2,4-dihydroxy-5-isopropylphenyl)-N-(2,2,2-trifluoroethyl)-4H-1,2,4-triazole-3-carboxamide |
| 190 | 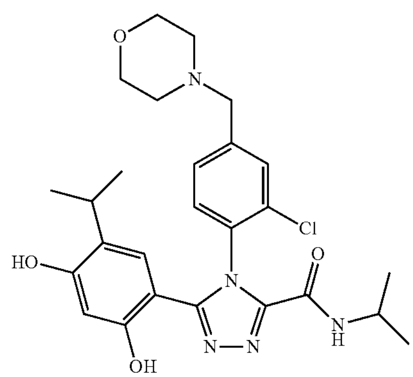 [SMILES: CC(C)NC(=O)c1nnc(-c2cc(C(C)C)c(O)cc2O)n1-c1ccc(CN2CCOCC2)cc1Cl] | 4-(2-chloro-4-(morpholinomethyl)phenyl)-5-(2,4-dihydroxy-5-isopropylphenyl)-N-isopropyl-4H-1,2,4-triazole-3-carboxamide |
| 191 | 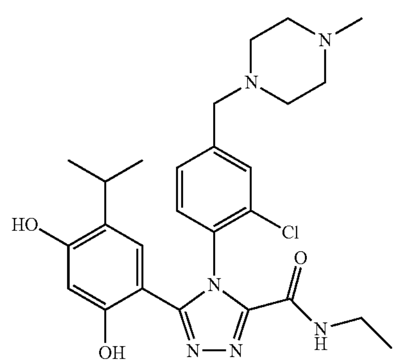 [SMILES: CCNC(=O)c1nnc(-c2cc(C(C)C)c(O)cc2O)n1-c1ccc(CN2CCN(C)CC2)cc1Cl] | 4-(2-chloro-4-((4-methylpiperazin-1-yl)methyl)phenyl)-5-(2,4-dihydroxy-5-isopropylphenyl)-N-ethyl-4H-1,2,4-triazole-3-carboxamide |

| No. | Structure | Name |
|---|---|---|
| 192 | 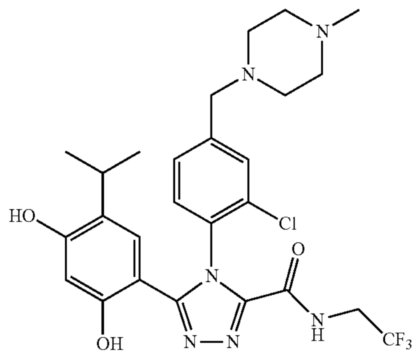 [SMILES: CC(C)c1cc(-c2nnc(C(=O)NCC(F)(F)F)n2-c2ccc(CN3CCN(C)CC3)cc2Cl)c(O)cc1O] | 4-(2-chloro-4-((4-methylpiperazin-1-yl)methyl)phenyl)-5-(2,4-dihydroxy-5-isopropylphenyl)-N-(2,2,2-trifluoroethyl)-4H-1,2,4-triazole-3-carboxamide |
| 193 | 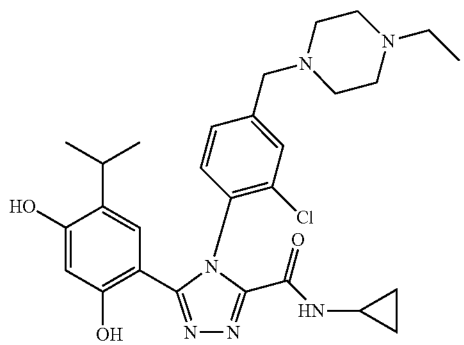 [SMILES: CCN1CCN(Cc2ccc(-n3c(C(=O)NC4CC4)nnc3-c3cc(C(C)C)c(O)cc3O)c(Cl)c2)CC1] | 4-(2-chloro-4-((4-ethylpiperazin-1-yl)methyl)phenyl)-N-cyclopropyl-5-(2,4-dihydroxy-5-isopropylphenyl)-4H-1,2,4-triazole-3-carboxamide |
| 194 | 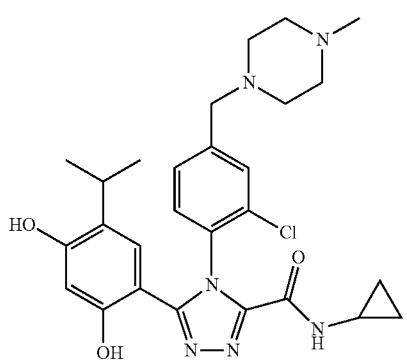 [SMILES: CC(C)c1cc(-c2nnc(C(=O)NC3CC3)n2-c2ccc(CN3CCN(C)CC3)cc2Cl)c(O)cc1O] | 4-(2-chloro-4-((4-methylpiperazin-1-yl)methyl)phenyl)-N-cyclopropyl-5-(2,4-dihydroxy-5-isopropylphenyl)-4H-1,2,4-triazole-3-carboxamide |
| 195 | 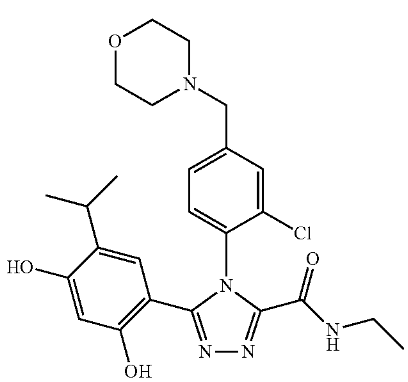 [SMILES: CCNC(=O)c1nnc(-c2cc(C(C)C)c(O)cc2O)n1-c1ccc(CN2CCOCC2)cc1Cl] | 4-(2-chloro-4-(morpholinomethyl)phenyl)-5-(2,4-dihydroxy-5-isopropylphenyl)-N-ethyl-4H-1,2,4-triazole-3-carboxamide |

TABLE 1-continued

| No. | Structure | Name |
|---|---|---|
| 196 | 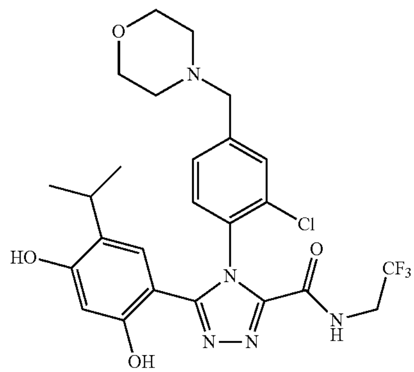 [SMILES: CC(C)c1cc(-c2nnc(C(=O)NCC(F)(F)F)n2-c2ccc(CN3CCOCC3)cc2Cl)c(O)cc1O] | 4-(2-chloro-4-(morpholinomethyl)phenyl)-5-(2,4-dihydroxy-5-isopropylphenyl)-N-(2,2,2-trifluoroethyl)-4H-1,2,4-triazole-3-carboxamide |
| 197 | 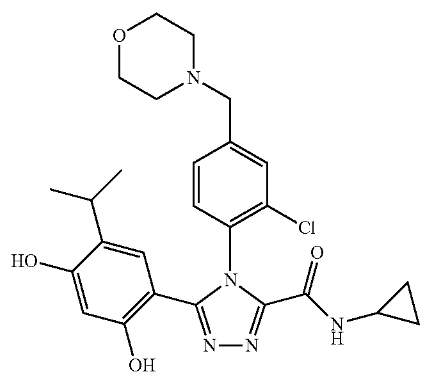 [SMILES: CC(C)c1cc(-c2nnc(C(=O)NC3CC3)n2-c2ccc(CN3CCOCC3)cc2Cl)c(O)cc1O] | 4-(2-chloro-4-(morpholinomethyl)phenyl)-N-cyclopropyl-5-(2,4-dihydroxy-5-isopropylphenyl)-4H-1,2,4-triazole-3-carboxamide |
| 198 | 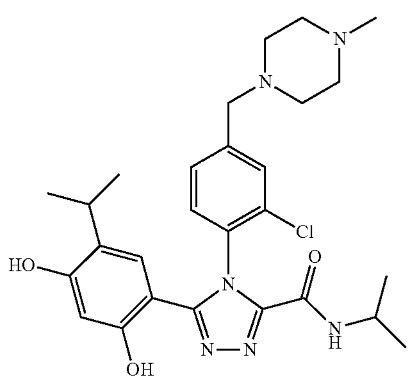 [SMILES: CC(C)NC(=O)c1nnc(-c2cc(C(C)C)c(O)cc2O)n1-c1ccc(CN2CCN(C)CC2)cc1Cl] | 4-(2-chloro-4-((4-methylpiperazin-1-yl)methyl)phenyl)-5-(2,4-dihydroxy-5-isopropylphenyl)-N-isopropyl-4H-1,2,4-triazole-3-carboxamide |
| 199 | 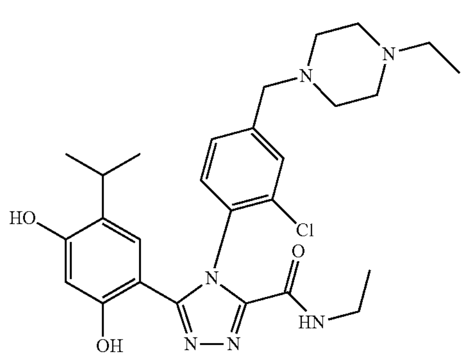 [SMILES: CCNC(=O)c1nnc(-c2cc(C(C)C)c(O)cc2O)n1-c1ccc(CN2CCN(CC)CC2)cc1Cl] | 4-(2-chloro-4-((4-ethylpiperazin-1-yl)methyl)phenyl)-5-(2,4-dihydroxy-5-isopropylphenyl)-N-ethyl-4H-1,2,4-triazole-3-carboxamide |

TABLE 1-continued

| No. | Structure | Name |
|---|---|---|
| 200 | 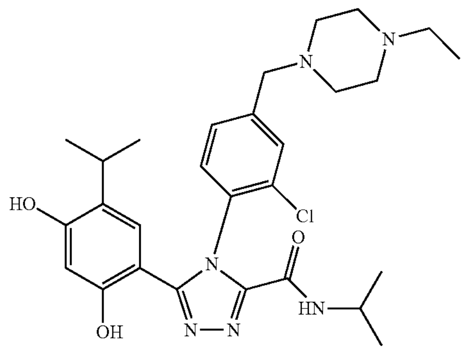 [SMILES: CCN1CCN(Cc2ccc(-n3c(C(=O)NC(C)C)nnc3-c3cc(C(C)C)c(O)cc3O)c(Cl)c2)CC1] | 4-(2-chloro-4-((4-ethylpiperazin-1-yl)methyl)phenyl)-5-(2,4-dihydroxy-5-isopropylphenyl)-N-isopropyl-4H-1,2,4-triazole-3-carboxamide |
| 201 | 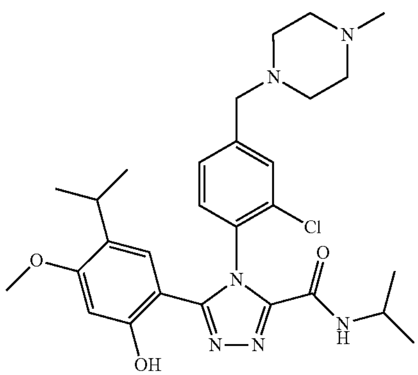 [SMILES: COc1cc(O)c(-c2nnc(C(=O)NC(C)C)n2-c2ccc(CN3CCN(C)CC3)cc2Cl)cc1C(C)C] | 4- (2-chloro-4-((4-methylpiperazin-1-yl)methyl)phenyl)-5-(2-hydroxy-5-isopropyl-4-methoxyphenyl)-N-isopropyl-4H-1,2,4-triazole-3-carboxamide |
| 202 | 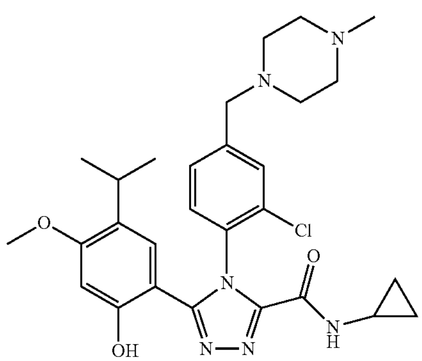 [SMILES: COc1cc(O)c(-c2nnc(C(=O)NC3CC3)n2-c2ccc(CN3CCN(C)CC3)cc2Cl)cc1C(C)C] | 4-(2-chloro-4-((4-methylpiperazin-1-yl)methyl)phenyl)-N-cyclopropyl-5-(2-hydroxy-5-isopropyl-4-methoxyphenyl)-4H-1,2,4-triazole-3-carboxamide |
| 203 | 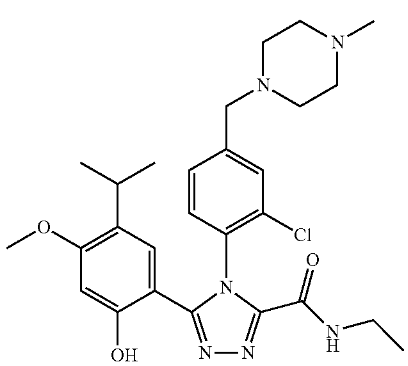 | 4-(2-chloro-4-((4-methylpiperazin-1-yl)methyl)phenyl)-N-ethyl-5-(2-hydroxy-5-isopropyl-4-methoxyphenyl)-4H-1,2,4-triazole-3-carboxamide |

TABLE 1-continued

| No. | Structure | Name |
|---|---|---|
| 204 | 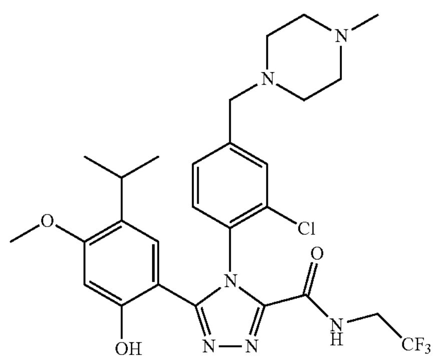 [SMILES: COc1cc(O)c(-c2nnc(C(=O)NCC(F)(F)F)n2-c2ccc(CN3CCN(C)CC3)cc2Cl)cc1C(C)C] | 4-(2-chloro-4-((4-methylpiperazin-1-yl)methyl)phenyl)-5-(2-hydroxy-5-isopropyl-4-methoxyphenyl)-N-(2,2,2-trifluoroethyl)-4H-1,2,4-triazole-3-carboxamide |
| 205 | 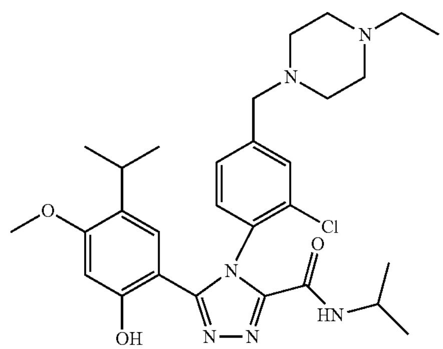 [SMILES: CCN1CCN(Cc2ccc(-n3c(C(=O)NC(C)C)nnc3-c3cc(C(C)C)c(OC)cc3O)c(Cl)c2)CC1] | 4-(2-chloro-4-((4-ethylpiperazin-1-yl)methyl)phenyl)-5-(2-hydroxy-5-isopropyl-4-methoxyphenyl)-N-isopropyl-4H-1,2,4-triazole-3-carboxamide |
| 206 | 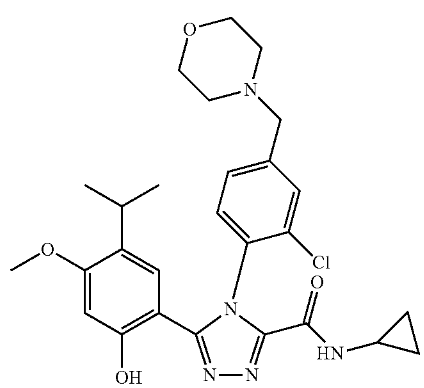 [SMILES: COc1cc(O)c(-c2nnc(C(=O)NC3CC3)n2-c2ccc(CN3CCOCC3)cc2Cl)cc1C(C)C] | 4-(2-chloro-4-(morpholinomethyl)phenyl)-N-cyclopropyl-5-(2-hydroxy-5-isopropyl-4-methoxyphenyl)-4H-1,2,4-triazole-3-carboxamide |
| 207 | 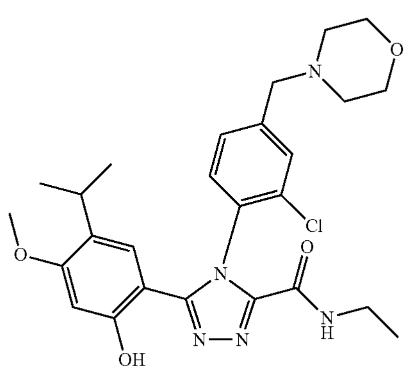 [SMILES: CCNC(=O)c1nnc(-c2cc(C(C)C)c(OC)cc2O)n1-c1ccc(CN2CCOCC2)cc1Cl] | 4-(2-chloro-4-(morpholinomethyl)phenyl)-N-ethyl-5-(2-hydroxy-5-isopropyl-4-methoxyphenyl)-4H-1,2,4-triazole-3-carboxamide |

TABLE 1-continued

| No. | Structure | Name |
|---|---|---|
| 208 | 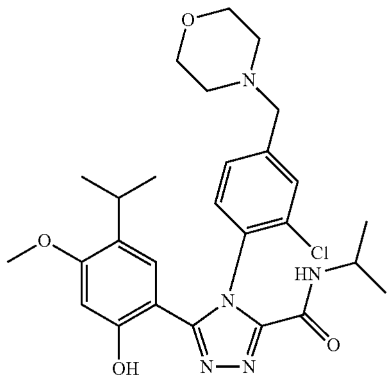 [SMILES: COc1cc(O)c(-c2nnc(C(=O)NC(C)C)n2-c2ccc(CN3CCOCC3)cc2Cl)cc1C(C)C] | 4-(2-chloro-4-(morpholinomethyl)phenyl)-5-(2-hydroxy-5-isopropyl-4-methoxyphenyl)-N-isopropyl-4H-1,2,4-triazole-3-carboxamide |
| 209 | 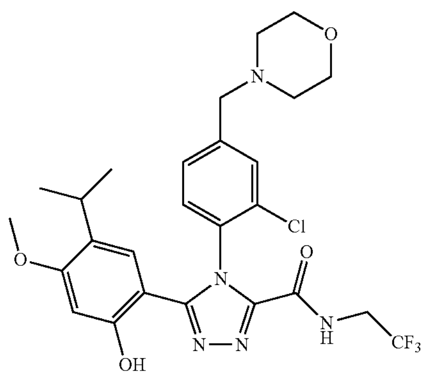 [SMILES: COc1cc(O)c(-c2nnc(C(=O)NCC(F)(F)F)n2-c2ccc(CN3CCOCC3)cc2Cl)cc1C(C)C] | 4-(2-chloro-4-(morpholinomethyl)phenyl)-5-(2-hydroxy-5-isopropyl-4-methoxyphenyl)-N-(2,2,2-trifluoroethyl)-4H-1,2,4-triazole-3-carboxamide |
| 210 | 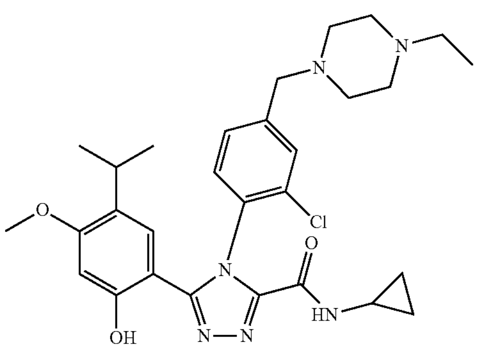 [SMILES: CCN1CCN(Cc2ccc(-n3c(C(=O)NC4CC4)nnc3-c3cc(C(C)C)c(OC)cc3O)c(Cl)c2)CC1] | 4-(2-chloro-4-((4-ethylpiperazin-1-yl)methyl)phenyl)-N-cyclopropyl-5-(2-hydroxy-5-isopropyl-4-methoxyphenyl)-4H-1,2,4-triazole-3-carboxamide |
| 211 | 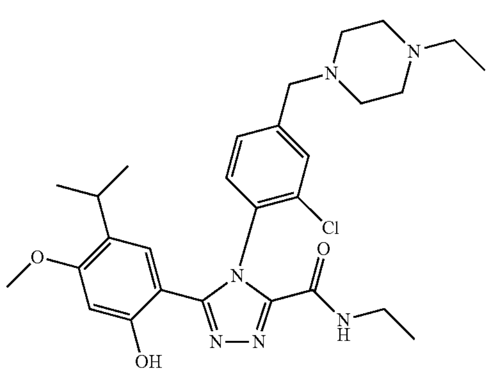 [SMILES: CCNC(=O)c1nnc(-c2cc(C(C)C)c(OC)cc2O)n1-c1ccc(CN2CCN(CC)CC2)cc1Cl] | 4-(2-chloro-4-((4-ethylpiperazin-1-yl)methyl)phenyl)-N-ethyl-5-(2-hydroxy-5-isopropyl-4-methoxyphenyl)-4H-1,2,4-triazole-3-carboxamide |

TABLE 1-continued

| No. | Structure | Name |
|---|---|---|
| 212 | 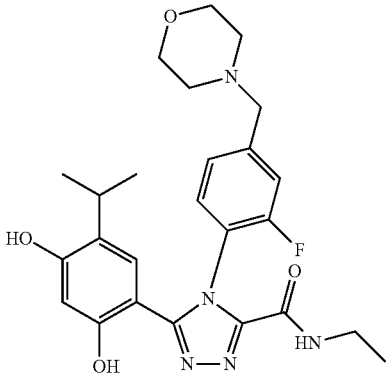 [SMILES: CCNC(=O)c1nnc(-c2cc(C(C)C)c(O)cc2O)n1-c1ccc(CN2CCOCC2)cc1F] | 5-(2,4-dihydroxy-5-isopropylphenyl)-N-ethyl-4-(2-fluoro-4-(morpholino-methyl)phenyl)-4H-1,2,4-triazole-3-carboxamide |
| 213 | 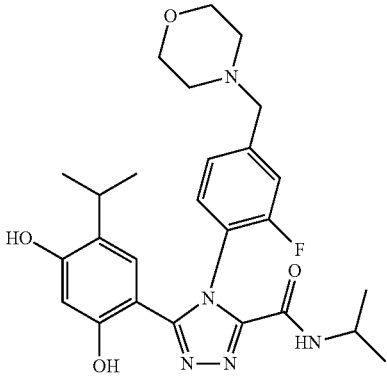 [SMILES: CC(C)NC(=O)c1nnc(-c2cc(C(C)C)c(O)cc2O)n1-c1ccc(CN2CCOCC2)cc1F] | 5-(2,4-dihydroxy-5-isopropylphenyl)-4-(2-fluoro-4-(morpholinomethyl)-phenyl)-N-isopropyl-4H-1,2,4-triazole-3-carboxamide |
| 214 | 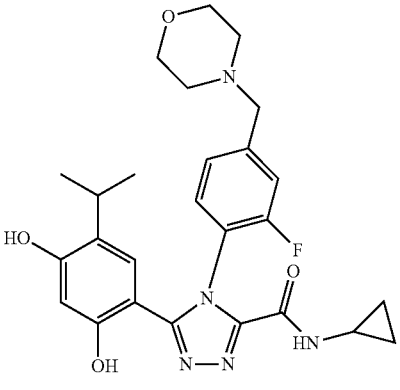 [SMILES: CC(C)c1cc(-c2nnc(C(=O)NC3CC3)n2-c2ccc(CN3CCOCC3)cc2F)c(O)cc1O] | N-cyclopropyl-5-(2,4-dihydroxy-5-isopropylphenyl)-4-(2-fluoro-4-(morpholinomethyl)-phenyl)-4H-1,2,4-triazole-3-carboxamide |
| 215 | 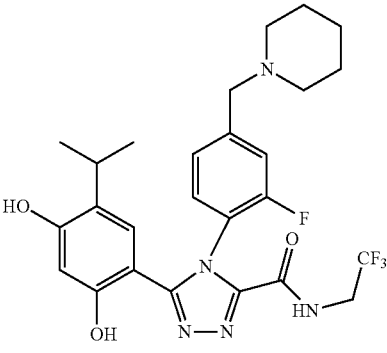 [SMILES: CC(C)c1cc(-c2nnc(C(=O)NCC(F)(F)F)n2-c2ccc(CN3CCCCC3)cc2F)c(O)cc1O] | 5-(2,4-dihydroxy-5-isopropylphenyl)-4-(2-fluoro-4-(morpholinomethyl)-phenyl)-N-(2,2,2-trifluoroethyl)-4H-1,2,4-triazole-3-carboxamide |

TABLE 1-continued

| No. | Structure | Name |
|---|---|---|
| 216 | 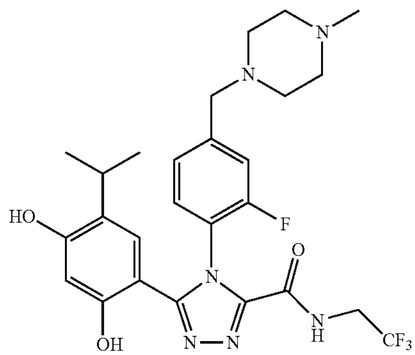 | 5-(2,4-dihydroxy-5-isopropylphenyl)-4-(2-fluoro-4-((4-methylpiperazin-1-yl)methyl)phenyl)-N-(2,2,2-trifluoroethyl)-4H-1,2,4-triazole-3-carboxamide |
| 217 | 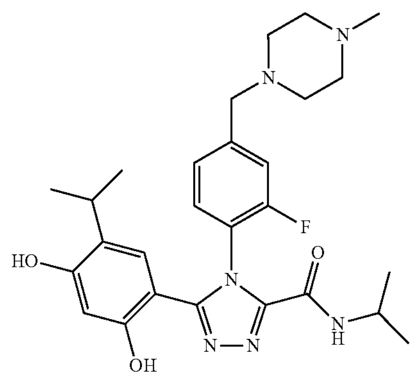 [SMILES: CC(C)NC(=O)c1nnc(-c2cc(C(C)C)c(O)cc2O)n1-c1ccc(CN2CCN(C)CC2)cc1F] | 5-(2,4-dihydroxy-5-isopropylphenyl)-4-(2-fluoro-4-((4-methylpiperazin-1-yl)methyl)phenyl)-N-isopropyl-4H-1,2,4-triazole-3-carboxamide |
| 218 | 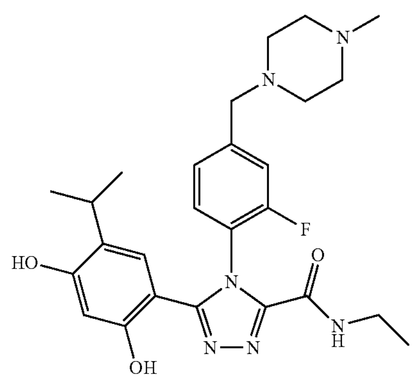 [SMILES: CCNC(=O)c1nnc(-c2cc(C(C)C)c(O)cc2O)n1-c1ccc(CN2CCN(C)CC2)cc1F] | 5-(2,4-dihydroxy-5-isopropylphenyl)-N-ethyl-4-(2-fluoro-4-((4-methylpiperazin-1-yl)methyl)phenyl)-4H-1,2,4-triazole-3-carboxamide |
| 219 | 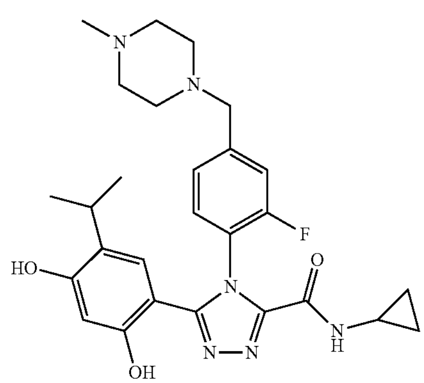 [SMILES: CC(C)c1cc(-c2nnc(C(=O)NC3CC3)n2-c2ccc(CN3CCN(C)CC3)cc2F)c(O)cc1O] | N-cyclopropyl-5-(2,4-dihydroxy-5-isopropylphenyl)-4-(2-fluoro-4-((4-methylpiperazin-1-yl)methyl)phenyl)-4H-1,2,4-triazole-3-carboxamide |

TABLE 1-continued

| No. | Structure | Name |
|---|---|---|
| 220 | 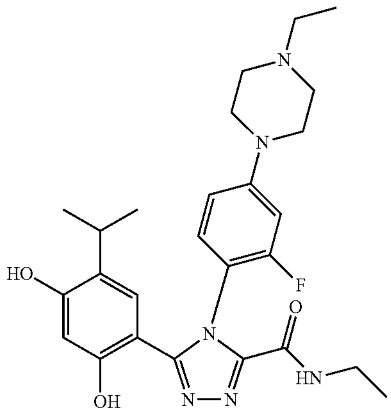 [SMILES: CCNC(=O)c1nnc(-c2cc(C(C)C)c(O)cc2O)n1-c1ccc(N2CCN(CC)CC2)cc1F] | 5-(2,4-dihydroxy-5-isopropylphenyl)-N-ethyl-4-(4-(4-ethylpiperazin-1-yl)-2-fluorophenyl)-4H-1,2,4-triazole-3-carboxamide |
| 221 | 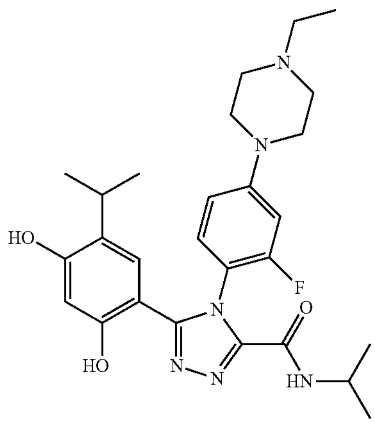 [SMILES: CCN1CCN(c2ccc(-n3c(C(=O)NC(C)C)nnc3-c3cc(C(C)C)c(O)cc3O)c(F)c2)CC1] | 5-(2,4-dihydroxy-5-isopropylphenyl)-4-(4-(4-ethylpiperazin-1-yl)-2-fluorophenyl)-N-isopropyl-4H-1,2,4-triazole-3-carboxamide |
| 222 | 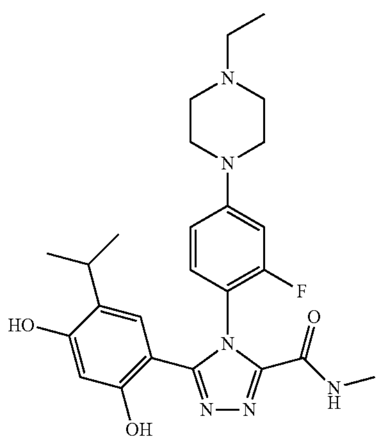 [SMILES: CCN1CCN(c2ccc(-n3c(C(=O)NC)nnc3-c3cc(C(C)C)c(O)cc3O)c(F)c2)CC1] | 5-(2,4-dihydroxy-5-isopropylphenyl)-4-(4-(4-ethylpiperazin-1-yl)-2-fluorophenyl)-N-methyl-4H-1,2,4-triazole-3-carboxamide |
| 223 | 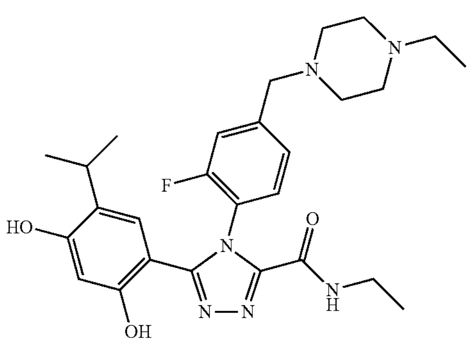 [SMILES: CCNC(=O)c1nnc(-c2cc(C(C)C)c(O)cc2O)n1-c1ccc(CN2CCN(CC)CC2)cc1F] | 5-(2,4-dihydroxy-5-isopropylphenyl)-N-ethyl-4-(4-((4-ethylpiperazin-1-yl)methyl)-2-fluorophenyl)-4H-1,2,4-triazole-3-carboxamide |

| No. | Structure | Name |
|---|---|---|
| 224 | 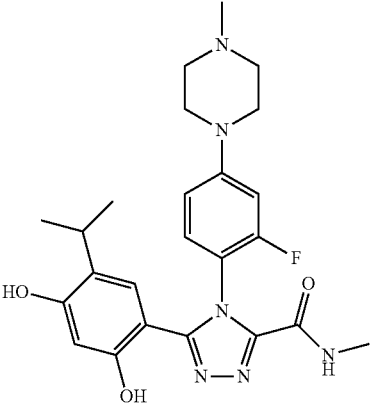 [SMILES: CNC(=O)c1nnc(-c2cc(C(C)C)c(O)cc2O)n1-c1ccc(N2CCN(C)CC2)cc1F] | 5-(2,4-dihydroxy-5-isopropylphenyl)-4-(2-fluoro-4-(4-methylpiperazin-1-yl)phenyl)-N-methyl-4H-1,2,4-triazole-3-carboxamide |
| 225 | 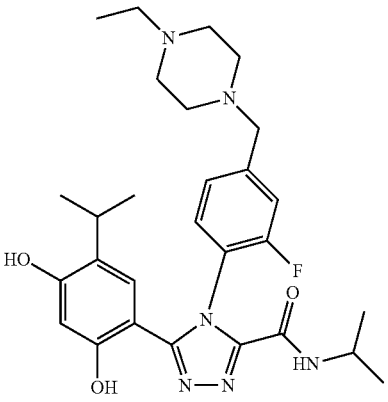 [SMILES: CCN1CCN(Cc2ccc(-n3c(C(=O)NC(C)C)nnc3-c3cc(C(C)C)c(O)cc3O)c(F)c2)CC1] | 5-(2,4-dihydroxy-5-isopropylphenyl)-4-(4-((4-ethylpiperazin-1-yl)methyl)-2-fluorophenyl)-N-isopropyl-4H-1,2,4-triazole-3-carboxamide |
| 226 | 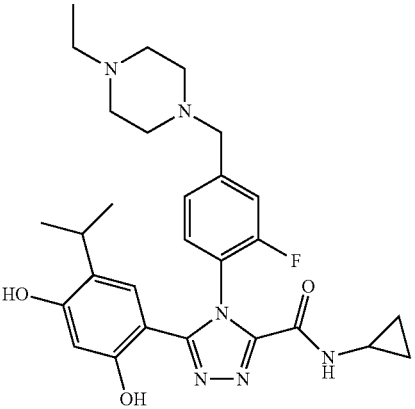 [SMILES: CCN1CCN(Cc2ccc(-n3c(C(=O)NC4CC4)nnc3-c3cc(C(C)C)c(O)cc3O)c(F)c2)CC1] | N-cyclopropyl-5-(2,4-dihydroxy-5-isopropylphenyl)-4-(4-((4-ethylpiperazin-1-yl)methyl)-2-fluorophenyl)-4H-1,2,4-triazole-3-carboxamide |

TABLE 1-continued

| No. | Structure | Name |
|---|---|---|
| 227 | 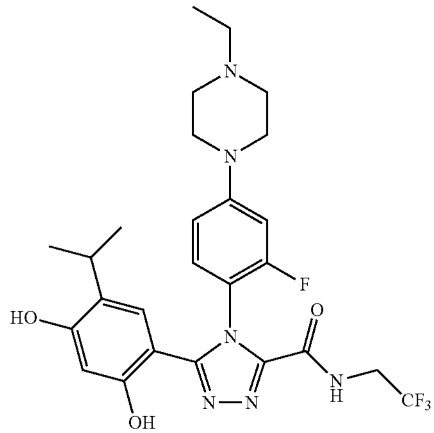 [SMILES: CCN1CCN(c2ccc(-n3c(C(=O)NCC(F)(F)F)nnc3-c3cc(C(C)C)c(O)cc3O)c(F)c2)CC1] | 5-(2,4-dihydroxy-5-isopropylphenyl)-4-(4-(4-ethylpiperazin-1-yl)-2-fluorophenyl)-N-(2,2,2-trifluoroethyl)-4H-1,2,4-triazole-3-carboxamide |
| 228 | 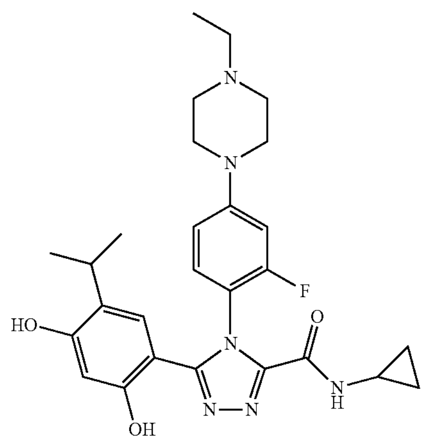 [SMILES: CCN1CCN(c2ccc(-n3c(C(=O)NC4CC4)nnc3-c3cc(C(C)C)c(O)cc3O)c(F)c2)CC1] | N-cyclopropyl-5-(2,4-dihydroxy-5-isopropylphenyl)-4-(4-(4-ethylpiperazin-1-yl)-2-fluorophenyl)-4H-1,2,4-triazole-3-carboxamide |
| 229 | 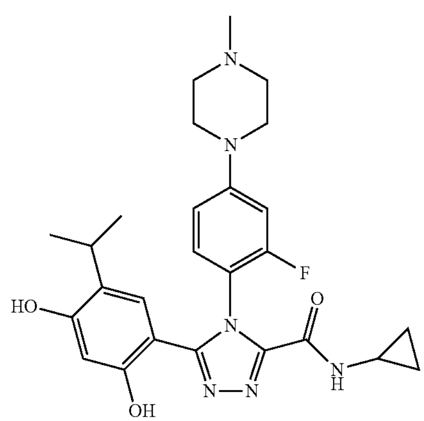 [SMILES: CC(C)c1cc(-c2nnc(C(=O)NC3CC3)n2-c2ccc(N3CCN(C)CC3)cc2F)c(O)cc1O] | N-cyclopropyl-5-(2,4-dihydroxy-5-isopropylphenyl)-4-(2-fluoro-4-(4-methylpiperazin-1-yl)phenyl)-4H-1,2,4-triazole-3-carboxamide |

TABLE 1-continued

| No. | Structure | Name |
|---|---|---|
| 230 | 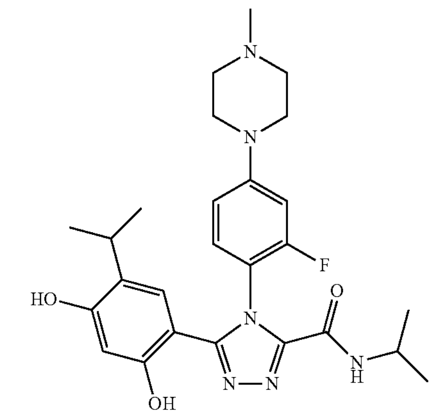 [SMILES: CC(C)NC(=O)c1nnc(-c2cc(C(C)C)c(O)cc2O)n1-c1ccc(N2CCN(C)CC2)cc1F] | 5-(2,4-dihydroxy-5-isopropylphenyl)-4-(2-fluoro-4-(4-methylpiperazin-1-yl)phenyl)-N-isopropyl-4H-1,2,4-triazole-3-carboxamide |
| 231 | 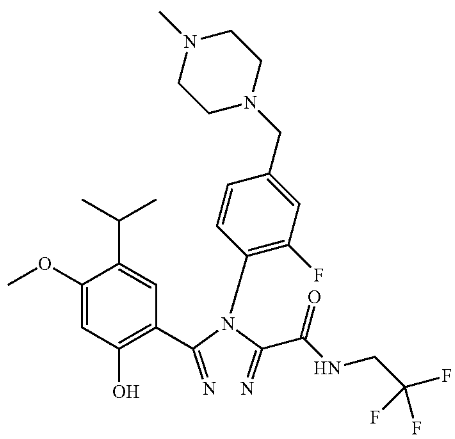 [SMILES: COc1cc(O)c(C(=N)N(C(=N)C(=O)NCC(F)(F)F)c2ccc(CN3CCN(C)CC3)cc2F)cc1C(C)C] | 4-(2-fluoro-4-((4-methylpiperazin-1-yl)methyl)phenyl)-5-(2-hydroxy-5-isopropyl-4-methoxyphenyl)-N-(2,2,2-trifluoroethyl)-4H-1,2,4-triazole-3-carboxamide |
| 232 | 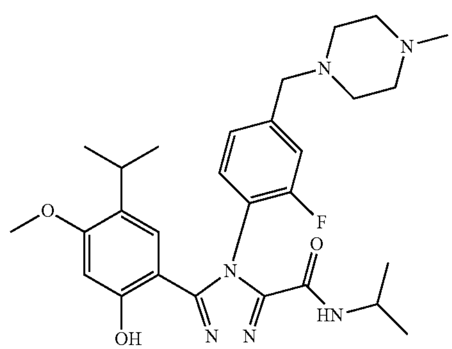 | 4-(2-fluoro-4-((4-methylpiperazin-1-yl)methyl)phenyl)-5-(2-hydroxy-5-isopropyl-4-methoxyphenyl)-N-isopropyl-4H-1,2,4-triazole-3-carboxamide |
| 233 | 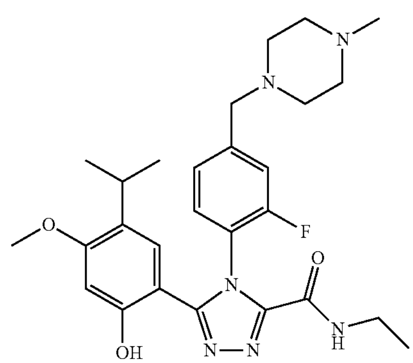 [SMILES: CCNC(=O)c1nnc(-c2cc(C(C)C)c(OC)cc2O)n1-c1ccc(CN2CCN(C)CC2)cc1F] | N-ethyl-4-(2-fluoro-4-((4-methylpiperazin-1-yl)methyl)phenyl)-5-(2-hydroxy-5-isopropyl-4-methoxyphenyl)-4H-1,2,4-triazole-3-carboxamide |

| No. | Structure | Name |
|---|---|---|
| 234 | 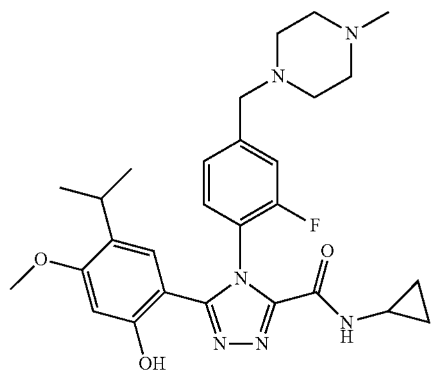 [SMILES: COc1cc(O)c(-c2nnc(C(=O)NC3CC3)n2-c2ccc(CN3CCN(C)CC3)cc2F)cc1C(C)C] | N-cyclopropyl-4-(2-fluoro-4-((4-methylpiperazin-1-yl)methyl)phenyl)-5-(2-hydroxy-5-isopropyl-4-methoxyphenyl)-4H-1,2,4-triazole-3-carboxamide |
| 235 | 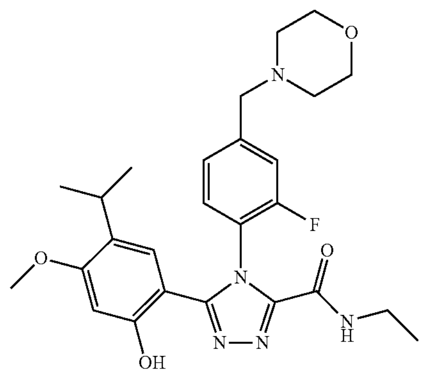 [SMILES: CCNC(=O)c1nnc(-c2cc(C(C)C)c(OC)cc2O)n1-c1ccc(CN2CCOCC2)cc1F] | N-ethyl-4-(2-fluoro-4-(morpholinomethyl)phenyl)-5-(2-hydroxy-5-isopropyl-4-methoxyphenyl)-4H-1,2,4-triazole-3-carboxamide |
| 236 | 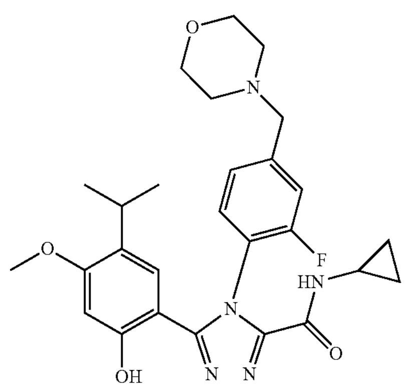 [SMILES: COc1cc(O)c(C(=N)N(C(=N)C(=O)NC2CC2)c2ccc(CN3CCOCC3)cc2F)cc1C(C)C] | N-cyclopropyl-4-(2-fluoro-4-(morpholinomethyl)phenyl)-5-(2-hydroxy-5-isopropyl-4-methoxyphenyl)-4H-1,2,4-triazole-3-carboxamide |
| 237 | 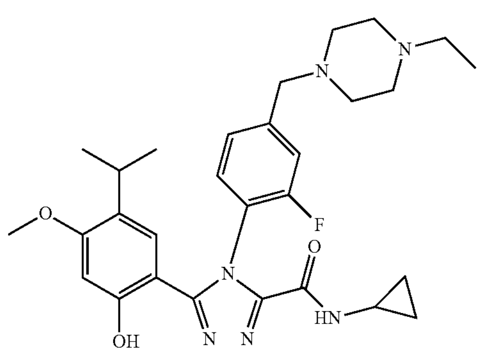 [SMILES: CCN1CCN(Cc2ccc(N(C(=N)C(=O)NC3CC3)C(=N)c3cc(C(C)C)c(OC)cc3O)c(F)c2)CC1] | N-cyclopropyl-4-(4-((4-ethylpiperazin-1-yl)methyl)-2-fluorophenyl)-5-(2-hydroxy-5-isopropyl-4-methoxyphenyl)-4H-1,2,4-triazole-3-carboxamide |

TABLE 1-continued

| No. | Structure | Name |
|---|---|---|
| 238 | 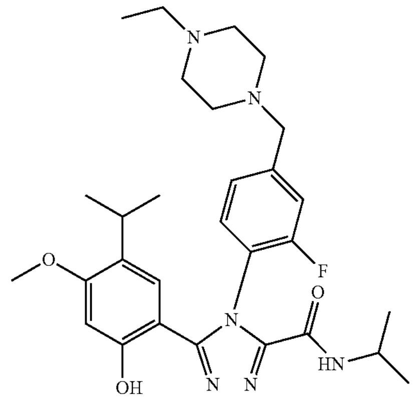 [SMILES: CCN1CCN(Cc2ccc(N(C(=N)C(=O)NC(C)C)C(=N)c3cc(C(C)C)c(OC)cc3O)c(F)c2)CC1] | 4-(4-((4-ethylpiperazin-1-yl)methyl)-2-fluorophenyl)-5-(2-hydroxy-5-isopropyl-4-methoxyphenyl)-N-isopropyl-4H-1,2,4-triazole-3-carboxamide |
| 239 | 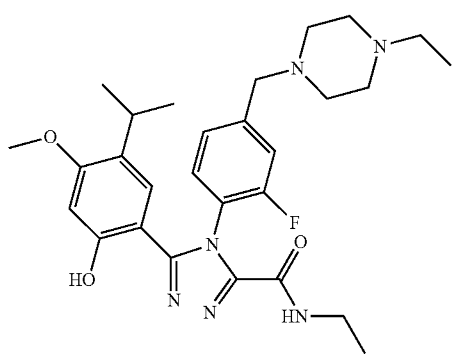 [SMILES: CCNC(=O)C(=N)N(C(=N)c1cc(C(C)C)c(OC)cc1O)c1ccc(CN2CCN(CC)CC2)cc1F] | N-ethyl-4-(4-((4-ethylpiperazin-1-yl)methyl)-2-fluorophenyl)-5-(2-hydroxy-5-isopropyl-4-methoxyphenyl)-4H-1,2,4-triazole-3-carboxamide |
| 240 | 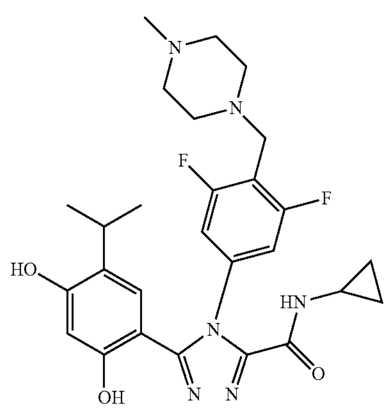 [SMILES: CC(C)c1cc(C(=N)N(C(=N)C(=O)NC2CC2)c2cc(F)c(CN3CCN(C)CC3)c(F)c2)c(O)cc1O] | N-cyclopropyl-4-(3,5-difluoro-4-((4-methylpiperazin-1-yl)methyl)phenyl)-5-(2,4-dihydroxy-5-isopropylphenyl)-4H-1,2,4-triazole-3-carboxamide |
| 241 | 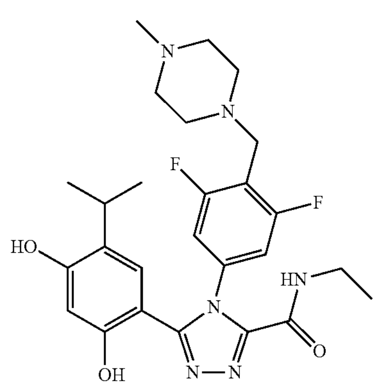 [SMILES: CCNC(=O)c1nnc(-c2cc(C(C)C)c(O)cc2O)n1-c1cc(F)c(CN2CCN(C)CC2)c(F)c1] | 4-(3,5-difluoro-4-((4-methylpiperazin-1-yl)methyl)phenyl)-5-(2,4-dihydroxy-5-isopropylphenyl)-N-ethyl-4H-1,2,4-triazole-3-carboxamide |

| No. | Structure | Name |
|---|---|---|
| 242 | 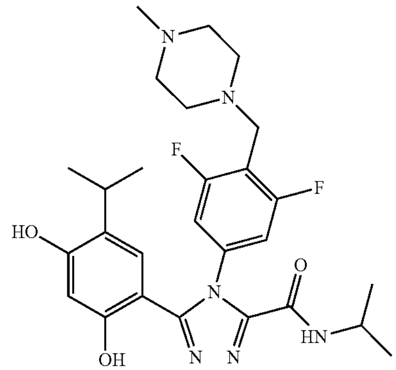 [SMILES: CC(C)NC(=O)C(=N)N(C(=N)c1cc(C(C)C)c(O)cc1O)c1cc(F)c(CN2CCN(C)CC2)c(F)c1] | 4-(3,5-difluoro-4-((4-methylpiperazin-1-yl)methyl)phenyl)-5-(2,4-dihydroxy-5-isopropylphenyl)-N-isopropyl-4H-1,2,4-triazole-3-carboxamide |
| 243 | 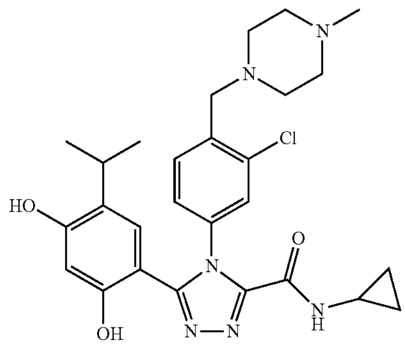 [SMILES: CC(C)c1cc(-c2nnc(C(=O)NC3CC3)n2-c2ccc(CN3CCN(C)CC3)c(Cl)c2)c(O)cc1O] | 4-(3-chloro-4-((4-methylpiperazin-1-yl)methyl)phenyl)-N-cyclopropyl-5-(2,4-dihydroxy-5-isopropylphenyl)-4H-1,2,4-triazole-3-carboxamide |
| 244 | 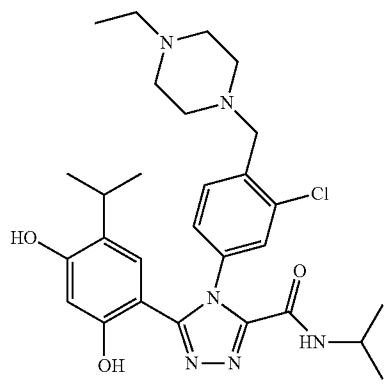 [SMILES: CCN1CCN(Cc2ccc(-n3c(C(=O)NC(C)C)nnc3-c3cc(C(C)C)c(O)cc3O)cc2Cl)CC1] | 4-(3-chloro-4-((4-ethylpiperazin-1-yl)methyl)phenyl)-5-(2,4-dihydroxy-5-isopropylphenyl)-N-isopropyl-4H-1,2,4-triazole-3-carboxamide |
| 245 | 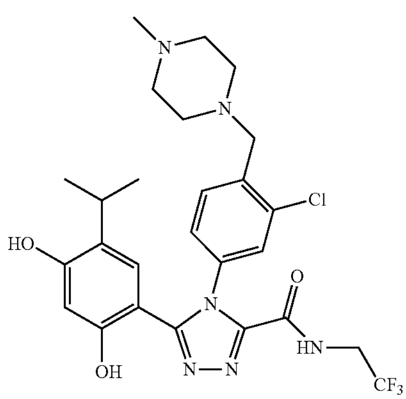 [SMILES: CC(C)c1cc(-c2nnc(C(=O)NCC(F)(F)F)n2-c2ccc(CN3CCN(C)CC3)c(Cl)c2)c(O)cc1O] | 4-(3-chloro-4-((4-methylpiperazin-1-yl)methyl)phenyl)-5-(2,4-dihydroxy-5-isopropylphenyl)-N-(2,2,2-trifluoroethyl)-4H-1,2,4-triazole-3-carboxamide |

TABLE 1-continued

| No. | Structure | Name |
|---|---|---|
| 246 | 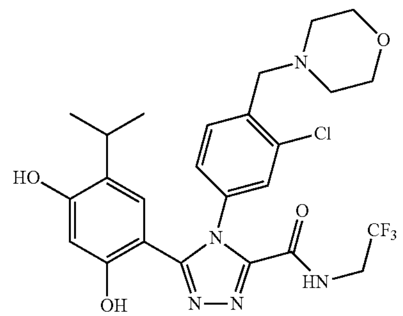 [SMILES: CC(C)c1cc(-c2nnc(C(=O)NCC(F)(F)F)n2-c2ccc(CN3CCOCC3)c(Cl)c2)c(O)cc1O] | 4-(3-chloro-4-(morpholinomethyl)phenyl)-5-(2,4-dihydroxy-5-isopropylphenyl)-N-(2,2,2-trifluoroethyl)-4H-1,2,4-triazole-3-carboxamide |
| 247 | 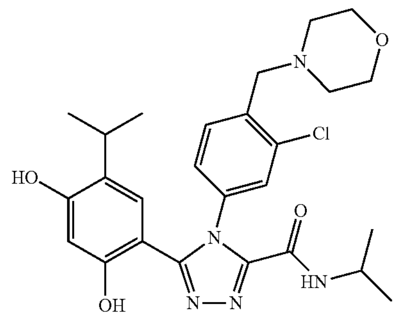 [SMILES: CC(C)NC(=O)c1nnc(-c2cc(C(C)C)c(O)cc2O)n1-c1ccc(CN2CCOCC2)c(Cl)c1] | 4-(3-chloro-4-(morpholinomethyl)phenyl)-5-(2,4-dihydroxy-5-isopropylphenyl)-N-isopropyl-4H-1,2,4-triazole-3-carboxamide |
| 248 | 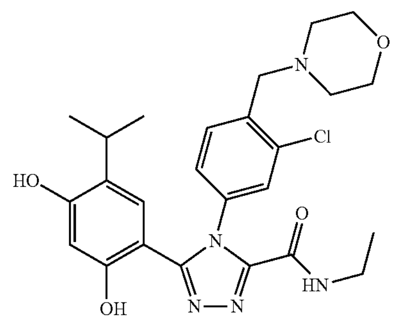 [SMILES: CCNC(=O)c1nnc(-c2cc(C(C)C)c(O)cc2O)n1-c1ccc(CN2CCOCC2)c(Cl)c1] | 4-(3-chloro-4-(morpholinomethyl)phenyl)-5-(2,4-dihydroxy-5-isopropylphenyl)-N-ethyl-4H-1,2,4-triazole-3-carboxamide |
| 249 | 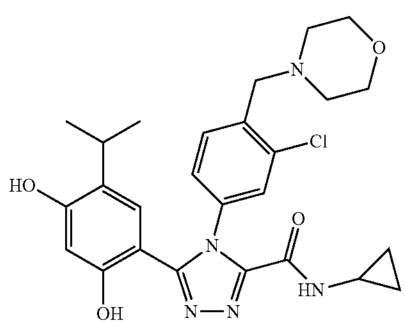 [SMILES: CC(C)c1cc(-c2nnc(C(=O)NC3CC3)n2-c2ccc(CN3CCOCC3)c(Cl)c2)c(O)cc1O] | 4-(3-chloro-4-(morpholinomethyl)phenyl)-N-cyclopropyl-5-(2,4-dihydroxy-5-isopropylphenyl)-4H-1,2,4-triazole-3-carboxamide |
| 250 | 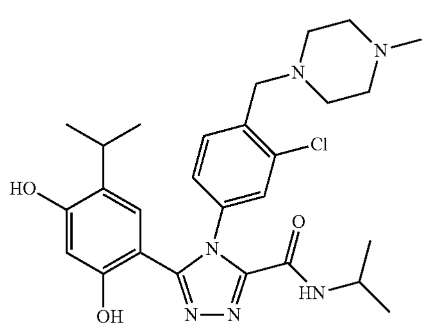 [SMILES: CC(C)NC(=O)c1nnc(-c2cc(C(C)C)c(O)cc2O)n1-c1ccc(CN2CCN(C)CC2)c(Cl)c1] | 4-(3-chloro-4-((4-methylpiperazin-1-yl)methyl)phenyl)-5-(2,4-dihydroxy-5-isopropylphenyl)-N-isopropyl-4H-1,2,4-triazole-3-carboxamide |

TABLE 1-continued

| No. | Structure | Name |
|---|---|---|
| 251 | 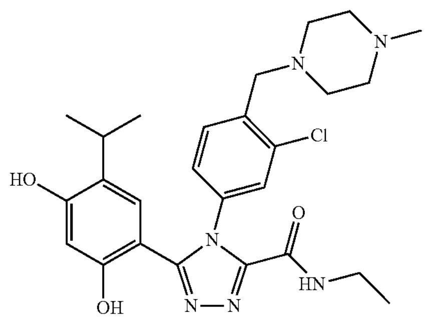 [SMILES: CCNC(=O)c1nnc(-c2cc(C(C)C)c(O)cc2O)n1-c1ccc(CN2CCN(C)CC2)c(Cl)c1] | 4-(3-chloro-4-((4-methylpiperazin-1-yl)methyl)phenyl)-5-(2,4-dihydroxy-5-isopropylphenyl)-N-ethyl-4H-1,2,4-triazole-3-carboxamide |
| 252 | 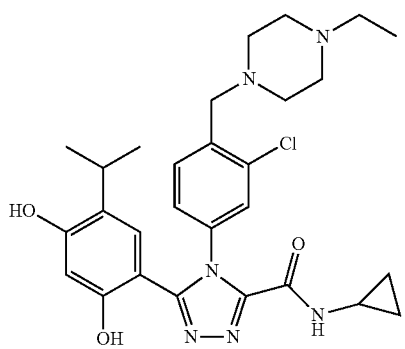 [SMILES: CCN1CCN(Cc2ccc(-n3c(C(=O)NC4CC4)nnc3-c3cc(C(C)C)c(O)cc3O)cc2Cl)CC1] | 4-(3-chloro-4-((4-ethylpiperazin-1-yl)methyl)phenyl)-N-cyclopropyl-5-(2,4-dihydroxy-5-isopropylphenyl)-4H-1,2,4-triazole-3-carboxamide |
| 253 | 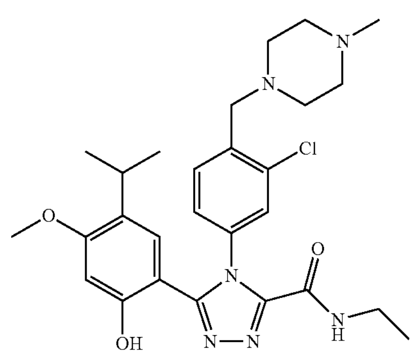 [SMILES: CCNC(=O)c1nnc(-c2cc(C(C)C)c(OC)cc2O)n1-c1ccc(CN2CCN(C)CC2)c(Cl)c1] | 4-(3-chloro-4-((4-methylpiperazin-1-yl)methyl)phenyl)-N-ethyl-5-(2-hydroxy-5-isopropyl-4-methoxyphenyl)-4H-1,2,4-triazole-3-carboxamide |
| 254 | 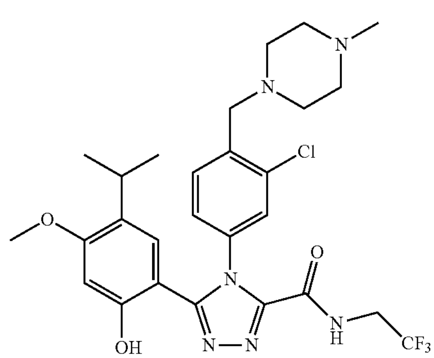 [SMILES: COc1cc(O)c(-c2nnc(C(=O)NCC(F)(F)F)n2-c2ccc(CN3CCN(C)CC3)c(Cl)c2)cc1C(C)C] | 4-(3-chloro-4-((4-methylpiperazin-1-yl)methyl)phenyl)-5-(2-hydroxy-5-isopropyl-4-methoxyphenyl)-N-(2,2,2-trifluoroethyl)-4H-1,2,4-triazole-3-carboxamide |

TABLE 1-continued

| No. | Structure | Name |
|---|---|---|
| 255 | 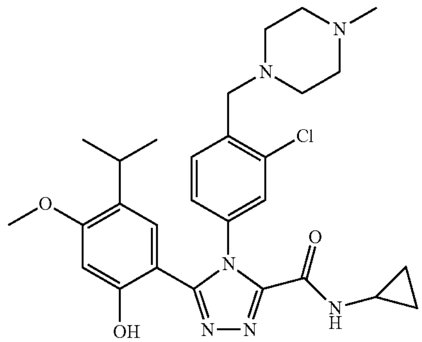 [SMILES: COc1cc(O)c(-c2nnc(C(=O)NC3CC3)n2-c2ccc(CN3CCN(C)CC3)c(Cl)c2)cc1C(C)C] | 4-(3-chloro-4-((4-methylpiperazin-1-yl)methyl)phenyl)-N-cyclopropyl-5-(2-hydroxy-5-isopropyl-4-methoxyphenyl)-4H-1,2,4-triazole-3-carboxamide |
| 256 | 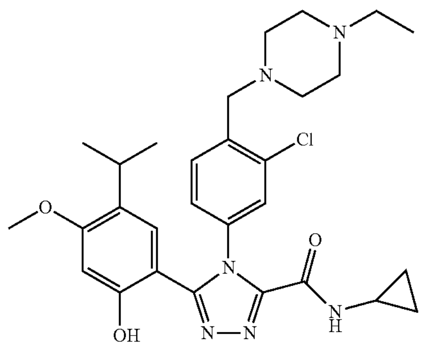 [SMILES: CCN1CCN(Cc2ccc(-n3c(C(=O)NC4CC4)nnc3-c3cc(C(C)C)c(OC)cc3O)cc2Cl)CC1] | 4-(3-chloro-4-((4-ethylpiperazin-1-yl)methyl)phenyl)-N-cyclopropyl-5-(2-hydroxy-5-isopropyl-4-methoxyphenyl)-4H-1,2,4-triazole-3-carboxamide |
| 257 | 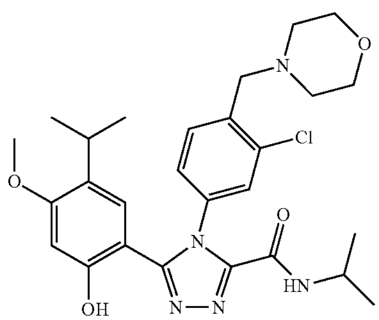 [SMILES: COc1cc(O)c(-c2nnc(C(=O)NC(C)C)n2-c2ccc(CN3CCOCC3)c(Cl)c2)cc1C(C)C] | 4-(3-chloro-4-(morpholinomethyl)phenyl)-5-(2-hydroxy-5-isopropyl-4-methoxyphenyl)-N-isopropyl-4H-1,2,4-triazole-3-carboxamide |
| 258 | 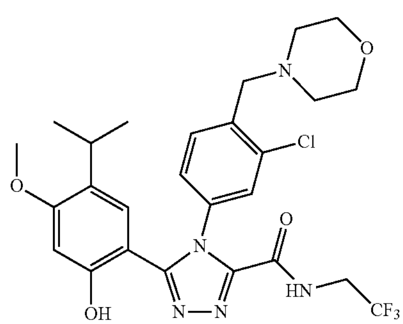 [SMILES: COc1cc(O)c(-c2nnc(C(=O)NCC(F)(F)F)n2-c2ccc(CN3CCOCC3)c(Cl)c2)cc1C(C)C] | 4-(3-chloro-4-(morpholinomethyl)phenyl)-5-(2-hydroxy-5-isopropyl-4-methoxyphenyl)-N-(2,2,2-trifluoroethyl)-4H-1,2,4-triazole-3-carboxamide |

TABLE 1-continued

| No. | Structure | Name |
|---|---|---|
| 259 | 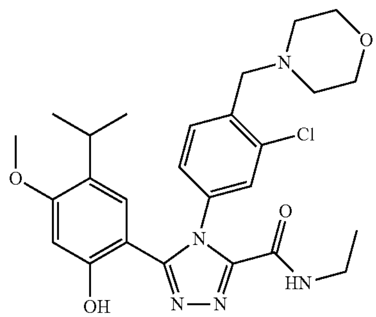 [SMILES: CCNC(=O)c1nnc(-c2cc(C(C)C)c(OC)cc2O)n1-c1ccc(CN2CCOCC2)c(Cl)c1] | 4-(3-chloro-4-(morpholinomethyl)phenyl)-N-ethyl-5-(2-hydroxy-5-isopropyl-4-methoxyphenyl)-4H-1,2,4-triazole-3-carboxamide |
| 260 | 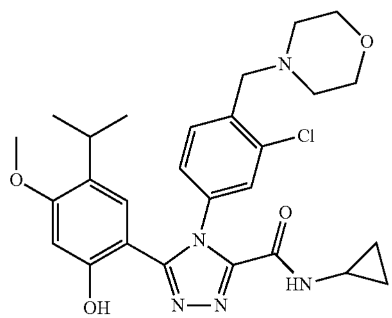 [SMILES: COc1cc(O)c(-c2nnc(C(=O)NC3CC3)n2-c2ccc(CN3CCOCC3)c(Cl)c2)cc1C(C)C] | 4-(3-chloro-4-(morpholinomethyl)phenyl)-N-cyclopropyl-5-(2-hydroxy-5-isopropyl-4-methoxyphenyl)-4H-1,2,4-triazole-3-carboxamide |
| 261 | 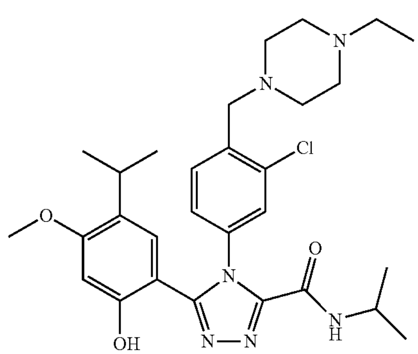 [SMILES: CCN1CCN(Cc2ccc(-n3c(C(=O)NC(C)C)nnc3-c3cc(C(C)C)c(OC)cc3O)cc2Cl)CC1] | 4-(3-chloro-4-((4-ethylpiperazin-1-yl)methyl)phenyl)-5-(2-hydroxy-5-isopropyl-4-methoxyphenyl)-N-isopropyl-4H-1,2,4-triazole-3-carboxamide |
| 262 | 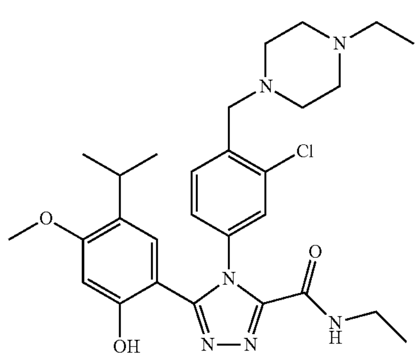 [SMILES: CCNC(=O)c1nnc(-c2cc(C(C)C)c(OC)cc2O)n1-c1ccc(CN2CCN(CC)CC2)c(Cl)c1] | 4-(3-chloro-4-((4-ethylpiperazin-1-yl)methyl)phenyl)-N-ethyl-5-(2-hydroxy-5-isopropyl-4-methoxyphenyl)-4H-1,2,4-triazole-3-carboxamide |

TABLE 1-continued

| No. | Structure | Name |
|---|---|---|
| 263 | 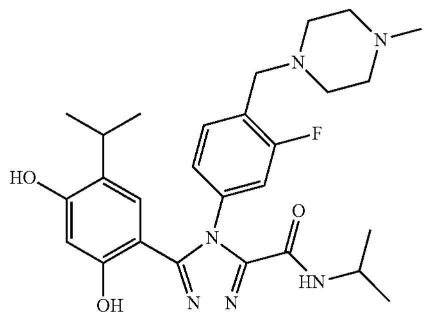 | 5-(2,4-dihydroxy-5-isopropylphenyl)-4-(3-fluoro-4-((4-methylpiperazin-1-yl)methyl)phenyl)-N-isopropyl-4H-1,2,4-triazole-3-carboxamide |
| 264 | 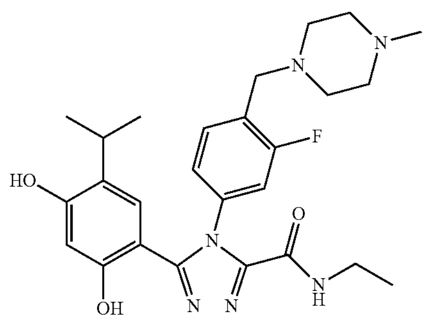 [SMILES: CCNC(=O)C(=N)N(C(=N)c1cc(C(C)C)c(O)cc1O)c1ccc(CN2CCN(C)CC2)c(F)c1] | 5-(2,4-dihydroxy-5-isopropylphenyl)-N-ethyl-4-(3-fluoro-4-((4-methylpiperazin-1-yl)methyl)phenyl)-4H-1,2,4-triazole-3-carboxamide |
| 265 | 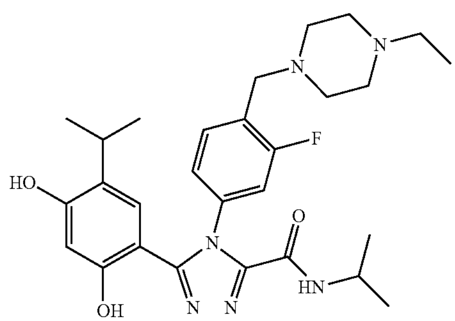 [SMILES: CCN1CCN(Cc2ccc(N(C(=N)C(=O)NC(C)C)C(=N)c3cc(C(C)C)c(O)cc3O)cc2F)CC1] | 5-(2,4-dihydroxy-5-isopropylphenyl)-4-(4-((4-ethylpiperazin-1-yl)methyl)-3-fluorophenyl)-N-isopropyl-4H-1,2,4-triazole-3-carboxamide |
| 266 | 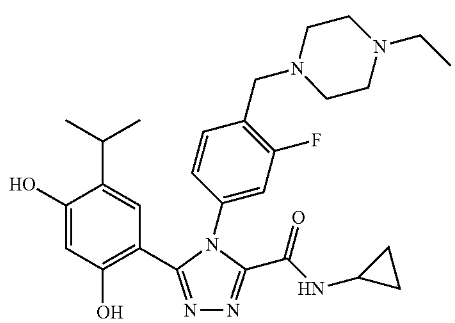 [SMILES: CCN1CCN(Cc2ccc(-n3c(C(=O)NC4CC4)nnc3-c3cc(C(C)C)c(O)cc3O)cc2F)CC1] | N-cyclopropyl-5-(2,4-dihydroxy-5-isopropylphenyl)-4-(4-((4-ethylpiperazin-1-yl)methyl)-3-fluorophenyl)-4H-1,2,4-triazole-3-carboxamide |
| 267 | 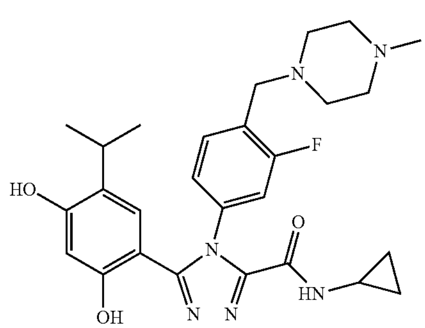 [SMILES: CC(C)c1cc(C(=N)N(C(=N)C(=O)NC2CC2)c2ccc(CN3CCN(C)CC3)c(F)c2)c(O)cc1O] | N-cyclopropyl-5-(2,4-dihydroxy-5-isopropylphenyl)-4-(3-fluoro-4-((4-methylpiperazin-1-yl)methyl)phenyl)-4H-1,2,4-triazole-3-carboxamide |

| No. | Structure | Name |
|---|---|---|
| 268 | 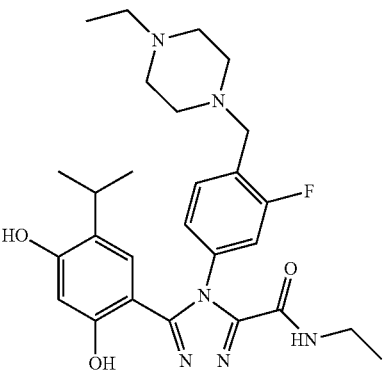 [SMILES: CCNC(=O)C(=N)N(C(=N)c1cc(C(C)C)c(O)cc1O)c1ccc(CN2CCN(CC)CC2)c(F)c1] | 5-(2,4-dihydroxy-5-isopropylphenyl)-N-ethyl-4-(4-((4-ethylpiperazin-1-yl)methyl)-3-fluorophenyl)-4H-1,2,4-triazole-3-carboxamide |
| 269 | 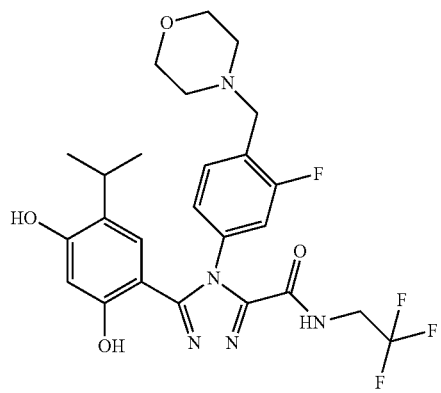 [SMILES: CC(C)c1cc(C(=N)N(C(=N)C(=O)NCC(F)(F)F)c2ccc(CN3CCOCC3)c(F)c2)c(O)cc1O] | 5-(2,4-dihydroxy-5-isopropylphenyl)-4-(3-fluoro-4-(morpholinomethyl)phenyl)-N-(2,2,2-trifluoroethyl)-4H-1,2,4-triazole-3-carboxamide |
| 270 | 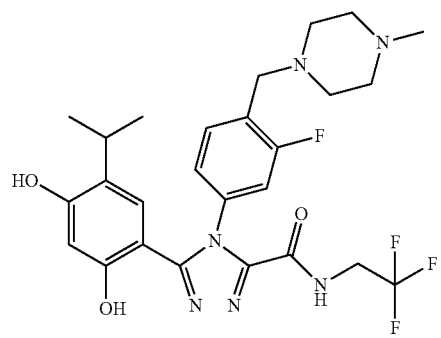 [SMILES: CC(C)c1cc(C(=N)N(C(=N)C(=O)NCC(F)(F)F)c2ccc(CN3CCN(C)CC3)c(F)c2)c(O)cc1O] | 5-(2,4-dihydroxy-5-isopropylphenyl)-4-(3-fluoro-4-((4-methylpiperazin-1-yl)methyl)phenyl)-N-(2,2,2-trifluoroethyl)-4H-1,2,4-triazole-3-carboxamide |
| 271 | 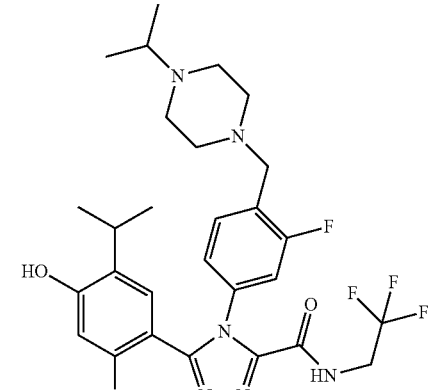 | 5-(2,4-dihydroxy-5-isopropylphenyl)-4-(3-fluoro-4-((4-isopropylpiperazin-1-yl)methyl)phenyl)-N-(2,2,2-trifluoroethyl)-4H-1,2,4-triazole-3-carboxamide |

TABLE 1-continued

| No. | Structure | Name |
|---|---|---|
| 272 | 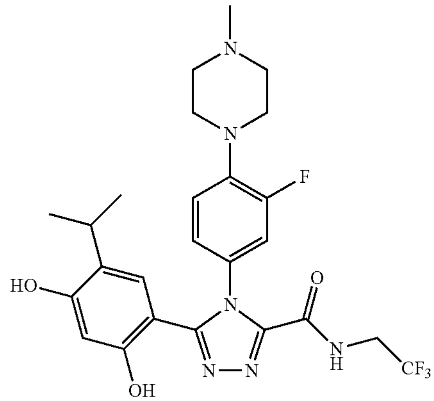 [SMILES: CC(C)c1cc(-c2nnc(C(=O)NCC(F)(F)F)n2-c2ccc(N3CCN(C)CC3)c(F)c2)c(O)cc1O] | 5-(2,4-dihydroxy-5-isopropylphenyl)-4-(3-fluoro-4-(4-methylpiperazin-1-yl)phenyl)-N-(2,2,2-trifluoroethyl)-4H-1,2,4-triazole-3-carboxamide |
| 273 | 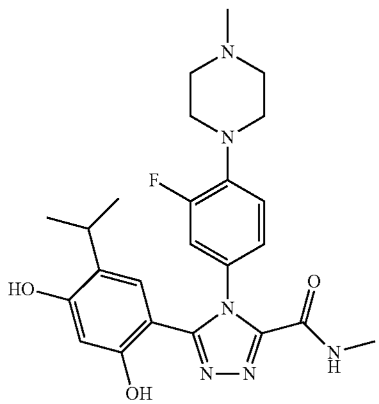 [SMILES: CNC(=O)c1nnc(-c2cc(C(C)C)c(O)cc2O)n1-c1ccc(N2CCN(C)CC2)c(F)c1] | 5-(2,4-dihydroxy-5-isopropylphenyl)-4-(3-fluoro-4-(4-methylpiperazin-1-yl)phenyl)-N-methyl-4H-1,2,4-triazole-3-carboxamide |
| 274 | 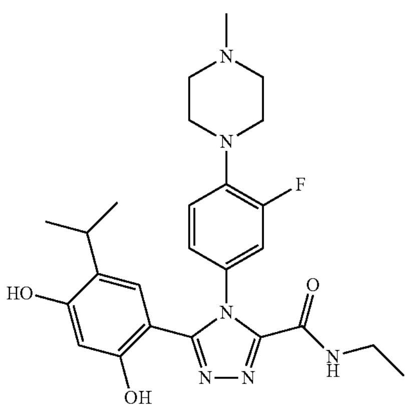 [SMILES: CCNC(=O)c1nnc(-c2cc(C(C)C)c(O)cc2O)n1-c1ccc(N2CCN(C)CC2)c(F)c1] | 5-(2,4-dihydroxy-5-isopropylphenyl)-N-ethyl-4-(3-fluoro-4-(4-methylpiperazin-1-yl)phenyl)-4H-1,2,4-triazole-3-carboxamide |
| 275 | 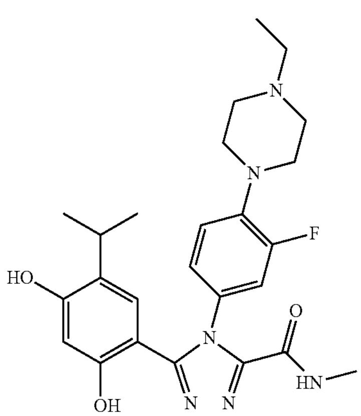 [SMILES: CCN1CCN(c2ccc(N(C(=N)C(=O)NC)C(=N)c3cc(C(C)C)c(O)cc3O)cc2F)CC1] | 5-(2,4-dihydroxy-5-isopropylphenyl)-4-(4-(4-ethylpiperazin-1-yl)-3-fluorophenyl)-N-methyl-4H-1,2,4-triazole-3-carboxamide |

TABLE 1-continued

| No. | Structure | Name |
|---|---|---|
| 276 | 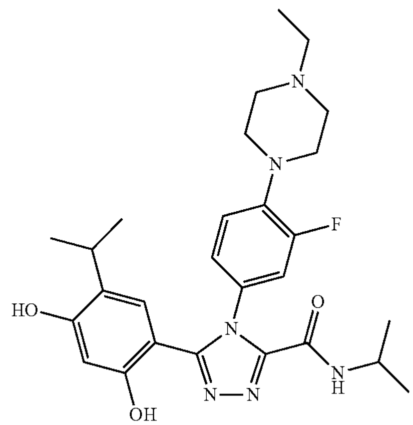 [SMILES: CCN1CCN(c2ccc(-n3c(C(=O)NC(C)C)nnc3-c3cc(C(C)C)c(O)cc3O)cc2F)CC1] | 5-(2,4-dihydroxy-5-isopropylphenyl)-4-(4-(4-ethylpiperazin-1-yl)-3-fluorophenyl)-N-isopropyl-4H-1,2,4-triazole-3-carboxamide |
| 277 | 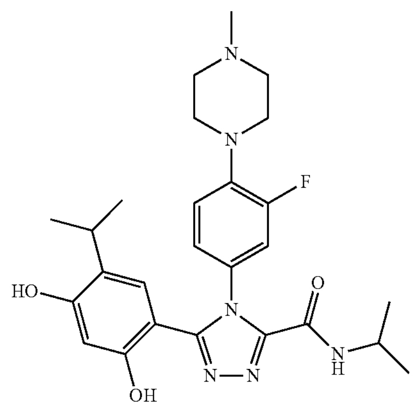 [SMILES: CC(C)NC(=O)c1nnc(-c2cc(C(C)C)c(O)cc2O)n1-c1ccc(N2CCN(C)CC2)c(F)c1] | 5-(2,4-dihydroxy-5-isopropylphenyl)-4-(3-fluoro-4-(4-methylpiperazin-1-yl)phenyl)-N-isopropyl-4H-1,2,4-triazole-3-carboxamide |
| 278 | 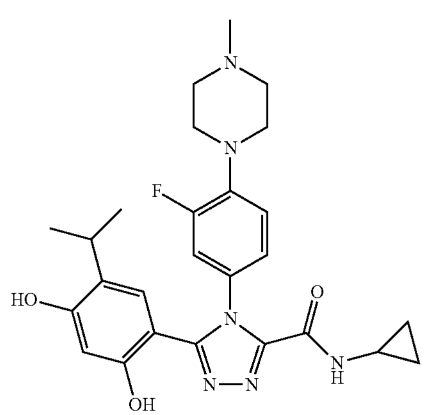 [SMILES: CC(C)c1cc(-c2nnc(C(=O)NC3CC3)n2-c2ccc(N3CCN(C)CC3)c(F)c2)c(O)cc1O] | N-cyclopropyl-5-(2,4-dihydroxy-5-isopropylphenyl)-4-(3-fluoro-4-(4-methylpiperazin-1-yl)phenyl)-4H-1,2,4-triazole-3-carboxamide |

TABLE 1-continued

| No. | Structure | Name |
|-----|-----------|------|
| 279 | 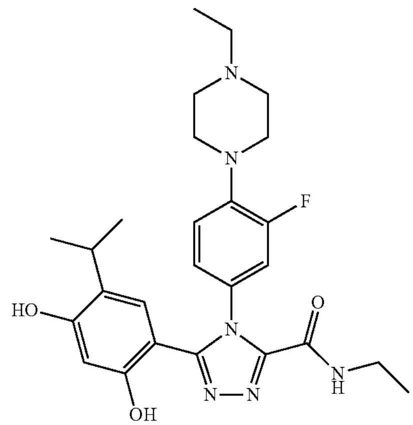 [SMILES: CCNC(=O)c1nnc(-c2cc(C(C)C)c(O)cc2O)n1-c1ccc(N2CCN(CC)CC2)c(F)c1] | 5-(2,4-dihydroxy-5-isopropylphenyl)-N-ethyl-4-(4-(4-ethylpiperazin-1-yl)-3-fluorophenyl)-4H-1,2,4-triazole-3-carboxamide |
| 280 | 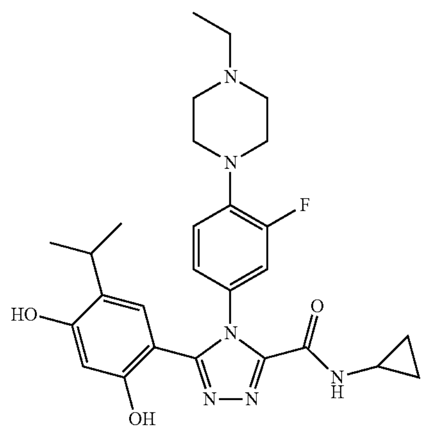 [SMILES: CCN1CCN(c2ccc(-n3c(C(=O)NC4CC4)nnc3-c3cc(C(C)C)c(O)cc3O)cc2F)CC1] | N-cyclopropyl-5-(2,4-dihydroxy-5-isopropylphenyl)-4-(4-(4-ethylpiperazin-1-yl)-3-fluorophenyl)-4H-1,2,4-triazole-3-carboxamide |
| 281 | 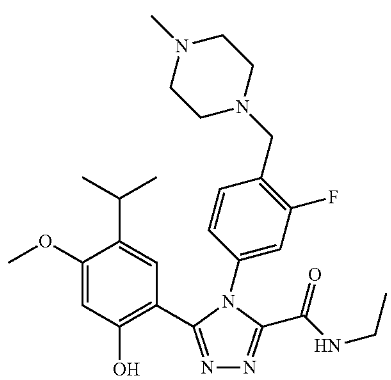 [SMILES: CCNC(=O)c1nnc(-c2cc(C(C)C)c(OC)cc2O)n1-c1ccc(CN2CCN(C)CC2)c(F)c1] | N-ethyl-4-(3-fluoro-4-((4-methylpiperazin-1-yl)methyl)phenyl)-5-(2-hydroxy-5-isopropyl-4-methoxyphenyl)-4H-1,2,4-triazole-3-carboxamide |
| 282 | 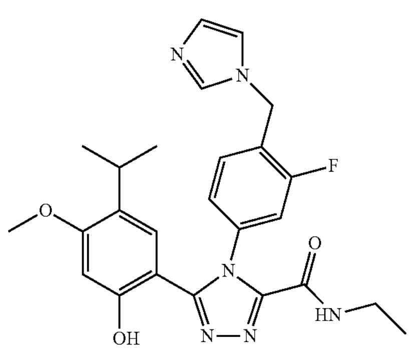 [SMILES: CCNC(=O)c1nnc(-c2cc(C(C)C)c(OC)cc2O)n1-c1ccc(Cn2ccnc2)c(F)c1] | 4-(4-((1H-imidazol-1-yl)methyl)-3-fluorophenyl)-N-ethyl-5-(2-hydroxy-5-isopropyl-4-methoxyphenyl)-4H-1,2,4-triazole-3-carboxamide |

TABLE 1-continued

| No. | Structure | Name |
|---|---|---|
| 283 | 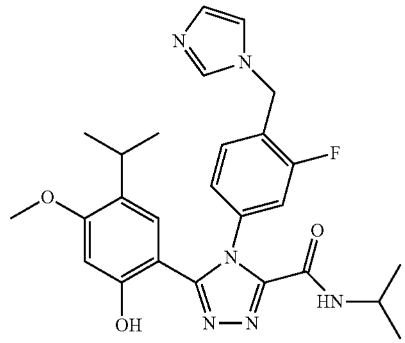 [SMILES: COc1cc(O)c(-c2nnc(C(=O)NC(C)C)n2-c2ccc(Cn3ccnc3)c(F)c2)cc1C(C)C] | 4-(4-((1H-imidazol-1-yl)methyl)-3-fluorophenyl)-5-(2-hydroxy-5-isopropyl-4-methoxyphenyl)-N-isopropyl-4H-1,2,4-triazole-3-carboxamide |
| 284 | 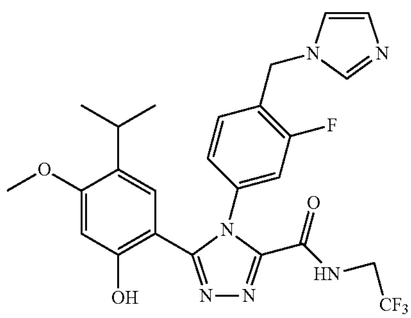 [SMILES: COc1cc(O)c(-c2nnc(C(=O)NCC(F)(F)F)n2-c2ccc(Cn3ccnc3)c(F)c2)cc1C(C)C] | 4-(4-((1H-imidazol-1-yl)methyl)-3-fluorophenyl)-5-(2-hydroxy-5-isopropyl-4-methoxyphenyl)-N-(2,2,2-trifluoroethyl)-4H-1,2,4-triazole-3-carboxamide |
| 285 | 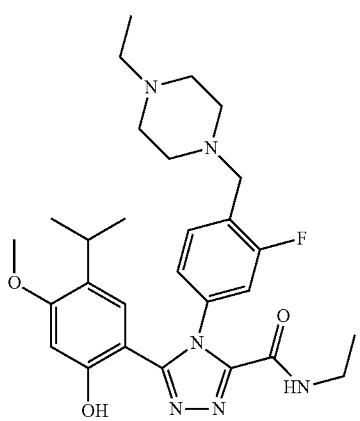 [SMILES: CCNC(=O)c1nnc(-c2cc(C(C)C)c(OC)cc2O)n1-c1ccc(CN2CCN(CC)CC2)c(F)c1] | N-ethyl-4-(4-((4-ethylpiperazin-1-yl)methyl)-3-fluorophenyl)-5-(2-hydroxy-5-isopropyl-4-methoxyphenyl)-4H-1,2,4-triazole-3-carboxamide |
| 286 | 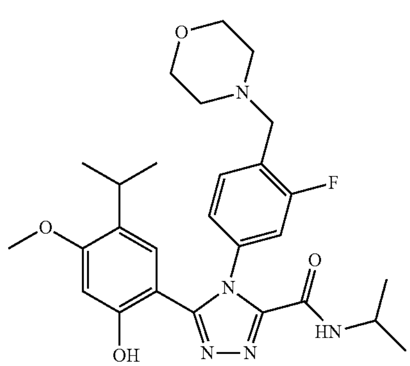 [SMILES: COc1cc(O)c(-c2nnc(C(=O)NC(C)C)n2-c2ccc(CN3CCOCC3)c(F)c2)cc1C(C)C] | 4-(3-fluoro-4-(morpholinomethyl)phenyl)-5-(2-hydroxy-5-isopropyl-4-methoxyphenyl)-N-isopropyl-4H-1,2,4-triazole-3-carboxamide |

TABLE 1-continued

| No. | Structure | Name |
|---|---|---|
| 287 | 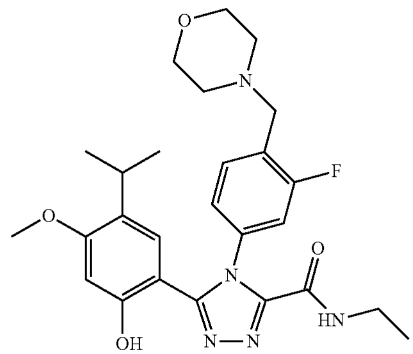 [SMILES: CCNC(=O)c1nnc(-c2cc(C(C)C)c(OC)cc2O)n1-c1ccc(CN2CCOCC2)c(F)c1] | N-ethyl-4-(3-fluoro-4-(morpholinomethyl)phenyl)-5-(2-hydroxy-5-isopropyl-4-methoxyphenyl)-4H-1,2,4-triazole-3-carboxamide |
| 288 | 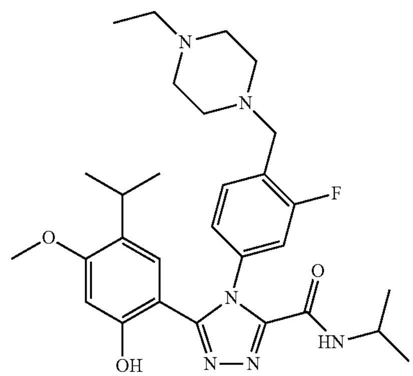 [SMILES: CCN1CCN(Cc2ccc(-n3c(C(=O)NC(C)C)nnc3-c3cc(C(C)C)c(OC)cc3O)cc2F)CC1] | 4-(4-((4-ethylpiperazin-1-yl)methyl)-3-fluorophenyl)-5-(2-hydroxy-5-isopropyl-4-methoxyphenyl)-N-isopropyl-4H-1,2,4-triazole-3-carboxamide |
| 289 | 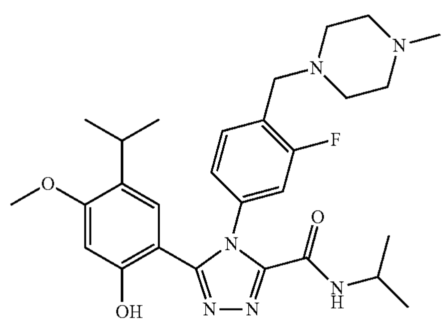 | 4-(3-fluoro-4-((4-methylpiperazin-1-yl)methyl)phenyl)-5-(2-hydroxy-5-isopropyl-4-methoxyphenyl)-N-isopropyl-4H-1,2,4-triazole-3-carboxamide |
| 290 | 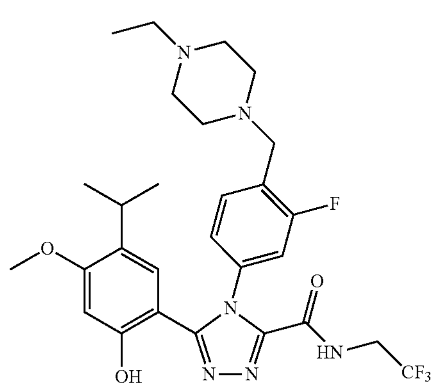 [SMILES: CCN1CCN(Cc2ccc(-n3c(C(=O)NCC(F)(F)F)nnc3-c3cc(C(C)C)c(OC)cc3O)cc2F)CC1] | 4-(4-((4-ethylpiperazin-1-yl)methyl)-3-fluorophenyl)-5-(2-hydroxy-5-isopropyl-4-methoxyphenyl)-N-(2,2,2-trifluoroethyl)-4H-1,2,4-triazole-3-carboxamide |

TABLE 1-continued

| No. | Structure | Name |
|---|---|---|
| 291 | 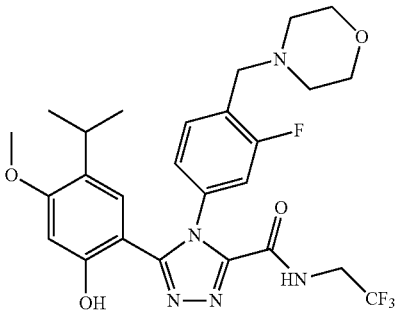 [SMILES: COc1cc(O)c(-c2nnc(C(=O)NCC(F)(F)F)n2-c2ccc(CN3CCOCC3)c(F)c2)cc1C(C)C] | 4-(3-fluoro-4-(morpholinomethyl)phenyl)-5-(2-hydroxy-5-isopropyl-4-methoxyphenyl)-N-(2,2,2-trifluoroethyl)-4H-1,2,4-triazole-3-carboxamide |
| 292 | 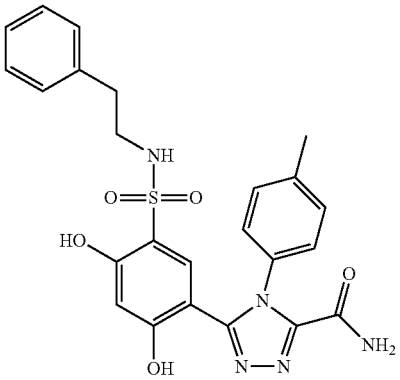 [SMILES: Cc1ccc(-n2c(C(N)=O)nnc2-c2cc(S(=O)(=O)NCCc3ccccc3)c(O)cc2O)cc1] | 5-(2,4-dihydroxy-5-(N-phenethylsulfamoyl)phenyl)-4-p-tolyl-4H-1,2,4-triazole-3-carboxamide |
| 293 | 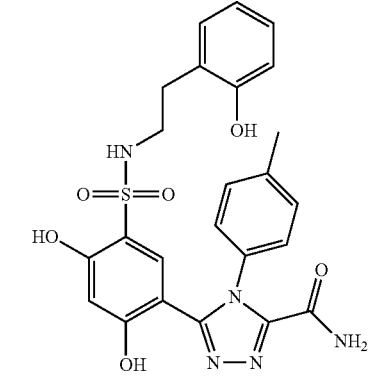 [SMILES: Cc1ccc(-n2c(C(N)=O)nnc2-c2cc(S(=O)(=O)NCCc3ccccc3O)c(O)cc2O)cc1] | 5-(2,4-dihydroxy-5-(N-(2-hydroxyphenethyl)sulfamoyl)phenyl)-4-p-tolyl-4H-1,2,4-triazole-3-carboxamide |
| 294 | 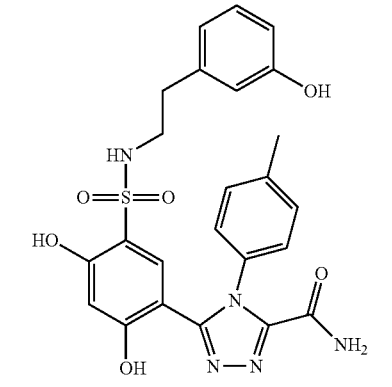 [SMILES: Cc1ccc(-n2c(C(N)=O)nnc2-c2cc(S(=O)(=O)NCCc3cccc(O)c3)c(O)cc2O)cc1] | 5-(2,4-dihydroxy-5-(N-(3-hydroxyphenethyl)sulfamoyl)phenyl)-4-p-tolyl-4H-1,2,4-triazole-3-carboxamide |

TABLE 1-continued

| No. | Structure | Name |
|---|---|---|
| 295 | 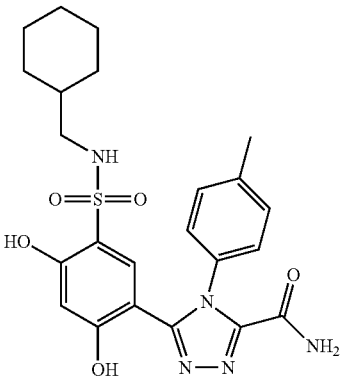 [SMILES: Cc1ccc(-n2c(C(N)=O)nnc2-c2cc(S(=O)(=O)NCC3CCCCC3)c(O)cc2O)cc1] | 5-(5-(N-(cyclohexylmethyl)sulfamoyl)-2,4-dihydroxyphenyl)-4-p-tolyl-4H-1,2,4-triazole-3-carboxamide |
| 296 | 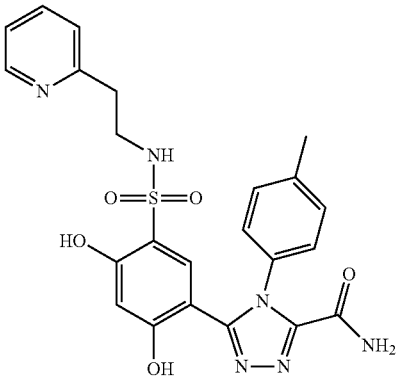 [SMILES: Cc1ccc(-n2c(C(N)=O)nnc2-c2cc(S(=O)(=O)NCCc3ccccn3)c(O)cc2O)cc1] | 5-(2,4-dihydroxy-5-(N-(2-(pyridin-2-yl)ethyl)sulfamoyl)phenyl)-4-p-tolyl-4H-1,2,4-triazole-3-carboxamide |
| 297 | 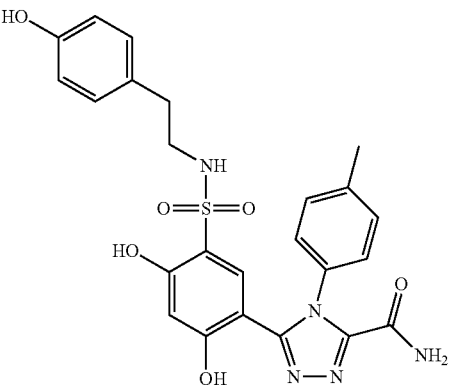 [SMILES: Cc1ccc(-n2c(C(N)=O)nnc2-c2cc(S(=O)(=O)NCCc3ccc(O)cc3)c(O)cc2O)cc1] | 5-(2,4-dihydroxy-5-(N-(4-hydroxyphenethyl)sulfamoyl)phenyl)-4-p-tolyl-4H-1,2,4-triazole-3-carboxamide |
| 298 | 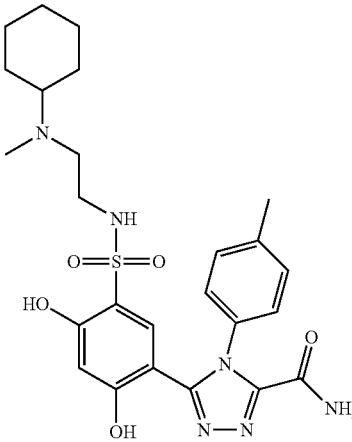 | 5-(5-(N-(2-(cyclohexyl(methyl)amino)ethyl)sulfamoyl)-2,4-dihydroxyphenyl)-4-p-tolyl-4H-1,2,4-triazole-3-carboxamide |

TABLE 1-continued

| No. | Structure | Name |
|---|---|---|
| 299 | 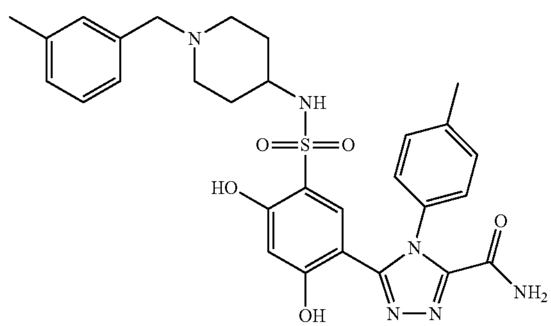 [SMILES: Cc1ccc(-n2c(C(N)=O)nnc2-c2cc(S(=O)(=O)NC3CCN(Cc4cccc(C)c4)CC3)c(O)cc2O)cc1] | 5-(2,4-dihydroxy-5-(N-(1-(3-methylbenzyl)piperidin-4-yl)sulfamoyl)phenyl)-4-p-tolyl-4H-1,2,4-triazole-3-carboxamide |
| 300 | 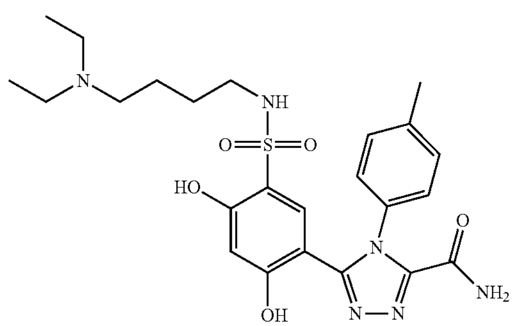 [SMILES: CCN(CC)CCCCNS(=O)(=O)c1cc(-c2nnc(C(N)=O)n2-c2ccc(C)cc2)c(O)cc1O] | 5-(5-(N-(4-(diethylamino)butyl)sulfamoyl)-2,4-dihydroxyphenyl)-4-p-tolyl-4H-1,2,4-triazole-3-carboxamide |
| 301 | 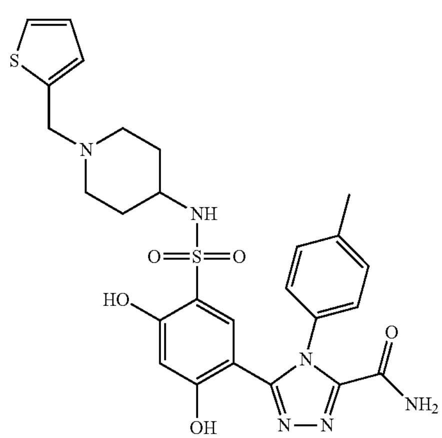 [SMILES: Cc1ccc(-n2c(C(N)=O)nnc2-c2cc(S(=O)(=O)NC3CCN(Cc4cccs4)CC3)c(O)cc2O)cc1] | 5-(2,4-dihydroxy-5-(N-(1-(thiophen-2-ylmethyl)piperidin-4-yl)sulfamoyl)phenyl)-4-p-tolyl-4H-1,2,4-triazole-3-carboxamide |
| 302 | 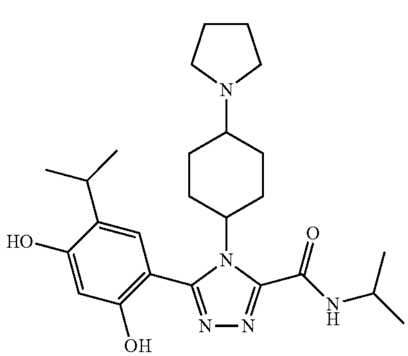 [SMILES: CC(C)NC(=O)c1nnc(-c2cc(C(C)C)c(O)cc2O)n1C1CCC(N2CCCC2)CC1] | 5-(2,4-dihydroxy-5-isopropylphenyl)-N-isopropyl-4-(4-(pyrrolidin-1-yl)cyclohexyl)-4H-1,2,4-triazole-3-carboxamide |

TABLE 1-continued

| No. | Structure | Name |
|---|---|---|
| 303 | 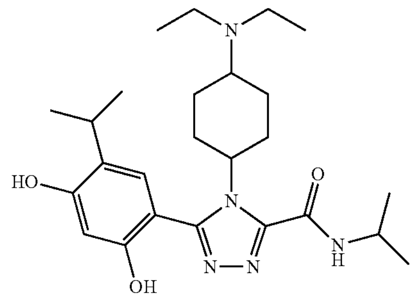 [SMILES: CCN(CC)C1CCC(n2c(C(=O)NC(C)C)nnc2-c2cc(C(C)C)c(O)cc2O)CC1] | 4-(4-(diethylamino)cyclohexyl)-5-(2,4-dihydroxy-5-isopropylphenyl)-N-isopropyl-4H-1,2,4-triazole-3-carboxamide |
| 304 | 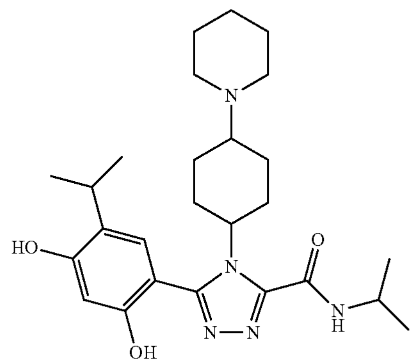 [SMILES: CC(C)NC(=O)c1nnc(-c2cc(C(C)C)c(O)cc2O)n1C1CCC(N2CCCCC2)CC1] | 5-(2,4-dihydroxy-5-isopropylphenyl)-N-isopropyl-4-(4-(piperidin-1-yl)cyclohexyl)-4H-1,2,4-triazole-3-carboxamide |
| 305 | 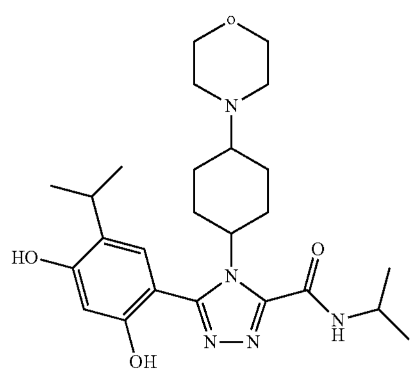 | 5-(2,4-dihydroxy-5-isopropylphenyl)-N-isopropyl-4-(4-morpholinocyclohexyl)-4H-1,2,4-triazole-3-carboxamide |
| 306 | 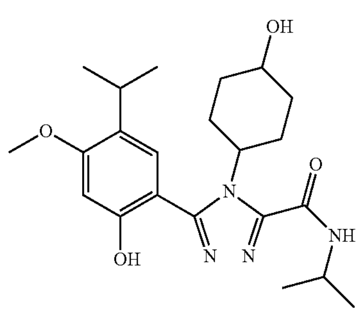 [SMILES: COc1cc(O)c(C(=N)N(C(=N)C(=O)NC(C)C)C2CCC(O)CC2)cc1C(C)C] | 5-(2-hydroxy-5-isopropyl-4-methoxyphenyl)-4-(4-hydroxycyclohexyl)-N-isopropyl-4H-1,2,4-triazole-3-carboxamide |

TABLE 1-continued

| No. | Structure | Name |
|---|---|---|
| 307 | 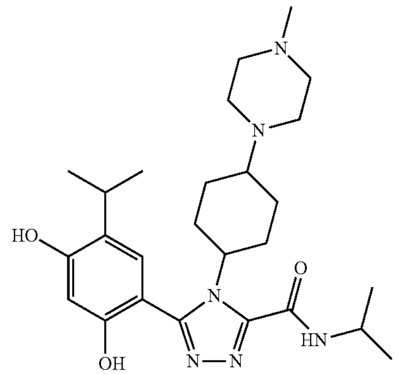 [SMILES: CC(C)NC(=O)c1nnc(-c2cc(C(C)C)c(O)cc2O)n1C1CCC(N2CCN(C)CC2)CC1] | 5-(2,4-dihydroxy-5-isopropylphenyl)-N-isopropyl-4-(4-(4-methylpiperazin-1-yl)cyclohexyl)-4H-1,2,4-triazole-3-carboxamide |
| 308 | 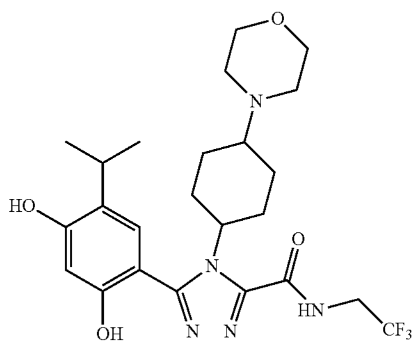 [SMILES: CC(C)c1cc(C(=N)N(C(=N)C(=O)NCC(F)(F)F)C2CCC(N3CCOCC3)CC2)c(O)cc1O] | 5-(2,4-dihydroxy-5-isopropylphenyl)-4-(4-morpholinocyclohexyl)-N-(2,2,2-trifluoroethyl)-4H-1,2,4-triazole-3-carboxamide |
| 309 | 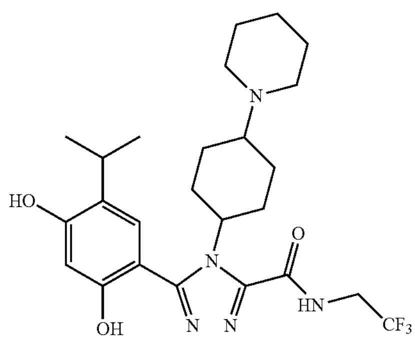 [SMILES: CC(C)c1cc(C(=N)N(C(=N)C(=O)NCC(F)(F)F)C2CCC(N3CCCCC3)CC2)c(O)cc1O] | 5-(2,4-dihydroxy-5-isopropylphenyl)-4-(4-(piperidin-1-yl)cyclohexyl)-N-(2,2,2-trifluoroethyl)-4H-1,2,4-triazole-3-carboxamide |
| 310 | 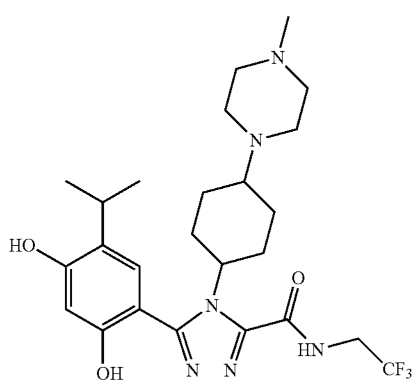 [SMILES: CC(C)c1cc(C(=N)N(C(=N)C(=O)NCC(F)(F)F)C2CCC(N3CCN(C)CC3)CC2)c(O)cc1O] | 5-(2,4-dihydroxy-5-isopropylphenyl)-4-(4-(4-methylpiperazin-1-yl)cyclohexyl)-N-(2,2,2-trifluoroethyl)-4H-1,2,4-triazole-3-carboxamide |

TABLE 1-continued

| No. | Structure | Name |
|---|---|---|
| 311 | 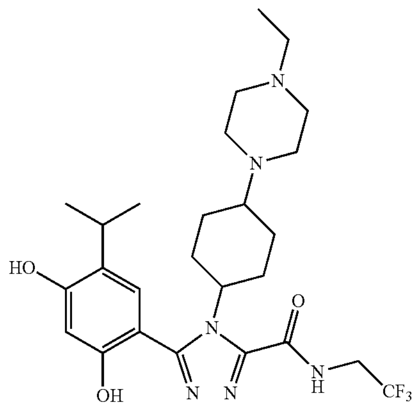 [SMILES: CCN1CCN(C2CCC(N(C(=N)C(=O)NCC(F)(F)F)C(=N)c3cc(C(C)C)c(O)cc3O)CC2)CC1] | 5-(2,4-dihydroxy-5-isopropylphenyl)-4-(4-(4-ethylpiperazin-1-yl)cyclohexyl |
| 312 | 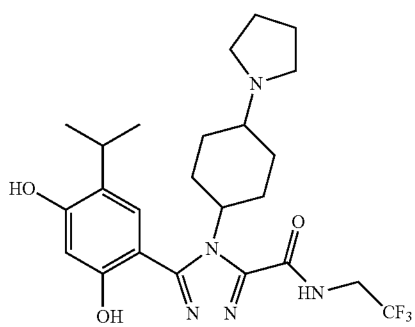 [SMILES: CC(C)c1cc(C(=N)N(C(=N)C(=O)NCC(F)(F)F)C2CCC(N3CCCC3)CC2)c(O)cc1O] | 5-(2,4-dihydroxy-5-isopropylphenyl)-4-(4-(pyrrolidin-1-yl)cyclohexyl)-N-(2,2,2-trifluoroethyl)-4H-1,2,4-triazole-3-carboxamide |
| 313 | 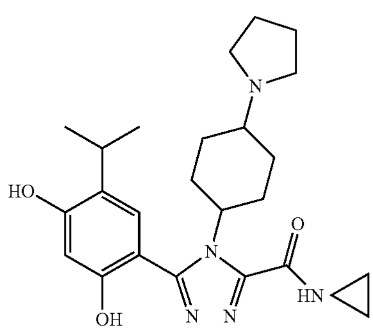 | N-cyclopropyl-5-(2,4-dihydroxy-5-isopropylphenyl)-4-(4-(pyrrolidin-1-yl)cyclohexyl)-4H-1,2,4-triazole-3-carboxamide |
| 314 | 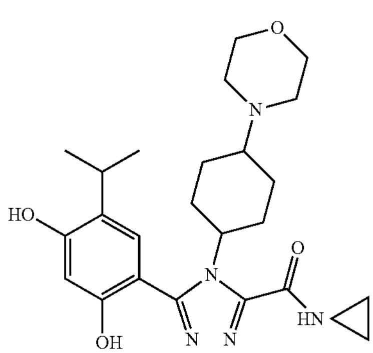 | N-cyclopropyl-5-(2,4-dihydroxy-5-isopropylphenyl)-4-(4-morpholinocyclohexyl)-4H-1,2,4-triazole-3-carboxamide |

TABLE 1-continued

| No. | Structure | Name |
|---|---|---|
| 315 | 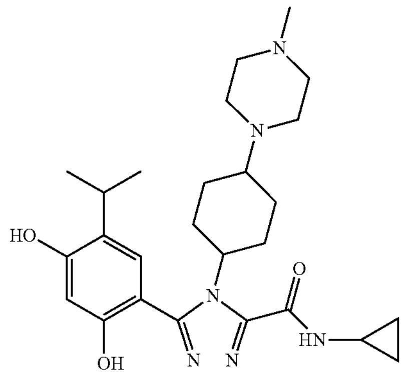 [SMILES: CC(C)c1cc(C(=N)N(C(=N)C(=O)NC2CC2)C2CCC(N3CCN(C)CC3)CC2)c(O)cc1O] | N-cyclopropyl-5-(2,4-dihydroxy-5-isopropylphenyl)-4-(4-(4-methylpiperazin-1-yl)cyclohexyl)-4H-1,2,4-triazole-3-carboxamide |
| 316 | 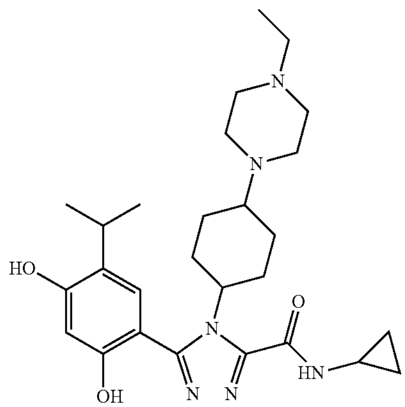 [SMILES: CCN1CCN(C2CCC(N(C(=N)C(=O)NC3CC3)C(=N)c3cc(C(C)C)c(O)cc3O)CC2)CC1] | N-cyclopropyl-5-(2,4-dihydroxy-5-isopropylphenyl)-4-(4-(4-ethylpiperazin-1-yl)cyclohexyl)-4H-1,2,4-triazole-3-carboxamide |
| 317 | 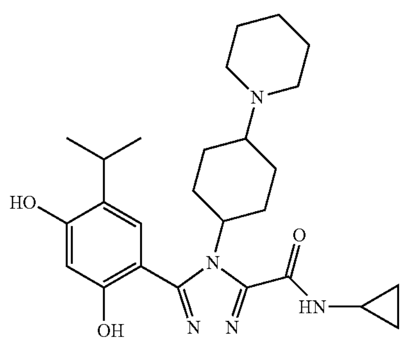 [SMILES: CC(C)c1cc(C(=N)N(C(=N)C(=O)NC2CC2)C2CCC(N3CCCCC3)CC2)c(O)cc1O] | N-cyclopropyl-5-(2,4-dihydroxy-5-isopropylphenyl)-4-(4-(piperidin-1-yl)cyclohexyl)-4H-1,2,4-triazole-3-carboxamide |
| 318 | 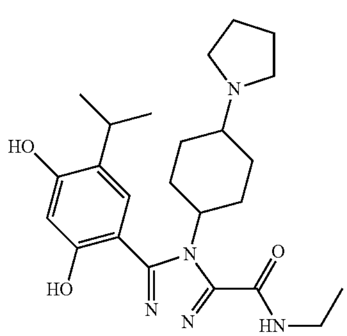 [SMILES: CCNC(=O)C(=N)N(C(=N)c1cc(C(C)C)c(O)cc1O)C1CCC(N2CCCC2)CC1] | 5-(2,4-dihydroxy-5-isopropylphenyl)-N-ethyl-4-(4-(pyrrolidin-1-yl)cyclohexyl)-4H-1,2,4-triazole-3-carboxamide |

TABLE 1-continued

| No. | Structure | Name |
|---|---|---|
| 319 | 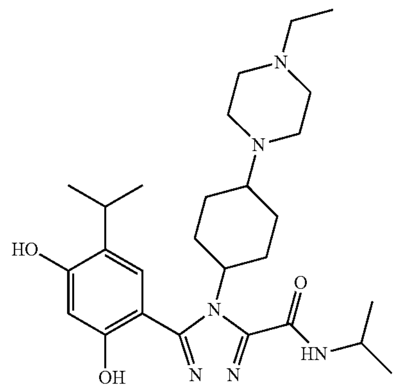 [SMILES: CCN1CCN(C2CCC(N(C(=N)C(=O)NC(C)C)C(=N)c3cc(C(C)C)c(O)cc3O)CC2)CC1] | 5-(2,4-dihydroxy-5-isopropylphenyl)-4-(4-(4-ethylpiperazin-1-yl)cyclohexyl)-N-isopropyl-4H-1,2,4-triazole-3-carboxamide |
| 320 | 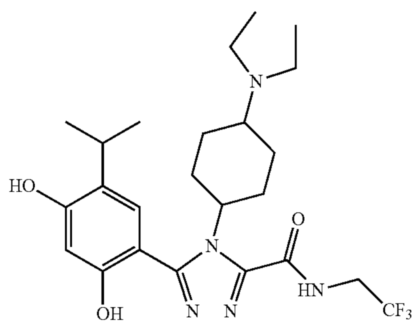 [SMILES: CCN(CC)C1CCC(N(C(=N)C(=O)NCC(F)(F)F)C(=N)c2cc(C(C)C)c(O)cc2O)CC1] | 4-(4-(diethylamino)cyclohexyl)-5-(2,4-dihydroxy-5-isopropylphenyl)-N-(2,2,2-trifluoroethyl)-4H-1,2,4-triazole-3-carboxamide |
| 321 | 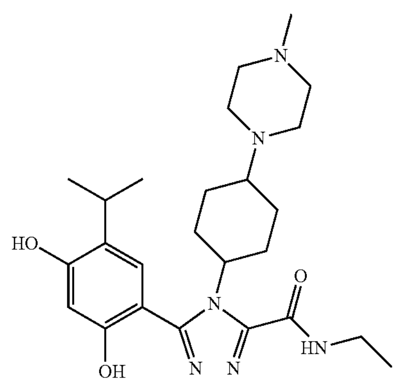 [SMILES: CCNC(=O)C(=N)N(C(=N)c1cc(C(C)C)c(O)cc1O)C1CCC(N2CCN(C)CC2)CC1] | 5-(2,4-dihydroxy-5-isopropylphenyl)-N-ethyl-4-(4-(4-methylpiperazin-1-yl)cyclohexyl)-4H-1,2,4-triazole-3-carboxamide |
| 322 | 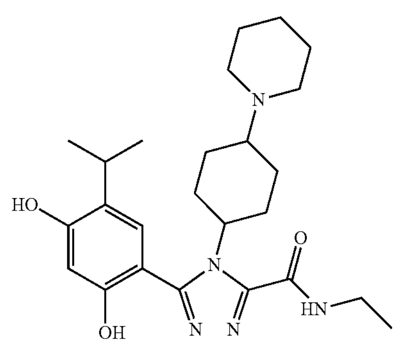 [SMILES: CCNC(=O)C(=N)N(C(=N)c1cc(C(C)C)c(O)cc1O)C1CCC(N2CCCCC2)CC1] | 5-(2,4-dihydroxy-5-isopropylphenyl)-N-ethyl-4-(4-(piperidin-1-yl)cyclohexyl)-4H-1,2,4-triazole-3-carboxamide |

TABLE 1-continued

| No. | Structure | Name |
|---|---|---|
| 323 | 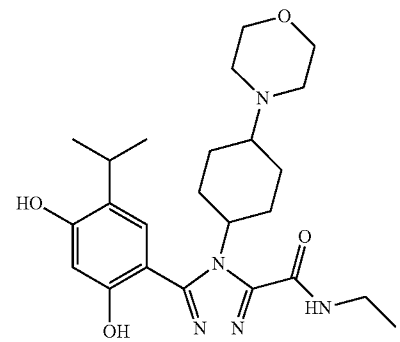 [SMILES: CCNC(=O)C(=N)N(C(=N)c1cc(C(C)C)c(O)cc1O)C1CCC(N2CCOCC2)CC1] | 5-(2,4-dihydroxy-5-isopropylphenyl)-N-ethyl-4-(4-morpholinocyclohexyl)-4H-1,2,4-triazole-3-carboxamide |
| 324 | 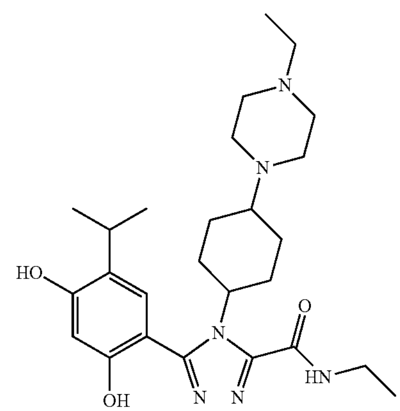 [SMILES: CCNC(=O)C(=N)N(C(=N)c1cc(C(C)C)c(O)cc1O)C1CCC(N2CCN(CC)CC2)CC1] | 5-(2,4-dihydroxy-5-isopropylphenyl)-N-ethyl-4-(4-(4-ethylpiperazin-1-yl)cyclohexyl)-4H-1,2,4-triazole-3-carboxamide |
| 325 | 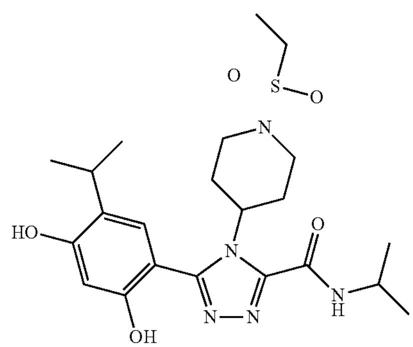 | 5-(2,4-dihydroxy-5-isopropylphenyl)-4-(1-(ethylsulfonyl)piperidin-4-yl)-N-isopropyl-4H-1,2,4-triazole-3-carboxamide |
| 326 | 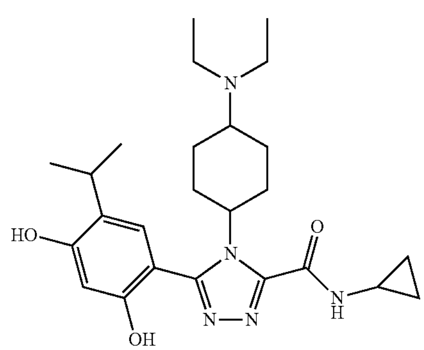 [SMILES: CCN(CC)C1CCC(n2c(C(=O)NC3CC3)nnc2-c2cc(C(C)C)c(O)cc2O)CC1] | N-cyclopropyl-4-(4-(diethylamino)cyclohexyl)-5-(2,4-dihydroxy-5-isopropylphenyl)-4H-1,2,4-triazole-3-carboxamide |

TABLE 1-continued

| No. | Structure | Name |
|---|---|---|
| 327 | 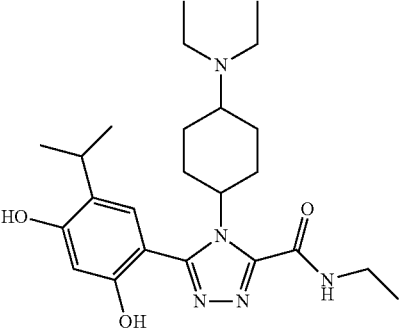 [SMILES: CCNC(=O)c1nnc(-c2cc(C(C)C)c(O)cc2O)n1C1CCC(N(CC)CC)CC1] | 4-(4-(diethylamino)cyclohexyl)-5-(2,4-dihydroxy-5-isopropylphenyl)-N-ethyl-4H-1,2,4-triazole-3-carboxamide |
| 328 | 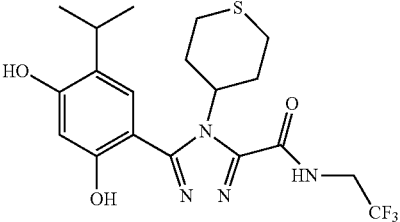 [SMILES: CC(C)c1cc(C(=N)N(C(=N)C(=O)NCC(F)(F)F)C2CCSCC2)c(O)cc1O] | 5-(2,4-dihydroxy-5-isopropylphenyl)-4-(tetrahydro-2H-thiopyran-4-yl)-N-(2,2,2-trifluoroethyl)-4H-1,2,4-triazole-3-carboxamide |
| 329 | 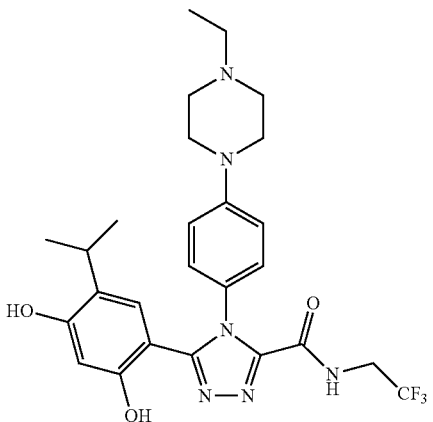 [SMILES: CCN1CCN(c2ccc(-n3c(C(=O)NCC(F)(F)F)nnc3-c3cc(C(C)C)c(O)cc3O)cc2)CC1] | 5-(2,4-dihydroxy-5-isopropylphenyl)-4-(4-(4-ethylpiperazin-1-yl)phenyl)-N-(2,2,2-trifluoroethyl)-4H-1,2,4-triazole-3-carboxamide |
| 330 | 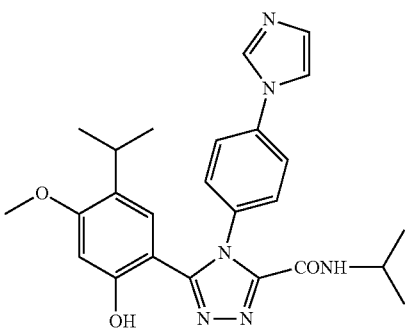 | 4-(4-(1H-imidazol-1-yl)phenyl)-5-(2-hydroxy-5-isopropyl-4-methoxyphenyl)-N-isopropyl-4H-1,2,4-triazole-3-carboxamide |

TABLE 1-continued

| No. | Structure | Name |
|---|---|---|
| 331 | 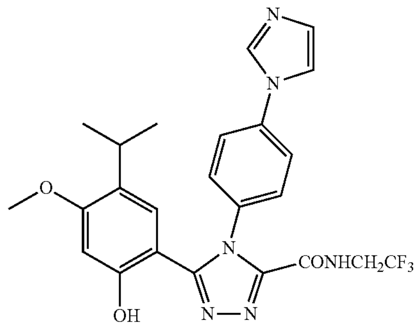 | 4-(4-(1H-imidazol-1-yl)phenyl)-5-(2-hydroxy-5-isopropyl-4-methoxyphenyl)-N-(2,2,2-trifluoroethyl)-4H-1,2,4-triazole-3-carboxamide |
| 332 | 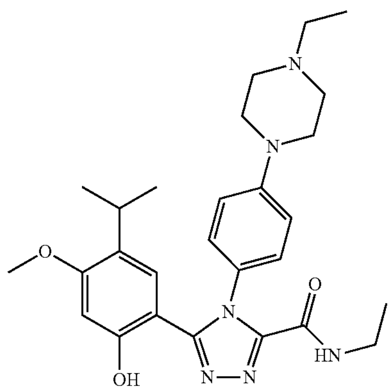 [SMILES: CCNC(=O)c1nnc(-c2cc(C(C)C)c(OC)cc2O)n1-c1ccc(N2CCN(CC)CC2)cc1] | N-ethyl-4-(4-(4-ethylpiperazin-1-yl)phenyl)-5-(2-hydroxy-5-isopropyl-4-methoxyphenyl)-4H-1,2,4-triazole-3-carboxamide |
| 333 | 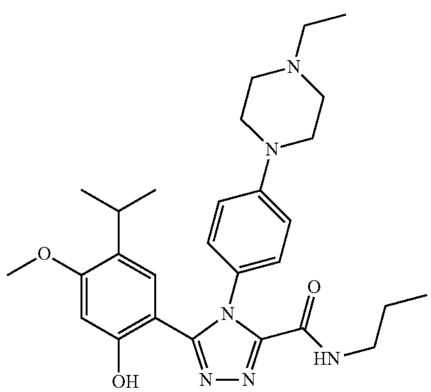 [SMILES: CCCNC(=O)c1nnc(-c2cc(C(C)C)c(OC)cc2O)n1-c1ccc(N2CCN(CC)CC2)cc1] | 4-(4-(4-ethylpiperazin-1-yl)phenyl)-5-(2-hydroxy-5-isopropyl-4-methoxyphenyl)-N-propyl-4H-1,2,4-triazole-3-carboxamide |
| 334 | 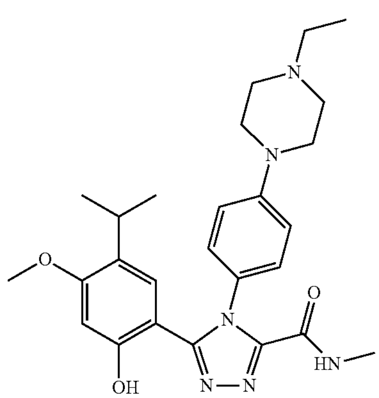 | 4-(4-(4-ethylpiperazin-1-yl)phenyl)-5-(2-hydroxy-5-isopropyl-4-methoxyphenyl)-N-methyl-4H-1,2,4-triazole-3-carboxamide |

TABLE 1-continued

| No. | Structure | Name |
|---|---|---|
| 335 | 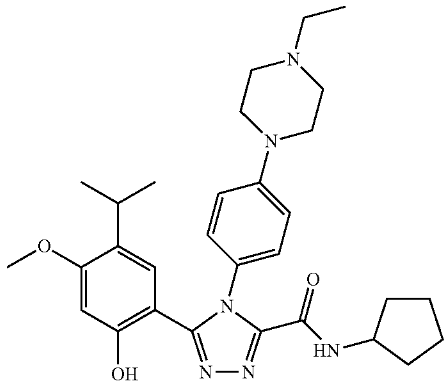 [SMILES: CCN1CCN(c2ccc(-n3c(C(=O)NC4CCCC4)nnc3-c3cc(C(C)C)c(OC)cc3O)cc2)CC1] | N-cyclopentyl-4-(4-(4-ethylpiperazin-1-yl)pheny l)-5-(2-hydroxy-5-isopropyl-4-methoxyphenyl)-4H-1,2,4-triazole-3-carboxamide |
| 336 | 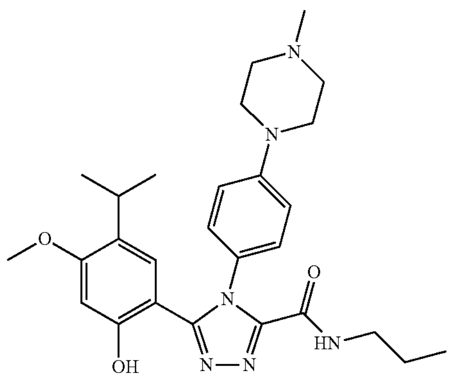 [SMILES: CCCNC(=O)c1nnc(-c2cc(C(C)C)c(OC)cc2O)n1-c1ccc(N2CCN(C)CC2)cc1] | 5-(2-hydroxy-5-isopropyl-4-methoxyphenyl)-4-(4-(4-methylpiperazin-1-yl)phenyl)-N-propyl-4H-1,2,4-triazole-3-carboxamide |
| 337 | 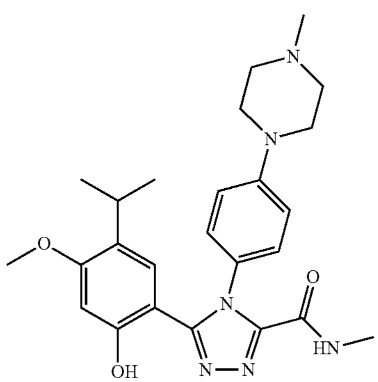 | 5-(2-hydroxy-5-isopropyl-4-methoxyphenyl)-N-methyl-4-(4-(4-methylpiperazin-1-yl)phenyl)-4H-1,2,4-triazole-3-carboxamide |
| 338 | 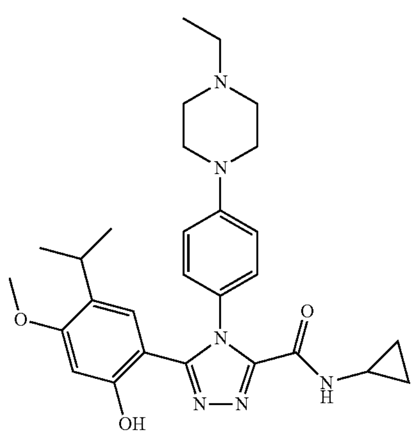 [SMILES: CCN1CCN(c2ccc(-n3c(C(=O)NC4CC4)nnc3-c3cc(C(C)C)c(OC)cc3O)cc2)CC1] | N-cyclopropyl-4-(4-(4-ethylpiperazin-1-yl)phenyl)-5-(2-hydroxy-5-isopropyl-4-methoxyphenyl)-4H-1,2,4-triazole-3-carboxamide |

TABLE 1-continued

| No. | Structure | Name |
|---|---|---|
| 339 | 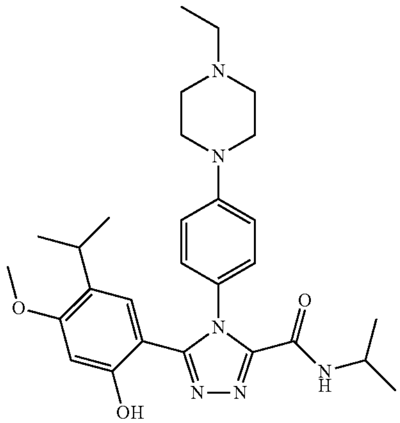 [SMILES: CCN1CCN(c2ccc(-n3c(C(=O)NC(C)C)nnc3-c3cc(C(C)C)c(OC)cc3O)cc2)CC1] | 4-(4-(4-ethylpiperazin-1-yl)phenyl)-5-(2-hydroxy-5-isopropyl-4-methoxyphenyl)-N-isopropyl-4H-1,2,4-triazole-3-carboxainide |
| 340 | 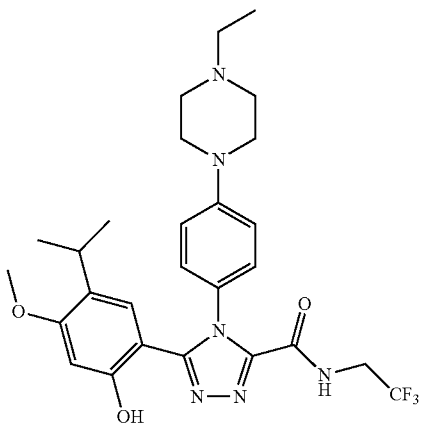 [SMILES: CCN1CCN(c2ccc(-n3c(C(=O)NCC(F)(F)F)nnc3-c3cc(C(C)C)c(OC)cc3O)cc2)CC1] | 4-(4-(4-ethylpiperazin-1-yl)phenyl)-5-(2-hydroxy-5-isopropyl-4-methoxyphenyl)-N-(2,2,2-trifluoroethyl)-4H-1,2,4-triazole-3-carboxamide |
| 341 | 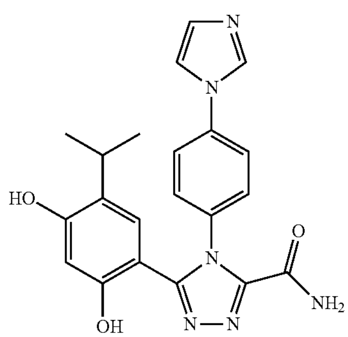 [SMILES: CC(C)c1cc(-c2nnc(C(N)=O)n2-c2ccc(-n3ccnc3)cc2)c(O)cc1O] | 4-(4-(1H-imidazol-1-yl)phenyl)-5-(2,4-dihydroxy-5-isopropylphenyl)-4H-1,2,4-triazole-3-carboxamide |
| 342 | 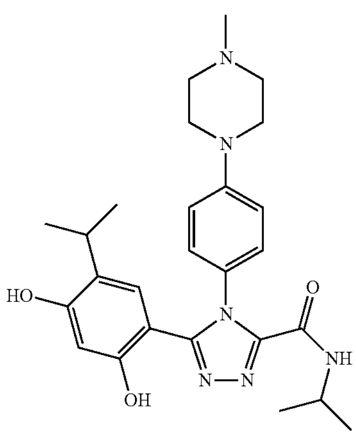 [SMILES: CC(C)NC(=O)c1nnc(-c2cc(C(C)C)c(O)cc2O)n1-c1ccc(N2CCN(C)CC2)cc1] | 5-(2,4-dihydroxy-5-isopropylphenyl)-N-isopropyl-4-(4-(4-methylpiperazin-1-yl)phenyl)-4H-1,2,4-triazole-3-carboxamide |

TABLE 1-continued

| No. | Structure | Name |
|---|---|---|
| 343 | 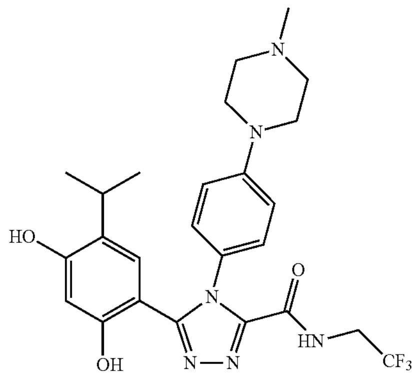 [SMILES: CC(C)c1cc(-c2nnc(C(=O)NCC(F)(F)F)n2-c2ccc(N3CCN(C)CC3)cc2)c(O)cc1O] | 5-(2,4-dihydroxy-5-isopropylphenyl)-4-(4-(4-methylpiperazin-1-yl)phenyl)-N-(2,2,2-trifluoroethyl)-4H-1,2,4-triazole-3-carboxamide |
| 345 | 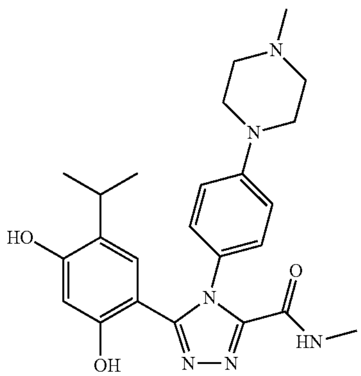 [SMILES: CNC(=O)c1nnc(-c2cc(C(C)C)c(O)cc2O)n1-c1ccc(N2CCN(C)CC2)cc1] | 5-(2,4-dihydroxy-5-isopropylphenyl)-N-methyl-4-(4-(4-methylpiperazin-1-yl)phenyl)-4H-1,2,4-triazole-3-carboxamide |
| 346 | 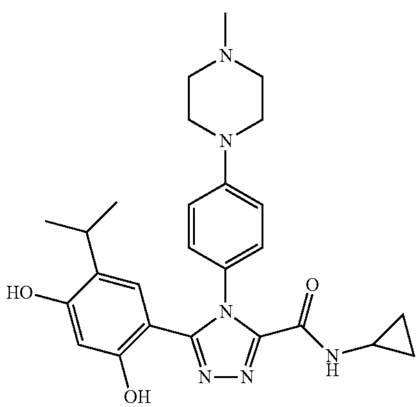 [SMILES: CC(C)c1cc(-c2nnc(C(=O)NC3CC3)n2-c2ccc(N3CCN(C)CC3)cc2)c(O)cc1O] | N-cyclopropyl-5-(2,4-dihydroxy-5-isopropylphenyl)-4-(4-(4-methylpiperazin-1-yl)phenyl)-4H-1,2,4-triazole-3-carboxamide |
| 347 | 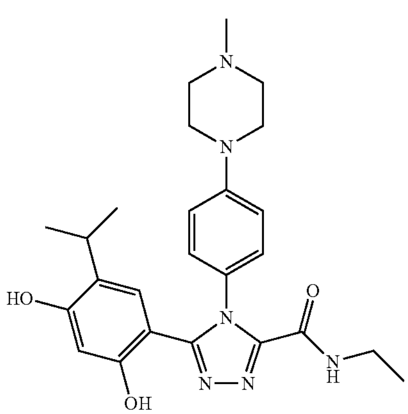 [SMILES: CCNC(=O)c1nnc(-c2cc(C(C)C)c(O)cc2O)n1-c1ccc(N2CCN(C)CC2)cc1] | 5-(2,4-dihydroxy-5-isopropylphenyl)-N-ethyl-4-(4-(4-methylpiperazin-1-yl)phenyl)-4H-1,2,4-triazole-3-carboxamide |

TABLE 1-continued

| No. | Structure | Name |
|---|---|---|
| 348 | 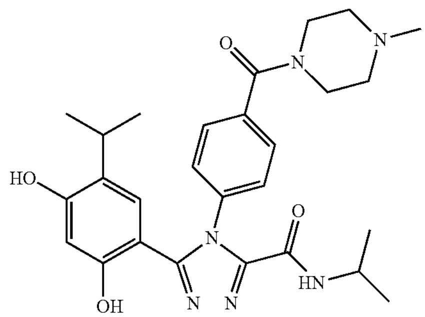 [SMILES: CC(C)NC(=O)C(=N)N(C(=N)c1cc(C(C)C)c(O)cc1O)c1ccc(C(=O)N2CCN(C)CC2)cc1] | 5-(2,4-dihydroxy-5-isopropylphenyl)-N-isopropyl-4-(4-(4-methylpiperazine-1-carbonyl)phenyl)-4H-1,2,4-triazole-3-carboxamide |
| 349 | 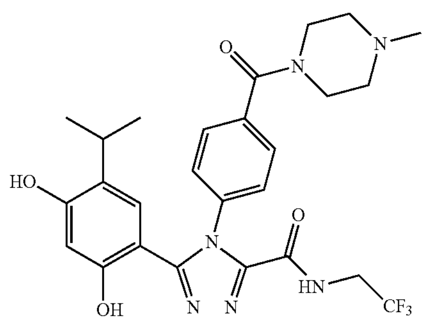 [SMILES: CC(C)c1cc(C(=N)N(C(=N)C(=O)NCC(F)(F)F)c2ccc(C(=O)N3CCN(C)CC3)cc2)c(O)cc1O] | 5-(2,4-dihydroxy-5-isopropylphenyl)-4-(4-(4-methylpiperazine-1-carbonyl)phenyl)-N-(2,2,2-trifluoroethyl)-4H-1,2,4-triazole-3-carboxamide |
| 350 | 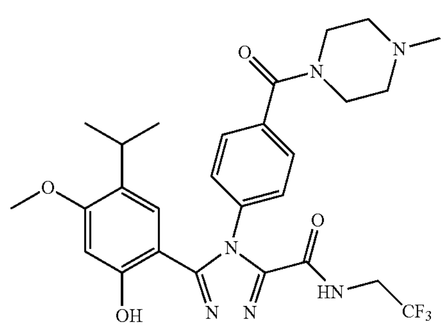 | 5-(2-hydroxy-5-isopropyl-4-methoxyphenyl)-4-(4-(4-methylpiperazine-1-carbonyl)phenyl)-N-(2,2,2-trifluoroethyl)-4H-1,2,4-triazole-3-carboxamide |
| 351 | 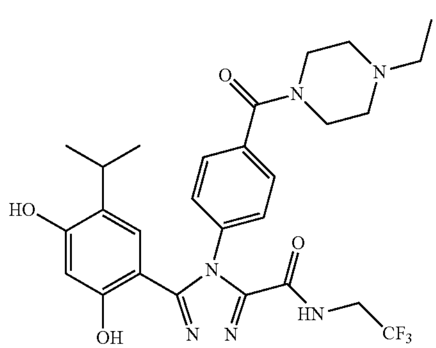 [SMILES: CCN1CCN(C(=O)c2ccc(N(C(=N)C(=O)NCC(F)(F)F)C(=N)c3cc(C(C)C)c(O)cc3O)cc2)CC1] | 5-(2,4-dihydroxy-5-isopropylphenyl)-4-(4-(4-ethylpiperazine-1-carbonyl)phenyl)-N-(2,2,2-trifluoroethyl)-4H-1,2,4-triazole-3-carboxamide |

| No. | Structure | Name |
|---|---|---|
| 352 | 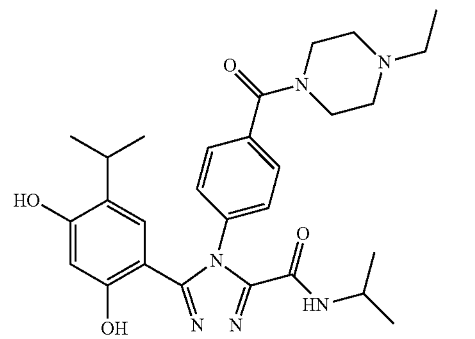 [SMILES: CCN1CCN(C(=O)c2ccc(N(C(=N)C(=O)NC(C)C)C(=N)c3cc(C(C)C)c(O)cc3O)cc2)CC1] | 5-(2,4-dihydroxy-5-isopropylphenyl)-4-(4-(4-ethylpiperazine-1-carbonyl)phenyl)-N-isopropyl-4H-1,2,4-triazole-3-carboxamide |
| 353 | 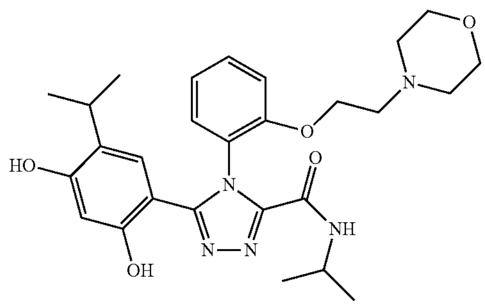 [SMILES: CC(C)NC(=O)c1nnc(-c2cc(C(C)C)c(O)cc2O)n1-c1ccccc1OCCN1CCOCC1] | 5-(2,4-dihydroxy-5-isopropylphenyl)-N-isopropyl-4-(2-(2-morpholinoethoxy)phenyl)-4H-1,2,4-triazole-3-carboxamide |
| 354 | 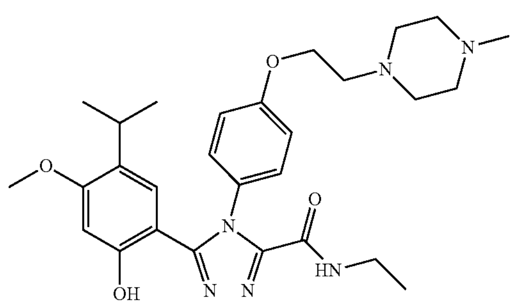 | N-ethyl-5-(2-hydroxy-5-isopropyl-4-methoxyphenyl)-4-(4-(2-(4-methylpiperazin-1-yl)ethoxy)phenyl)-4H-1,2,4-triazole-3-carboxamide |
| 355 | 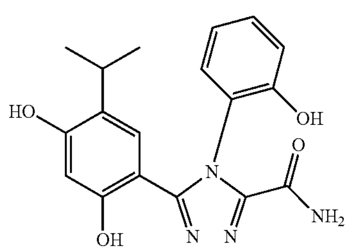 [SMILES: CC(C)c1cc(C(=N)N(C(=N)C(N)=O)c2ccccc2O)c(O)cc1O] | 5-(2,4-dihydroxy-5-isopropylphenyl)-4-(2-hydroxyphenyl)-4H-1,2,4-triazole-3-carboxamide |
| 356 | 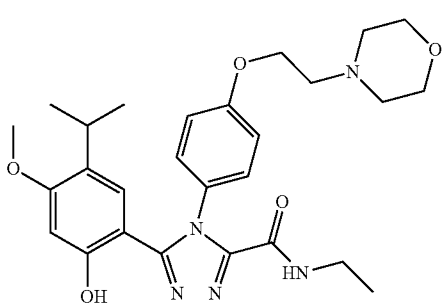 [SMILES: CCNC(=O)C(=N)N(C(=N)c1cc(C(C)C)c(OC)cc1O)c1ccc(OCCN2CCOCC2)cc1] | N-ethyl-5-(2-hydroxy-5-isopropyl-4-methoxyphenyl)-4-(4-(2-morpholinoethoxy)phenyl)-4H-1,2,4-triazole-3-carboxamide |

TABLE 1-continued

| No. | Structure | Name |
|---|---|---|
| 357 | 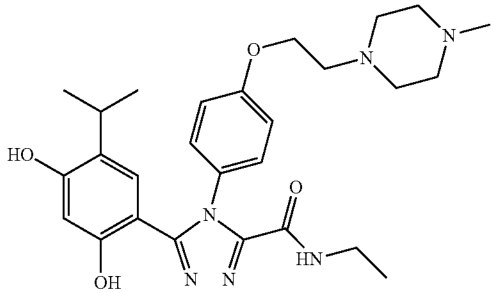 [SMILES: CCNC(=O)C(=N)N(C(=N)c1cc(C(C)C)c(O)cc1O)c1ccc(OCCN2CCN(C)CC2)cc1] | 5-(2,4-dihydroxy-5-isopropylphenyl)-N-ethyl-4-(4-(2-(4-methylpiperazin-1-yl)ethoxy)phenyl)-4H-1,2,4-triazole-3-carboxamide |
| 358 | 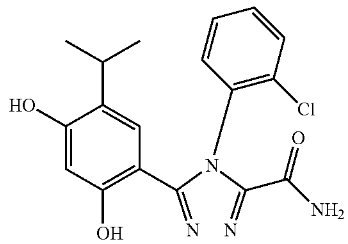 [SMILES: CC(C)c1cc(C(=N)N(C(=N)C(N)=O)c2ccccc2Cl)c(O)cc1O] | 4-(2-chlorophenyl)-5-(2,4-dihydroxy-5-isopropylphenyl)-4H-1,2,4-triazole-3-carboxamide |
| 359 | 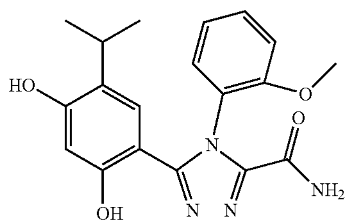 [SMILES: COc1ccccc1N(C(=N)C(N)=O)C(=N)c1cc(C(C)C)c(O)cc1O] | 5-(2,4-dihydroxy-5-isopropylphenyl)-4-(2-methoxyphenyl)-4H-1,2,4-triazole-3-carboxamide |
| 360 | 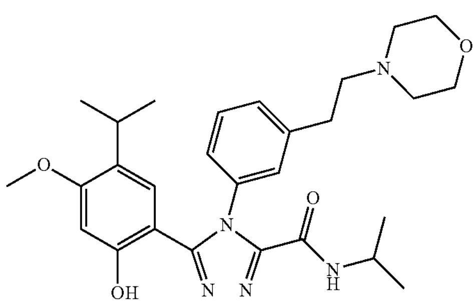 [SMILES: COc1cc(O)c(C(=N)N(C(=N)C(=O)NC(C)C)c2cccc(CCN3CCOCC3)c2)cc1C(C)C] | 5-(2-hydroxy-5-isopropyl-4-methoxyphenyl)-N-isopropyl-4-(3-(2-morpholinoethyl)phenyl)-4H-1,2,4-triazole-3-carboxamide |
| 361 | 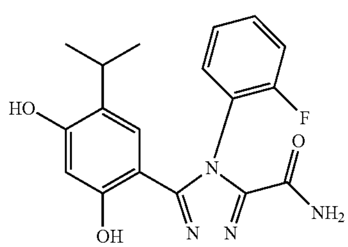 [SMILES: CC(C)c1cc(C(=N)N(C(=N)C(N)=O)c2ccccc2F)c(O)cc1O] | 5-(2,4-dihydroxy-5-isopropylphenyl)-4-(2-fluorophenyl)-4H-1,2,4-triazole-3-carboxamide |
| 362 | 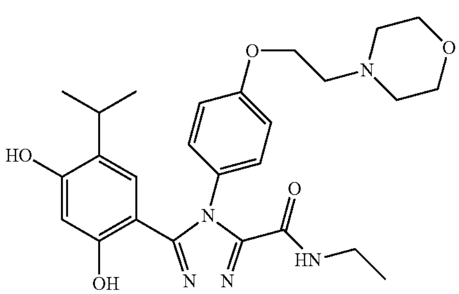 [SMILES: CCNC(=O)C(=N)N(C(=N)c1cc(C(C)C)c(O)cc1O)c1ccc(OCCN2CCOCC2)cc1] | 5-(2,4-dihydroxy-5-isopropylphenyl)-N-ethyl-4-(4-(2-morpholinoethoxy)-phenyl)-4H-1,2,4-triazole-3-carboxamide |

TABLE 1-continued

| No. | Structure | Name |
|---|---|---|
| 363 | 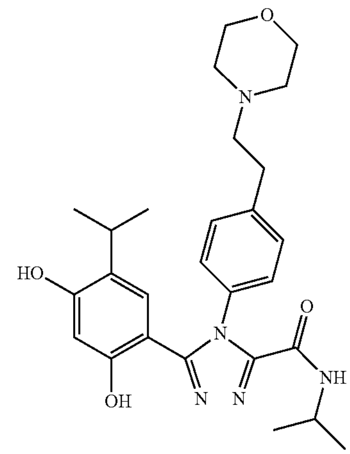 [SMILES: CC(C)NC(=O)C(=N)N(C(=N)c1cc(C(C)C)c(O)cc1O)c1ccc(CCN2CCOCC2)cc1] | 5-(2,4-dihydroxy-5-isopropylphenyl)-N-isopropyl-4-(4-(2-morpholinoethyl)phenyl)-4H-1,2,4-triazole-3-carboxamide |
| 364 | 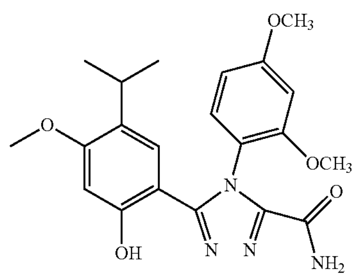 [SMILES: COc1ccc(N(C(=N)C(N)=O)C(=N)c2cc(C(C)C)c(OC)cc2O)c(OC)c1] | 4-(2,4-dimethoxyphenyl)-5-(2-hydroxy-5-isopropyl-4-methoxyphenyl)-4H-1,2,4-triazole-3-carboxamide |
| 365 | 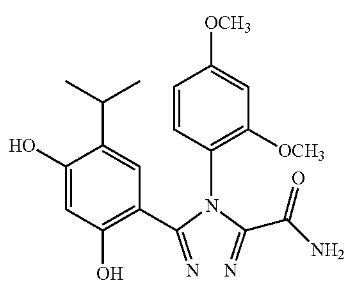 [SMILES: COc1ccc(N(C(=N)C(N)=O)C(=N)c2cc(C(C)C)c(O)cc2O)c(OC)c1] | 5-(2,4-dihydroxy-5-isopropylphenyl)-4-(2,4-dimethoxyphenyl)-4H-1,2,4-triazole-3-carboxamide |
| 366 | 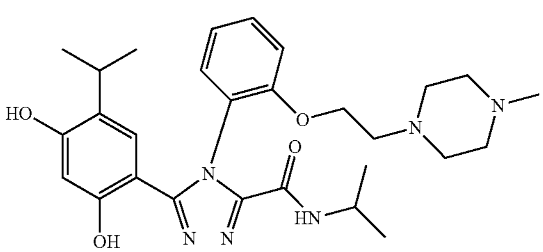 [SMILES: CC(C)NC(=O)C(=N)N(C(=N)c1cc(C(C)C)c(O)cc1O)c1ccccc1OCCN1CCN(C)CC1] | 5-(2,4-dihydroxy-5-isopropylphenyl)-N-isopropyl-4-(2-(2-(4-methylpiperazin-1-yl)ethoxy)phenyl)-4H-1,2,4-triazole-3-carboxamide |
| 367 | 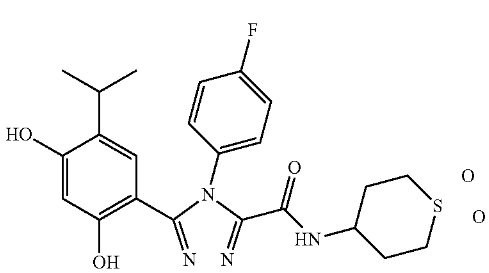 | |

TABLE 1-continued

| No. | Structure | Name |
|---|---|---|
| 368 | 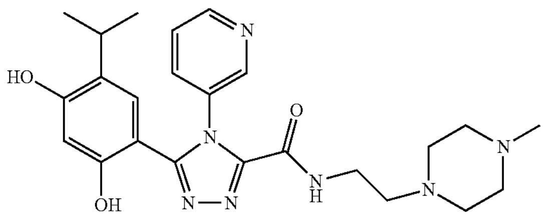 [SMILES: CC(C)c1cc(-c2nnc(C(=O)NCCN3CCN(C)CC3)n2-c2cccnc2)c(O)cc1O] | 5-(2,4-dihydroxy-5-isopropylphenyl)-N-(2-(4-methylpiperazin-1-yl)ethyl)-4-(pyridin-3-yl)-4H-1,2,4-triazole-3-carboxamide |
| 369 | 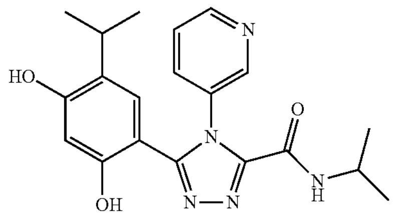 [SMILES: CC(C)NC(=O)c1nnc(-c2cc(C(C)C)c(O)cc2O)n1-c1cccnc1] | 5-(2,4-dihydroxy-5-isopropylphenyl)-N-isopropyl-4-(pyridin-3-yl)-4H-1,2,4-triazole-3-carboxamide |
| 370 | 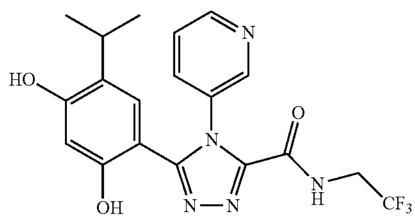 [SMILES: CC(C)c1cc(-c2nnc(C(=O)NCC(F)(F)F)n2-c2cccnc2)c(O)cc1O] | 5-(2,4-dihydroxy-5-isopropylphenyl)-4-(pyridin-3-yl)-N-(2,2,2-trifluoroethyl)-4H-1,2,4-triazole-3-carboxamide |
| 371 | 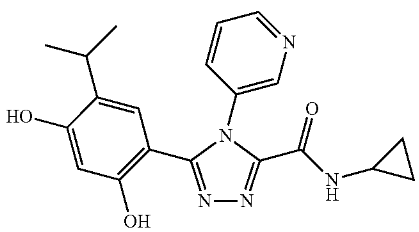 [SMILES: CC(C)c1cc(-c2nnc(C(=O)NC3CC3)n2-c2cccnc2)c(O)cc1O] | N-cyclopropyl-5-(2,4-dihydroxy-5-isopropylphenyl)-4-(pyridin-3-yl)-4H-1,2,4-triazole-3-carboxamide |
| 372 | 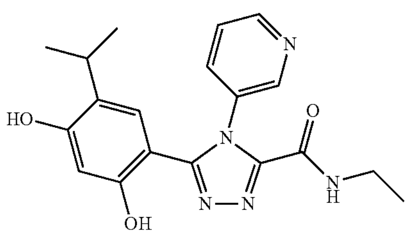 [SMILES: CCNC(=O)c1nnc(-c2cc(C(C)C)c(O)cc2O)n1-c1cccnc1] | 5-(2,4-dihydroxy-5-isopropylphenyl)-N-ethyl-4-(pyridin-3-yl)-4H-1,2,4-triazole-3-carboxamide |
| 373 | 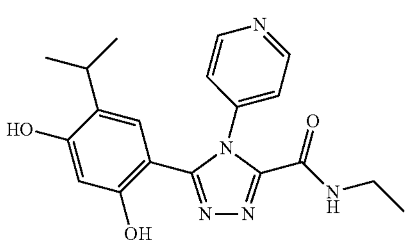 [SMILES: CCNC(=O)c1nnc(-c2cc(C(C)C)c(O)cc2O)n1-c1ccncc1] | 5-(2,4-dihydroxy-5-isopropylphenyl)-N-ethyl-4-(pyridin-4-yl)-4H-1,2,4-triazole-3-carboxamide |
| 374 | 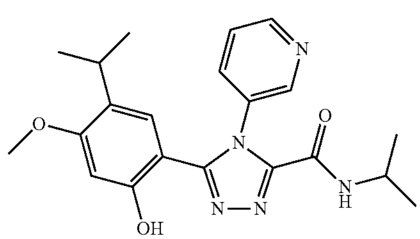 [SMILES: COc1cc(O)c(-c2nnc(C(=O)NC(C)C)n2-c2cccnc2)cc1C(C)C] | 5-(2-hydroxy-5-isopropyl-4-methoxyphenyl)-N-isopropyl-4-(pyridin-3-yl)-4H-1,2,4-triazole-3-carboxamide |

TABLE 1-continued

| No. | Structure | Name |
|---|---|---|
| 375 | 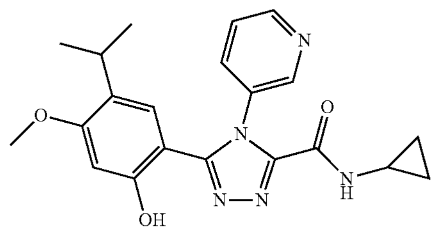 [SMILES: COc1cc(O)c(-c2nnc(C(=O)NC3CC3)n2-c2cccnc2)cc1C(C)C] | N-cyclopropyl-5-(2-hydroxy-5-isopropyl-4-methoxyphenyl)-4-(pyridin-3-yl)-4H-1,2,4-triazole-3-carboxamide |
| 376 | 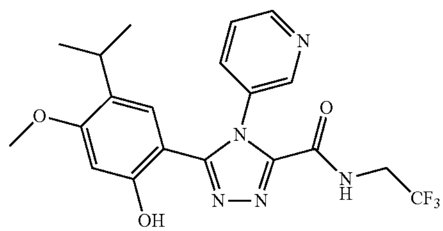 [SMILES: COc1cc(O)c(-c2nnc(C(=O)NCC(F)(F)F)n2-c2cccnc2)cc1C(C)C] | 5-(2-hydroxy-5-isopropyl-4-methoxyphenyl)-4-(pyridin-3-yl)-N-(2,2,2-trifluoroethyl)-4H-1,2,4-triazole-3-carboxamide |
| 377 | 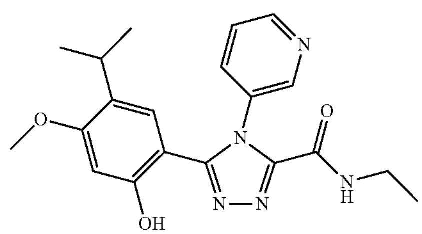 [SMILES: CCNC(=O)c1nnc(-c2cc(C(C)C)c(OC)cc2O)n1-c1cccnc1] | N-ethyl-5-(2-hydroxy-5-isopropyl-4-methoxyphenyl)-4-(pyridin-3-yl)-4H-1,2,4-triazole-3-carboxamide |
| 378 | 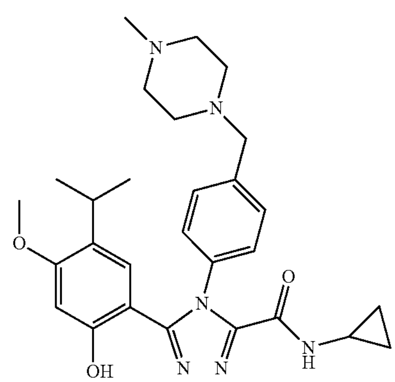 [SMILES: COc1cc(O)c(C(=N)N(C(=N)C(=O)NC2CC2)c2ccc(CN3CCN(C)CC3)cc2)cc1C(C)C] | N-cyclopropyl-5-(2-hydroxy-5-isopropyl-4-methoxyphenyl)-4-(4-((4-methylpiperazin-1-yl)methyl)phenyl)-4H-1,2,4-triazole-3-carboxamide |
| 379 | 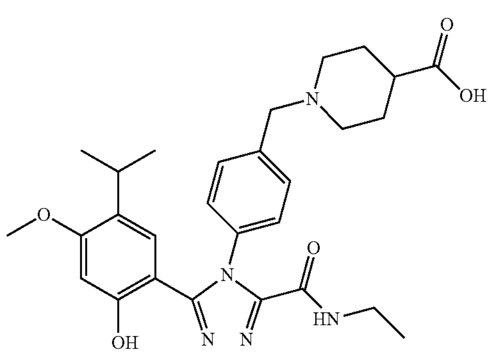 [SMILES: CCNC(=O)C(=N)N(C(=N)c1cc(C(C)C)c(OC)cc1O)c1ccc(CN2CCC(C(=O)O)CC2)cc1] | 1-(4-(3-(ethylcarbamoyl)-5-(2-hydroxy-5-isopropyl-4-methoxyphenyl)-4H-1,2,4-triazol-4-yl)benzyl)piperidine-4-carboxylic acid |

TABLE 1-continued

| No. | Structure | Name |
|---|---|---|
| 380 | 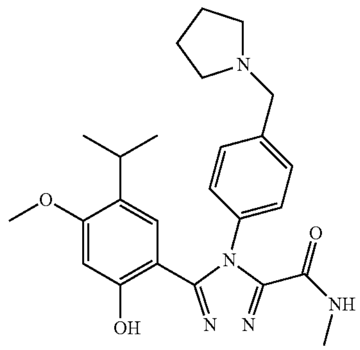 [SMILES: CNC(=O)C(=N)N(C(=N)c1cc(C(C)C)c(OC)cc1O)c1ccc(CN2CCCC2)cc1] | 5-(2-hydroxy-5-isopropyl-4-methoxyphenyl)-N-methyl-4-(4-(pyrrolidin-1-ylmethyl)phenyl)-4H-1,2,4-triazole-3-carboxamide |
| 381 | 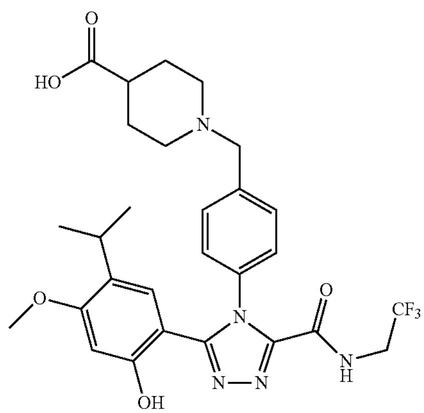 [SMILES: COc1cc(O)c(-c2nnc(C(=O)NCC(F)(F)F)n2-c2ccc(CN3CCC(C(=O)O)CC3)cc2)cc1C(C)C] | 1-(4-(3-(2-hydroxy-5-isopropyl-4-methoxyphenyl)-5-(2,2,2-trifluoroethyl-carbamoyl)-4H-1,2,4-triazol-4-yl)benzyl)piperidine-4-carboxylic acid |
| 382 | 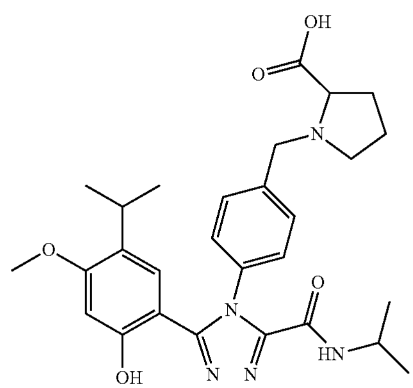 [SMILES: COc1cc(O)c(C(=N)N(C(=N)C(=O)NC(C)C)c2ccc(CN3CCCC3C(=O)O)cc2)cc1C(C)C] | 1-(4-(3-(2-hydroxy-5-isopropyl-4-methoxyphenyl)-5-(isopropylcarbamoyl)-4H-1,2,4-triazol-4-yl)benzyl)pyrrolidine-2-carboxylic acid |
| 383 | 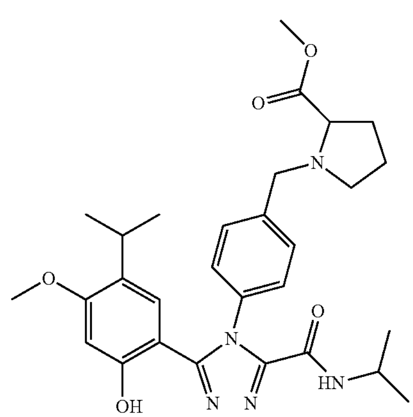 [SMILES: COC(=O)C1CCCN1Cc1ccc(N(C(=N)C(=O)NC(C)C)C(=N)c2cc(C(C)C)c(OC)cc2O)cc1] | methyl 1-(4-(3-(2-hydroxy-5-isopropyl-4-methoxyphenyl)-5-(isopropylcarbamoyl)-4H-1,2,4-triazol-4-yl)benzyl)pyrrolidine-2-carboxylate |

TABLE 1-continued

| No. | Structure | Name |
|---|---|---|
| 384 | 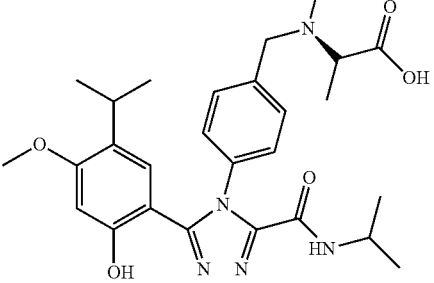 | (S)-2-((4-(3-(2-hydroxy-5-isopropyl-4-methoxyphenyl)-5-(isopropylcarbamoyl)-4H-1,2,4-triazol-4-yl)benzyl)(methyl)-amino)propanoic acid |
| 385 | 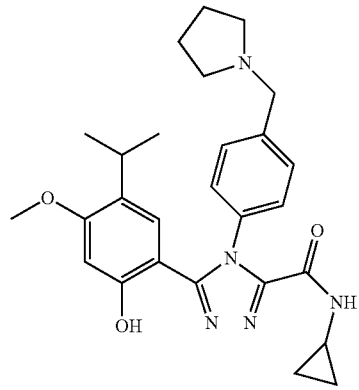 [SMILES: COc1cc(O)c(C(=N)N(C(=N)C(=O)NC2CC2)c2ccc(CN3CCCC3)cc2)cc1C(C)C] | N-cyclopropyl-5-(2-hydroxy-5-isopropyl-4-methoxyphenyl)-4-(4-(pyrrolidin-1-ylmethyl)phenyl)-4H-1,2,4-triazole-3-carboxamide |
| 386 | 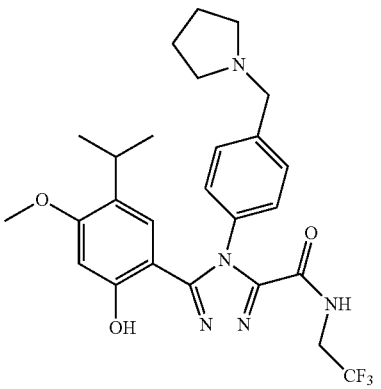 [SMILES: COc1cc(O)c(C(=N)N(C(=N)C(=O)NCC(F)(F)F)c2ccc(CN3CCCC3)cc2)cc1C(C)C] | 5-(2-hydroxy-5-isopropyl-4-methoxyphenyl)-4-(4-(pyrrolidin-1-ylmethyl)phenyl)-N-(2,2,2-trifluoroethyl)-4H-1,2,4-triazole-3-carboxamide |
| 387 | 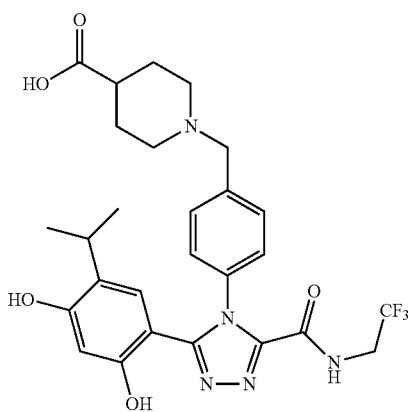 [SMILES: CC(C)c1cc(-c2nnc(C(=O)NCC(F)(F)F)n2-c2ccc(CN3CCC(C(=O)O)CC3)cc2)c(O)cc1O] | 1-(4-(3-(2,4-dihydroxy-5-isopropylphenyl)-5-(2,2,2-trifluoroethylcarbamoyl)-4H-1,2,4-triazol-4-yl)benzyl)piperidine-4-carboxylic acid |

TABLE 1-continued

| No. | Structure | Name |
|---|---|---|
| 388 | 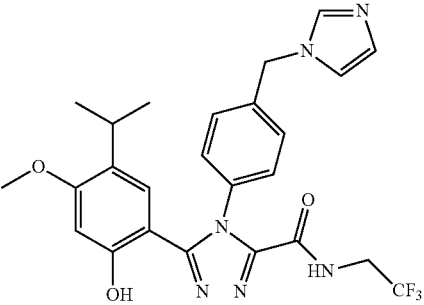 [SMILES: COc1cc(O)c(C(=N)N(C(=N)C(=O)NCC(F)(F)F)c2ccc(Cn3ccnc3)cc2)cc1C(C)C] | 4-(4-((1H-imidazol-1-yl)methyl)phenyl)-5-(2-hydroxy-5-isopropyl-4-methoxyphenyl)-N-(2,2,2-trifluoroethyl)-4H-1,2,4-triazole-3-carboxamide |
| 389 | 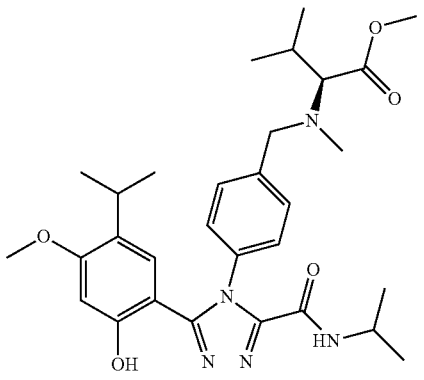 | (S)-methyl 2-((4-(3-(2-hydroxy-5-isopropyl-4-methoxyphenyl)-5-(isopropylcarbamoyl)-4H-1,2,4-triazol-4-yl)benzyl)(methyl)amino)-3-methylbutanoate |
| 390 | 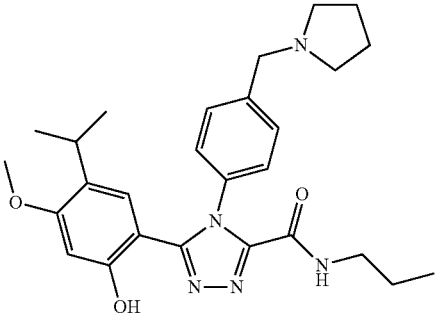 [SMILES: CCCNC(=O)c1nnc(-c2cc(C(C)C)c(OC)cc2O)n1-c1ccc(CN2CCCC2)cc1] | 5-(2-hydroxy-5-isopropyl-4-methoxyphenyl)-N-propyl-4-(4-(pyrrolidin-1-ylmethyl)phenyl)-4H-1,2,4-triazole-3-carboxamide |
| 391 | 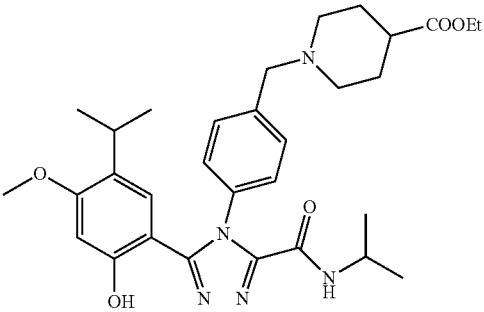 [SMILES: CCOC(=O)C1CCN(Cc2ccc(N(C(=N)C(=O)NC(C)C)C(=N)c3cc(C(C)C)c(OC)cc3O)cc2)CC1] | ethyl 1-(4-(3-(2-hydroxy-5-isopropyl-4-methoxyphenyl)-5-(isopropylcarbamoyl)-4H-1,2,4-triazol-4-yl)benzyl)piperidine-4-carboxylate |

TABLE 1-continued

| No. | Structure | Name |
|---|---|---|
| 392 | 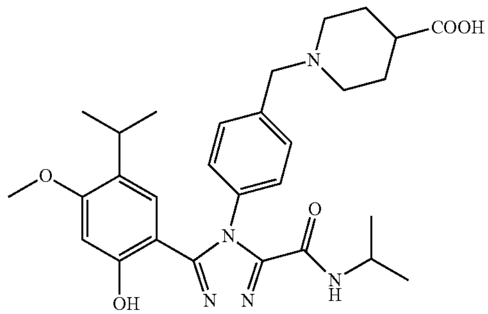 [SMILES: COc1cc(O)c(C(=N)N(C(=N)C(=O)NC(C)C)c2ccc(CN3CCC(C(=O)O)CC3)cc2)cc1C(C)C] | 1-(4-(3-(2-hydroxy-5-isopropyl-4-methoxyphenyl)-5-(isopropylcarbamoyl)-4H-1,2,4-triazol-4-yl)benzyl)piperidine-4-carboxylic acid |
| 393 | 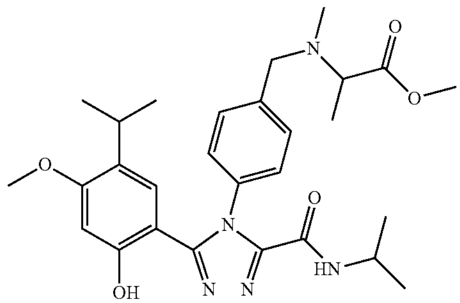 | methyl 2-((4-(3-(2-hydroxy-5-isopropyl-4-methoxyphenyl)-5-(isopropylcarbamoyl)-4H-1,2,4-triazol-4-yl)benzyl)(methyl)amino)-propanoate |
| 394 | 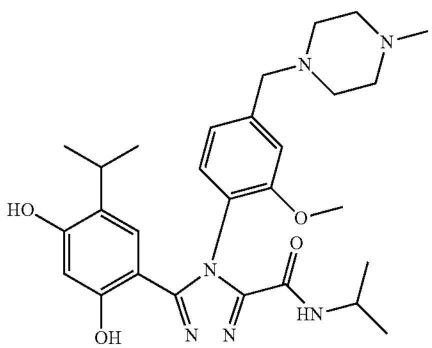 [SMILES: COc1cc(CN2CCN(C)CC2)ccc1N(C(=N)C(=O)NC(C)C)C(=N)c1cc(C(C)C)c(O)cc1O] | 5-(2,4-dihydroxy-5-isopropylphenyl)-N-isopropyl-4-(2-methoxy-4-((4-methylpiperazin-1-yl)methyl)phenyl)-4H-1,2,4-triazole-3-carboxamide |
| 395 | 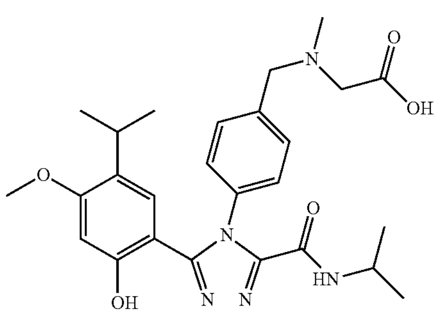 [SMILES: COc1cc(O)c(C(=N)N(C(=N)C(=O)NC(C)C)c2ccc(CN(C)CC(=O)O)cc2)cc1C(C)C] | 2-((4-(3-(2-hydroxy-5-isopropyl-4-methoxyphenyl)-5-(isopropylcarbamoyl)-4H-1,2,4-triazol-4-yl)benzyl)(methyl)amino)acetic acid |
| 396 | 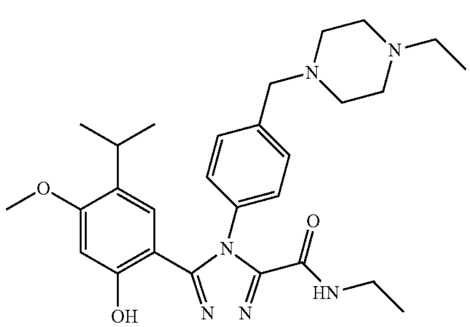 [SMILES: CCNC(=O)C(=N)N(C(=N)c1cc(C(C)C)c(OC)cc1O)c1ccc(CN2CCN(CC)CC2)cc1] | N-ethyl-4-(4-((4-ethylpiperazin-1-yl)methyl)phenyl)-5-(2-hydroxy-5-isopropyl-4-methoxyphenyl)-4H-1,2,4-triazole-3-carboxamide |

TABLE 1-continued

| No. | Structure | Name |
|---|---|---|
| 397 | 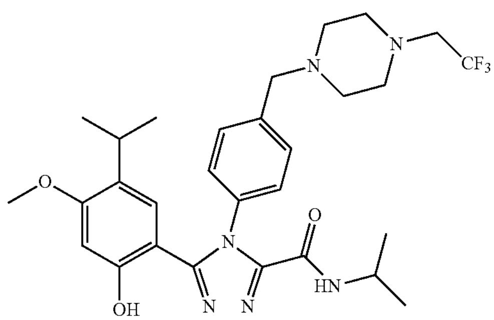 [SMILES: COc1cc(O)c(C(=N)N(C(=N)C(=O)NC(C)C)c2ccc(CN3CCN(CC(F)(F)F)CC3)cc2)cc1C(C)C] | 5-(2-hydroxy-5-isopropyl-4-methoxyphenyl)-N-isopropyl-4-(4-((4-(2,2,2-trifluoroethyl)piperazin-1-yl)methyl)phenyl)-4H-1,2,4-triazole-3-carboxamide |
| 398 | 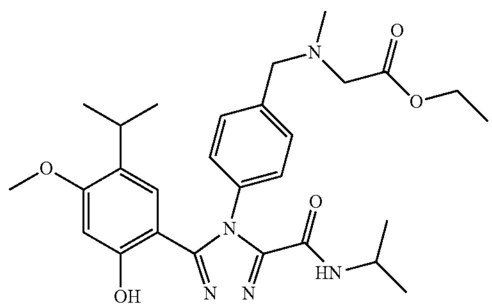 [SMILES: CCOC(=O)CN(C)Cc1ccc(N(C(=N)C(=O)NC(C)C)C(=N)c2cc(C(C)C)c(OC)cc2O)cc1] | ethyl 2-((4-(3-(2-hydroxy-5-isopropyl-4-methoxyphenyl)-5-(isopropylcarbamoyl)-4H-1,2,4-triazol-4-yl)benzyl)-(methyl)amino)acetate |
| 399 | 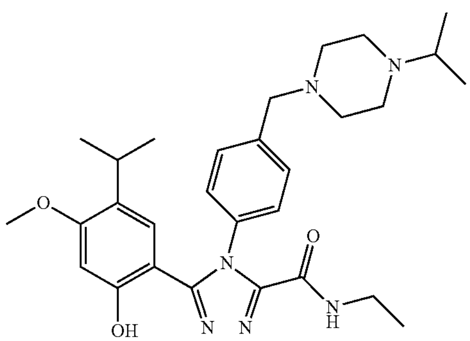 [SMILES: CCNC(=O)C(=N)N(C(=N)c1cc(C(C)C)c(OC)cc1O)c1ccc(CN2CCN(C(C)C)CC2)cc1] | N-ethyl-5-(2-hydroxy-5-isopropyl-4-methoxyphenyl)-4-(4-((4-isopropylpiperazin-1-yl)methyl)phenyl)-4H-1,2,4-triazole-3-carboxamide |
| 400 | 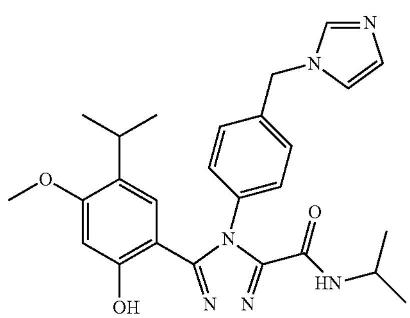 | 4-(4-((1H-imidazol-1-yl)methyl)phenyl)-5-(2-hydroxy-5-isopropyl-4-methoxyphenyl)-N-isopropyl-4H-1,2,4-triazole-3-carboxamide |
| 401 | 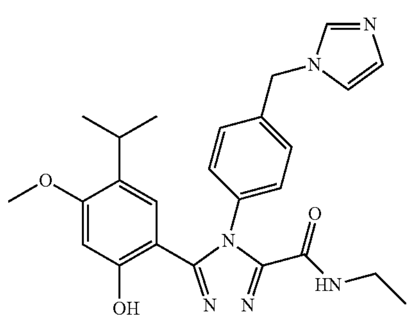 [SMILES: CCNC(=O)C(=N)N(C(=N)c1cc(C(C)C)c(OC)cc1O)c1ccc(Cn2ccnc2)cc1] | 4-(4-((1H-imidazol-1-yl)methyl)phenyl)-N-ethyl-5-(2-hydroxy-5-isopropyl-4-methoxyphenyl)-4H-1,2,4-triazole-3-carboxamide |

| No. | Structure | Name |
|---|---|---|
| 402 | 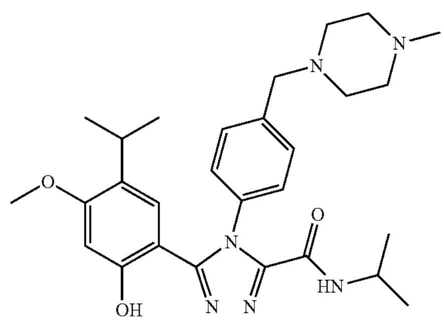 | 5-(2-hydroxy-5-isopropyl-4-methoxyphenyl)-N-isopropyl-4-(4-((4-methylpiperazin-1-yl)methyl)phenyl)-4H-1,2,4-triazole-3-carboxamide |
| 403 | 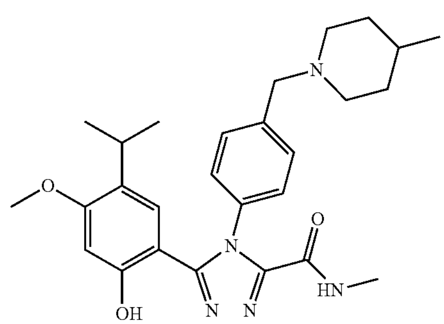 | 5-(2-hydroxy-5-isopropyl-4-methoxyphenyl)-N-methyl-4-(4-((4-methylpiperidin-1-yl)methyl)phenyl)-4H-1,2,4-triazole-3-carboxamide |
| 404 | 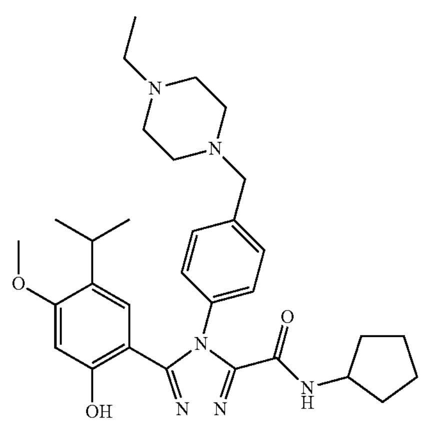 [SMILES: CCN1CCN(Cc2ccc(N(C(=N)C(=O)NC3CCCC3)C(=N)c3cc(C(C)C)c(OC)cc3O)cc2)CC1] | N-cyclopentyl-4-(4-((4-ethylpiperazin-1-yl)methyl)phenyl)-5-(2-hydroxy-5-isopropyl-4-methoxyphenyl)-4H-1,2,4-triazole-3-carboxamide |
| 405 | 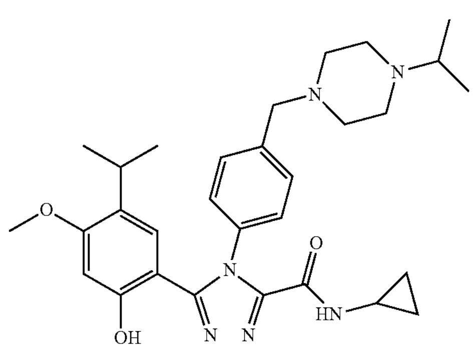 [SMILES: COc1cc(O)c(C(=N)N(C(=N)C(=O)NC2CC2)c2ccc(CN3CCN(C(C)C)CC3)cc2)cc1C(C)C] | N-cyclopropyl-5-(2-hydroxy-5-isopropyl-4-methoxyphenyl)-4-(4-((4-isopropylpiperazin-1-yl)methyl)phenyl)-4H-1,2,4-triazole-3-carboxamide |

TABLE 1-continued

| No. | Structure | Name |
|---|---|---|
| 406 | 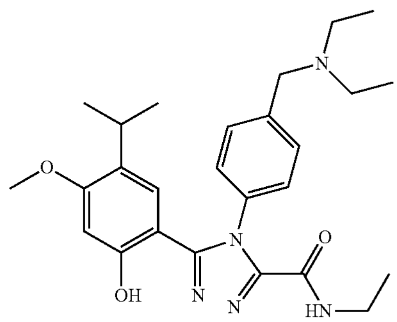 [SMILES: CCNC(=O)C(=N)N(C(=N)c1cc(C(C)C)c(OC)cc1O)c1ccc(CN(CC)CC)cc1] | 4-(4-((diethylamino)methyl)phenyl)-N-ethyl-5-(2-hydroxy-5-isopropyl-4-methoxyphenyl)-4H-1,2,4-triazole-3-carboxamide |
| 407 | 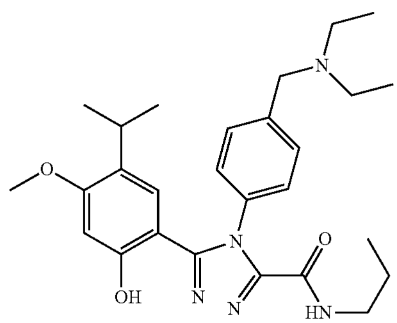 [SMILES: CCCNC(=O)C(=N)N(C(=N)c1cc(C(C)C)c(OC)cc1O)c1ccc(CN(CC)CC)cc1] | 4-(4-((diethylamino)methyl)phenyl)-5-(2-hydroxy-5-isopropyl-4-methoxyphenyl)-N-propyl-4H-1,2,4-triazole-3-carboxamide |
| 408 | 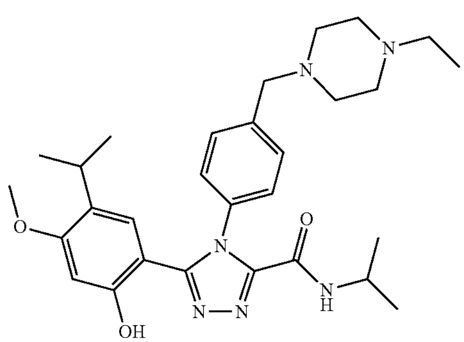 [SMILES: CCN1CCN(Cc2ccc(-n3c(C(=O)NC(C)C)nnc3-c3cc(C(C)C)c(OC)cc3O)cc2)CC1] | 4-(4-((4-ethylpiperazin-1-yl)methyl)phenyl)-5-(2-hydroxy-5-isopropyl-4-methoxyphenyl)-N-isopropyl-4H-1,2,4-triazole-3-carboxamide |
| 409 | 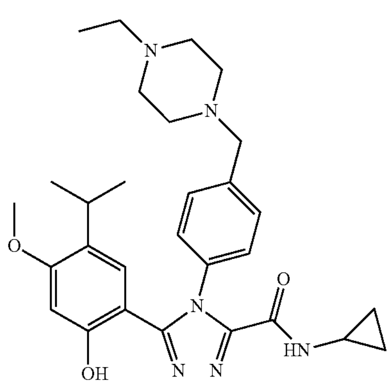 [SMILES: CCN1CCN(Cc2ccc(N(C(=N)C(=O)NC3CC3)C(=N)c3cc(C(C)C)c(OC)cc3O)cc2)CC1] | N-cyclopropyl-4-(4-((4-ethylpiperazin-1-yl)methyl)phenyl)-5-(2-hydroxy-5-isopropyl-4-methoxyphenyl)-4H-1,2,4-triazole-3-carboxamide |

TABLE 1-continued

| No. | Structure | Name |
|---|---|---|
| 410 | 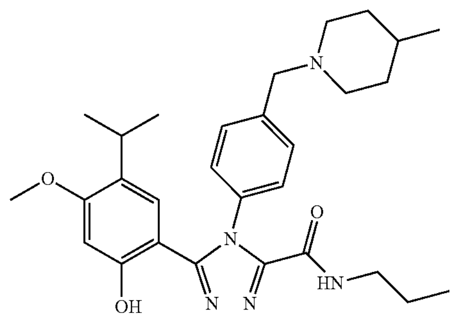 [SMILES: CCCNC(=O)C(=N)N(C(=N)c1cc(C(C)C)c(OC)cc1O)c1ccc(CN2CCC(C)CC2)cc1] | 5-(2-hydroxy-5-isopropyl-4-methoxyphenyl)-4-(4-((4-methylpiperidin-1-yl)methyl)phenyl)-N-propyl-4H-1,2,4-triazole-3-carboxamide |
| 411 | 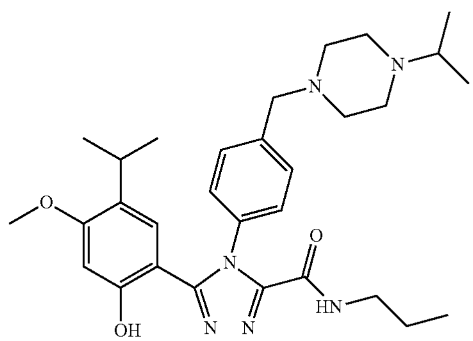 [SMILES: CCCNC(=O)C(=N)N(C(=N)c1cc(C(C)C)c(OC)cc1O)c1ccc(CN2CCN(C(C)C)CC2)cc1] | 5-(2-hydroxy-5-isopropyl-4-methoxyphenyl)-4-(4-((4-isopropylpiperazin-1-yl)methyl)phenyl)-N-propyl-4H-1,2,4-triazole-3-carboxamide |
| 412 | 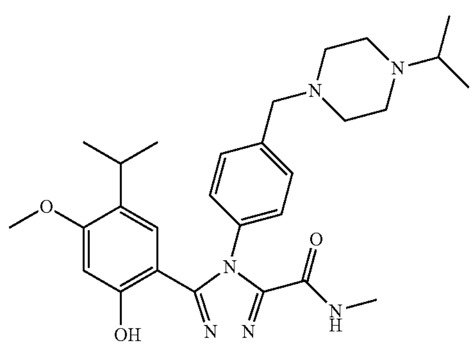 [SMILES: CNC(=O)C(=N)N(C(=N)c1cc(C(C)C)c(OC)cc1O)c1ccc(CN2CCN(C(C)C)CC2)cc1] | 5-(2-hydroxy-5-isopropyl-4-methoxyphenyl)-4-(4-((4-isopropylpiperazin-1-yl)methyl)phenyl)-N-methyl-4H-1,2,4-triazole-3-carboxamide |
| 413 | 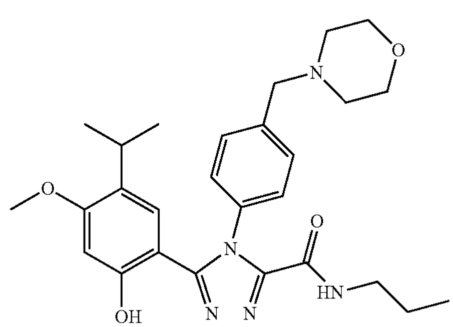 | 5-(2-hydroxy-5-isopropyl-4-methoxyphenyl)-4-(4-(morpholinomethyl)phenyl)-N-propyl-4H-1,2,4-triazole-3-carboxamide |

TABLE 1-continued

| No. | Structure | Name |
|---|---|---|
| 414 | 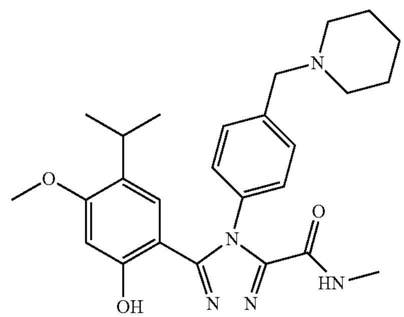 [SMILES: CNC(=O)C(=N)N(C(=N)c1cc(C(C)C)c(OC)cc1O)c1ccc(CN2CCCCC2)cc1] | 5-(2-hydroxy-5-isopropyl-4-methoxyphenyl)-N-methyl-4-(4-(piperidin-1-ylmethyl)phenyl)-4H-1,2,4-triazole-3-carboxamide |
| 415 | 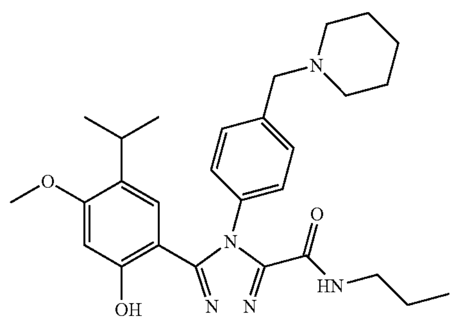 [SMILES: CCCNC(=O)C(=N)N(C(=N)c1cc(C(C)C)c(OC)cc1O)c1ccc(CN2CCCCC2)cc1] | 5-(2-hydroxy-5-isopropyl-4-methoxyphenyl)-4-(4-(piperidin-1-ylmethyl)phenyl)-N-propyl-4H-1,2,4-triazole-3-carboxamide |
| 416 | 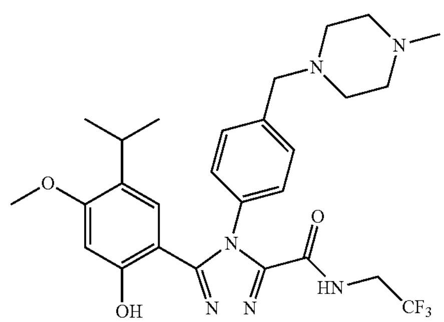 | 5-(2-hydroxy-5-isopropyl-4-methoxyphenyl)-4-(4-((4-methylpiperazin-1-yl)methyl)phenyl)-N-(2,2,2-trifluoroethyl)-4H-1,2,4-triazole-3-carboxamide |
| 417 | 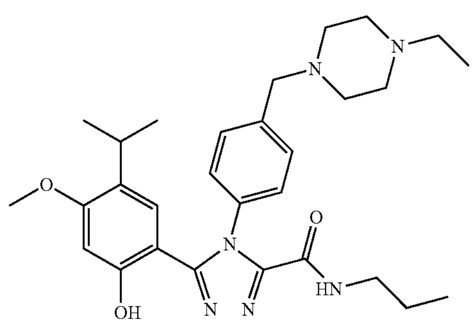 [SMILES: CCCNC(=O)C(=N)N(C(=N)c1cc(C(C)C)c(OC)cc1O)c1ccc(CN2CCN(CC)CC2)cc1] | 4-(4-((4-ethylpiperazin-1-yl)methyl)phenyl)-5-(2-hydroxy-5-isopropyl-4-methoxyphenyl)-N-propyl-4H-1,2,4-triazole-3-carboxamide |
| 418 | 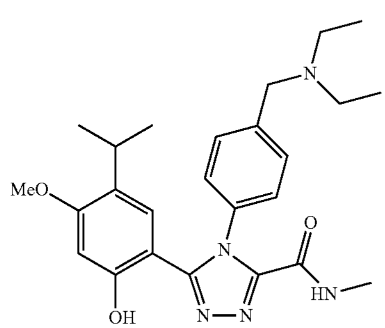 [SMILES: CCN(CC)Cc1ccc(-n2c(C(=O)NC)nnc2-c2cc(C(C)C)c(OC)cc2O)cc1] | 4-(4-((diethylamino)methyl)phenyl)-5-(2-hydroxy-5-isopropyl-4-methoxy-phenyl)-N-methyl-4H-1,2,4-triazole-3-carboxamide |

TABLE 1-continued

| No. | Structure | Name |
|---|---|---|
| 419 | 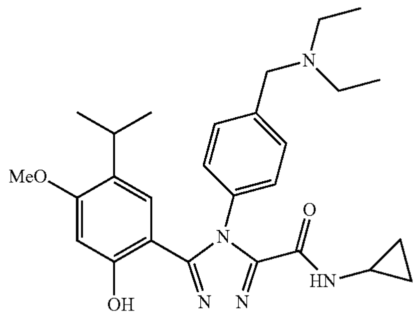 [SMILES: CCN(CC)Cc1ccc(N(C(=N)C(=O)NC2CC2)C(=N)c2cc(C(C)C)c(OC)cc2O)cc1] | N-cyclopropyl-4-(4-((diethylamino)methyl)phenyl)-5-(2-hydroxy-5-isopropyl-4-methoxyphenyl)-4H-1,2,4-triazole-3-carboxamide |
| 420 | 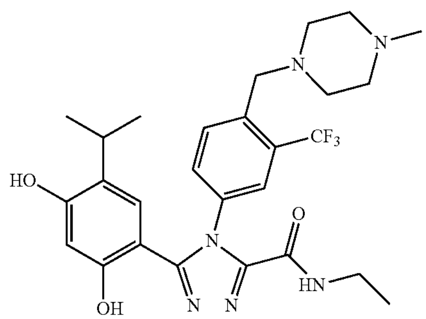 [SMILES: CCNC(=O)C(=N)N(C(=N)c1cc(C(C)C)c(O)cc1O)c1ccc(CN2CCN(C)CC2)c(C(F)(F)F)c1] | 5-(2,4-dihydroxy-5-isopropylphenyl)-N-ethyl-4-(4-((4-methylpiperazin-1-yl)methyl)-3-(trifluoromethyl)phenyl)-4H-1,2,4-triazole-3-carboxamide |
| 421 | 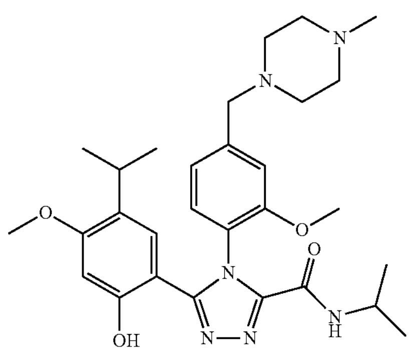 [SMILES: COc1cc(O)c(-c2nnc(C(=O)NC(C)C)n2-c2ccc(CN3CCN(C)CC3)cc2OC)cc1C(C)C] | 5-(2-hydroxy-5-isopropyl-4-methoxyphenyl)-N-isopropyl-4-(2-methoxy-4-((4-methylpiperazin-1-yl)methyl)phenyl)-4H-1,2,4-triazole-3-carboxamide |
| 422 | 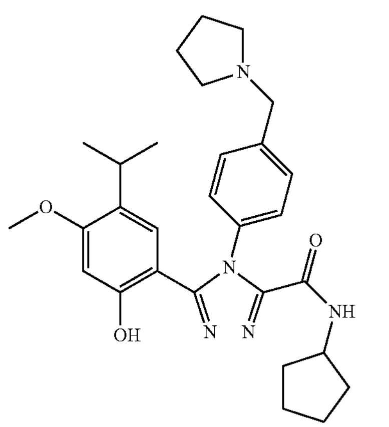 [SMILES: COc1cc(O)c(C(=N)N(C(=N)C(=O)NC2CCCC2)c2ccc(CN3CCCC3)cc2)cc1C(C)C] | N-cyclopentyl-5-(2-hydroxy-5-isopropyl-4-methoxyphenyl)-4-(4-(pyrrolidin-1-ylmethyl)phenyl)-4H-1,2,4-triazole-3-carboxamide |

TABLE 1-continued

| No. | Structure | Name |
|---|---|---|
| 423 | 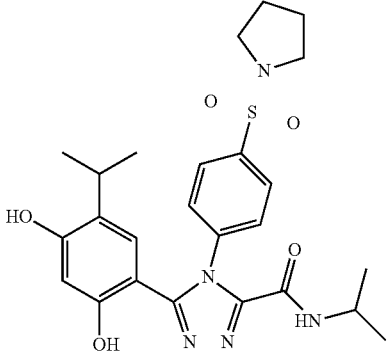 | 5-(2,4-dihydroxy-5-isopropylphenyl)-N-isopropyl-4-(4-(pyrrolidin-1-ylsulfonyl)phenyl)-4H-1,2,4-triazole-3-carboxamide |
| 424 | 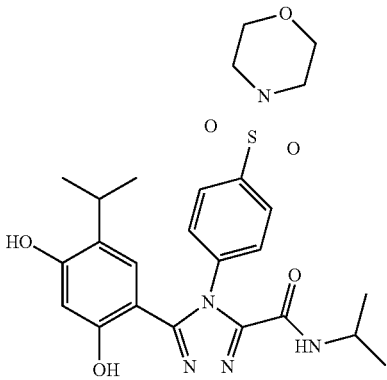 | 5-(2,4-dihydroxy-5-isopropylphenyl)-N-isopropyl-4-(4-(morpholino-sulfonyl)phenyl)-4H-1,2,4-triazole-3-carboxamide |
| 425 | 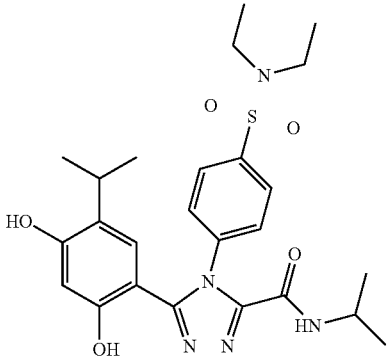 | 4-(4-(N,N-diethylsulfamoyl)phenyl)-5-(2,4-dihydroxy-5-isopropylphenyl)-N-isopropyl-4H-1,2,4-triazole-3-carboxamide |
| 426 | 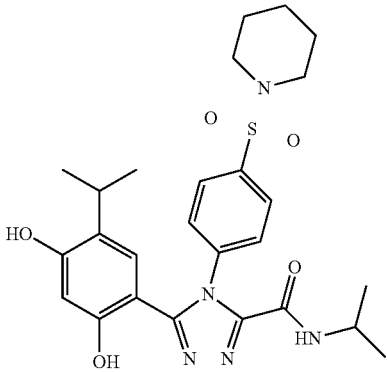 | 5-(2,4-dihydroxy-5-isopropylphenyl)-N-isopropyl-4-(4-(piperidin-1-ylsulfonyl)phenyl)-4H-1,2,4-triazole-3-carboxamide |

TABLE 1-continued

| No. | Structure | Name |
|---|---|---|
| 427 | 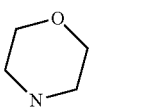 | 5-(2,4-dihydroxy-5-isopropylphenyl)-N-ethyl-4-(4-(morpholino-sulfonyl)phenyl)-4H-1,2,4-triazole-3-carboxamide |
| 428 | 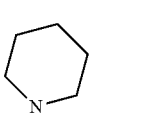 | 5-(2,4-dihydroxy-5-isopropylphenyl)-4-(4-(piperidin-1-ylsulfonyl)phenyl)-N-(2,2,2-trifluoroethyl)-4H-1,2,4-triazole-3-carboxamide |
| 429 | 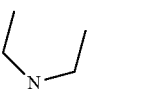 | 4-(4-(N,N-diethylsulfamoyl)phenyl)-5-(2,4-dihydroxy-5-isopropylphenyl)-N-(2,2,2-trifluoroethyl)-4H-1,2,4-triazole-3-carboxamide |
| 430 | 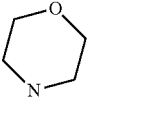 | 5-(2,4-dihydroxy-5-isopropylphenyl)-4-(4-(morpholinosulfonyl)phenyl)-N-(2,2,2-trifluoroethyl)-4H-1,2,4-triazole-3-carboxamide |

TABLE 1-continued

| No. | Structure | Name |
|---|---|---|
| 431 | 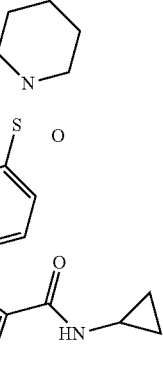 | N-cyclopropyl-5-(2,4-dihydroxy-5-isopropylphenyl)-4-(4-(piperidin-1-ylsulfonyl)phenyl)-4H-1,2,4-triazole-3-carboxamide |
| 432 | 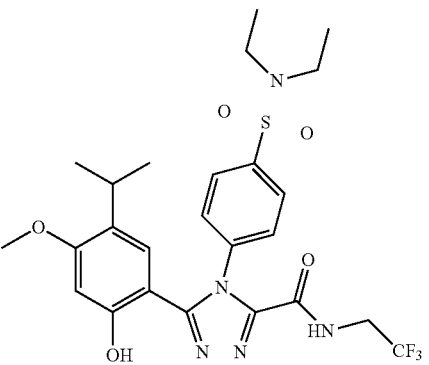 | 4-(4-(N,N-diethylsulfamoyl)phenyl)-5-(2-hydroxy-5-isopropyl-4-methoxyphenyl)-N-(2,2,2-trifluoroethyl)-4H-1,2,4-triazole-3-carboxamide |
| 433 | 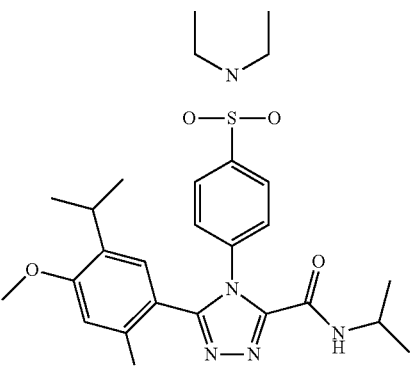 | 4-(4-(N,N-diethylsulfamoyl)phenyl)-5-(2-hydroxy-5-isopropyl-4-methoxyphenyl)-N-isopropyl-4H-1,2,4-triazole-3-carboxamide |
| 434 | 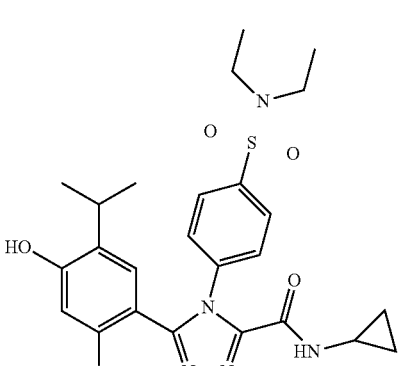 | N-cyclopropyl-4-(4-(N,N-diethylsulfamoyl)phenyl)-5-(2,4-dihydroxy-5-isopropylphenyl)-4H-1,2,4-triazole-3-carboxamide |

TABLE 1-continued

| No. | Structure | Name |
|---|---|---|
| 435 | 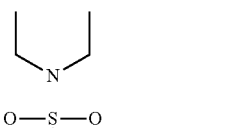 | 4-(4-(N,N-diethylsulfamoyl)phenyl)-5-(2,4-dihydroxy-5-isopropylphenyl)-N-ethyl-4H-1,2,4-triazole-3-carboxamide |
| 436 | 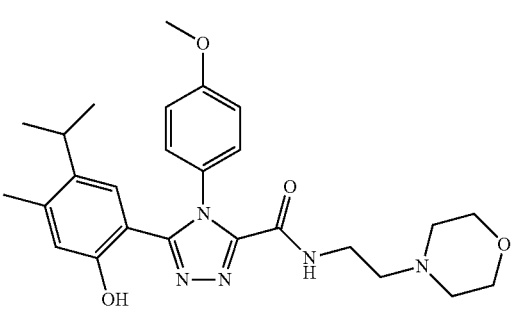 [SMILES: COc1ccc(-n2c(C(=O)NCCN3CCOCC3)nnc2-c2cc(C(C)C)c(C)cc2O)cc1] | 5-(2-hydroxy-5-isopropyl-4-methylphenyl)-4-(4-methoxyphenyl)-N-(2-morpholinoethyl)-4H-1,2,4-triazole-3-carboxamide |
| 437 | 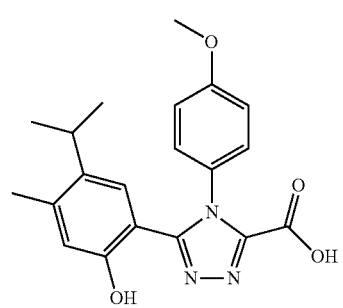 [SMILES: COc1ccc(-n2c(C(=O)O)nnc2-c2cc(C(C)C)c(C)cc2O)cc1] | 5-(2-hydroxy-5-isopropyl-4-methylphenyl)-4-(4-methoxyphenyl)-4H-1,2,4-triazole-3-carboxylic acid |
| 438 | 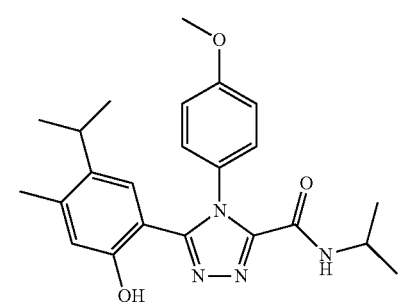 [SMILES: COc1ccc(-n2c(C(=O)NC(C)C)nnc2-c2cc(C(C)C)c(C)cc2O)cc1] | 5-(2-hydroxy-5-isopropyl-4-methylphenyl)-N-isopropyl-4-(4-methoxyphenyl)-4H-1,2,4-triazole-3-carboxamide |
| 439 | 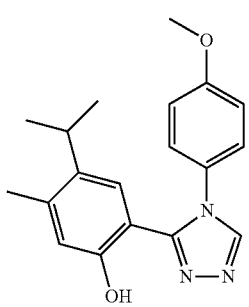 [SMILES: COc1ccc(-n2cnnc2-c2cc(C(C)C)c(C)cc2O)cc1] | 4-isopropyl-2-(4-(4-methoxyphenyl)-4H-1,2,4-triazol-3-yl)-5-methylphenol |

TABLE 1-continued

| No. | Structure | Name |
|---|---|---|
| 440 | 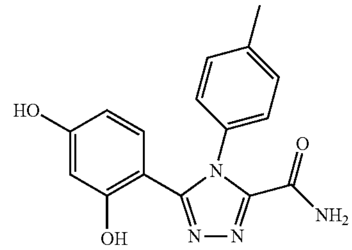 [SMILES: Cc1ccc(-n2c(C(N)=O)nnc2-c2ccc(O)cc2O)cc1] | 5-(2,4-Dihydroxyphenyl)-4-p-tolyl-4H-1,2,4-triazole-3-carboxamide |
| 441 | 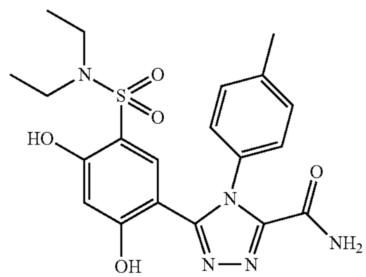 [SMILES: CCN(CC)S(=O)(=O)c1cc(-c2nnc(C(N)=O)n2-c2ccc(C)cc2)c(O)cc1O] | 5-(5-(N,N-Diethylsulfamoyl)-2,4-dihydroxyphenyl)-4-p-tolyl-4H-1,2,4-triazole-3-carboxamide |
| 442 | 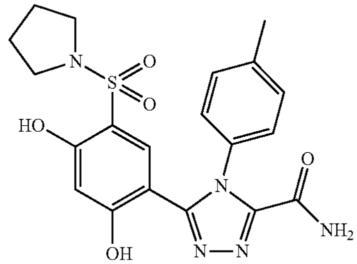 [SMILES: Cc1ccc(-n2c(C(N)=O)nnc2-c2cc(S(=O)(=O)N3CCCC3)c(O)cc2O)cc1] | 5-(2,4-Dihydroxy-5-(pyrrolidin-1-ylsulfonyl)phenyl)-4-p-tolyl-1,2,4-triazole-3-carboxamide |
| 443 | 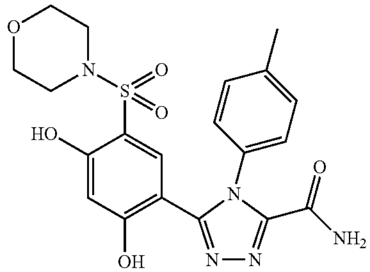 [SMILES: Cc1ccc(-n2c(C(N)=O)nnc2-c2cc(S(=O)(=O)N3CCOCC3)c(O)cc2O)cc1] | 5-(2,4-Dihydroxy-5-(morpholinosulfonyl)phenyl)-4-p-tolyl-4H-1,2,4-triazole-3-carboxamide |
| 444 | 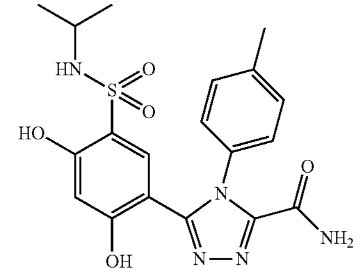 [SMILES: Cc1ccc(-n2c(C(N)=O)nnc2-c2cc(S(=O)(=O)NC(C)C)c(O)cc2O)cc1] | 5-(2,4-Dihydroxy-5-(N-isopropylsulfamoyl)phenyl)-4-p-tolyl-4H-1,2,4-triazole-3-carboxamide |

TABLE 1-continued

| No. | Structure | Name |
|---|---|---|
| 445 | 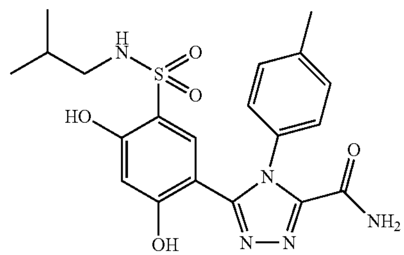 [SMILES: Cc1ccc(-n2c(C(N)=O)nnc2-c2cc(S(=O)(=O)NCC(C)C)c(O)cc2O)cc1] | 5-(2,4-Dihydroxy-5-(N-isobutylsulfamoyl)phenyl)-4-tolyl-4H-1,2,4-triazole-3-carboxamide |
| 446 | 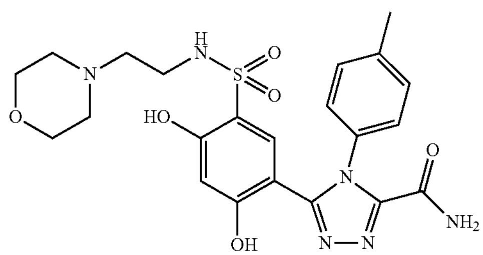 [SMILES: Cc1ccc(-n2c(C(N)=O)nnc2-c2cc(S(=O)(=O)NCCN3CCOCC3)c(O)cc2O)cc1] | 5-(2,4-Dihydroxy-5-(N-(2-morpholinoethyl)sulfamoyl)phenyl)-4-p-tolyl-4H-1,2,4-triazole-3-carboxamide |
| 447 | 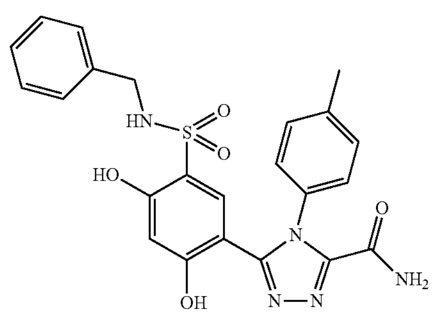 [SMILES: Cc1ccc(-n2c(C(N)=O)nnc2-c2cc(S(=O)(=O)NCc3ccccc3)c(O)cc2O)cc1] | 5-(5-(N-Benzylsulfamoyl)-2,4-dihydroxyphenyl)-4-p-tolyl-4H-1,2,4-triazole-3-carboxamide |
| 448 | 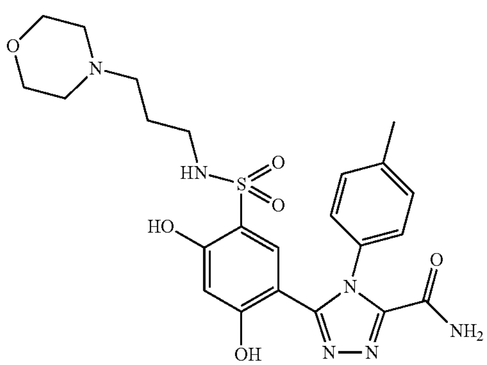 [SMILES: Cc1ccc(-n2c(C(N)=O)nnc2-c2cc(S(=O)(=O)NCCCN3CCOCC3)c(O)cc2O)cc1] | 5-(2,4-Dihydroxy-5-(N-(3-morpholinopropyl)sulfamoyl)phenyl)-4-p-tolyl-4H-1,2,4-triazole-3-carboxamide |
| 449 | 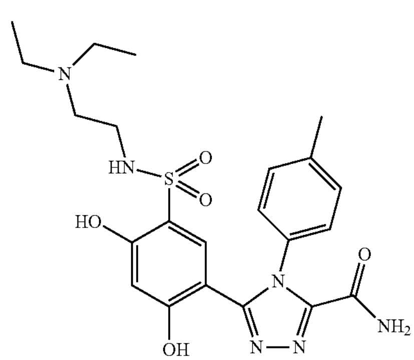 [SMILES: CCN(CC)CCNS(=O)(=O)c1cc(-c2nnc(C(N)=O)n2-c2ccc(C)cc2)c(O)cc1O] | 5-(5-(N-(2-(Diethylamino)ethyl)sulfamoyl)-2,4-dihydroxyphenyl)-4-p-tolyl-4H-1,2,4-triazole-3-carboxamide |

TABLE 1-continued

| No. | Structure | Name |
|---|---|---|
| 450 | 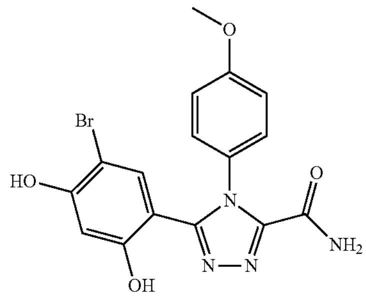 [SMILES: COc1ccc(-n2c(C(N)=O)nnc2-c2cc(Br)c(O)cc2O)cc1] | 5-(5-bromo-2,4-dihydroxyphenyl)-4-(4-methoxyphenyl)-4H-1,2,4-triazole-3-carboxamide |
| 451 | 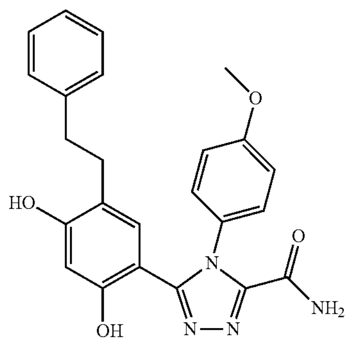 [SMILES: COc1ccc(-n2c(C(N)=O)nnc2-c2cc(CCc3ccccc3)c(O)cc2O)cc1] | 5-(2,4-Dihydroxy-5-phenethylphenyl)-4-(4-methoxyphenyl)-4H-1,2,4-triazole-3-carboxamide |
| 452 | 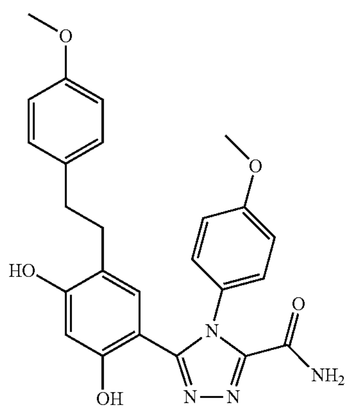 [SMILES: COc1ccc(CCc2cc(-c3nnc(C(N)=O)n3-c3ccc(OC)cc3)c(O)cc2O)cc1] | 5-(2,4-Dihydroxy-5-(4-methoxyphenethyl)phenyl)-4-(4-methoxyphenyl)-4H-1,2,4-triazole-3-carboxamide |
| 453 | 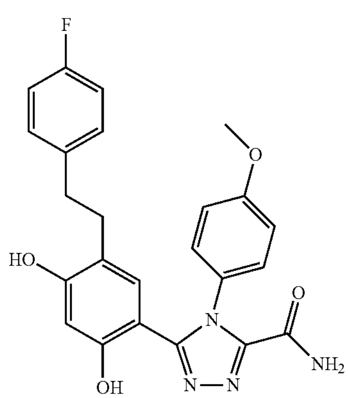 [SMILES: COc1ccc(-n2c(C(N)=O)nnc2-c2cc(CCc3ccc(F)cc3)c(O)cc2O)cc1] | 5-(5-(4-Fluorophenethyl)-2,4-dihydroxyphenyl)-4-(4-methoxyphenyl)-4H-1,2,4-triazole-3-carboxamide |

TABLE 1-continued

| No. | Structure | Name |
|---|---|---|
| 454 | 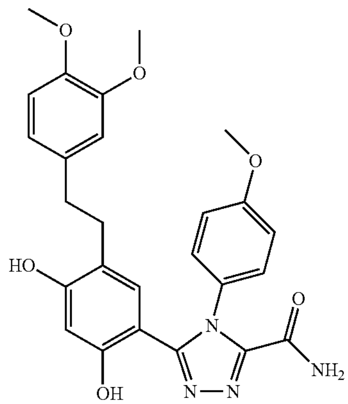 [SMILES: COc1ccc(-n2c(C(N)=O)nnc2-c2cc(CCc3ccc(OC)c(OC)c3)c(O)cc2O)cc1] | 5-(5-(3,4-Dimethoxyphenethyl)-2,4-dihydroxyphenyl)-4-(4-methoxyphenyl)-4H-1,2,4-triazole-3-carboxamide |
| 455 | 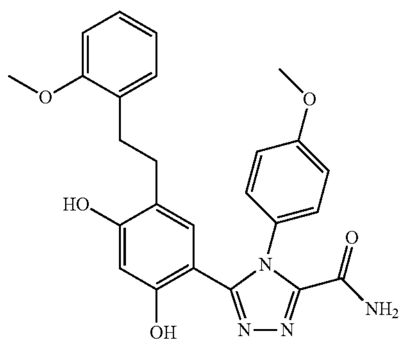 [SMILES: COc1ccc(-n2c(C(N)=O)nnc2-c2cc(CCc3ccccc3OC)c(O)cc2O)cc1] | 5-(2,4-Dihydroxy-5-(2-methoxyphenethyl)phenyl)-4-(4-methoxyphenyl)-4H-1,2,4-triazole-3-carboxamide |
| 456 | 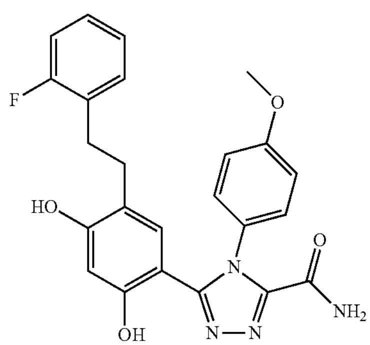 [SMILES: COc1ccc(-n2c(C(N)=O)nnc2-c2cc(CCc3ccccc3F)c(O)cc2O)cc1] | 5-(5-(2-Fluorophenethyl)-2,4-dihydroxyphenyl)-4-(4-methoxyphenyl)-4H-1,2,4-triazole-3-carboxamide |
| 457 | 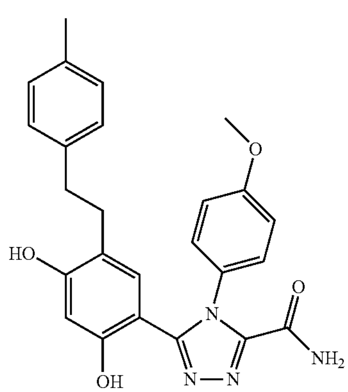 [SMILES: COc1ccc(-n2c(C(N)=O)nnc2-c2cc(CCc3ccc(C)cc3)c(O)cc2O)cc1] | 5-(2,4-Dihydroxy-5-(4-methylphenethyl)phenyl)-4-(4-methoxyphenyl)-4H-1,2,4-triazole-3-carboxamide |

TABLE 1-continued

| No. | Structure | Name |
|---|---|---|
| 458 | 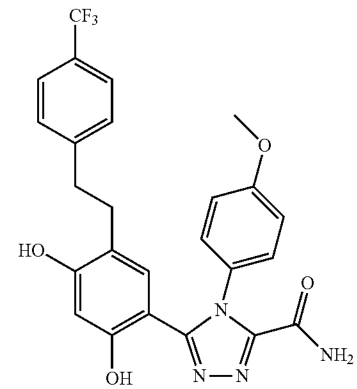 [SMILES: COc1ccc(-n2c(C(N)=O)nnc2-c2cc(CCc3ccc(C(F)(F)F)cc3)c(O)cc2O)cc1] | 5-(2,4-Dihydroxy-5-(4-(trifluoromethyl)phenethyl)phenyl)-4-(4-methoxy-phenyl)-4H-1,2,4-triazole-3-carboxamide |
| 459 | 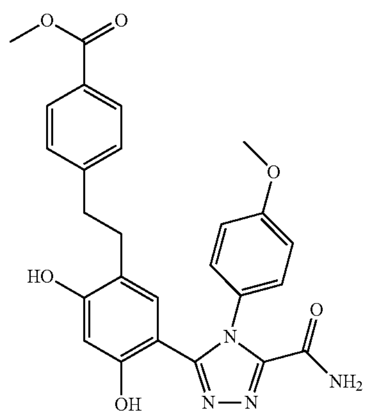 [SMILES: COC(=O)c1ccc(CCc2cc(-c3nnc(C(N)=O)n3-c3ccc(OC)cc3)c(O)cc2O)cc1] | Methyl 4-(5-(5-carbamoyl-4-(4-methoxyphenyl)-4H-1,2,4-triazol-3-yl)-2,4-di-hydroxyphenethyl)benzoate |
| 460 | 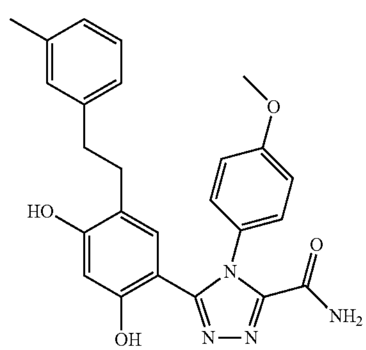 [SMILES: COc1ccc(-n2c(C(N)=O)nnc2-c2cc(CCc3cccc(C)c3)c(O)cc2O)cc1] | 5-(2,4-Dihydroxy-5-(3-methylphenethyl)phenyl)-4-(4-methoxyphenyl)-4H-1,2,4-triazole-3-carboxamide |
| 461 | 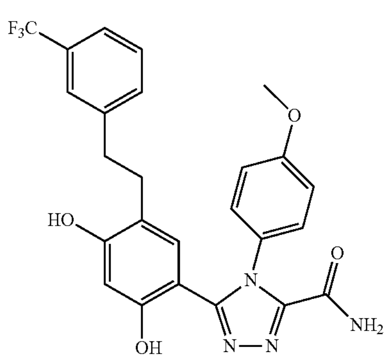 [SMILES: COc1ccc(-n2c(C(N)=O)nnc2-c2cc(CCc3cccc(C(F)(F)F)c3)c(O)cc2O)cc1] | 5-(2,4-Dihydroxy-5-(3-(trifluoromethyl)phenethyl)phenyl)-4-(4-methoxy-phenyl)-4H-1,2,4-triazole-3-carboxamide |

TABLE 1-continued

| No. | Structure | Name |
|-----|-----------|------|
| 462 | 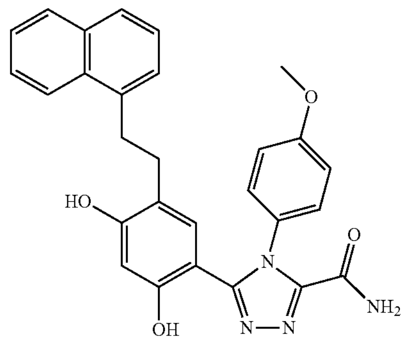 [SMILES: COc1ccc(-n2c(C(N)=O)nnc2-c2cc(CCc3cccc4ccccc34)c(O)cc2O)cc1] | 5-(2,4-Dihydroxy-5-(2-(naphthalen-1-yl)ethyl)phenyl)-4-(4-methoxyphenyl)-4H-1,2,4-triazole-3-carboxamide |
| 463 | 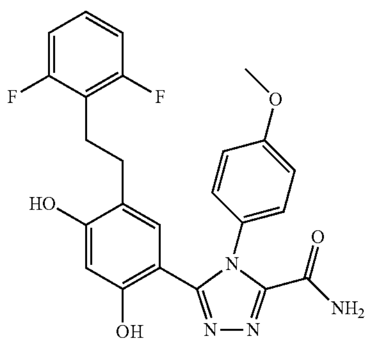 [SMILES: COc1ccc(-n2c(C(N)=O)nnc2-c2cc(CCc3c(F)cccc3F)c(O)cc2O)cc1] | 5-(5-(2,6-Difluorophenethyl)-2,4-dihydroxyphenyl)-4-(4-methoxyphenyl)-4H-1,2,4-triazole-3-carboxamide |
| 464 | 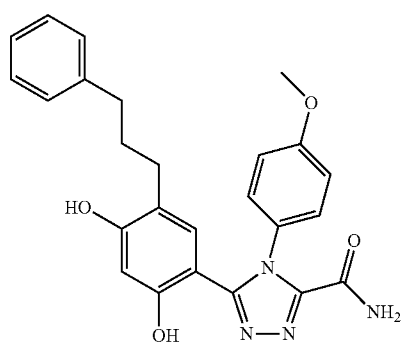 [SMILES: COc1ccc(-n2c(C(N)=O)nnc2-c2cc(CCCc3ccccc3)c(O)cc2O)cc1] | 5-(2,4-Dihydroxy-5-(3-phenylpropyl)phenyl)-4-(4-methoxyphenyl)-4H-1,2,4-triazole-3-carboxamide |
| 465 | 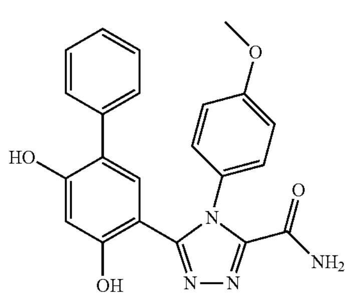 [SMILES: COc1ccc(-n2c(C(N)=O)nnc2-c2cc(-c3ccccc3)c(O)cc2O)cc1] | 5-(4,6-Dihydroxybiphenyl-3-yl)-4-(4-methoxyphenyl)-4H-1,2,4-triazole-3-carboxamide |

TABLE 1-continued

| No. | Structure | Name |
|---|---|---|
| 466 | 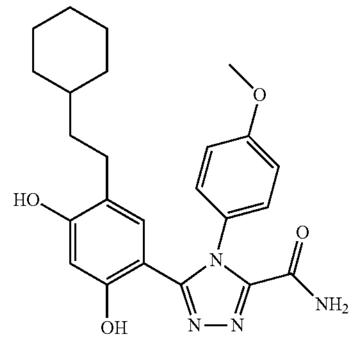 [SMILES: COc1ccc(-n2c(C(N)=O)nnc2-c2cc(CCC3CCCCC3)c(O)cc2O)cc1] | 5-(5-(2-Cyclohexylethyl)-2,4-dihydroxyphenyl)-4-(4-methoxyphenyl)-4H-1,2,4-triazole-3-carboxamide |
| 467 | 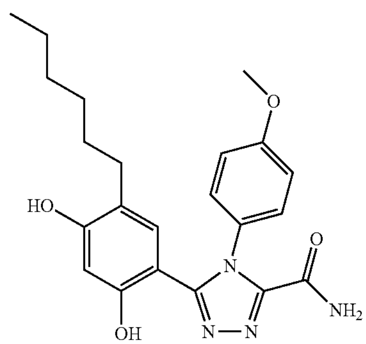 [SMILES: CCCCCCc1cc(-c2nnc(C(N)=O)n2-c2ccc(OC)cc2)c(O)cc1O] | 5-(5-Hexyl-2,4-dihydroxyphenyl)-4-(4-methoxyphenyl)-4H-1,2,4-triazole-3-carboxamide |
| 468 | 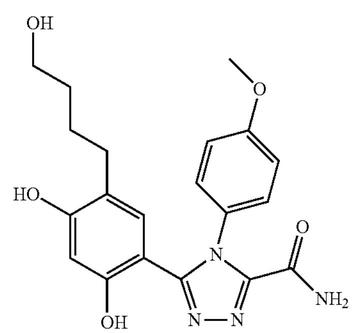 [SMILES: COc1ccc(-n2c(C(N)=O)nnc2-c2cc(CCCCO)c(O)cc2O)cc1] | 5-(2,4-Dihydroxy-5-(4-hydroxybutyl)phenyl)-4-(4-methoxyphenyl)-4H-1,2,4-triazole-3-carboxamide |
| 469 | 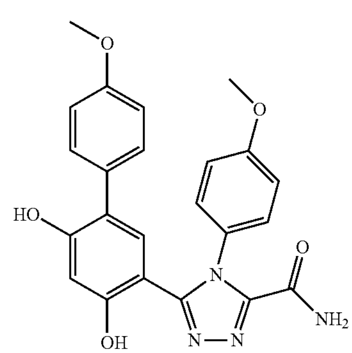 [SMILES: COc1ccc(-c2cc(-c3nnc(C(N)=O)n3-c3ccc(OC)cc3)c(O)cc2O)cc1] | 5-(4,6-Dihydroxy-4'-methoxybiphenyl-3-yl)-4-(4-methoxyphenyl)-4H-1,2,4-triazole-3-carboxamide |

TABLE 1-continued

| No. | Structure | Name |
|---|---|---|
| 470 | 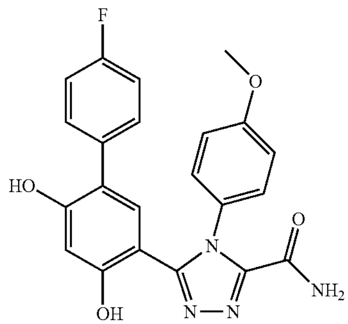 [SMILES: COc1ccc(-n2c(C(N)=O)nnc2-c2cc(-c3ccc(F)cc3)c(O)cc2O)cc1] | 5-(4'-Fluoro-4,6-dihydroxybiphenyl-3-yl)-4-(4-methoxyphenyl)-4H-1,2,4-triazole-3-carboxamide |
| 471 | 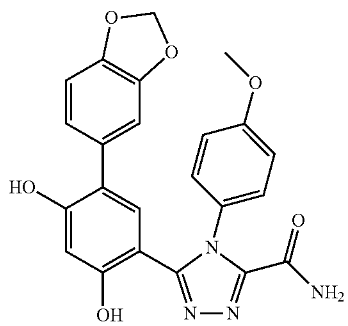 | 5-(5-(Benzo[d][1,3]dioxol-5-yl)-2,4-dihydroxyphenyl)-4-(4-methoxyphenyl)-4H-1,2,4-triazole-3-carboxamide |
| 472 | 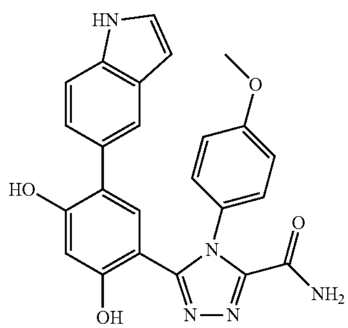 | 5-(2,4-Dihydroxy-5-(1H-indol-5-yl)phenyl)-4-(4-methoxyphenyl)-4H-1,2,4-triazole-3-carboxamide |
| 473 | 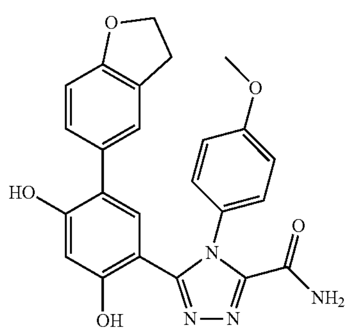 [SMILES: COc1ccc(-n2c(C(N)=O)nnc2-c2cc(-c3ccc4c(c3)OCO4)c(O)cc2O)cc1] | 5-(5-(2,3-Dihydrobenzofuran-5-yl)-2,4-dihydroxyphenyl)-4-(4-methoxy-phenyl)-4H-1,2,4-triazole-3-carboxamide |
| 474 | 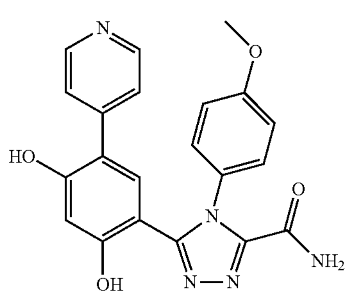 [SMILES: COc1ccc(-n2c(C(N)=O)nnc2-c2cc(-c3ccncc3)c(O)cc2O)cc1] | 5-(2,4-Dihydroxy-5-(pyridin-4-yl)phenyl)-4-(4-methoxyphenyl)-4H-1,2,4-triazole-3-carboxamide |

TABLE 1-continued

| No. | Structure | Name |
|---|---|---|
| 475 | 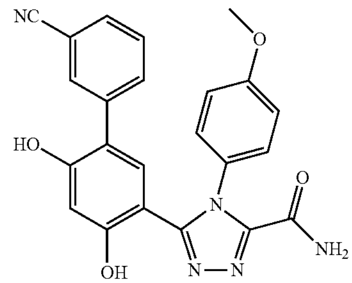 [SMILES: COc1ccc(-n2c(C(N)=O)nnc2-c2cc(-c3cccc(C#N)c3)c(O)cc2O)cc1] | 5-(3'-Cyano-4,6-dihydroxybiphenyl-3-yl)-4-(4-methoxyphenyl)-4H-1,2,4-triazole-3-carboxamide |
| 476 | 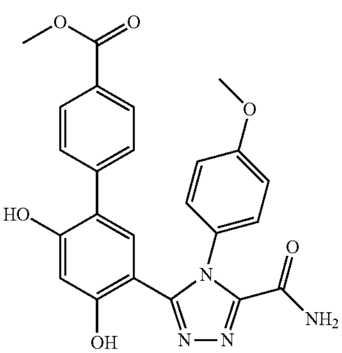 [SMILES: COC(=O)c1ccc(-c2cc(-c3nnc(C(N)=O)n3-c3ccc(OC)cc3)c(O)cc2O)cc1] | Methyl 5'-(5-carbamoyl-4-(4-methoxyphenyl)-4H-1,2,4-triazol-3-yl)-2',4'-di-hydroxybiphenyl-4-carboxylate |
| 477 | 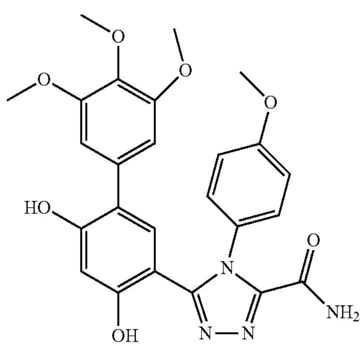 [SMILES: COc1ccc(-n2c(C(N)=O)nnc2-c2cc(-c3cc(OC)c(OC)c(OC)c3)c(O)cc2O)cc1] | 5-(4,6-Dihydroxy-3',4',5'-trimethoxybiphenyl-3-yl)-4-(4-methoxyphenyl)-4H-1,2,4-triazole-3-carboxamide |
| 478 | 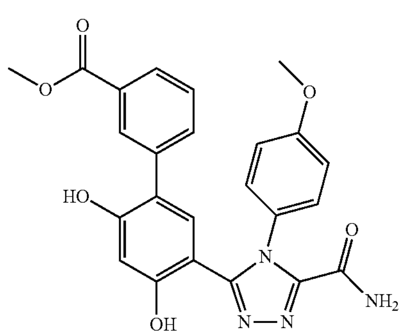 [SMILES: COC(=O)c1cccc(-c2cc(-c3nnc(C(N)=O)n3-c3ccc(OC)cc3)c(O)cc2O)c1] | Methyl 5'-(5-carbamoyl-4-(4-methoxyphenyl)-4H-1,2,4-triazol-3-yl)-2',4'-di-hydroxybiphenyl-3-carboxylate |

TABLE 1-continued

| No. | Structure | Name |
|---|---|---|
| 479 | 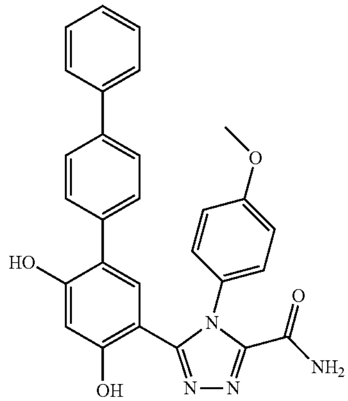 [SMILES: COc1ccc(-n2c(C(N)=O)nnc2-c2cc(-c3ccc(-c4ccccc4)cc3)c(O)cc2O)cc1] | 5-(5-(Biphenyl-4-yl)-2,4-dihydroxyphenyl)-4-(4-methoxyphenyl)-4H-1,2,4-triazole-3-carboxamide |
| 480 | 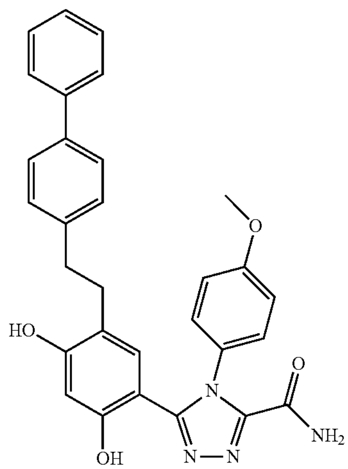 [SMILES: COc1ccc(-n2c(C(N)=O)nnc2-c2cc(CCc3ccc(-c4ccccc4)cc3)c(O)cc2O)cc1] | 5-(5-(2-(Biphenyl-4-yl)ethyl)-2,4-dihydroxyphenyl)-4-(4-methoxyphenyl)-4H-1,2,4-triazole-3-carboxamide |

In certain instances, tautomeric forms of a disclosed compound exist. It is to be understood that when a compound is represented by a structural formula herein, all other tautomeric forms which may exist for the compound are encompassed the structural formula. Compounds represented by formulas disclosed herein that can form analogous tautomeric structures are also preferred.

One skilled in the art will understand that other hydrolyzable protecting groups can be employed with the compounds of the present invention to obtain prodrugs encompassed by the present description.

C. Methods for Making Compounds of the Invention

Compounds of the invention can be obtained via standard, well-known synthetic methodology. See e.g., MARCH, J., ADVANCED ORGANIC CHEMISTRY: REACTIONS MECHANISMS AND STRUCTURE, (4th ed., (1992)). In addition to the synthesis included in the Example section and the synthetic schemes shown below, compounds of the invention can be made using methods disclosed in PCT Application No. PCT/US2008/01693, and U.S. application Ser. Nos. 11/282,119, 11/506,185, and 11/807,331, each of which is incorporated herein by reference.

Reactive functional groups can be protected during one or more reaction step, and then deprotected to restore the original functionality. Examples of suitable protecting groups for hydroxyl groups include benzyl, methoxymethyl, allyl, trimethylsilyl, tert-butyldimethylsilyl, acetate, and the like. Examples of suitable amine protecting groups include benzyloxycarbonyl, tert-butoxycarbonyl, tert-butyl, benzyl and fluorenylmethyloxy-carbonyl (Fmoc). Examples of suitable thiol protecting groups include benzyl, tert-butyl, acetyl, methoxymethyl and the like. Other suitable protecting groups are well known to those of ordinary skill in the art and include those found in T. W. GREENE, PROTECTING GROUPS IN ORGANIC SYNTHESIS (John Wiley & Sons (1981)).

Reactive functional groups can be protected during one or more reaction step, then deprotected to restore the original functionality. Examples of suitable protecting groups for hydroxyl groups include benzyl, methoxymethyl, allyl, trimethylsilyl, tert-butyldimethylsilyl, acetate, and the like. Examples of suitable amine protecting groups include benzyloxycarbonyl, tert-butoxycarbonyl, tert-butyl, benzyl and fluorenylmethyloxy-carbonyl (Fmoc). Examples of suitable thiol protecting groups include benzyl, tert-butyl, acetyl, methoxymethyl and the like. Other suitable protecting groups are well known to those of ordinary skill in the art and include those found in T. W. Greene, Protecting Groups in Organic Synthesis, John Wiley & Sons, Inc. 1981.

Scheme I: Synthesis of triazole compounds of the invention

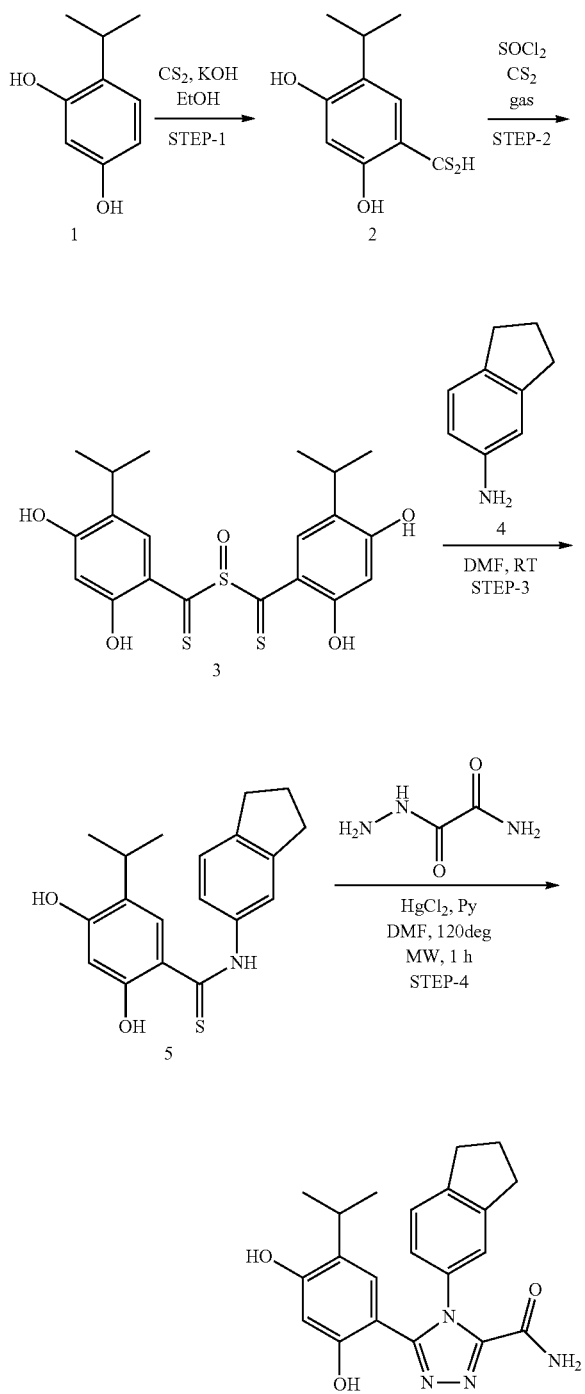

Scheme II: Synthesis of substituted amide compounds

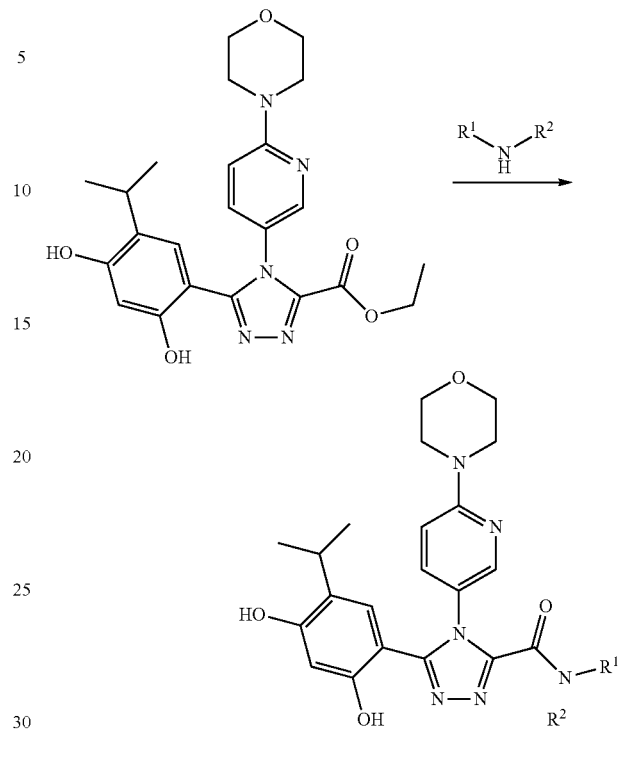

STEP-1 involves the thiocarbonylation of a tri-substituted phenyl (1) to produce (2). STEP-2 forms a sulfoxy bridged dimmer (3) which is then subject to nucleophilic attack by (4) in STEP-3 to produce (5). The final step in the synthesis, STEP-4, is the cyclization/dehydration reaction of (5) with 2-hydrazinyl-2-oxoacetamide (6) in which the tri-substituted 1,3,4-triazole moiety is formed.

Di-substituted amides can be produced from the corresponding ethers by reaction with a primary or secondary amine, as shown in Scheme II.

D. Uses of Compounds of the Invention

The present invention is directed to therapies which involve administering one of more compounds of the invention, and pharmaceutical compositions comprising said one or more compounds to a subject, preferably a human subject, to inhibit the activity of Hsp90 to treat a disease or disorder, such as a proliferative disorder, or one or more symptoms thereof. In one embodiment, the proliferative disorder is cancer.

In another embodiment, the present invention is directed to treating cancers in which aberrant expression and/or activation of c-Kit has been implicated as a contributing factor. The method comprises administering to a subject an effective amount of a compound represented by Formulae (I)-(V) or a compound shown in Table 1.

In one embodiment, the present invention is directed to treating cancers in which expression of BCR-ABL has been implicated as a contributing factor. The method comprises administering to a subject an effective amount of a compound represented by Formulae (I)-(V) or a compound shown in Table 1.

In one embodiment, the present invention is directed to treating cancers in which aberrant expression and/or activation of FLT3 has been implicated as a contributing factor. The method comprises administering to a subject an effective amount of a compound represented by Formulae (I)-(V) or a compound shown in Table 1.

In one embodiment, the present invention is directed to treating cancers in which aberrant expression and/or activation of EGFR has been implicated as a contributing factor.

The method comprises administering to a subject an effective amount of a compound represented by Formulae (I)-(V) or a compound shown in Table 1.

In one embodiment, the present invention is directed to treating cancers in which Hsp90 is over expressed, as compared with normal cells. The method comprises administering to a subject an effective amount of a compound represented by Formulae (I)-(V) or a compound shown in Table 1. Examples of cancers in which Hsp90 is over expressed include diffuse large B-cell lymphomas (DLBCL).

In one aspect, the invention provides a method of inhibiting the activity of Hsp90 in a cell, comprising administering to the cell an effective amount of a compound represented by Formulae (I)-(V) or a compound shown in Table 1. In one embodiment, the compound is administered to a cell in a subject, preferably a mammal, and more preferably a human.

In another aspect, the invention provides a method of treating a proliferation disorder in a subject, comprising administering to the subject an effective amount of a compound represented by Formulae (I)-(V) or a compound shown in Table 1. In one embodiment, the compound is administered to a mammal to treat a proliferative disorder. In another embodiment, the mammal is a human. In another embodiment, the proliferation disorder is cancer. In another embodiment, the compound is administered with one or more additional therapeutic agents. In a preferred embodiment, the additional therapeutic agent(s) is an anti-cancer agent.

In another aspect, the invention provides a method for treating a c-Kit associated cancer in a subject, comprising administering to the subject an effective amount of a compound represented by Formulae (I)-(V) or a compound shown in Table 1. In one embodiment the subject is a mammal, preferably a human. In one embodiment, the compound is administered to a human to treat the c-Kit associated cancer. In another embodiment, the compound is administered with one or more additional therapeutic agents. In a preferred embodiment, the one or more additional therapeutic agents are anti-cancer agents.

In another aspect, the invention provides a method for treating a BCR-ABL associated cancer in a subject, comprising administering to the subject an effective amount of a compound represented by Formulae (I)-(V) or a compound shown in Table 1. In one embodiment the subject is a mammal, preferably a human. In one embodiment, the compound is administered to a human to treat or prevent the BCR-ABL associated cancer. In another embodiment, the compound is administered with one or more additional therapeutic agents. In a preferred embodiment, the one or more additional therapeutic agents are anti-cancer agents.

In another aspect, the invention provides a method for treating a FLT3 associated cancer in a subject, comprising administering to the subject an effective amount of a compound represented by Formulae (I)-(V) or a compound shown in Table 1. In one embodiment the subject is a mammal, preferably a human. In one embodiment, the compound is administered to a human to treat the FLT3 associated cancer. In another embodiment, the compound is administered with one or more additional therapeutic agents. In a preferred embodiment, the one or more additional therapeutic agents are anti-cancer agents.

In another aspect, the invention provides a method for treating an EGFR associated cancer in a subject, comprising administering to the subject an effective amount of a compound represented by Formulae (I)-(V) or a compound shown in Table 1. In one embodiment the subject is a mammal, preferably a human. In one embodiment, the compound is administered to a human to treat the EGFR associated cancer. In another embodiment, the compound is administered with one or more additional therapeutic agents. In a preferred embodiment, the one or more additional therapeutic agents are anti-cancer agents.

In another aspect, the invention provides a method for treating a cancer in a subject which is characterized by the upregulation of Hsp90, compared to normal cells of the same type, comprising administering to the subject an effective amount of a compound represented by Formulae (I)-(V) or a compound shown in Table 1. In one embodiment the subject is a mammal, preferably a human. In one embodiment, the compound is administered to a human to treat or prevent the cancer associated with the upregulation of Hsp90. In another embodiment, the cancer associated with the upregulation of Hsp90 is DLBCL. In another embodiment, the compound is administered with one or more additional therapeutic agents. In a preferred embodiment, the one or more additional therapeutic agents are anti-cancer agents.

In another aspect, the invention provides a method for treating or inhibiting angiogenesis in a subject in need thereof, comprising administering to the subject an effective amount of a compound represented by Formulae (I)-(V) or a compound shown in Table 1.

In another aspect, the invention provides a method of blocking, occluding, or otherwise disrupting blood flow in neovasculature in a subject, comprising contacting the neovasculature with an effective amount of a compound represented by Formulae (I)-(V) or a compound shown in Table 1. In one aspect, the neovasculature is in a subject and blood flow in the neovasculature is blocked, occluded, or otherwise disrupted in the subject by administering to the subject an effective amount of a compound represented by Formulae (I)-(V) or a compound shown in Table 1. In one aspect, the subject is human.

The present invention provides a method for treating an infection in a subject in need thereof, comprising administering an effective amount of a compound represented by Formulae (I)-(V), or a compound shown in Table 1. In one embodiment the subject is a mammal, preferably a human. In one aspect, the invention is directed to a method of treating a fungal infection. In one aspect, the invention is directed to a method of treating a yeast infection. In one aspect, the invention is directed to a method of treating a yeast infection caused by *Candida* yeast.

In another embodiment the invention is directed to a method of treating fungal drug resistance a subject in need thereof, comprising administering an effective amount of a compound represented by Formulae (I)-(V), or a compound shown in Table 1. In one aspect, the fungal drug resistance is associated with an azole drug. In another aspect, the fungal drug resistance is associated with a non-azole fungal drug. In one aspect, the non-azole drug is an echinocandin. In one aspect, the azole fungal drug is ketoconazole, miconazole, fluconazole, itraconazole, posaconazole, ravuconazole, voriconazole, clotrimazole, econazole, oxiconazole, sulconazole, terconazole, butoconazole, isavuconazole or tioconazole. In one aspect, the azole fugnal drug is fluconazole.

In one aspect, the invention is directed to a method of treating a bacterial infection in a subject in need thereof, comprising administering to the subject an effective amount of a compound according to Formulae (I)-(V) or a compound shown in Table 1. In one aspect, the invention is directed to a method of treating a bacterial infection caused by Gram positive bacteria. In one aspect, the invention is directed to a method of treating a bacterial infection caused by Gram negative bacteria.

In one aspect, the invention is directed to a method of treating a viral infection in a subject in need thereof, comprising administering to the subject an effective amount of a compound according to Formulae (I)-(V) or a compound shown in Table 1. In one aspect, the invention is directed to a method of treating a viral infection caused by an influenza virus, a herpes virus, a hepatitis virus, or an HIV virus. In one aspect, the invention is directed to a method of treating a viral infection caused by influenza A virus, herpes simplex virus type 1, hepatitis C virus, hepatitis B virus, HIV-1 virus, or Epstein-Barr Virus.

In one aspect, the invention is directed to a method of treating a parasitic infection in a subject in need thereof, comprising administering to the subject an effective amount of a compound according to Formulae (I)-(V) or a compound shown in Table 1. In one aspect, the invention is directed to a method of treating a protozoal infection. In one aspect, the invention is directed to a method of treating an infection caused by *plasmodium falciparum* or *trypsanosoma cruzi*. In one aspect, the invention is directed to a method of treating an infection caused by a *leishmania* protozoa. In one aspect, the invention is directed to a method of treating an amoebic infection. In one aspect, the invention is directed to a method of treating a helminth infection. In one aspect, the invention is directed to a method of treating an infection caused by *schistostoma mansoni*.

In one aspect, compounds of the invention are administered in combination with one or more additional anti-infective therapeutic agents, such as antibiotics, anti-viral agents, anti-fungal agents, and/or anti-parasitic agents.

The present invention provides a method for inhibiting topoisomerase II in a subject in need thereof, comprising administering to the subject an effective amount of a compound according to Formulae (I)-(V) or a compound shown in Table 1. In one embodiment, topoisomerase II is associated with a disease, and administering the compound will treat the disease. In one aspect, the disease is a proliferative disease. In another aspect, the proliferative disease is cancer. In one aspect, the disease is an infection.

The present invention provides a method of treating an inflammatory disease or disorder in a subject in need thereof, comprising administering an effective amount of a compound of Formulae (I)-(V) or a compound shown in Table 1. In one embodiment, the inflammatory disease or disorder is selected from the group consisting of transplant rejection, skin graft rejection, arthritis, rheumatoid arthritis, osteoarthritis, bone diseases associated with increased bone resorption; inflammatory bowel disease, ileitis, ulcerative colitis, Barrett's syndrome, Crohn's disease; asthma, adult respiratory distress syndrome, chronic obstructive airway disease; corneal dystrophy, trachoma, onchocerciasis, uveitis, sympathetic ophthalmitis, endophthalmitis; gingivitis, periodontitis; tuberculosis; leprosy; uremic complications, glomerulonephritis, nephrosis; sclerodermatitis, psoriasis, eczema; chronic demyelinating diseases of the nervous system, multiple sclerosis, AIDS-related neurodegeneration, Alzheimer's disease, infectious meningitis, encephalomyelitis, Parkinson's disease, Huntington's disease, amyotrophic lateral sclerosis viral, autoimmune encephalitis; autoimmune disorders, immune-complex vasculitis, systemic lupus erythematosus (SLE); cardiomyopathy, ischemic heart disease hypercholesterolemia, atherosclerosis, preeclampsia; chronic liver failure, and brain and spinal cord trauma.

The present invention provides a method of treating an immune disease or disorder in a subject in need thereof, comprising administering an effective amount of a compound of Formulae (I)-(V) or a compound shown in Table 1. In one embodiment, the immune disease or disorder is selected from the group consisting of multiple sclerosis, myasthenia gravis, Guillain-Barré, autoimmune uveitis, autoimmune hemolytic anemia, pernicious anemia, autoimmune thrombocytopenia, temporal arteritis, anti-phospholipid syndrome, vasculitides such as Wegener's granulomatosis, Behcet's disease, psoriasis, dermatitis herpetiformis, pemphigus vulgaris, vitiligo, Crohn's disease, ulcerative colitis, primary biliary cirrhosis, autoimmune hepatitis, Type 1 or immune-mediated diabetes mellitus, Grave's disease, Hashimoto's thyroiditis, autoimmune oophoritis and orchitis, autoimmune disorder of the adrenal gland, rheumatoid arthritis, systemic lupus erythematosus, scleroderma, polymyositis, dermatomyositis, ankylosing spondylitis and Sjogren's syndrome.

The present invention provides a method of suppressing an immune response in a subject in need thereof, comprising administering an effective amount of a compound represented by Formulae (I)-(V) or a compound shown in Table 1. In one embodiment, the subject in need of immunosuppression is a subject that has received an organ or tissue transplant, such as a skin graft, or a heart, kidney, lung, liver, pancreas, cornea, bowel, or stomach transplant, and the like. In another embodiment, the subject in need of immunosuppression is a subject that has received stem cell transplantation. The transplant may be a syngeneic transplant (i.e., from a donor that has the same genetic make up), an allographic transplant (i.e., from a donor of the same species) or a xenographic transplant (i.e., from a donor that is a different species).

The present invention provides a method of inhibiting the production of inflammatory cytokines, such as G-CSF, GM-CSF, IL-12, IL-1l3, IL-23, IL-6, IL-8, and TNF-α, in a subject in need of such treatment. The method comprises administering to the subject an effective amount of a compound represented by Formulae (I)-(V) or a compound shown in Table 1.

1. c-Kit Associated Cancers

SCF binding to c-Kit protects hematopoietic stem and progenitor cells from apoptosis, thereby contributing to colony formation and hematopoiesis. Lee, et al., *J. Immunol.*, (1997) 159:3211-3219. Expression of c-Kit is frequently observed in acute myelocytic leukemia (AML) and is sometimes observed in acute lymphocytic leukemia (ALL). For reviews, see Sperling, et al., *Haemat.*, (1997) 82:617-621; Escribano, et al., *Leuk. Lymph.*, (1998) 30:459-466. Although c-Kit is expressed in the majority of AML cells, its expression does not appear to be prognostic of disease progression. Sperling, et al, *Haemat.* (1997) 82:617-621. However, AML cells are protected from apoptosis induced by chemotherapeutic agents when the SCF is bound to c-Kit proteins. Hassan, et al., *Acta. Hem.*, (1996) 95:257-262). Therefore, degradation of c-Kit caused by the inhibition of Hsp90 by the compounds of the invention will result in less SCF protected cell, and thus will enhance the efficacy of chemotherapeutic agents and may induce apoptosis of AML cells.

The clonal growth of cells from patients with myelodysplastic syndrome (Sawada, et al., *Blood,* (1996) 88:319-327) or chronic myelogenous leukemia (CML) (Sawai, et al., *Exp. Hem.*, (1996) 2:116-122) was found to be significantly enhanced by SCF in combination with other cytokines. CML is characterized by expansion of Philadelphia chromosome positive cells of the marrow (Verfaillie, et al., *Leuk.*, (1998) 12:136-138), which appears to primarily result from inhibition of apoptotic cell death (Jones, *Curr. Opin. One.*, (1997) 9:3-7). The product of the Philadelphia chromosome, p210.sup.BCR-ABL, has been reported to mediate inhibition of apoptosis. Bedi, et al., *Blood*, (1995) 86:1148-1158. Since p210.sup.BCR-ABL and the c-Kit RTK both inhibit apoptosis, and p62.sup.dok has been suggested as a substrate. Carpino, et al., *Cell*, (1997) 88:197-204. It is possible that clonal expansion mediated by these kinases occurs through a common signaling pathway. However, c-Kit has also been reported to interact directly with p210.sup.BCR-ABL which suggests that c-Kit may have a more causative role in CML pathology. Hallek, et al., *Brit. J. Haem.*, (1996) 94:5-16. Therefore, degradation of c-Kit caused by the inhibition of Hsp90 by the compounds of the invention will prove useful in the treatment of CML.

Normal colorectal mucosa does not express c-Kit. Bellone, et al., *J. Cell Physiol.*, (1997) 172:1-11. However, c-Kit is frequently expressed in colorectal carcinoma, and autocrine loops of SCF and c-Kit have been observed in several colon carcinoma cell lines. Bellone, et al., *J. Cell Physiol.*, (1997) 172: 1-11; Toyota, et al., *Turn. Biol.*, (1993) 14:295-302; Lahm, et al., *Cell Growth & Differ.*, (1995) 6:1111-1118. Furthermore, disruption of the autocrine loop by the use of neutralizing antibodies and downregulation of c-Kit and/or SCF significantly inhibits cell proliferation. Lahm, et al., *Cell Growth & Differ.*, (1995) 6:1111-1118; Bellone, et al., *J. Cell Physiol.*, (1997) 172:1-11.

SCF/c-Kit autocrine loops have been observed in gastric carcinoma cell lines, and constitutive c-Kit activation also appears to be important for gastrointestinal stromal tumors (GISTs). Turner, et al., *Blood*, (1992) 80:374-381; Hassan, et al., *Digest. Dis. Science*, (1998) 43:8-14. GISTs are the most common mesenchymal tumor of the digestive system. More than 90% of GISTs express c-Kit, which is consistent with the putative origin of these tumor cells from interstitial cells of Cajal (ICCs). Hirota, et al., *Science*, (1998) 279:577-580. The c-Kit expressed in GISTs from several different patients was observed to have mutations in the intracellular juxtamembrane domain leading to constitutive activation. Hirota, et al., *Science*, (1998) 279:577-580. Therefore, degradation of c-Kit caused by the inhibition of Hsp90 by the compounds of the invention will be an efficacious means for the treatment of these cancers. Male germ cell tumors have been histologically categorized into seminomas which retain germ cell characteristics and nonseminomas which can display characteristics of embryonal differentiation. Both seminomas and nonseminomas are thought to arise from a preinvasive stage designated carcinoma in situ (CIS). Murty, et al., *Sem. Oncol.*, (1998) 25:133-144. Both c-Kit and SCF have been reported to be essential for normal gonadal development during embryogenesis. Loveland, et al., *J. Endocrinol.*, (1997) 153:337-344. Loss of either the receptor or the ligand resulted in animals devoid of germ cells. In postnatal testes, c-Kit has been found to be expressed in Leydig cells and spermatogonia, while SCF was expressed in Sertoli cells. Loveland, et al., *J. Endocrinol.*, (1997) 153:337-344. Testicular tumors develop from Leydig cells with high frequency in transgenic mice expressing human papilloma virus 16 (HPV16) E6 and E7 oncogenes. Kondoh, et al., *J. Virol.*, (1991) 65:3335-3339; Kondoh, et al., *J. Urol.*, (1994) 152:2151-2154. These tumors express both c-Kit and SCF, and an autocrine loop may contribute to the tumorigenesis associated with the cellular loss of functional p53 and the retinoblastoma gene product by association with E6 and E7. Kondoh, et al., *Oncogene*, (1995)10:341-347; Dyson, et al., *Science*, (1989) 243:934-937; Werness, et al., *Science*, (1990) 248:76-79; Scheffner, et al., *Cell*, (1990) 63:1129-1136. Defective signaling mutants of SCF or c-Kit inhibited formation of testicular tumors in mice expressing HPV16 E6 and E7. Kondoh, et al., *Oncogene*, (1995) 10:341-347; Li, et al., *Canc. Res.*, (1996) 56:4343-4346. Since c-Kit kinase activation is pivotal to tumorigenesis in these animals, the compounds of the invention which inhibit Hsp90, and thereby cause the degradation of c-Kit, will be useful for treating testicular tumors associated with the human papilloma virus.

Expression of c-Kit in germ cell tumors shows that the receptor is expressed by the majority of carcinomas in situ and seminomas, but c-Kit is expressed in only a minority of nonseminomas. Strohmeyer, et al., *Canc. Res.*, (1991) 51:1811-1816; Rajpert-de Meyts, et al., *Int. J. Androl.*, (1994)17:85-92; Izquierdo, et al., *J. Pathol.*, (1995) 177: 253-258; Strohmeyer, et al., *J. Urol.*, (1995) 153:511-515; Bokenmeyer, et al., *J. Cancer Res. & Clin. Oncol.*, (1996) 122:301-306; Sandlow, et al., *J. Androl.*, (1996) 17:403-408. Therefore, degradation of c-Kit caused by the inhibition of Hsp90 by the compounds of the invention will be an efficacious means for the treatment of these cancers.

SCF and c-Kit are expressed throughout the central nervous system of developing rodents, and the pattern of expression suggests a role in growth, migration and differentiation of neuroectodermal cells. The expression of SCF and c-Kit have also been reported in the adult brain. Hamel, et al., *J. Neuro-One.*, (1997) 35:327-333). Expression of c-Kit has also been observed in normal human brain tissue. Tada, et al., *J. Neuro.*, (1994) 80:1063-1073). Glioblastoma and astrocytoma, which define the majority of intracranial tumors, arise from neoplastic transformation of astrocytes. Levin, V. A., et al., *Neoplasms of the central nervous system, In* CANCER: PRINCIPLES AND PRACTICE OF ONCOLOGY (DeVita, V. T., et al., Eds., Philadelphia: Lippincott-Raven (1997)) 2022-2082. Expression of c-Kit has been observed in glioblastoma cell lines and tissues. Berdel, et al., *Canc. Res.*, (1992) 52:3498-3502; Tada, et al., *J. Neuro.*, (1994) 80:1063-1073; Stanulla, et al., *Act. Neuropath.*, (1995) 89:158-165). Therefore, glioblastomas can be treated by degrading c-Kit. The inhibition of Hsp90 using compounds of the invention leads to the degredation of c-Kit, and other client proteins.

The association of c-Kit with astrocytoma pathology is less clear. Reports of expression of c-Kit in normal astrocytes have been made. Natali, et al., *Int. J. Canc.*, (1992) 52:197-201; Tada, et al., *J. Neuro.*, (1994) 80:1063-1073. However, others report it is not expressed. Kristt, et al., *Neuro.*, (1993) 33:106-115. In the former case, high levels of c-Kit expression in high grade tumors were observed, whereas in the latter case researchers were unable to detect any expression in astrocytomas. In addition, contradictory reports of c-Kit and SCF expression in neuroblastomas also exist. One study found that neuroblastoma cell lines often express SCF, but rarely express c-Kit. In primary tumors, c-Kit was detected in about 8% of neuroblastomas, while SCF was found in 18% of tumors. Beck, et al., *Blood*, (1995) 86:3132-3138. In contrast, other studies have reported that all 14 neuroblastoma cell lines examined contained c-Kit/SCF autocrine loops, and expression of both the receptor and ligand were observed in 45% of tumor samples examined. Cohen, et al., *Blood*, (1994) 84:3465-3472. In two cell lines, anti-c-Kit antibodies inhibited cell proliferation, suggesting that the SCF/c-Kit autocrine loop contributed to growth. Cohen, et al., *Blood*, (1994) 84:3465-3472. Therefore, degradation of c-Kit caused by the inhibition of Hsp90 by the compounds of the invention will be an efficacious means for treating some cancers of the central nervous system.

2. BCR-ABL Associated Cancers

The Philadelphia chromosome which generates the fusion protein BCR-ABL is associated with the bulk of chronic myelogenous leukemia (CML) patients (more than 95%), 10-25% of acute lymphocytic leukemia (ALL) patients, and about 2-3% of acute myelogenous leukemias (AML). In addition, BCR-ABL is a factor in a variety of other hematological malignancies, including granulocytic hyperplasia resembling CML, myelomonocytic leukemia, lymphomas, and erythroid leukemia. See Lugo, et al., *Molecular Cell Bio*. (1989), 9:1263-1270; Daley, et al., *Science* (1990), 247:824-830; Honda, *Blood* (1998), 91:2067-2075.

A number of different kinds of evidence support the contention that BCR-ABL oncoproteins, such as p210 and p185 BCR-ABL, are causative factors in these leukemias. Campbell & Arlinghaus, *Current Status of Bcr Gene Involvement with Human Leukemia, In* ADVANCES IN CANCER RESEARCH, (Klein, VandeWoude Eds., Orlando, Fla. Academic Press, Inc., (1991)), 57:227-256. The malignant activity is due in large part to the BCR-ABL protein's highly activated protein tyrosine kinase activity and its abnormal interaction with protein substrates. Arlinghaus, et al., In: UCLA SYMPOSIA ON MOLECULAR AND CELLULAR BIOLOGY, NEW SERIES, ACUTE LYMPHOBLASTIC LEUKEMIA (R. P. Gale & D. Hoelzer, Eds., N.Y.: Alan R. Liss, Inc. (1990)) 108:81-90. The BCR-ABL oncoprotein p210 BCR-ABL is associated with both CML and ALL, whereas the smaller oncoprotein, p185 BCR-ABL, is associated with ALL patients, although some CML patients also express p185. Campbell & Arlinghaus, *Current Status of Bcr Gene Involvement with Human Leukemia, In* ADVANCES IN CANCER RESEARCH, (Klein, VandeWoude Eds., Orlando, Fla. Academic Press, Inc., (1991)), 57:227-256.

3. FLT3 Associated Cancers

FLT3 associated cancers are cancers in which inappropriate FLT3 activity is detected. FLT3 associated cancers include hematologic malignancies such as leukemia and lymphoma. In some embodiments of the present invention, FLT3 associated cancers include acute myelogenous leukemia (AML), B-precursor cell acute lymphoblastic leukemia, myelodysplastic leukemia, T-cell acute lymphoblastic leukemia, mixed lineage leukemia (MLL) and chronic myelogenous leukemia (CML).

4. EGFR Associated Cancers

EGFR associated cancers are cancers in which inappropriate EGFR activity (e.g., overexpression of EGFR or mutation of EGFR which causes constitutive tyrosine kinase activity) has been implicated as a contributing factor. Inappropriate EGFR activity has been associated with an adverse prognosis in a number of human cancers, such as neuroblastoma; intestinal carcinomas, such as rectum carcinoma, colon carcinomas, familiary adenomatous polyposis carcinoma and hereditary non-polyposis colorectal cancer; esophageal carcinoma; labial carcinoma; larynx carcinoma; hypopharynx carcinoma; tongue carcinoma; salivary gland carcinoma; gastric carcinoma; adenocarcinoma; medullary thyroidea carcinoma; papillary thyroidea carcinoma; renal carcinoma; kidney parenchym carcinoma; ovarian carcinoma; cervix carcinoma; uterine corpus carcinoma; endometrium carcinoma; chorion carcinoma; pancreatic carcinoma; prostate carcinoma; testis carcinoma; breast carcinoma; urinary carcinoma; melanoma; brain tumors such as glioblastoma, astrocytoma, meningioma, medulloblastoma and peripheral neuroectodermal tumors; Hodgkin lymphoma; non-Hodgkin lymphoma; Burkitt lymphoma; acute lymphatic leukemia (ALL); chronic lymphatic leukemia (CLL); acute myeloid leukemia (AML); chronic myeloid leukemia (CML); adult T-cell leukemia lymphoma; hepatocellular carcinoma; gall bladder carcinoma; bronchial carcinoma; small cell lung carcinoma; non-small cell lung carcinoma; multiple myeloma; basalioma; teratoma; retinoblastoma; choroidea melanoma; seminoma; rhabdomyo sarcoma; craniopharyngeoma; osteosarcoma; chondrosarcoma; myosarcoma; liposarcoma; fibrosarcoma; Ewing sarcoma and plasmocytoma.

In particular, EGFR appears to have an important role in the development of human brain tumors. A high incidence of overexpression, amplification, deletion and structural rearrangement of the gene coding for EGFR has been found in biopsies of brain tumors. In fact, the amplification of the EGFR gene in glioblastoma multiforme tumors is one of the most consistent genetic alterations known, with EGFR being overexpressed in approximately 40% of malignant gliomas and the EGFRvIII mutation being found in about 50% of all glioblastomas. In addition to gliomas, abnormal EGFR expression has also been reported in a number of squamous epidermoid cancers and breast cancers. Interestingly, evidence also suggests that many patients with tumors that over-express EGFR have a worse prognosis than those having tumors that do not over-express EGFR.

Non-small cell lung cancer (NSCLC) includes squamous cell carcinomas, adenocarcinoma, bronchioloalveolar carcinoma (BAC) and large cell undifferentiated carcinoma. A subset of patients with NSCLC have been shown to have mutations in the tyrosine kinase domain of EGFR which is thought to be necessary for the maintenance of the disease. Treatment of this subset of patients with NSCLC with Gefitinib, a tyrosine kinase inhibitor which targets EGFR, has shown rapid and dramatic clinical response. Consequently, therapeutic strategies that can potentially inhibit or reduce the aberrant expression of EGFR are of great interest as potential anti-cancer agents.

5. Combination Therapies and Treatment of Refractory Cancers

The therapeutic agents of the combination therapies of the invention can be administered sequentially or concurrently. In a specific embodiment, the combination therapies of the invention comprise one or more compounds of the invention and at least one other therapeutic agent which has the same mechanism of action as said compounds. In another specific embodiment, the combination therapies of the invention comprise one or more compounds of the invention and at least one other therapeutic agent which has a different mechanism of action than said compounds. In certain embodiments, the combination therapies of the present invention improve the therapeutic effect of one or more compounds of the invention by functioning together with the additional therapeutic agent(s) to produce an additive or synergistic effect. In certain embodiments, the combination therapies of the present invention reduce the side effects associated with the additional therapeutic agent(s). In certain embodiments, the combination therapies of the present invention reduce the effective dosage of a compound of the invention and/or an additional therapeutic agent.

The therapeutic agents of the combination therapies can be administered to a subject, preferably a human subject, in the same pharmaceutical composition. In alternative embodiments, the therapeutic agents of the combination therapies can be administered concurrently to a subject in separate pharmaceutical compositions. In another embodiment, the therapeutic agents may be administered to a subject by the same or different routes of administration.

In a specific embodiment, a pharmaceutical composition comprising one or more compounds of the invention is administered to a subject, preferably a human, to treat, manage, or ameliorate a proliferative disorder, such as cancer, or one or more symptom thereof. In accordance with the invention, pharmaceutical compositions of the invention may also comprise one or more additional therapeutic agents which are currently being used, have been used, or are known to be useful in the treatment of a proliferative disorder, or a symptom thereof.

The invention provides methods for treating a proliferative disorder, such as cancer, or one or more symptoms thereof, in a subject refractory (either completely or partially) to an existing therapeutic agent for the proliferative disorder The method comprises administering to a subject an effective amount of one or more compounds of the invention in conjunction with an effective amount of one or more additional therapeutic agents useful for the treatment of the proliferative disorder, or a symptom thereof. The invention also provides a method for treating, a proliferative disorder, or a symptom thereof, by administering to a subject in need thereof, an effective amount of one or more compounds of the invention in combination with one or more additional therapeutic agent(s) wherein the subject has proven refractory to said additional therapeutic agent(s).

The compounds of the invention and/or any additional therapeutic agents can be administered to a subject by any route known to one of skill in the art. Examples of routes of administration include, but are not limited to, parenteral, e.g., intravenous, intradermal, subcutaneous, oral (e.g., inhalation), intranasal, transdermal (topical), transmucosal and rectal administration.

6. Agents Useful in Combination with the Compounds of the Invention

Without being bound by any particular theory, it is believed that the compounds of the invention can be particularly effective at treating subjects whose cancer has become drug resistant or multi-drug resistant. Although currently available chemotherapeutic agents may initially cause tumor regression, most agents that are currently used to treat cancer target only one pathway to tumor progression. Therefore, in many instances, after treatment with one or more chemotherapeutic agents, the tumor may become resistant to said one or more agents, and no longer responds positively to treatment. One of the advantages of inhibiting Hsp90 activity is that several of its client proteins, which are mostly protein kinases or transcription factors involved in signal transduction, have been shown to be involved in the progression of cancer. Thus, inhibition of Hsp90 provides a method of short circuiting several pathways for tumor progression simultaneously. Therefore, it is believed that treatment of cancer with an Hsp90 inhibitor of the invention either alone, or in combination with additional therapeutic agents, is more likely to result in regression or elimination of the tumor, and less likely to result in the development of more aggressive multidrug resistant tumors than other currently available therapies.

In one embodiment, one or more compounds of the invention can be administered with additional therapeutic agents that are tyrosine kinase inhibitors (e.g., Gefitinib or Erlotinib, which inhibit EGFR tyrosine kinase activity). In another embodiment, the compounds of the invention can be administered to a subject whose cancer has become resistant to a tyrosine kinase inhibitor (e.g., Gefitinib or Erlotinib). In this embodiment, the compounds of the invention can be administered either alone or in combination with the tyrosine kinase inhibitor.

In another embodiment, the compounds of the invention are useful for treating a subject with a hematological cancer that have become resistant to Imatinib, a chemotherapeutic agent that acts by inhibiting tyrosine kinase activity of BCR-ABL. In patients with CML in the chronic phase, as well as in a blast crisis, treatment with Imatinib typically will induce remission. However, in many cases, particularly in those subjects who were in a blast crisis before remission, the remission is not durable because the BCR-ABL fusion protein develops mutations in the tyrosine kinase domain that cause it to be resistance to Imatinib. Nimmanapalli, et al., *Cancer Research* (2001), 61:1799-1804; Gorre, et al., *Blood* (2002), 100:3041-3044. Compounds of the invention act by inhibiting the activity of Hsp90, which disrupts BCR-ABL/Hsp90 complexes. When BCR-ABL is not complexed to Hsp90, it is rapidly degraded. Therefore, compounds of the invention are effective in treating Imatinib resistant cancers since they act through a different mechanism than Imatinib. One or more compound(s) of the invention can be administered alone or with Imatinib to a subject that has a BCR-ABL associated cancer that is not resistant to Imatinib, or to a subject whose cancer has become resistant to Imatinib.

Anti-cancer agents that can be co-administered with the compounds of the invention include Taxol™, also referred to as "paclitaxel", and analogs of Taxol™, such as Taxotere™. Paclitaxel is a well-known anti-cancer drug which acts by enhancing and stabilizing microtubule formation. Compounds that have the basic taxane skeleton as a common structural feature have also been shown to have the ability to arrest cells in the G2-M phases due to the stabilization or inhibition of microtubules.

Other anti-cancer agents that can be employed in combination with the compounds of the invention include: Avastin; Adriamycin; Dactinomycin; Bleomycin; Vinblastine; Cisplatin; acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2); interferon α-2a; interferon α-2b; interferon α-n1; interferon α-n3; interferon β-I a; interferon γ-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs that can be employed in combination with the compounds of the invention include: 20-epi-1,25 dihydroxyvitamin D3; 5-ethynyluracil; abiraterone; aclarubicin; acylfulvene; adecypenol; aldesleukin; ALL-TK antagonists; ambamustine; amidox; amifostine; aminolevulinic acid; amrubicin; amsacrine; anagrelide; andrographolide; angiogenesis inhibitors; antagonist D; antagonist G; antarelix; anti-dorsalizing morphogenetic protein-1; antiandrogen; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; BCR/ABL antagonists; benzochlorins; benzoylstaurosporine; beta lactam derivatives; beta-alethine; betaclamycin B; betulinic acid; bFGF inhibitor; bisantrene; bisaziridinylspermine; bisnafide; bistrene A; breflate; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; dehydrodidemnin B; deslorelin; dexamethasone; dexifosfamide; dexrazoxane; dexverapamil; didemnin B; didox; diethylnorspermine; dihydro-5-azacytidine; 9-dioxamycin; diphenyl spiromustine; docosanol; dolasetron; doxifluridine; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; exemestane; fadrozole; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; glutathione inhibitors; hepsulfam; heregulin; hexamethylene bisacetamide; hypericin; ibandronic acid; idarubicin; idoxifene; idramantone; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti-cancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; osaterone; oxaliplatin; oxaunomycin; palauamine; palmitoylrhizoxin; pamidronic acid; panaxytriol; panomifene; parabactin; pazelliptine; peldesine; pentosan polysulfate sodium; pentostatin; pentrozole; perflubron; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; prednisone; propyl bisacridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; saintopin; SarCNU; sarcophytol A; sargramostim; Sdi 1 mimetics; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tellurapyrylium; telomerase inhibitors; temozolomide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; titanocene bichloride; topsentin; toremifene; totipotent stem cell factor; translation inhibitors; tretinoin; triacetyluridine; triciribine; tropisetron; turosteride; tyrosine kinase inhibitors; tyrphostins; UBC inhibitors; ubenimex; urogenital sinus-derived growth inhibitory factor; urokinase receptor antagonists; variolin B; vector system, erythrocyte gene therapy; velaresol; veramine; verdins; vinxaltine; vitaxin; zanoterone; zilascorb and zinostatin stimalamer. Preferred anti-cancer drugs are 5-fluorouracil and leucovorin.

Other chemotherapeutic agents that can be employed in combination with the compounds of the invention include but are not limited to alkylating agents, antimetabolites, natural products or hormones. Examples of alkylating agents useful for the treatment of T-cell malignancies in the methods and compositions of the invention include, but are not limited to, nitrogen mustards (e.g., mechloroethamine, cyclophosphamide, chlorambucil, etc.), alkyl sulfonates (e.g., busulfan), nitrosoureas (e.g., carmustine, lomusitne, etc.) and triazenes (e.g., decarbazine, etc.). Examples of antimetabolites useful for the treatment of T-cell malignancies in the methods and compositions of the invention include, but are not limited to, folic acid analogs (e.g., methotrexate), pyrimidine analogs (e.g., Cytarabine) and purine analogs (e.g., mercaptopurine, thioguanine, pentostatin). Examples of natural products useful for the treatment of T-cell malignancies in the methods and compositions of the invention include, but are not limited to, vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase) and biological response modifiers (e.g., interferon alpha).

Examples of alkylating agents that can be employed in combination with the compounds of the invention include, but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.) and triazenes (e.g., decarbazine, etc.). Examples of antimetabolites useful for the treatment of cancer in the methods and compositions of the invention include, but are not limited to, folic acid analogs (e.g., methotrexate), pyrimidine analogs (e.g., fluorouracil, floxouridine, Cytarabine) and purine analogs (e.g., mercaptopurine, thioguanine, pentostatin). Examples of natural products useful for the treatment of cancer in the methods and compositions of the invention include, but are not limited to, vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin), enzymes (e.g., L-asparaginase) and biological response modifiers (e.g., interferon α). Examples of hormones and antagonists useful for the treatment of cancer in the methods and compositions of the invention include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide) and gonadotropin releasing hormone analog (e.g., leuprolide). Other agents that can be used in the methods and compositions of the invention for the treatment of cancer include platinum coordination complexes (e.g., cisplatin, carboblatin), anthracenedione (e.g., mitoxantrone), substituted ureas (e.g., hydroxyurea), methyl hydrazine derivatives (e.g., procarbazine) and adrenocortical suppressants (e.g., mitotane, aminoglutethimide).

Examples of anti-cancer agents which act by arresting cells in the G2-M phases due to stabilization or inhibition of microtubules, and which can be used in combination with the compounds of the invention include, without limitation, the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8 and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF) and 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39-HCl), AC-7700 (Ajinomoto, also known as AVE-8062, AVE-8062A, CS-39-L-SerHCl and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, Isoeleutherobin A and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (Wyeth, also known as SPA-110, trifluoroacetate salt), D-82317 (Zentaris), D-82318 (Zentaris), SC-12983 (NCI), Resverastatin phosphate sodium, BPR-0Y-007 (National Health Research Institutes) and SSR-250411 (Sanofi).

7. Anti-Infective Agents Useful in Combination with the Compounds of the Invention In one embodiment relating to infections, the other therapeutic agent may be an anti-infective agent. In one embodiment, an anti-infective agent is selected from an anti-fungal, anti-bacterial, anti-viral or anti-parasitic agent.

Anti-fungal agents that can be co-administered with the compounds of the invention include, but are not limited to, polyene antifungals (e.g., amphotericin and nystatin), azole antifungals (e.g., ketoconazole, miconazole, fluconazole, itraconazole, posaconazole, ravuconazole, voriconazole, clotrimazole, econazole, oxiconazole, sulconazole, terconazole, butoconazole, and tioconazole), amorolfine, butenafine, naftifine, terbinafine, flucytosine, nikkomycin Z, caspofungin, micafungin (FK463), anidulafungin (LY303366), griseofulvin, ciclopiroxolamine, tolnaftate, intrathecal, haloprogrin and undecylenate.

Anti-bacterial agents that can be co-administered with the compounds of the invention include, but are not limited to, sulfa drugs (e.g., sulfanilamide), folic acid analogs (e.g., trimethoprim), beta-lactams (e.g., penacillin, cephalosporins), aminoglycosides (e.g., stretomycin, kanamycin, neomycin, gentamycin), tetracyclines (e.g., chlorotetracycline, oxytetracycline and doxycycline), macrolides (e.g., erythromycin, azithromycin and clarithromycin), lincosamides (e.g., clindamycin), streptogramins (e.g., quinupristin and dalfopristin), fluoroquinolones (e.g., ciprofloxacin, levofloxacin and moxifloxacin), polypeptides (e.g., polymixins), rifampin, mupirocin, cycloserine, aminocyclitol (e.g., spectinomycin), glycopeptides (e.g., vancomycin), oxazolidinones (e.g., linezolid), ribosomes, chloramphenicol, fusidic acid and metronidazole.

Anti-viral agents that can be co-administered with the compounds of the invention include, but are not limited to, Emtricitabine (FTC); Lamivudine (3TC); Carbovir; Acyclovir; Interferon; Famciclovir; Penciclovir; Zidovudine (AZT); Didanosine (ddI); Zalcitabine (ddC); Stavudine (d4T); Tenofovir DF (Viread); Abacavir (ABC); L-(−)-FMAU; L-DDA phosphate prodrugs; β-D-dioxolane nucleosides such as β-D-dioxolanyl-guanine (DG), β-D-dioxolanyl-2,6-diaminopurine (DAPD) and β-D-dioxolanyl-6-chloropurine (ACP); non-nucleoside RT inhibitors such as Nevirapine (Viramune), MKC-442, Efavirenz (Sustiva), Delavirdine (Rescriptor); protease inhibitors such as Amprenavir, Atazanavir, Fosamprenavir, Indinavir, Kaletra, Nelfinavir, Ritonavir, Saquinavir, AZT, DMP-450; combination treatments such as Epzicom (ABC+3TC), Trizivir (ABC+3TC+AZT) and Truvada (FTC+Viread); Omega IFN (BioMedicines Inc.); BILN-2061 (Boehringer Ingelheim); Summetrel (Endo Pharmaceuticals); Roferon A (F. Hoffman-La Roche); Pegasys (F. Hoffman-La Roche); Pegasys/Ribaravin (F. Hoffman-La Roche); CellCept (F. Hoffman-La Roche); Wellferon (GlaxoSmithKline); Albuferon-α (Human Genome Sciences); Levovirin (ICN Pharmaceuticals); IDN-6556 (Idun Pharmaceuticals); IP-501 (Indevus Pharmaceuticals); Actimmune (InterMune); Infergen A (InterMune); ISIS 14803 (ISIS Pharmaceuticals); JTK-003 (Japan Tobacco); Pegasys/Ceplene (Maxim Pharmaceuticals); Ceplene (Maxim Pharmaceuticals); Civacir (Nabi Biopharmaceuticals); Intron A/Zadaxin (RegeneRx); Levovirin (Ribapharm); Viramidine (Ribapharm); Heptazyme (Ribozyme Pharmaceuticals); Intron A (Schering-Plough); PEG-Intron (Schering-Plough); Rebetron (Schering-Plough); Ribavirin (Schering-Plough); PEG-Intron/Ribavirin (Schering-Plough); Zadazim (SciClone); Rebif (Serono); IFN-13/EMZ701 (Transition Therapeutics); T67 (Tularik Inc.); VX-497 (Vertex Pharmaceuticals); VX-950/LY-570310 (Vertex Pharmaceuticals); Omniferon (Viragen); XTL-002 (XTL Biopharmaceuticals); SCH 503034 (Schering-Plough); isatoribine and its prodrugs ANA971 and ANA975 (Anadys); R1479 (Roche Biosciences); Valopicitabine (Idenix); NIM811 (Novartis); Actilon (Coley Pharmaceuticals); Pradefovir (Metabasis Therapeutics); zanamivir; adefovir, adefovir dipivoxil, oseltamivir; vidarabine; gancyclovir; valganciclovir; amantadine; rimantadine; relenza; tamiflu; amantadine; entecavir and pleconaril.

Anti-parasitic agents that can be co-administered with the compounds of the invention include, but are not limited to, avermectins, milbemycins, lufenuron, imidacloprid, organophosphates, pyrethroids, sufanamides, iodquinol, diloxanide furoate, metronidazole, paromycin, azithromycin, quinacrine, furazolidone, timidazole, ornidazole, bovine colostrum, bovine dialyzable leukocyte extract, chloroquine, chloroquine phosphate, diclazuril, eflornithine, paromomycin, pentamidine, pyrimethamine, spiramycin, trimethoprim-sulfamethoxazole, albendazole, quinine, quinidine, tetracycline, pyrimethamine-sulfadoxine, mefloquine, doxycycline, proguanil, clindamycin, suramin, melarsoprol, diminazene, nifurtimox, spiroarsoranes, ketoconazole, terbinafine, lovastatin, sodium stibobgluconate, N-methylglucamine antimonate, amphotericin B, allopurinol, itraconazole, sulfadiazine, dapsone, trimetrexate, clarithromycin, roxithromycin, atovaquone, aprinocid, timidazole, mepacrine hydrochloride, emetine, polyaminopropyl biguanide, paromomycin, benzimidazole, praziquantel and albendazole.

8. Steroid or Non-Steroidal Anti-Inflammatory Agents Useful in Combination with the Compounds of the Invention In one embodiment, relating to autoimmune, allergic and inflammatory conditions, the one or more additional therapeutic agent(s) may be a steroid or a non-steroidal anti-inflammatory agent. Particularly useful non-steroidal anti-inflammatory agents include, but are not limited to, aspirin; ibuprofen; diclofenac; naproxen; benoxaprofen; flurbiprofen; fenoprofen; flubufen; ketoprofen; indoprofen; piroprofen; carprofen; oxaprozin; pramoprofen; muroprofen; trioxaprofen; suprofen; aminoprofen; tiaprofenic acid; fluprofen; bucloxic acid; indomethacin; sulindac; tolmetin; zomepirac; tiopinac; zidometacin; acemetacin; fentiazac; clidanac; oxpinac; mefenamic acid; meclofenamic acid; flufenamic acid; niflumic acid; tolfenamic acid; diflurisal; flufenisal; salicylic acid derivatives, including aspirin, sodium salicylate, choline magnesium trisalicylate, salsalate, diflunisal, salicylsalicylic acid, sulfasalazine and olsalazin; para-aminophennol derivatives including acetaminophen and phenacetin; indole and indene acetic acids including indomethacin, sulindac and etodolac; heteroaryl acetic acids including tolmetin, diclofenac and ketorolac; anthranilic acids (fenamates) including mefenamic acid and meclofenamic acid; enolic acids including oxicams (piroxicam, sudoxicam, isoxicam and tenoxicam); pyrazolidinediones (phenylbutazone, oxyphenthartazone); and alkanones, including nabumetone; and pharmaceutically acceptable salts thereof and mixtures thereof. For a more detailed description of the NSAIDs, see Paul A. Insel, *Analgesic-Antipyretic and Anninflammatory Agents and Drugs Employed in the Treatment of Gout, In* GOODMAN & GILMAN's THE PHARMACOLOGICAL BASIS OF THERAPEUTICS (P. B. Molinhoff & R. W. Ruddon Eds., 9th ed (1996)) 617-57; 2 GLEN R. HANSON, ANALGESIC, ANTIPYRETIC AND ANTI-INFLAMMATORY DRUGS IN REMINGTON: THE SCIENCE AND PRACTICE OF PHARMACY (A. R. Gennaro Ed., 19th ed. (1995)) 1196-1221.

Of particular relevance to allergic disorders, the additional therapeutic agent used in combination with a compound of the invention may be an antihistamine. Useful antihistamines include, but are not limited to, loratadine, cetirizine, fexofenadine, desloratadine, diphenhydramine, chlorpheniramine, chlorcyclizine, pyrilamine, promethazine, terfenadine, doxepin, carbinoxamine, clemastine, tripelennamine, brompheniramine, hydroxyzine, cyclizine, meclizine, cyproheptadine, phenindamine, acrivastine, azelastine, levocabastine and mixtures thereof. For a more detailed description of antihistamines, see GOODMAN & GILMAN'S THE PHARMACOLOGICAL BASIS OF THERAPEUTICS (10th ed. (2001)) 651-57.

Immunosuppressive agents include glucocorticoids, corticosteroids, such as Prednisone or Solumedrol; T cell blockers, such as cyclosporin A and FK506; purine analogs, such as azathioprine (Imuran); pyrimidine analogs, such as cytosine arabinoside; alkylating agents, such as nitrogen mustard, phenylalanine mustard, buslfan and cyclophosphamide; folic acid analogs, such as aminopterin and methotrexate; antibiotics, such as rapamycin, actinomycin D, mitomycin C, puramycin, and chloramphenicol; human IgG; antilymphocyte globulin (ALG); and antibodies, such as anti-CD3 (OKT3), anti-CD4 (OKT4), anti-CD5, anti-CD7, anti-IL-2 receptor, anti-alpha/beta TCR, anti-ICAM-1, anti-CD20 (Rituxan), anti-IL-12 and antibodies to immunotoxins.

E. Compositions and Methods for Administering Therapies

The present invention provides compositions for the treatment of proliferative disorders, such as cancer. In a specific embodiment, a composition comprises one or more compounds of the invention, or a pharmaceutically acceptable salt, solvate, clathrate, hydrate or prodrug thereof. In another embodiment, a composition of the invention comprises one or more therapeutic agents in addition to a compound of the invention, or a pharmaceutically acceptable salt, solvate, clathrate, hydrate, or prodrug thereof. In another embodiment, a composition of the invention comprises one or more compounds of the invention, or a pharmaceutically acceptable salt, solvate, clathrate, hydrate or prodrug thereof, and one or more additional therapeutic agents. In another embodiment, the composition comprises a compound of the invention, or a pharmaceutically acceptable salt, solvate, clathrate, hydrate, or prodrug thereof, and a pharmaceutically acceptable carrier, diluent or excipient.

In a preferred embodiment, a composition of the invention is a pharmaceutical composition in a single unit dosage form. Pharmaceutical compositions and dosage forms of the invention comprise one or more active ingredients in relative amounts and are formulated in such a way that a given pharmaceutical composition or dosage form can be used to treat or prevent proliferative disorders, such as cancer. Preferred pharmaceutical compositions and dosage forms comprise a compound of Formulae (I)-(V) or a compound in Table 1, optionally in combination with one or more additional therapeutic agents. In one embodiment, the pharmaceutical composition includes one or more additional therapeutic agent, such as one or more additional anti-inflammatory agent or one or more immunosuppressant.

The pharmaceutical compositions can be used in therapy, e.g., to treat a mammal with an infection. In one embodiment, the pharmaceutical composition includes one or more additional therapeutic agents, such as one or more additional anti-infective agent(s).

In another embodiment, the present invention is the use of a compound of any one of Formulae (I)-(V), or a compound in Table 1, disclosed herein for the manufacture of a medicament for treating a mammal with an infection.

In another embodiment, the present invention is the use of a compound of any one of Formulae (I)-(V), or a compound in Table 1, disclosed herein for the manufacture of a medicament for treatment of a mammal with an inflammatory or autoimmune disorder or for treatment of a mammal in need of immunosuppression.

A pharmaceutical composition of the invention is formulated to be compatible with its intended route of administration. Examples of routes of administration include, but are not limited to, parenteral, e.g., intravenous, intradermal, subcutaneous, oral (e.g., inhalation), intranasal, transdermal (topical), transmucosal, and rectal administration. In a specific embodiment, the composition is formulated in accordance with routine procedures as a pharmaceutical composition adapted for intravenous, subcutaneous, intramuscular, oral, intranasal or topical administration to human beings. In a preferred embodiment, a pharmaceutical composition is formulated in accordance with routine procedures for subcutaneous administration to human beings.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape and type of dosage forms of the invention will typically vary depending on their use. For example, a dosage form suitable for mucosal administration may contain a smaller amount of active ingredient(s) than an oral dosage form used to treat the same indication. This aspect of the invention will be readily apparent to those skilled in the art. See, e.g., REMINGTON'S PHARMACEUTICAL SCIENCES (18th ed., Mack Publishing, Easton Pa. (1990)).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art, including, but not limited to, the way in which the dosage form will be administered to a patient. For example, oral dosage forms such as tablets may contain excipients not suited for use in parenteral dosage forms.

The suitability of a particular excipient may also depend on the specific active ingredients in the dosage form. For example, the decomposition of some active ingredients can be accelerated by some excipients such as lactose, or when exposed to water. Active ingredients that comprise primary or secondary amines (e.g., N-desmethylvenlafaxine and N,N-didesmethylvenlafaxine) are particularly susceptible to such accelerated decomposition. Consequently, this invention encompasses pharmaceutical compositions and dosage forms that contain little, if any, lactose. As used herein, the term "lactose-free" means that the amount of lactose present, if any, is insufficient to substantially increase the degradation rate of an active ingredient. Lactose-free compositions of the invention can comprise excipients that are well known in the art and are listed, for example, in the U.S. PHARMOCOPIA (USP)SP(XXI)/NF (XVI). In general, lactose-free compositions comprise active ingredients, a binder/filler and a lubricant in pharmaceutically compatible and pharmaceutically acceptable amounts. Preferred lactose-free dosage forms comprise active ingredients, microcrystalline cellulose, pre-gelatinized starch and magnesium stearate.

This invention further encompasses anhydrous pharmaceutical compositions and anhydrous dosage forms, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., JENS T. CARSTENSEN, DRUG STABILITY: PRINCIPLES & PRACTICE (2d. ed. (1995)) 379-80. In effect, water and heat accelerate the decomposition of some compounds. Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that has a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs and strip packs.

The invention further encompasses pharmaceutical compositions and dosage forms that comprise one or more compounds that reduce the rate by which an active ingredient will decompose. Such compounds, which are referred to herein as "stabilizer" include, but are not limited to, antioxidants such as ascorbic acid, pH buffers or salt buffers.

1) Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, REMINGTON'S PHARMACEUTICAL SCIENCES (18th ed., Mack Publishing, Easton, Pa. (1990)).

Typical oral dosage forms of the invention are prepared by combining the active ingredient(s) in an admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives and coloring agents. Examples of excipients suitable for use in solid oral dosage forms (e.g., powders, tablets, capsules and caplets) include, but are not limited to, starches, sugars, micro-crystalline cellulose, diluents, granulating agents, lubricants, binders and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation, if necessary.

For example, a tablet can be prepared by compression or molding. Compressed tablets can be prepared by compressing the active ingredients in a free-flowing form such as powder or granules, optionally mixed with an excipient, in a suitable machine. Molded tablets can be made by molding a mixture of the powdered active ingredient moistened with an inert liquid diluent in a suitable machine.

Examples of excipients that can be used in oral dosage forms of the invention include, but are not limited to, binders, fillers, disintegrants and lubricants. Binders suitable for use in pharmaceutical compositions and dosage forms include, but are not limited to, corn starch, potato starch or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose and mixtures thereof.

Suitable forms of microcrystalline cellulose include, but are not limited to, the materials sold as AVICEL-PH-101, AVICEL-PH-103, AVICEL RC-581, AVICEL-PH-105 (available from FMC Corporation, Marcus Hook, Pa.), and mixtures thereof. One specific binder is a mixture of microcrystalline cellulose and sodium carboxymethyl cellulose sold as AVICEL RC-581. Suitable anhydrous or low moisture excipients or additives include AVICEL-PH-103J and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch and mixtures thereof. The binder or filler in pharmaceutical compositions of the invention is typically present in from about 50 to about 99 weight percent of the pharmaceutical composition or dosage form.

Disintegrants can be used in the pharmaceutical compositions of the invention to provide tablets that disintegrate when exposed to an aqueous environment. Tablets that contain too much disintegrant may disintegrate in storage, while those that contain too little may not disintegrate at a desired rate or under the desired conditions. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, other algins, calcium carbonate, microcrystalline cellulose, croscarmellose sodium, other celluloses, crospovidone, polacrilin potassium, sodium starch glycolate, pre-gelatinized starch, potato or tapioca starch, other starches, clays, gums and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and/or soybean oil), zinc stearate, ethyl oleate, ethyl laureate, agar and mixtures thereof. Additional lubricants include, for example, a syloid silica gel (AEROSIL 200, manufactured by W.R. Grace Co., Baltimore, Md.), a coagulated aerosol of synthetic silica (marketed by Degussa Co., Plano, Tex.), CAB-O-SIL (sold by Cabot Co., Boston, Mass.) and mixtures thereof. If used at all, lubricants are typically used in an amount of less than about 1 weight percent of the pharmaceutical compositions or dosage forms into which they are incorporated.

2) Controlled Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719, 5,674,533, 5,059,595, 5,591,767, 5,120,548, 5,073,543, 5,639,476, 5,354,556 and 5,733,566. Such dosage forms can be used to provide slow or controlled-release of one or more active ingredients using, for example, hydropropylmethyl cellulose, polymer matrices, gels, permeable membranes, osmotic systems, multilayer coatings, microparticles, liposomes, microspheres or a combination thereof. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency and increased patient compliance.

Most controlled-release formulations are designed to initially release an initial amount of a drug (active ingredient) that produces the desired therapeutic effect, and thereafter gradually and continually release of other amounts of the drug to maintain this level of therapeutic effect over an extended period of time. In order to maintain a relatively consistent level of drug in the body, the drug must be released at a rate similar to the rate at which the drug is metabolized and excreted from the body. Controlled-release of an active ingredient can be stimulated by various conditions including, but not limited to, pH, temperature, enzymes, water, or other physiological conditions or compounds.

3) Parenteral Dosage Forms

Parenteral dosage forms can be administered to patients by various routes including, but not limited to, subcutaneous, intravenous (including bolus injection), intramuscular and intraarterial. Because parental administration typically bypasses a patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection and emulsions.

Suitable vehicles that can be used to provide parenteral dosage forms of the invention are well known to those skilled in the art. Examples include, but are not limited to: water for injection USP; aqueous vehicles such as, but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol and polypropylene glycol; and non-aqueous vehicles such as, but not limited to, corn oil, cottonseed oil, peanut oil, sesame oil, ethyl oleate, isopropyl myristate and benzyl benzoate.

Compounds that increase the solubility of one or more of the active ingredients disclosed herein can also be incorporated into the parenteral dosage forms of the invention.

4) Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., REMINGTON'S PHARMACEUTICAL SCIENCES (16th and 18th eds., Mack Publishing, Easton Pa. (1980 & 1990)) and INTRODUCTION TO PHARMACEUTICAL DOSAGE FORMS (4th ed., Lea & Febiger, Philadelphia (1985)). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredient(s).

Suitable excipients (e.g., carriers and diluents) and other materials that can be used to provide transdermal, topical and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil and mixtures thereof to form lotions, tinctures, creams, emulsions, gels or ointments which are non-toxic and pharmaceutically acceptable. Moisturizers or humectants can also be added to pharmaceutical compositions and dosage forms if desired. Examples of such additional ingredients are well known in the art. See, e.g., REMINGTON'S PHARMACEUTICAL SCIENCES (16th and 18th eds., Mack Publishing, Easton Pa. (1980 & 1990)).

Depending on the specific tissue to be treated, additional components may be used prior to, in conjunction with, or subsequent to treatment with active ingredient(s) of the invention. For example, penetration enhancers can be used to assist in delivery of the active ingredient(s) to the tissue. Suitable penetration enhancers include, but are not limited to: acetone; various alcohols such as ethanol, oleyl and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant and as a delivery-enhancing or penetration-enhancing agent. Different salts, hydrates or solvates of the active ingredients can be used to further adjust the properties of the resulting composition.

5) Dosage & Frequency of Administration

The amount of the compound or pharmaceutical composition of the invention which will be effective in the treatment of a disease or disorder, e.g. a proliferative disorder, such as cancer, or one or more symptoms thereof, will depend on the nature and severity of the disease and the route by which the active ingredient is administered. The frequency and dosage will also vary according to factors specific for each patient depending on the specific therapy (e.g., therapeutic agent) administered, the severity of the disorder or disease, the route of administration, and the age, body, weight, response and the past medical history of the patient. Effective doses may be extrapolated from dose-response curves derived from in vitro or animal model test systems. Suitable regiments can be selected by one skilled in the art by considering such factors and by following, for example, dosages reported in the literature and recommended in the PHYSICIAN'S DESK REFERENCE (57th ed., 2003).

Exemplary doses of a small molecule include milligram or microgram amounts of the small molecule per kilogram of subject or sample weight (e.g., about 1 mg/kg to about 500 mg/kg, about 0.1 mg/kg to about 5 mg/kg, or about 0.001 mg/kg to about 0.05 mg/kg).

In general, the recommended daily dose range of a compound of the invention for the conditions described herein lies within the range of from about 0.01 mg to about 1000 mg per day, given as a single, once-a-day dose preferably as divided doses throughout a day. In one embodiment, the daily dose is administered twice daily in equally divided doses. Specifically, a daily dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 1000 mg per day as either a single dose or divided doses, depending on the patient's global response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Different therapeutically effective amounts may be applicable for different disease or disorder, as will be readily known by those of ordinary skill in the art. Similarly, amounts sufficient to prevent, manage, treat or ameliorate such a disease or disorder, e.g. proliferative disorders, but insufficient to cause, or sufficient to reduce, adverse effects associated with the compounds of the invention are also encompassed by the above described dosage amounts and dose frequency schedules. Further, when a patient is administered multiple dosages of a compound of the invention, not all of the dosages need be the same. For example, the dosage administered to the patient may be increased to improve the prophylactic or therapeutic effect of the compound or it may be decreased to reduce one or more side effects that a particular patient is experiencing.

In a specific embodiment, the dosage of the composition of the invention or a compound of the invention administered to prevent, treat, manage, or ameliorate a disorders, such as cancer, or one or more symptoms thereof in a patient is 150 µg/kg, preferably 250 µg/kg, 500 µg/kg, 1 mg/kg, 5 mg/kg, 10 mg/kg, 25 mg/kg, 50 mg/kg, 75 mg/kg, 100 mg/kg, 125 mg/kg, 150 mg/kg, or 200 mg/kg or more of a patient's body weight. In another embodiment, the dosage of the composition of the invention or a compound of the invention administered to prevent, treat, manage, or ameliorate a proliferative disorders, such as cancer, or one or more symptoms thereof in a patient is a unit dose of 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosages of prophylactic or therapeutic agents other than compounds of the invention, which have been or are currently being used to prevent, treat, manage, or ameliorate diseases or disorders, e.g. proliferative disorders, such as cancer, or one or more symptoms thereof can be used in the combination therapies of the invention. Preferably, dosages lower than those which have been or are currently being used to prevent, treat, manage, or ameliorate a disease or disorder, e.g. proliferative disorders, or one or more symptoms thereof, are used in the combination therapies of the invention. The recommended dosages of agents currently used for the prevention, treatment, management, or amelioration of a disease or disorder, e.g. proliferative disorders, such as cancer, or one or more symptoms thereof, can obtained from any reference in the art including, but not limited to, Hardman et al., eds., 1996, Goodman & Gilman's The Pharmacological Basis Of Basis Of Therapeutics $9^{th}$ Ed, Mc-Graw-Hill, New York; Physician's Desk Reference (PDR) $57^{th}$ Ed., 2003, Medical Economics Co., Inc., Montvale, N.J., which are incorporated herein by reference in its entirety.

In certain embodiments, when the compounds of the invention are administered in combination with another therapy, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In one embodiment, two or more therapies are administered within the same patent visit.

In certain embodiments, one or more compounds of the invention and one or more other the therapies are cyclically administered. Cycling therapy involves the administration of a first therapy for a period of time, followed by the administration of a second therapy for a period of time, followed by the administration of a third therapy for a period of time and so forth, and repeating this sequential administration, i.e., the cycle in order to reduce the development of resistance to one of the agents, to avoid or reduce the side effects of one of the agents, and/or to improve the efficacy of the treatment.

In certain embodiments, administration of the same compound of the invention may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In a specific embodiment, the invention provides a method of preventing, treating, managing, or ameliorating proliferative disorders, such as cancer, or one or more symptoms thereof, said methods comprising administering to a subject in need thereof a dose of at least 150 µg/kg, preferably at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds of the invention once every day, preferably, once every 2 days, once every 3 days, once every 4 days, once every 5 days, once every 6 days, once every 7 days, once every 8 days, once every 10 days, once every two weeks, once every three weeks, or once a month.

F. Other Embodiments

The compounds of the invention may be used as research tools (for example, to evaluate the mechanism of action of new drug agents, to isolate new drug discovery targets using affinity chromatography, as antigens in an ELISA or ELISA-like assay, or as standards in in vitro or in vivo assays). These and other uses and embodiments of the compounds and compositions of this invention will be apparent to those of ordinary skill in the art.

The invention is further defined by reference to the following examples describing in detail the preparation of compounds of the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Example 1

Synthesis of Compound 95

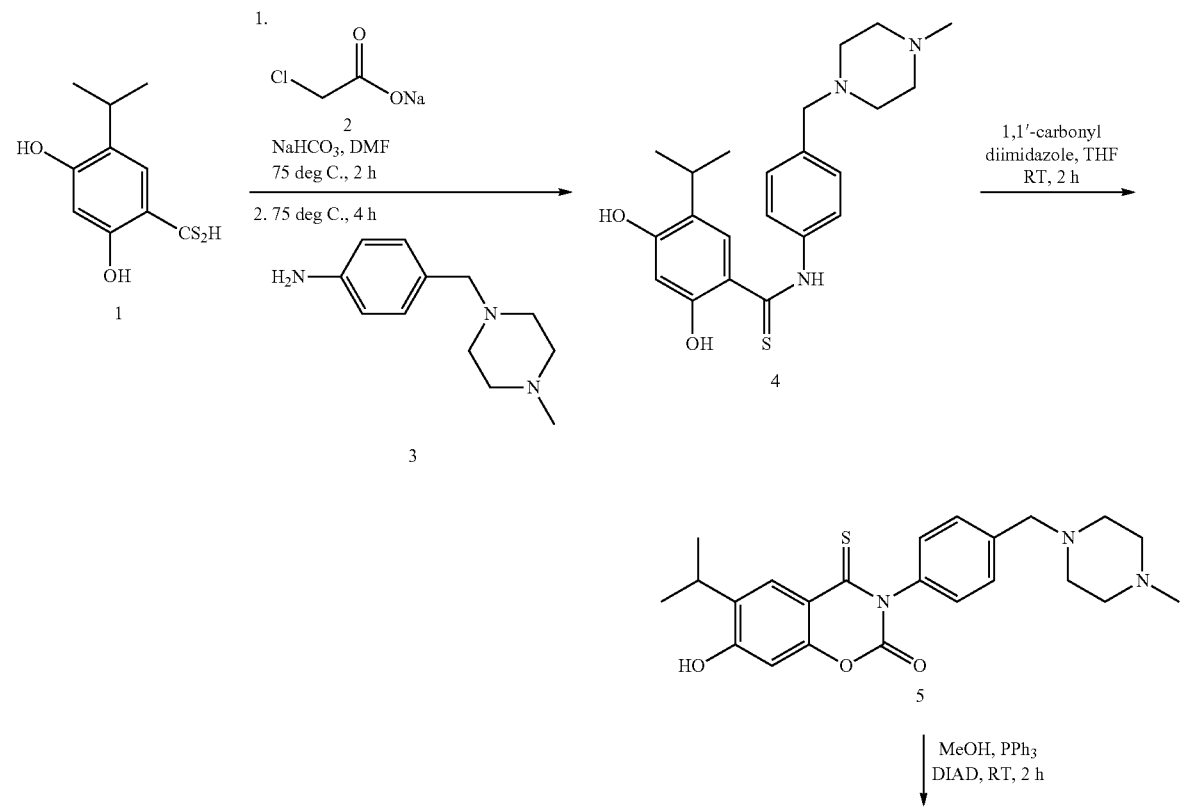

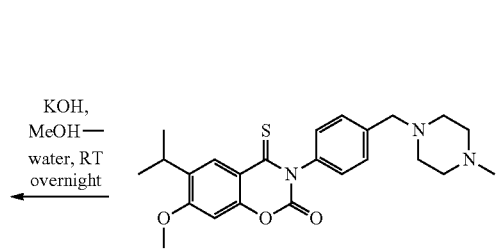

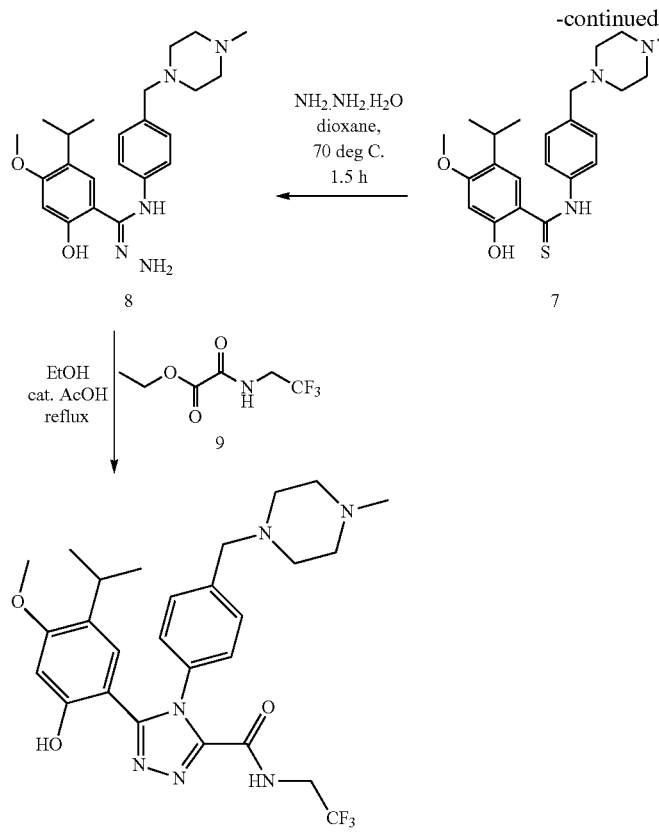

STEP-1:

To the solution of compound 1 (16.7 g, 73 mmol) and NaHCO$_3$ (18.5 g, 219 mmol) in anhydrous DMF, was added sodium chloroacetate 2 (12.8 g, 109.5 mmol). After the addition, the mixture was stirred at 75° C. for 2 h, and to the resultant mixture, was added compound 3 (15 g, 73 mmol) in portion at the same temperature and the solution was stirred for 4 h. The mixture was cooled to room temperature and poured into ice water. The resultant precipitate was filtered, washed with water and dried to give target compound. Quantity: 20 g; yellow solid; yield: 75%.

STEP2:

To a suspension of compound 4 (13.7 g, 33.17 mmol) in THF (150 ml) was add 1,1'-carbonyldiimidazole (5.37 g, 33.17 mmol) portion-wise at 0° C. and the resultant mixture was stirred at room temperature for 2 h. Water was added and organic layer separated and aqueous layer was extracted by ethylacetate. The organics were combined, washed with water, brine and dried over Na$_2$SO$_4$. The organic solution was filtered and concentrated in vacuum to give the desired product 11.2 g, yield 77.2%.

STEP-3:

To a solution of PPh$_3$ (15.4 g, 58.8 mmol) and DIAD (11.9 g, 58.8 mmol) in THF (200 ml) at 0° C. was added compound 5 (10 g, 58.8 mmol) followed by CH$_3$OH (1.88 g) dropwise. The mixture was slowly warmed up to room temperature over about 2 h. After confirming the consumption of the starting material 5, the mixture was quenched by water, extracted with ethylacetate, dried over Na$_2$SO$_4$ and concentrated in vacuum to give 6 g of a yellow solid. Yield 58.2%.

STEP-4:

A suspension of compound 6 (6 g, 13.7 mmol) and KOH (3.8 g, 68 mmol) in MeOH/H$_2$O (200 ml/30 ml) was stirred at room temperature overnight. Concentration of methanol followed by neutralization of base (to pH 6-7) and regular work up using ethylacetate extraction afforded compound 7 as oil. This was further purified by passing through a short silica gel column (CH$_2$Cl$_2$: MeOH=10:1) to give desired product 4 g with 71% yield.

STEP-5:

A suspension of compound 10 (3.0 g, 7.26 mmol) and compound 11 (2.2 g, 44.0 mmol) was stirred in 100 mL dioxane at 80° C. under N$_2$ atmosphere for 1.5 hours. After confirming the completion of the reaction the mixture was poured into 250 mL H$_2$O and extracted with ethylacetate. The ethylacatate phase was washed with brine, dried over Na$_2$SO$_4$, concentrated to give crude product as yellow semisolid.

STEP-6:

Compound 8 (crude from previous step), compound 9 (2.0 g, 10.1 mmol) and 8 drops of AcOH were stirred in 25 mL EtOH at reflux under N$_2$ atmosphere for 6 hours and at r.t. over night. The precipitate formed was filtered and the mother liquor was concentrated to precipitate the product in EtOH/Et$_2$O to give desired product (1.8 g, pink solid) yield: 45% (2 steps).

$^1$H NMR (400 MHz, DMSO), δ (ppm): 10.69 (s, 1H), 9.63 (t, J=6.8 Hz, 1H), 7.37 (q, J=8.0 Hz, 4H), 6.68 (s, 1H), 6.48 (s, 1H), 3.95-3.99 (m, 2H), 3.75 (s, 3H), 3.49 (s, 2H), 2.94-2.97 (m, 1H), 2.33-2.38 (m, 7H), 2.16 (s, 3H), 0.83 (d, J=6.8 Hz, 6H). ESMS calculated for C$_{27}$H$_{36}$N$_6$O$_3$: 492.28. ESMS found: 493.3 (M$^+$).

Compounds I-94, 96-124, and 130-147 were made by methods analogous to that exemplified for Compound 95.

Compound 1

¹H NMR (400 MHz, DMSO), δ (ppm): 10.60 (s, 1H), 9.77 (s, 1H), 8.29 (s, 1H), 7.75 (s, 1H), 7.29-7.39 (dd, $J_1$=8.0 Hz, $J_2$=8.0 Hz, 4H), 6.58 (s, 1H), 6.34 (s, 1H), 3.49 (s, 2H), 2.88-2.90 (m, 1H), 2.28-2.39 (m, 8H), 1.00 (t, J=7.2 Hz, 3H), 0.83 (d, J=7.2 Hz, 6H). ESMS calculated for $C_{25}H_{32}N_6O_3$: 464.56. Found: 465.3 (M⁺).

Compound 4

¹H NMR (400 MHz, DMSO-$d_6$), δ (ppm): 10.61 (s, 1H), 9.79 (s, 1H), 8.93 (t, J=5.6 Hz, 1H), 7.29-7.38 (dd, $J_1$=8.0 Hz, $J_2$=8.0 Hz, 4H), 6.58 (s, 1H), 6.35 (s, 1H), 3.45-3.49 (m, 2H), 3.18 (s, 2H), 2.87-2.94 (m, 1H), 2.67-2.69 (m, 3H), 2.37-2.39 (m, 6H), 2.17 (s, 3H), 0.76 (d, J=6.0 Hz, 6H). ESMS calculated for $C_{25}H_{32}N_6O_3$: 464.56. Found: 465.3 (M⁺).

Compound 7

¹H NMR (400 MHz, DMSO), δ (ppm): 10.58 (s, 1H), 9.80 (s, 1H), 8.95-8.97 (m, 1H), 7.30-7.37 (dd, $J_1$=8.4 Hz, $J_2$=8.4 Hz, 4H), 6.59 (s, 1H), 6.35 (s, 1H), 3.50 (s, 2H), 3.20 (q, J=6.8 Hz, 2H), 2.85-2.87 (m, 1H), 2.51 (s, 8H), 1.48-1.50 (m, 2H), 1.01 (s, 3H), 0.82 (q, J=8.0 Hz, 6H), 0.79 (t, J=6.8 Hz, 3H). ESMS calculated for $C_{28}H_{38}N_6O_3$: 506.6. Found: 505.4 (M⁻).

Compound 8

¹H NMR (400 MHz, DMSO-$d_6$), δ (ppm): 10.59 (s, 1H), 9.77 (s, 1H), 8.95-8.97 (m, 1H), 7.29-7.38 (dd, $J_1$=8.4 Hz, $J_2$=8.4 Hz, 4H), 6.59 (s, 1H), 6.34 (s, 1H), 3.48 (s, 2H), 3.11 (q, J=6.8 Hz, 2H), 2.90-2.92 (m, 1H), 2.28-2.33 (m, 8H), 2.16 (s, 3H), 1.45 (q, J=8.0 Hz, 2H), 0.82 (q, J=8.0 Hz, 6H), 0.79 (t, J=6.8 Hz, 3H). ESMS calculated for $C_{27}H_{36}N_6O_3$: 492.61. Found: 491.4 (M⁻).

Compound 9

¹H NMR (400 MHz, CDCl₃), δ (ppm): 11.70 (s, 1H), 7.36 (s, 1H), 6.99 (d, J=7.6 Hz, 1H), 6.86-6.88 (m, 2H), 6.57-6.63 (m, 2H), 6.10 (s, 2H), 3.83 (s, 3H), 3.44 (t, J=6.8 Hz, 2H), 3.05 (t, J=6.8 Hz, 1H), 1.26 (t, J=6.8 Hz, 3H), 0.85 (s, 6H). ESMS calculated for $C_{22}H_{24}N_4O_5$: 424.45. Found: 423.2 (M⁻).

Compound 10

¹H NMR (400 MHz, DMSO), δ (ppm): 10.61 (s, 1H), 9.76 (s, 1H), 8.95 (t, J=5.6 Hz, 1H), 7.29-7.39 (dd, $J_1$=8.0 Hz, $J_2$=8.0 Hz, 4H), 6.58 (s, 1H), 6.35 (s, 1H), 3.49-3.52 (m, 2H), 3.14-3.17 (m, 5H), 2.87-2.94 (m, 1H), 2.34-2.40 (m, 6H), 2.17 (s, 3H), 1.06 (t, J=6.8 Hz, 3H), 0.83 (d, J=6.0 Hz, 6H). ESMS calculated for $C_{26}H_{34}N_6O_3$: 478.59. Found: 501.3 (M⁺).

Compound 11

¹H NMR (400 MHz, DMSO-$d_6$), δ (ppm): 10.55 (s, 1H), 9.78 (s, 1H), 9.08 (t, J=5.6 Hz, 1H), 7.29-7.40 (dd, $J_1$=8.0 Hz, $J_2$=8.0 Hz, 4H), 6.60 (s, 1H), 6.34 (s, 1H), 3.58-3.60 (m, 4H), 3.50 (s, 2H), 3.15-3.20 (m, 2H), 2.89-2.92 (m, 1H), 2.35-2.45 (m, 10H), 1.56 (t, J=7.2 Hz, 2H), 0.94 (t, J=6.8 Hz, 6H), 0.83 (d, J=6.8 Hz, 6H). ESMS calculated for $C_{30}H_{42}N_6O_4$: 550.69. Found: 549.4 (M⁻).

Compound 12

¹H NMR (400 MHz, DMSO-$d_6$), δ (ppm): 10.55 (s, 1H), 9.79 (s, 1H), 8.75 (t, J=5.6 Hz, 1H), 7.27-7.38 (dd, $J_1$=8.0 Hz, $J_2$=8.0 Hz, 4H), 6.60 (s, 1H), 6.34 (s, 1H), 3.61 (s, 2H), 3.18-3.21 (m, 2H), 2.88-2.95 (m, 1H), 2.44-2.51 (m, 10H), 1.71 (s, 4H), 0.94 (t, J=6.8 Hz, 6H), 0.83 (d, J=6.8 Hz, 6H). ESMS calculated for $C_{29}H_{40}N_6O_3$: 520.67. Found: 521.4 (M⁺).

Compound 17

¹H NMR (300 MHz, DMSO-$d_6$), δ 11.72 (s, 1H), 7.23 (d, J=6.9 Hz, 2H), 7.17 (d, J=6.3 Hz, 1H), 7.01 (d, J=6.9 Hz, 2H), 6.54 (s, 1H), 6.53 (s, 1H), 4.13 (sept., J=4.8 Hz, 2H), 3.87 (t, J=3.6 Hz, 4H), 3.80 (s, 3H), 3.23 (t, J=3.6 Hz, 4H), 2.98 (sept., J=5.1 Hz, 1H), 1.23 (d, J=4.8 Hz, 6H), 0.75 (d, J=5.1 Hz, 6H). ESMS calculated for C26H33N5O4: 479.25. Found: 480.2 (M+H)⁺.

Compound 18

¹H NMR (400 MHz, CDCl₃), δ (ppm): 7.99 (d, J=8.0 Hz, 2H), 7.35 (d, J=8.0 Hz, 2H), 7.29 (d, J=7.2 Hz, 2H), 6.57 (d, J=7.6 Hz, 2H), 4.15-4.18 (m, 1H), 3.82 (s, 3H), 3.75 (s, 2H), 2.98-3.01 (m, 1H), 2.60-2.62 (m, 4H), 2.10 (s, 2H), 1.26 (d, J=6.8 Hz, 6H), 1.13 (t, J=6.4 Hz, 6H), 0.76 (d, J=7.2 Hz, 6H). ESMS calculated for $C_{27}H_{37}N_5O_3$: 479.61. Found: 480.6 (M⁺).

Compound 19

¹H NMR (300 MHz, DMSO-$d_6$), δ 11.64 (bs, 1H), 7.54 (d, J=6.3 Hz, 2H), 7.31 (d, J=6.3 Hz, 2H), 7.21 (bs, 1H), 6.52 (s, 1H), 6.51 (s, 1H), 5.60 (bs, 1H), 4.01 (q, J=5.1 Hz, 2H), 3.72 (s, 2H), 2.96 (sept, J=5.1 Hz, 1H), 2.57 (bs, 4H), 1.81 (q, J=2.4 Hz, 4H), 1.39 (t, J=5.1 Hz, 3H), 0.73 (d, J=5.1 Hz, 6H). ESMS calculated for C25H31N5O3: 449.24. Found: 450.2 (M+H)⁺.

Compound 20

¹H NMR (400 MHz, DMSO-$d_6$), δ (ppm): 10.56 (s, 1H), 9.77 (s, 1H), 8.73 (t, J=6.0 Hz, 1H), 7.26-7.37 (dd, $J_1$=8.4 Hz, $J_2$=8.4 Hz, 4H), 6.58 (s, 1H), 6.34 (s, 1H), 3.48 (s, 2H), 3.14-3.25 (m, 2H), 2.89-2.91 (m, 1H), 2.45-2.50 (m, 13H), 2.08-2.10 (m, 3H), 1.10 (t, J=8 Hz, 1H), 0.93 (t, J=8 Hz, 6H), 0.81 (d, J=4 Hz, 6H). ESMS calculated for $C_{30}H_{43}N_7O_3$: 549.7. Found: 548.4 (M⁻).

Compound 21

¹H NMR (400 MHz, DMSO), δ (ppm): 10.50 (s, 1H), 9.76 (s, 1H), 8.77 (t, J=5.2 Hz, 1H), 7.28-7.38 (dd, $J_1$=8.0 Hz, $J_2$=8.0 Hz, 4H), 6.59 (s, 1H), 6.33 (s, 1H), 3.58-3.59 (m, 4H), 3.49 (s, 2H), 3.24-3.26 (m, 2H), 2.90-2.92 (m, 1H), 2.25-2.31 (m, 15H), 0.99 (t, J=6.8 Hz, 3H), 0.82 (d, J=7.2 Hz, 6H). ESMS calculated for $C_{31}H_{43}N_7O_4$: 577.72. Found: 576.5 (M⁻).

Compound 22

¹H NMR (400 MHz, DMSO-$d_6$), δ (ppm): 10.45 (s, 1H), 9.82 (s, 1H), 9.07 (t, J=6.0 Hz, 1H), 7.39 (d, J=8 Hz, 2H), 7.30 (d, J=8 Hz, 2H), 6.58 (s, 1H), 6.36 (s, 1H), 3.56-3.58 (m, 8H), 3.49 (s, 2H), 3.19 (d, J=6.4 Hz, 2H), 2.86-2.93 (m, 1H), 1.99-2.37 (m, 10H), 1.59 (t, J=6.8 Hz, 2H), 0.82 (d, J=6.8 Hz, 6H). ESMS calculated for C30H40N6O5: 564.68. Found: 563.3 (M⁻).

Compound 23

¹H NMR (400 MHz, DMSO-$d_6$), δ (ppm): 10.54 (s, 1H), 9.76 (s, 1H), 9.08 ((t, J=5.2 Hz, 1H), 7.37-739 (m, 2H), 7.28-7.30 (m, 2H), 6.59 (s, 1H), 6.33 (s, 1H), 3.59 (s, 4H), 3.49 (s, 2H), 3.17 (s, 2H), 2.86-2.93 (m, 1H), 2.34-2.38 (m, 10H), 1.56-1.67 (m, 6H), 0.82 (d, J=8 Hz, 6H). ESMS calculated for $C_{30}H_{40}N_6O_4$: 548.68. Found: 547.4 (M⁻).

Compound 24

¹H NMR (400 MHz, DMSO-$d_6$), δ (ppm): 10.53 (s, 1H), 9.76 (s, 1H), 8.81 (t, J=6.0 Hz, 1H), 7.27-7.37 (dd, $J_1$=8.4 Hz, $J_2$=8.4 Hz, 4H), 6.58 (s, 1H), 6.33 (s, 1H), 3.47-3.55 (m, 4H), 3.37-3.41 (m, 2H), 3.24-3.29 (m, 2H), 2.88-2.92 (m, 2H), 2.36-2.49 (m, 12H), 2.15 (s, 3H), 1.09 (t, J=4.0 Hz, 1H), 0.82 (d, J=8.0 Hz, 6H). ESMS calculated for $C_{30}H_{41}N_7O_4$: 563.7. Found: 562.4 (M⁻).

Compound 25

¹H NMR (400 MHz, DMSO), δ (ppm): 10.79 (s, 1H), 9.00 (t, J=5.6 Hz, 1H), 7.32-7.41 (dd, $J_1$=8.0 Hz, $J_2$=8.0 Hz, 4H), 6.64 (s, 1H), 6.45 (s, 1H), 3.98 (q, J=5.2 Hz, 2H), 3.58-3.60 (m, 4H), 3.51 (s, 2H), 3.14-3.21 (m, 2H), 2.91-2.98 (m, 1H), 2.38 (s, 4H), 1.31 (t, J=7.2 Hz, 3H), 1.04 (t, J=7.2 Hz, 3H), 0.82 (d, J=7.2 Hz, 6H). ESMS calculated for $C_{27}H_{35}N_5O_4$: 493.6. Found: 494.4 (M⁺).

Compound 26

¹H NMR (400 MHz, DMSO), δ (ppm): 10.59 (s, 1H), 9.74 (s, 1H), 8.78 (t, J=5.2 Hz, 1H), 7.26-7.38 (dd, J₁=8.0 Hz, J₂=8.0 Hz, 4H), 6.55 (s, 1H), 6.32 (s, 1H), 3.52-3.54 (m, 6H), 3.24-3.26 (m, 2H), 2.86-2.89 (m, 1H), 2.43-2.45 (m, 2H), 2.34-2.38 (m, 6H), 0.97 (t, J=6.8 Hz, 6H), 0.80 (d, J=6.8 Hz, 6H). ESMS calculated for $C_{29}H_{40}N_6O_4$: 536.67. Found: 537.3 (M⁺).

Compound 27

¹H NMR (400 MHz, DMSO), δ (ppm): 10.59 (s, 1H), 9.74 (s, 1H), 8.78 (t, J=5.2 Hz, 1H), 7.26-7.38 (dd, J₁=8.0 Hz, J₂=8.0 Hz, 4H), 6.55 (s, 1H), 6.32 (s, 1H), 3.58-3.61 (m, 6H), 3.18-3.22 (m, 2H), 2.90-2.93 (m, 1H), 2.32-2.33 (m, 4H), 2.26-2.30 (m, 6H), 1.71 (s, 4H), 1.61 (t, J=7.2 Hz, 2H), 0.82 (d, J=7.2 Hz, 6H). ESMS calculated for $C_{30}H_{40}N_6O_4$: 548.68. Found: 547.4 (M⁻).

Compound 28

¹H NMR (400 MHz, DMSO), δ (ppm): 10.79 (s, 1H), 8.98 (t, J=6.0 Hz, 1H), 7.30-7.39 (dd, J₁=8.0 Hz, J₂=8.0 Hz, 4H), 6.53 (s, 1H), 6.46 (s, 1H), 3.72 (s, 3H), 3.57 (t, J=4.4 Hz, 4H), 3.48 (s, 2H), 0.12-3.19 (m, 2H), 2.89-2.96 (m, 1H), 2.36 (s, 4H), 1.02 (t, J=6.8 Hz, 3H), 0.79 (d, J=7.2 Hz, 6H). ESMS calculated for $C_{26}H_{33}N_5O_4$: 479.6. Found: 480.3 (M⁺).

Compound 29

¹H NMR (400 MHz, DMSO), δ (ppm): 10.26 (s, 1H), 8.31 (s, 1H), 7.76 (s, 1H), 7.20-7.31 (dd, J₁=8.0 Hz, J₂=8.0 Hz, 4H), 6.98 (d, J=8.8 Hz, 1H), 6.31-6.33 (m, 2H), 3.92 (q, J=6.8 Hz, 2H), 3.57-3.59 (m, 4H), 3.46-3.47 (m, 2H), 2.33 (s, 4H), 1.28 (t, J=6.8 Hz, 3H). ESMS calculated for $C_{22}H_{25}N_5O_4$: 423.47. Found: 422.3 (M⁻).

Compound 30

¹H NMR (400 MHz, DMSO-d₆), δ (ppm): 10.23 (s, 1H), 8.30 (s, 1H), 7.75 (s, 1H), 7.21-7.31 (dd, J₁=8.0 Hz, J₂=8.0 Hz, 4H), 7.00 (d, J=8.0 Hz, 1H), 6.33-6.35 (m, 2H), 3.68 (s, 3H), 3.58 (s, 4H), 3.47 (s, 2H), 2.34 (s, 4H). ESMS calculated for $C_{21}H_{23}N_5O_4$: 409.44. Found: 432.3 (M⁺).

Compound 31

¹H NMR (400 MHz, DMSO-d₆), δ (ppm): 10.89 (s, 1H), 9.82 (s, 1H), 8.94 (t, J=6.0 Hz, 1H), 7.11-7.26 (dd, J₁=8.0 Hz, J₂=8.0 Hz, 4H), 6.61 (s, 1H), 6.37 (s, 1H), 3.88 (s, 4H), 3.11-3.21 (m, 6H), 2.90-2.97 (m, 1H), 1.05 (t, J=7.2 Hz, 3H), 0.83 (d, J=6.8 Hz, 6H). ESMS calculated for $C_{24}H_{29}N_5O_5S$: 499.58. Found: 522.3 (M⁺).

Compound 32

ESMS calculated for $C_{24}H_{29}N_5O_3$: 435.23. Found: 436.2 (M+H)⁺.

Compound 33

¹H NMR (400 MHz, DMSO-d₆), δ (ppm): 10.55 (s, 1H), 9.84 (s, 1H), 8.76 (t, J=5.2 Hz, 1H), 7.28-7.38 (dd, J₁=8.0 Hz, J₂=8.0 Hz, 4H), 6.59 (s, 1H), 6.39 (s, 1H), 3.48 (s, 2H), 3.24-3.28 (q, J=8.0 Hz, 2H), 2.87-2.92 (m, 1H), 2.16-2.40 (m, 20H), 2.10 (s, 3H), 0.98 (t, J=7.2 Hz, 3H), 0.82 (d, J=7.2 Hz, 6H). ESMS calculated for $C_{32}H_{46}N_8O_3$: 590.76. Found: 589.4 (M⁺).

Compound 34

¹H NMR (400 MHz, DMSO-d₆), δ (ppm): 10.55 (s, 1H), 9.78 (s, 1H), 8.74 (s, 1H), 7.29-7.38 (dd, J₁=8.0 Hz, J₂=8.0 Hz, 4H), 6.59 (s, 1H), 6.34 (s, 1H), 3.49 (s, 2H), 3.25-3.27 (m, 2H), 2.91 (t, J=6.0 Hz, 1H), 2.20-2.38 (m, 18H), 2.14-2.16 (m, 6H), 0.83 (d, J=6.4 Hz, 6H). ESMS calculated for $C_{31}H_{44}N_8O_3$: 576.73. Found: 575.4 (M⁺).

Compound 35

¹H NMR (400 MHz, DMSO), δ (ppm): 10.61 (s, 1H), 9.79 (s, 1H), 8.77 (t, J=5.2 Hz, 1H), 7.28-7.41 (dd, J₁=8.0 Hz, J₂=8.0 Hz, 4H), 6.58 (s, 1H), 6.35 (s, 1H), 3.57 (s, 2H), 3.25-3.27 (m, 2H), 2.46-2.51 (m, 1H), 2.26-2.32 (m, 10H), 0.96-1.01 (m, 9H), 0.82 (d, J=6.4 Hz, 6H). ESMS calculated for $C_{31}H_{45}N_7O_3$: 563.73. Found: 562.4 (M⁻).

Compound 36

¹H NMR (400 MHz, DMSO), δ (ppm): 10.53 (s, 1H), 9.77 (s, 1H), 8.87 (d, J=8.4 Hz, 1H), 7.40 (d, J=8.4 Hz, 2H), 7.31 (d, J=8.4 Hz, 2H), 6.61 (s, 1H), 6.34 (s, 1H), 3.58-3.60 (m, 5H), 3.50 (s, 2H), 2.90-2.92 (m, 1H), 2.67-2.70 (m, 2H), 2.38 (s, 4H), 2.12 (s, 3H), 1.85 (t, J=8.8 Hz, 2H), 1.56-1.59 (m, 4H), 0.83 (d, J=8.8 Hz, 6H). ESMS calculated for $C_{29}H_{38}N_6O_4$: 534.65. Found: 535.3 (M⁺).

Compound 37

¹H NMR (400 MHz, DMSO), δ (ppm): 10.53 (s, 1H), 9.79 (s, 1H), 8.78 (t, J=5.2 Hz, 1H), 7.27-7.38 (dd, J₁=8.0 Hz, J₂=8.0 Hz, 4H), 6.60 (s, 1H), 6.35 (s, 1H), 3.57 (s, 2H), 3.25-3.27 (m, 2H), 2.88-2.94 (m, 1H), 2.31-2.39 (m, 8H), 2.14 (s, 3H), 0.99 (t, J=7.2 Hz, 6H), 0.82 (d, J=6.8 Hz, 6H). ESMS calculated for $C_{30}H_{43}N_7O_3$: 549.71. Found: 548.5 (M⁻).

Compound 38

¹H NMR (400 MHz, DMSO), δ (ppm): 10.53 (s, 1H), 9.79 (s, 1H), 8.78 (t, J=5.2 Hz, 1H), 7.27-7.38 (dd, J₁=8.0 Hz, J₂=8.0 Hz, 4H), 6.60 (s, 1H), 6.35 (s, 1H), 3.57-3.59 (m, 6H), 3.17-3.20 (m, 2H), 2.89-2.92 (m, 1H), 2.25-2.32 (m, 6H), 1.58-1.62 (m, 2H), 0.99 (t, J=7.2 Hz, 6H), 0.82 (d, J=8.0 Hz, 6H). ESMS calculated for $C_{30}H_{42}N_6O_4$: 550.69. Found: 551.3 (M⁺).

Compound 39

¹H NMR (400 MHz, DMSO), δ (ppm): 10.53 (s, 1H), 9.79 (s, 1H), 8.79 (t, J=5.2 Hz, 1H), 7.27-7.39 (dd, J₁=8.0 Hz, J₂=8.0 Hz, 4H), 6.53 (s, 1H), 6.35 (s, 1H), 3.56 (s, 2H), 3.22-3.27 (m, 4H), 2.88-2.94 (m, 1H), 2.41-2.46 (m, 8H), 1.65 (s, 4H), 0.98 (t. J=6.8 Hz, 6H), 0.82 (d, J=6.8 Hz, 6H). ESMS calculated for $C_{29}H_{40}N_6O_3$: 520.67. Found: 543.4 (M⁺).

Compound 40

¹H NMR (300 MHz, DMSO-d₆), δ 11.02 (s, 1H), 8.24 (s, 1H), 7.73 (s, 1H), 7.54-7.51 (m, 2H), 7.45 (d, J=2.4 Hz, 1H), 7.14-7.11 (m, 1H), 6.46-6.44 (m, 3H), 3.83 (s, 3H), 3.70 (s, 3H), 2.83 (sept, J=5.1 Hz, 1H), 0.59 (d, J=5.1 Hz, 6H). ESMS calculated for C22H23N5O3: 405.18. Found: 406.1 (M+H)⁺.

Compound 41

¹H NMR (400 MHz, DMSO), δ (ppm): 10.78 (s, 1H), 9.00 (t, J=4.0 Hz, 1H), 7.32-7.41 (dd, J₁=8.0 Hz, J₂=8.0 Hz, 4H), 6.64 (s, 1H), 6.45 (s, 1H), 3.88 (t, J=5.6 Hz, 2H), 3.59 (s, 4H), 3.51 (s, 2H), 3.14-3.19 (m, 2H), 2.92-2.97 (m, 1H), 2.36-2.37 (m, 4H), 1.69-1.74 (m, 2H), 1.18 (t, J=7.2 Hz, 3H), 0.97 (t, J=7.2 Hz, 3H), 0.82 (d, J=6.8 Hz, 6H). ESMS calculated for $C_{28}H_{37}N_5O_4$: 507.62. Found: 530.3 (M⁺).

Compound 42

¹H NMR (400 MHz, DMSO), δ (ppm): 10.77 (s, 1H), 9.00 (t, J=4.0 Hz, 1H), 7.31-7.40 (dd, J₁=8.0 Hz, J₂=8.0 Hz, 4H), 6.61 (s, 1H), 6.46 (s, 1H), 4.51-4.57 (m, 1H), 3.56-3.57 (m, 4H), 3.49 (s, 2H), 3.12-3.17 (m, 2H), 2.86-2.93 (m, 1H), 2.36 (s, 4H), 1.23 (d, J=6.4 Hz, 6H), 1.03 (t, J=7.2 Hz, 3H), 0.79 (d, J=7.2 Hz, 6H). ESMS calculated for $C_{28}H_{37}N_5O_4$: 507.62. Found: 508.3 (M⁺).

Compound 43

¹H NMR (400 MHz, DMSO), δ (ppm): 10.10 (s, 1H), 9.70 (s, 1H), 8.30 (s, 1H), 7.74 (s, 1H), 7.20-7.31 (dd, J₁=8.0 Hz, J₂=8.0 Hz, 4H), 6.84 (d, J=8.4 Hz, 1H), 6.21 (s, 1H), 6.15 (d, J=6.4 Hz, 1H), 3.58 (s, 4H), 3.48 (s, 2H), 2.34 (s, 4H). ESMS calculated for $C_{20}H_{21}N_5O_4$: 395.41. Found: 418.2 (M⁺).

Compound 44

¹H NMR (400 MHz, DMSO), δ (ppm): 10.65 (s, 1H), 9.80 (s, 1H), 9.08 (t, J=6.0 Hz, 1H), 7.28-7.41 (dd, J₁=8.0 Hz, $J_2$=8.0 Hz, 4H), 6.57 (s, 1H), 6.35 (s, 1H), 3.57 (s, 2H), 3.17-3.21 (m, 2H), 2.89-2.92 (m, 1H), 2.46-2.49 (m, 4H), 2.35-2.38 (m, 6H), 1.57-1.60 (m, 6H), 1.00 (t, J=7.2 Hz, 6H), 0.80 (d, J=7.2 Hz, 6H). ESMS calculated for $C_{30}H_{42}N_6O_3$: 534.69. Found: 535.3 (M⁺).

Compound 45

¹H NMR (400 MHz, DMSO), δ (ppm): 10.62 (s, 1H), 9.80 (s, 1H), 8.88 (d, J=8.0 Hz, 1H), 7.28-7.41 (dd, $J_1$=8.0 Hz, $J_2$=8.0 Hz, 4H), 6.59 (s, 1H), 6.35 (s, 1H), 3.57 (s, 3H), 2.89-2.93 (m, 1H), 2.69-2.72 (m, 2H), 2.45-2.49 (m, 4H), 2.14 (s, 3H), 1.87-1.89 (m, 2H), 1.55-1.60 (m, 4H), 1.00 (t, J=6.8 Hz, 6H), 0.83 (d, J=7.2 Hz, 6H). SMS calculated for $C_{29}H_{40}N_6O_3$: 520.67. Found: 521.3 (M⁺).

Compound 46

¹H NMR (300 MHz, CDCl₃), δ (ppm): 11.59 (br s, 1H); 7.26-7.32 (m, 3H); 7.08 (d, J=6.9 Hz, 2H); 6.53 (s, 1H); 6.44 (s, 1H); 5.38 (br s, 1H); 4.66 (s, 2H); 4.30 (q, J=5.4 Hz, 2H); 3.97 (m, 2H); 2.90 (hept, J=5.1 Hz, 1H); 1.32 (t, J=6.3 Hz, 3H); 1.22 (t, J=5.4 Hz, 3H); 0.81 (d, J=5.1 Hz, 6H). ESMS calculated. for $C_{24}H_{29}N_4O_6$ (M+H)⁺: 469.2. Found: 469.2.

Compound 47

¹H NMR (300 MHz, DMSO-d₆), δ (ppm): 13.08 (br s, 1H); 10.49 (br s, 1H); 9.73 (s, 1H); 8.96 (s, 1H); 7.26 (d, J=6.9 Hz, 2H); 6.96 (d, J=6.9 Hz, 2H); 6.93 (s, 1H); 6.34 (s, 1H); 4.69 (s, 2H); 3.17 (m, 2H); 2.93 (hept, J=5.1 Hz, 1H); 1.05 (t, J=5.4 Hz, 3H); 0.87 (d, J=5.1 Hz, 6H). ESMS calculated. for $C_{22}H_{25}N_4O_6$ (M+H)⁺: 440.2. Found: 440.2.

Compound 48

¹H NMR (400 MHz, DMSO) δ 10.27 (s, 1H), 8.25 (s, 1H), 7.75 (s, 1H), 7.27 (d, J=8.8 Hz, 2H), 6.97 (d, J=8.8 Hz, 2H), 6.77 (s, 1H), 6.65 (s, 1H), 3.77 (s, 3H), 2.93-2.82 (m, 1H), 2.18 (s, 3H), 0.90 (s, 6H). ESMS calculated for $C_{20}H_{22}N_4O_3$ m/z 366.17. found m/z 367.2 (M⁺+H).

Compound 49

¹H-NMR (DMSO-d₆): δ 0.77 (d, J=6.9 Hz, 6H), 2.89 (hept., J=6.9 Hz, 1H), 3.81 (s, 3H), 6.44 (d, J=2.9 Hz, 1H), 6.59 (s, 1H), 6.85 (s, 1H), 7.10 (dd, J=8.6, 1.8 Hz, 1H), 7.18 (t, J=73.8 Hz, 1H), 7.43 (d, J=2.9 Hz, 1H), 7.47 (d, J=8.6 Hz, 1H), 7.53 (d, J=1.7 Hz, 1H), 7.76 (bs, 1H), 8.28 (bs, 1H), 10.78 (bs, 1H). ESMS ($C_{22}H_{21}F_2N_5O_3$): calc. 441.16. found: 442.2 [M+H⁺].

Compound 50

¹H NMR (300 MHz, DMSO-d₆), δ 10.90 (bs, 1H), 7.32 (bs, 1H), 7.12 (s, 1H), 6.78 (d, J=6.0 Hz, 1H), 6.60 (s, 1H), 6.55 (J=1.2 Hz, 1H), 6.51 (dd, J=1.2 Hz, 6.0 Hz, 1H), 5.95 (s, 2H), 5.83 (s, 2H), 5.57 (bs, 1H), 3.83 (s, 3H), 3.13 (sept, J=5.1 Hz, 1H), 0.93 (d. J=5.1 Hz, 6H). ESMS calculated for $C_{21}H_{22}N_4O_5$: 410.16. Found: 411.1 (M+H)⁺.

Compound 51

¹H NMR (400 MHz, DMSO-d₆), δ (ppm): 10.28 (s, 1H), 8.31 (s, 1H), 7.76 (s, 1H), 7.20-7.31 (dd, $J_1$=8.4 Hz, $J_2$=8.4 Hz, 4H), 6.98 (d, J=8.8 Hz, 1H), 6.31-6.33 (m, 2H), 3.84 (t, J=5.6 Hz, 2H), 3.57-3.59 (m, 4H), 3.47 (s, 2H), 2.33 (s, 4H), 1.63-1.72 (m, 2H), 0.94 (t, J=7.2 Hz, 3H). ESMS calculated for $C_{23}H_{27}N_5O_4$: 437.49. Found: 438.3 (M⁺).

Compound 52

¹H NMR (400 MHz, DMSO-d₆), δ (ppm): 10.24 (s, 1H), 8.30 (s, 1H), 7.75 (s, 1H), 7.21-7.31 (dd, $J_1$=8.4 Hz, $J_2$=8.4 Hz, 4H), 6.95 (d, J=8.8 Hz, 1H), 6.30-6.31 (m, 2H), 4.78-4.54 (m, 1H), 3.56-3.58 (m, 4H), 3.48 (s, 2H), 2.33 (s, 4H), 1.22 (d, J=6.4 Hz, 6H). ESMS calculated for $C_{23}H_{27}N_5O_4$: 437.49. Found: 438.4 (M⁺).

Compound 53

¹H NMR (400 MHz, DMSO-d₆), δ (ppm): 10.58 (s, 1H), 9.87 (s, 1H), 8.28 (s, 1H), 7.74 (s, 1H), 7.29-7.40 (dd, $J_1$=8.4 Hz, $J_2$=8.4 Hz, 4H), 6.67 (s, 1H), 6.36 (s, 1H), 0.58-3.60 (m, 4H), 3.50 (s, 2H), 2.38 (s, 4H), 1.03 (s, 9H). ESMS calculated for $C_{24}H_{29}N_5O_4$: 451.52. Found: 452.3 (M⁺).

Compound 56

¹H NMR (400 MHz, DMSO), δ (ppm): 10.55 (s, 1H), 9.77 (s, 1H), 8.76 (t, J=6.8 Hz, 1H), 7.28-7.38 (dd, $J_1$=8.0 Hz, $J_2$=8.0 Hz, 4H), 6.59 (s, 1H), 6.35 (s, 1H), 3.48 (s, 2H), 3.24-3.35 (q, J=6.4 Hz, 2H), 2.89-2.93 (m, 1H), 2.28-2.34 (m, 17H), 2.15 (s, 3H), 0.99 (t, J=6.4 Hz, 3H), 0.83 (d, J=6.4 Hz, 6H). ESMS calculated for $C_{32}H_{46}N_8O_3$: 590.76. Found: 591.4 (M⁺).

Compound 57

¹H NMR (400 MHz, DMSO), δ (ppm): 10.53 (s, 1H), 9.77 (s, 1H), 8.76 (t, J=6.8 Hz, 1H), 7.27-7.36 (dd, $J_1$=8.0 Hz, $J_2$=8.0 Hz, 4H), 6.58 (s, 1H), 6.33 (s, 1H), 3.47 (s, 2H), 3.23-3.25 (m, 2H), 2.88-2.90 (m, 1H), 2.25-2.32 (m, 18H), 1.00 (t, J=6.8 Hz, 6H), 0.81 (d, J=6.8 Hz, 6H). ESMS calculated for $C_{33}H_{48}N_8O_3$: 604.79. Found: 605.4 (M⁺).

Compound 58

¹H NMR (400 MHz, DMSO), δ (ppm): 10.62 (s, 1H), 8.29 (s, 1H), 7.76 (s, 1H), 7.28-7.38 (dd, $J_1$=8.0 Hz, $J_2$=8.0 Hz, 4H), 6.61 (s, 1H), 6.45 (s, 1H), 3.73 (s, 3H), 3.57-3.60 (m, 4H), 3.51 (s, 2H), 2.51 (s, 4H), 2.36 (s, 2H), 0.83 (t, J=6.8 Hz, 3H). ESMS calculated for $C_{23}H_{27}N_5O_4$: 437.49. Found: 438.3 (M⁺).

Compound 59

¹H NMR (400 MHz, DMSO-d₆), δ (ppm): 8.31 (s, 1H), 7.76 (s, 1H), 7.32 (d, J=8.4 Hz, 1H), 7.23 (d, J=8.4 Hz, 2H), 7.07 (d, J=8.0 Hz, 2H), 6.55-6.58 (m, 1H), 6.41 (s, 1H), 3.74 (s, 3H), 3.55 (s, 4H), 3.43 (s, 2H), 3.37 (s, 3H), 2.29 (s, 4H). ESMS calculated for $C_{22}H_{25}N_5O_4$: 423.47. Found: 424.2 (M⁺).

Compound 60

¹H NMR (400 MHz, CDCl₃), δ (ppm): 11.57 (s, 1H), 8.03 (s, 1H), 7.58 (d, J=8.0 Hz, 2H), 7.36 (d, J=8.0 Hz, 2H), 6.56 (s, 1H), 6.47 (s, 1H), 5.61 (s, 1H), 3.75 (t, J=8.4 Hz, 4H), 3.60 (s, 2H), 2.88-2.95 (m, 1H), 2.68 (s, 6H), 2.52 (s, 4H), 0.77 (d, J=8.8 Hz, 6H). ESMS calculated for $C_{25}H_{32}N_6O_4$: 480.56. Found: 479.3 (M⁻).

Compound 61

¹H NMR (400 MHz, DMSO), δ (ppm): 10.56 (s, 1H), 9.88 (s, 1H), 8.81 (t, J=6.0 Hz, 1H), 7.27-7.38 (dd, $J_1$=8.0 Hz, $J_2$=8.0 Hz, 4H), 6.60 (s, 1H), 6.34 (s, 1H), 3.49 (s, 2H), 3.24-3.29 (m, 2H), 2.89-2.93 (m, 1H), 2.28-2.33 (m, 14H), 1.67 (s, 4H), 0.99 (t, J=6.8 Hz, 3H), 0.83 (d, J=6.0 Hz, 6H). ESMS calculated for $C_{31}H_{43}N_7O_3$: 561.72. Found: 560.5 (M⁻).

Compound 62

¹H NMR (400 MHz, DMSO), δ (ppm): 10.32 (s, 1H), 9.71 (s, 1H), 8.28 (s, 1H), 7.73 (s, 1H), 7.23-7.35 (dd, $J_1$=8.4 Hz, $J_2$=8.4 Hz, 4H), 6.55 (s, 1H), 6.30 (s, 1H), 3.56 (t, J=4.4 Hz, 4H), 3.48 (s, 2H), 2.34 (s, 4H), 2.17-2.23 (m, 2H), 0.82 (t, J=7.2 Hz, 3H). ESMS calculated for $C_{22}H_{25}N_5O_4$: 423.47. Found: 424.2 (M⁺).

Compound 63

¹H NMR (400 MHz, DMSO-d₆), δ (ppm): 9.88 (s, 1H), 9.71 (s, 1H), 8.33 (s, 1H), 7.75 (s, 1H), 7.56-7.58 (m, 2H), 7.39 (d, J=7.2 Hz, 2H), 6.74 (s, 1H), 6.30 (s, 1H), 4.35-4.38 (m, 2H), 3.96-3.99 (m, 2H), 3.74-3.75 (m, 2H), 3.10-3.18 (m, 4H), 1.88 (s, 3H). ESMS calculated for $C_{21}H_{23}N_5O_4$: 409.44. Found: 410.3 (M⁺).

Compound 64

¹H NMR (400 MHz, DMSO), δ (ppm): 10.60 (s, 1H), 8.29 (s, 1H), 7.76 (s, 1H), 7.28-7.38 (dd, $J_1$=8.0 Hz, $J_2$=8.0 Hz, 4H), 6.60 (s, 1H), 6.42 (s, 1H), 3.95-3.97 (m, 4H), 3.57-3.60 (m, 4H), 3.51 (s, 2H), 2.36 (s, 4H), 2.23-2.25 (m, 2H), 1.30 (t, J=7.2 Hz, 3H), 0.84 (t, J=7.2 Hz, 3H). ESMS calculated for $C_{24}H_{29}N_5O_4$: 451.52. Found: 452.2 (M⁺).

Compound 65

¹H NMR (400 MHz, DMSO), δ (ppm): 9.84 (s, 1H), 9.73 (s, 1H), 8.24 (s, 1H), 7.79 (s, 1H), 6.99 (s, 1H), 6.51 (s, 1H), 4.34 (t, J=5.6 Hz, 2H), 3.34-3.37 (m, 4H), 3.10-3.18 (m, 1H), 2.37 (t, J=6.0 Hz, 2H), 2.11 (s, 4H), 1.15 (d, J=6.4 Hz, 6H). ESMS calculated for $C_{18}H_{25}N_5O_4$: 375.42. Found: 376.4 (M⁺).

Compound 66

¹H NMR (400 MHz, DMSO), δ (ppm): 10.39 (s, 1H), 8.31 (s, 1H), 7.76 (s, 1H), 7.25-7.35 (dd, $J_1$=8.4 Hz, $J_2$=8.4 Hz, 4H), 6.67 (s, 1H), 6.40 (s, 1H), 3.72 (s, 3H), 3.58 (s, 4H), 3.50 (s, 2H), 2.35 (s, 4H), 1.85 (s, 3H). ESMS calculated for $C_{22}H_{25}N_5O_4$: 423.47. Found: 424.2 (M⁺).

Compound 67

¹H NMR (400 MHz, DMSO) δ 10.07 (s, 1H), 8.29 (s, 1H), 7.76 (s, 1H), 7.22 (d, J=8.4 Hz, 2H), 7.10 (dd, J=8.4, 1.4 Hz, 1H), 6.92 (d, J=8.4 Hz, 2H), 6.91 (s, 1H), 6.74 (d, J=8.4 Hz, 1H), 3.75 (s, 3H), 2.75-2.65 (m, 1H), 1.02 (d, J=6.8 Hz, 6H). ESMS calculated for $C_{19}H_{20}N_4O_3$ m/z 352.15. found m/z 353.2 (M⁺+H).

Compound 68

¹H NMR (300 MHz, CDCl₃), δ (ppm): 11.60 (br s, 1H); 7.53 (d, J=6.3 Hz, 2H); 7.30-7.40 (m, 3H); 6.54 (s, 1H); 6.42 (s, 1H); 6.17 (br s, 1H); 4.66 (s, 2H); 4.15 (q, J=5.4 Hz, 2H); 3.56 (s, 2H); 3.44 (m, 2H); 2.84-2.94 (m, 3H); 1.77-2.36 (m, 8H); 1.28 (t, J=6.3 Hz, 3H); 1.19 (t, J=5.4 Hz, 3H); 0.74 (d, J=5.1 Hz, 6H). ESMS calculated. for $C_{30}H_{39}N_4O_5$ (M+H)⁺: 536.3. Found: 536.3.

Compound 69

¹H NMR (300 MHz, DMSO-d₆), δ (ppm): 13.08 (br s, 1H); 10.67 (br s, 2H); 8.97 (s, 1H); 7.37 (d, J=6.3 Hz, 2H); 7.29 (d, J=6.3 Hz, 2H); 6.58 (s, 1H); 6.35 (s, 1H); 3.48 (s, 2H); 3.13-3.20 (m, 2H); 2.91 (hept, J=5.1 Hz, 1H); 2.76-2.79 (m, 2H); 1.50-2.21 (m, 8H); 1.0 (t, J=5.4 Hz, 3H); 0.81 (d, J=5.1 Hz, 6H). ESMS calculated for $C_{28}H_{35}N_4O_5$ (M+H)⁺: 508.3. Found: 508.3.

Compound 70

¹H NMR (400 MHz, DMSO) δ 10.17 (s, 1H), 8.26 (s, 1H), 7.74 (s, 1H), 7.22 (d, J=8.0 Hz, 2H), 7.00 (d, J=8.0 Hz, 1H), 6.91 (d, J=8.0 Hz, 2H), 6.69 (s, 1H), 6.66 (d, J=8.0 Hz, 1H), 3.76 (s, 3H), 2.84-2.74 (m, 1H), 1.13 (d, J=6.4 Hz, 6H). ESMS calculated for $C_{19}H_{20}N_4O_3$ m/z 352.15. found m/z 353.1 (M⁺+H).

Compound 71

¹H NMR (400 MHz, DMSO) δ 9.68 (s, 1H), 8.25 (s, 1H), 7.73 (s, 1H), 7.16 (d, J=8.8 Hz, 2H), 6.99 (d, J=8.4 Hz, 1H), 6.87 (d, J=8.8 Hz, 2H), 6.60 (s, 1H), 6.51 (d, J=8.4 Hz, 1H), 3.73 (s, 3H), 2.03 (s, 3H). ESMS calculated for $C_{17}H_{16}N_4O_3$ m/z 324.12. found m/z 325.1 (M⁺+H).

Compound 72

¹H NMR (400 MHz, DMSO), δ (ppm): 10.81 (s, 1H), 8.88 (d, J=7.6 Hz, 1H), 7.32-7.42 (dd, $J_1$=8.4 Hz, $J_2$=8.4 Hz, 4H), 6.65 (s, 1H), 6.48 (s, 1H), 4.00-4.10 (m, 1H), 3.74 (s, 3H), 3.59 (t, J=4.0 Hz, 4H), 3.51 (s, 2H), 2.92-2.98 (m, 1H), 2.38 (s, 4H), 1.76-1.77 (m, 2H), 1.63 (s, 3H), 1.47 (s, 4H), 0.82 (d, J=6.8 Hz, 6H). ESMS calculated for $C_{29}H_{37}N_5O_4$: 519.64. Found: 520.6 (M⁺).

Compound 74

¹H NMR (400 MHz, DMSO-d₆), δ (ppm): 10.83 (s, 1H), 8.80 (d, J=7.6 Hz, 1H), 7.31-7.40 (dd, $J_1$=8.4 Hz, $J_2$=8.4 Hz, 4H), 6.65 (s, 1H), 6.49 (s, 1H), 3.90-3.95 (m, 1H), 3.75 (s, 3H), 3.49 (s, 2H), 2.91-2.97 (m, 1H), 2.34-2.39 (m, 7H), 2.16 (s, 3H), 1.10 (d, J=6.4 Hz, 6H), 0.82 (d, J=6.8 Hz, 6H). ESMS calculated for $C_{28}H_{38}N_6O_3$: 506.64. Found: 507.5 (M⁺).

Compound 75

¹H NMR (400 MHz, DMSO-d₆), δ (ppm): 10.85 (s, 1H), 8.89-8.93 (m, 1H), 7.32-7.40 (dd, $J_1$=8.4 Hz, $J_2$=8.4 Hz, 4H), 6.64 (s, 1H), 6.49 (s, 1H), 3.75 (s, 3H), 3.50 (s, 2H), 2.91-2.98 (m, 1H), 2.71 (d, J=4.8 Hz, 3H), 2.34-2.40 (m, 8H), 2.17 (s, 3H), 0.81 (d, J=6.8 Hz, 6H). ESMS calculated for $C_{26}H_{34}N_6O_3$: 478.5. Found: 479.5 (M⁺).

Compound 76

¹H NMR (400 MHz, DMSO), δ (ppm): 10.38 (s, 1H), 8.28 (s, 1H), 7.75 (s, 1H), 7.25-7.35 (dd, $J_1$=8.0 Hz, $J_2$=8.8 Hz, 4H), 6.65 (s, 1H), 6.38 (s, 1H), 3.93-3.95 (m, 2H), 3.58 (t, J=4.0 Hz, 4H), 3.50 (s, 2H), 2.35 (s, 4H), 1.85 (s, 3H), 1.31 (t, J=6.8 Hz, 3H). ESMS calculated for $C_{23}H_{27}N_5O_4$: 437.49. Found: 438.5 (M⁺).

Compound 77

¹H NMR (400 MHz, DMSO), δ (ppm): 10.83 (s, 1H), 8.92 (d, J=4.8 Hz, 1H), 7.33-7.41 (dd, $J_1$=8.0 Hz, $J_2$=8.4 Hz, 4H), 6.64 (s, 1H), 6.49 (s, 1H), 3.74 (s, 3H), 3.60 (t, J=4.0 Hz, 4H), 3.51 (s, 2H), 2.91-2.98 (m, 1H), 2.70 (d, J=4.8 Hz, 3H), 2.39 (s, 4H), 0.81 (d, J=6.8 Hz, 6H). ESMS calculated for $C_{25}H_{31}N_5O_4$: 465.54. Found: 466.5 (M⁺).

Compound 78

¹H NMR (400 MHz, DMSO-d₆), δ (ppm): 10.83 (s, 1H), 8.86 (d, J=8.0 Hz, 1H), 7.31-7.40 (dd, $J_1$=8.4 Hz, $J_2$=8.4 Hz, 4H), 6.65 (s, 1H), 6.49 (s, 1H), 4.03-4.08 (m, 1H), 3.75 (s, 3H), 3.49 (s, 2H), 2.91-2.98 (m, 1H), 2.34-2.36 (m, 7H), 2.16 (s, 3H), 2.10 (s, 3H), 1.73-1.77 (m, 2H), 1.63 (s, 2H), 1.47 (s, 4H), 0.82 (d, J=6.8 Hz, 6H). ESMS calculated for $C_{30}H_{40}N_6O_3$: 532.68. Found: 531.6 (M⁻).

Compound 78

¹H NMR (400 MHz, DMSO-d₆), δ (ppm): 10.84 (s, 1H), 8.87 (d, J=6.8 Hz, 1H), 7.31-7.41 (dd, $J_1$=8.4 Hz, $J_2$=8.4 Hz, 4H), 6.65 (s, 1H), 6.49 (s, 1H), 4.02-4.02 (m, 1H), 3.75 (s, 4H), 3.49 (s, 3H), 2.95-2.98 (m, 1H), 2.34-2.39 (m, 6H), 2.17 (s, 3H), 2.70-2.73 (m, 2H), 1.61-1.63 (m, 2H), 1.45-1.47 (m, 4H), 0.82 (d, J=7.2 Hz, 6H). ESMS calculated for $C_{30}H_{40}N_6O_3$: 532.68. Found: 533.5 (M⁺).

Compound 79

¹H NMR (400 MHz, DMSO-d₆), δ (ppm): 10.80 (s, 1H), 8.80 (d, J=8.0 Hz, 1H), 7.32-7.42 (dd, $J_1$=8.4 Hz, $J_2$=8.0 Hz, 4H), 6.65 (s, 1H), 6.48 (s, 1H), 3.88-3.97 (m, 1H), 3.74 (s, 3H), 3.58 (t, J=4.0 Hz, 4H), 3.51 (s, 2H), 2.91-2.98 (m, 1H), 2.38 (s, 4H), 1.10 (d, J=6.4 Hz, 6H), 0.82 (d, J=7.2 Hz, 6H). ESMS calculated for $C_{27}H_{35}N_5O_4$: 493.6. Found: 494.5 (M⁺).

Compound 80

¹H NMR (400 MHz, DMSO-d₆), δ (ppm): 10.45 (s, 1H), 9.91 (s, 1H), 9.78 (s, 1H), 7.28-7.41 (dd, $J_1$=8.0 Hz, $J_2$=8.8 Hz, 4H), 6.63 (s, 1H), 6.34 (s, 1H), 3.58-3.60 (m, 4H), 3.50 (s, 2H), 2.90-2.94 (m, 1H), 2.86-2.88 (m, 4H), 2.51 (s, 4H), 1.50-1.52 (m, 4H), 1.30-1.33 (m. 2H), 0.84 (d, J=7.2 Hz, 6H). ESMS calculated for $C_{28}H_{36}N_6O_4$: 520.62. Found: 519.6 (M⁻).

Compound 81

¹H NMR (400 MHz, DMSO-d₆), δ (ppm): 10.44 (s, 1H), 10.10 (s, 1H), 9.76 (s, 1H), 7.28-7.41 (dd, $J_1$=8.4 Hz, $J_2$=8.4 Hz, 4H), 6.63 (s, 1H), 6.34 (s, 1H), 3.58-3.60 (m, 8H), 3.50 (s, 2H), 2.90-2.92 (m, 1H), 2.76 (t, J=4.8 Hz, 4H), 2.36-2.38 (m, 4H), 0.85 (d, J=6.8 Hz, 6H). ESMS calculated for $C_{27}H_{34}N_6O_5$: 522.6. Found: 521.5 (M⁻).

Compound 82

¹H NMR (400 MHz, DMSO) δ 9.81 (s, 1H), 8.19 (s, 1H), 7.69 (s, 1H), 7.26 (d, J=8.8 Hz, 2H), 7.22 (dd, J=8.4, 2.4 Hz, 1H), 7.00 (d, J=8.8 Hz, 2H), 6.91 (d, J=2.0 Hz, 1H), 6.76 (d, J=8.4 Hz, 1H), 3.79 (s, 3H), 3.12-3.01 (m, 1H), 0.91 (d, J=6.8 Hz, 6H). ESMS calculated for $C_{19}H_{20}N_4O_3$ m/z 352.15. found m/z 353.2 (M⁺+H).

Compound 83

¹H NMR (400 MHz, DMSO) δ 9.56 (s, 1H), 8.23 (s, 1H), 7.72 (s, 1H), 7.16 (d, J=8.8 Hz, 2H), 6.87 (d, J=8.8 Hz, 2H), 6.80 (s, 1H), 6.60 (s, 1H), 3.72 (s, 3H), 3.07-2.97 (m, 1H), 2.09 (s, 3H), 0.93 (d, J=6.8 Hz, 6H). ESMS calculated for $C_{20}H_{22}N_4O_3$ m/z 366.17. found m/z 367.2 (M⁺+H).

Compound 84

¹H NMR (400 MHz, DMSO) δ 9.67 (s, 1H), 8.26 (s, 1H), 7.72 (s, 1H), 7.14 (d, J=8.0 Hz, 2H), 6.85 (d, J=8.0 Hz, 2H), 6.47 (s, 1H), 6.44 (s, 1H), 3.72 (s, 3H), 2.14 (s, 3H), 1.92 (s, 3H). ESMS calculated for $C_{18}H_{18}N_4O_3$ m/z 338.14. found m/z 339.1 (M⁺+H).

Compound 85

¹H NMR (400 MHz, DMSO), δ (ppm): 10.86 (s, 1H), 8.78 (d, J=8.4 Hz, 1H), 7.31-7.40 (dd, $J_1$=8.4 Hz, $J_2$=8.8 Hz, 4H), 6.64 (s, 1H), 6.49 (s, 1H), 3.88-3.97 (m, 1H), 3.75 (s, 3H), 3.46 (s, 2H), 2.91-2.98 (m, 1H), 1.49-1.52 (m, 4H), 1.41-1.42 (m, 2H), 1.10 (d, J=6.4 Hz, 6H), 0.82 (d, J=6.8 Hz, 6H). ESMS calculated for $C_{28}H_{37}N_5O_3$: 491.63. Found: 492.3 (M⁺).

Compound 86

¹H NMR (400 MHz, DMSO), δ (ppm): 10.42 (s, 1H), 9.75 (s, 1H), 9.59 (d, J=5.6 Hz, 1H), 7.31-7.40 (dd, $J_1$=8.4 Hz, $J_2$=8.4 Hz, 4H), 6.64 (s, 1H), 6.34 (s, 1H), 3.92-4.00 (m, 2H), 3.59 (t, J=4.4 Hz, 4H), 3.50 (s, 2H), 2.89-2.95 (m, 1H), 2.51 (s, 4H), 0.84 (d, J=6.8 Hz, 6H). ESMS calculated for $C_{25}H_{28}F_3N_5O_4$: 519.52. Found: 520.1 (M⁺).

Compound 87

¹H NMR (400 MHz, DMSO), δ (ppm): 10.85 (s, 1H), 8.91 (d, J=4.8 Hz, 1H), 7.32-7.40 (dd, $J_1$=8.0 Hz, $J_2$=8.4 Hz, 4H), 6.64 (s, 1H), 6.49 (s, 1H), 3.75 (s, 3H), 3.50 (s, 2H), 2.69-2.70 (m, 1H), 2.51 (s, 3H), 2.29-2.34 (m, 9H), 0.99 (t, J=6.8 Hz, 3H), 0.81 (d, J=6.8 Hz, 6H). ESMS calculated for $C_{27}H_{36}N_6O_3$: 492.61. Found: 491.6 (M⁻).

Compound 88

¹H NMR (400 MHz, DMSO), δ (ppm): 10.45 (s, 1H), 9.75 (s, 1H), 9.58 (t, J=6.4 Hz, 1H), 7.29-7.37 (dd, $J_1$=8.4 Hz, $J_2$=8.4 Hz, 4H), 6.61 (s, 1H), 6.34 (s, 1H), 3.91-3.99 (m, 2H), 3.41-3.48 (m, 2H), 2.87-2.94 (m, 1H), 2.32-2.37 (m, 7H), 2.12 (s, 3H), 1.90 (s, 1H), 1.05 (t, J=6.8 Hz, 1H), 0.83 (d, J=6.8 Hz, 6H). ESMS calculated for $C_{26}H_{31}F_3N_6O_3$: 532.56. Found: 531.5 (M⁻).

Compound 89

¹H NMR (400 MHz, DMSO), δ (ppm): 10.75 (s, 1H), 8.80 (d, J=8.4 Hz, 1H), 7.32-7.42 (dd, $J_1$=8.4 Hz, $J_2$=8.4 Hz, 4H), 6.66 (s, 1H), 6.49 (s, 1H), 3.91-3.94 (m, 1H), 3.74 (s, 3H), 3.57 (s, 2H), 2.92-2.99 (m, 4H), 2.78-2.83 (m, 7H), 1.08-1.14 (m, 9H), 0.83 (d, J=6.4 Hz, 6H). ESMS calculated for $C_{29}H_{40}N_6O_3$: 520.67. Found: 521.6 (M⁺).

Compound 90

¹H NMR (400 MHz, DMSO), δ (ppm): 10.78 (s, 1H), 8.87 (d, J=7.6 Hz, 1H), 7.32-7.42 (dd, $J_1$=8.4 Hz, $J_2$=8.4 Hz, 4H), 6.66 (s, 1H), 6.49 (s, 1H), 4.04-4.06 (m, 1H), 3.75 (s, 3H), 3.60 (s, 2H), 2.92-2.98 (m, 1H), 2.51 (s, 6H), 1.74-1.76 (m, 2H), 1.63 (s, 2H), 1.48-1.50 (m, 4H), 1.11 (s, 3H), 0.83 (d, J=6.8 Hz, 6H). ESMS calculated for $C_{31}H_{42}N_6O_3$: 546.70. Found: 545.7 (M⁻).

Compound 91

¹H NMR (400 MHz, DMSO-d₆), δ (ppm): 9.71 (d, J=6.4 Hz, 2H), 8.24 (s, 1H), 7.81 (s, 1H), 7.23-7.32 (m, 5H), 6.91 (s, 1H), 6.50 (s, 1H), 4.24-4.26 (m, 1H), 3.42 (s, 2H), 3.11-3.14 (m, 1H), 2.79-2.82 (m, 2H), 2.32-2.35 (m, 1H), 1.84-1.90 (m, 2H), 1.65-1.68 (m, 1H), 1.40 (d, J=7.2 Hz, 6H). ESMS calculated for $C_{24}H_{29}N_5O_3$: 435.52. Found: 434.6 (M⁻).

Compound 92

¹H NMR (400 MHz, DMSO-d₆), δ (ppm): 10.44 (s, 1H), 9.75 (s, 1H), 9.43 (d, J=7.2 Hz, 1H), 7.30-7.40 (dd, $J_1$=8.4 Hz, $J_2$=8.4 Hz, 4H), 6.63 (s, 1H), 6.39 (s, 1H), 4.53-4.59 (m, 1H), 3.58-3.60 (t, J=4.4 Hz, 4H), 3.55 (s, 2H), 3.06-3.16 (m, 3H), 2.88-2.95 (m, 1H), 2.35-2.50 (m, 5H), 2.18-2.23 (m, 2H), 0.83 (d, J=7.2 Hz, 6H). ESMS calculated for $C_{27}H_{33}N_5O_6S$: 555.65. Found: 556.5 (M⁺).

Compound 93

¹H NMR (400 MHz, DMSO) δ 11.39 (s, 1H), 8.31 (s, 1H), 7.87 (d, J=7.6 Hz, 1H), 7.23 (s, 1H), 7.35 (d, J=8.8 Hz, 2H), 7.00 (d, J=8.8 Hz, 2H), 6.66 (d, J=7.6 Hz, 1H), 6.61 (d, J=7.6 Hz, 1H), 3.80 (s, 3H), 1.35 (s, 9H). ESMS calculated for $C_{20}H_{22}N_4O_3$ m/z 366.17. found m/z 367.2 (M⁺+H).

Compound 94

¹H NMR (400 MHz, DMSO) δ 9.58 (s, 1H), 8.24 (s, 1H), 7.72 (s, 1H), 7.15 (d, J=8.8 Hz, 2H), 6.91 (s, 1H), 6.87 (d, J=8.8 Hz, 2H), 6.57 (s, 1H), 3.72 (s, 3H), 1.97 (s, 3H), 1.95 (s, 3H). ESMS calculated for $C_{18}H_{18}N_4O_3$ m/z 338.14. found m/z 339.1 (M⁺+H).

Compound 95

¹H NMR (400 MHz, DMSO), δ (ppm): 10.69 (s, 1H), 9.63 (t, J=6.8 Hz, 1H), 7.37 (q, J=8.0 Hz, 4H), 6.68 (s, 1H), 6.48 (s, 1H), 3.95-3.99 (m, 2H), 3.75 (s, 3H), 3.49 (s, 2H), 2.94-2.97 (m, 1H), 2.33-2.38 (m, 7H), 2.16 (s, 3H), 0.83 (d, J=6.8 Hz, 6H). ESMS calculated for $C_{27}H_{33}F_3N_6O_3$: 546.58. Found: 547.3 (M⁺).

Compound 96

¹H NMR (400 MHz, DMSO), δ (ppm): 10.55 (s, 1H), 9.75 (s, 1H), 8.77 (d, J=8.0 Hz, 1H), 7.40 (d, J=8.4 Hz, 2H), 7.30 (d, J=8.4 Hz, 2H), 6.60 (s, 1H), 6.35 (s, 1H), 3.91-3.94 (m, 1H), 3.63 (s, 2H), 2.90-2.94 (m, 1H), 2.45-2.47 (m, 4H), 1.72 (s, 4H), 1.10 (d, J=6.4 Hz, 6H), 0.84 (d, J=6.8 Hz, 6H). ESMS calculated for $C_{26}H_{33}N_5O_3$: 463.57. Found: 462.6 (M⁻).

Compound 97

¹H NMR (400 MHz, DMSO) δ 9.75 (s, 1H), 8.19 (s, 1H), 7.68 (s, 1H), 7.24 (d, J=8.8 Hz, 2H), 7.10 (dd, J=8.8, 2.0 Hz, 1H), 6.87 (d, J=8.8 Hz, 2H), 6.96 (s, 1H), 6.60 (d, J=8.8 Hz, 1H), 3.79 (s, 3H), 2.35 (t, J=7.6 Hz, 2H), 1.42-1.29 (m, 2H), 0.73 (t, J=7.6 Hz, 3H). ESMS calculated for $C_{19}H_{20}N_4O_3$ m/z 352.15. found m/z 353.2 (M⁺+H).

Compound 98

¹H NMR (400 MHz, DMSO) δ 9.79 (s, 1H), 8.19 (s, 1H), 7.69 (s, 1H), 7.26 (d, J=8.4 Hz, 3H), 7.00 (d, J=8.4 Hz, 2H), 6.86 (s, 1H), 6.76 (d, J=8.4 Hz, 1H), 3.79 (s, 3H), 3.19-3.03 (m, 1H), 1.86-1.67 (m, 2H), 1.64-1.42 (m, 4H), 1.21-1.02 (m, 2H). ESMS calculated for $C_{21}H_{22}N_4O_3$ m/z 378.17. found m/z 379.2 (M⁺+H).

Compound 99

¹H NMR (400 MHz, DMSO-d₆), δ (ppm): 10.80 (s, 1H), 8.78 (d, J=8.0 Hz, 1H), 7.41 (d, J=8.4 Hz, 2H), 7.32 (d, J=8.4 Hz, 2H), 6.65 (s, 1H), 6.48 (s, 1H), 3.90-3.95 (m, 1H), 3.74 (s, 3H), 3.63 (s, 2H), 2.91-2.98 (m, 1H), 2.46-2.50 (m, 4H), 1.71 (s, 4H), 1.10 (t, J=6.8 Hz, 6H), 0.83 (d, J=7.2 Hz, 6H). ESMS calculated for $C_{27}H_{35}N_5O_3$: 477.6. Found: 476.5 (M⁻).

Compound 100

¹H NMR (400 MHz, DMSO-d₆), δ (ppm): 10.81 (s, 1H), 8.78 (d, J=7.6 Hz, 1H), 7.40 (d, J=8.4 Hz, 2H), 7.33 (d, J=8.4 Hz, 2H), 6.65 (s, 1H), 6.48 (s, 1H), 3.90-3.97 (m, 1H), 3.75 (s, 3H), 3.48 (s, 2H), 2.92-2.98 (m, 1H), 2.58-2.64 (m, 1H), 2.34-2.44 (m, 8H), 1.10 (d, J=6.8 Hz, 6H), 0.97 (d, J=6.4 Hz, 6H), 0.82 (d, J=6.8 Hz, 6H). ESMS calculated for $C_{30}H_{42}N_6O_3$: 534.69. Found: 535.5 (M⁺).

Compound 100

¹H NMR (400 MHz, DMSO), δ (ppm): 10.80 (s, 1H), 8.77 (d, J=8.0 Hz, 1H), 7.39 (d, J=8.4 Hz, 2H), 7.30 (d, J=8.4 Hz, 2H), 6.64 (s, 1H), 6.48 (s, 1H), 3.91-3.93 (m, 1H), 3.74 (s, 3H), 3.49 (s, 2H), 2.92-2.96 (m, 1H), 2.35-2.43 (m, 6H), 1.08 (d, J=6.8 Hz, 6H), 0.97 (s, 6H), 0.82 (d, J=6.8 Hz, 6H). ESMS calculated for $C_{30}H_{42}N_6O_3$: 534.69. Found: 535.5 ($M^+$).

Compound 101

$^1$H NMR (400 MHz, DMSO), δ (ppm): 10.86 (s, 1H), 8.78 (d, J=8.0 Hz, 1H), 7.40 (d, J=8.4 Hz, 2H), 7.33 (d, J=8.4 Hz, 2H), 6.64 (s, 1H), 6.49 (s, 1H), 3.88-3.97 (m, 1H), 3.75 (s, 3H), 3.47 (s, 2H), 2.91-2.98 (m, 1H), 2.77-2.80 (m, 2H), 1.93 (t, J=10.4 Hz, 2H), 1.55-1.58 (m, 2H), 1.32-1.34 (m, 1H), 1.08-1.19 (m, 8H), 0.89 (d, J=6.8 Hz, 3H), 0.80 (d, J=7.2 Hz, 6H). ESMS calculated for $C_{29}H_{39}N_5O_3$: 505.65. Found: 506.4 ($M^+$).

Compound 102

$^1$H NMR (400 MHz, DMSO), δ (ppm): 9.68 (d, J=12.0 Hz, 2H), 8.22 (s, 1H), 7.79 (s, 1H), 6.89 (s, 1H), 6.49 (s, 1H), 4.29-4.32 (m, 1H), 3.10-3.17 (m, 1H), 3.90-3.94 (m, 2H), 2.29-2.35 (m, 2H), 2.11-2.15 (m, 2H), 1.61-1.64 (m, 2H), 1.13 (d, J=6.8 Hz, 6H). ESMS calculated for $C_{17}H_{23}N_5O_3$: 345.4. Found: 368.3 ($M^+$).

Compound 103

$^1$H-NMR (CDCl$_3$): δ 0.82 (d, J=6.9 Hz, 6H), 2.93 (hept., J=6.9 Hz, 1H), 3.89 (s, 3H), 6.56 (d, J=8.4 Hz, 1H), 6.72 (d, J=11.5 Hz, 1H), 7.07 (d, J=8.9 Hz, 2H), 7.27 (d, J=8.9 Hz, 2H). ESMS ($C_{19}H_{19}FN_4O_3$): calc. 370.14. found: 371.2 [M+H$^+$].

Compound 104

$^1$H NMR (400 MHz, DMSO) δ 9.80 (s, 1H), 8.20 (s, 1H), 7.69 (s, 1H), 7.25 (d, J=7.6 Hz, 2H), 7.06 (d, J=8.4 Hz, 1H), 7.03 (s, 1H), 6.98 (d, J=7.6 Hz, 2H), 6.71 (d, J=8.0 Hz, 1H), 3.79 (s, 3H), 2.40 (q, J=7.2 Hz, 2H), 0.94 (t, J=7.2 Hz, 3H). ESMS calculated for $C_{18}H_{18}N_4O_3$ m/z 338.14. found m/z 339.2 ($M^+$+H).

Compound 105

$^1$H NMR (400 MHz, DMSO) δ 9.76 (s, 1H), 8.19 (s, 1H), 7.69 (s, 1H), 7.25 (d, J=8.8 Hz, 3H), 6.98 (d, J=8.8 Hz, 2H), 6.82 (d, J=2.0 Hz, 1H), 6.78 (d, J=8.4 Hz, 1H), 3.78 (s, 3H), 2.91-2.82 (m, 1H), 1.33-1.20 (m, 2H), 0.88 (d, J=7.2 Hz, 3H), 0.59 (t, J=7.2 Hz, 3H). ESMS calculated for $C_{20}H_{22}N_4O_3$ m/z 366.17. found m/z 367.2 ($M^+$+H).

Compound 106

$^1$H NMR (400 MHz, DMSO), δ (ppm): 10.72 (s, 1H), 9.61 (t, J=6.4 Hz, 1H), 7.39 (q, J=8.4 Hz, 4H), 6.68 (s, 1H), 6.49 (s, 1H), 3.93-4.02 (m, 2H), 3.75 (s, 3H), 3.46 (s, 2H), 2.92-2.99 (m, 1H), 2.77-2.80 (m, 2H), 1.93 (t, J=11.2 Hz, 2H), 1.55-1.58 (m, 2H), 1.32-1.33 (m, 1H), 1.10-1.18 (m, 2H), 0.91 (d, J=6.8 Hz, 3H), 0.83 (d, J=6.8 Hz, 6H). ESMS calculated for $C_{28}H_{34}F_3N_5O_3$: 545.6. Found: 546.6 ($M^+$).

Compound 107

$^1$H NMR (400 MHz, DMSO), δ (ppm): 10.77 (s, 1H), 8.74 (s, 1H), 7.41 (d, J=8.0 Hz, 2H), 7.32 (d, J=8.4 Hz, 2H), 6.65 (s, 1H), 6.48 (s, 1H), 3.74 (s, 3H), 3.58-3.60 (m, 4H), 3.51 (s, 2H), 3.20-3.22 (m, 2H), 2.93-2.96 (m, 2H), 2.39-2.48 (m, 4H), 0.96 (t, J=7.2 Hz, 6H), 0.82 (d, J=6.8 Hz, 6H). ESMS calculated for $C_{30}H_{42}N_6O_4$: 550.69. Found: 551.6 ($M^+$).

Compound 108

$^1$H NMR (400 MHz, DMSO), δ (ppm): 10.88 (s, 1H), 8.97 (t, J=6.0 Hz, 1H), 7.31-7.40 (dd, $J_1$=8.4 Hz, $J_2$=8.4 Hz, 4H), 6.64 (s, 1H), 6.50 (s, 1H), 3.75 (s, 3H), 3.48 (s, 2H), 3.15-3.20 (m, 2H), 2.91-2.98 (m, 1H), 2.78-2.81 (m, 2H), 1.94 (m, 2H), 1.34-1.36 (m, 2H), 1.19-1.20 (m, 1H), 1.13-1.14 (m, 2H), 1.05 (t, J=6.8 Hz, 3H), 0.91 (d, J=6.4 Hz, 3H), 0.81 (d, J=6.8 Hz, 6H). ESMS calculated for $C_{28}H_{37}N_5O_3$: 491.6. Found: 492.6 ($M^+$).

Compound 109

$^1$H NMR (400 MHz, DMSO-d$_6$), δ (ppm): 10.96 (s, 1H), 8.80 (d, J=7.6 Hz, 1H), 7.12 (d, J=8.8 Hz, 2H), 6.68 (s, 1H), 6.56 (d, J=8.4 Hz, 2H), 6.48 (s, 1H), 3.75 (s, 3H), 3.22-3.25 (m, 4H), 2.94-2.98 (m, 2H), 2.69-2.72 (m, 2H), 2.15 (s, 3H), 1.91-1.98 (m, 5H), 1.55-1.65 (m, 4H), 0.84 (d, J=6.8 Hz, 6H). ESMS calculated for $C_{29}H_{38}N_6O_3$: 518.65. Found: 519.6 ($M^+$).

Compound 110

$^1$H NMR (400 MHz, DMSO-d$_6$), δ (ppm): 10.49 (s, 1H), 8.78 (d, J=8.4 Hz, 1H), 7.64 (s, 1H), 7.58 (d, J=8.4 Hz, 2H), 7.28 (d, J=8.4 Hz, 2H), 6.75 (s, 1H), 6.42 (s, 1H), 3.91-3.95 (m, 2H), 3.72 (s, 4H), 3.10-3.13 (m, 5H), 2.93-3.00 (m, 2H), 2.21 (s, 3H), 1.11 (d, J=6.4 Hz, 6H), 0.88 (d, J=7.2 Hz, 6H). ESMS calculated for $C_{28}H_{37}N_7O_3$: 519.64. Found: 518.6 ($M^-$).

Compound 111

$^1$H NMR (400 MHz, DMSO), δ (ppm): 10.65 (s, 1H), 9.62 (t, J=6.4 Hz, 1H), 7.33-7.39 (dd, $J_1$=8.8 Hz, $J_2$=8.8 Hz, 4H), 6.68 (s, 1H), 6.46 (s, 1H), 3.94-3.99 (m, 2H), 3.73 (s, 3H), 3.58 (t, J=4.4 Hz, 4H), 3.49 (s, 2H), 2.92-2.96 (m, 1H), 2.35-2.37 (m, 4H), 0.82 (d, J=6.8 Hz, 6H). ESMS calculated for $C_{26}H_{30}F_3N_5O_4$: 533.54. Found: 534.5 ($M^+$).

Compound 112

$^1$H NMR (400 MHz, DMSO), δ (ppm): 10.67 (s, 1H), 9.62 (t, J=8.4 Hz, 1H), 7.31-7.37 (dd, $J_1$=8.4 Hz, $J_2$=8.4 Hz, 4H), 6.68 (s, 1H), 6.47 (s, 1H), 3.94-3.98 (m, 2H), 3.73 (s, 3H), 3.47 (s, 2H), 2.92-2.95 (m, 1H), 2.58-2.60 (m, 1H), 2.38-2.43 (m, 8H), 0.96 (d, J=6.8 Hz, 6H), 0.83 (d, J=6.8 Hz, 6H). ESMS calculated for $C_{29}H_{37}F_3N_6O_3$: 574.64. Found: 575.5 ($M^+$).

Compound 113

$^1$H NMR (400 MHz, DMSO), δ (ppm): 10.57 (s, 1H), 9.79 (s, 1H), 8.77 (d, J=8.4 Hz, 1H), 7.39 (d, J=8.0 Hz, 2H), 7.28 (d, J=8.0 Hz, 2H), 6.59 (s, 1H), 6.35 (s, 1H), 3.91-3.92 (m, 1H), 2.89-2.93 (m, 1H), 2.59-2.61 (m, 1H), 2.40-2.44 (m, 7H), 1.08 (t, J=6.0 Hz, 6H), 0.97 (d, J=6.4 Hz, 6H), 0.83 (d, J=6.8 Hz, 6H). ESMS calculated for $C_{29}H_{40}N_6O_3$: 520.67. Found: 521.6 ($M^+$).

Compound 114

$^1$H NMR (400 MHz, DMSO), δ (ppm): 10.62 (s, 1H), 9.79 (s, 1H), 8.74 (d, J=8.4 Hz, 1H), 7.39 (d, J=8.0 Hz, 2H), 7.28 (d, J=8.4 Hz, 2H), 6.59 (s, 1H), 6.35 (s, 1H), 4.01-4.04 (m, 1H), 2.89-2.93 (m, 1H), 2.78-2.81 (m, 2H), 1.91-1.95 (m, 3H), 1.55-1.59 (m, 2H), 1.07-1.10 (m, 7H), 0.91 (d, J=6.4 Hz, 3H), 0.83 (d, J=6.8 Hz, 6H). ESMS calculated for $C_{28}H_{37}N_5O_3$: 491.63. Found: 492.5 ($M^+$).

Compound 115

$^1$H NMR (400 MHz, DMSO), δ (ppm): 10.69 (s, 1H), 9.61 (t, J=6.4 Hz, 1H), 7.39 (q, J=8.4 Hz, 4H), 6.68 (s, 1H), 6.48 (s, 1H), 3.95-3.99 (m, 2H), 3.75 (s, 3H), 3.49 (s, 2H), 2.92-2.96 (m, 1H), 2.28-2.38 (m, 10H), 0.99 (t, J=7.2 Hz, 3H), 0.87 (d, J=6.4 Hz, 6H). ESMS calculated for $C_{28}H_{35}F_3N_6O_3$: 560.61. Found: 561.5 ($M^+$).

Compound 116

$^1$H NMR (400 MHz, DMSO-d$_6$), δ (ppm): 11.00 (s, 1H), 8.74 (d, J=8.0 Hz, 1H), 7.20 (d, J=8.4 Hz, 2H), 7.01 (d, J=8.4 Hz, 2H), 6.64 (s, 1H), 6.50 (s, 1H), 3.90-3.98 (m, 1H), 3.76 (s, 3H), 3.19-3.22 (m, 4H), 2.94-3.00 (m, 1H), 2.45 (t, J=8.4 Hz, 4H), 2.23 (s, 3H), 1.11 (d, J=6.8 Hz, 6H), 0.83 (d, J=6.8 Hz, 6H). ESMS calculated for $C_{27}H_{36}N_6O_3$: 492.61. Found: 493.6 ($M^+$).

Compound 117

$^1$H NMR (400 MHz, DMSO), δ (ppm): 10.71 (s, 1H), 9.60 (t, J=8.8 Hz, 1H), 7.31-7.38 (dd, $J_1$=8.4 Hz, $J_2$=8.4 Hz, 4H), 6.68 (s, 1H), 6.48 (s, 1H), 3.93-4.01 (m, 2H), 3.74 (s, 3H), 2.91-2.98 (m, 1H), 2.33 (s, 4H), 1.48-1.51 (m, 4H), 1.39-

1.40 (m, 2H), 0.83 (d, J=7.2 Hz, 6H). ESMS calculated for $C_{27}H_{33}F_3N_5O_3$: 531.57. Found: 532.5 (M$^+$).

Compound 118

$^1$H NMR (400 MHz, DMSO), δ (ppm): 10.79 (s, 1H), 9.05 (d, J=4.4 Hz, 1H), 7.32-7.42 (dd, J$_1$=8.8 Hz, J$_2$=8.8 Hz, 4H), 6.65 (s, 1H), 6.48 (s, 1H), 3.74 (s, 3H), 3.58-3.60 (m, 4H), 3.52 (s, 2H), 2.93-2.97 (m, 1H), 2.73-2.75 (m, 1H), 2.38-2.39 (m, 4H), 0.82 (d, J=6.8 Hz, 6H), 0.64 (d, J=7.2 Hz, 2H), 0.56-0.58 (m, 2H). ESMS calculated for $C_{27}H_{33}N_5O_4$: 491.58. Found: 492.6 (M$^+$).

Compound 119

$^1$H NMR (400 MHz, DMSO), δ (ppm): 10.43 (s, 1H), 9.66 (t, J=6.4 Hz, 1H), 7.40-7.48 (m, 2H), 7.19-7.21 (d, J=7.2 Hz, 2H), 6.79 (s, 1H), 6.46 (s, 1H), 3.94-4.03 (m, 2H), 3.74 (s, 3H), 3.56 (s, 2H), 2.96-3.03 (m, 1H), 2.67-2.69 (m, 4H), 2.40 (s, 3H), 0.90 (d, J=7.2 Hz, 6H). ESMS calculated for $C_{27}H_{32}F_4N_6O_3$: 564.57. Found: 565.5 (M$^+$).

Compound 120

$^1$H NMR (400 MHz, DMSO-d$_6$), δ (ppm): 11.02 (s, 1H), 8.85 (d, J=7.6 Hz, 1H), 7.19 (d, J=8.8 Hz, 2H), 7.01 (d, J=8.8 Hz, 2H), 6.64 (s, 1H), 6.50 (s, 1H), 4.04-4.11 (m, 1H), 3.75 (s, 3H), 3.21 (t, J=4.8 Hz, 4H), 2.93-3.00 (m, 1H), 2.51 (s, 4H), 2.45 (t, J=4.8 Hz, 3H), 2.23 (s, 2H), 1.78-1.79 (m, 2H), 1.48-1.51 (m, 4H), 0.82 (d, J=6.8 Hz, 6H). ESMS calculated for $C_{29}H_{38}N_6O_3$: 518.65. Found: 519.6 (M$^+$).

Compound 121

$^1$H NMR (400 MHz, DMSO-d$_6$), δ (ppm): 10.83 (s, 1H), 8.88 (d, J=8.4 Hz, 1H), 7.31-7.40 (dd, J$_1$=8.4 Hz, J$_2$=8.4 Hz, 4H), 6.65 (s, 1H), 6.48 (s, 1H), 4.04-4.06 (m, 1H), 3.75 (s, 3H), 3.49 (s, 2H), 2.94-2.97 (m, 1H), 2.60-2.63 (m, 1H), 2.40-2.51 (m, 8H), 1.76-1.77 (m, 2H), 1.62-1.63 (m, 2H), 1.47 (s, 4H), 0.97 (d, J=6.4 Hz, 6H), 0.82 (d, J=7.2 Hz, 6H). ESMS calculated for $C_{32}H_{44}N_6O_3$: 560.73. Found: 559.6 (M$^-$).

Compound 121

$^1$H NMR (400 MHz, DMSO), δ (ppm): 10.81 (s, 1H), 8.85 (d, J=7.6 Hz, 1H), 7.39 (d, J=8.4 Hz, 2H), 7.30 (d, J=8.4 Hz, 2H), 6.64 (s, 1H), 6.48 (s, 1H), 3.98-4.05 (m, 1H), 3.74 (s, 3H), 3.48 (s, 2H), 2.92-2.96 (m, 1H), 2.51-2.53 (m, 1H), 2.39-2.44 (m, 7H), 1.74-1.76 (m, 2H), 1.60-1.62 (m, 2H), 1.46-1.48 (m, 4H), 0.97 (d, J=6.8 Hz, 6H), 0.81 (d, J=7.2 Hz, 6H). ESMS calculated for $C_{32}H_{44}N_6O_3$: 534.69. Found: 535.5 (M$^+$).

Compound 122

$^1$H-NMR (CD$_3$OD): δ 0.74 (d, J=6.9 Hz, 6H), 2.97 (hept., J=6.9 Hz, 1H), 3.82 (s, 3H), 6.48 (d, J=2.4 Hz, 1H), 6.57 (s, 1H), 6.75 (t, J=73.9 Hz, 1H), 6.83 (d, J=1.8 Hz, 1H), 7.06 (d, J=8.6 Hz, 1H), 7.27 (d, J=2.4 Hz, 1H), 7.47 (d, J=8.6 Hz, 1H), 7.51 9 s, 1H). ESMS ($C_{21}H_{20}F_2N_4O_3$): calc. 414.15. found: 415.1 [M+H$^+$].

Compound 124

$^1$H NMR (400 MHz, DMSO) δ 9.77 (s, 1H), 8.17 (s, 1H), 7.68 (s, 1H), 7.28-7.23 (m, 3H), 7.01 (d, J=8.8 Hz, 2H), 6.79-6.75 (m, 2H), 3.79 (s, 3H), 2.75-2.65 (m, 1H), 1.69-0.85 (m, 10H). ESMS calculated for $C_{22}H_{24}N_4O_3$ m/z 392.18. found m/z 393.2 (M$^+$+H).

Compound 130

$^1$H NMR (400 MHz, DMSO), δ (ppm): 10.88 (s, 1H), 8.87 (d, J=6.8 Hz, 1H), 7.31-7.40 (dd, J$_1$=8.0 Hz, J$_2$=8.0 Hz, 4H), 6.65 (s, 1H), 6.50 (s, 1H), 4.04-4.06 (m, 3H), 3.75 (s, 1H), 3.48 (s, 2H), 2.95 (t, J=6.8 Hz, 1H), 2.77-2.80 (m, 2H), 1.91-1.96 (m, 2H), 1.75-1.77 (m, 2H), 1.56-1.63 (m, 4H), 1.46-1.47 (m, 4H), 1.33-1.35 (m, 1H), 1.11-1.19 (m, 2H), 0.91 (d, J=6.0 Hz, 3H), 0.82 (d, J=6.4 Hz, 6H). ESMS calculated for $C_{31}H_{41}N_5O_3$: 531.6. Found: 532.6 (M$^+$).

Compound 131

$^1$H NMR (400 MHz, DMSO-d$_6$), δ (ppm): 10.30 (s, 1H), 9.76 (s, 1H), 8.75 (t, J=4.8 Hz, 1H), 7.46 (t, J=8.4 Hz, 1H), 7.34 (d, J=8.0 Hz, 1H), 7.65 (t, J=8.4 Hz, 1H), 6.69 (s, 1H), 6.33 (s, 1H), 3.57-3.59 (m, 6H), 3.20-3.25 (m, 2H), 2.93-2.96 (m, 1H), 2.40-2.46 (m, 4H), 0.95 (t, J=7.2 Hz, 6H), 0.87 (d, J=7.2 Hz, 6H). ESMS calculated for $C_{29}H_{39}FN_6O_4$: 554.65. Found: 555.7 (M$^+$).

Compound 132

$^1$H NMR (400 MHz, DMSO-d$_6$), δ (ppm): 10.84 (s, 1H), 8.87 (t, J=6.8 Hz, 1H), 7.32-7.40 (dd, J$_1$=8.4 Hz, J$_2$=8.4 Hz, 4H), 6.54 (s, 1H), 6.49 (s, 1H), 3.75 (s, 3H), 3.50 (s, 2H), 3.16-3.19 (m, 2H), 2.93-2.95 (m, 1H), 2.34-2.40 (m, 6H), 2.18 (s, 3H), 1.05 (t, J=7.6 Hz, 3H), 0.81 (d, J=7.2 Hz, 6H). ESMS calculated for $C_{22}H_{36}N_6O_3$: 492.61. Found: 493.5 (M$^+$).

Compound 133

$^1$H NMR (400 MHz, DMSO), δ (ppm): 10.87 (s, 1H), 8.97 (t, J=6.0 Hz, 1H), 7.31-7.39 (dd, J$_1$=8.4 Hz, J$_2$=8.4 Hz, 4H), 6.65 (s, 1H), 6.49 (s, 1H), 3.74 (s, 3H), 3.44-3.46 (m, 2H), 3.14-3.21 (m, 2H), 2.90-2.97 (m, 1H), 2.34 (s, 4H), 1.49-1.52 (m, 4H), 1.40-1.41 (m, 2H), 1.05 (t, J=6.8 Hz, 3H), 0.82 (d, J=6.8 Hz, 6H). ESMS calculated for $C_{27}H_{35}N_5O_3$: 477.6. Found: 476.5 (M$^-$).

Compound 134

$^1$H NMR (400 MHz, DMSO-d$_6$), δ (ppm): 10.86 (s, 1H), 8.85 (d, J=6.8 Hz, 1H), 7.30-7.40 (dd, J$_1$=8.4 Hz, J$_2$=8.4 Hz, 4H), 6.64 (s, 1H), 6.49 (s, 1H), 4.00-4.09 (m, 1H), 3.74 (s, 3H), 3.43-3.46 (m, 2H), 2.89-2.96 (m, 1H), 2.34 (s, 4H), 1.76-1.79 (m, 2H), 1.71-1.73 (m, 2H), 1.40-1.51 (m, 10H), 0.82 (d, J=6.8 Hz, 6H). ESMS calculated for $C_{30}H_{39}N_5O_3$: 517.66. Found: 518.6 (M$^+$).

Compound 135

$^1$H NMR (400 MHz, DMSO-d$_6$), δ (ppm): 10.49 (s, 1H), 8.81 (d, J=8.0 Hz, 1H), 7.72 (s, 1H), 7.62 (d, J=8.4 Hz, 2H), 7.31 (d, J=8.4 Hz, 2H), 6.77 (s, 1H), 6.43 (s, 1H), 3.89-3.97 (m, 1H), 3.77 (t, J=8.4 Hz, 4H), 3.73 (s, 3H), 3.121-3.13 (m, 4H), 2.95-3.01 (m, 1H), 1.11 (d, J=6.4 Hz, 6H), 0.87 (d, J=6.8 Hz, 6H). ESMS calculated for $C_{27}H_{34}N_6O_4$: 506.6. Found: 505.5 (M$^-$).

Compound 136

$^1$H NMR (400 MHz, DMSO), δ (ppm): 10.56 (s, 2H), 9.77 (s, 2H), 8.92 (t, J=5.6 Hz, 2H), 7.29-7.40 (dd, J$_1$=8.4 Hz, J$_2$=8.4 Hz, 8H), 6.60 (s, 2H), 6.35 (s, 2H), 3.58-3.60 (m, 8H), 3.50 (s, 4H), 3.10-3.15 (m, 4H), 2.89-2.93 (m, 2H), 2.38 (s, 8H), 104-1.43 (m, 4H), 1.17-1.24 (m, 29H), 0.82 (d, J=6.8 Hz, 12H). ESMS calculated for $C_{58}H_{76}N_{10}O_8$: 1041.29. Found: 1042.0 (M$^+$).

Compound 137

$^1$H NMR (400 MHz, DMSO-d$_6$), δ (ppm): 10.55 (s, 1H), 8.89 (d, J=8.4 Hz, 1H), 7.45 (t, J=8.0 Hz, 1H), 7.33-7.36 (m, 1H), 7.15-7.17 (m, 1H), 6.73 (s, 1H), 6.46 (s, 1H), 4.06-4.08 (m, 1H), 3.74 (s, 3H), 3.50 (s, 2H), 2.96-2.99 (m, 1H), 2.26-2.39 (m, 7H), 2.14 (s, 3H), 1.75-1.79 (m, 2H), 1.62-1.66 (m, 2H), 1.45-1.52 (m, 4H), 0.82 (d, J=8.0 Hz, 6H). ESMS calculated for $C_{30}H_{39}FN_6O_3$: 550.67. Found: 551.5 (M$^+$).

Compound 138

$^1$H NMR (400 MHz, DMSO), δ (ppm): 10.84 (s, 1H), 9.03 (d, J=4.8 Hz, 1H), 7.40 (d, J=8.4 Hz, 2H), 7.30 (d, J=8.4 Hz, 2H), 6.63 (s, 1H), 6.48 (s, 1H), 3.74 (s, 3H), 3.46 (s, 2H), 2.90-2.97 (m, 1H), 2.69-2.76 (m, 1H), 2.34 (s, 4H), 1.49-1.51 (m, 4H), 1.39-1.40 (m, 2H), 0.81 (d, J=7.2 Hz, 6H), 0.53-0.65 (m, 4H). ESMS calculated for $C_{28}H_{35}N_5O_3$: 489.61. Found: 488.6 (M$^-$).

Compound 139

$^1$H NMR (400 MHz, DMSO-d$_6$), δ (ppm): 10.86 (s, 1H), 9.59 (t, J=6.0 Hz, 1H), 7.21 (d, J=8.8 Hz, 2H), 7.00 (d, J=8.8 Hz, 2H), 6.68 (s, 1H), 6.50 (s, 1H), 3.94-4.02 (m, 2H), 3.76 (s, 3H), 3.01 (s, 4H), 2.96-3.00 (m, 1H), 2.45-2.46 (m, 4H), 2.23 (s, 3H), 0.86 (d, J=7.2 Hz, 6H). ESMS calculated for C$_{26}$H$_{31}$F$_3$N$_6$O$_3$: 532.56. Found: 531.5 (M$^-$).

Compound 140

$^1$H NMR (400 MHz, DMSO-d$_6$), δ (ppm): 11.00 (s, 1H), 8.93 (t, J=5.6 Hz, 1H), 7.17 (d, J=8.8 Hz, 2H), 6.99 (d, J=8.8 Hz, 2H), 6.62 (s, 1H), 6.49 (s, 1H), 3.74 (s, 3H), 3.14-3.19 (m, 6H), 2.94-2.99 (m, 1H), 2.43-2.45 (m, 4H), 2.22 (s, 3H), 1.05 (t, J=6.8 Hz, 3H), 0.83 (d, J=6.8 Hz, 6H). ESMS calculated for C$_{26}$H$_{34}$N$_6$O$_3$: 478.59. Found: 479.5 (M$^+$).

Compound 141

$^1$H NMR (400 MHz, DMSO), δ (ppm): 10.89 (s, 1H), 8.85 (d, J=8.0 Hz, 1H), 7.40 (d, J=8.0 Hz, 2H), 7.32 (d, J=8.0 Hz, 2H), 6.62 (s, 1H), 6.49 (s, 1H), 4.03-4.05 (m, 1H), 3.74 (s, 3H), 3.57 (s, 2H), 2.92-2.95 (m, 1H), 1.73-1.75 (m, 2H), 1.60-1.62 (m, 2H), 1.46 (s, 4H), 1.00 (t, J=6.8 Hz, 6H), 0.81 (d, J=7.2 Hz, 6H). ESMS calculated for C$_{29}$H$_{39}$N$_5$O$_3$: 505.65. Found: 506.5 (M$^+$).

Compound 142

$^1$H NMR (400 MHz, DMSO), δ (ppm): 10.85 (s, 1H), 9.04 (t, J=5.0 Hz, 1H), 7.40 (d, J=8.0 Hz, 2H), 7.33 (d, J=8.0 Hz, 2H), 6.64 (s, 1H), 6.49 (s, 1H), 3.75 (s, 3H), 3.48 (s, 2H), 2.93-2.96 (m, 1H), 2.80-2.82 (m, 2H), 2.71-2.77 (m, 1H), 1.91-1.97 (m, 2H), 1.55-1.59 (m, 2H), 1.18-1.20 (m, 1H), 1.13-1.16 (m, 2H), 0.91 (d, J=6.8 Hz, 3H), 0.82 (d, J=6.8 Hz, 6H), 0.63-0.66 (m, 2H), 0.50-0.55 (m, 2H). ESMS calculated for C$_{29}$H$_{37}$N$_5$O$_3$: 503.64. Found: 504.3 (M$^+$).

Compound 143

$^1$H NMR (400 MHz, DMSO) δ 9.52 (s, 1H), 9.34 (s, 1H), 7.42-7.37 (m, 2H), 7.69 (d, J=2.8 Hz, 1H), 6.92 (dd, J=8.8, 2.0 Hz, 1H), 6.82 (s, 1H), 6.40 (d, J=2.8 Hz, 1H), 6.20 (s, 1H), 3.77 (s, 3H), 3.44 (s, 3H), 2.98-2.87 (m, 1H), 0.91 (d, J=7.2 Hz, 6H). ESMS calculated for C$_{21}$H$_{22}$N$_4$O$_3$ m/z 378.17. found m/z 379.1 (M$^+$+H).

Compound 144

$^1$H NMR (400 MHz, DMSO) δ 11.79 (s, 1H), 9.65 (s, 1H), 7.38-7.32 (m, 2H), 7.30 (d, J=1.6 Hz, 1H), 7.07 (s, 1H), 6.83 (dd, J=8.8, 2.0 Hz, 1H), 6.38 (d, J=3.2 Hz, 1H), 6.24 (s, 1H), 3.75 (s, 3H), 3.28 (s, 3H), 3.10-3.00 (m, 1H), 1.06 (d, J=7.2 Hz, 6H). ESMS calculated for C$_{21}$H$_{22}$N$_4$O$_3$ m/z 378.17. found m/z 379.1 (M$^+$+H).

Compound 145

$^1$H NMR (400 MHz, DMSO) δ 9.70 (s, 1H), 7.45-7.39 (m, 2H), 7.38 (d, J=3.2 Hz, 1H), 6.95 (dd, J=8.8, 2.0 Hz, 1H), 6.82 (s, 1H), 6.41 (d, J=2.4 Hz, 1H), 6.31 (s, 1H), 3.78 (s, 3H), 3.67 (s, 3H), 3.00-2.89 (m, 1H), 0.85 (d, J=6.8 Hz, 6H). ESMS calculated for C$_{21}$H$_{22}$N$_4$O$_3$ m/z 378.17. found m/z 379.1 (M$^+$+H).

Compound 146

$^1$H NMR (400 MHz, DMSO) δ 11.95 (s, 1H), 9.36 (s, 2H), 7.49 (d, J=8.4 Hz, 1H), 7.46-7.41 (m, 2H), 6.94 (dd, J=8.4, 1.6 Hz, 1H), 6.47 (d, J=2.8 Hz, 1H), 6.17 (s, 3H), 3.83 (s, 3H). ESMS calculated for C$_{17}$H$_{14}$N$_4$O$_3$ m/z 322.11. found m/z 323.1 (M$^+$+H).

Example 2

Synthesis of Compound 129

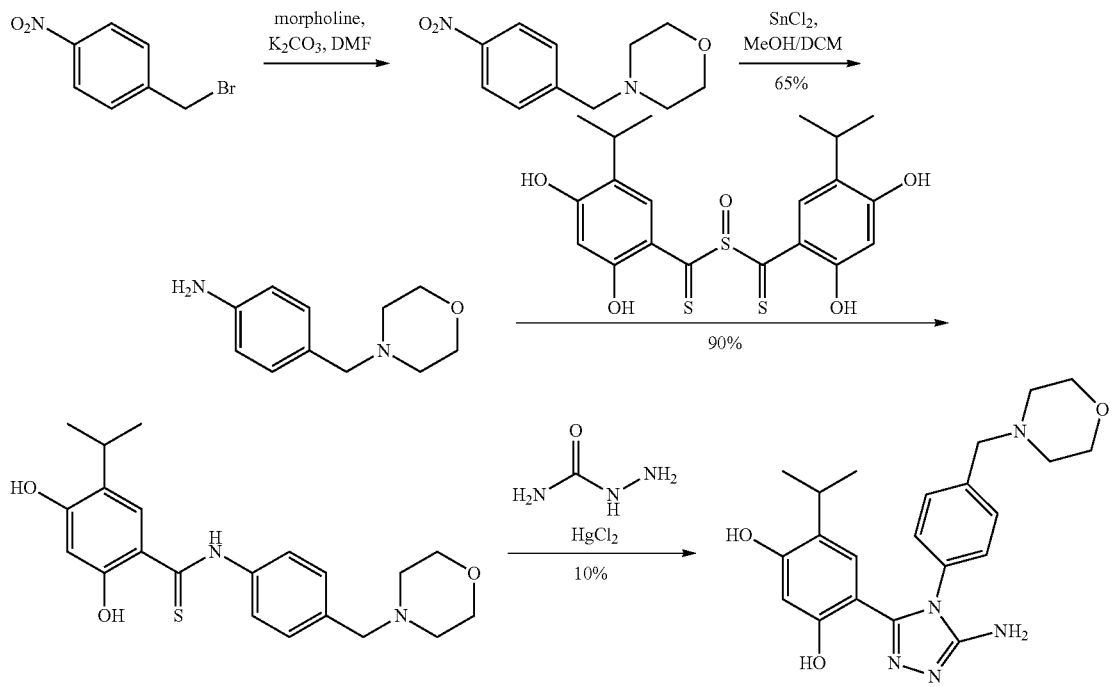

4-(morpholinomethyl)aniline (577 mg, 3.0 mmol) was added to sulfinylbis((2,4-dihydroxy-5-isopropylphenyl)methanethione) (746 mg, 1.7 mmol) in 10 ml DMF at rt. It was stirred for 2 h and then added into 20 ml water. The pH was adjusted to 7-8 and then extracted with ethyl acetate. The combined extracts were dried over Na$_2$SO$_4$, filtered and the solvent removed. The crude product was purified by chromatography on silica with DCM/MeOH (5-10%) to yield 1.23 g (2.8 mmol). The thioamide (289 mg, 0.66 mmol) was then added to hydrazinecarboxamide (147 mg, 1.32 mmol) and mercury chloride (210 mg, 0.79 mmol) in 8 ml DMF. Pyridine (244 ul, 3.0 mmol) was added and the mixture heated in a microwave reactor at 120° C. for 2 h. The crude mixture was filtered, concentrated and purified by chromatography on silica with DCM/MeOH (0-10%) to yield 28 mg (0.07 mmol) 4-(5-amino-4-(4-(morpholinomethyl)phenyl)-4H-1,2,4-triazol-3-yl)-6-isopropylbenzene-1,3-diol.

NMR (400 MHz, CD$_3$OD) δ 7.47 (d, J=8.2, 2H), 7.27 (d, J=8.3, 2H), 6.63 (s, 1H), 6.33 (d, J=2.3, 1H), 3.71 (m, 4H), 3.56 (s, 2H), 3.00 (dt, J=6.8, 13.6, 1H), 2.49 (m, 4H), 0.85 (dd, J=2.1, 6.9, 6H). ESMS (C$_{22}$H$_{27}$N$_5$O$_3$): calculated 409.21. found: 411.2 [M+2H$^+$].

Example 3

Synthesis of Compounds 127 and 128

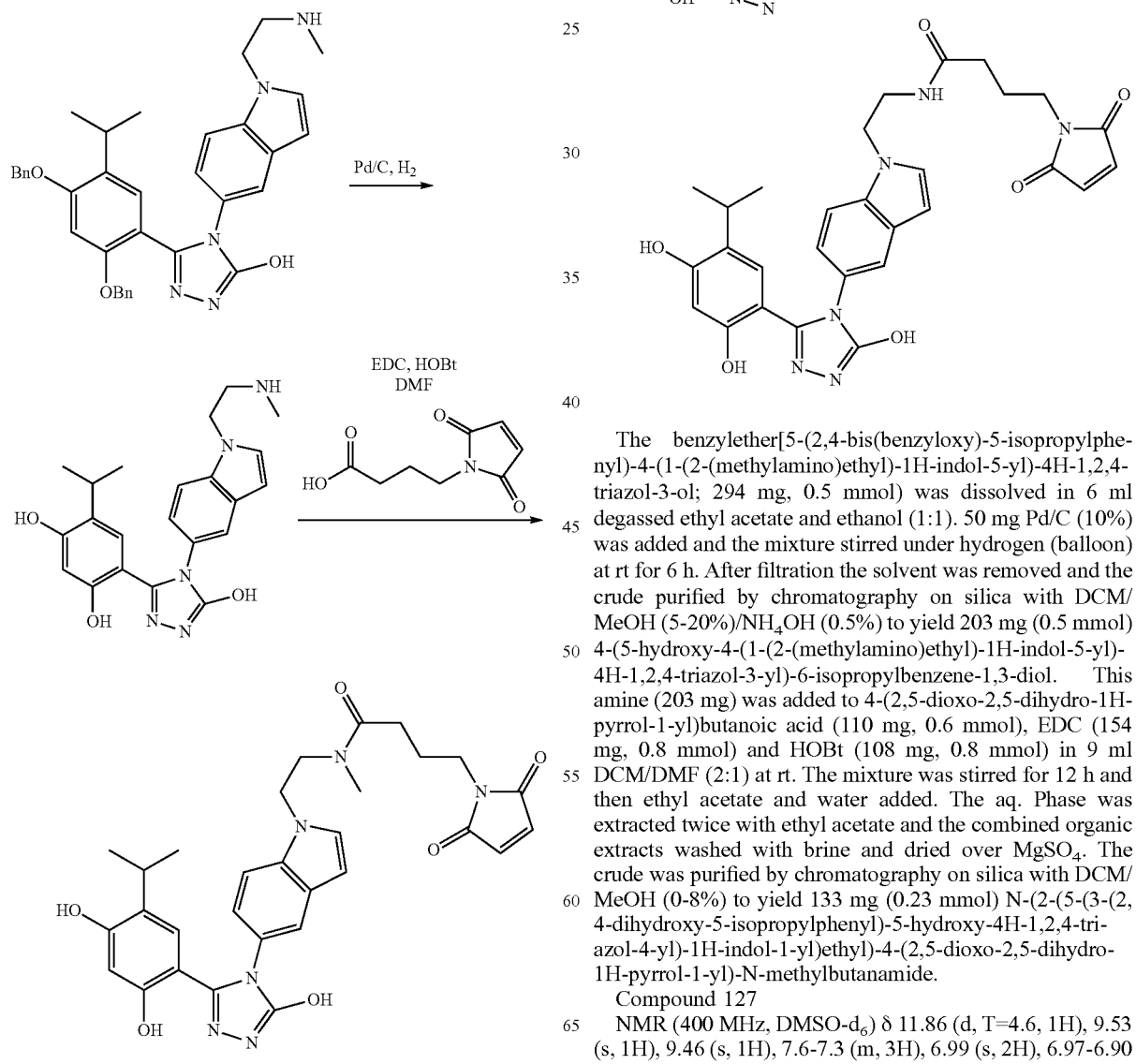

The benzylether[5-(2,4-bis(benzyloxy)-5-isopropylphenyl)-4-(1-(2-(methylamino)ethyl)-1H-indol-5-yl)-4H-1,2,4-triazol-3-ol; 294 mg, 0.5 mmol) was dissolved in 6 ml degassed ethyl acetate and ethanol (1:1). 50 mg Pd/C (10%) was added and the mixture stirred under hydrogen (balloon) at rt for 6 h. After filtration the solvent was removed and the crude purified by chromatography on silica with DCM/MeOH (5-20%)/NH$_4$OH (0.5%) to yield 203 mg (0.5 mmol) 4-(5-hydroxy-4-(1-(2-(methylamino)ethyl)-1H-indol-5-yl)-4H-1,2,4-triazol-3-yl)-6-isopropylbenzene-1,3-diol. This amine (203 mg) was added to 4-(2,5-dioxo-2,5-dihydro-1H-pyrrol-1-yl)butanoic acid (110 mg, 0.6 mmol), EDC (154 mg, 0.8 mmol) and HOBt (108 mg, 0.8 mmol) in 9 ml DCM/DMF (2:1) at rt. The mixture was stirred for 12 h and then ethyl acetate and water added. The aq. Phase was extracted twice with ethyl acetate and the combined organic extracts washed with brine and dried over MgSO$_4$. The crude was purified by chromatography on silica with DCM/MeOH (0-8%) to yield 133 mg (0.23 mmol) N-(2-(5-(3-(2,4-dihydroxy-5-isopropylphenyl)-5-hydroxy-4H-1,2,4-triazol-4-yl)-1H-indol-1-yl)ethyl)-4-(2,5-dioxo-2,5-dihydro-1H-pyrrol-1-yl)-N-methylbutanamide.

Compound 127

NMR (400 MHz, DMSO-d$_6$) δ 11.86 (d, T=4.6, 1H), 9.53 (s, 1H), 9.46 (s, 1H), 7.6-7.3 (m, 3H), 6.99 (s, 2H), 6.97-6.90 (m, 1H), 6.74 (d, T=5.7, 1H), 6.48-6.41 (m, 1H), 6.22 (s,

1H), 4.25 (t, J=6.3, 2H), 3.55 (dd, J=6.8, 13.9, 2H), 3.44 (t, J=6.8, 2H), 3.33 (s, 3H), 2.89 (dt, J=6.9, 13.6, 1H), 2.20 (t, T=7.0, 2H), 1.78-1.66 (m, 2H), 0.87-0.76 (m, 6H). ESMS ($C_{30}H_{32}N_6O_6$): calculated 572.24. found: 573.2 [M+H$^+$].

Compound 128

NMR (400 MHz, CDCl$_3$) δ 7.50 (d, J=1.8, 1H), 7.4 (m, 1H), 7.15 (d, J=3.2, 1H), 7.06 (dd, J=1.9, 8.6, 1H), 6.66 (s, 2H), 6.42-6.37 (m, 2H), 6.36 (s, 1H), 4.27 (t, J=6.0, 2H), 3.51 (m, 4H), 2.80 (dt, J=8.1, 16.2, 1H), 2.13 (t, J=7.3, 2H), 1.90 (dt, J=7.1, 13.9, 2H), 0.46 (d, J=6.9, 6H). ESMS ($C_{29}H_{30}N_6O_6$): calculated 558.22. found: 559.2 [M+H$^+$].

Compound 180

$^1$H NMR (400 MHz, DMSO), δ (ppm): 9.890 (s, 1H), 9.762 (s, 1H), 9.037 (t, J=4.4 Hz, 1H), 6.813 (s, 1H), 6.743 (d, J=10.6 Hz, 2H), 6.316 (s, 1H), 3.682 (t, J=4.0 Hz, 4H), 3.191-3.206 (m, 6H), 2.989-3.097 (m, 1H), 2.479-2.496 (m, 4H), 1.060 (t, J=7.2 Hz, 3H), 0.970 (d, J=6.8 Hz, 6H).

ESMS clcd for C24H27F2N5O4: 487.5. Found: 488.6 (M$^+$).

Compound 181

$^1$H NMR (400 MHz, DMSO), δ (ppm): 9.903 (s, 1H), 9.769 (s, 1H), 8.885 (d, J=8.4 Hz, 1H), 6.830 (s, 1H), 6.764 (d, J=12.4 Hz, 2H), 6.328 (s, 1H), 3.970-3.987 (m, 1H), 3.698 (s, 4H), 3.186 (s, 4H), 2.998-3.023 (m, 1H), 1.104-1.145 (m, 6H), 1.006 (d, J=6.8 Hz, 6H). ESMS clcd for C25H29F2N5O4: 501.53. Found: 502.5 (M$^+$).

Compound 182

$^1$H NMR (400 MHz, DMSO), δ (ppm): 9.951 (s, 1H), 9.774 (s, 1H), 8.874 (d, J=9.6 Hz, 1H), 6.814 (s, 1H), 6.727 (d, J=11.2 Hz, 2H), 6.328 (s, 1H), 3.975-3.963 (m, 1H), 3.237 (m, 4H), 3.020-2.985 (m, 1H), 2.437 (m, 4H), 2.361-2.346 (m, 2H), 1.138-0.975 (m, 15H). ESMS clcd for $C_{27}H_{34}F_2N_6O_3$: 528.59. Found: 528.9 (M$^+$).

Compound 183

$^1$H NMR (400 MHz, DMSO), δ (ppm): 9.808 (s, 1H), 9.743 (s, 1H), 9.683 (t, J=6.4 Hz, 1H), 6.815 (s, 1H), 6.686 (d, J=12.0 Hz, 2H), 6.289 (s, 1H), 3.968-3.928 (m, 2H), 3.202 (m, 4H), 2.995-2.960 (m, 1H), 2.395 (m, 4H), 2.337-2.286 (m, 2H), 1.001-0.0957 (m, 9H). ESMS clcd for $C_{26}H_{29}F_5N_6O_3$: 568.54. Found: 569.2 (M$^+$).

Compound 184

$^1$H NMR (400 MHz, DMSO), δ (ppm): 9.963 (s, 1H), 9.800 (s, 1H), 9.059 (m, 1H), 6.811 (s, 1H), 6.721 (d, J=11.2 Hz, 2H), 6.325 (s, 1H), 3.233-3.197 (m, 4H), 3.002 (m, 1H), 2.356 (m, 4H), 2.335 (m, 2H), 1.080-0.0970 (m, 12H).

ESMS clcd for $C_{26}H_{32}F_2N_6O_3$: 514.57. Found: 515.1 (M$^+$).

Compound 185

$^1$H NMR (400 MHz, DMSO), δ (ppm): 9.963 (s, 1H), 9.711 (s, 1H), 8.910-8.898 (m, 1H), 6.770 (s, 1H), 6.686 (d, J=12.8 Hz, 2H), 6.303 (s, 1H), 3.211 (m, 4H), 2.988-2.949 (m, 1H), 2.678 (d, J=4.4 Hz, 3H), 2.408 (m, 4H), 2.354-2.301 (m, 2H), 0.989 (t, J=7.6 Hz, 3H), 0.936 (d, J=7.2 Hz, 6H).

ESMS clcd for $C_{25}H_{30}F_2N_6O_3$: 500.54. Found: 501.1 (M$^+$).

Compound 186

$^1$H NMR (400 MHz, DMSO), δ (ppm): 9.966 (s, 1H), 9.779 (s, 1H), 8.982 (m, 1H), 6.812 (s, 1H), 6.728 (d, J=12.0 Hz, 2H), 6.330 (s, 1H), 3.243 (m, 4H), 3.002 (m, 1H), 2.711 (m, 3H), 2.387 (m, 4H), 2.203 (s, 3H), 0.982 (d, J=4.8 Hz, 6H).

ESMS clcd for $C_{24}H_{28}F_2N_6O_3$: 486.51. Found: 487.2 (M$^+$).

Compound 187

$^1$H NMR (400 MHz, DMSO), δ (ppm): 9.964 (s, 1H), 9.779 (s, 1H), 8.877 (d, J=7.2 Hz, 1H), 6.813 (s, 1H), 6.732 (d, J=12.4 Hz, 2H), 6.328 (s, 1H), 3.983-3.966 (m, 1H), 3.243 (m, 4H), 3.022-2.991 (m, 1H), 2.390 (m, 4H), 2.208 (s, 3H), 1.134 (d, J=6.8 Hz, 6H), 0.984 (d, J=7.2 Hz, 6H). ESMS clcd for $C_{26}H_{32}F_2N_6O_3$: 514.57. Found: 515.2 (M$^+$).

Compound 188

$^1$H NMR (400 MHz, DMSO), δ (ppm): 9.962 (s, 1H), 9.775 (s, 1H), 9.060 (m, 1H), 6.807 (s, 1H), 6.731 (d, J=12.8 Hz, 2H), 6.332 (s, 1H), 3.249 (m, 4H), 3.211-3.195 (m, 2H), 3.021-2.990 (m, 1H), 2.411 (m, 4H), 2.216 (s, 3H), 1.070 (t, J=7.2 Hz, 3H), 0.979 (d, J=8.0 Hz, 6H).

ESMS clcd for $C_{25}H_{30}F_2N_6O_3$: 500.54. Found: 501.2 (M$^+$).

Compound 189

$^1$H NMR (400 MHz, DMSO), δ (ppm): 9.859 (s, 1H), 9.766 (s, 1H), 9.695 (t, J=6.4 Hz, 1H), 6.846 (s, 1H), 6.724 (d, J=11.6 Hz, 2H), 6.333 (s, 1H), 4.005-3.966 (m, 2H), 3.242 (m, 4H), 3.033-2.999 (m, 1H), 2.386 (m, 4H), 2.205 (s, 3H), 1.000 (d, J=6.8 Hz, 6H).

ESMS clcd for $C_{25}H_{27}F_5N_6O_3$: 554.51. Found: 555.0 (M$^+$).

Compound 190

$^1$H NMR (400 MHz, DMSO), δ (ppm): 10.51 (s, 1H), 9.815 (s, 1H), 8.845 (d, J=8.4 Hz, 1H), 7.567 (s, 1H), 7.369-7.504 (dd, J$_1$=8.0 Hz, 1H, J$_2$=4.4 Hz, 1H), 6.593 (s, 1H), 6.356 (s, 1H), 3.918-3.971 (m, 1H), 3.602 (t, J$_1$=4.4 Hz, 4H), 3.528 (s, 2H), 2.911-2.944 (m, 1H), 2.394 (s, 4H), 1.112-1.137 (m, 6H), 0.804-0.862 (dd, J$_1$=6.8 Hz, J$_2$=9.69 Hz, 6H).

ESMS clcd for C26H32ClN5O4: 514.02. Found: 514.2 (M$^+$).

Compound 191

$^1$H NMR (400 MHz, DMSO), δ (ppm): 10.471 (s, 1H), 9.875 (s, 1H), 9.054 (t, J=5.6 Hz, 1H), 7.581 (s, 1H), 7.521 (d, J=12.0 Hz, 1H), 7.389 (d, J=8.8 Hz, 1H), 6.594 (s, 1H), 6.389 (s, 1H), 3.600 (s, 2H), 3.145-3.213 (m, 3H), 3.058-3.076 (m, 2H), 2.918-2.935 (m, 1H), 2.510 (s, 6H), 1.062 (t, J=6.8 Hz, 3H), 0.813-0.869 0.804-0.862 (dd, J$_1$=7.2 Hz, J$_2$=9.69 Hz, 6H).

ESMS clcd for C26H33ClN6O3: 513.03. Found: 513.5 (M$^+$).

Compound 192

$^1$H NMR (400 MHz, DMSO), δ (ppm): 10.333 (s, 1H), 9.870 (s, 1H), 9.690 (t, J=6.8 Hz, 1H), 7.556 (s, 1H), 7.501 (d, J=8.8 Hz, 1H), 7.369 (d, J=6.0 Hz, 1H), 6.629 (s, 1H), 6.373 (s, 1H), 3.936-3.995 (m, 3H), 3.553 (s, 2H), 2.919-2.953 (m, 1H), 2.500-2.518 (m, 3H), 2.366 (s, 6H), 0.827-0.884 (m, 6H).

ESMS clcd for C26H30ClF3N6O3: 567. Found: 567.2 (M$^+$).

Compound 193

$^1$H NMR (400 MHz, DMSO), δ (ppm): 10.477 (s, 1H), 10.013 (s, 1H), 9.118 (d, J=4.4 Hz, 1H), 7.578 (s, 1H), 7.506 (d, J=8.0 Hz, 1H), 7.394 (d, J=8.0 Hz, 1H), 6.593 (s, 1H), 6.460 (s, 1H), 3.585 (s, 2H), 2.895-2.963 (m, 2H), 2.734-2.745 (m, 3H), 2.608-2.673 (m, 2H), 2.512 (s, 3H), 1.155 (s, 1H), 0.814-0.870 (m, 6H), 0.621-0.640 (m, 4H).

ESMS clcd for C28H35ClN6O3: 539.07. Found: 539.3 (M$^+$).

Compound 194

$^1$H NMR (400 MHz, DMSO), δ (ppm): 10.469 (s, 1H), 9.853 (s, 1H), 9.117 (d, J=4.8 Hz, 1H), 7.573 (s, 1H), 7.492 (d, J=8.4 Hz, 1H), 7.382 (d, J=4.0 Hz, 1H), 6.589 (s, 1H), 6.360 (s, 1H), 3.569 (s, 2H), 2.913-2.930 (m, 1H), 2.728-2.748 (m, 3H), 2.481-2.506 (m, 2H), 0.806-0.861 (m, 6H), 0.608-0.639 (m, 4H).

ESMS clcd for C27H33ClN6O3: 525.04. Found: 523.3 (M$^-$).

Compound 195

¹H NMR (400 MHz, DMSO), δ (ppm): 10.521 (s, 1H), 9.807 (s, 1H), 9.017 (t, J=5.6 Hz, 1H), 7.565 (s, 1H), 7.513 (d, J=8.4 Hz, 1H), 7.391 (d, J=6.4 Hz, 1H), 6.590 (s, 1H), 6.359 (s, 1H), 3.577-3.615 (m, 4H), 3.530 (s, 2H), 3.147-3.198 (m, 2H), 2.910-2.944 (m, 1H), 2.408 (s, 4H), 1.062 (t, J=6.8 Hz, 3H), 0.801-0.857 (m, 6H).

ESMS clcd for C25H30ClN5O4: 499.99. Found: 500.3 (M⁺).

Compound 196

¹H NMR (400 MHz, DMSO), δ (ppm): 10.357 (s, 1H), 9.805 (s, 1H), 9.667 (t, J=6.8 Hz, 1H), 7.564 (s, 1H), 7.505 (d, J=8.0 Hz, 1H), 7.371 (d, J=6.4 Hz, 1H), 6.635 (s, 1H), 6.356 (s, 1H), 3.930-4.000 (m, 2H), 3.587 (t, J=4.8 Hz, 4H), 3.525 (s, 2H), 2.901-2.970 (m, 1H), 2.387 (s, 4H), 0.822-0.880 (dd, $J_1$=6.8 Hz, $J_2$=9.6 Hz, 6H).

ESMS clcd for C25H27ClF3N5O4: 553.96. Found: 554.5 (M⁺).

Compound 197

¹H NMR (400 MHz, DMSO), δ (ppm): 10.485 (s, 1H), 9.826 (s, 1H), 9.119 (d, J=4.8 Hz, 1H), 7.567 (s, 1H), 7.485 (d, J=7.6 Hz, 1H), 7.375 (d, J=6.8 Hz, 1H), 6.595 (s, 1H), 6.347 (s, 1H), 3.592 (d, J=4.4 Hz, 4H), 3.529 (s, 2H), 2.907-2.941 (m, 1H), 2.506-2.519 (m, 1H), 2.396 (s, 4H), 0.805-0.861 (dd, $J_1$=7.2 Hz, $J_2$=8.8 Hz, 6H), 0.612-0.642 (m, 4H).

ESMS clcd for C26H30ClN5O4: 512. Found: 512.5 (M⁺).

Compound 198

¹H NMR (400 MHz, DMSO), δ (ppm): 10.528 (s, 1H), 9.820 (s, 1H), 8.845 (d, J=8.4 Hz, 1H), 7.536 (s, 1H), 7.486 (d, J=8.4 Hz, 1H), 7.364 (d, J=8.4 Hz, 1H), 6.573 (s, 1H), 6.348 (s, 1H), 3.923-3.943 (m, 1H), 3.501 (s, 2H), 2.898-2.932 (m, 1H), 2.301-2.391 (m, 7H), 2.166 (s, 3H), 1.053-1.125 (m, 6H), 0.790-0.847 (dd, $J_1$=6.8 Hz, $J_1$=9.2 Hz, 6H).

ESMS clcd for C27H35ClN6O3: 527.06. Found: 525.7 (M⁻).

Compound 199

¹H NMR (400 MHz, DMSO), δ (ppm): 8.975 (t, 1H), 7.516 (s, 1H), 7.464 (d, J=8.8 Hz, 1H), 7.343 (d, 1H), 6.467 (s, 1H), 6.244 (s, 1H), 3.480 (s, 2H), 3.151-3.117 (m, 2H), 2.375-2.250 (m, 10H), 1.016 (t, J=7.2 Hz, 3H), 0.950 (t, J=7.2 Hz, 3H), 0.787-0.731 (dd, $J_1$=6.4 Hz, $J_2$=16.0 Hz, 6H).

ESMS clcd for $C_{27}H_{35}ClN_6O_3$: 527.06. Found: 527.3 (M⁺).

Compound 200

¹H NMR (400 MHz, DMSO), δ (ppm): 10.450 (s, 1H), 9.816 (s, 1H), 8.824 (d, J=9.2 Hz, 1H), 7.529 (s, 1H), 7.458 (d, J=8.4 Hz, 1H), 7.334 (d, J=8.0 Hz, 1H), 6.554 (s, 1H), 6.332 (s, 1H), 3.524 (s, 2H), 2.912-2.876 (m, 1H), 1.100-1.043 (m, 9H), 0.831-0.776 (dd, $J_1$=7.2 Hz, $J_2$=15.2 Hz, 6H).

ESMS clcd for $C_{28}H_{37}ClN_6O_3$: 541.08. Found: 539.2 (M⁻).

Compound 201

¹H NMR (400 MHz, DMSO), δ (ppm): 10.705 (s, 1H), 8.836 (d, J=8.4 Hz, 1H), 7.559 (s, 1H), 7.518 (d, J=8.0 Hz, 1H), 7.353 (d, J=7.6 Hz, 1H), 6.625 (s, 1H), 6.487 (s, 1H), 3.916-3.935 (m, 1H), 3.725 (s, 3H), 3.553 (s, 2H), 2.931-2.966 (m, 1H), 2.728-2.748 (m, 4H), 1.220 (s, 3H), 1.093-1.114 (m, 6H), 0.784-0.840 (dd, $J_1$=6.8 Hz, $J_1$=6.8 Hz, 6H).

ESMS clcd for C28H37ClN6O3: 541.08. Found: 539.6 (M⁻).

Compound 202

¹H NMR (400 MHz, DMSO), δ (ppm): 10.729 (s, 1H), 9.133 (d, J=6.4 Hz, 1H), 7.573 (s, 1H), 7.534 (d, J=8.4 Hz, 1H), 7.384 (d, J=7.6 Hz, 1H), 6.639 (s, 1H), 6.489 (s, 1H), 3.743 (s, 3H), 3.550 (s, 2H), 2.979-2.947 (m, 1H), 2.747-2.669 (m, 4H), 2.378 (m, 4H), 0.849-0.795 (dd, $J_1$=6.0 Hz, $J_2$=15.2 Hz, 4H), 0.643-0.612 (m, 4H).

ESMS clcd for $C_{28}H_{35}ClN_6O_3$: 539.07. Found: 539.3 (M⁺).

Compound 203

¹H NMR (400 MHz, DMSO), δ (ppm): 10.781 (s, 1H), 9.068 (t, 1H), 7.546-7.512 (m, 2H), 7.370 (d, J=8.8 Hz, 1H), 6.632 (s, 1H), 6.495 (s, 1H), 3.745 (s, 3H), 3.507 (s, 2H), 3.196-3.162 (m, 2H), 2.975-2.940 (m, 1H), 2.395-2.294 (m, 8H), 2.160 (s, 3H), 1.058 (t, J=7.2 Hz, 3H), 0.844-0.788 (dd, $J_1$=6.8 Hz, $J_2$=15.6 Hz, 6H).

ESMS clcd for $C_{27}H_{35}ClN_6O_3$: 527.06. Found: 527.2 (M⁺).

Compound 204

¹H NMR (400 MHz, DMSO), δ (ppm): 9.751 (s, 1H), 7.518 (d, J=8.8 Hz, 2H), 7.306 (m, 1H), 6.674 (s, 1H), 6.423 (s, 1H), 3.990-3.943 (m, 2H), 3.694 (s, 3H), 3.478 (s, 2H), 2.974-2.940 (m, 1H), 2.365-2.332 (m, 8H), 2.153 (s, 3H), 1.058 (t, J=7.2 Hz, 3H), 0.883-0.822 (dd, $J_1$=7.2 Hz, $J_2$=17.6 Hz, 6H).

ESMS clcd for $C_{27}H_{32}ClF_3N_6O_3$: 581.03. Found: 581.2 (M⁺).

Compound 205

¹H NMR (400 MHz, DMSO), δ (ppm): 10.681 (s, 1H), 8.894 (d, J=8.0 Hz, 1H), 7.601 (s, 1H), 7.533 (d, J=8.0 Hz, 1H), 7.396 (d, J=8.0 Hz, 1H), 6.663 (s, 1H), 6.515 (s, 1H), 3.975-3.922 (m, 1H), 3.745 (s, 3H), 3.624 (s, 2H), 3.448-3.421 (m, 2H), 3.089 (t, J=6.0 Hz, 2H), 2.996-2.945 (m, 3H), 2.898-2.868 (m, 2H), 2.562 (m, 2H), 1.256 (t, J=7.2 Hz, 3H), 1.140-1.116 (dd, $J_1$=3.2 Hz, $J_2$=6.4 Hz, 6H), 0.874-0.819 (dd, $J_1$=6.8 Hz, $J_2$=15.2 Hz, 6H).

ESMS clcd for $C_{29}H_{39}ClN_6O_3$: 555.11. Found: 555.2 (M⁺).

Compound 206

¹H NMR (400 MHz, DMSO), δ (ppm): 10.734 (s, 1H), 9.148 (d, J=4.8 Hz, 1H), 7.580 (s, 1H), 7.530 (d, J=7.6 Hz, 1H), 7.394 (d, J=8.4 Hz, 1H), 6.646 (s, 1H), 6.484 (s, 1H), 3.742 (s, 3H), 3.609-3.587 (m, 4H), 3.528 (s, 2H), 2.975-2.940 (m, 1H), 2.748-2.735 (m, 1H), 2.392 (m, 4H), 0.850-0.792 (dd, $J_1$=7.2 Hz, $J_2$=16.4 Hz, 6H), 0.642-0.610 (m, 4H).

ESMS clcd for $C_{27}H_{32}ClN_5O_4$: 526.03. Found: 526.3 (M⁺).

Compound 207

¹H NMR (400 MHz, DMSO), δ (ppm): 10.753 (s, 1H), 9.082 (t, J=6.4 Hz, 1H), 7.574 (d, J=1.2 Hz 1H), 7.532 (d, J=8.0 Hz, 1H), 7.390 (d, J=8.0 Hz, 1H), 6.641 (s, 1H), 6.492 (s, 1H), 3.746 (s, 3H), 3.607-3.586 (m, 4H), 3.525 (s, 2H), 3.198-3.163 (m, 2H), 2.978-2.944 (m, 1H), 2.390 (m, 4H), 1.061 (t, J=7.2 Hz, 3H), 0.850-0.794 (dd, $J_1$=7.2 Hz, $J_2$=15.6 Hz, 6H).

ESMS clcd for $C_{26}H_{32}ClN_5O_4$: 514.02. Found: 514.3 (M⁺).

Compound 208

¹H NMR (400 MHz, DMSO), δ (ppm): 10.730 (s, 1H), 8.886 (d, J=6.4 Hz, 1H), 7.562 (d, J=1.6 Hz 1H), 7.510 (d, J=8.0 Hz, 1H), 7.387-7.362 (dd, $J_1$=1.6 Hz, $J_2$=8.0 Hz, 1H), 6.631 (s, 1H), 6.474 (s, 1H), 3.959-3.907 (m, 1H), 3.732 (s, 3H), 3.595-3.574 (m, 4H), 3.512 (s, 2H), 2.966-2.930 (m, 1H), 2.374 (m, 4H), 1.123-1.098 (dd, $J_1$=3.2 Hz, $J_2$=6.4 Hz, 6H), 0.851-0.773 (m, 6H).

ESMS clcd for $C_{27}H_{34}ClN_5O_4$: 528.04. Found: 528.3 (M⁺).

Compound 209

¹H NMR (400 MHz, DMSO), δ (ppm): 10.588 (s, 1H), 9.680 (m, 1H), 7.564-7.528 (m, 2H), 7.380 (d, J=8.0 Hz, 1H), 6.673 (s, 1H), 6.478 (s, 1H), 3.994-3.936 (m, 2H), 3.735 (s, 3H), 3.597-3.575 (m, 4H), 3.517 (s, 2H), 2.977-2.945 (m, 1H), 2.376 (m, 4H), 0.864-0.805 (dd, J$_1$=6.8 Hz, J$_2$=16.4 Hz, 6H).

ESMS clcd for C$_{26}$H$_{29}$ClF$_3$N$_5$O$_4$: 567.99. Found: 568.2 (M$^+$).

Compound 210

$^1$H NMR (400 MHz, DMSO), δ (ppm): 10.751 (s, 1H), 9.136 (d, J=4.8 Hz, 1H), 7.549-7.504 (m, 2H), 7.370 (d, J=8.0 Hz, 1H), 6.631 (s, 1H), 6.482 (s, 1H), 3.736 (s, 3H), 3.507 (s, 2H), 2.969-2.935 (m, 1H), 2.743-2.733 (m, 1H), 2.398-2.276 (m, 9H), 0.976 (t, J=7.2 Hz, 3H), 0.843-0.789 (dd, J$_1$=6.8 Hz, J$_2$=14.8 Hz, 6H), 0.638-0.606 (m, 4H).

ESMS clcd for C$_{29}$H$_{37}$ClN$_6$O$_3$: 553.1. Found: 552.9 (M$^+$).

Compound 211

$^1$H NMR (400 MHz, DMSO), δ (ppm): 10.780 (s, 1H), 9.018 (t, 1H), 7.552-7.519 (m, 2H), 7.376 (d, J=7.6 Hz, 1H), 6.631 (s, 1H), 6.504 (s, 1H), 3.753 (s, 3H), 3.524 (s, 2H), 3.204-3.172 (m, 2H), 2.963 (m, 1H), 2.411-2.336 (m, 9H), 1.069 (t, J=7.2 Hz, 3H), 0.998 (t, J=6.4 Hz, 3H), 0.849-0.796 (dd, J$_1$=6.8 Hz, J$_2$=14.4 Hz, 6H).

ESMS clcd for C$_{28}$H$_{37}$ClN$_6$O$_3$: 541.08. Found: 541.2 (M$^+$).

Compound 212

$^1$H NMR (400 MHz, DMSO), δ (ppm): 10.108 (s, 1H), 9.750 (s, 1H), 9.025 (t, J=12.0 Hz, 1H), 7.360 (s, 1H), 7.155-7.311 (dd, J$_1$=8.8 Hz, J$_2$=4.4 Hz, 2H), 6.743 (s, 1H), 6.327 (s, 1H), 3.599 (s, 4H), 3.508 (s, 2H), 3.177-3.211 (m, 2H), 2.924-2.972 (m, 1H), 2.385 (s, 4H), 1.049 (t, J=8.8 Hz, 3H), 0.898-0.968 (m, 6H).

ESMS clcd for C$_{25}$H$_{30}$FN$_5$O$_4$: 483.54. Found: 482.1 (M$^-$).

Compound 213

$^1$H NMR (400 MHz, DMSO), δ (ppm): 10.082 (s, 1H), 9.751 (s, 1H), 8.866 (d, J=7.6 Hz, 1H), 7.311 (s, 1H), 7.293 (d, J=4.4 Hz, 1H), 7.168 (d, J=8.0 Hz, 1H), 6.744 (s, 1H), 6.301 (s, 1H), 3.948-3.968 (m, 1H), 3.581 (s, 4H), 3.500 (s, 2H), 2.946-2.979 (m, 1H), 2.371 (s, 4H), 1.078-1.139 (m, 6H), 0.899-0.941 (m, 6H).

ESMS clcd for C26H32FN5O4: 497.56. Found: 496.3 (M$^-$).

Compound 214

$^1$H NMR (400 MHz, DMSO), δ (ppm): 10.069 (s, 1H), 9.753 (s, 1H), 9.105 (d, J=3.6 Hz, 1H), 7.297-7.317 (m, 2H), 7.155 (d, J=7.6 Hz, 1H), 6.746 (s, 1H), 6.296 (s, 1H), 3.689 (s, 4H), 3.597 (s, 2H), 2.928-2.975 (m, 1H), 2.748 (s, 1H), 2.378 (s, 4H), 0.878-0.939 (m, 6H), 0.584-0.647 (m, 4H).

ESMS clcd for C$_{26}$H$_{30}$FN5O4: 495.55. Found: 494.1 (M$^-$).

Compound 215

$^1$H NMR (400 MHz, DMSO), δ (ppm): 9.956 (s, 1H), 9.757 (s, 1H), 9.691 (t, J=5.6 Hz, 1H), 7.280-7.318 (m, 2H), 7.137 (d, J=8.8 Hz, 1H), 6.795 (s, 1H), 6.295 (s, 1H), 3.950-4.005 (m, 2H), 3.589 (s, 4H), 3.499 (s, 2H), 2.953-2.986 (m, 1H), 2.362 (s, 4H), 0.924-0.961 (m, 6H).

ESMS clcd for C$_{25}$H$_{27}$F$_4$N$_5$O$_4$: 537.20. Found: 536.1 (M$^-$).

Compound 216

$^1$H NMR (400 MHz, DMSO), δ (ppm): 9.960 (s, 1H), 9.780 (s, 1H), 9.701 (t, J=5.6 Hz, 1H), 7.322-7.270 (m, 2H), 7.138 (d, J=8.0 Hz, 1H), 6.786 (s, 1H), 6.315 (s, 1H), 3.990 (m, 2H), 3.521 (s, 2H), 2.987-2.954 (m, 3H), 0.943 (t, J=7.2 Hz, 6H).

ESMS clcd for C$_{26}$H$_{30}$F$_4$N$_6$O$_3$: 550.55. Found: 551.2 (M$^+$).

Compound 217

$^1$H NMR (400 MHz, DMSO), δ (ppm): 10.109 (s, 1H), 9.759 (s, 1H), 8.863 (d, J=8.0 Hz, 1H), 7.315-7.260 (m, 2H), 7.147 (d, J=8.0 Hz, 1H), 6.736 (s, 1H), 6.311 (s, 1H), 3.971-3.951 (m, 1H), 3.498 (s, 2H), 2.980-2.945 (m, 1H), 2.399-2.343 (m, 7H), 2.208 (s, 3H), 1.141-1.099 (dd, J$_1$=5.6 Hz, J$_2$=11.2 Hz, 6H), 0.940-0.900 (dd, J$_1$=7.2 Hz, J$_2$=8.8 Hz, 6H). ESMS clcd for C$_{27}$H$_{35}$FN$_6$O$_3$: 510.6. Found: 511.3 (M$^+$).

Compound 218

$^1$H NMR (400 MHz, DMSO), δ (ppm): 10.120 (s, 1H), 9.767 (s, 1H), 9.056 (t, J=6.0 Hz, 1H), 7.323-7.263 (m, 2H), 7.145 (d, J=7.2 Hz, 1H), 6.732 (s, 1H), 6.316 (s, 1H), 3.502 (s, 2H), 0.3207-3.174 (m, 2H), 2.978-2.943 (m, 1H), 2.416-2.306 (m, 6H), 2.225 (s, 3H), 1.066 (t, J=3.2 Hz, 3H), 0.935-0.895 (dd, J$_1$=7.2 Hz, J$_2$=9.2 Hz, 6H).

ESMS clcd for C$_{26}$H$_{33}$FN$_6$O$_3$: 496.58. Found: 497.3 (M$^+$).

Compound 219

$^1$H NMR (400 MHz, DMSO), δ (ppm): 10.108 (s, 1H), 9.781 (s, 1H), 9.134 (d, J=4.4 Hz, 1H), 7.332-7.284 (m, 2H), 7.165 (d, J=7.2 Hz, 1H), 6.749 (s, 1H), 6.320 (s, 1H), 3.520 (s, 2H), 2.990-2.955 (m, 1H), 2.772-2.758 (m, 1H), 2.351-2.302 (m, 6H), 2.254 (s, 3H), 0.930 (t, J=7.6 Hz, 6H), 0.662-0.601 (m, 4H).

ESMS clcd for C$_{27}$H$_{33}$FN$_6$O$_3$: 508.59. Found: 509.2 (M$^+$).

Compound 220

$^1$H NMR (400 MHz, DMSO), δ (ppm): 10.664 (s, 1H), 9.830 (s, 1H), 9.017 (d, J=7.6 Hz, 1H), 7.448 (d, J=7.2 Hz, 1H), 7.044-6.992 (m, 2H), 6.537 (s, 1H), 6.368 (s, 1H), 3.230-3.144 (m, 2H), 2.964-2.887 (m, 1H), 2.595-2.543 (m, 2H), 2.452-2.424 (m, 2H), 2.223-2.171 (m, 2H), 2.064 (m, 4H), 1.067 (t, J=7.2 Hz, 3H), 0.901 (t, J=7.2 Hz, 3H), 0.832 (d, J=5.6 Hz, 6H).

ESMS clcd for C$_{26}$H$_{33}$FN$_6$O$_3$: 496.58. Found: 497.1 (M$^+$).

Compound 221

$^1$H NMR (400 MHz, DMSO), δ (ppm): 10.682 (s, 1H), 9.822 (s, 1H), 8.848 (d, J=7.6 Hz, 1H), 7.462-7.425 (dd, J$_1$=2.8 Hz, J$_2$=8.4 Hz, 1H), 7.055-6.993 (m, 2H), 6.541 (s, 1H), 6.375 (s, 1H), 3.958-3.906 (m, 1H), 2.967-2.898 (m, 1H), 2.615-2.565 (m, 2H), 2.459-2.419 (m, 2H), 2.230-2.177 (m, 2H), 2.079 (m, 4H), 1.130 (d, J=6.4 Hz, 6H), 0.907 (t, J=7.2 Hz, 3H), 0.838 (d, J=7.2 Hz, 6H).

ESMS clcd for C$_{27}$H$_{35}$FN$_6$O$_3$: 510.6. Found: 511.2 (M$^+$).

Compound 222

$^1$H NMR (400 MHz, DMSO), δ (ppm): 10.620 (m, 1H), 8.944 (d, J=4.0 Hz, 1H), 7.460-7.424 (dd, J$_1$=5.6 Hz, J$_1$=7.2 Hz, 1H), 7.035-6.982 (m, 2H), 6.527 (s, 1H), 6.359 (s, 1H), 2.967-2.899 (m, 1H), 2.696 (d, J=4.0 Hz, 3H), 2.577-2.549 (m, 2H), 2.446-2.419 (m, 2H), 2.221-2.169 (m, 2H), 2.058 (m, 4H), 0.900 (t, J=7.2 Hz, 3H), 0.835 (d, J=6.4 Hz, 6H).

ESMS clcd for C$_{25}$H$_{31}$FN$_6$O$_3$: 482.55. Found: 483.1 (M$^+$).

Compound 223

$^1$H NMR (400 MHz, DMSO), δ (ppm): 10.087 (s, 1H), 9.782 (s, 1H), 9.032 (m, 1H), 7.305-7.289 (m, 2H), 7.162 (m, 1H), 6.733 (s, 1H), 6.335 (s, 1H), 3.549 (s, 2H), 3.253-3.186 (m, 4H), 2.963-2.945 (m, 2H), 1.062-0.915 (m, 12H).

ESMS clcd for C$_{27}$H$_{35}$FN$_6$O$_3$: 510.6. Found: 509.1 (M$^-$).

Compound 224

$^1$H NMR (400 MHz, DMSO), δ (ppm): 9.780 (s, 1H), 8.916 (d, J=4.4 Hz, 1H), 7.158 (t, J=8.8 Hz, 1H), 6.905-6.866 (dd, J$_1$=2.0 Hz, J$_2$=14.0 Hz, 1H), 6.753-6.713 (m, 1H), 6.335 (s, 1H), 3.222 (d, J=4.4 Hz, 4H), 3.000-2.931 (m, 1H), 2.728-2.692 (m, 3H), 2.420 (t, J=4.4 Hz, 4H), 2.216 (s, 3H), 0.909 (t, J=6.4 Hz, 6H).

ESMS clcd for C₂₄H₂₉FN₆O₃: 468.52. Found: 469.2 (M⁺).

Compound 225

¹H NMR (400 MHz, DMSO), δ (ppm): 10.048 (s, 1H), 9.722 (s, 1H), 8.815 (d, J=8.0 Hz, 1H), 7.271-7.221 (m, 2H), 7.102 (d, J=7.6 Hz, 1H), 6.694 (s, 1H), 6.268 (s, 1H), 3.917-3.903 (m, 1H), 3.468 (s, 2H), 2.935-2.900 (m, 1H), 1.094-1.032 (m, 6H), 0.985 (m, 3H), 0.872 (t, J=7.6 Hz, 6H).

ESMS clcd for C₂₈H₃₇FN₆O₃: 524.63. Found: 525.2 (M⁺).

Compound 226

¹H NMR (400 MHz, DMSO), δ (ppm): 10.098 (s, 1H), 9.750 (s, 1H), 9.103 (d, J=4.0 Hz, 1H), 7.310-7.257 (m, 2H), 7.146 (d, J=8.4 Hz, 1H), 6.727 (s, 1H), 6.298 (s, 1H), 3.488 (s, 2H), 2.970-2.936 (m, 1H), 2.754-2.743 (m, 1H), 2.381-2.275 (m, 9H), 0.979 (t, J=7.2 Hz, 3H), 0.909 (t, J=7.6 Hz, 6H), 0.644-0.606 (m, 4H).

ESMS clcd for C₂₈H₃₅FN₆O₃: 522.61. Found: 523.3 (M⁺).

Compound 227

¹H NMR (400 MHz, DMSO), δ (ppm): 10.515 (s, 1H), 9.833 (s, 1H), 9.645 (t, J=6.4 Hz, 1H), 7.495-7.455 (dd, J₁=6.4 Hz, J₂=9.2 Hz, 1H), 7.067-7.002 (m, 2H), 6.616 (s, 1H), 6.378 (s, 1H), 3.998-3.907 (m, 2H), 2.984-2.916 (m, 1H), 2.552 (m, 2H), 2.482-2.453 (m, 2H), 2.239-2.187 (m, 2H), 2.086 (m, 4H), 0.910 (t, J=7.2 Hz, 3H), 0.868 (d, J=7.6 Hz, 6H). ESMS clcd for C₂₆H₃₀F₄N₆O₃: 550.55. Found: 551.1 (M⁺).

Compound 228

¹H NMR (400 MHz, DMSO), δ (ppm): 10.622 (s, 1H), 9.790 (s, 1H), 9.068 (d, J=4.8 Hz, 1H), 7.459-7.422 (dd, J₁=6.4 Hz, J₂=8.4 Hz, 1H), 7.054-6.989 (m, 2H), 6.542 (s, 1H), 6.373 (s, 1H), 2.969-2.899 (m, 1H), 2.779-2.733 (m, 1H), 2.611-2.559 (m, 2H), 2.462-2.423 (m, 2H), 2.235-2.180 (m, 2H), 2.075 (m, 4H), 0.909 (t, J=7.2 Hz, 3H), 0.851-0.833 (m, 6H), 0.653-0.617 (m, 4H).

ESMS clcd for C₂₇H₃₃FN₆O₃: 508.59. Found: 507.2 (M⁻).

Compound 229

¹H NMR (400 MHz, DMSO), δ (ppm): 10.611 (s, 1H), 9.845 (s, 1H), 9.106 (d, J=4.4 Hz, 1H), 7.455-7.419 (dd, J₁=6.0 Hz, J₂=8.4 Hz, 1H), 7.064-7.012 (m, 2H), 6.551 (s, 1H), 6.372 (s, 1H), 2.953-2.919 (m, 1H), 2.773-2.752 (m, 1H), 2.592-2.563 (m, 2H), 2.458-2.428 (m, 2H), 2.057-2.033 (m, 7H), 0.844 (d, J=6.8 Hz, 6H), 0.654-0.620 (m, 4H). ESMS clcd for C₂₆H₃₁FN₆O₃: 494.56. Found: 495.1 (M⁺).

Compound 230

¹H NMR (400 MHz, DMSO), δ (ppm): 10.675 (s, 1H), 9.821 (s, 1H), 8.858 (d, J=8.0 Hz, 1H), 7.461-7.425 (m, 1H), 7.056-7.001 (m, 2H), 6.543 (s, 1H), 6.376 (s, 1H), 3.975-3.889 (m, 1H), 2.967-2.899 (m, 1H), 2.610-2.569 (m, 2H), 2.454-2.413 (m, 2H), 2.055-2.031 (m, 7H), 1.130 (d, J=7.2 Hz, 6H), 0.838 (d, J=6.0 Hz, 6H).

ESMS clcd for C₂₆H₃₃FN₆O₃: 496.58. Found: 495.2 (M⁻).

Compound 231

¹H NMR (400 MHz, DMSO), δ (ppm): 10.248 (s, 1H), 9.707 (t, J=8.0 Hz, 1H), 7.294-7.377 (m, 2H), 7.156 (d, J=13.2 Hz, 1H), 6.850 (s, 1H), 6.436 (s, 1H), 3.969-3.978 (m, 2H), 3.734 (s, 3H), 3.526 (s, 2H), 2.983-3.034 (m, 1H), 2.728-2.736 (m, 4H), 2.435-2.444 (m, 3H), 0.921-0.957 (m, 6H).

ESMS clcd for C27H32F4N6O3: 564.57. Found: 565.5 (M⁺).

Compound 232

¹H NMR (400 MHz, DMSO), δ (ppm): 10.391 (s, 1H), 8.870 (d, J=8.4 Hz, 1H), 7.343 (t, J=8.4 Hz, 1H), 7.299 (d, J=10.8 Hz, 1H), 7.173 (d, J=8.4 Hz, 1H), 6.781 (s, 1H), 6.436 (s, 1H), 3.920-4.004 (m, 1H), 3.730 (s, 3H), 3.502 (s, 2H), 2.962-3.030 (m, 1H), 2.416 (s, 7H), 2.226 (s, 3H), 1.126 (t, J=5.6 Hz, 6H), 0.901 (m, 6H).

ESMS clcd for C28H37FN6O3: 524.63. Found: 525.5 (M⁺).

Compound 233

¹H NMR (400 MHz, DMSO), δ (ppm): 10.383 (s, 1H), 9.070 (t, J=6.0 Hz, 1H), 7.363-7.271 (m, 2H), 7.158 (d, J=7.6 Hz, 1H), 6.784 (s, 1H), 6.434 (s, 1H), 3.728 (s, 3H), 3.508 (s, 2H), 3.224-3.155 (m, 2H), 3.027-2.956 (m, 1H), 2.508-2.435 (m, 6H), 2.271 (s, 3H), 1.064 (t, J=7.6 Hz, 3H), 0.901 (t, J=7.6 Hz, 6H).

ESMS clcd for C₂₇H₃₅FN₆O₃: 510.6. Found: 511.3 (M⁺).

Compound 234

¹H NMR (400 MHz, DMSO), δ (ppm): 10.355 (s, 1H), 9.128 (d, J=4.4 Hz, 1H), 7.360 (m, 2H), 7.191 (d, J=7.2 Hz, 1H), 6.796 (s, 1H), 6.438 (s, 1H), 3.735 (s, 3H), 3.549 (s, 2H), 2.768-2.757 (m, 1H), 2.514-2.510 (m, 1H), 2.423-2.410 (m, 4H), 0.913 (t, J=3.2 Hz, 6H), 0.658-0.623 (m, 4H).

ESMS clcd for C₂₈H₃₅FN₆O₃: 522.61. Found: 523.6 (M⁺).

Compound 235

¹H NMR (400 MHz, DMSO), δ (ppm): 10.257 (s, 1H), 8.984 (t, J=2.4 Hz, 1H), 7.254-7.189 (m, 2H), 7.065 (d, J=8.0 Hz, 1H), 6.694 (s, 1H), 6.319 (s, 1H), 3.622 (s, 3H), 3.496-3.475 (m, 4H), 3.399 (s, 2H), 3.121-3.053 (m, 2H), 2.909-2.874 (m, 1H), 2.265 (m, 4H), 0.959 (t, J=7.2 Hz, 3H), 0.803 (t, J=7.2 Hz, 6H).

ESMS clcd for C₂₆H₃₂FN₅O₄: 497.56. Found: 498.2 (M⁺).

Compound 236

¹H NMR (400 MHz, DMSO), δ (ppm): 10.234 (s, 1H), 9.050 (d, 1H), 7.260-7.195 (m, 2H), 7.079-7.044 (m, 1H), 6.701 (s, 1H), 6.308 (s, 1H), 3.619 (s, 3H), 3.488 (m, 4H), 3.401 (s, 2H), 2.907-2.873 (m, 1H), 2.675-2.617 (m, 1H), 2.269 (m, 4H), 0.806 (t, J=7.2 Hz, 6H), 0.545-0.490 (m, 4H).

ESMS clcd for C₂₇H₃₂FN₅O₄: 509.57. Found: 510.2 (M⁺).

Compound 237

¹H NMR (400 MHz, DMSO), δ (ppm): 10.334 (s, 1H), 9.090 (d, J=2.8 Hz, 1H), 7.326-7.243 (m, 2H), 7.131 (d, J=8.0 Hz, 1H), 6.751 (s, 1H), 6.393 (s, 1H), 3.690 (s, 3H), 3.475 (s, 2H), 2.959 (m, 1H), 2.728-2.715 (m, 1H), 2.469-2.378 (m, 8H), 0.974 (m, 3H), 0.867 (t, J=7.2 Hz, 6H), 0.614-0.577 (m, 4H).

ESMS clcd for C₂₉H₃₇FN₆O₃: 536.64. Found: 537.0 (M⁺).

Compound 238

¹H NMR (400 MHz, DMSO), δ (ppm): 10.380 (s, 1H), 8.852 (d, J=8.4 Hz, 1H), 7.338-7.268 (m, 2H), 7.160 (d, J=8.0 Hz, 1H), 6.778 (s, 1H), 6.432 (s, 1H), 3.952 (m, 1H), 3.729 (s, 3H), 3.499 (s, 2H), 2.993 (m, 1H), 2.397-2.330 (m, 8H), 1.140-1.111 (dd, J₁=5.2 Hz, J₂=6.4 Hz, 6H), 0.996 (t, 3H), 0.902 (t, J=7.2 Hz, 6H).

ESMS clcd for C₂₉H₃₉FN₆O₃: 538.66. Found: 539.1 (M⁺).

Compound 239

¹H NMR (400 MHz, DMSO), δ (ppm): 10.312 (s, 1H), 9.088 (m, 1H), 7.360-7.299 (m, 2H), 7.163 (d, J=7.2 Hz, 1H), 6.804 (s, 1H), 6.432 (s, 1H), 3.722 (s, 3H), 3.575 (s, 2H), 3.202-3.170 (m, 2H), 2.018-2.959 (m, 2H), 1.166-1.045 (m, 6H), 0.916 (t, J=7.2 Hz, 6H). ESMS clcd for C₂₈H₃₇FN₆O₃: 524.63. Found: 525.0 (M⁺).

Compound 240

¹H NMR (400 MHz, DMSO), δ (ppm): 10.162 (s, 1H), 9.790 (s, 1H), 9.135 (d, J=4.8 Hz, 1H), 7.270 (d, J=7.2 Hz, 2H), 6.771 (s, 1H), 6.314 (s, 1H), 3.542 (s, 2H), 3.024-2.931 (m, 1H), 2.789-2.728 (m, 1H), 2.133 (s, 3H), 0.931 (d, J=12.8 Hz, 6H), 0.640-0.620 (m, 4H). ESMS clcd for $C_{27}H_{32}F_2N_6O_3$: 526.58. Found: 527.1 (M⁺).

Compound 241

¹H NMR (400 MHz, DMSO), δ (ppm): 9.102 (d, J=6.0 Hz, 1H), 7.398 (d, J=6.8 Hz, 2H), 6.765 (s, 1H), 6.345 (s, 1H), 3.658 (s, 2H), 3.341-3.291 (m, 2H), 3.101-3.050 (m, 1H), 2.242 (s, 3H), 1.175 (t, J=7.6 Hz, 3H), 1.000 (d, J=6.8 Hz, 6H).

ESMS clcd for $C_{26}H_{32}F_2N_6O_3$: 514.57. Found: 515.1 (M⁺).

Compound 242

¹H NMR (400 MHz, DMSO), δ (ppm): 10.131 (s, 1H), 9.719 (s, 1H), 8.777 (d, J=8.8 Hz, 1H), 7.244 (d, J=7.6 Hz, 2H), 6.769 (s, 1H), 6.340 (s, 1H), 4.007-3.954 (m, 1H), 3.551 (s, 2H), 3.019-2.955 (m, 1H), 2.457-2.330 (m, 8H), 2.169 (s, 3H), 1.133 (d, J=7.2 Hz, 6H), 0.942 (d, J=6.8 Hz, 6H).

ESMS clcd for $C_{27}H_{34}F_2N_6O_3$: 528.59. Found: 527.2 (M⁻).

Compound 243

¹H NMR (400 MHz, DMSO), δ (ppm): 10.494 (s, 1H), 9.066 (d, J=4.0 Hz, 1H), 7.569 (s, 1H), 7.549 (d, J=8.8 Hz, 1H), 7.307 (d, J=6.4 Hz, 1H), 6.607 (s, 1H), 6.290 (s, 1H), 3.569 (s, 2H), 2.916-2.984 (m, 1H), 2.719-2.766 (m, 1H), 2.272-2.370 (m, 8H), 2.164 (s, 3H), 0.845-0.862 (m, 6H), 0.571-0.667 (m, 4H).

ESMS clcd for C27H33ClN6O3: 525.04. Found: 523.3 (M⁻).

Compound 244

¹H NMR (400 MHz, DMSO), δ (ppm): 10.359 (s, 1H), 9.796 (s, 1H), 8.835 (d, J=8.4 Hz, 1H), 7.559 (s, 1H), 7.522 (d, J=9.6 Hz, 1H), 7.310 (d, J=5.6 Hz, 1H), 6.673 (s, 1H), 6.333 (s, 1H), 3.913-3.999 (m, 1H), 3.565 (s, 2H), 2.922-2.991 (m, 1H), 2.288-2.341 (m, 11H), 1.111-1.127 (m, 6H), 0.992 (t, J=7.2 Hz, 3H), 0.874-0.891 (m, 6H).

ESMS clcd for C28H37ClN6O3: 541.08. Found: 539.3 (M⁻).

Compound 245

¹H NMR (400 MHz, DMSO), δ (ppm): 10.261 (s, 1H), 9.770 (s, 1H), 9.637 (t, J=6.0 Hz, 1H), 7.587 (s, 1H), 7.527 (d, J=7.6 Hz, 1H), 7.330 (d, J=5.6 Hz, 1H), 6.704 (s, 1H), 6.330 (s, 1H), 3.930-4.019 (m, 2H), 3.555 (s, 2H), 2.916-2.984 (m, 1H), 2.333-2.338 (m, 8H), 2.159 (s, 3H), 0.872-0.890 (m, 6H).

ESMS clcd for C26H30ClF3N6O3: 567.00. Found: 567.4 (M⁺).

Compound 246

¹H NMR (400 MHz, DMSO), δ (ppm): 10.234 (s, 1H), 9.768 (s, 1H), 9.637 (t, J=5.6 Hz, 1H), 7.600 (s, 1H), 7.556 (d, J=8.8 Hz, 1H), 7.316 (d, J=8.0 Hz, 1H), 6.712 (s, 1H), 6.328 (s, 1H), 3.934-4.018 (m, 2H), 3.596 (s, 4H), 3.569 (s, 2H), 2.920-2.984 (m, 1H), 2.431 (s, 4H), 0.876 (d, J=7.2 Hz, 6H).

ESMS clcd for C25H27ClF3N5O4: 553.96. Found: 554.5 (M⁺).

Compound 247

¹H NMR (400 MHz, DMSO), δ (ppm): 10.250 (s, 1H), 9.751 (s, 1H), 8.834 (d, J=8.4 Hz, 1H), 7.535-7.551 (m, 2H), 7.300 (d, J=6.0 Hz, 1H), 6.679 (s, 1H), 6.321 (s, 1H), 3.900-3.989 (m, 1H), 3.583 (t, J=8.8 Hz, 4H), 3.569 (s, 2H), 2.910-2.981 (m, 1H), 2.430 (t, J=4.0 Hz, 4H), 1.100 (d, J=6.4 Hz, 6H), 0.860 (d, J=9.6 Hz, 6H).

ESMS clcd for C26H32ClN5O4: 514.02. Found: 512.5 (M⁻).

Compound 248

¹H NMR (400 MHz, DMSO), δ (ppm): 10.344 (s, 1H), 9.757 (s, 1H), 9.009 (t, J=6.4 Hz, 1H), 7.533-7.567 (m, 2H), 7.310 (d, J=6.0 Hz, 1H), 6.662 (s, 1H), 6.324 (s, 1H), 3.593 (t, J=4.4 Hz, 4H), 3.569 (s, 2H), 3.146-3.213 (m, 2H), 2.906-2.972 (m, 1H), 2.440 (s, 4H), 1.034-1.089 (m, 3H), 0.873 (d, J=7.2 Hz, 6H).

ESMS clcd for $C_{25}H_{30}ClN_5O_4$: 499.99. Found: 498.5 (M⁻).

Compound 249

¹H NMR (400 MHz, DMSO), δ (ppm): 10.310 (s, 1H), 9.762 (s, 1H), 9.076 (d, J=4.8 Hz, 1H), 7.542-7.567 (m, 2H), 7.307 (d, J=6.0 Hz, 1H), 6.672 (s, 1H), 6.320 (s, 1H), 3.600 (t, J=4.8 Hz, 4H), 3.575 (s, 2H), 2.909-2.977 (m, 1H), 2.717-2.763 (m, 1H), 2.438 (t, J=4.4 Hz, 4H), 0.863 (d, J=6.8 Hz, 6H), 0.596-0.645 (m, 4H).

ESMS clcd for C26H30ClN5O4: 512. Found: 510.5 (M⁺).

Compound 250

¹H NMR (400 MHz, DMSO), δ (ppm): 10.334 (s, 1H), 9.756 (s, 1H), 8.803 (d, J=8.8 Hz, 1H), 7.543 (s, 1H), 7.509 (d, J=8.0 Hz, 1H), 7.283 (d, J=7.6 Hz, 1H), 6.667 (s, 1H), 6.325 (s, 1H), 4.017-4.034 (m, 1H), 3.558 (s, 2H), 2.927-2.960 (m, 1H), 2.391-2.456 (m, 8H), 2.193 (s, 3H), 1.114 (d, J=6.4 Hz, 6H), 0.861 (d, J=7.6 Hz, 6H).

ESMS clcd for C27H35ClN6O3: 527.06. Found: 527.2 (M⁺).

Compound 251

¹H NMR (400 MHz, DMSO), δ (ppm): 10.372 (s, 1H), 9.753 (s, 1H), 9.000 (t, J=5.6 Hz, 1H), 7.552 (s, 1H), 7.527 (d, J=8.4 Hz, 1H), 7.310 (d, J=6.4 Hz, 1H), 6.651 (s, 1H), 6.327 (s, 1H), 3.554 (s, 2H), 3.162-3.194 (m, 2H), 2.921-2.954 (m, 1H), 2.293-2.450 (m, 8H), 2.158 (s, 3H), 1.050 (t, J=7.2 Hz, 6H), 0.851 (d, J=6.8 Hz, 6H).

ESMS clcd for C26H33ClN6O3: 513.03. Found: 511.5 (M⁻).

Compound 252

¹H NMR (400 MHz, DMSO), δ (ppm): 10.358 (s, 1H), 9.778 (s, 1H), 9.070 (d, J=3.6 Hz, 1H), 7.561-7.521 (m, 2H), 7.303 (d, J=6.4 Hz, 1H), 6.665 (s, 1H), 6.329 (s, 1H), 3.563 (s, 2H), 2.963-2.929 (m, 1H), 2.757-2.722 (m, 1H), 2.454-2.300 (m, 10H), 0.982 (t, J=7.2 Hz, 3H), 0.869 (d, J=6.8 Hz, 6H), 0.646-0.598 (m, 4H).

ESMS clcd for $C_{28}H_{35}ClN_6O_3$: 539.07. Found: 537.2 (M⁻).

Compound 253

¹H NMR (400 MHz, DMSO), δ (ppm): 9.670 (s, 1H), 9.062 (t, J=4.8 Hz, 1H), 7.638 (s, 1H), 7.541 (d, J=8.4 Hz, 1H), 7.348 (d, J=6.0 Hz, 1H), 6.745 (s, 1H), 6.460 (s, 1H), 3.737 (s, 3H), 3.681 (s, 2H), 3.412 (d, J=11.6 Hz, 2H), 3.155-3.225 (m, 2H), 3.042-3.092 (m, 2H), 2.929-3.027 (m, 3H), 2.804 (s, 3H), 2.446-2.473 (m, 2H), 1.065 (t, J=6.8 Hz, 3H), 0.867-0.886 (m, 6H).

ESMS clcd for C27H35ClN6O3: 527.06. Found: 527.4 (M⁺).

Compound 254

¹H NMR (400 MHz, DMSO), δ (ppm): 10.500 (s, 1H), 9.662 (t, J=6.0 Hz, 1H), 7.625 (s, 1H), 7.513 (d, J=8.0 Hz, 1H), 7.357 (d, J=6.0 Hz, 1H), 6.761 (s, 1H), 6.457 (s, 1H), 3.937-4.025 (m, 2H), 3.739 (s, 3H), 3.555 (s, 2H), 2.952-3.020 (m, 1H), 2.209-2.400 (m, 8H), 2.162 (s, 3H), 0.866-0.883 (m, 6H).

ESMS clcd for C27H32ClF3N6O3: 581.03. Found: 581.3 (M⁺).

Compound 255

¹H NMR (400 MHz, DMSO), δ (ppm): 10.624 (s, 1H), 9.109 (s, 1H), 7.604 (s, 1H), 7.527 (d, J=8.4 Hz, 1H), 7.323 (d, J=8.0 Hz, 1H), 6.722 (s, 1H), 6.460 (s, 1H), 3.737 (s, 3H), 3.564 (s, 2H), 2.963-2.998 (m, 1H), 2.728-2.773 (m, 1H), 2.340-2.368 (m, 8H), 2.163 (s, 3H), 0.852-0.869 (m, 6H), 0.605-0.641 (m, 4H).

ESMS clcd for C28H35ClN6O3: 539.07. Found: 539.4 (M⁺).

Compound 256

¹H NMR (400 MHz, DMSO), δ (ppm): 10.602 (s, 1H), 9.110 (s, 1H), 7.604 (s, 1H), 7.530 (d, J=7.6 Hz, 1H), 7.340 (d, J=6.4 Hz, 1H), 6.722 (s, 1H), 6.458 (s, 1H), 3.740 (s, 3H), 3.572 (s, 2H), 2.949-3.016 (m, 1H), 2.727-2.775 (m, 1H), 2.341-2.466 (m, 10H), 0.997 (t, J=7.2 Hz, 3H), 0.856-0.875 (m, 6H), 0.609-0.655 (m, 4H).

ESMS clcd for C29H37ClN6O3: 553.10. Found: 553.2 (M⁺).

Compound 257

¹H NMR (400 MHz, DMSO), δ (ppm): 10.581 (s, 1H), 8.855 (d, J=8.4 Hz, 1H), 7.604 (s, 1H), 7.550 (d, J=8.0 Hz, 1H), 7.320 (d, J=6.8 Hz, 1H), 6.732 (s, 1H), 6.457 (s, 1H), 3.911-3.998 (m, 1H), 3.738 (s, 3H), 3.576-3.596 (m, 6H), 2.948-3.018 (m, 1H), 2.506 (s, 4H), 1.116 (d, J=5.6 Hz, 1H), 0.857 (d, J=6.8 Hz, 6H).

ESMS clcd for C27H34ClN5O4: 528.04. Found: 528.6 (M⁺).

Compound 258

¹H NMR (400 MHz, DMSO), δ (ppm): 10.481 (s, 1H), 9.662 (t, J=6.0 Hz, 1H), 7.639 (s, 1H), 7.545 (d, J=8.0 Hz, 1H), 7.363 (d, J=6.4 Hz, 1H), 6.771 (s, 1H), 6.457 (s, 1H), 3.941-4.027 (m, 2H), 3.742 (s, 3H), 3.575-3.608 (m, 6H), 2.955-3.023 (m, 1H), 2.434 (s, 4H), 0.871 (d, J=6.4 Hz, 6H).

ESMS clcd for C26H29ClF3N5O4: 567.99. Found: 568.3 (M⁺).

Compound 259

¹H NMR (400 MHz, DMSO), δ (ppm): 10.610 (s, 1H), 9.035 (t, J=6.0 Hz, 1H), 7.613 (s, 1H), 7.548 (d, J=8.4 Hz, 1H), 7.347 (d, J=6.4 Hz, 1H), 6.720 (s, 1H), 6.462 (s, 1H), 3.739 (s, 3H), 3.588-3.609 (m, 2H), 3.576 (s, 4H), 3.156-3.224 (m, 2H), 3.945-3.011 (m, 1H), 2.436 (s, 4H), 1.060 (t, J=7.2 Hz, 3H), 0.865 (d, J=6.8 Hz, 6H).

ESMS clcd for C26H32ClN5O4: 514.02. Found: 512.7 (M⁻).

Compound 260

¹H NMR (400 MHz, DMSO), δ (ppm): 10.589 (s, 1H), 9.105 (d J=4.0 Hz, 1H), 7.610 (s, 1H), 7.576 (d, J=8.0 Hz, 1H), 7.341 (d, J=5.6 Hz, 1H), 6.728 (s, 1H), 6.456 (s, 1H), 3.737 (s, 3H), 3.590-3.613 (m, 2H), 3.581 (s, 4H), 2.947-3.015 (m, 1H), 2.716-2.784 (m, 1H), 2.442 (s, 4H), 0.871 (d, J=6.8 Hz, 6H), 0.593-0.653 (m, 4H).

ESMS clcd for C27H32ClN5O4: 526.03. Found: 526.4 (M⁺).

Compound 261

¹H NMR (400 MHz, DMSO), δ (ppm): 10.605 (s, 1H), 8.838 (d, J=7.6 Hz, 1H), 7.590 (s, 1H), 7.534 (d, J=6.8 Hz, 1H), 7.326 (d, J=8.8 Hz, 1H), 6.723 (s, 1H), 6.460 (s, 1H), 3.977-3.926 (m, 1H), 3.738 (s, 3H), 3.559 (s, 2H), 3.017-2.948 (m, 1H), 2.449-2.281 (m, 10H), 1.112 (d, J=5.2 Hz, 6H), 0.980 (t, J=7.6 Hz, 3H), 0.863 (d, J=8.0 Hz, 6H).

ESMS clcd for $C_{29}H_{39}ClN_6O_3$: 554.28. Found: 555.2 (M⁺).

Compound 262

¹H NMR (400 MHz, DMSO), δ (ppm): 10.642 (s, 1H), 9.033 (t, 1H), 7.601 (s, 1H), 7.530 (d, J=8.8 Hz, 1H), 7.329 (d, J=6.8 Hz, 1H), 6.713 (s, 1H), 6.463 (s, 1H), 3.734 (s, 3H), 3.557 (s, 2H), 3.222-3.155 (m, 2H), 3.009-2.976 (m, 1H), 2.448-2.294 (m, 10H), 1.051 (t, J=4.8 Hz, 3H), 0.982 (t, J=7.2 Hz, 3H), 0.854 (d, J=8.0 Hz, 6H).

ESMS clcd for $C_{28}H_{37}ClN_6O_3$: 541.08. Found: 541.3 (M⁺).

Compound 263

¹H NMR (400 MHz, DMSO), δ (ppm): 8.761 (d, J=8.0 Hz, 1H), 7.463 (t, J=8.0 Hz, 1H), 7.351 (d, J=9.2 Hz, 1H), 7.174 (d, J=8.0 Hz, 1H), 6.590 (s, 1H), 6.269 (s, 1H), 3.901-3.988 (m, 1H), 3.621 (s, 2H), 3.103-3.168 (m, 1H), 2.211-2.419 (s, 8H), 2.155 (s, 3H), 1.116 (d, J=6.4 Hz, 6H), 0.814-0.859 (m, 6H).

ESMS clcd for C27H35FN6O3: 510.6. Found: 509.5 (M⁻).

Compound 264

¹H NMR (400 MHz, DMSO), δ (ppm): 10.375 (s, 1H), 9.742 (s, 1H), 9.017 (t, J=12.8 Hz, 1H), 7.412 (t, J=3.2 Hz, 1H), 7.341 (d, J=3.2 Hz, 1H), 7.140 (t, J=8.0 Hz, 1H), 6.687 (s, 1H), 6.355 (s, 1H), 3.522 (s, 2H), 3.154-3.219 (m, 2H), 2.898-2.963 (m, 1H), 2.313-2.393 (m, 7H), 2.161 (s, 3H), 1.059 (t, J=7.2 Hz, 3H), 0.855 (d, J=12.4 Hz, 6H). ESMS clcd for C26H33FN6O3: 496.58. Found: 495.6 (M⁻).

Compound 265

¹H NMR (400 MHz, DMSO), δ (ppm): 8.776 (d, J=8.0 Hz, 1H), 7.465 (t, J=8.4 Hz, 1H), 7.356 (d, J=9.2 Hz, 1H), 7.157 (d, J=7.6 Hz, 1H), 6.584 (s, 1H), 6.259 (s, 1H), 3.930-3.956 (m, 1H), 3.531 (s, 2H), 2.937-2.972 (m, 1H), 2.274-2.423 (m, 9H), 1.100 (d, J=6.8 Hz, 6H), 0.983 (t, J=6.8 Hz, 3H), 0.842 (d, J=6./Hz, 6H).

ESMS clcd for C28H37FN6O3: 524.63. Found: 525.5 (M⁺).

Compound 266

¹H NMR (400 MHz, DMSO), δ (ppm): 9.027 (d, J=4.4 Hz, 1H), 7.473 (t, J=8.8 Hz, 1H), 7.373 (d, J=11.2 Hz, 1H), 7.160 (d, J=9.2 Hz, 1H), 6.560 (s, 1H), 6.238 (s, 1H), 3.538 (s, 2H), 2.920-2.985 (m, 1H), 2.730-2.747 (m, 1H), 2.278-2.332 (m, 9H), 0.985 (t, J=7.2 Hz, 3H), 0.831 (d, J=6.8 Hz, 6H), 0.595-0.646 (m, 4H).

ESMS clcd for C28H35FN6O3: 522.61. Found: 523.5 (M⁺).

Compound 267

¹H NMR (400 MHz, DMSO), δ (ppm): 10.268 (s, 1H), 9.781 (s, 1H), 9.062 (d, J=4.8 Hz, 1H), 7.464 (t, J=8.0 Hz, 1H), 7.344 (d, J=10.4 Hz, 1H), 7.146 (t, J=8.4 Hz, 1H), 6.693 (s, 1H), 6.351 (s, 1H), 3.556 (s, 2H), 2.923-2.991 (m, 1H), 2.645-2.772 (m, 1H), 2.507-2.514 (s, 3H), 0.884 (d, J=6.8 Hz, 6H), 0.606-0.673 (m, 4H).

ESMS clcd for C27H33FN6O3: 508.59. Found: 509.4 (M⁺).

Compound 268

¹H NMR (400 MHz, DMSO), δ (ppm): 10.219 (s, 1H), 9.761 (s, 1H), 8.985 (t, J=6.0 Hz, 1H), 7.478 (t, J=8.0 Hz, 1H), 7.350 (d, J=7.6 Hz, 1H), 7.145 (d, J=8.4 Hz, 1H), 6.673 (s, 1H), 6.332 (s, 1H), 3.589 (s, 2H), 3.147-3.580 (m, 2H), 2.889-2.967 (m, 1H), 1.155 (s, 3H), 1.037 (t, J=6.8 Hz, 3H), 0.861 (d, J=6.8 Hz, 6H).

ESMS clcd for C27H35FN6O3: 510.6. Found: 512.6 (M⁺).

Compound 269

¹H NMR (400 MHz, DMSO), δ (ppm): 10.208 (s, 1H), 9.747 (s, 1H), 9.630 (t, J=5.2 Hz, 1H), 7.457 (t, J=9.6 Hz, 1H), 7.379 (d, J=9.6 Hz, 1H), 7.176 (d, J=6.8 Hz, 1H), 6.717 (s, 1H), 6.328 (s, 1H), 3.933-4.023 (m, 2H), 3.574 (t, J=4.0 Hz, 4H), 3.533 (s, 2H), 2.935-2.979 (m, 1H), 2.385 (s, 4H), 0.870 (d, J=8.4 Hz, 6H).

ESMS clcd for C25H27F4N5O4: 537.51. Found: 538.2 (M⁺).

Compound 270
¹H NMR (400 MHz, DMSO), δ (ppm): 10.234 (s, 1H), 9.770 (s, 1H), 9.629 (t, J=6.4 Hz, 1H), 7.445 (t, J=7.6 Hz, 1H), 7.385 (d, J=6.0 Hz, 1H), 7.183 (d, J=8.4 Hz, 1H), 6.719 (s, 1H), 6.343 (s, 1H), 3.961-4.001 (m, 2H), 3.529 (s, 2H), 2.938-2.972 (m, 1H), 2.421 (s, 6H), 2.205 (s, 3H), 0.903 (d, J=6.8 Hz, 6H).
ESMS clcd for C26H30F4N6O3: 550.55. Found: 551.2 (M⁺).

Compound 271
¹H NMR (400 MHz, DMSO), δ (ppm): 10.222 (s, 1H), 9.754 (s, 1H), 9.619 (t, J=6.8 Hz, 1H), 7.429 (t, J=8.0 Hz, 1H), 7.366 (d, J=8.0 Hz, 1H), 7.143 (d, J=8.0 Hz, 1H), 6.706 (s, 1H), 6.327 (s, 1H), 3.950-3.990 (m, 2H), 3.504 (s, 2H), 2.925-2.960 (m, 1H), 2.591-2.622 (m, 1H), 2.429 (s, 8H), 0.957 (d, J=6.0 Hz, 6H), 0.877 (d, J=6.8 Hz, 6H). ESMS clcd for C28H34F4N6O3: 578.6. Found: 579.2 (M⁺).

Compound 272
¹H NMR (400 MHz, DMSO), δ (ppm): 10.404 (s, 1H), 9.783 (s, 1H), 9.590 (m, 1H), 7.338 (d, J=13.2 Hz, 1H), 7.097-7.032 (m, 2H), 6.654 (s, 1H), 6.338 (s, 1H), 3.982-3.944 (m, 2H), 3.042 (m, 4H), 2.963-2.929 (m, 1H), 2.218 (s, 3H), 0.874 (d, J=7.6 Hz, 6H). ESMS clcd for $C_{25}H_{28}F_4N_6O_3$: 536.52. Found: 537.1 (M⁺).

Compound 273
¹H NMR (400 MHz, DMSO), δ (ppm): 10.563 (s, 1H), 9.799 (s, 1H), 8.906-8.894 (m, 1H), 7.325 (d, J=14.4 Hz, 1H), 7.065-7.042 (m, 2H), 6.614 (s, 1H), 6.345 (s, 1H), 3.049 (m, 4H), 2.962-2.927 (m, 1H), 2.694 (d, J=4.4 Hz, 3H), 2.227 (s, 3H), 0.861 (d, J=6.4 Hz, 6H). ESMS clcd for $C_{24}H_{29}FN_6O_3$: 468.52. Found: 467.2 (M⁻).

Compound 274
¹H NMR (400 MHz, DMSO), δ (ppm): 10.555 (s, 1H), 9.778 (s, 1H), 8.968 (t, J=6.4 Hz, 1H), 7.319 (d, J=13.6 Hz, 1H), 7.087-7.021 (m, 2H), 6.610 (s, 1H), 6.347 (s, 1H), 3.214-3.143 (m, 2H), 3.050 (m, 4H), 2.980-2.908 (m, 1H), 2.223 (s, 3H), 1.055 (t, J=7.6 Hz, 3H), 0.864 (d, J=6.0 Hz, 6H).
ESMS clcd for $C_{25}H_{31}FN_6O_3$: 482.55. Found: 483.1 (M⁺).

Compound 275
¹H NMR (400 MHz, DMSO), δ (ppm): 10.561 (s, 1H), 9.797 (s, 1H), 8.921-8.887 (m, 1H), 7.345-7.308 (dd, J₁=2.0 Hz, J₂=12.8 Hz, 1H), 7.094-7.019 (m, 2H), 6.617 (s, 1H), 6.344 (s, 1H), 3.056 (m, 4H), 2.979-2.911 (m, 1H), 2.695 (d, J=4.8 Hz, 3H), 2.406-2.356 (m, 2H), 1.029 (t, J=7.2 Hz, 3H), 0.864 (d, J=6.8 Hz, 6H).
ESMS clcd for $C_{25}H_{31}FN_6O_3$: 482.55. Found: 483.1 (M⁺).

Compound 276
¹H NMR (400 MHz, DMSO), δ (ppm): 10.520 (s, 1H), 9.791 (s, 1H), 8.779 (d, J=8.0 Hz, 1H), 7.310 (d, J=13.2 Hz, 1H), 7.064-7.025 (m, 2H), 6.626 (s, 1H), 6.345 (s, 1H), 3.972-3.922 (m, 1H), 3.055 (m, 4H), 2.994-2.884 (m, 1H), 2.393-2.278 (m, 2H), 1.162-0.865 (m, 9H), 0.786-0.705 (m, 6H).
ESMS clcd for $C_{27}H_{35}FN_6O_3$: 510.6. Found: 511.1 (M⁺).

Compound 277
¹H NMR (400 MHz, DMSO), δ (ppm): 10.522 (s, 1H), 9.760 (s, 1H), 9.752 (d, J=8.0 Hz, 1H), 7.320-7.284 (m, 1H), 7.063-7.045 (m, 2H), 6.618 (s, 1H), 6.340 (s, 1H), 3.969-3.932 (m, 1H), 3.051 (m, 4H), 2.965-2.931 (m, 1H), 2.226 (s, 3H), 1.106 (d, J=6.4 Hz, 6H), 0.868 (d, J=6.8 Hz, 6H).
ESMS clcd for $C_{26}H_{33}FN_6O_3$: 496.58. Found: 497.1 (M⁺).

Compound 278
¹H NMR (400 MHz, DMSO), δ (ppm): 10.520 (s, 1H), 9.792 (s, 1H), 9.738 (d, J=4.8 Hz, 1H), 7.334-7.296 (m, 1H), 7.065-7.047 (m, 2H), 6.622 (s, 1H), 6.339 (s, 1H), 3.054 (m, 4H), 2.965-2.930 (m, 1H), 2.755-2.731 (m, 1H), 2.227 (s, 3H), 0.870 (d, J=6.8 Hz, 6H), 0.665-0.591 (m, 4H).
ESMS clcd for $C_{26}H_{31}FN_6O_3$: 494.56. Found: 495.1 (M⁺).

Compound 279
¹H NMR (400 MHz, DMSO), δ (ppm): 10.554 (s, 1H), 9.811 (s, 1H), 8.963 (t, J=5.6 Hz, 1H), 7.314 (d, J=13.2 Hz, 1H), 7.087-7.016 (m, 2H), 6.611 (s, 1H), 6.343 (s, 1H), 3.193-3.161 (m, 2H), 3.052-3.011 (m, 4H), 2.977-2.907 (m, 1H), 2.402-2.347 (m, 2H), 1.069-1.007 (m, 6H), 0.870-0.822 (m, 6H).
ESMS clcd for $C_{26}H_{33}FN_6O_3$: 496.58. Found: 495.2 (M⁻).

Compound 280
¹H NMR (400 MHz, DMSO), δ (ppm): 10.517 (s, 1H), 9.784 (s, 1H), 9.036 (d, J=3.6 Hz, 1H), 7.314 (d, J=12.0 Hz, 1H), 7.062-7.043 (m, 2H), 6.622 (s, 1H), 6.334 (s, 1H), 3.056 (m, 4H), 2.963-2.929 (m, 1H), 2.743-2.733 (m, 1H), 2.405-2.353 (m, 2H), 1.025 (t, J=6.8 Hz, 3H), 0.868 (d, J=6.0 Hz, 6H), 0.634-0.590 (m, 4H).
ESMS clcd for $C_{27}H_{33}FN_6O_3$: 508.59. Found: 507.2 (M⁻).

Compound 281
¹H NMR (400 MHz, DMSO), δ (ppm): 10.578 (s, 1H), 8.991 (t, J=10.0 Hz, 1H), 7.433 (s, 1H), 7.370 (d, J=4.0 Hz, 1H), 7.152 (d, J=8.0 Hz, 1H), 6.712 (s, 1H), 6.448 (s, 1H), 3.723 (s, 3H), 3.509 (s, 2H), 3.157-3.190 (m, 2H), 2.908-2.996 (m, 1H), 2.398 (s, 7H), 2.176 (s, 3H), 1.042 (t, J=7.2 Hz, 3H), 0.839-0.857 (m, 6H).
ESMS clcd for C27H35FN6O3: 510.60. Found: 511.2 (M⁺).

Compound 282
¹H NMR (400 MHz, DMSO), δ (ppm): 10452 (s, 1H), 9.163 (s, 1H), 9.057 (t, J=5.6 Hz, 1H), 7.675 (d, J=8.0 Hz, 2H), 7.489-7.557 (m, 2H), 7.288 (d, J=8.0 Hz, 1H), 6.703 (s, 1H), 6.439 (s, 1H), 6.541 (s, 1H), 3.724 (s, 4H), 3.143-3.209 (m, 2H), 2.911-2.978 (m, 1H), 1.051 (t, J=6.8 Hz, 3H), 0.6785 (d, J=6.8 Hz, 7H).
ESMS clcd for C25H27FN6O3: 478.52. Found: 477.5 (M⁻).

Compound 283
¹H NMR (400 MHz, DMSO), δ (ppm): 10.425 (s, 1H), 8.42 (d, J=8.0 Hz, 1H), 7.719 (s, 1H), 7.460 (d, J=10.4 Hz, 1H), 7.270 (t, J=8.0 Hz, 1H), 7.159-7.208 (m, 2H), 6.921 (s, 1H), 6.726 (s, 1H), 6.425 (s, 1H), 5.301 (s, 2H), 3.919-3.987 (m, 1H), 3.729 (s, 3H), 2.927-2.992 (m, 1H), 1.118 (d, J=6.4 Hz, 6H), 0.831-0.847 (d, J=6.4 Hz, 6H).
ESMS clcd for C26H29FN6O3: 492.55. Found: 491.6 (M⁻).

Compound 284
¹H NMR (400 MHz, DMSO), δ (ppm): 10.339 (s, 1H), 9.660 (t, J=6.4 Hz, 1H), 7.721 (s, 1H), 7.500 (d, J=11.2 Hz, 1H), 7.211-7.285 (m, 2H), 7.162 (s, 1H), 6.924 (s, 1H), 6.767 (s, 1H), 6.424 (s, 1H), 6.300 (s, 2H), 3.923-4.008 (m, 2H), 3.728 (s, 3H), 2.929-2.997 (m, 1H), 0.788-0.856 (dd, J₁=6.8 Hz, J₂=12.8 Hz, 6H).
ESMS clcd for C25H24F4N6O3: 532.49. Found: 531.4 (M⁻).

Compound 285
¹H NMR (400 MHz, DMSO), δ (ppm): 10.583 (s, 1H), 9.012 (t, J=5.2 Hz, 1H), 7.443 (t, J=8.0 Hz, 1H), 7.360 (d, J=8.8 Hz, 1H), 7.178 (d, J=6.0 Hz, 1H), 6.724 (s, 1H), 6.456 (s, 1H), 3.733 (s, 3H), 3.523 (s, 2H), 3.149-3.218 (m, 2H), 2.955-2.989 (m, 1H), 2.337-2.414 (m, 9H), 1.052 (t, J=7.2 Hz, 3H), 0.983 (t, J=7.2 Hz, 3H), 0.852 (d, J=6.8 Hz, 6H). ESMS clcd for C28H37FN6O3: 524.63. Found: 525.2 (M$^+$).

Compound 286

$^1$H NMR (400 MHz, DMSO), δ (ppm): 10.559 (s, 1H), 8.823 (d, J=8.0 Hz, 1H), 7.479 (t, J=8.0 Hz, 1H), 7.387 (d, J=8.4 Hz, 1H), 7.188 (d, J=6.0 Hz, 1H), 6.746 (s, 1H), 6.463 (s, 1H), 3.947-3.968 (m, 1H), 3.745 (s, 3H), 3.544-3.590 (m, 6H), 2.969-3.004 (m, 1H), 2.397 (t, J=4.4 Hz, 4H), 1.108 (d, J=6.4 Hz, 6H), 0.868 (d, J=7.2 Hz, 6H).

ESMS clcd for C27H34FN5O4: 511.59. Found: 512.6 (M$^+$).

Compound 287

$^1$H NMR (400 MHz, DMSO), δ (ppm): 10.597 (s, 1H), 9.013 (t, J=6.4 Hz, 1H), 7.474 (t, J=8.4 Hz, 1H), 7.401 (d, J=8.4 Hz, 1H), 7.194 (d, J=6.0 Hz, 1H), 6.738 (s, 1H), 6.466 (s, 1H), 3.744 (s, 3H), 3.543-3.592 (m, 6H), 3.178-3.211 (m, 2H), 2.966-3.000 (m, 1H), 2.411 (t, J=4.4 Hz, 4H), 1.063 (t, J=7.6 Hz, 3H), 0.862 (d, J=6.8 Hz, 6H).

ESMS clcd for C26H32FN5O4: 497.56. Found: 498.5 (M$^+$).

Compound 288

$^1$H NMR (400 MHz, DMSO), δ (ppm): 10.526 (s, 1H), 8.848 (d, J=7.6 Hz, 1H), 7.470 (t, J=8.8 Hz, 1H), 7.390 (d, J=8.8 Hz, 1H), 7.191 (d, J=8.8 Hz, 1H), 6.762 (s, 1H), 6.477 (s, 1H), 3.954-3.971 (m, 1H), 3.746 (s, 3H), 3.578 (s, 2H), 2.981-3.014 (m, 1H), 1.131 (t, J=6.4 Hz, 9H), 0.884 (d, J=6.8 Hz, 6H).

ESMS clcd for C29H39FN6O3: 538.66. Found: 539.3 (M$^+$).

Compound 289

$^1$H NMR (400 MHz, DMSO), δ (ppm): 10.511 (s, 1H), 8.832 (d, J=7.6 Hz, 1H), 7.463 (t, J=7.6 Hz, 1H), 7.384 (d, J=8.8 Hz, 1H), 7.189 (d, J=8.8 Hz, 1H), 6.745 (s, 1H), 6.455 (s, 1H), 3.945-3.968 (m, 1H), 3.740 (s, 3H), 3.569 (s, 2H), 2.970-3.008 (m, 1H), 2.712 (s, 4H), 2.430 (s, 3H), 1.107 (d, J=6.8 Hz, 6H), 0.889 (d, J=7.6 Hz, 6H).

ESMS clcd for C28H37FN6O3: 524.63. Found: 525.3 (M$^+$).

Compound 290

$^1$H NMR (400 MHz, DMSO), δ (ppm): 10.401 (s, 1H), 9.569 (t, J=5.6 Hz, 1H), 7.407-7.491 (m, 2H), 7.200 (d, J=10.4 Hz, 1H), 6.800 (s, 1H), 6.472 (s, 1H), 3.968-4.009 (m, 2H), 3.746 (s, 3H), 3.599 (s, 2H), 2.986-3.020 (m, 1H), 1.139 (s, 1H), 0.894 (d, J=6.4 Hz, 6H). ESMS clcd for C28H34F4N6O3: 578.6. Found: 579.4 (M$^+$).

Compound 291

$^1$H NMR (400 MHz, DMSO), δ (ppm): 10.457 (s, 1H), 9.644 (t, J=8.0 Hz, 1H), 7.472 (t, J=8.0 Hz, 2H), 7.424 (d, J=10.0 Hz, 1H), 7.215 (d, J=8.0 Hz, 1H), 6.784 (s, 1H), 6.461 (s, 1H), 3.966-4.006 (m, 2H), 3.744 (s, 3H), 3.540-3.587 (m, 6H), 2.973-2.997 (m, 1H), 2.392 (s, 4H), 0.878 (d, J=6.8 Hz, 6H).

ESMS clcd for C26H29F4N5O4: 551.53. Found: 552.5 (M$^+$).

Compound 292

$^1$H NMR (400 MHz, DMSO), δ (ppm): 10.975 (s, 1H), 10.756 (s, 1H), 8.285 (s, 1H), 7.775 (s, 1H), 7.482 (s, 1H), 7.303-6.983 (m, 10H), 6.445 (s, 1H), 2.642 (m, 2H), 2.511 (m, 2H), 2.204 (s, 3H).

ESMS clcd for $C_{24}H_{23}N_5O_5S$: 493.53. Found: 492.1 (M$^-$).

Compound 293

$^1$H NMR (400 MHz, DMSO), δ (ppm): 10.944 (s, 1H), 10.730 (s, 1H), 9.377 (s, 1H), 8.276 (s, 1H), 7.748 (s, 2H), 7.459 (s, 1H), 7.069-7.047 (m, 2H), 6.994-6.960 (m, 4H), 6.901 (m, 1H), 6.776 (d, J=9.2 Hz, 1H), 6.697 (t, J=8.0 Hz, 1H), 6.437 (s, 1H), 2.828-2.780 (m, 2H), 2.591 (m, 2H), 2.193 (s, 3H).

ESMS clcd for $C_{24}H_{23}N_5O_6S$: 509.53. Found: 510.3 (M$^+$).

Compound 294

$^1$H NMR (400 MHz, DMSO), δ (ppm): 10.806 (s, 1H), 9.341 (s, 1H), 8.274 (s, 1H), 7.750 (s, 2H), 7.466 (s, 1H), 7.078-7.039 (m, 1H), 7.006 (d, J=8.4 Hz, 1H), 6.931 (m, 1H), 6.600 (d, J=8.4 Hz, 1H), 6.542-6.516 (m, 3H), 2.810-2.775 (m, 2H), 2.538 (m, 2H), 2.202 (s, 3H).

ESMS clcd for $C_{24}H_{23}N_5O_6S$: 509.53. Found: 510.3 (M$^+$).

Compound 295

$^1$H NMR (400 MHz, DMSO), δ (ppm): 10.745 (m, 2H), 8.274 (s, 1H), 7.747 (s, 2H), 7.425 (s, 1H), 7.152-7.099 (dd, $J_1$=8.0 Hz, $J_2$=13.2, 4H), 6.842 (m, 1H), 6.410 (s, 1H), 2.430 (d, J=6.8 Hz, 2H), 2.290 (s, 3H), 1.628-1.605 (m, 5H), 1.271 (m, 1H), 1.091-1.075 (m, 3H), 0.781-0.683 (m, 2H).

ESMS clcd for $C_{23}H_{27}N_5O_5S$: 485.56. Found: 486.2 (M$^+$).

Compound 296

$^1$H NMR (400 MHz, DMSO), δ (ppm): 10.751 (m, 1H), 8.465 (d, J=4.0 Hz, 1H), 8.275 (s, 1H), 7.743 (s, 1H), 7.682 (t, J=6.4 Hz, 1H), 7.440 (s, 1H), 7.227-7.172 (m, 2H), 7.095-7.027 (dd, $J_1$=8.8 Hz, $J_2$=18.4 Hz, 4H), 6.393 (s, 1H), 2.984 (t, J=8.0 Hz, 2H), 2.801 (t, J=8.0 Hz, 2H), 2.215 (s, 3H).

ESMS clcd for $C_{23}H_{22}N_6O_5S$: 494.52. Found: 495.1 (M$^+$).

Compound 297

$^1$H NMR (400 MHz, DMSO), δ (ppm): 10.756 (m, 2H), 9.215 (s, 1H), 8.276 (s, 1H), 7.746 (s, 1H), 7.460 (s, 1H), 7.086-6.993 (dd, $J_1$=8.8 Hz, $J_2$=28.0 Hz, 4H), 6.910 (d, J=8.4 Hz, 2H), 6.662 (d, J=7.6 Hz, 2H), 6.398 (s, 1H), 2.760 (t, J=7.6 Hz, 2H), 2.206 (s, 3H). ESMS clcd for $C_{24}H_{23}N_5O_6S$: 509.5. Found: 508.0 (M$^-$).

Compound 298

$^1$H NMR (400 MHz, CD$_3$OD), δ (ppm): 7.364 (s, 1H), 7.142-7.067 (dd, $J_1$=8.4 Hz, $J_2$=21.6 Hz, 4H), 6.095 (s, 1H), 3.116-3.089 (m, 2H), 2.985-2.957 (m, 2H), 2.596 (s, 3H), 2.237 (s, 3H), 1.918-1.885 (m, 2H), 1.608-1.578 (m, 1H), 1.339-1.244 (m, 4H), 1.088 (m, 2H), 0.800 (m, 2H).

ESMS clcd for $C_{25}H_{32}N_6O_5S$: 528.6. Found: 529.0 (M$^+$).

Compound 299

$^1$H NMR (400 MHz, CD$_3$OD), δ (ppm): 7.197 (s, 1H), 7.110-6.972 (m, 8H), 5.978 (s, 1H), 3.363 (s, 2H), 2.634-2.610 (m, 2H), 2.220-2.212 (m, 6H), 1.967-1.901 (m, 2H), 1.547-1.521 (m, 2H), 1.398-1.298 (m, 2H), 0.816-0.771 (m, 2H).

ESMS clcd for $C_{29}H_{32}N_6O_5S$: 576.7. Found: 577.3 (M$^+$).

Compound 300

$^1$H NMR (400 MHz, DMSO), δ (ppm): 10.912 (s, 1H), 10.711 (s, 1H), 8.954 (m, 1H), 8.251 (s, 1H), 7.748 (s, 1H), 7.471 (s, 1H), 7.165-7.096 (dd, $J_1$=8.0 Hz, $J_2$=19.6 Hz, 4H), 6.418 (s, 1H), 3.109-3.057 (m, 4H), 2.971 (t, J=8.4 Hz, 2H), 2.675-2.646 (m, 2H), 2.300 (s, 3H), 1.586 (m, 2H), 1.420-1.404 (m, 2H), 1.179 (t, J=7.2 Hz, 6H).

ESMS clcd for $C_{24}H_{32}N_5O_6S$: 516.6. Found: 517.2 (M$^+$).

Compound 301

$^1$H NMR (400 MHz, CD$_3$OD), δ (ppm): 7.541-7.502 (m, 2H), 7.237-7.230 (m, 1H), 7.124-7.032 (s, 6H), 6.291 (s, 1H), 4.433 (s, 2H), 3.401-3.375 (m, 2H), 2.945-2.886 (m, 2H), 2.258 (s, 3H), 1.904-1.790 (m, 3H), 1.655-1.570 (m, 2H).

ESMS clcd for $C_{28}H_{26}N_6O_5S_2$: 568.67. Found: 569.3 (M$^+$).

Compound 302

¹H NMR (400 MHz, DMSO), δ (ppm): 6.878 (s, 1H), 6.331 (s, 1H), 4.469-4.530 (m, 1H), 4.066-4.132 (m, 1H), 3.087-3.158 (m, 1H), 2.406 (s, 3H), 2.250-2.321 (m, 3H), 2.157 (s, 1H), 1.858-1.894 (m, 2H), 1.673 (s, 4H), 1.571-1.597 (m, 2H), 1.307-1.370 (m, 2H), 1.197-1.213 (m, 6H), 1.088-1.108 (m, 6H).

ESMS clcd for $C_{25}H_{37}N_5O3$: 455.59. Found: 456.5 (M⁺).

Compound 303

¹H NMR (400 MHz, DMSO), δ (ppm): 9.604 (s, 1H), 9.538 (s, 1H), 8.749 (d, J=7.6 Hz, 1H), 6.812 (s, 1H), 6.462 (s, 1H), 4.491-4.559 (m, 1H), 4.056-4.107 (m, 1H), 3.063-3.129 (m, 1H), 2.422-2.439 (m, 5H), 2.141-2.233 (m, 2H), 1.853-1.906 (m, 2H), 1.456-1.481 (m, 2H), 1.498-1.259 (m, 2H), 1.072-1.235 (m, 12H), 0.810 (t, J=6.8 Hz, 6H).

ESMS clcd for C25H39N5O3: 457.61. Found: 458.4 (M⁺).

Compound 304

¹H NMR (400 MHz, DMSO), δ (ppm): 9.560-9.653 (m, 2H), 8.878 (s, 1H), 6.846 (s, 1H), 6.500 (s, 1H), 4.570 (s, 1H), 4.073-4.142 (m, 1H), 3.397 (s, 1H), 3.080-3.149 (m, 1H), 2.174-2.236 (m, 4H), 2.000 (s, 2H), 1.917 (s, 1H), 1.489 (s, 6H), 1.413 (s, 3H), 1.363 (s, 2H), 1.194-1.292 (m, 6H), 1.121 (d, J=6.8 Hz, 6H).

ESMS clcd for C26H39N5O3: 469.62. Found: 470.5 (M⁺).

Compound 305

¹H NMR (400 MHz, DMSO), δ (ppm): 9.640 (s, 1H), 9.560 (s, 1H), 8.733 (d, J=7.6 Hz, 1H), 6.808 (s, 1H), 6.477 (s, 1H), 4.661-4.722 (m, 1H), 4.080-4.132 (m, 1H), 3.470 (s, 4H), 3.394 (s, 1H), 3.076-3.141 (m, 1H), 2.144-2.174 (m, 6H), 1.890-1.965 (m, 3H), 1.436 (d, J=9.2 Hz, 2H), 1.238 (s, 2H), 1.159-1.194 (m, 6H), 1.118 (d, J=6.8 Hz, 6H). ESMS clcd for C25H37N5O4: 471.59. Found: 472.5 (M⁺).

Compound 306

¹H NMR (400 MHz, DMSO), δ (ppm): 9.718 (d, J=10.0 Hz, 2H), 8.748 (d, J=8.8 Hz, 1H), 6.881 (s, 1H), 6.485 (s, 1H), 4.585 (d, J=4.0 Hz, 1H), 4.063-4.115 (m, 2H), 3.255-3.311 (m, 1H), 3.089-3.123 (m, 1H), 2.163-2.191 (m, 2H), 1.792 (d, J=10.0 Hz, 2H), 1.713 (d, J=10.8 Hz, 2H), 1.105-1.175 (dd, $J_1$=6.0 Hz, $J_2$=7.6 Hz, 12H), 1.039-1.071 (m, 2H). ESMS clcd for C22H32N4O4: 416.51. Found: 417.5 (M⁺).

Compound 307

¹H NMR (400 MHz, CD3OD), δ (ppm): 6.904 (s, 1H), 6.362 (s, 1H), 4.700-4.642 (m, 2H), 4.161-4.094 (m, 1H), 3.179-3.102 (m, 1H), 2.683-2.643 (m, 5H), 2.494 (s, 3H), 2.355-2.185 (m, 4H), 1.990-1.954 (m, 2H), 1.579-1.550 (m, 2H), 1.365-1.269 (m, 2H), 1.214 (d, J=6.4, 6H), 1.104 (d, J=7.6 Hz, 6H)

ESMS clcd for $C_{26}H_{40}N_6O_3$: 484.63. Found: 485.3 (M⁺).

Compound 308

¹H NMR (400 MHz, CD3OD), δ (ppm): 6.895 (s, 1H), 6.367 (s, 1H), 4.770-4.707 (m, 1H), 4.076-4.009 (m, 2H), 3.586 (t, J=7.6 Hz, 4H), 3.170-3.115 (m, 1H), 2.365 (m, 4H), 2.317-2.215 (m, 2H), 2.151 (m, 1H), 2.006-1.962 (m, 2H), 1.570-1.546 (m, 2H), 1.358-1.288 (m, 2H), 1.099 (d, J=7.2 Hz, 6H).

ESMS clcd for $C_{24}H_{32}F_3N_5O_4$: 511.54. Found: 512.3 (M⁺).

Compound 309

¹H NMR (400 MHz, CD3OD), δ (ppm): 6.945 (s, 1H), 6.374 (s, 1H), 4.552-4.527 (m, 1H), 4.097-4.029 (m, 2H), 3.160-3.091 (m, 1H), 2.824 (m, 4H), 2.303-2.206 (m, 2H), 2.165-2.131 (m, 2H), 1.811-1.726 (m, 7H), 1.523 (m, 4H), 1.109 (d, J=6.8 Hz, 6H).

ESMS clcd for $C_{25}H_{34}F_3N_5O_3$: 509.56. Found: 510.2 (M⁺).

Compound 310

¹H NMR (400 MHz, CD3OD), δ (ppm): 6.907 (s, 1H), 6.359 (s, 1H), 4.076-4.006 (m, 2H), 3.172-3.105 (m, 1H), 2.645-2.433 (m, 10H), 2.311-2.219 (m, 3H), 2.113 (m, 1H), 1.976-1.938 (m, 2H), 1.549-1.525 (m, 2H), 1.349-1.282 (m, 2H), 1.106 (d, J=7.2 Hz, 6H). ESMS clcd for $C_{25}H_{35}F_3N_6O_3$: 524.58. Found: 525.2 (M⁺).

Compound 311

¹H NMR (400 MHz, CD3OD), δ (ppm): 6.917 (s, 1H), 6.356 (s, 1H), 4.758-4.718 (m, 1H), 4.075-4.005 (m, 2H), 3.162-3.092 (m, 1H), 2.833-2.531 (m, 9H), 2.334-2.244 (m, 3H), 2.148 (m, 1H), 1.984-1.948 (m, 2H), 1.558-1.532 (m, 2H), 1.365-1.294 (m, 2H), 1.190 (t, J=7.2 Hz, 3H), 1.109 (d, J=6.4 Hz, 6H).

ESMS clcd for $C_{26}H_{37}F_3N_6O_3$: 538.61. Found: 539.3 (M⁺).

Compound 312

¹H NMR (400 MHz, CD3OD), δ (ppm): 6.922 (s, 1H), 6.343 (s, 1H), 4.542-4.526 (m, 1H), 4.067-3.998 (m, 2H), 3.161-3.074 (m, 1H), 2.934-2.755 (m, 4H), 2.305-2.215 (m, 2H), 1.999-1.966 (m, 2H), 1.911-1.889 (m, 4H), 1.795 (m, 3H), 1.574-1.511 (m, 2H), 1.090 (d, J=6.8 Hz, 6H).

ESMS clcd for $C_{24}H_{32}F_3N_5O_3$: 495.54. Found: 494.1 (M⁻).

Compound 313

¹H NMR (400 MHz, CD3OD), δ (ppm): 6.978 (s, 1H), 6.383 (s, 1H), 4.803 (m, 1H), 4.370-4.295 (m, 1H), 3.343 (m, 1H), 3.154-3.085 (m, 4H), 2.850-2.813 (m, 1H), 2.373-2.259 (m, 2H), 2.192-2.125 (m, 6H), 2.044-2.009 (m, 2H), 1.796-1.726 (m, 2H), 1.109 (d, J=6.4 Hz, 6H), 0.800-0.748 (m, 2H), 0.700-0.670 (m, 2H).

ESMS clcd for $C_{25}H_{35}N_5O_3$: 453.58. Found: 454.2 (M⁺).

Compound 314

¹H NMR (400 MHz, CD3OD), δ (ppm): 6.871 (s, 1H), 6.359 (s, 1H), 4.692 (m, 1H), 3.583 (m, 4H), 3.149-3.115 (m, 1H), 2.847-2.812 (m, 1H), 2.320-2.184 (m, 6H), 2.082 (m, 1H), 1.997-1.959 (m, 2H), 1.564-1.530 (m, 2H), 1.336-1.270 (m, 2H), 1.094 (d, J=6.8 Hz, 6H), 0.779-0.759 (m, 2H), 0.629 (m, 2H).

ESMS clcd for $C_{25}H_{35}N_5O_4$: 469.58. Found: 470.2 (M⁺).

Compound 315

¹H NMR (400 MHz, CD3OD), δ (ppm): 6.870 (s, 1H), 6.345 (s, 1H), 4.744-4.727 (m, 1H), 3.150-3.099 (m, 1H), 2.837-2.792 (m, 1H), 2.323-2.161 (m, 12H), 2.051-1.941 (m, 2H), 1.541-1.516 (m, 2H), 1.328-1.246 (m, 4H), 1.098 (d, J=6.8 Hz, 6H), 0.772-0.743 (m, 2H), 0.642-0.624 (m, 2H).

ESMS clcd for $C_{26}H_{38}N_6O_3$: 482.62. Found: 483.2 (M⁺).

Compound 316

¹H NMR (400 MHz, CD3OD), δ (ppm): 6.905 (s, 1H), 6.354 (s, 1H), 4.663 (m, 1H), 3.112-3.088 (m, 1H), 2.918-2.792 (m, 6H), 2.298-2.187 (m, 4H), 1.992-1.974 (m, 2H), 1.603-1.567 (m, 2H), 1.381-1.327 (m, 2H), 1.198 (t, J=7.2 Hz, 3H), 1.104 (d, J=6.4 Hz, 6H), 0.790-0.741 (m, 2H), 0.648-0.621 (m, 2H).

ESMS clcd for $C_{27}H_{40}N_6O_3$: 496.64. Found: 497.3 (M⁺).

Compound 317

¹H NMR (400 MHz, CD3OD), δ (ppm): 6.956 (s, 1H), 6.375 (s, 1H), 4.402 (m, 1H), 3.154-2.814 (m, 7H), 2.355-2.222 (m, 5H), 1.925 (m, 6H), 1.650-1.588 (m, 4H), 1.106 (d, J=6.8 Hz, 6H), 0.800-0.776 (m, 2H), 0.687-0.680 (m, 2H).

ESMS clcd for $C_{26}H_{37}N_5O_3$: 467.6. Found: 468.0 (M⁺).

Compound 318

¹H NMR (400 MHz, CD3OD), δ (ppm): 6.977 (s, 1H), 6.378 (s, 1H), 4.343 (m, 1H), 3.410-3.355 (m, 2H), 3.135-

3.120 (m, 5H), 2.371-1.992 (m, 11H), 1.747-1.693 (m, 2H), 1.189 (t, J=7.2 Hz, 3H), 1.110 (d, J=6.8 Hz, 6H).

ESMS clcd for $C_{24}H_{35}N_5O_3$: 441.57. Found: 442.1 ($M^+$).

Compound 319

$^1$H NMR (400 MHz, CD3OD), δ (ppm): 8.523 (s, 1H), 7.913 (s, 1H), 6.934 (s, 1H), 6.377 (s, 1H), 4.696 (m, 1H), 4.118 (m, 1H), 3.464-3.437 (m, 2H), 3.136-3.072 (m, 4H), 3.036-3.006 (m, 2H), 2.912 (m, 1H), 2.807-2.778 (m, 1H), 2.694 (m, 2H), 2.284-2.046 (m, 5H), 1.968-1.915 (m, 2H), 1.557 (m, 2H), 1.314-1.200 (m, 14H), 1.106 (d, J=6.0 Hz, 6H). ESMS clcd for $C_{27}H_{42}N_6O_3$: 498.66. Found: 499.1 ($M^+$).

Compound 320

$^1$H NMR (400 MHz, CD3OD), δ (ppm): 6.966 (s, 1H), 6.374 (s, 1H), 4.493-4.436 (m, 1H), 4.099-4.030 (m, 2H), 3.149-3.046 (m, 5H), 2.316-2.210 (m, 2H), 2.142-2.103 (m, 2H), 1.893-1.868 (m, 2H), 1.650-1.582 (m, 2H), 1.201-1.140 (m, 7H), 1.111 (d, J=7.2 Hz, 6H). ESMS clcd for $C_{24}H_{34}F_3N_5O_3$: 497.55. Found: 496.3 ($M^-$).

Compound 321

$^1$H NMR (400 MHz, CD3OD), δ (ppm): 6.996 (s, 1H), 6.455 (s, 1H), 4.838 (m, 1H), 3.488-3.434 (m, 2H), 3.230-2.589 (m, 11H), 2.377-2.267 (m, 4H), 2.085-2.046 (m, 2H), 1.668-1.637 (m, 2H), 1.460-1.387 (m, 2H), 1.275 (t, J=7.2 Hz, 3H), 1.198 (d, J=6.8 Hz, 6H). ESMS clcd for $C_{25}H_{38}N_6O_3$: 470.61. Found: 471.2 ($M^+$).

Compound 322

$^1$H NMR (400 MHz, CD3OD), δ (ppm): 7.067 (s, 1H), 6.482 (s, 1H), 4.463 (m, 1H), 3.514-3.496 (m, 2H), 3.236-3.201 (m, 6H), 2.475-2.328 (m, 4H), 2.020 (m, 6H), 1.782-1.718 (m, 4H), 1.316 (t, J=8.0 Hz, 3H), 1.208 (d, J=6.8 Hz, 6H).

ESMS clcd for $C_{25}H_{37}N_5O_3$: 455.59. Found: 456.2 ($M^+$).

Compound 323

$^1$H NMR (400 MHz, CD3OD), δ (ppm): 6.873 (s, 1H), 6.359 (s, 1H), 4.709 (m, 1H), 3.557-3.509 (m, 4H), 3.376-3.358 (m, 2H), 3.158-3.114 (m, 1H), 2.311-1.947 (m, 9H), 1.555-1.533 (m, 2H), 1.324-1.249 (m, 2H), 1.180 (t, J=7.2 Hz, 3H), 1.094 (d, J=6.4 Hz, 6H). ESMS clcd for $C_{24}H_{35}N_5O_4$: 457.57. Found: 458.2 ($M^+$).

Compound 324

$^1$H NMR (400 MHz, CD3OD), δ (ppm): 6.870 (s, 1H), 6.328 (s, 1H), 4.739 (m, 1H), 3.374-3.309 (m, 2H), 3.147-3.076 (m, 1H), 2.608-2.073 (m, 13H), 1.965-1.926 (m, 2H), 1.544-1.512 (m, 2H), 1.343-1.256 (m, 2H), 1.163 (t, J=7.2 Hz, 3H), 1.089 (d, J=7.2 Hz, 6H). ESMS clcd for $C_{26}H_{40}N_6O_3$: 484.63. Found: 485.2 ($M^+$).

Compound 325

$^1$H NMR (400 MHz, CD3OD), δ (ppm): 6.936 (s, 1H), 6.347 (s, 1H), 4.510 (m, 1H), 4.103-4.070 (m, 1H), 3.732-3.699 (m, 2H), 3.122-3.086 (m, 1H), 2.902-2.847 (m, 2H), 2.773-2.710 (m, 2H), 2.435-2.394 (m, 2H), 1.857-1.835 (m, 2H), 1.204-1.061 (m, 21H).

ESMS clcd for $C_{22}H_{33}N_5O_5S$: 479.59. Found: 478.1 ($M^-$).

Compound 326

$^1$H NMR (400 MHz, CD$_3$OD), δ (ppm): 6.843 (s, 1H), 6.309 (s, 1H), 4.580-4.539 (m, 1H), 3.114-3.080 (m, 1H), 2.798-2.780 (m, 1H), 2.553-2.539 (m, 5H), 2.247-2.214 (m, 2H), 1.938-1.904 (m, 2H), 1.582-1.559 (m, 2H), 1.082 (d, J=6.8 Hz, 6H), 0.874 (t, J=7.2 Hz, 3H), 0.746-0.733 (m, 2H), 0.608-0.588 (m, 2H).

ESMS clcd for $C_{25}H_{37}N_5O_3$: 455.59. Found: 456.1 ($M^+$).

Compound 327

$^1$H NMR (400 MHz, CD$_3$OD), δ (ppm): 6.936 (s, 1H), 6.354 (s, 1H), 4.401-4.355 (m, 1H), 3.379-3.361 (m, 2H), 3.134-3.088 (m, 6H), 2.327-2.228 (m, 2H), 2.143-2.094 (m, 2H), 1.896 (m, 2H), 1.612 (m, 2H), 1.187-1.085 (m, 15H).

ESMS clcd for $C_{24}H_{37}N_5O_3$: 443.58. Found: 444.2 ($M^+$).

Compound 328

$^1$H NMR (400 MHz, DMSO), δ (ppm): 9.708 (m, 2H), 9.558 (t, J=6.4 Hz, 1H), 6.894 (s, 1H), 6.460 (s, 1H), 4.223-4.148 (m, 1H), 4.090-4.002 (m, 2H), 3.150-3.037 (m, 1H), 2.615-2.526 (m, 4H), 2.391-2.310 (m, 2H), 2.014-1.984 (m, 2H), 1.088 (d, J=6.8 Hz, 6H). ESMS clcd for $C_{19}H_{23}F_3N_4O_3S$: 444.47. Found: 445.2 ($M^+$).

Compound 329

$^1$H NMR (400 MHz, DMSO), δ (ppm): 10.584 (s, 1H), 9.773 (s, 1H), 9.519 (t, J=6.4 Hz, 1H), 7.158 (d, J=9.2 Hz, 2H), 6.952 (d, J=9.2 Hz, 2H), 6.601 (s, 1H), 6.322 (s, 1H), 3.896-3.984 (m, 2H), 3.172 (t, J=4.4 Hz, 4H), 2.877-2.947 (m, 1H), 2.321-2.374 (m, 2H), 1.014 (t, J=7.2 Hz, 3H), 0.840 (d, J=7.2 Hz, 6H).

ESMS clcd for C26H31F3N6O3: 532.56. Found: 533.4 ($M^+$).

Compound 330

$^1$H NMR (400 MHz, DMSO), δ (ppm): 10.463 (s, 1H), 8.889 (d, J=6.4 Hz, 1H), 8.375 (s, 1H), 7.835 (s, 1H), 7.797 (d, J=8.8 Hz, 2H), 7.541 (d, J=8.8 Hz, 2H), 7.162 (s, 1H), 6.817 (s, 1H), 6.460 (s, 1H), 3.975-3.987 (m, 2H), 3.754 (s, 3H), 2.522-2.540 (m, 1H), 1.145 (d, J=6.0 Hz, 6H), 0.911 (d, J=12.8 Hz, 6H).

ESMS clcd for C25H28N6O3: 460.53. Found: 461.4 ($M^+$).

Compound 331

$^1$H NMR (400 MHz, DMSO), δ (ppm): 10.377 (s, 1H), 9.720 (t, J=6.0 Hz, 1H), 8.358 (s, 1H), 7.836 (s, 1H), 7.794 (d, J=9.2 Hz, 2H), 7.550 (d, J=8.8 Hz, 2H), 7.161 (s, 1H), 6.860 (s, 1H), 6.458 (s, 1H), 3.984-4.031 (m, 2H), 3.753 (s, 3H), 2.999-3.033 (m, 1H), 0.922 (d, J=6.8 Hz, 6H).

ESMS clcd for C24H23F3N6O3: 500.47. Found: 501.5 (W).

Compound 332

$^1$H NMR (400 MHz, DMSO), δ (ppm): 11.011 (s, 1H), 8.944 (t, J=5.6 Hz, 1H), 7.201 (d, J=8.8 Hz, 2H), 7.001 (d, J=9.2 Hz, 2H), 6.639 (s, 1H), 6.495 (s, 1H), 3.754 (s, 3H), 3.150-3.217 (m, 6H), 2.949-2.983 (m, 1H), 2.352-2.406 (m, 2H), 1.027-1.07 (m, 6H), 0.807 (d, J=7.2 Hz, 6H).

ESMS clcd for C27H36N6O3: 492.61. Found: 493.4 (W).

Compound 333

$^1$H NMR (400 MHz, DMSO), δ (ppm): 10.993 (s, 1H), 8.925 (t, J=6.0 Hz, 1H), 7.198 (d, J=8.8 Hz, 2H), 7.000 (d, J=5.2 Hz, 2H), 6.645 (s, 1H), 6.494 (s, 1H), 3.754 (s, 3H), 3.204 (s, 4H), 3.089-3.139 (m, 2H), 2.933-3.002 (m, 1H), 2.350-2.408 (m, 2H), 1.436-1.490 (s, 2H), 1.046 (t, J=7.2 Hz, 3H), 0.844 (d, J=7.2 Hz, 9H).

ESMS clcd for C28H38N6O3: 506.64. Found: 507.2 (W).

Compound 334

$^1$H NMR (400 MHz, DMSO), δ (ppm): 11.010 (s, 1H), 8.68 (d, J=4.8 Hz, 1H), 7.200 (d, J=4.8 Hz, 2H), 7.000 (d, J=5.2 Hz, 2H), 6.638 (s, 1H), 6.496 (s, 1H), 3.754 (s, 3H), 3.207 (s, 4H), 2.931-2.999 (m, 1H), 2.511 (s, 3H), 2.355-2.408 (m, 2H), 1.045 (t, J=7.6 Hz, 3H), 0.823 (d, J=6.8 Hz, 6H).

ESMS clcd for C26H34N6O3: 478.59. Found: 477.2 ($M^-$).

Compound 335

$^1$H NMR (400 MHz, DMSO), δ (ppm): 11.013 (s, 1H), 8.831 (d, J=7.6 Hz, 1H), 7.175 (d, J=8.8 Hz, 2H), 7.009 (d, J=8.8 Hz, 2H), 6.644 (s, 1H), 6.496 (s, 1H), 4.021-4.113 (m, 1H), 3.755 (s, 3H), 3.206 (s, 4H), 2.933-3.001 (m, 1H), 2.350-2.403 (m, 2H), 1.751-1.854 (m, 2H), 1.643 (s, 2H), 1.484 (s, 4H), 1.043 (t, J=7.2 Hz, 3H), 0.826 (d, J=6.8 Hz, 6H). ESMS clcd for C30H40N6O3: 532.68. Found: 531.3 (M⁻).

Compound 336

¹H NMR (400 MHz, DMSO), δ (ppm): 11.066 (s, 1H), 8.922 (t, J=6.0 Hz, 1H), 7.175 (t, J=8.4 Hz, 2H), 7.000 (d, J=8.8 Hz, 2H), 6.641 (s, 1H), 6.495 (s, 1H), 3.755 (s, 3H), 3.205 (s, 4H), 3.090-3.140 (m, 2H), 2.933-3.002 (m, 1H), 2.454 (s, 4H), 2.232 (s, 3H), 1.419-1.509 (m, 2H), 0.806-0.843 (m, 9H).

ESMS clcd for C27H36N6O3: 492.61. Found: 493.6 (M⁺).

Compound 337

¹H NMR (400 MHz, DMSO), δ (ppm): 11.014 (s, 1H), 8.878 (d, J=4.8 Hz, 1H), 7.199 (d, J=9.2 Hz, 2H), 7.001 (d, J=8.8 Hz, 2H), 6.634 (s, 1H), 6.496 (s, 1H), 3.754 (s, 3H), 3.208 (s, 4H), 2.931-3.000 (m, 1H), 2.706 (d, J=4.4 Hz, 3H), 2.458 (s, 4H), 2.235 (s, 3H), 0.840 (d, J=6.8 Hz, 6H).

ESMS clcd for C25H32N6O3: 464.56. Found: 465.6 (M⁺).

Compound 338

¹H NMR (400 MHz, DMSO), δ (ppm): 10.978 (s, 1H), 9.003 (d, J=4.4 Hz, 1H), 7.173 (d, J=8.8 Hz, 2H), 7.010 (d, J=9.2 Hz, 2H), 6.645 (s, 1H), 6.490 (s, 1H), 3.752 (s, 3H), 3.215 (s, 4H), 2.948-2.967 (m, 1H), 2.432-2.511 (m, 1H), 2.384-2.402 (m, 2H), 1.049 (t, J=7.2 Hz, 3H), 0.828 (d, J=6.8 Hz, 6H), 0.563-0.652 (m, 4H).

ESMS clcd for C28H36N6O3: 504.62. Found: 505.5 (M⁺).

Compound 339

¹H NMR (400 MHz, DMSO), δ (ppm): 11.011 (s, 1H), 8.755 (d, J=8.0 Hz, 1H), 7.177 (d, J=8.8 Hz, 2H), 7.005 (d, J=8.8 Hz, 2H), 6.644 (s, 1H), 6.496 (s, 1H), 3.980-3.999 (m, 1H), 3.756 (s, 3H), 3.026 (s, 4H), 2.948-2.968 (m, 1H), 2.350-2.404 (m, 1H), 1.097 (d, J=6.4 Hz, 6H), 1.043 (d, J=7.2 Hz, 3H), 0.827 (d, J=6.8 Hz, 6H).

ESMS clcd for C28H38N6O3: 506.64. Found: 507.3 (M⁺).

Compound 340

¹H NMR (400 MHz, DMSO), δ (ppm): 10.831 (s, 1H), 9.568 (t, J=6.4 Hz, 1H), 7.120 (d, J=4.4 Hz, 2H), 6.977 (d, J=8.8 Hz, 2H), 6.677 (s, 1H), 6.478 (s, 1H), 3.946-3.986 (m, 2H), 3.7544 (s, 3H), 3.190 (s, 4H), 2.947-2.981 (m, 1H), 2.337-2.391 (m, 2H), 1.030 (t, J=7.6 Hz, 3H), 0.834 (d, J=6.8 Hz, 6H).

ESMS clcd for C27H33F3N6O3: 546.58. Found: 547.2 (M⁺).

Compound 341

¹H NMR (400 MHz, DMSO), δ (ppm): 10.225 (s, 1H), 9.715 (s, 1H), 8.331 (s, 1H), 7.745-7.810 (m, 4H), 7.501 (d, J=8.8 Hz, 2H), 7.138 (s, 1H), 6.715 (s, 1H), 6.326 (s, 1H), 899-2.943 (m, 1H), 0.887 (d, J=7.2 Hz, 6H).

ESMS clcd for C21H20N6O3: 404.42. Found: 405.4 (M⁺).

Compound 342

¹H NMR (400 MHz, DMSO), δ (ppm): 10.742 (s, 1H), 9.755 (s, 1H), 8.722 (d, J=8.4 Hz, 1H), 7.150 (d, J=8.4 Hz, 2H), 6.974 (d, J=8.8 Hz, 2H), 6.578 (s, 1H), 6.340 (s, 1H), 3.964-3.878 (m, 2H), 3.193-3.179 (m, 4H), 2.956-2.886 (m, 1H), 2.453-2.430 (m, 4H), 2.222 (s, 3H), 1.089 (d, J=7.2 Hz, 6H), 0.834 (d, J=6.8 Hz, 6H).

ESMS clcd for $C_{26}H_{34}N_6O_3$: 478.59. Found: 479.2 (M⁺).

Compound 343

¹H NMR (400 MHz, DMSO), δ (ppm): 10.560 (s, 1H), 9.749 (s, 1H), 9.555-9.544 (m, 1H), 7.137 (d, J=9.6 Hz 2H), 6.933 (d, J=6.4 Hz, 2H), 6.598 (s, 1H), 6.311 (s, 1H), 3.954-3.915 (m, 2H), 3.164 (m, 4H), 2.938-2.887 (m, 1H), 2.409 (m, 4H), 2.192 (s, 3H), 0.826 (d, J=7.6 Hz, 6H).

ESMS clcd for $C_{25}H_{29}F_3N_6O_3$: 518.53. Found: 519.2 (M⁺).

Compound 345

¹H NMR (400 MHz, DMSO), δ (ppm): 10.762 (s, 1H), 9.768 (s, 1H), 8.870-8.848 (m, 1H), 7.154 (d, J=9.2 Hz, 2H), 6.972 (d, J=9.6 Hz, 2H), 6.574 (s, 1H), 6.343 (s, 1H), 3.206-3.183 (m, 4H), 2.939-2.905 (m, 1H), 2.683 (d, J=4.0 Hz, 3H), 2.457-2.434 (m, 4H), 2.223 (s, 3H), 0.830 (d, J=6.8 Hz, 6H).

ESMS clcd for $C_{24}H_{30}N_6O_3$: 450.53. Found: 451.3 (M⁺).

Compound 346

¹H NMR (400 MHz, DMSO), δ (ppm): 10.719 (s, 1H), 9.751 (s, 1H), 8.982 (m, 1H), 7.142 (d, J=9.2 Hz, 2H), 6.983 (d, 2H), 6.330 (s, 1H), 3.191 (m, 4H), 2.934-2.881 (m, 1H), 2.728 (m, 1H), 2.444 (m, 4H), 2.215 (s, 3H), 0.830 (d, J=6.8 Hz, 6H), 0.632-0.552 (m, 4H). ESMS clcd for $C_{26}H_{32}N_6O_3$: 476.57. Found: 477.4 (M⁺).

Compound 347

¹H NMR (400 MHz, DMSO), δ (ppm): 10.752 (s, 1H), 9.772 (s, 1H), 8.932 (t, J=5.6 Hz, 1H), 7.152 (d, J=8.8 Hz, 2H), 6.972 (d, J=9.2 Hz, 2H), 6.576 (s, 1H), 6.338 (s, 1H), 3.184 (m, 6H), 2.957-2.890 (m, 1H), 2.445 (m, 4H), 2.222 (s, 3H), 1.042 (t, J=7.2 Hz, 1H), 0.833 (d, J=6.4 Hz, 6H).

ESMS clcd for $C_{25}H_{32}N_6O_3$: 464.56. Found: 465.2 (M⁺).

Compound 348

¹H NMR (400 MHz, DMSO), δ (ppm): 10.252 (s, 1H), 9.740 (s, 1H), 8.820 (d, J=8.4 Hz, 1H), 7.451-7.367 (dd, J₁=8.8 Hz, J₂=24.8 Hz, 4H), 6.677 (s, 1H), 6.312 (s, 1H), 3.962-3.908 (m, 1H), 3.635-3.615 (m, 2H), 2.961-2.898 (m, 1H), 2.391-2.267 (m, 4H), 2.193 (s, 3H), 1.095 (d, J=6.4 Hz, 6H), 0.870 (d, J=6.8 Hz, 6H).

ESMS clcd for $C_{27}H_{34}N_6O_4$: 506.6. Found: 507.3 (M⁺).

Compound 349

¹H NMR (400 MHz, DMSO), δ (ppm): 10.161 (s, 1H), 9.763 (s, 1H), 9.650 (t, J=8.0 Hz, 1H), 7.446-7.402 (m, 4H), 6.711 (s, 1H), 6.315 (s, 1H), 3.987-3.974 (m, 2H), 3.621 (m, 2H), 2.952-2.920 (m, 1H), 2.384-2.307 (m, 4H), 2.213 (s, 3H), 0.882 (d, J=6.0 Hz, 6H). ESMS clcd for $C_{26}H_{29}F_3N_6O_4$: 546.54. Found: 547.2 (M⁺).

Compound 350

¹H NMR (400 MHz, DMSO), δ (ppm): 10.349 (s, 1H), 9.622 (t, J=6.4 Hz, 1H), 7.400 (m, 4H), 6.741 (s, 1H), 6.399 (s, 1H), 3.954-3.891 (m, 2H), 3.690 (s, 3H), 3.573 (m, 2H), 3.295 (m, 2H), 2.955-2.921 (m, 1H), 2.306-2.226 (m, 4H), 2.154 (s, 3H), 0.840 (d, J=8.0 Hz, 6H). ESMS clcd for $C_{27}H_{31}F_3N_6O_4$: 560.57. Found: 559.2 (M⁻).

Compound 351

¹H NMR (400 MHz, DMSO), δ (ppm): 9.787-9.754 (m, 1H), 7.587-7.538 (dd, J₁=8.0 Hz, J₂=11.2 Hz, 4H), 6.804 (s, 1H), 6.413 (s, 1H), 4.135-4.064 (m, 2H), 3.749-3.711 (m, 2H), 3.107-3.037 (m, 1H), 2.540-2.456 (m, 6H), 1.135 (t, J=7.2 Hz, 3H), 1.003 (d, J=5.6 Hz, 6H).

ESMS clcd for $C_{27}H_{31}F_3N_6O_4$: 560.57. Found: 561.2 (M⁺).

Compound 352

¹H NMR (400 MHz, DMSO), δ (ppm): 8.803 (d, J=8.0 Hz, 1H), 7.478-7.402 (dd, J₁=8.0 Hz, J₂=22.0 Hz, 4H), 6.588 (s, 1H), 6.248 (s, 1H), 3.979-3.912 (m, 1H), 3.633 (m, 2H), 2.982-2.910 (m, 1H), 2.385-2.334 (m, 6H), 1.100 (d, J=6.4 Hz, 6H), 1.008 (t, J=6.0 Hz, 3H), 0.846 (d, J=6.4 Hz, 6H).

ESMS clcd for $C_{28}H_{36}N_6O_4$: 520.62. Found: 519.3 (M⁻).

Compound 353

¹H NMR (400 MHz, DMSO), δ (ppm): 10.809 (s, 1H), 9.804 (s, 1H), 8.727 (d, J=8.0 Hz, 1H), 7.434-7.478 (m, 1H), 7.362 (d, J=6.0 Hz, 1H), 7.183 (d, J=8.4 Hz, 1H), 7.036 (d, J=7.6 Hz, 1H), 6.560 (s, 1H), 6.354 (s, 1H), 4.043-4.083 (m, 1H), 3.885-3.975 (m, 2H), 3.390-3.401 (m, 4H), 2.878-2.931 (m, 1H), 2.440 (t, J=5.2 Hz, 2H), 2.172 (s, 4H), 1.108-1.130 (m, 6H), 0.776-0.830 (dd, $J_1$=6.4 Hz, $J_2$=8.4 Hz, 6H).

ESMS clcd for C27H35N5O5: 509.6. Found: 510.3 (M$^+$).

Compound 354

$^1$H NMR (400 MHz, DMSO), δ (ppm): 10.290 (s, 1H), 8.956 (t, J=5.6 Hz, 1H), 7.272 (d, J=9.2 Hz, 2H), 7.097 (d, J=8.8 Hz, 2H), 6.652 (s, 1H), 6.478 (s, 1H), 4.100 (t, J=5.6 Hz, 2H), 3.747 (s, 3H), 3.150-3.218 (m, 2H), 2.958-3.008 (m, 1H), 2.693 (t, J=6.0 Hz, 2H), 2.309-2.315 (m, 6H), 2.149 (s, 1H), 1.058 (t, J=6.8 Hz, 3H), 0.861 (d, J=6.4 Hz, 6H). ESMS clcd for C28H38N6O4: 522.64. Found: 523.6 (M$^+$).

Compound 355

$^1$H NMR (400 MHz, DMSO), δ (ppm): 11.034 (s, 1H), 10.100 (s, 1H), 9.729 (s, 1H), 8.178 (s, 1H), 7.860 (s, 1H), 7.230-7.337 (m, 2H), 6.868-6.992 (m, 2H), 6.640 (s, 1H), 6.374 (s, 1H), 2.886-2.922 (m, 1H), 0.759-0.812 (dd, $J_1$=6.8 Hz, $J_1$=7.2 Hz, 6H).

ESMS clcd for C18H18N4O4: 354.36. Found: 355.3 (M$^+$).

Compound 356

$^1$H NMR (400 MHz, DMSO), δ (ppm): 10.795 (s, 1H), 8.959 (t, J=6.4 Hz, 1H), 7.291 (d, J=8.8 Hz, 2H), 7.017 (d, J=8.8 Hz, 2H), 6.560 (s, 1H), 6.470 (s, 1H), 4.115 (t, J=5.9 Hz, 2H), 3.743 (s, 3H), 3.578 (t, J=4.4 Hz, 4H), 3.143-3.211 (m, 2H), 2.937-3.004 (m, 1H), 2.689-2.716 (m, 2H), 2.090 (s, 4H), 1.054 (t, J=6.8 Hz, 3H), 0.842 (d, J=6.8 Hz, 6H). ESMS clcd for C27H35N5O5: 509.6. Found: 508.5 (M$^-$).

Compound 357

$^1$H NMR (400 MHz, DMSO), δ (ppm): 10.471 (s, 1H), 9.769 (s, 1H), 8.936 (t, J=6.0 Hz, 1H), 7.225 (d, J=8.8 Hz, 2H), 6.966 (d, J=8.8 Hz, 2H), 6.602 (s, 1H), 6.341 (s, 1H), 4.107 (s, 2H), 3.118-3.188 (m, 2H), 2.887-2.953 (m, 2H), 2.766 (s, 2H), 2.650 (s, 3H), 1.032 (t, J=6.8 Hz, 3H), 0.843 (d, J=6.8 Hz, 6H).

ESMS clcd for C27H36N6O4: 508.61. Found: 509.4 (M$^+$).

Compound 358

$^1$H NMR (400 MHz, DMSO), δ (ppm): 10.451 (s, 1H), 9.852 (s, 1H), 8.328 (s, 1H), 7.762 (s, 1H), 7.645 (d, J=7.2 Hz, 1H), 7.422-7.560 (m, 3H), 6.577 (s, 1H), 6.378 (s, 1H), 2.928-2.935 (m, 1H), 0.820-0.873 (dd, $J_1$=6.8 Hz, $J_2$=7.6 Hz, 6H).

ESMS clcd for C18H17ClN4O3: 372.81. Found: 373.3 (M$^+$).

Compound 359

$^1$H NMR (400 MHz, DMSO), δ (ppm): 10.696 (s, 1H), 9.770 (s, 1H), 8.216 (s, 1H), 7.675 (s, 1H), 7.450 (t, J=7.2 Hz, 1H), 7.313 (d, J=6.4 Hz, 1H), 7.204 (d, J=7.6 Hz, 1H), 7.024 (t, J=7.2 Hz, 1H), 6.568 (s, 1H), 6.345 (s, 1H), 3.665 (s, 1H), 2.905-2.939 (m, 1H), 0.788-0.849 (dd, $J_1$=4.0 Hz, $J_2$=10.4 Hz, 6H).

ESMS clcd for C19H20N4O4: 368.39. Found: 367.4 (M$^-$).

Compound 360

$^1$H NMR (400 MHz, DMSO), δ (ppm): 10.751 (s, 1H), 8.808 (d, J=8.4 Hz, 1H), 7.320-7.372 (m, 2H), 7.191 (d, J=5.6 Hz, 2H), 6.648 (s, 1H), 6.456 (s, 1H), 3.916-3.936 (m, 1H), 3.729 (s, 3H), 3.527 (s, 3H), 2.936-2.971 (m, 1H), 2.687-2.726 (m, 2H), 2.338-2.403 (m, 1H), 1.102 (d, J=10.4 Hz, 6H), 0.874 (d, J=6.4 Hz, 6H).

ESMS clcd for C28H37N5O4: 507.62. Found: 508.2 (M$^+$).

Compound 361

$^1$H NMR (400 MHz, DMSO), δ (ppm): 10.002 (s, 1H), 9.721 (s, 1H), 8.336 (s, 1H), 7.770 (s, 1H), 7.485 (t, J=7.2 Hz, 1H), 7.322-7.375 (m, 2H), 7.224 (d, J=7.6 Hz, 1H), 6.748 (s, 1H), 6.287 (s, 1H), 2.946-2.980 (m, 1H), 0.911-0.948 (m, 6H).

ESMS clcd for C18H17FN4O3: 356.35. Found: 357.4 (M$^+$).

Compound 362

$^1$H NMR (400 MHz, DMSO), δ (ppm): 10.585 (s, 1H), 9.780 (s, 1H), 80974 (d, J=6.0 Hz, 1H), 7.272 (d, J=9.2 Hz, 2H), 7.016 (d, J=8.8 Hz, 2H), 3.165-3.215 (m, 4H), 2.928-2.995 (m, 1H), 2.729 (t, J=5.2 Hz, 2H), 2.496-2.532 (m, 3H), 1.075 (t, J=7.2 Hz, 6H), 0.874 (d, J=6.8 Hz, 6H).

ESMS clcd for C26H33N5O5: 495.57. Found: 496.5 (M$^+$).

Compound 363

$^1$H NMR (400 MHz, DMSO), δ (ppm): 10.800 (s, 1H), 9.954 (s, 1H), 8.776 (d, J=8.0 Hz, 1H), 7.276-7.344 (m, 4H), 6.632 (s, 1H), 6.378 (s, 1H), 4.028-4.057 (m, 2H), 3.852-3.935 (m, 3H), 3.583-3.692 (m, 3H), 3.174-3.264 (m, 3H), 2.928-2.963 (m, 1H), 1.099 (t, J=7.2 Hz, 28H), 0.870 (d, J=7.2 Hz, 6H).

ESMS clcd for C27H35N5O4: 493.6. Found: 494.5 (M$^+$).

Compound 364

$^1$H NMR (400 MHz, DMSO), δ (ppm): 11.033 (s, 1H), 8.203 (s, 1H), 7.686 (s, 1H), 7.262 (d, J=8.4 Hz, 1H), 6.746 (s, 1H), 6.591-6.648 (m, 2H), 6.499 (s, 1H), 3.816 (s, 3H), 3.757 (s, 3H), 3.651 (s, 3H), 2.980-2.979 (m, 1H), 0.868 (m, 6H).

ESMS clcd for C21H24N4O5: 412.44. Found: 413.1 (M$^+$).

Compound 365

$^1$H NMR (400 MHz, DMSO), δ (ppm): 10.789 (s, 1H), 9.771 (s, 1H), 8.179 (s, 1H), 7.661 (s, 2H), 7.234 (d, J=8.8 Hz, 1H), 6.730 (s, 1H), 6.580-6.608 (m, 2H), 3.353 (s, 1H), 3.813 (s, 3H), 3.650 (s, 3H), 2.899-2.943 (m, 1H), 0.818-0.872 (dd, $J_1$=6.8 Hz, $J_2$=7.6 Hz, 6H). ESMS clcd for C20H22N4O5: 398.41. Found: 399.3 (M$^+$).

Compound 366

$^1$H NMR (400 MHz, DMSO), δ (ppm): 10.743 (s, 1H), 9.779 (s, 1H), 8.742 (d, J=8.4 Hz, 1H), 7.443 (t, J=8.0 Hz, 1H), 7.338 (d, J=7.2 Hz, 1H), 7.182 (d, J=6.8 Hz, 1H), 7.021 (t, J=8.0 Hz, 1H), 6.559 (s, 1H), 6.351 (s, 1H), 4.053-4.001 (m, 1H), 3.953-3.886 (m, 2H), 2.944-2.874 (m, 1H), 2.420 (t, J=5.6 Hz, 2H), 2.188 (m, 6H), 2.077 (s, 3H), 1.131-1.104 (dd, $J_1$=4.0 Hz, $J_2$=6.8 Hz, 6H), 0.834-0.775 (dd, $J_1$=6.8 Hz, $J_2$=16.8 Hz, 6H). ESMS clcd for $C_{28}H_{38}N_6O_4$: 522.64. Found: 523.3 (M$^+$).

Compound 367

$^1$H NMR (400 MHz, DMSO), δ (ppm): 10.185 (s, 1H), 9.742 (s, 1H), 9.187 (d, J=7.6 Hz, 1H), 7.417-7.384 (m, 2H), 7.284 (t, J=8.4 Hz, 2H), 6.701 (s, 1H), 6.322 (s, 1H), 4.050-4.010 (m, 1H), 3.242-3.169 (m, 2H), 3.091-3.062 (m, 2H), 3.001-2.928 (m, 1H), 2.132-2.017 (m, 6H), 0.923 (d, J=6.4 Hz, 6H).

ESMS clcd for $C_{23}H_{25}FN_4O_5S$: 488.53. Found: 487.3 (M$^-$).

Compound 368

$^1$H NMR (400 MHz, DMSO), δ (ppm): 9.817 (s, 1H), 9.684 (s, 1H), 8.834 (t, J=6.4 Hz, 1H), 8.561-8.548 (m, 1H), 8.462 (d, J=2.0 Hz, 1H), 7.751-7.722 (dd, $J_1$=1.6 Hz, $J_2$=10.0 Hz, 1H), 7.453-7.420 (dd, $J_1$=4.8 Hz, $J_2$=8.4 Hz, 1H), 6.837 (s, 1H), 6.256 (s, 1H), 3.295-3.246 (m, 2H), 2.994-2.960 (m, 1H), 2.418-2.306 (m, 11H), 2.147 (s, 3H), 0.974 (d, J=6.8 Hz, 6H). ESMS clcd for $C_{24}H_{31}N_7O_4$: 465.55. Found: 466.2 (M$^+$).

Compound 369

¹H NMR (400 MHz, DMSO), δ (ppm): 9.831 (s, 1H), 9.690 (s, 1H), 8.880 (d, J=8.4 Hz, 1H), 8.573-8.558 (dd, J₁=1.6 Hz, J₂=4.4 Hz, 1H), 8.466 (d, J=2.0 Hz, 1H), 7.766-7.736 (m, 1H), 7.471-7.436 (dd, J₁=5.2 Hz, J₂=8.8 Hz, 1H), 6.846 (s, 1H), 6.261 (s, 1H), 3.970-3.933 (m, 1H), 3.006-2.971 (m, 1H), 1.126 (d, J=6.8 Hz, 6H), 0.986 (d, J=7.6 Hz, 6H). ESMS clcd for $C_{20}H_{23}N_5O_4$: 381.43. Found: 380.1 (M⁻).

Compound 370

¹H NMR (400 MHz, DMSO), δ (ppm): 9.700 (s, 1H), 9.627-9.595 (m, 2H), 8.468 (d, J=4.8 Hz, 1H), 8.392 (d, J=6.4 Hz, 1H), 7.675 (d, J=8.8 Hz, 1H), 7.367-7.336 (dd, J₁=4.8 Hz, J₂=7.2 Hz, 1H), 6.779 (s, 1H), 6.157 (s, 1H), 3.892-3.850 (m, 1H), 2.883-2.866 (m, 1H), 0.886 (d, J=6.8 Hz, 6H). ESMS clcd for $C_{19}H_{18}F_3N_5O_4$: 421.37. Found: 420.1 (M⁻).

Compound 371

¹H NMR (400 MHz, DMSO), δ (ppm): 9.826 (s, 1H), 9.681 (s, 1H), 9.113 (d, J=4.8 Hz, 1H), 8.566 (d, J=4.4 Hz, 1H), 8.462 (d, J=2.0 Hz, 1H), 7.750 (d, J=9.2 Hz, 1H), 7.469-7.437 (m, 1H), 6.832 (s, 1H), 6.252 (s, 1H), 3.013-2.943 (m, 1H), 2.769-2.725 (m, 1H), 0.978 (d, J=6.8 Hz, 6H), 0.665-0.612 (m, 4H). ESMS clcd for $C_{20}H_{21}N_5O_3$: 379.41. Found: 380.2 (M⁺).

Compound 372

¹H NMR (400 MHz, DMSO), δ (ppm): 9.873-9.846 (m, 1H), 9.686-9.649 (m, 1H), 9.057 (t, J=5.6 Hz, 1H), 8.561-8.548 (m, 1H), 8.466 (d, J=2.0 Hz, 1H), 7.765-7.735 (dd, J₁=1.6 Hz, J₂=10.4 Hz, 1H), 7.460-7.428 (m, 1H), 6.829 (s, 1H), 6.257 (s, 1H), 3.220-3.151 (m, 2H), 3.012-2.943 (m, 1H), 1.078-1.029 (m, 3H), 0.982-0.899 (dd, J₁=6.8 Hz, J₂=26.0 Hz, 6H). ESMS clcd for $C_{19}H_{21}N_5O_3$: 367.4. Found: 366.2 (M⁻).

Compound 373

¹H NMR (400 MHz, DMSO), δ (ppm): 9.832-9.821 (m, 2H), 9.341-9.329 (m, 1H), 8.719 (d, J=4.8 Hz, 1H), 7.664-7.648 (m, 3H), 6.389 (s, 1H), 3.298-3.228 (m, 2H), 3.108-3.075 (m, 1H), 1.135-1.078 (m, 9H). ESMS clcd for $C_{19}H_{21}N_5O_3$: 367.4. Found: 368.1 (M⁺).

Compound 374

¹H NMR (400 MHz, DMSO), δ (ppm): 10.042 (s, 1H), 8.837 (d, J=8.0 Hz, 1H), 8.528 (d, J=3.6 Hz, 1H), 8.445 (s, 1H), 7.734 (d, J=6.8 Hz, 1H), 7.430-7.400 (m, 1H), 6.868 (s, 1H), 6.316 (s, 1H), 3.942-3.893 (m, 1H), 3.669 (s, 3H), 2.996-2.961 (m, 1H), 1.081 (d, J=7.2 Hz, 6H), 0.932 (d, J=7.6 Hz, 6H). ESMS clcd for $C_{21}H_{25}N_5O_3$: 395.45. Found: 396.1 (M⁺).

Compound 375

¹H NMR (400 MHz, DMSO), δ (ppm): 10.048 (s, 1H), 9.092 (d, J=4.8 Hz, 1H), 8.539 (d, J=4.8 Hz, 1H), 8.453 (s, 1H), 7.744 (d, J=8.0 Hz, 1H), 7.439-7.405 (m, 1H), 6.860 (s, 1H), 6.316 (s, 1H), 3.669 (s, 3H), 3.012-2.945 (m, 1H), 2.719-2.708 (m, 1H), 0.932 (d, J=7.2 Hz, 6H), 0.606-0.580 (m, 4H). ESMS clcd for $C_{21}H_{23}N_5O_3$: 393.44. Found: 394.2 (M⁺).

Compound 376

¹H NMR (400 MHz, DMSO), δ (ppm): 10.005 (s, 1H), 9.660 (t, J=6.0 Hz, 1H), 8.532 (d, J=5.6 Hz, 1H), 8.474 (s, 1H), 7.768 (d, J=8.4 Hz, 1H), 7.433-7.399 (m, 1H), 6.897 (s, 1H), 6.316 (s, 1H), 3.978-3.892 (m, 2H), 3.668 (s, 3H), 3.014-2.948 (m, 1H), 0.937 (d, J=5.6 Hz, 6H). ESMS clcd for $C_{20}H_{20}F_3N_5O_3$: 435.4. Found: 436.3 (M⁺).

Compound 377

¹H NMR (400 MHz, DMSO), δ (ppm): 10.109 (s, 1H), 9.092 (m, 1H), 8.576 (d, J=5.2 Hz, 1H), 8.502 (s, 1H), 7.792 (d, J=6.0 Hz, 1H), 7.474-7.448 (m, 1H), 6.908 (s, 1H), 6.362 (s, 1H), 3.712 (s, 3H), 3.212-3.180 (m, 2H), 3.039-3.004 (m, 1H), 1.067 (t, J=6.0 Hz, 3H), 0.976 (d, J=6.8 Hz, 6H). ESMS clcd for $C_{20}H_{23}N_5O_3$: 381.43. Found: 382.3 (M⁺).

Compound 378

¹H NMR (400 MHz, DMSO), δ (ppm): 10.834 (s, 1H), 9.027 (s, 1H), 7.406 (d, J=7.6 Hz, 2H), 7.313 (d, J=8.4 Hz, 2H), 6.642 (s, 1H), 6.485 (s, 1H), 3.758 (s, 3H), 3.500 (s, 2H), 2.893-2.973 (m, 1H), 2.722-2.748 (m, 1H), 2.351-2.379 (m, 7H), 2.157 (s, 3H), 0.782-0.844 (m, 6H), 0.565-0.625 (m, 4H). ESMS clcd for C28H36N6O3: 504.62. Found: 505.3 (M⁺).

Compound 379

¹H NMR (400 MHz, DMSO), δ (ppm): 12.145 (s, 1H), 10.874 (s, 1H), 8.985 (s, 1H), 7.318-7.382 (m, 4H), 6.646 (s, 1H), 6.515 (s, 1H), 3.747 (s, 3H), 3.490 (s, 2H), 3.165-3.194 (m, 2H), 2.938-2.968 (m, 1H), 2.771-2.782 (m, 2H), 2.187-2.264 (m, 1H), 2.002-2.028 (m, 2H), 1.780-1.806 (m, 2H), 1.552-1.578 (m, 2H), 1.049 (t, J=6.8 Hz, 3H), 0.809-0.824 (m, 6H). ESMS clcd for C28H35N5O5: 521.61. Found: 522.1 (M⁺).

Compound 380

¹H NMR (400 MHz, DMSO), δ (ppm): 10.595 (s, 1H), 8.936 (d, J=4.4 Hz, 1H), 7.401 (s, 2H), 7.383 (s, 2H), 6.706 (s, 1H), 6.469 (s, 1H), 3.739 (s, 3H), 2.967 (m, 2H), 2.707 (d, J=4.4 Hz, 4H), 1.833-1.874 (m, 4H), 0.867 (d, J=6.4 Hz, 6H). ESMS clcd for C25H31N5O3: 449.55. Found: 450.4 (M⁺).

Compound 381

¹H NMR (400 MHz, DMSO), δ (ppm): 10.720 (s, 1H), 9.624 (t, J=6.8 Hz, 1H), 7.321-7.387 (m, 4H), 6.680 (s, 1H), 6.509 (s, 1H), 3.953-3.993 (m, 2H), 3.740 (s, 3H), 3.476 (s, 2H), 2.937-2.971 (m, 1H), 2.749-2.776 (m, 2H), 2.189-2.193 (m, 1H), 1.983-2.034 (m, 2H), 1.768-1.794 (m, 2H), 1.541-1.594 (m, 2H), 0.836 (d, J=6.4 Hz, 6H). ESMS clcd for C28H32F3N5O5: 575.58. Found: 576.4 (M⁺).

Compound 382

¹H NMR (400 MHz, DMSO), δ (ppm): 8.806 (d, J=8.0 Hz, 1H), 7.416 (d, J=7.6 Hz, 2H), 7.245 (d, J=8.0 Hz, 2H), 6.713 (s, 1H), 6.496 (s, 1H), 4.046 (d, J=13.6 Hz, 1H), 3.885-3.971 (m, 1H), 3.722 (s, 3H), 3.616 (d, J=12.4 Hz, 1H), 3.216 (t, J=7.2 Hz, 1H), 3.163 (s, 2H), 2.927-2.979 (m, 2H), 2.365-2.423 (m, 1H), 2.018-2.071 (m, 1H), 1.786-1.882 (m, 1H), 1.710-1.732 (m, 2H), 1.097 (d, J=6.4 Hz, 6H), 0.870 (d, J=7.2 Hz, 6H). ESMS clcd for C28H35N5O5: 521.61. Found: 520.6 (M⁺).

Compound 383

¹H NMR (400 MHz, DMSO), δ (ppm): 10.746 (s, 1H), 8.881 (d, J=8.4 Hz, 1H), 7.370 (d, J=8.4 Hz, 2H), 7.288 (d, J=8.0 Hz, 2H), 6.647 (s, 1H), 6.496 (s, 1H), 3.898 (d, J=8.0 Hz, 2H), 3.732 (s, 3H), 3.582 (s, 3H), 3.517-3.553 (m, 1H), 3.296-3.308 (m, 1H), 2.905-2.981 (m, 1H), 2.834-2.871 (m, 1H), 2.316-2.376 (m, 1H), 2.054-2.115 (m, 1H), 1.725-1.891 (m, 3H), 1.080 (d, J=6.8 Hz, 6H), 0.814 (d, J=7.2 Hz, 6H). ESMS clcd for C29H37N5O5: 535.63. Found: 536.3 (M⁺).

Compound 384

¹H NMR (400 MHz, DMSO), δ (ppm): 10.797 (s, 1H), 8.805 (d, J=9.6 Hz, 1H), 7.413 (d, J=7.2 Hz, 2H), 7.303 (d, J=9.6 Hz, 2H), 6.643 (s, 1H), 6.473 (s, 1H), 4.046 (d, J=13.6 Hz, 1H), 3.880-3.966 (m, 6H), 3.652-3.776 (m, 6H), 2.908-2.977 (m, 1H), 2.234 (s, 3H), 1.228 (d, J=8.0 Hz, 3H), 1.095 (d, J=6.8 Hz, 6H), 0.804 (d, J=6.8 Hz, 6H).

ESMS clcd for C27H35N5O5: 509.6. Found: 508.5 (M⁻).

Compound 385

¹H NMR (400 MHz, DMSO), δ (ppm): 10.505 (s, 1H), 9.085 (d, J=4.4 Hz, 1H), 7.577 (s, 2H), 7.402 (d, J=7.6 Hz, 2H), 6.720 (s, 1H), 6.446 (s, 1H), 4.190-4.299 (m, 1H), 3.722 (s, 3H), 2.931-3.015 (m, 2H), 2.700-2.769 (m, 1H), 1.988 (s, 4H), 0.877 (d, J=6.8 Hz, 6H), 0.557-0.660 (m, 4H).

ESMS clcd for C27H33N5O3: 475.58. Found: 476.2 (M⁺).

Compound 386

¹H NMR (400 MHz, DMSO), δ (ppm): 10.674 (s, 1H), 9.622 (t, J=4.4 Hz, 1H), 7.317-7.394 (dd, J₁=8.0 Hz, J₁=8.0 Hz, 4H), 6.691 (s, 1H), 6.477 (s, 1H), 3.953-3.994 (m, 2H), 3.744 (s, 3H), 3.611 (s, 2H), 2.940-2.973 (m, 1H), 2.446 (s, 4H), 1.708 (s, 4H), 0.845 (d, J=6.8 Hz, 6H).

ESMS clcd for C26H30F3N5O3: 517.54. Found: 518.3 (M⁺).

Compound 387

¹H NMR (400 MHz, DMSO), δ (ppm): 10.546 (s, 1H), 10.108 (s, 1H), 9.608 (t, J=6.8 Hz, 1H), 7.292-7.371 (dd, J₁=8.4 Hz, J₁=11.2 Hz, 4H), 6.600 (s, 1H), 6.490 (s, 1H), 3.944-3.983 (m, 2H), 3.449 (s, 2H), 2.89-2.923 (m, 1H), 2.740 (d, J=10.4 Hz, 2H), 1.926-1.980 (m, 3H), 1.721-1.756 (m, 1H), 1.511-1.543 (m, 2H), 0.815 (d, J=7.2 Hz, 6H). ESMS clcd for C27H30F3N5O5: 561.55. Found: 562.1 (M⁺).

Compound 388

¹H NMR (400 MHz, DMSO), δ (ppm): 10.498 (s, 1H), 9.632 (t, J=6.8 Hz, 1H), 7.750 (s, 1H), 7.363 (d, J=9.2 Hz, 2H), 7.318 (t, J=8.4 Hz, 2H), 7.191 (s, 1H), 6.919 (s, 1H), 6.668 (s, 1H), 6.430 (s, 1H), 5.244 (s, 2H), 3.909-3.997 (m, 2H), 3.723 (s, 3H), 2.896-2.965 (m, 1H), 0.806 (d, J=7.2 Hz, 6H).

ESMS clcd for C25H25F3N6O3: 514.5. Found: 513.5 (M⁻).

Compound 389

¹H NMR (400 MHz, DMSO), δ (ppm): 11.677 (s, 1H), 7.608 (d, J=8.8 Hz, 2H), 7.370 (d, J=8.4 Hz, 2H), 7.242 (d, J=8.4 Hz, 1H), 6.590 (s, 1H), 6.534 (s, 1H), 4.131-4.218 (m, 1H), 3.930 (s, 1H), 3.893 (s, 3H), 3.842 (d, J=14.0 Hz, 3H), 3.674 (d, J=11.2 Hz, 1H), 2.964-3.031 (m, 2H), 2.315 (s, 3H), 2.113-2.206 (m, 1H), 1.218 (d, J=6.8 Hz, 6H), 1.129 (d, J=6.8 Hz, 3H), 0.967 (d, J=6.4 Hz, 3H), 0.763 (d, J=6.8 Hz, 6H).

ESMS clcd for C30H41N5O5: 551.68. Found: 550.7 (M⁻).

Compound 390

¹H NMR (400 MHz, DMSO), δ (ppm): 10.6434 (s, 1H), 9.013 (t, J=6.0 Hz, 1H), 7.420-7.667 (dd, J₁=8.0 Hz, J₁=8.0 Hz, 4H), 6.755 (s, 1H), 6.4755 (s, 1H), 4.384 (s, 2H), 3.7433 (s, 3H), 3.092-3.142 (m, 2H), 2.946-2.997 (m, 1H), 1.972-2.025 (m, 4H), 1.443-1.497 (m, 2H), 0.899 (d, J=6.8 Hz, 6H), 0.811 (t, J=7.2 Hz, 4H).

ESMS clcd for C27H35N5O3: 477.6. Found: 478.3 (M⁺).

Compound 391

¹H NMR (400 MHz, DMSO), δ (ppm): 10.821 (s, 1H), 8.807 (d, J=8.0 Hz, 1H), 7.394 (s, 2H), 7.316-7.335 (m, 2H), 6.538 (s, 1H), 6.498 (s, 1H), 4.042-4.095 (m, 2H), 3.903-3.955 (m, 1H), 3.742 (s, 3H), 3.493 (s, 2H), 2.920-2.970 (m, 1H), 2.774 (s, 2H), 2.320 (s, 1H), 1.997-2.037 (m, 2H), 1.791 (s, 2H), 1.589 (s, 2H), 1.183 (t, J=7.2 Hz, 3H), 1.099 (d, J=6.4 Hz, 6H), 0.812 (d, J=6.8 Hz, 6H).

ESMS clcd for C31H41N5O5: 563.69. Found: 562.5 (M⁻).

Compound 392

¹H NMR (400 MHz, DMSO), δ (ppm): 10.849 (s, 1H), 8.792 (d, J=8.0 Hz, 1H), 7.390 (d, J=8.4 Hz, 2H), 7.729 (d, J=8.4 Hz, 2H), 6.644 (s, 1H), 6.516 (s, 1H), 3.909-3.928 (m, 1H), 3.735 (s, 3H), 3.474 (s, 2H), 2.928-2.962 (m, 2H), 2.746 (d, J=10.8 Hz, 2H), 2.198 (s, 1H), 1.979-2.032 (m, 2H), 1.789 (d, J=10.4 Hz, 2H), 1.531-1.586 (m, 2H), 1.089 (d, J=6.4 Hz, 6H), 0.819 (d, J=6.4 Hz, 6H).

ESMS clcd for C29H37N5O5: 535.63. Found: 536.3 (M⁺).

Compound 393

¹H NMR (400 MHz, DMSO), δ (ppm): 11.757 (s, 1H), 7.602 (d, J=7.6 Hz, 2H), 7.375 (d, J=8.0 Hz, 2H), 7.235 (d, J=8.4 Hz, 1H), 6.590 (s, 1H), 6.537 (s, 1H), 4.144-4.212 (m, 1H), 3.842 (s, 3H), 3.794 (s, 3H), 3.560-3.613 (m, 1H), 2.959-3.082 (m, 1H), 2.937 (s, 3H), 1.401 (d, J=7.6 Hz, 3H), 1.262-1.295 (m, 8H), 0.742 (d, J=6.8 Hz, 6H).

ESMS clcd for C28H37N5O5: 523.62. Found: 522.5 (M⁻).

Compound 394

¹H NMR (400 MHz, DMSO), δ (ppm): 10.777 (s, 1H), 9.818 (s, 1H), 8.732 (d, J=7.6 Hz, 1H), 7.259 (d, J=7.6 Hz, 1H), 7.129 (s, 1H), 6.960 (d, J=8.0 Hz, 1H), 6.593 (s, 1H), 6.367 (s, 1H), 3.870-3.998 (m, 1H), 3.665 (s, 3H), 3.548 (s, 2H), 2.906-2.922 (m, 1H), 2.453 (s, 3H), 1.100-1.122 (dd, J₁=6.0 Hz, J₂=4.8 Hz, 6H), 0.773-0.837 (dd, J₁=6.8 Hz, J₂=12.0 Hz, 6H).

ESMS clcd for C28H38N6O4: 522.64. Found: 523.5 (M⁺).

Compound 395

¹H NMR (400 MHz, DMSO), δ (ppm): 10.737 (s, 1H), 8.796 (d, J=8.4 Hz, 1H), 7.422 (d, J=8.4 Hz, 2H), 7.305 (d, J=8.4 Hz, 2H), 6.667 (s, 1H), 6.482 (s, 1H), 3.877-3.965 (m, 1H), 3.727 (s, 6H), 3.220 (s, 2H), 2.909-2.978 (m, 1H), 2.292 (s, 3H), 1.090 (d, J=6.8 Hz, 6H), 0.812 (d, J=6.4 Hz, 6H).

ESMS clcd for C26H33N5O5: 495.57. Found: 494.5 (M⁻).

Compound 396

¹H NMR (400 MHz, DMSO), δ (ppm): 10.813 (s, 1H), 8.990 (t, J=6.0 Hz, 1H), 7.378 (d, J=7.6 Hz, 2H), 7.314 (d, J=8.0 Hz, 2H), 6.649 (s, 1H), 6.508 (s, 1H), 3.741 (s, 3H), 3.520 (s, 2H), 3.143-3.210 (m, 2H), 2.932-2.966 (m, 1H), 1.046 (t, J=7.2 Hz, 6H), 0.807 (d, J=7.2 Hz, 6H).

ESMS clcd for C28H38N6O3: 506.64. Found: 507.3 (W).

Compound 397

¹H NMR (400 MHz, DMSO), δ (ppm): 10.831 (s, 1H), 8.788 (d, J=8.4 Hz, 1H), 7.382 (d, J=8.4 Hz, 2H), 7.337 (d, J=8.0 Hz, 2H), 6.649 (s, 1H), 6.488 (s, 1H), 3.884-3.970 (m, 1H), 3.745 (s, 3H), 3.508 (s, 2H), 3.126-3.203 (m, 2H), 2.913-2.982 (m, 1H), 2.635 (s, 4H), 2.412 (s, 4H), 1.099 (d, J=6.8 Hz, 6H), 0.801 (d, J=6.8 Hz, 6H).

ESMS clcd for C29H37F3N6O3: 574.64. Found: 576.3 (W).

Compound 398

¹H NMR (400 MHz, DMSO), δ (ppm): 10.784 (s, 1H), 8.773 (d, J=8.4 Hz, 1H), 7.415 (d, J=8.0 Hz, 2H), 7.339 (d, J=8.4 Hz, 2H), 6.664 (s, 1H), 6.482 (s, 1H), 4.081-4.134 (m, 2H), 3.888-3.974 (m, 1H), 3.745 (s, 3H), 3.688 (s, 2H), 3.313 (s, 2H), 2.918-2.987 (m, 1H), 2.281 (s, 3H), 1.206 (d, J=7.6 Hz, 3H), 1.102 (d, J=6.8 Hz, 6H), 0.811 (d, J=7.2 Hz, 6H). ESMS clcd for C28H37N5O5: 523.62. Found: 525.7 (W).

Compound 399

¹H NMR (400 MHz, DMSO), δ (ppm): 10.835 (s, 1H), 8.982 (t, J=8.4 Hz, 1H), 7.395 (d, J=8.0 Hz, 2H), 7.334 (d, J=8.0 Hz, 2H), 6.641 (s, 1H), 6.489 (s, 1H), 3.747 (s, 3H), 3.488 (s, 2H), 3.162-3.196 (m, 2H), 2.930-2.965 (m, 1H), 2.512-2.623 (m, 1H), 2.364-2.449 (m, 8H), 1.050 (t, J=7.2

Hz, 3H), 0.960 (d, J=6.4 Hz, 6H), 0.802 (d, J=7.2 Hz, 6H). ESMS clcd for C29H40N6O3: 520.67. Found: 521.5 (W).

Compound 400

¹H NMR (400 MHz, DMSO), δ (ppm): 10.632 (s, 1H), 8.804 (d, J=8.8 Hz, 1H), 7.760 (s, 1H), 7.321-7.375 (m, 4H), 7.198 (s, 1H), 6.929 (s, 1H), 6.631 (s, 1H), 6.450 (s, 1H), 5.258 (s, 2H), 3.886-3.972 (m, 1H), 3.737 (s, 3H), 2.902-2.970 (m, 1H), 1.107 (d, J=6.4 Hz, 6H), 0.801 (d, J=6.8 Hz, 6H).

ESMS clcd for C26H30N6O3: 474.55. Found: 475.5 (M⁺).

Compound 401

¹H NMR (400 MHz, DMSO), δ (ppm): 10.658 (s, 1H), 8.991 (t, J=5.6 Hz, 1H), 7.766 (s, 1H), 7.317-7.378 (m, 4H), 7.205 (s, 1H), 6.934 (s, 1H), 6.622 (s, 1H), 6.453 (s, 1H), 5.259 (s, 2H), 3.735 (s, 3H), 3.138-3.207 (m, 2H), 2.895-2.965 (m, 1H), 1.047 (t, J=6.8 Hz, 3H), 0.776 (d, J=6.8 Hz, 6H).

ESMS clcd for C25H28N6O3: 460.53. Found: 461.5 (M⁺).

Compound 402

¹H NMR (400 MHz, DMSO), δ (ppm): 10.836 (s, 1H), 8.711 (d, J=10.0 Hz, 1H), 7.381 (d, J=8.8 Hz, 2H), 7.334 (d, J=6.4 Hz, 2H), 6.664 (s, 1H), 6.486 (s, 1H), 3.909-3.929 (m, 1H), 3.747 (s, 3H), 3.497 (s, 2H), 2.948-2.960 (m, 1H), 2.380-2.391 (s, 8H), 2.191 (s, 3H), 1.100 (d, J=6.8 Hz, 6H), 0.818 (d, J=4.0 Hz, 6H).

ESMS clcd for C28H38N6O3: 506.64. Found: 507.4 (M⁺).

Compound 403

¹H NMR (400 MHz, DMSO), δ (ppm): 10.886 (s, 1H), 8.903 (d, J=4.8 Hz, 1H), 7.373 (d, J=8.0 Hz, 2H), 7.314 (d, J=8.4 Hz, 2H), 6.633 (s, 1H), 6.497 (s, 1H), 3.748 (s, 3H), 3.475 (s, 2H), 2.926-2.960 (m, 1H), 2.782 (d, J=10.8 Hz, 2H), 2.689 (d, J=4.8 Hz, 3H), 1.911-1.956 (m, 2H), 1.590 (d, J=10.8 Hz, 2H), 1.353 (s, 1H), 1.138-1.166 (m, 2H), 0.910 (d, J=6.4 Hz, 3H), 0.810 (d, J=6.8 Hz, 6H).

ESMS clcd for C27H35N5O3: 477.6. Found: 478.5 (M⁺).

Compound 404

¹H NMR (400 MHz, DMSO), δ (ppm): 10.838 (s, 1H), 8.903 (d, J=4.8 Hz, 1H), 7.407 (d, J=8.0 Hz, 2H), 7.311 (d, J=8.4 Hz, 2H), 6.647 (s, 1H), 6.490 (s, 1H), 4.000-4.015 (m, 1H), 3.748 (s, 3H), 3.497 (s, 2H), 2.505-2.515 (m, 1H), 2.306-2.400 (m, 8H), 1.732 (s, 2H), 1.629 (s, 2H), 1.471 (s, 4H), 0.988 (d, J=7.2 Hz, 3H), 0.802 (d, J=6.8 Hz, 6H). ESMS clcd for C31H42N6O3: 546.7. Found: 547.5 (M⁺).

Compound 405

¹H NMR (400 MHz, DMSO), δ (ppm): 10.799 (s, 1H), 9.041 (d, J=4.4 Hz, 1H), 7.384 (d, J=8.8 Hz, 1H), 7.311 (d, J=8.8 Hz, 1H), 6.646 (s, 1H), 6.483 (s, 1H), 3.746 (s, 3H), 3.500 (s, 2H), 2.932-2.967 (m, 1H), 2.731-2.749 (m, 1H), 0.986 (d, J=5.6 Hz, 6H), 0.807 (d, J=6.8 Hz, 6H), 0.567-0.645 (m, 4H).

ESMS clcd for C30H40N6O3: 532.68. Found: 531.5 (M⁻).

Compound 406

¹H NMR (400 MHz, DMSO), δ (ppm): 10.907 (s, 1H), 8.979 (t, J=5.2 Hz, 1H), 7.315-7.427 (m, 4H), 6.629 (s, 1H), 6.494 (s, 1H), 3.748 (s, 3H), 3.578 (s, 2H), 3.144-3.213 (m, 2H), 2.930-2.963 (m, 1H), 0.983-1.067 (m, 9H), 0.815 (d, J=6.8 Hz, 6H).

ESMS clcd for C26H35N5O3: 465.59. Found: 464.6 (M⁻).

Compound 407

¹H NMR (400 MHz, DMSO), δ (ppm): 10.895 (s, 1H), 8.978 (t, J=5.2 Hz, 1H), 7.312-7.425 (m, 4H), 6.633 (s, 1H), 6.496 (s, 1H), 3.748 (s, 3H), 3.578 (s, 2H), 3.082-3.133 (m, 2H), 2.465-2.515 (m, 1H), 1.425-1.479 (m, 2H), 0.978 (t, J=7.2 Hz, 6H), 0.797-0.8321 (m, 9H). ESMS clcd for C27H37N5O3: 479.61. Found: 480.5 (M⁺).

Compound 408

¹H NMR (400 MHz, DMSO), δ (ppm): 10.832 (s, 1H), 8.793 (d, J=8.0 Hz, 1H), 7.381 (d, J=8.4 Hz, 2H), 7.311 (d, J=8.8 Hz, 2H), 6.648 (s, 1H), 6.488 (s, 1H), 3.980-3.997 (m, 1H), 3.747 (s, 3H), 3.494 (s, 2H), 2.936-2.949 (m, 1H), 2.281-2.393 (m, 9H), 1.100 (d, J=6.4 Hz, 6H), 0.986 (t, J=6.8 Hz, 3H), 0.804 (d, J=6.8 Hz, 6H).

ESMS clcd for C29H40N6O3: 520.67. Found: 519.6 (M⁻).

Compound 409

¹H NMR (400 MHz, DMSO), δ (ppm): 10.832 (s, 1H), 9.012 (d, J=8.0 Hz, 1H), 7.372 (d, J=8.4 Hz, 2H), 7.300 (d, J=8.8 Hz, 2H), 6.728 (s, 1H), 6.487 (s, 1H), 3.807 (s, 3H), 3.494 (s, 2H), 2.936-2.947 (m, 1H), 2.754-2.783 (m, 1H), 2.323-2.456 (m, 8H), 1.006 (t, J=6.4 Hz, 3H), 0.804 (d, J=6.8 Hz, 6H), 0.689-0.746 (m, 6H).

ESMS clcd for C29H38N6O3: 518.65. Found: 519.6 (M⁺).

Compound 410

¹H NMR (400 MHz, DMSO), δ (ppm): 10.865 (s, 1H), 8.962 (t, J=6.0 Hz, 1H), 7.393 (d, J=8.4 Hz, 2H), 7.330 (d, J=8.8 Hz, 2H), 6.641 (s, 1H), 6.494 (s, 1H), 3.747 (s, 3H), 3.471 (s, 2H), 3.081-3.131 (m, 2H), 2.929-22.963 (m, 1H), 2.776-2.804 (m, 2H), 1.934 (t, J=10.8 Hz, 2H), 1.556-1.584 (m, 2H), 1.421-1.476 (m, 2H), 1.331 (s, 1H), 1.134-1.156 (m, 2H), 0.908 (d, J=6.4 Hz, 3H), 0.797-0.830 (m, 9H).

ESMS clcd for C29H39N5O3: 505.65. Found: 506.5 (M⁺).

Compound 411

¹H NMR (400 MHz, DMSO), δ (ppm): 10.826 (s, 1H), 8.898 (t, J=6.4 Hz, 1H), 7.378 (d, J=8.4 Hz, 2H), 7.312 (d, J=8.4 Hz, 2H), 6.641 (s, 1H), 6.495 (s, 1H), 3.751 (s, 3H), 3.491 (s, 2H), 3.098-3.139 (m, 2H), 2.932-2.966 (m, 1H), 2.615-2.628 (m, 1H), 2.405-2.514 (m, 8H), 1.431-1.484 (m, 2H), 0.978 (d, J=6.8 Hz, 6H), 0.804-0.837 (m, 9H). ESMS clcd for C30H42N6O3: 534.69. Found: 535.5 (M⁺).

Compound 412

¹H NMR (400 MHz, DMSO), δ (ppm): 10.846 (s, 1H), 8.846 (s, 1H), 7.401 (d, J=8.4 Hz, 2H), 7.317 (d, J=8.4 Hz, 2H), 6.633 (s, 1H), 6.498 (s, 1H), 3.752 (s, 3H), 3.498 (s, 2H), 2.930-2.964 (m, 1H), 2.698-2.709 (m, 3H), 2.681 (s, 1H), 2.416-2.463 (m, 7H), 0.966 (d, J=6.4 Hz, 6H), 0.801 (d, J=6.8 Hz, 6H).

ESMS clcd for C28H38N6O3: 506.64. Found: 507.3 (M⁺).

Compound 413

¹H NMR (400 MHz, DMSO), δ (ppm): 10.807 (s, 1H), 8.957 (t, J=6.0 Hz, 1H), 7.394 (d, J=8.4 Hz, 2H), 7.323 (d, J=8.0 Hz, 2H), 6.650 (s, 1H), 6.485 (s, 1H), 3.745 (s, 3H), 3.593 (t, J=4.4 Hz, 4H), 3.332 (s, 12H), 3.082-23.133 (m, 2H), 2.930-2.7964 (m, 1H), 2.387 (s, 4H), 1.426-2.1.479 (m, 2H), 0.799-0.832 (m, 9H).

ESMS clcd for C27H35N5O4: 493.6. Found: 494.5 (M⁺).

Compound 414

¹H NMR (400 MHz, DMSO), δ (ppm): 10.886 (s, 1H), 8.914 (d, J=4.8 Hz, 1H), 7.376 (d, J=8.4 Hz, 2H), 7.315 (d, J=8.4 Hz, 2H), 6.634 (s, 1H), 6.497 (s, 1H), 3.748 (s, 3H), 3.462 (s, 2H), 2.909-2.976 (m, 1H), 2.702 (d, J=4.8 Hz, 3H), 2.353 (s, 4H), 1.510 (t, J=4.8 Hz, 4H), 1.406 (s, 2H), 0.795 (d, J=6.8 Hz, 6H).

ESMS clcd for C26H33N5O3: 463.57. Found: 464.5 (M⁺).

Compound 415

$^1$H NMR (400 MHz, DMSO), δ (ppm): 10.864 (s, 1H), 8.971 (d, J=8.8 Hz, 1H), 7.376 (d, J=8.0 Hz, 2H), 7.313 (d, J=7.6 Hz, 2H), 6.642 (s, 1H), 6.495 (s, 1H), 3.749 (s, 3H), 3.460 (s, 2H), 3.082-3.132 (m, 2H), 2.911-2.979 (m, 1H), 2.350 (s, 4H), 1.423-1.509 (m, 8H), 0.800-0.830 (m, 9H).

ESMS clcd for C28H37N5O3: 491.63. Found: 492.6 (M$^+$).

Compound 416

$^1$H NMR (400 MHz, DMSO), δ (ppm): 10.695 (s, 1H), 9.613 (d, J=6.0 Hz, 1H), 7.334-7.390 (m, 4H), 6.682 (s, 1H), 6.482 (s, 1H), 3.931-4.015 (m, 2H), 3.745 (s, 3H), 3.488 (s, 2H), 2.922-2.987 (m, 1H), 2.335-2.388 (m, 7H), 2.160 (s, 3H), 0.831 (d, J=6.4 Hz, 6H). ESMS clcd for C27H33F3N6O3: 546.58. Found: 547.5 (M$^+$).

Compound 417

$^1$H NMR (400 MHz, DMSO), δ (ppm): 10.826 (s, 1H), 8.964 (t, J=6.0 Hz, 1H), 7.314-7.396 (m, 4H), 6.645 (s, 1H), 6.488 (s, 1H), 3.746 (s, 3H), 3.496 (s, 2H), 3.081-3.132 (m, 2H), 2.930-2.964 (m, 1H), 2.299-2.352 (m, 8H), 1.423-1.478 (m, 2H), 0.991 (t, J=7.2 Hz, 3H), 0.794-0.831 (m, 9H).

ESMS clcd for C29H40N6O3: 520.67. Found: 521.3 (M$^+$).

Compound 418

$^1$H NMR (400 MHz, DMSO), δ (ppm): 10.915 (s, 1H), 8.918 (d, J=4.8 Hz, 1H), 7.316-7.426 (m, 4H), 6.625 (s, 1H), 6.497 (s, 1H), 3.748 (s, 3H), 3.581 (s, 2H), 2.943-2.960 (m, 1H), 2.702 (s, 3H), 0.999 (t, J=7.2 Hz, 6H), 0.793 (d, J=6.8 Hz, 6H).

ESMS clcd for C25H33N5O3: 451.56. Found: 452.4 (M$^+$).

Compound 419

$^1$H NMR (400 MHz, DMSO), δ (ppm): 10.880 (s, 1H), 9.038 (d, J=4.8 Hz, 1H), 7.309-7.435 (m, 4H), 6.6231 (s, 1H), 6.492 (s, 1H), 3.748 (s, 3H), 3.584 (s, 2H), 2.929-2.964 (m, 1H), 2.713-2.759 (m, 1H), 1.001 (t, J=6.8 Hz, 6H), 0.799 (d, J=6.8 Hz, 6H), 0.543-0.664 (m, 4H).

ESMS clcd for C27H35N5O3: 477.6. Found: 478.5 (M$^+$).

Compound 420

$^1$H NMR (400 MHz, CDCl$_3$), δ (ppm): 8.049 (d, J=7.2 Hz, 1H), 7.692 (s, 1H), 7.573 (d, J=8.0 Hz, 1H), 7.348 (m, 1H), 6.466 (s, 1H), 6.337 (s, 1H), 3.768 (s, 2H), 3.392 (m, 2H), 2.879 (m, 1H), 2.682-2.638 (m, 8H), 2.439 (s, 3H), 1.244 (m, 3H), 0.716 (d, J=5.6 Hz, 6H). ESMS clcd for $C_{27}H_{33}F_3N_6O_3$: 546.58. Found: 547.3 (M$^+$).

Compound 421

$^1$H NMR (400 MHz, DMSO), δ (ppm): 11.067 (s, 1H), 8.754 (d, J=8.0 Hz, 1H), 7.250 (d, J=8.0 Hz 1H), 7.113 (s, 1H), 6.956 (d, J=7.2 Hz, 1H), 6.632 (s, 1H), 6.493 (s, 1H), 3.945-3.891 (m, 1H), 3.739 (s, 3H), 3.647 (s, 3H), 3.484 (d, J=2.8 Hz, 2H), 2.956-2.922 (m, 1H), 2.497-2.294 (m, 7H), 2.155 (s, 3H), 1.108-1.085 (dd, J$_1$=2.4 Hz, J$_2$=6.8 Hz, 6H), 0.810-0.744 (dd, J$_1$=3.2 Hz, J$_2$=19.6 Hz, 6H).

ESMS clcd for $C_{29}H_{40}N_6O_4$: 536.67. Found: 537.1 (M$^+$).

Compound 422

$^1$H NMR (400 MHz, DMSO), δ (ppm): 10.802 (s, 1H), 8.860 (d, J=8.4 Hz, 1H), 7.392 (d, J=9.2 Hz, 2H), 7.298 (d, J=7.6 Hz, 2H), 6.641 (s, 1H), 6.468 (s, 1H), 3.733 (s, 3H), 3.618 (s, 2H), 1.767-1.623 (m, 8H), 1.487-1.461 (m, 4H), 0.812 (d, J=6.4 Hz, 6H).

ESMS clcd for $C_{29}H_{37}N_5O_3$: 503.29. Found: 504.2 (M$^+$).

Compound 423

$^1$H NMR (400 MHz, DMSO), δ (ppm): 9.961 (s, 1H), 9.924 (s, 1H), 8.876 (d, J=8.4 Hz, 1H), 7.803 (d, J=8.0 Hz, 2H), 7.504 (d, J=7.6 Hz, 2H), 6.734 (s, 1H), 6.387 (s, 1H), 3.957-3.904 (m, 1H), 3.124 (m, 4H), 2.966-2.919 (m, 1H), 1.092 (d, J=6.0 Hz, 6H), 0.927 (d, J=7.2 Hz, 6H).

ESMS clcd for $C_{25}H_{31}N_5O_5S$: 513.61. Found: 512.1 (M$^-$).

Compound 424

$^1$H NMR (400 MHz, DMSO), δ (ppm): 10.025 (s, 1H), 9.763 (s, 1H), 8.890 (d, J=8.4 Hz, 1H), 7.814 (d, J=8.8 Hz, 2H), 7.616 (d, J=8.0 Hz, 2H), 6.780 (s, 1H), 6.327 (s, 1H), 3.996 (m, 1H), 3.672 (m, 4H), 2.977 (m, 1H), 2.920 (m, 4H), 1.144 (d, J=6.0 Hz, 6H), 0.968 (d, J=4.4 Hz, 6H).

ESMS clcd for $C_{25}H_{31}N_5O_6S$: 529.61. Found: 530.1 (M$^+$).

Compound 425

$^1$H NMR (400 MHz, DMSO), δ (ppm): 9.943 (s, 1H), 9.684 (s, 1H), 8.846 (d, 1H), 7.805 (d, J=7.2 Hz, 2H), 7.495 (d, J=8.8 Hz, 2H), 6.722 (s, 1H), 6.270 (s, 1H), 3.959-3.886 (m, 1H), 3.198-3.148 (m, 4H), 2.937 (m, 1H), 1.104 (d, J=6.4 Hz, 6H), 1.022 (t, 6H), 0.925 (d, J=7.2 Hz, 6H).

ESMS clcd for $C_{25}H_{33}N_5O_5S$: 515.63. Found: 516.5 (M$^+$).

Compound 426

$^1$H NMR (400 MHz, DMSO), δ (ppm): 9.926 (s, 1H), 9.703 (s, 1H), 8.856 (d, J=8.4 Hz, 1H), 7.746 (d, J=8.4 Hz, 2H), 7.536 (d, J=8.4 Hz, 2H), 6.743 (s, 1H), 6.277 (s, 1H), 3.991-3.905 (m, 1H), 2.991-2.924 (m, 1H), 2.879 (m, 4H), 1.528 (m, 4H), 1.374 (m, 2H), 1.108 (d, J=6.8 Hz, 6H), 0.942 (d, J=6.4 Hz, 6H).

ESMS clcd for $C_{26}H_{33}N_5O_5S$: 527.64. Found: 526.3 (M$^-$).

Compound 427

$^1$H NMR (400 MHz, DMSO), δ (ppm): 9.980 (s, 1H), 9.693 (s, 1H), 9.018 (t, 1H), 7.737 (d, J=8.8 Hz, 2H), 7.556 (d, J=7.6 Hz, 2H), 6.698 (s, 1H), 6.257 (s, 1H), 3.604 (m, 4H), 3.166-3.133 (m, 2H), 2.916-2.853 (m, 5H), 1.017 (t, J=7.2 Hz, 3H), 0.890 (d, J=6.4 Hz, 6H). ESMS clcd for $C_{24}H_{29}N_5O_6S$: 515.58. Found: 516.2 (M$^+$).

Compound 428

$^1$H NMR (400 MHz, DMSO), δ (ppm): 9.978 (s, 1H), 9.875 (s, 1H), 9.640 (m, 1H), 7.745-7.720 (m, 2H), 7.581-7.567 (m, 2H), 6.695 (s, 1H), 6.361 (s, 1H), 3.948-3.925 (m, 2H), 3.591 (m, 4H), 2.904 (m, 1H), 2.835 (m, 4H), 0.880 (d, J=7.2 Hz, 6H).

ESMS clcd for $C_{25}H_{28}F_3N_5O_5S$: 567.58. Found: 566.2 (M$^-$).

Compound 429

$^1$H NMR (400 MHz, DMSO), δ (ppm): 9.864 (s, 1H), 9.672 (s, 1H), 9.641 (t, J=6.4 Hz, 1H), 7.766 (d, J=8.4 Hz, 2H), 7.495 (d, J=8.0 Hz, 2H), 6.714 (s, 1H), 6.230 (s, 1H), 3.944-3.906 (m, 2H), 3.154-3.102 (m, 4H), 2.923-2.888 (m, 1H), 0.976 (t, J=4.8 Hz, 6H), 0.885 (d, J=6.4 Hz, 6H).

ESMS clcd for $C_{24}H_{28}F_3N_5O_5S$: 555.57. Found: 554.2 (M$^-$).

Compound 430

$^1$H NMR (400 MHz, DMSO), δ (ppm): 9.862 (s, 1H), 9.671 (s, 1H), 9.587 (t, J=7.6 Hz, 1H), 7.677 (d, J=8.8 Hz, 2H), 7.520 (d, J=7.6 Hz, 2H), 6.667 (s, 1H), 6.193 (s, 1H), 3.896-3.854 (m, 2H), 3.532 (m, 4H), 2.870-2.832 (m, 1H), 2.778 (m, 4H), 0.830 (d, J=8.4 Hz, 6H). ESMS clcd for $C_{24}H_{26}F_3N_5O_6S$: 569.55. Found: 568.3 (M$^-$).

Compound 431

$^1$H NMR (400 MHz, DMSO), δ (ppm): 9.953 (s, 1H), 9.762 (s, 1H), 9.125 (m, 1H), 7.760 (d, J=8.8 Hz, 2H), 7.550 (d, J=8.0 Hz, 2H), 6.747 (s, 1H), 6.316 (s, 1H), 2.983-2.905 (m, 5H), 2.762 (m, 1H), 1.543 (m, 4H), 1.405 (m, 2H), 0.946 (d, J=7.2 Hz, 6H), 0.654-0.612 (m, 4H).

ESMS clcd for $C_{26}H_{31}N_5O_5S$: 525.62. Found: 526.4 (M$^+$).

Compound 432

¹H NMR (400 MHz, DMSO), δ (ppm): 10.145 (s, 1H), 9.638 (t, 1H), 7.823 (d, J=8.0 Hz, 2H), 7.576 (d, J=8.4 Hz, 2H), 6.833 (s, 1H), 6.386 (s, 1H), 4.001-3.959 (m, 2H), 3.716 (s, 3H), 3.210-3.158 (m, 4H), 2.977 (m, 1H), 1.018 (t, J=6.4 Hz, 6H), 0.934 (d, J=6.8 Hz, 6H).

ESMS clcd for C₂₅H₃₀F₃N₅O₅S: 569.6. Found: 570.2 (M⁺).

Compound 433

¹H NMR (400 MHz, DMSO), δ (ppm): 10.195 (s, 1H), 8.886 (d, J=6.8 Hz, 1H), 7.824 (d, J=8.4 Hz, 2H), 7.538 (d, J=7.6 Hz, 2H), 6.808 (s, 1H), 6.385 (s, 1H), 3.974-3.928 (m, 1H), 3.713 (s, 3H), 3.209-3.159 (m, 4H), 3.013-2.979 (m, 1H), 1.116 (d, J=6.4 Hz, 6H), 1.020 (t, J=8.0 Hz, 6H), 0.930 (d, J=7.2 Hz, 6H).

ESMS clcd for C₂₆H₃₅N₅O₅S: 529.65. Found: 530.2 (M⁺).

Compound 434

¹H NMR (400 MHz, DMSO), δ (ppm): 9.854 (s, 1H), 9.639 (s, 1H), 9.000 (d, J=4.4 Hz, 1H), 7.706 (d, J=9.2 Hz, 2H), 7.399 (d, J=8.8 Hz, 2H), 6.618 (s, 1H), 6.161 (s, 1H), 3.138-3.051 (m, 4H), 2.859-2.825 (m, 1H), 2.638 (m, 1H), 0.926 (t, J=6.4 Hz, 6H), 0.818 (d, J=6.4 Hz, 6H), 0.537-0.490 (m, 4H).

ESMS clcd for C₂₅H₃₁N₅O₅S: 513.61. Found: 512.2 (M⁻).

Compound 435

¹H NMR (400 MHz, DMSO), δ (ppm): 9.980 (s, 1H), 9.709 (s, 1H), 9.052 (m, 1H), 7.810 (d, J=8.4 Hz, 2H), 7.515 (d, J=8.0 Hz, 2H), 6.726 (s, 1H), 6.284 (s, 1H), 3.191-3.175 (m, 6H), 2.950 (m, 1H), 1.074-1.015 (m, 9H), 0.926 (d, J=6.4 Hz, 6H).

ESMS clcd for C₂₄H₃₁N₅O₅S: 501.6. Found: 502.1 (M⁺).

Example 4

Synthesis of Compound 126

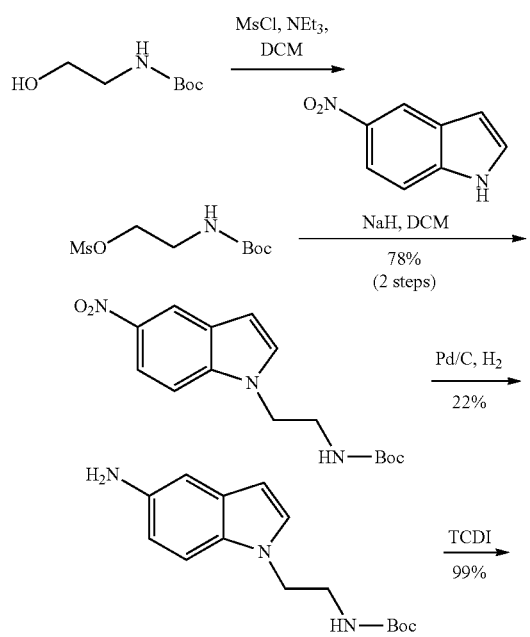

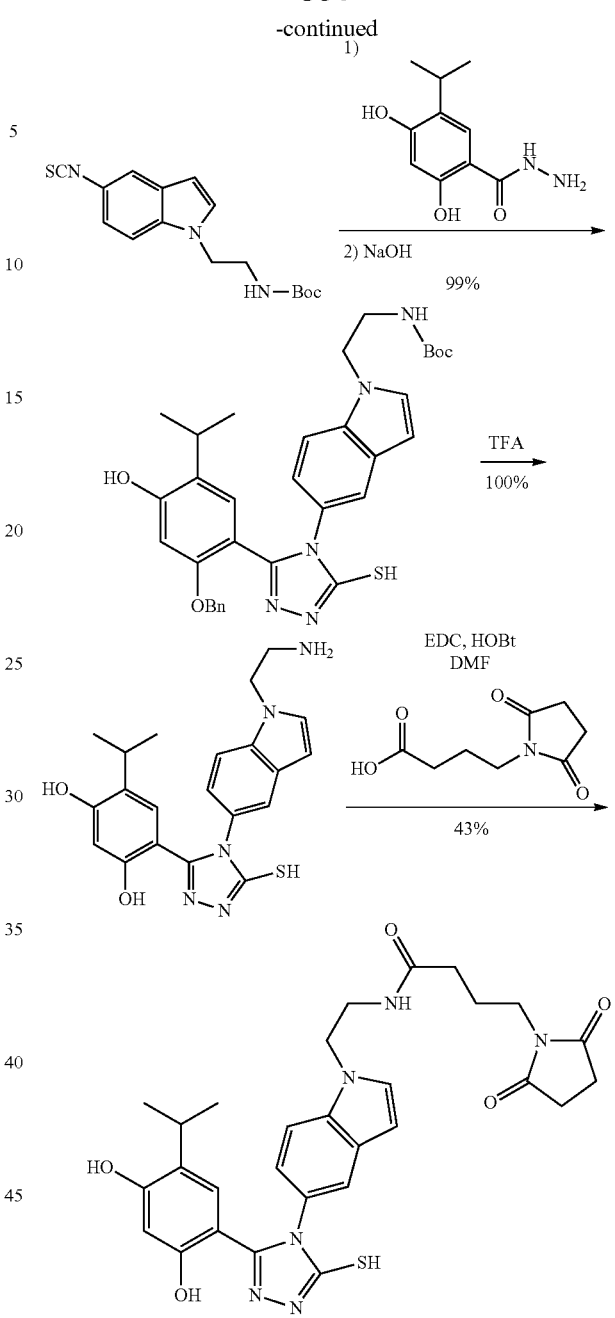

STEP-1:

Nitroindole (1.98 g, 12.2 mmol) was added to NaH (336 mg, 14.0 mmol) in 30 ml DMF at 0° C. After 30 min, 166 mg (1 mmol) sodium iodide and 3.35 g (14 mmol) 2-(tert-butoxycarbonylamino)ethyl methanesulfonate in 10 ml DMF were added successively at 0° C. The mixture was warmed up to rt and stirred overnight. It was quenched with water and extracted with ethyl acetate. The combined extracts were dried over Na₂SO₄ and purified by chromatography on silica with hexane/ethyl acetate (20-50%) to yield 2.90 g (9.5 mmol) product.

STEP-2:

The nitro compound (2.9 g, 9.5 mmol) was dissolved in 150 ml degassed ethyl acetate and ethanol (2:1). 500 mg Pd/C (10%) was added and the mixture stirred under hydrogen (balloon) at rt for 6 h. After filtration the solvent was removed and the crude purified by chromatography on silica with hexane/ethyl acetate to yield 566 mg (2.1 mmol) product.

STEP-3:

The amine, 280 mg (1 mmol), was added to di(1H-imidazol-1-yl)methanethione (214 mg, 1.2 mmol) in 2 ml ethyl acetate. The mixture was stirred for 1 h at 55° C. The reaction was quenched with water and extracted with ethyl acetate. The extracts were dried over Na₂SO₄, filtered and concentrated to yield 317 mg product.

STEP-4:

2,4-dihydroxy-5-isopropylbenzohydrazide (168 mg, 0.8 mmol) was added to the isothiocyanate (317 mg, 1 mmol) in 4 ml ethanol. It was stirred at 55° C. for 2 h and then concentrated under vacuum. 2 ml ethanol and 2 ml aq. NaOH (2 N) were added and the mixture heated in a microwave reactor at 110° C. for 1 h. Water was added and the pH adjusted to 7 with HCl (2 N). The precipitate was filtered off and yielded 417 mg (0.8 mmol) product.

STEP-5:

The Boc-triazole, 204 mg (0.4 mmol), was dissolved in 4 ml DCM and 2 ml trifluoroacetic acid. It was stirred for 3 h at 0° C. and then concentrated. The crude product was used in the next step.

STEP-6:

This amine (82 mg, 0.2 mmol) was added to 4-(2,5-dioxopyrrolidin-1-yl)butanoic acid (56 mg, 0.3 mmol), EDC (67 mg, 0.35 mmol) and HOBt (47 mg, 0.35 mmol) in 3 ml DMF at rt. The mixture was stirred for 12 h and then ethyl acetate and water added. The aq. phase was extracted twice with ethyl acetate and the combined organic extracts washed with brine and dried over MgSO₄. The crude was purified by chromatography on silica with DCM/MeOH (0-8%) to yield 50 mg (0.09 mmol) product.

NMR (400 MHz, DMSO-d₆) δ 13.81 (s, 1H), 9.52 (s, 1H), 9.39 (s, 1H), 7.97 (t, J=5.6, 1H), 7.44 (m, 2H), 7.37 (d, J=3.1, 1H), 6.97 (dd, J=1.9, 8.7, 1H), 6.84 (s, 1H), 6.42 (d, J=3.1, 1H), 6.20 (s, 1H), 4.20 (t, J=6.2, 2H), 3.2-3.4 (m, 4H), 2.91 (dt, J=6.8, 13.7, 1H), 2.60 (s, 4H), 2.07-1.98 (m, 2H), 1.74-1.62 (m, 2H), 0.91 (d, J=6.9, 6H). ESMS (C₂₉H₃₂N₆O₅S): calculated 576.22. found: 577.2 [M+H]⁺.

Example 5

Synthesis of Compound 125

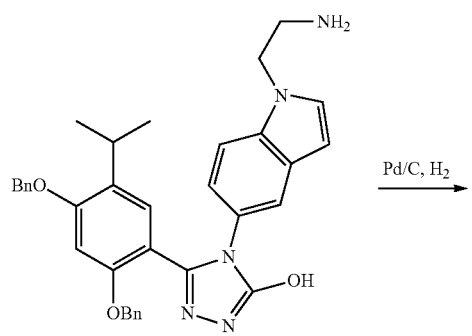

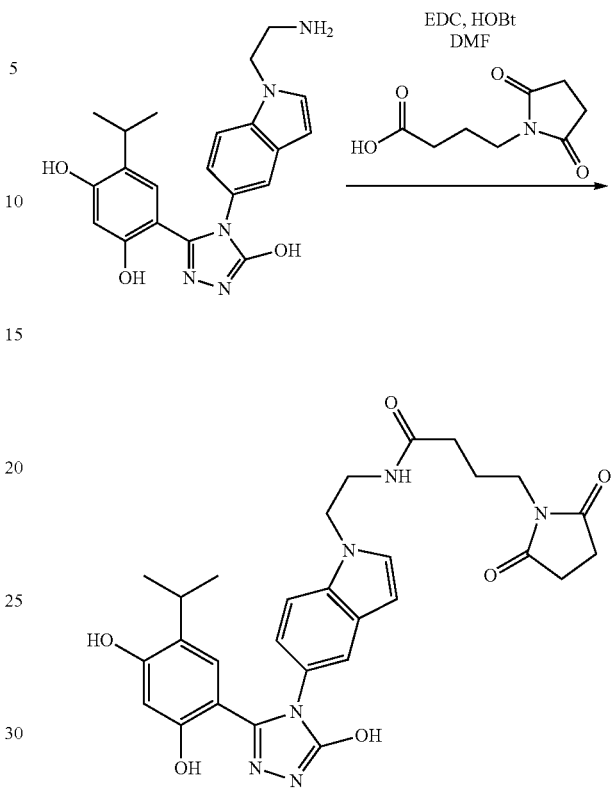

The benzylether[4-(1-(2-aminoethyl)-1H-indol-5-yl)-5-(2,4-bis(benzyloxy)-5-isopropylphenyl)-4H-1,2,4-triazol-3-ol; 188 mg, 0.33 mmol) was dissolved in 6 ml degassed THF/methanol (1:1). 50 mg Pd/C (10%) was added and the mixture stirred under hydrogen (balloon) at rt for 5 h. After filtration the solvent was removed and the crude purified by chromatography on silica with DCM/MeOH (5-20%)/NH₄OH (0.5%) to yield 71 mg (0.18 mmol) 4-(5-hydroxy-4-(1-(2-(methylamino)ethyl)-1H-indol-5-yl)-4H-1,2,4-triazol-3-yl)-6-isopropylbenzene-1,3-diol. This amine (50 mg, 0.125) was added to 4-(2,5-dioxopyrrolidin-1-yl)butanoic acid (26 mg, 0.14 mmol), EDC (38 mg, 0.2 mmol) and HOBt (27 mg, 0.2 mmol) in 1.5 ml DMF at rt. The mixture was stirred for 12 h and then ethyl acetate and water added. The aq. Phase was extracted twice with ethyl acetate and the combined organic extracts washed with brine and dried over MgSO₄. The crude was purified by chromatography on silica with DCM/MeOH (3-10%) to yield 34 mg (0.061 mmol) product.

NMR (400 MHz, DMSO-d₆) δ 11.85 (s, 1H), 9.52 (s, 1H), 9.45 (s, 1H), 8.00-7.90 (m, 1H), 7.54-7.48 (m, 2H), 7.41 (d, J=1.9, 1H), 6.93 (dd, J=1.9, 8.7, 1H), 6.76 (s, 1H), 6.41 (d, J=3.0, 1H), 6.21 (s, 1H), 4.20 (t, J=6.3, 2H), 3.3 (m, 4H), 2.97-2.83 (m, 1H), 2.59 (s, 4H), 2.02 (t, J=7.6, 2H), 1.67 (dt, J=7.4, 14.6, 2H), 0.86 (d, J=6.9, 6H). ESMS (C₂₉H₃₂N₆O₆): calculated 560.24. found: 561.2 [M+H⁺].

Example 6

Synthesis of 2-hydroxy-5-isopropyl-4-methylphenyl derivatives

Scheme 1. Synthesis of 2-hydroxy-5-isopropyl-4-methylphenyl derivatives.

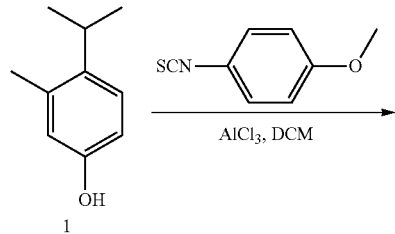

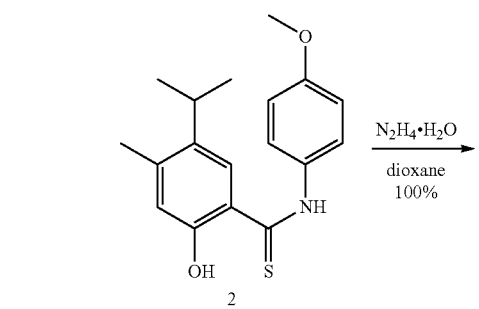

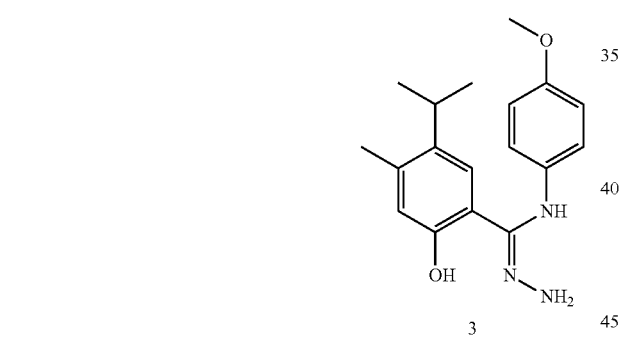

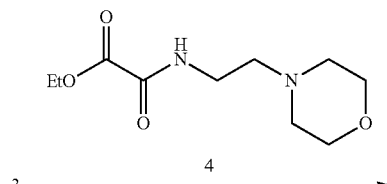

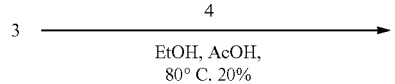

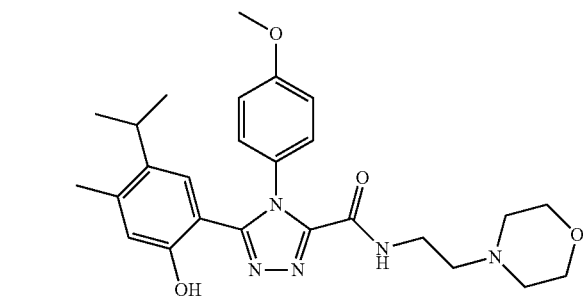

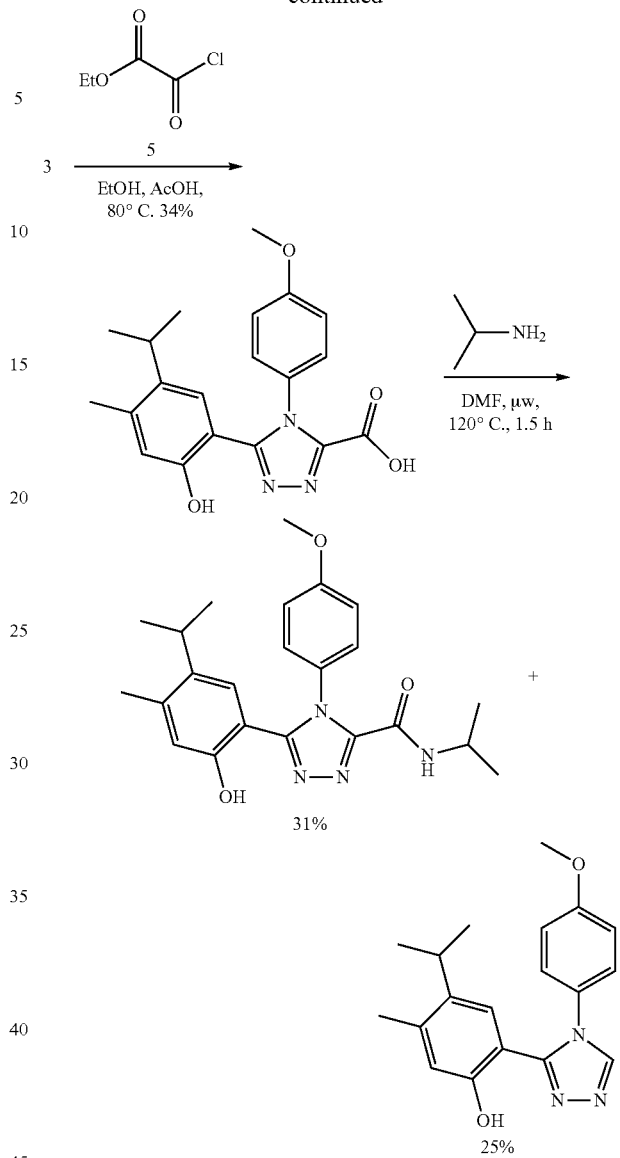

5-(2-Hydroxy-5-isopropyl-4-methylphenyl)-4-(4-methoxyphenyl)-N-(2-morpholinoethyl)-4H-1,2,4-triazole-3-carboxamide (436)

To a solution of 394 mg (1.26 mmol) of hydrazonamide 3 in 10 mL of ethanol was added 376 mg (1.64 mmol) of oxoactate 4 and one drop of acetic acid. The resulting solution was stirred at 70° C. for 15 h and then cooled to room temperature. The crude product was concentrated in vacuo, and chromatographed over $SiO_2$ (eluted with 1:1, hexanes→ethyl acetate→ethyl acetate→1:20, ethyl acetate-methanol) to afford 120 mg (20%) of STA-12-4262 as a white solid: $^1$H NMR (400 MHz, DMSO) δ 10.22 (s, 1H), 8.80 (t, J=5.6 Hz, 1H), 7.26 (d, J=8.8 Hz, 2H), 6.96 (d, J=8.8 Hz, 2H), 6.79 (s, 1H), 6.64 (s, 1H), 3.77 (s, 3H), 3.57-3.51 (m, 4H), 3.33-3.22 (m, 2H), 2.92-2.82 (m, 1H), 2.43-2.30 (m, 6H), 2.18 (s, 3H), 0.91 (d, J=6.8 Hz, 6H).

LCMS clcd. for $C_{26}H_{33}N_5O_4$ m/z 479.57. found m/z 480.4 (M$^+$+H).

5-(2-Hydroxy-5-isopropyl-4-methylphenyl)-4-(4-methoxyphenyl)-4H-1,2,4-triazole-3-carboxylic acid (437)

To a solution of 509 mg (1.63 mmol) of hydrazonamide 3 in 20 mL of THF at 0° C. was added dropwise a solution of ethyl chloroxoacetate (0.18 mL, 1.63 mmol) in 1 mL of THF. After stirring for 10 min, 0.43 mL of diisopropylethylamine (315 mg, 2.44 mmol) was added the mixture. The reaction was stirred at 0° C. for 30 min, 2 h at room temperature and then was quenched by slowly adding 15 mL of water. The aqueous solution was extracted three times with 20-mL portions of ethyl acetate. The combined organic fractions were dried (Na$_2$SO$_4$), concentrated in vacuo. The residue was chromatographed over silica gel (eluted with 1:1, hexanes→ethyl acetate→ethyl acetate→1:20, ethyl acetate-methanol) to afford 294 mg (49%) of 437 as a yellow solid: $^1$H NMR (400 MHz, DMSO) δ 12.50 (s, 1H), 9.22 (s, 1H), 7.13 (d, J=8.8 Hz, 2H), 6.94 (s, 1H), 6.77 (d, J=8.8 Hz, 2H), 6.38 (s, 1H), 3.66 (s, 3H), 2.88-2.78 (m, 1H), 2.08 (s, 3H), 1.00 (d, J=6.8 Hz, 6H).

LCMS clcd. for C$_{20}$H$_{21}$N$_3$O$_4$ m/z 367.15. found m/z 368.2 (M$^+$+H).

5-(2-Hydroxy-5-isopropyl-4-methylphenyl)-N-isopropyl-4-(4-methoxy-phenyl)-4H-1,2,4-triazole-3-carboxamide (438) and 4-isopropyl-2-(4-(4-methoxyphenyl)-4H-1,2,4-triazol-3-yl)-5-methylphenol (439)

To a solution of 229 mg (0.624 mmol) of acid 437 in 5 mL of DMF was added 0.5 mL of isopropylamine. The mixture was stirred while heated via microwave to 150° C. for 1 h. After cooling to room temperature, the mixture was poured into 15 mL of water, and was extracted three times with 15-mL portions of ethyl acetate. The combined organic fractions were dried (Na$_2$SO$_4$) and concentrated in vacuo. The residue was chromatographed over SiO$_2$ (9:1, hexanes-ethyl acetate→8:2→7:3) to afford 80 mg (31%) of 438 and 50 mg (25%) of 439 as off-white solids: 438: $^1$H NMR (400 MHz, DMSO) δ 10.25 (s, 1H), 8.78 (d, J=7.6 Hz, 1H), 7.26 (d, J=8.8 Hz, 2H), 6.97 (d, J=8.8 Hz, 2H), 6.79 (s, 1H), 6.64 (s, 1H), 3.97-3.87 (m, 1H), 3.77 (s, 3H), 2.92-2.82 (m, 1H), 2.18 (s, 3H), 1.10 (d, J=6.4 Hz, 6H), 0.91 (d, J=6.8 Hz, 6H).

LCMS clcd. for C$_{23}$H$_{28}$N$_4$O$_3$ m/z 408.22. found m/z 409.3 (M$^+$+H).

439

$^1$H NMR (400 MHz, DMSO) δ 10.53 (s, 1H), 8.79 (s, 1H), 7.36 (d, J=8.8 Hz, 2H), 7.08 (d, J=8.8 Hz, 2H), 6.83 (s, 1H), 6.69 (s, 1H), 3.80 (s, 3H), 2.96-2.82 (m, 1H), 2.21 (s, 3H), 0.90 (d, J=6.8 Hz, 6H).

LCMS clcd. for C$_{19}$H$_{21}$N$_3$O$_2$ m/z 323.16. found m/z 324.2 (M$^+$+H).

Example 7

Synthesis of 5-Sulfonamide Derivatives

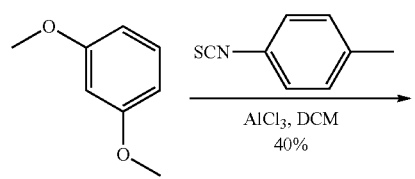

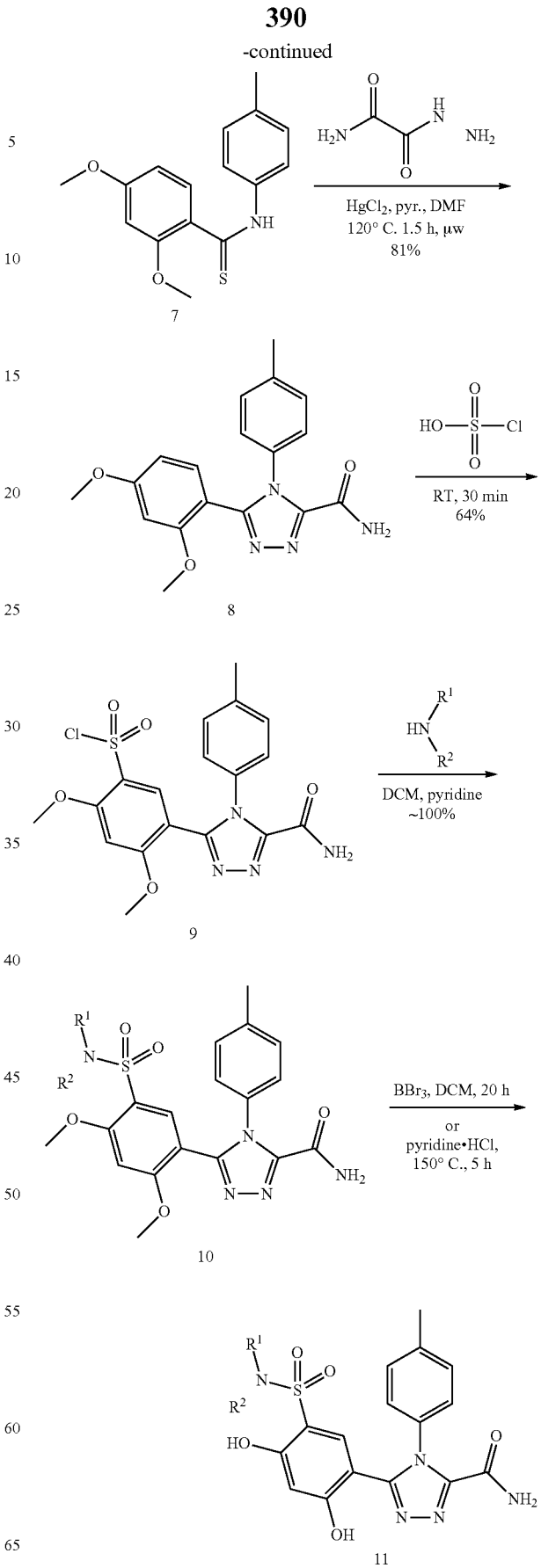

General Experimental

5-(5-Carbamoyl-4-p-tolyl-4H-1,2,4-triazol-3-yl)-2,4-dimethoxybenzene-1-sulfonyl chloride (9)

To 217 mg (0.642 mmol) of triazole 8 was added dropwise neat 1.5 mL of chlorosulfonic acid. The resulting yellow solution stirred for 45 min at room temperature and then was cooled to 0° C. The reaction mixture was quenched by adding dropwise addition of 50 mL of water (caution! Extremely exothermic!) After stirring for 5 min, the aqueous solution was extracted three times with 50-mL portions of ethyl acetate. The combined organic phases were dried ($Na_2SO_4$) and concentrated in vacuo to afford 180 mg (64%) of 9 as a colorless solid. The product was immediately used after preparation: LCMS clcd. for $C_{18}H_{17}ClN_4O_5S$ m/z 436.06. found m/z 437.1 ($M^++H$).

General Procedure to Prepare Sulfonamides.

To a solution 60 mg (0.138 mmol) of sulfonyl chloride 9 in 2 mL of methylene chloride was added 0.02 mL of amine and 0.02 mL of pyridine. The resulting solution was stirred for 4 h at room temperature, concentrated in vacuo, and dried under high vacuum to afford the sulfonamide in suitable purity. To the crude sulfonamide was added ~1 g of pyridine.HCl, and the mixture was heated to 150° C. for 7 h. After cooling to room temperature, the solid was dissolved in 40 mL of water. The aqueous solution was extracted three times with 50-mL portions of ethyl acetate. The combined organic fractions were dried ($Na_2SO_4$) and concentrated in vacuo. The residue was dissolved in ethyl acetate and precipitated by dropwise addition of hexanes. The solid was collected via filtration to afford the desired sulfonamide in 17%-53% (two steps) as a solid.

5-(2,4-Dihydroxyphenyl)-4-p-tolyl-4H-1,2,4-triazole-3-carboxamide (440)

$^1$H NMR (400 MHz, DMSO) δ 10.06 (s, 1H), 9.67 (s, 1H), 8.24 (s, 1H), 7.72 (s, 1H), 7.17 (d, J=8.4 Hz, 2H), 7.12 (d, J=8.4 Hz, 2H), 6.86 (d, J=8.4 Hz, 1H), 6.22 (d, J=2.0 Hz, 1H), 6.16 (dd, J=2.0, 8.4 Hz, 1H), 2.31 (s, 3H).
LCMS clcd. for $C_{16}H_{14}N_4O_3$ m/z 310.11. found m/z 311.2 ($M^++H$).

5-(5-(N,N-Diethylsulfamoyl)-2,4-dihydroxyphenyl)-4-p-tolyl-4H-1,2,4-triazole-3-carboxamide (441)

$^1$H NMR (400 MHz, DMSO) δ 10.86 (s, 1H), 10.78 (s, 1H), 8.27 (s, 1H), 7.74 (s, 1H), 7.42 (s, 1H), 7.15 (d, J=8.4 Hz, 2H), 7.11 (d, J=8.4 Hz, 2H), 6.40 (s, 1H), 3.10 (q, J=7.2 Hz, 4H), 2.29 (s, 3H), 0.94 (t, J=7.2 Hz, 6H).
LCMS clcd. for $C_{20}H_{23}N_5O_5S$ m/z 445.14. found m/z 446.2 ($M^++H$).

5-(2,4-Dihydroxy-5-(pyrrolidin-1-ylsulfonyl)phenyl)-4-p-tolyl-4H-1,2,4-triazole-3-carboxamide (442)

$^1$H NMR (400 MHz, DMSO) δ 10.98-10.72 (m, 1H), 8.28 (s, 1H), 7.75 (s, 1H), 7.42 (s, 1H), 7.25-7.01 (m, 4H), 6.43 (s, 1H), 3.18-2.98 (m, 4H), 2.29 (s, 3H), 1.78-1.54 (m, 4H).
LCMS clcd. for $C_{20}H_{21}N_5O_5S$ m/z 443.13. found m/z 444.2 ($M^++H$).

5-(2,4-Dihydroxy-5-(morpholinosulfonyl)phenyl)-4-p-tolyl-4H-1,2,4-triazole-3-carboxamide (443)

$^1$H NMR (400 MHz, DMSO) δ 10.93 (s, 1H), 8.28 (s, 1H), 7.75 (s, 1H), 7.38 (s, 1H), 7.30-6.98 (m, 4H), 6.46 (s, 1H), 3.75-3.49 (m, 4H), 2.84 (s, 3H), 2.40-2.12 (m, 4H).
LCMS clcd. for $C_{20}H_{21}N_5O_6S$ m/z 459.12. found m/z 460.2 ($M^++H$).

5-(2,4-Dihydroxy-5-(N-isopropylsulfamoyl)phenyl)-4-p-tolyl-4H-1,2,4-triazole-3-carboxamide (444)

$^1$H NMR (400 MHz, DMSO) δ 10.89 (s, 1H), 10.68 (s, 1H), 8.28 (s, 1H), 7.75 (s, 1H), 7.42 (s, 1H), 7.20-7.04 (m, 4H), 6.78 (d, J=8.0 Hz, 1H), 6.41 (s, 1H), 3.08-2.95 (m, 1H), 2.29 (s, 3H), 0.88 (d, J=6.4 Hz, 6H).
LCMS clcd. for $C_{19}H_{21}N_5O_5S$ m/z 431.13. found m/z 432.2 ($M^++H$).

5-(2,4-Dihydroxy-5-(N-isobutylsulfamoyl)phenyl)-4-p-tolyl-4H-1,2,4-triazole-3-carboxamide (445)

$^1$H NMR (400 MHz, DMSO) δ 10.89 (s, 1H), 10.70 (s, 1H), 8.28 (s, 1H), 7.75 (s, 1H), 7.44 (s, 1H), 7.14 (d, J=8.0 Hz, 2H), 7.11 (d, J=8.0 Hz, 2H), 6.90 (t, J=6.0 Hz, 1H), 6.41 (s, 1H), 2.42 (t, J=6.0 Hz, 2H), 2.29 (s, 3H), 1.64-1.51 (m, 1H), 0.77 (d, J=6.4 Hz, 6H).
LCMS clcd. for $C_{20}H_{23}N_5O_5S$ m/z 445.14. found m/z 446.2 ($M^++H$).

5-(2,4-Dihydroxy-5-(N-(2-morpholinoethyl)sulfamoyl)phenyl)-4-p-tolyl-4H-1,2,4-triazole-3-carboxamide (446)

$^1$H NMR (400 MHz, DMSO) δ 10.72 (s, 1H), 8.28 (s, 1H), 7.75 (s, 1H), 7.45 (s, 1H), 7.23-6.98 (m, 4H), 6.44 (s, 1H), 3.75-3.40 (m, 6H), 2.77-2.65 (m, 2H), 2.29 (s, 3H), 2.22-2.04 (m, 4H).
LCMS clcd. for $C_{22}H_{26}N_6O_6S$ m/z 502.16. found m/z 503.3 ($M^++H$).

5-(5-(N-Benzylsulfamoyl)-2,4-dihydroxyphenyl)-4-p-tolyl-4H-1,2,4-triazole-3-carboxamide (447)

$^1$H NMR (400 MHz, DMSO) δ 10.94 (s, 1H), 10.74 (s, 1H), 8.27 (s, 1H), 7.75 (s, 1H), 7.47 (s, 2H), 7.33-7.15 (m, 5H), 7.15-7.02 (m, 4H), 6.38 (s, 1H), 3.84 (s, 2H), 2.29 (s, 3H).
LCMS clcd. for $C_{23}H_{21}N_5O_5S$ m/z 479.13. found m/z 480.2 ($M^++H$).

5-(2,4-Dihydroxy-5-(N-(3-morpholinopropyl)sulfamoyl)phenyl)-4-p-tolyl-4H-1,2,4-triazole-3-carboxamide (448)

$^1$H NMR (400 MHz, DMSO) δ 10.74 (s, 1H), 8.27 (s, 1H), 7.75 (s, 1H), 7.44 (s, 1H), 7.25 (d, J=8.0 Hz, 1H), 7.15 (d, J=8.4 Hz, 2H), 7.11 (d, J=8.4 Hz, 2H), 6.42 (s, 1H), 3.63-3.48 (m, 4H), 2.66 (t, J=6.8 Hz, 2H), 2.38-2.12 (m, 9H), 1.56-1.40 (m, 2H).
LCMS clcd. for $C_{23}H_{28}N_6O_6S$ m/z 516.18. found m/z 517.3 ($M^++H$).

5-(5-(N-(2-(Diethylamino)ethyl)sulfamoyl)-2,4-dihydroxyphenyl)-4-p-tolyl-4H-1,2,4-triazole-3-carboxamide (449)

$^1$H NMR (400 MHz, DMSO) δ 8.26 (s, 1H), 7.74 (s, 1H), 7.42 (s, 1H), 7.15 (d, J=8.4 Hz, 2H), 7.11 (d, J=8.4 Hz, 2H), 6.34 (s, 1H), 2.71 (t, J=6.4 Hz, 2H), 2.48-2.35 (m, 6H), 2.29 (s, 3H), 0.90 (t, J=6.4 Hz, 6H).

LCMS clcd. for $C_{22}H_{28}N_6O_5S$ m/z 488.18. found m/z 489.3 (M$^+$+H).

Example 8

Synthesis of 5-phenethylresorcinol derivatives

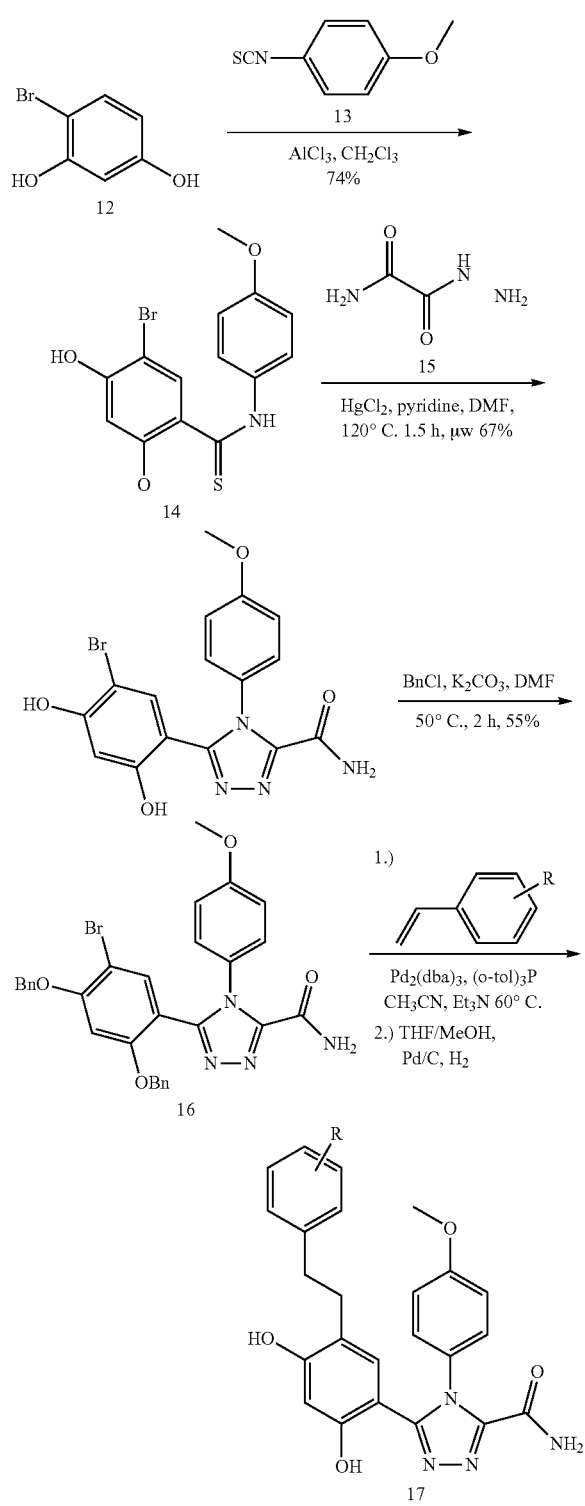

5-(5-Bromo-2,4-dihydroxyphenyl)-4-(4-methoxyphenyl)-4H-1,2,4-triazole-3-carboxamide (450)

To a well-stirred suspension of 500 mg (1.41 mmol) of thioamide 14, 290 mg (2.82 mmol) of oxamic hydrazide 15 and 460 mg (1.69 mmol) of mercury (II) chloride in 20 mL of DMF was added 0.28 mL (278 mg, 3.53 mmol) of pyridine. The suspension was heated to 120° C. for 1.5 h via microwave irradiation. After cooling to room temperature, the suspension was poured into 40 mL of water and extracted three times with 40-mL portions of ethyl acetate.

The combined organic fractions were dried (Na$_2$SO$_4$) and concentrated in vacuo. The residue was chromatographed over silica gel (eluted with 1:1→1:2 hexanes-ethyl acetate) to afford 380 mg (67%) of 450 as a yellow solid: $^1$H NMR (400 MHz, DMSO) δ 10.54 (s, 1H), 10.23 (s, 1H), 8.24 (s, 1H), 7.72 (s, 1H), 7.21 (s, 1H), 7.19 (d, J=9.0 Hz, 2H), 6.92 (d, J=9.0 Hz, 2H), 6.44 (s, 1H), 3.76 (s, 3H).

LCMS clcd. for $C_{16}H_{13}BrN_4O_4$ m/z 404.01. found m/z 405.0 (M$^+$+H).

5-(2,4-Bis(benzyloxy)-5-bromophenyl)-4-(4-methoxyphenyl)-4H-1,2,4-triazole-3-carboxamide (16)

To a well-stirred suspension of 702 mg (1.73 mmol) of STA-12-4145 and 1.19 g (8.65 mmol) of potassium carbonate in 10 mL of DMF was added 0.64 mL (704 mg, 5.54 mL) of benzyl chloride. The suspension stirred for 3 h at 45° C. and then was cooled to room temperature. The mixture was poured into 50 mL of water and extracted three times with 50-mL portions of ethyl acetate. The combined organic fractions were dried (Na$_2$SO$_4$) and concentrated in vacuo. The residue was chromatographed over SiO$_2$ (eluted with 1:1→3:7 hexanes-ethyl acetate) to afford 556 mg (55%) of compound 16 an off-white solid: $^1$H NMR (400 MHz, DMSO) δ 8.28 (s, 1H), 7.73 (s, 1H), 7.63 (s, 1H), 7.44-7.28 (m, 8H), 7.20 (dd, J=1.6, 7.2 Hz, 2H), 7.02 (d, J=9.0 Hz, 2H), 6.90 (s, 1H), 6.83 (d, J=9.0 Hz, 2H), 5.17 (s, 2H), 5.00 (s, 2H), 3.74 (s, 3H).

LCMS clcd. for $C_{30}H_{25}BrN_4O_4$ m/z 584.11. found m/z 585.0 (M$^+$+H).

General Procedure for Heck Coupling

To a solution of 60 mg (0.103 mmol) of 16 in 3 mL of acetonitrile were added 3.0 equivalents of styrene, 13 mg (41 wok 0.4 equ) of tri-o-tolylphosphine, and 43 mg (0.43 mmol) of triethylamine. The well-stirred mixture was degassed and then 10 mg (10 wok 0.1 equ) of tris(dibenzylideneacetone)-dipalladium [Pd$_2$(dba)$_3$] was added. The mixture was stirred at 50° C. for 15 h and then at 75° C. for 5 h. After cooling to room temperature, the mixture was filtered through a pad of silica gel (rinsed with ethyl acetate) and concentrated in vacuo. The residue was purified by chromatography (eluted with various mixtures of hexanes-ethyl acetate) to afford the stilbene (~40%-80% on average) as a solid. The benzyl protecting groups were removed by adding 5% Pd/C to a solution of the stilbene in 1:1 solution of THF-MeOH. The mixture was stirred under an atmosphere of hydrogen gas for overnight (balloon), filtered over a plug of Celite (rinsed with 1:1 ethyl acetate-MeOH), and then was concentrated in vacuo. The residue was taken up in ethyl acetate and precipitated by dropwise addition of hexanes. The product was collected by filtration to afford phenethyl derivative 17 (~50%-90%) as a solid.

5-(2,4-Dihydroxy-5-phenethylphenyl)-4-(4-methoxyphenyl)-4H-1,2,4-triazole-3-carboxamide (451)

$^1$H NMR (400 MHz, DMSO) δ 10.25 (s, 1H), 9.76 (s, 1H), 8.24 (s, 1H), 7.73 (s, 1H), 7.31-7.21 (m, 2H), 7.21-7.14 (m, 3H), 7.11 (d, J=7.2 Hz, 2H), 6.97 (d, J=8.8 Hz, 2H), 6.63 (s, 1H), 6.34 (s, 1H), 3.76 (s, 3H), 2.60-2.50 (m, 4H).
LCMS clcd. for $C_{24}H_{22}N_4O_4$ m/z 430.16. found m/z 431.2 (M$^+$+H).

5-(2,4-Dihydroxy-5-(4-methoxyphenethyl)phenyl)-4-(4-methoxyphenyl)-4H-1,2,4-triazole-3-carboxamide (452)

$^1$H NMR (400 MHz, DMSO) δ 10.25 (s, 1H), 9.72 (s, 1H), 8.24 (s, 1H), 7.73 (s, 1H), 7.32-7.12 (m, 2H), 7.12-6.88 (m, 4H), 6.88-6.77 (m, 2H), 6.63 (s, 1H), 6.32 (s, 1H), 3.76 (s, 3H), 3.71 (s, 3H), 2.60-2.40 (m, 4H).
LCMS clcd. for $C_{25}H_{24}N_4O_5$ m/z 460.17. found m/z 461.3 (M$^+$+H).

5-(5-(4-Fluorophenethyl)-2,4-dihydroxyphenyl)-4-(4-methoxyphenyl)-4H-1,2,4-triazole-3-carboxamide (453)

$^1$H NMR (400 MHz, DMSO) δ 10.25 (s, 1H), 9.74 (s, 1H), 8.24 (s, 1H), 7.73 (s, 1H), 7.18 (d, J=8.8 Hz, 2H), 7.14-7.02 (m, 4H), 6.95 (d, J=8.8 Hz, 2H), 6.63 (s, 1H), 6.31 (s, 1H), 3.76 (s, 3H), 2.60-2.45 (m, 4H).
LCMS clcd. for $C_{24}H_{21}FN_4O_4$ m/z 448.15. found ink 449.2 (M$^+$+H).

5-(5-(3,4-Dimethoxyphenethyl)-2,4-dihydroxyphenyl)-4-(4-methoxyphenyl)-4H-1,2,4-triazole-3-carboxamide (454)

$^1$H NMR (400 MHz, DMSO) δ 10.23 (s, 1H), 9.73 (s, 1H), 8.24 (s, 1H), 7.73 (s, 1H), 7.45-7.36 (m, 1H), 7.18 (d, J=8.4 Hz, 2H), 6.95 (d, J=8.4 Hz, 2H), 6.89-6.56 (m, 3H), 6.32 (s, 1H), 3.76 (s, 3H), 3.71 (s, 3H), 2.60-2.45 (m, 4H).
LCMS clcd. for $C_{26}H_{26}N_4O_6$ m/z 490.2. found m/z 491.3 (M$^+$+H).

5-(2,4-Dihydroxy-5-(2-methoxyphenethyl)phenyl)-4-(4-methoxyphenyl)-4H-1,2,4-triazole-3-carboxamide (455)

$^1$H NMR (400 MHz, DMSO) δ 10.26 (s, 1H), 9.71 (s, 1H), 8.24 (s, 1H), 7.73 (s, 1H), 7.22-7.12 (m, 3H), 7.02-6.88 (m, 4H), 6.83 (t, J=7.2 Hz, 1H), 6.62 (s, 1H), 6.32 (s, 1H), 3.76 (s, 3H), 3.75 (s, 3H), 2.60-2.45 (m, 4H). LCMS clcd. for $C_{25}H_{24}N_4O_5$ m/z 460.17. found m/z 461.3 (M$^+$+H).

5-(5-(2-Fluorophenethyl)-2,4-dihydroxyphenyl)-4-(4-methoxyphenyl)-4H-1,2,4-triazole-3-carboxamide (456)

$^1$H NMR (400 MHz, DMSO) δ 10.25 (s, 1H), 9.77 (s, 1H), 8.24 (s, 1H), 7.73 (s, 1H), 7.29-6.99 (m, 6H), 6.94 (d, J=8.8 Hz, 2H), 6.61 (s, 1H), 6.32 (s, 1H), 3.76 (s, 3H), 2.65-2.55 (m, 4H).
LCMS clcd. for $C_{24}H_{21}FN_4O_4$ m/z 448.15. found m/z 449.2 (M$^+$+H).

5-(2,4-Dihydroxy-5-(4-methylphenethyl)phenyl)-4-(4-methoxyphenyl)-4H-1,2,4-triazole-3-carboxamide (457)

$^1$H NMR (400 MHz, DMSO) δ 8.30 (s, 1H), 7.81 (s, 1H), 7.29-6.84 (m, 8H), 6.27 (s, 1H), 3.77 (s, 3H), 2.65-2.45 (m, 7H).
LCMS clcd. for $C_{25}H_{24}N_4O_4$ m/z 444.18. found m/z 445.2 (M$^+$+H).

5-(2,4-Dihydroxy-5-(4-(trifluoromethyl)phenethyl)phenyl)-4-(4-methoxy-phenyl)-4H-1,2,4-triazole-3-carboxamide (458)

LCMS clcd. for $C_{25}H_2T_3N_4O_4$ m/z 498.15. found m/z 499.2 (M$^+$+H).

Methyl 4-(5-(5-carbamoyl-4-(4-methoxyphenyl)-4H-1,2,4-triazol-3-yl)-2,4-di-hydroxyphenethyl)benzoate (459)

$^1$H NMR (400 MHz, DMSO) δ 8.29 (s, 1H), 7.89-7.72 (m, 3H), 7.43-7.38 (m, 2H), 7.28-7.10 (m, 4H), 7.01-6.89 (m, 2H), 3.84 (s, 3H), 3.76 (s, 3H), 3.12-3.01 (m, 2H), 3.00-2.61 (m, 2H).
LCMS clcd. for $C_{26}H_{24}N_4O_6$ m/z 488.17. found m/z 489.2 (M$^+$+H).

5-(2,4-Dihydroxy-5-(3-methylphenethyl)phenyl)-4-(4-methoxyphenyl)-4H-1,2,4-triazole-3-carboxamide (460)

$^1$H NMR (400 MHz, DMSO) δ 10.40 (s, 1H), 9.76 (s, 1H), 8.25 (s, 1H), 7.74 (s, 1H), 7.54-6.78 (m, 10H), 3.76 (s, 3H), 2.65-2.45 (m, 4H) 2.27 (s, 3H).
LCMS clcd. for $C_{25}H_{24}N_4O_4$ m/z 444.18. found m/z 445.2 (M$^+$+H).

5-(2,4-Dihydroxy-5-(3-(trifluoromethyl)phenethyl)phenyl)-4-(4-methoxy-phenyl)-4H-1,2,4-triazole-3-carboxamide (461)

$^1$H NMR (400 MHz, DMSO) δ 9.87 (s, 1H), 8.28 (s, 1H), 7.79 (s, 1H), 7.60-7.43 (m, 3H), 7.40 (d, J=7.6 Hz, 1H), 7.21 (d, J=8.8 Hz, 2H), 6.95 (d, J=8.8 Hz, 2H), 6.69 (s, 1H), 6.36 (s, 1H), 3.75 (s, 3H), 2.74-2.50 (m, 4H). LCMS clcd. for $C_{25}H_{21}F_3N_4O_4$ m/z 498.15. found m/z 499.2 (M$^+$+H).

5-(2,4-Dihydroxy-5-(2-(naphthalen-1-yl)ethyl)phenyl)-4-(4-methoxyphenyl)-4H-1,2,4-triazole-3-carboxamide (462)

$^1$H NMR (400 MHz, DMSO) δ 9.89 (s, 1H), 8.30 (s, 1H), 7.91-7.77 (m, 3H), 7.52-7.42 (m, 2H), 7.30 (d, J=8.8 Hz, 1H), 7.26 (d, J=8.8 Hz, 1H), 7.19 (d, J=8.8 Hz, 2H), 7.06 (s, 1H), 6.98 (d, J=8.8 Hz, 1H), 6.90 (d, J=8.8 Hz, 2H), 6.39 (s, 1H), 3.75 (s, 3H), 2.79-2.55 (m, 4H).
LCMS clcd. for $C_{28}H_{24}N_4O_4$ m/z 480.18. found m/z 481.3 (M$^+$+H).

5-(5-(2,6-Difluorophenethyl)-2,4-dihydroxyphenyl)-4-(4-methoxyphenyl)-4H-1,2,4-triazole-3-carboxamide (463)

$^1$H NMR (400 MHz, DMSO) δ 9.98 (s, 1H), 8.30 (s, 1H), 7.82 (s, 1H), 7.29 (t, J=7.6 Hz, 1H), 7.19 (d, J=8.8 Hz, 2H), 7.03 (d, J=7.6 Hz, 1H), 7.01 (d, J=7.6 Hz, 1H), 6.96 (d, J=8.8 Hz, 2H), 6.56 (s, 1H), 6.39 (s, 1H), 3.78 (s, 3H), 2.70-2.58 (m, 2H), 2.58-2.38 (m, 2H).
LCMS clcd. for $C_{24}H_{20}F_2N_4O_4$ m/z 466.15. found m/z 467.2 (M$^+$+H).

Example 9

Compounds with Various Linker Lengths and Saturation Via Suzuki Coupling

Compounds were made using the coupling strategy of Example 8 except commercially available boronic acids (ie. Suzuki procedure) were used instead of styrenes (ie. Heck procedure).

5-(2,4-Dihydroxy-5-(3-phenylpropyl)phenyl)-4-(4-methoxyphenyl)-4H-1,2,4-triazole-3-carboxamide (464)

$^1$H NMR (400 MHz, DMSO) δ 9.98 (s, 1H), 8.29 (s, 1H), 7.80 (s, 1H), 7.34-7.20 (m, 4H), 7.18 (d, J=6.8 Hz, 1H), 7.12 (d, J=7.6 Hz, 2H), 6.92 (d, J=7.6 Hz, 2H), 6.66 (s, 1H), 6.39 (s, 1H), 3.69 (s, 3H), 2.49-2.35 (m, 2H), 2.35-2.22 (m, 2H), 1.64-1.53 (m, 2H).
LCMS clcd. for $C_{25}H_{24}N_4O_4$ m/z 444.18. found m/z 445.2 (M$^+$+H).

5-(4,6-Dihydroxybiphenyl-3-yl)-4-(4-methoxyphenyl)-4H-1,2,4-triazole-3-carboxamide (465)

$^1$H NMR (400 MHz, DMSO) δ 10.25 (s, 1H), 8.34 (s, 1H), 7.85 (s, 1H), 7.39-7.15 (m, 7H), 7.00 (d, J=8.4 Hz, 2H), 6.91 (s, 1H), 6.56 (s, 1H), 3.80 (s, 3H). LCMS clcd. for $C_{22}H_{18}N_4O_4$ m/z 402.13. found m/z 403.1 (M$^+$+H).

5-(5-(2-Cyclohexylethyl)-2,4-dihydroxyphenyl)-4-(4-methoxyphenyl)-4H-1,2,4-triazole-3-carboxamide (466)

$^1$H NMR (400 MHz, DMSO) δ 9.98 (s, 1H), 8.33 (s, 1H), 7.86 (s, 1H), 7.29 (d, J=8.4 Hz, 2H), 6.99 (d, J=8.4 Hz, 2H), 6.58 (s, 1H), 6.41 (s, 1H), 3.79 (s, 3H), 2.22 (t, J=7.2 Hz, 2H), 1.70-1.52 (m, 5H), 1.22-0.98 (m, 6H), 0.88-0.73 (m, 2H).
LCMS clcd. for $C_{24}H_{28}N_4O_4$ m/z 436.21. found m/z 437.2 (M$^+$+H).

5-(5-Hexyl-2,4-dihydroxyphenyl)-4-(4-methoxyphenyl)-4H-1,2,4-triazole-3-carboxamide (467)

$^1$H NMR (400 MHz, DMSO) δ 9.98 (s, 1H), 8.30 (s, 1H), 7.83 (s, 1H), 7.31 (d, J=8.8 Hz, 2H), 6.99 (d, J=8.8 Hz, 2H), 6.58 (s, 1H), 6.40 (s, 1H), 3.78 (s, 3H), 1.25-0.68 (m, 13H).
LCMS clcd. for $C_{22}H_{26}N_4O_4$ m/z 410.20. found m/z 411.2 Or +H).

5-(2,4-Dihydroxy-5-(4-hydroxybutyl)phenyl)-4-(4-methoxyphenyl)-4H-1,2,4-triazole-3-carboxamide (468)

$^1$H NMR (400 MHz, DMSO) δ 9.77 (s, 1H), 8.28 (s, 1H), 7.79 (s, 1H), 7.24 (d, J=7.2 Hz, 2H), 6.95 (d, J=7.2 Hz, 2H), 6.63 (s, 1H), 6.35 (s, 1H), 3.78 (s, 3H), 3.39-3.28 (m, 2H), 2.30-2.20 (m, 2H), 1.34-1.21 (m, 4H). LCMS clcd. for $C_{20}H_{22}N_4O_5$ m/z 398.16. found m/z 399.3 (M$^+$+H).

Example 10

5-Phenylresorcinol Series

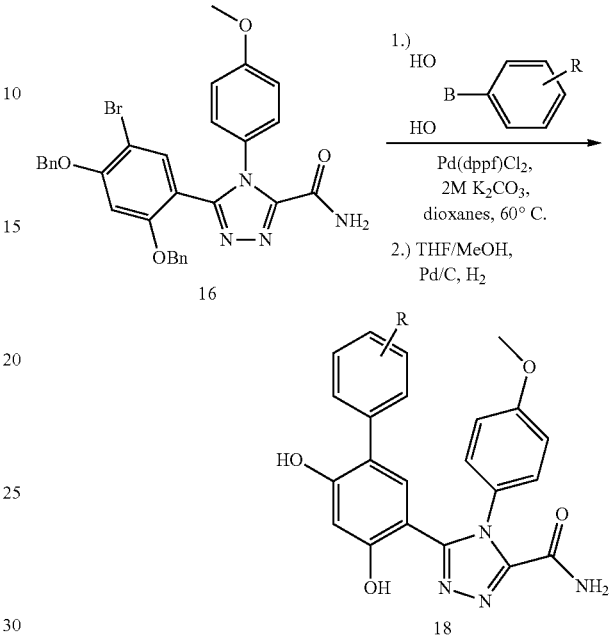

General Procedure for Suzuki Coupling:

To a solution of 65 mg (0.111 mmol) of 16 in 3 mL of 1,4-dioxanes were added 3.0 equivalents of boronic acid (or boronic ester) and 0.22 mL (0.44 mmol) of a 2 M potassium carbonate aqueous solution. The well-stirred mixture was degassed and then 3 mg (3.3 μmol, 0.03 equ) of [1,1'-bis(diphenylphosphino)-ferrocene]dichloropalladium (II) complex with dichloromethane (1:1) [PdCl$_2$(dppf).CH$_2$Cl$_2$] was added. The mixture was stirred at 50° C. for 15 h. After cooling to room temperature, the mixture was filtered through a plug of silica gel (rinsed with ethyl acetate) and concentrated in vacuo. The residue was purified by chromatography (eluted with various mixtures of hexanes-ethyl acetate) to afford the biphenyl derivative (~40%-80% on average) as a solid. The benzyl protecting groups were removed by adding 5% Pd/C to a solution of the biphenyl compound in 1:1 solution of THF-MeOH. The mixture was stirred under an atmosphere of hydrogen gas for overnight (balloon), filtered over a plug of Celite (rinsed with 1:1 ethyl acetate-MeOH), and then was concentrated in vacuo. The residue was taken up in ethyl acetate and precipitated by dropwise addition of hexanes. The product was collected by filtration to afford phenylresorcinol derivative 18 (~50%-90%) as a solid.

5-(4,6-Dihydroxy-4'-methoxybiphenyl-3-yl)-4-(4-methoxyphenyl)-4H-1,2,4-triazole-3-carboxamide (469)

$^1$H NMR (400 MHz, DMSO) δ 10.50 (s, 1H), 9.99 (s, 1H), 8.27 (s, 1H), 7.77 (s, 1H), 7.29 (dd, J=1.6, 8.0 Hz, 2H), 7.18 (dd, J=1.6, 8.0 Hz, 2H), 6.99 (dd, J=1.6, 8.4 Hz, 2H), 6.88-6.72 (m, 3H), 6.47 (s, 1H), 3.80 (s, 3H), 3.75 (s, 3H). LCMS clcd. for $C_{23}H_{20}N_4O_5$ m/z 432.14. found m/z 433.1 (M$^+$+H).

5-(4'-Fluoro-4,6-dihydroxybiphenyl-3-yl)-4-(4-methoxyphenyl)-4H-1,2,4-triazole-3-carboxamide (470)

$^1$H NMR (400 MHz, DMSO) δ 10.25 (s, 1H), 8.33 (s, 1H), 7.83 (s, 1H), 7.42-7.04 (m, 7H), 6.99 (d, J=8.4 Hz, 2H), 6.92 (s, 1H), 6.54 (s, 1H), 3.79 (s, 3H).
LCMS clcd. for $C_{22}H_{17}FN_4O_4$ m/z 420.12. found m/z 421.2 (M$^+$+H).

5-(5-(Benzo[d][1,3]dioxol-5-yl)-2,4-dihydroxyphenyl)-4-(4-methoxyphenyl)-4H-1,2,4-triazole-3-carboxamide (471)

$^1$H NMR (400 MHz, DMSO) δ 10.17 (s, 1H), 8.33 (s, 1H), 7.84 (s, 1H), 7.32 (d, J=8.8 Hz, 2H), 7.00 (d, J=8.8 Hz, 2H), 6.86 (s, 1H), 6.83 (d, J=8.4 Hz, 1H), 6.78 (s, 1H), 6.67 (d, J=8.4 Hz, 1H), 6.52 (s, 1H), 6.00 (s, 2H), 3.80 (s, 3H).
LCMS clcd. for $C_{23}H_{18}N_4O_6$ m/z 446.12. found m/z 447.1 (M$^+$+H).

5-(2,4-Dihydroxy-5-(1H-indol-5-yl)phenyl)-4-(4-methoxyphenyl)-4H-1,2,4-triazole-3-carboxamide (472)

LCMS clcd. for $C_{24}H_{19}N_5O_4$ m/z 441.14. found m/z 442.2 (M$^+$+H).

5-(5-(2,3-Dihydrobenzofuran-5-yl)-2,4-dihydroxyphenyl)-4-(4-methoxy-phenyl)-4H-1,2,4-triazole-3-carboxamide (473)

$^1$H NMR (400 MHz, DMSO) δ 10.25 (s, 1H), 8.36 (s, 1H), 7.88 (s, 1H), 7.35 (d, J=8.4 Hz, 2H), 7.03 (d, J=8.4 Hz, 2H), 6.97 (s, 1H), 6.95 (d, J=8.4 Hz, 1H), 6.81 (s, 1H), 6.66 (d, J=8.4 Hz, 1H), 6.52 (s, 1H), 4.52 (t, J=8.4 Hz, 2H), 3.81 (s, 3H), 3.15 (t, J=8.4 Hz, 2H).
LCMS clcd. for $C_{24}H_{20}N_4O_5$ m/z 444.14. found m/z 445.1 (M$^+$+H).

5-(2,4-Dihydroxy-5-(pyridin-4-yl)phenyl)-4-(4-methoxyphenyl)-4H-1,2,4-triazole-3-carboxamide (474)

$^1$H NMR (400 MHz, DMSO) δ 11.28 (s, 1H), 10.90 (s, 1H), 8.78 (d, J=4.4 Hz, 2H), 8.30 (s, 1H), 8.22 (d, J=4.4 Hz, 2H), 7.78 (s, 1H), 7.68 (s, 1H), 7.25 (d, J=7.6 Hz, 2H), 6.91 (d, J=7.6 Hz, 2H), 6.67 (s, 1H), 3.75 (s, 3H).
LCMS clcd. for $C_{21}H_{17}N_5O_4$ m/z 403.13. found m/z 404.1 (M$^+$+H).

5-(3'-Cyano-4,6-dihydroxybiphenyl-3-yl)-4-(4-methoxyphenyl)-4H-1,2,4-triazole-3-carboxamide (475)

$^1$H NMR (400 MHz, DMSO) δ 10.45 (s, 1H), 10.25 (s, 1H), 8.31 (s, 1H), 7.81 (s, 1H), 7.74-7.69 (m, 2H), 7.52 (t, J=8.0 Hz, 1H), 7.38-7.33 (m, 1H), 7.31 (d, J=8.8 Hz, 2H), 7.05 (s, 1H), 6.97 (d, J=8.8 Hz, 2H), 6.56 (s, 1H), 3.79 (s, 3H). LCMS clcd. for $C_{23}H_{17}N_5O_4$ m/z 427.13. found m/z 428.1 (M$^+$+H).

Methyl 5'-(5-carbamoyl-4-(4-methoxyphenyl)-4H-1,2,4-triazol-3-yl)-2',4'-di-hydroxybiphenyl-4-carboxylate (476)

$^1$H NMR (400 MHz, DMSO) δ 10.40 (s, 1H), 8.33 (s, 1H), 7.89 (d, J=8.4 Hz, 2H), 7.84 (s, 1H), 7.44 (d, J=8.4 Hz, 2H), 7.32 (d, J=8.8 Hz, 2H), 7.04 (s, 1H), 7.00 (d, J=8.8 Hz, 2H), 6.59 (s, 1H), 3.86 (s, 3H), 3.80 (s, 3H). LCMS clcd. for $C_{24}H_{20}N_4O_6$ m/z 460.14. found m/z 461.1 (M$^+$+H).

5-(4,6-Dihydroxy-3',4',5'-trimethoxybiphenyl-3-yl)-4-(4-methoxyphenyl)-4H-1,2,4-triazole-3-carboxamide (477)

$^1$H NMR (400 MHz, DMSO) δ 10.50 (s, 1H), 9.96 (s, 1H), 8.24 (s, 1H), 7.73 (s, 1H), 7.29 (d, J=8.8 Hz, 2H), 6.96 (d, J=8.8 Hz, 2H), 6.95 (s, 1H), 6.54 (s, 2H), 6.47 (s, 1H), 3.76 (s, 3H), 3.74 (s, 6H), 3.66 (s, 3H).
LCMS clcd. for $C_{25}H_{24}N_4O_7$ m/z 492.16. found m/z 493.1 (M$^+$+H).

Methyl 5'-(5-carbamoyl-4-(4-methoxyphenyl)-4H-1,2,4-triazol-3-yl)-2',4'-di-hydroxybiphenyl-3-carboxylate (478)

$^1$H NMR (400 MHz, DMSO) δ 10.60 (s, 1H), 10.15 (s, 1H), 8.25 (s, 1H), 7.96 (s, 1H), 7.82 (d, J=7.6 Hz, 1H), 7.74 (s, 1H), 7.54 (d, J=7.6 Hz, 1H), 7.45 (t, J=7.6 Hz, 1H), 7.29 (d, J=8.8 Hz, 2H), 6.98 (s, 1H), 6.96 (d, J=8.8 Hz, 2H), 6.50 (s, 1H), 3.87 (s, 3H), 3.76 (s, 3H).
LCMS clcd. for $C_{24}H_{20}N_4O_6$ m/z 460.14. found m/z 461.1 (M$^+$+H).

5-(5-(Biphenyl-4-yl)-2,4-dihydroxyphenyl)-4-(4-methoxyphenyl)-4H-1,2,4-triazole-3-carboxamide (479)

$^1$H NMR (400 MHz, DMSO) δ 10.23 (s, 1H), 8.32 (s, 1H), 7.83 (s, 1H), 7.67 (d, J=7.2 Hz, 2H), 7.59 (d, J=8.4 Hz, 2H), 7.48 (t, J=7.6 Hz, 2H), 7.37 (m, 3H), 7.33 (d, J=8.8 Hz, 2H), 7.01 (d, J=8.8 Hz, 2H), 6.99 (s, 1H), 6.56 (s, 1H), 3.80 (s, 3H).
LCMS clcd. for $C_{28}H_{22}N_4O_4$ m/z 478.16. found m/z 479.1 (M$^+$+H).

5-(5-(2-(Biphenyl-4-yl)ethyl)-2,4-dihydroxyphenyl)-4-(4-methoxyphenyl)-4H-1,2,4-triazole-3-carboxamide (480)

$^1$H NMR (400 MHz, DMSO) δ 9.95 (s, 1H), 8.32 (s, 1H), 7.84 (s, 1H), 7.65 (d, J=7.6 Hz, 2H), 7.57 (d, J=8.4 Hz, 2H), 7.45 (t, J=7.6 Hz, 2H), 7.34 (t, J=7.2 Hz, 1H), 7.25 (d, J=8.8 Hz, 2H), 7.20 (d, J=8.0 Hz, 2H), 6.97 (d, J=8.8 Hz, 2H), 6.71 (s, 1H), 6.43 (s, 1H), 3.75 (s, 3H), 2.65-2.52 (m, 4H).
LCMS clcd. for $C_{30}H_{26}N_4O_4$ m/z 506.20. found m/z 507.2 (M$^+$+H).

Example 11

Inhibition of Hsp90

Hsp90 protein is obtained from Stressgen (Cat# SPP-770). Assay buffer: 100 mM Tris-HCl, Ph 7.4, 20 mM KCl, 6 mM MgCl$_2$. Malachite green (0.0812% w/v) (M9636) and polyvinyl alcohol USP (2.32% w/v) (P1097) are obtained from Sigma. A Malachite Green Assay (see *Methods Mol. Med.*, 85:149 (2003) for method details) is used for examination of ATPase activity of Hsp90 protein. Briefly, Hsp90 protein in assay buffer (100 mM Tris-HCl, Ph 7.4, 20 mM KCl, 6 mM MgCl$_2$) is mixed with ATP alone (negative control) or in the presence of Geldanamycin (a positive control) or a compound of the invention in a 96-well plate. Malachite green reagent is added to the reaction. The mixtures are incubated at 37° C. for 4 hours and sodium citrate buffer (34% w/v sodium citrate) is added to the reaction. The plate is read by an ELISA reader with an absorbance at 620 nm.

Example 12

Degradation of Hsp90 Client Proteins Via Inhibition of Hsp90 Activity

A. Cells and Cell Culture

Human high-Her2 breast carcinoma BT474 (HTB-20), SK-BR-3 (HTB-30) and MCF-7 breast carcinoma (HTB-22) from American Type Culture Collection, Va., USA were grown in Dulbecco's modified Eagle's medium with 4 mM L-glutamine and antibiotics (100 IU/ml penicillin and 100 µg/ml streptomycine; GibcoBRL). To obtain exponential cell growth, cells were trypsinized, counted and seeded at a cell density of $0.5 \times 10^6$ cells/ml regularly, every 3 days. All experiments were performed on day 1 after cell passage.

B. Degradation of her2 in Cells after Treatment with a Compound of the Invention 1. Method 1

BT-474 cells are treated with 0.5 µM, 2 µM, or 5 µM of 17AAG (a positive control) or 0.5 µM, 2 µM, or 5 µM of a compound of the invention overnight in DMEM medium. After treatment, each cytoplasmic sample is prepared from $1 \times 10^6$ cells by incubation of cell lysis buffer (#9803, Cell Signaling Technology) on ice for 10 minutes. The resulting supernatant used as the cytosol fractions is dissolved with sample buffer for SDS-PAGE and run on a SDS-PAGE gel, blotted onto a nitrocellulose membrane by using semi-dry transfer. Non-specific binding to nitrocellulose is blocked with 5% skim milk in TBS with 0.5% Tween at room temperature for 1 hour, then probed with anti-Her2/ErB2 mAb (rabbit IgG, #2242, Cell Signaling) and anti-Tubulin (T9026, Sigma) as housekeeping control protein. HRP-conjugated goat anti-rabbit IgG (H+L) and HRP-conjugated horse anti-mouse IgG (H+L) are used as secondary Ab (#7074, #7076, Cell Signaling) and LumiGLO reagent, 20× Peroxide (#7003, Cell Signaling) is used for visualization.

Her2, an Hsp90 client protein, is expected to be degraded when cells are treated with compounds of the invention. 0.5 µM of 17AAG, a known Hsp90 inhibitor which is used as a positive control, causes partial degradation of Her2.

2. Method 2

MV-4-11 cells (20,000 cells/well) were cultured in 96-well plates and maintained at 37° C. for several hours. The cells were treated with a compound of the invention or 17AAG (a positive control) at various concentrations and incubated at 37° C. for 72 hours. Cell survival was measured with Cell Counting Kit-8 (Dojindo Laboratories, Cat. # CK04).

The $IC_{50}$ range for Her2 degradation by compounds of the invention are listed below in Table 2.

TABLE 2

Her2 $IC_{50}$ range of compounds of the invention for inhibition of Hsp90

| $IC_{50}$ (µM) | Compound Number |
|---|---|
| ≤0.05 | 1-4, 7, 8, 10, 11, 14, 21-23, 27, 31, 35, 36, 38, 44, 46, 60, 68, 80, 86, 88, 96, 113, 114, 180, 181, 190-192, 194, 195, 197-200, 213-219, 240, 241, 243-252, 264, 266-271, 273, 275, 320, 342-345, 347, 348, 351, 352, 357, 362, 369, 420, 425, 426, 430 |

TABLE 2-continued

Her2 $IC_{50}$ range of compounds of the invention for inhibition of Hsp90

| $IC_{50}$ (µM) | Compound Number |
|---|---|
| 0.5 ≥ x > 0.05 | 5, 12, 13, 15-17, 20, 24, 26, 28, 32-34, 37, 39, 45, 54, 55, 57, 61, 62, 69, 72, 73, 77-79, 81, 85, 87, 89-92, 95, 99-101, 108, 111, 112, 115, 117-119, 121, 129, 131-134, 137, 138, 141, 142, 147, 187, 202-204, 206, 207, 231-233, 235-237, 253-262, 265, 272, 274, 276, 281, 282, 284, 286, 287, 289, 302-305, 308, 309, 311-315, 321-324, 330, 331, 337, 346, 349, 350, 354, 355, 358, 359, 361, 363, 366-368, 370, 371, 373, 379, 380, 382, 383, 385, 386, 392, 398, 400, 403, 405, 421-424, 427-429, 431-435, 450, 452, 453, 455-458, 463, 466, 467, 471 |
| 1 ≥ x > 0.5 | 6, 9, 53, 56, 63, 74, 109, 110, 116, 120, 123, 130, 208, 307, 310, 325, 375-377, 381, 384, 391, 454, 473 |
| 5 ≥ x > 1 | 40, 43, 47, 48, 50, 75, 106, 107, 125, 126, 135, 136, 139, 140, 234, 263, 332, 333, 353, 356, 360, 364, 387, 417, 451, 459-462, 464, 465, 468-470, 475, 479 |
| 20 ≥ x > 5 | 19, 25, 29, 49, 51, 52, 58, 64-67, 76, 82, 98, 102, 122, 127, 143, 295, 301, 436, 438, 440, 442-449, 474, 480 |
| 20 < x ≤ 50 | 30, 41, 42, 59, 93, 97, 103, 105, 296, 437, 441 |
| >50 | 70, 71, 83, 84, 94, 104, 124, 144-146, 439 |

C. Fluorescent Staining of her2 on the Surface of Cells Treated with a Compound of the Invention After treatment with a compound of the invention, cells are washed twice with 1×PBS/1% FBS, and then stained with anti-Her2-FITC (#340553, BD) for 30 min at 4° C. Cells are then washed three times in FACS buffer before the fixation in 0.5 ml 1% paraformadehyrede. Data is acquired on a FACSCalibur system. Isotype-matched controls are used to establish the non-specific staining of samples and to set the fluorescent markers. A total 10,000 events are recorded from each sample. Data are analyzed by using CellQuest software (BD Biosciences).

D. Apoptosis Analysis

After treatment with the compounds of the invention, cells are washed once with 1×PBS/1% FBS, and then stained in binding buffer with FITC-conjugated Annexin V and Propidium iodide (PI) (all obtained from BD Biosciences) for 30 min at 4° C. Flow cytometric analysis is performed with FACSCalibur (BD Biosciences) and a total 10,000 events are recorded from each sample. Data is analyzed by using CellQuest software (BD Biosciences). The relative fluorescence is calculated after subtraction of the fluorescence of control.

E. Degradation of c-Kit in Cells after Treatment with a Compound of the Invention Two leukemia cell lines, HEL92.1.7 and Kasumi-1, are used for testing c-Kit degradation induced by Hsp90 inhibitors of the invention. The cells ($3 \times 10^5$ per well) are treated with 17AAG (0.5 µM), or a compound of the invention for about 18 h. The cells are collected and centrifuged (SORVALL RT 6000D) at 1200 rpm for 5 min. The supernatants are discarded, and the cells are washed one time with 1×PBS. After centrifugation the cells are stained with FITC conjugated c-Kit antibody (MBL International, Cat# K0105-4) in 100 ml 1×PBS at 4° C. for 1 h. The samples are read and analyzed with FACSCalibur flow cytometer (Becton Dicknson). The results of the FACS analysis can be confirmed with Western blot analysis.

c-Kit, a tyrosine kinase receptor and one of the Hsp90 client proteins, is selected and used in a FACS-based degradation assay. Compounds of the invention are expected to induce c-Kit degradation in a dose-dependent manner. Compounds of the invention are expected to be effective in the treatment of c-Kit associated tumors, such as leukemias, mast cell tumors, small cell lung cancer, testicular cancer, some cancers of the gastrointestinal tract (including GIST), and some central nervous system.

The $IC_{50}$ range for c-Kit degradation by select compounds of the invention are listed below in Table 3.

TABLE 3 c-Kit $IC_{50}$ range of compounds of the invention for inhibition of Hsp90

| $IC_{50}$ (μM) | Compound Number |
|---|---|
| $0.5 \geq x > 0.05$ | 80 |
| $1 \geq x > 0.5$ | 75, 85, 101 |
| $2 \geq x > 1$ | 87, 95 |

F. Degradation of c-Met in Cells after Treatment with a Compound of the Invention The ability of the Hsp90 inhibitors of the invention to induce the degradation of c-Met, an Hsp90 client protein that is expressed at high levels in several types of non-small cell lung cancer can be examined. NCI-H1993 (ATCC, cat# CRL-5909) are seeded in 6-well plates at $5 \times 10^5$ cells/well. The cells are treated with 17AAG (100 nM or 400 nM) or a compound of the invention (100 nM or 400 nM), and cell lysis is prepared 24 h after treatment. Equal amount of proteins are used for Western blot analysis. The compounds of the invention are expected to potently induce degradation of c-Met in this cell line due to inhibition of Hsp90.

Example 13

Alternative Method of Determination of Efficacy of Compounds: (ICW)

A. Cells and Cell Culture

Human BT474 (HTB-20), SK-BR-3 (HTB-30) and MCF-7 breast carcinoma cells (HTB-22) from American Type Culture Collection, Va., USA were grown in Dulbecco's modified Eagle's medium with 4 mM L-glutamine and antibiotics (100 IU/ml penicillin and 100 μg/ml streptomycine; GibcoBRL). To obtain exponential cell growth, cells were trypsinized, counted and seeded at a cell density of $0.5 \times 10^6$ cells/ml regularly, every 3 days. All experiments were performed on day 1 after cell passage.

B. Degradation of her2 in Cells after Treatment with a Compound of the Invention 1. Method 1

BT-474 cells were treated with 0.5 μM, 2 μM, or 5 μM of 17AAG (a positive control) or 0.5 μM, 2 μM, or 5 μM of a compound of the invention overnight in DMEM medium. After treatment, each cytoplasmic sample is prepared from $1 \times 10^6$ cells by incubation of cell lysis buffer (#9803, Cell Signaling Technology) on ice for 10 minutes. The resulting supernatant used as the cytosol fractions is dissolved with sample buffer for SDS-PAGE and run on a SDS-PAGE gel, blotted onto a nitrocellulose membrane by using semi-dry transfer. Non-specific binding to nitrocellulose is blocked with 5% skim milk in TBS with 0.5% Tween at room temperature for 1 hour, then probed with anti-Her2/ErB2 mAb (rabbit IgG, #2242, Cell Signaling) and anti-Tubulin (T9026, Sigma) as housekeeping control protein. HRP-conjugated goat anti-rabbit IgG (H+L) and HRP-conjugated horse anti-mouse IgG (H+L) are used as secondary Ab (#7074, #7076, Cell Signaling) and LumiGLO reagent, 20× Peroxide (#7003, Cell Signaling) is used for visualization.

Her2, an Hsp90 client protein, is expected to be degraded when cells are treated with compounds of the invention. 0.5 μM of 17AAG, a known Hsp90 inhibitor which is used as a positive control, causes partial degradation of Her2.

2. Method 2

BT-474 cells were plated in the interior 60 wells of a 96 well black clear bottom plate (20,000 cells/well) in DMEM medium, with DMEM media in the surrounding 36 wells, and incubated at 37° C. with 5% $CO_2$ overnight. On the second day, concentration response curve source plates were produced (10 point, 3-fold dilution of compounds in DMSO) followed by a 1:30 dilution in an intermediate dilution plate containing DMEM. Compound was transferred from the intermediate plate to the cell plate at a dilution of 1:10. The cells were incubated at 37° C. with 5% $CO_2$ for 24 hours.

Cells were fixed in 4% phosphate buffered paraformaldehyde for 30 minutes at room temperature and then permeabilized by washing five times with 0.1% Triton X-100 in PBS for 5 minutes at room temperature on a shaker. Cells were blocked with Odyssey Blocking Buffer (LI-COR, #927-40000) on a shaker at room temperature for 1.5 hours followed by incubation with Her2 antibody (CST, #2165) diluted 1:400 in blocking buffer overnight on a shaker at 4° C. Cells were washed five times with 0.1% Tween-20 in PBS for 5 minutes at room temperature on a shaker and incubated with fluorescently labeled secondary antibody (LI-COR, #926-32211) diluted 1:1000 in blocking buffer, and DRAQ5 nuclear stain (Biostatus Limited, #DRAQ5) diluted 1:10,000, at room temperature on a shaker for 1 hour. Cells were washed 5 times with 0.1% Tween-20 in PBS for 5 minutes at room temperature on a shaker and imaged on a LI-COR Odyssey imaging station. The raw data was normalized to DRAQ5 and the Her2 $EC_{50}$ were calculated using XLfit C. In Vitro Cytotoxicity Assay MV-4-11 cells (20,000 cells/well) were cultured in 96-well plates and maintained at 37° C. for several hours. The cells were treated with a compound of the invention or 17AAG (a positive control) at various concentrations and incubated at 37° C. for 72 hours. Cell survival was measured with Cell Counting Kit-8 (Dojindo Laboratories, Cat. # CK04).

The $eC_{50}$ range for Her2 degradation by compounds of the invention are listed below in Table 4.

| $EC_{50}$ (μM) | Compound Number |
|---|---|
| $\leq 0.05$ | 148, 150, 153, 155, 158, 160, 162, 165, 166, 168, 173, 174, 176-179, 182-186, 188, 189, 210, 223, 225, 226, 242, 277-279, 280, 326, 327, 372 |
| $0.5 \geq x > 0.05$ | 149, 151, 152, 154, 156, 157, 159, 161, 163, 164, 167, 169, 172, 175, 209, 221, 328, 334 |
| $1 \geq x > 0.5$ | 171, 335 |
| $5 \geq x > 1$ | 227-230 |
| $20 \geq x > 5$ | 297, 299 |
| $20 < x \leq 50$ | 298, 300 |
| $>50$ | 170 |

D. Fluorescent Staining of Her2 on the Surface of Cells Treated with a Compound of the Invention After treatment with a compound of the invention, cells are washed twice with 1×PBS/1% FBS, and then stained with anti-Her2-FITC (#340553, BD) for 30 min at 4° C. Cells are then washed three times in FACS buffer before the fixation in 0.5 ml 1% paraformadehyrede. Data is acquired on a FACSCalibur system. Isotype-matched controls are used to establish the non-specific staining of samples and to set the fluorescent markers. A total 10,000 events are recorded from each sample. Data are analyzed by using CellQuest software (BD Biosciences).

E. Apoptosis Analysis

After treatment with the compounds of the invention, cells are washed once with 1×PBS/1% FBS, and then stained in binding buffer with FITC-conjugated Annexin V and Propidium iodide (PI) (all obtained from BD Biosciences) for 30 min at 4° C. Flow cytometric analysis is performed with FACSCalibur (BD Biosciences) and a total 10,000 events are recorded from each sample. Data is analyzed by using CellQuest software (BD Biosciences). The relative fluorescence is calculated after subtraction of the fluorescence of control.

Example 14

Anti-Tumor Activity Against the Human Tumor Cell Line MDA-MB-435S in a Nude Mouse Xenograft Model The human tumor cell line, MDA-MB-435S (ATCC #HTB-129; G. Ellison, et al., *Mol. Pathol.* 55:294-299, 2002), is obtained from the American Type Culture Collection (Manassus, Va., USA). The cell line is cultured in growth media prepared from 50% Dulbecco's Modified Eagle Medium (high glucose), 50% RPMI Media 1640, 10% fetal bovine serum (FBS), 1% 100×L-glutamine, 1% 100× Penicillin-Streptomycin, 1% 100× sodium pyruvate and 1% 100×MEM non-essential amino acids. FBS is obtained from Sigma-Aldrich Corp. (St. Louis, Mo., USA), and all other reagents are obtained from Invitrogen Corp. (Carlsbad, Calif., USA). Approximately 4-5×10$^6$ cells that have been cryopreserved in liquid nitrogen are rapidly thawed at 37° C. and transferred to a 175 cm$^2$ tissue culture flask containing 50 ml of growth media and then incubated at 37° C. in a 5% $CO_2$ incubator. The growth media is replaced every 2-3 days until the flask becomes 90% confluent, typically in 5-7 days. To passage and expand the cell line, a 90% confluent flask is washed with 10 ml of room temperature phosphate buffered saline (PBS) and the cells are disassociated by adding 5 ml 1× Trypsin-EDTA (Invitrogen) and incubating at 37° C. until the cells detach from the surface of the flask. To inactivate the trypsin, 5 ml of growth media is added and then the contents of the flask are centrifuged to pellet the cells. The supernatant is aspirated and the cell pellet is resuspended in 10 ml of growth media and the cell number determined using a hemocytometer. Approximately 1-3×10$^6$ cells per flask are seeded into 175 cm$^2$ flasks containing 50 ml of growth media and incubated at 37° C. in a 5% $CO_2$ incubator. When the flasks reach 90% confluence, the above passaging process is repeated until sufficient cells have been obtained for implantation into mice.

Six to eight week old, female Crl:CD-1-nuBR (nude) mice are obtained from Charles River Laboratories (Wilmington, Mass., USA). Animals are housed 4-5/cage in microisolators, with a 12 hr/12 hr light/dark cycle, acclimated for at least 1 week prior to use and fed normal laboratory chow ad libitum. Studies are conducted on animals between 7 and 12 weeks of age at implantation. To implant tumor cells into nude mice, the cells are trypsinized as above, washed in PBS and resusupended at a concentration of 50×10$^6$ cells/ml in PBS. Using a 27 gauge needle and 1 cc syringe, 0.1 ml of the cell suspension is injected into the corpus adiposum of nude mice. The corpus adiposum is a fat body located in the ventral abdominal vicera in the right quadrant of the abdomen at the juncture of the os coxae (pelvic bone) and the os femoris (femur). Tumors are then permitted to develop in vivo until they reach approximately 150 mm$^3$ in volume, which typically requires 2-3 weeks following implantation. Tumor volumes (V) are calculated by caliper measurement of the width (W), length (L) and thickness (T) of tumors using the following formula: V=0.5326×(L×W×T) Animals are randomized into treatment groups so that the average tumor volumes of each group are similar at the start of dosing.

Stock solutions of test compounds are prepared by dissolving the appropriate amounts of each compound in dimethyl sulfoxide (DMSO) by sonication in an ultrasonic water bath. Stock solutions are prepared at the start of the study, stored at −20° C. and diluted fresh each day for dosing. A solution of 20% Cremophore RH40 (polyoxyl 40 hydrogenated castor oil (BASF Corp., Aktiengesellschaft, Ludwigshafen, Germany)) in 80% D5W (5% dextrose in water (Abbott Laboratories, North Chicago, Ill., USA)) is also prepared by first heating 100% Cremophore RH40 at 50-60° C. until liquefied and clear, diluting 1:5 with 100% D5W, reheating again until clear and then mixing well. This solution is stored at room temperature for up to 3 months prior to use. To prepare formulations for daily dosing, DMSO stock solutions are diluted 1:10 with 20% Cremophore RH40. The final formulation for dosing contains 10% DMSO, 18% Cremophore RH40, 3.6% dextrose and 68.4% water and the appropriate amount of test article. Animals are intraperitoneal (IP) injected with this solution at 10 ml per kg body weight on a schedule of 5 days per week (Monday thru Friday, with no dosing on Saturday and Sunday) for 3 weeks.

Compounds of the invention are expected to result in decreased the growth rate of MDA-MB-435S cells in nude mice to a greater extent than a dose of 100 mg/kg body weight of the Hsp90 inhibitor 17-AAG.

Example 15

Anti-Tumor Activity Against Human

Tumor Cells in a Nude Mouse Xenograft Model

The human squamous non-small cell lung cancer cell line, RERF-LC-AI (RCB0444; S. Kyoizumi, et al., *Cancer. Res.* 45:3274-3281, 1985), is obtained from the Riken Cell Bank (Tsukuba, Ibaraki, Japan). The cell line is cultured in growth media prepared from 50% Dulbecco's Modified Eagle Medium (high glucose), 50% RPMI Media 1640, 10% fetal bovine serum (FBS), 1% 100×L-glutamine, 1% 100× penicillin-streptomycin, 1% 100× sodium pyruvate and 1% 100×MEM non-essential amino acids. FBS is obtained from American Type Culture Collection (Manassas, Va., USA) and all other reagents are obtained from Invitrogen Corp. (Carlsbad, Calif., USA). Approximately 4-5×10$^6$ cells that have been cryopreserved in liquid nitrogen are rapidly thawed at 37° C. and transferred to a 175 cm$^2$ tissue culture flask containing 50 ml of growth media and then incubated at 37° C. in a 5% $CO_2$ incubator.

The growth media is replaced every 2-3 days until the flask becomes 90% confluent, typically in 5-7 days. To passage and expand the cell line, a 90% confluent flask is washed with 10 ml of room temperature phosphate buffered saline (PBS) and the cells are disassociated by adding 5 ml 1× trypsin-EDTA (Invitrogen) and incubating at 37° C. until the cells detach from the surface of the flask. To inactivate the trypsin, 5 ml of growth media is added and then the contents of the flask are centrifuged to pellet the cells. The supernatant is aspirated and the cell pellet is resuspended in 10 ml of growth media and the cell number determined using a hemocytometer. Approximately 1-3×10⁶ cells per flask are seeded into 175 cm² flasks containing 50 ml of growth media and incubated at 37° C. in a 5% CO₂ incubator. When the flasks reach 90% confluence, the above passaging process is repeated until sufficient cells have been obtained for implantation into mice.

Seven to eight week old, female Crl:CD-1-nuBR (nude) mice are obtained from Charles River Laboratories (Wilmington, Mass., USA). Animals are housed 4-5/cage in microisolators, with a 12 hr/12 hr light/dark cycle, acclimated for at least 1 week prior to use and fed normal laboratory chow ad libitum. Studies are conducted on animals between 8 and 12 weeks of age at implantation. To implant RERF-LC-AI tumor cells into nude mice, the cells are trypsinized as above, washed in PBS and resuspended at a concentration of 50×10⁶ cells/ml in 50% non-supplemented RPMI Media 1640 and 50% Matrigel Basement Membrane Matrix (#354234; BD Biosciences; Bedford, Mass., USA). Using a 27 gauge needle and 1 cc syringe, 0.1 ml of the cell suspension is injected subcutaneously into the flank of each nude mouse. Tumor volumes (V) are calculated by caliper measurement of the width (W), length (L) and thickness (T) of tumors using the following formula: $V=0.5236 \times (L \times W \times T)$.

In vivo passaged RERF-LC-AI tumor cells (RERF-LC-AI$^{IVP}$) are isolated to improve the rate of tumor implantation relative to the parental cell line in nude mice. RERF-LC-AI tumors are permitted to develop in vivo until they reach approximately 250 mm³ in volume, which requires approximately 3 weeks following implantation. Mice are euthanized via CO₂ asphyxiation and their exteriors sterilized with 70% ethanol in a laminar flow hood. Using sterile technique, tumors are excised and diced in 50 ml PBS using a scalpel blade. A single cell suspension is prepared using a 55 ml Wheaton Safe-Grind tissue grinder (catalog #62400-358; VWR International, West Chester, Pa., USA) by plunging the pestle up and down 4-5 times without twisting. The suspension is strained through a 70 µM nylon cell strainer and then centrifuged to pellet the cells. The resulting pellet is resuspended in 0.1 M NH₄Cl to lyse contaminating red blood cells and then immediately centrifuged to pellet the cells. The cell pellet is resuspended in growth media and seeded into 175 cm² flasks containing 50 ml of growth media at 1-3 tumors/flask or approximately 10×10⁶ cells/flask. After overnight incubation at 37° C. in a 5% CO₂ incubator, non-adherent cells are removed by rinsing two times with PBS and then the cultures are fed with fresh growth media. When the flasks reach 90% confluence, the above passaging process is repeated until sufficient cells have been obtained for implantation into mice.

RERF-LC-AI$^{IVP}$ cells are then implanted as above and tumors are permitted to develop in vivo until the majority reached an average of 100-200 mm³ in tumor volume, which typically requires 2-3 weeks following implantation Animals with oblong or very small or large tumors are discarded, and only animals carrying tumors that display consistent growth rates are selected for studies. Animals are randomized into treatment groups so that the average tumor volumes of each group are similar at the start of dosing.

The HSP90 inhibitor, 17-allylamino-17-demethoxygeldanamycin (17-AAG), can be employed as a positive control (Albany Molecular Research, Albany, N.Y., USA). Stock solutions of test articles are prepared by dissolving the appropriate amounts of each compound in dimethyl sulfoxide (DMSO) by sonication in an ultrasonic water bath. Stock solutions are prepared weekly, stored at −20° C. and diluted fresh each day for dosing. A solution of 20% Cremophore RH40 (polyoxyl 40 hydrogenated castor oil; BASF Corp., Aktiengesellschaft, Ludwigshafen, Germany) in 80% D5W (5% dextrose in water; Abbott Laboratories, North Chicago, Ill., USA) is also prepared by first heating 100% Cremophore RH40 at 50-60° C. until liquefied and clear, diluting 1:5 with 100% D5W, reheating again until clear and then mixing well. This solution is stored at room temperature for up to 3 months prior to use. To prepare formulations for daily dosing, DMSO stock solutions are diluted 1:10 with 20% Cremophore RH40. The final formulation for dosing contains 10% DMSO, 18% Cremophore RH40, 3.6% dextrose, 68.4% water and the appropriate amount of test article. Animals are intraperitoneally (i.p.) injected with this solution at 10 ml per kg body weight on a schedule of 5 days per week (Monday, Tuesday, Wednesday, Thursday and Friday, with no dosing on Saturday and Sunday) for a total of 15 doses.

Treatment with compounds of the invention is expected to result in the decreased growth rate of RERF-LC-AI$^{IVP}$ human lung tumor cells in nude mice.

Example 16

Necrosis in a Nude Mouse Tumor Model

The mouse mammary carcinoma cell line, EMT6 (ATCC #CRL-2755), is obtained from the American Type Culture Collection (ATCC; Manassas, Va., USA). The cell line is cultured in growth media prepared from 50% Dulbecco's Modified Eagle Medium (high glucose), 50% RPMI Media 1640, 10% fetal bovine serum (FBS), 1% 100×L-glutamine, 1% 100× Penicillin-Streptomycin, 1% 100× sodium pyruvate and 1% 100×MEM non-essential amino acids. FBS is obtained from ATCC and all other reagents are obtained from Invitrogen Corp. (Carlsbad, Calif., USA). Approximately 4-5×10⁶ cells that have been cryopreserved in liquid nitrogen are rapidly thawed at 37° C. and transferred to a 175 cm² tissue culture flask containing 50 ml of growth media and then incubated at 37° C. in a 5% CO₂ incubator. The growth media is replaced every 2-3 days until the flask became 90% confluent, typically in 5-7 days. To passage and expand the cell line, a 90% confluent flask is washed with 10 ml of room temperature phosphate buffered saline (PBS) and the cells are disassociated by adding 5 ml 1× Trypsin-EDTA (Invitrogen) and incubating at 37° C. until the cells detach from the surface of the flask. To inactivate the trypsin, 5 ml of growth media is added and then the contents of the flask are centrifuged to pellet the cells. The supernatant is aspirated and the cell pellet is resuspended in 10 ml of growth media and the cell number determined using a hemocytometer. Approximately 1-3×10⁶ cells per flask are seeded into 175 cm² flasks containing 50 ml of growth media and incubated at 37° C. in a 5% CO₂ incubator. When the flasks reach 90% confluence, the above passaging process is repeated until sufficient cells have been obtained for implantation into mice.

Seven to eight week old, female Crl:CD-1-nuBR (nude) mice are obtained from Charles River Laboratories (Wilmington, Mass., USA). Animals are housed 4-5/cage in microisolators, with a 12 hr/12 hr light/dark cycle, acclimated for at least 1 week prior to use and fed normal laboratory chow ad libitum. Studies are conducted on animals between 8 and 10 weeks of age at implantation. To implant EMT6 tumor cells into nude mice, the cells are trypsinized as above, washed in PBS and resuspended at a concentration of 10×10⁶ cells/ml in PBS. Using a 27 gauge needle and 1 cc syringe, 0.1 ml of the cell suspension is injected subcutaneously into the flank of each nude mouse.

Tumors are then permitted to develop in vivo until the majority reached 75-125 mm$^3$ in tumor volume, which typically requires 1 week following implantation Animals with oblong, very small or large tumors are discarded, and only animals carrying tumors that display consistent growth rates are selected for studies. Tumor volumes (V) are calculated by caliper measurement of the width (W), length (L) and thickness (T) of tumors using the following formula: V=0.5236×(L×W×T) Animals are randomized into treatment groups so that each group had median tumor volumes of approximately 100 mm$^3$ at the start of dosing.

To formulate a compound of the invention in DRD, a stock solution of the test article is prepared by dissolving an appropriate amount of the compound in dimethyl sulfoxide (DMSO) by sonication in an ultrasonic water bath. A solution of 20% Cremophore RH40 (polyoxyl 40 hydrogenated castor oil; BASF Corp., Aktiengesellschaft, Ludwigshafen, Germany) in 5% dextrose in water (Abbott Laboratories, North Chicago, Ill., USA) is also prepared by first heating 100% Cremophore RH40 at 50-60° C. until liquefied and clear, diluting 1:5 with 100% D5W, reheating again until clear and then mixing well. This solution is stored at room temperature for up to 3 months prior to use. To prepare a DRD formulation for dosing, the DMSO stock solution is diluted 1:10 with 20% Cremophore RH40. The final DRD formulation for dosing contains 10% DMSO, 18% Cremophore RH40, 3.6% dextrose, 68.4% water and the appropriate amount of test article.

Tumor-bearing animals are given a single intravenous (i.v.) bolus injections of either DRD vehicle or a compound of the invention formulated in DRD, both at 10 mL per kg body weight. Then, 4-24 hr after drug treatment, tumors are excised, cut in half and fixed overnight in 10% neutral-buffered formalin. Each tumor is embedded in paraffin with the cut surfaces placed downwards in the block, and rough cut until a complete section is obtained. From each tumor, 5 µM serial sections are prepared and stained with hematoxylin and eosin. Slides are evaluated manually using light microscopy with a 10×10 square gridded reticle. The percentage of necrosis in a tumor is quantified at 200× magnification by scoring the total number of grid squares containing necrosis and the total number of grid squares containing viable tumor cells.

It is expected that compounds of the invention will result in an increase in necrotic tissue in the center of EMT6 tumors relative to the baseline necrosis observed in vehicle treated tumors. As would be expected for a vascular targeting mechanism of action, rapid onset of necrosis is consistent with there being a loss of blood flow to tumors resulting in hypoxia and tumor cell death.

Example 17

Vascular Disrupting Activities in a Nude Mouse Tumor Model

The mouse mammary carcinoma cell line, EMT6 (ATCC #CRL-2755), is obtained from the American Type Culture Collection (ATCC; Manassas, Va., USA). The cell line is cultured in growth media prepared from 50% Dulbecco's Modified Eagle Medium (high glucose), 50% RPMI Media 1640, 10% fetal bovine serum (FBS), 1% 100×L-glutamine, 1% 100× Penicillin-Streptomycin, 1% 100× sodium pyruvate and 1% 100×MEM non-essential amino acids. FBS is obtained from ATCC and all other reagents are obtained from Invitrogen Corp. (Carlsbad, Calif., USA). Approximately 4-5×10$^6$ cells that have been cryopreserved in liquid nitrogen are rapidly thawed at 37° C. and transferred to a 175 cm$^2$ tissue culture flask containing 50 mL of growth media and then incubated at 37° C. in a 5% CO$_2$ incubator. The growth media is replaced every 2-3 days until the flask became 90% confluent, typically in 5-7 days. To passage and expand the cell line, a 90% confluent flask is washed with 10 mL of room temperature phosphate buffered saline (PBS) and the cells are disassociated by adding 5 mL 1× Trypsin-EDTA (Invitrogen) and incubating at 37° C. until the cells detach from the surface of the flask. To inactivate the trypsin, 5 mL of growth media is added and then the contents of the flask are centrifuged to pellet the cells. The supernatant is aspirated and the cell pellet is resuspended in 10 mL of growth media and the cell number determined using a hemocytometer. Approximately 1-3×10$^6$ cells per flask are seeded into 175 cm$^2$ flasks containing 50 mL of growth media and incubated at 37° C. in a 5% CO$_2$ incubator. When the flasks reach 90% confluence, the above passaging process is repeated until sufficient cells have been obtained for implantation into mice.

Seven to eight week old, female Crl:CD-1-nuBR (nude) mice are obtained from Charles River Laboratories (Wilmington, Mass., USA). Animals are housed 4-5/cage in microisolators, with a 12 hr/12 hr light/dark cycle, acclimated for at least 1 week prior to use and fed normal laboratory chow ad libitum. Studies are conducted on animals between 8 and 10 weeks of age at implantation. To implant EMT6 tumor cells into nude mice, the cells are trypsinized as above, washed in PBS and resuspended at a concentration of 10×10$^6$ cells/mL in PBS. Using a 27 gauge needle and 1 cc syringe, 0.1 mL of the cell suspension is injected subcutaneously into the flank of each nude mouse.

For the Evans Blue dye assay, tumors are permitted to develop in vivo until the majority reach 40-90 mm$^3$ in tumor volume (to minimize the extent of tumor necrosis), which typically require 4-6 days following implantation. Animals with visibly necrotic, oblong, very small or very large tumors are discarded and only animals carrying tumors that display consistent growth rates are selected for use. Tumor volumes (V) are calculated by caliper measurement of the width (W), length (L) and thickness (T) of tumors using the following formula: V=0.5236×(L×W×T). Animals are randomized into treatment groups so that at the start of dosing each group have median tumor volumes of approximately 125 mm$^3$ or approximately 55 mm$^3$ for the Evans Blue dye assay.

To formulate compounds of the invention for dosing, the appropriate amount of compound is dissolved in 5% dextrose in water (D5W; Abbott Laboratories, North Chicago, Ill., USA). Vehicle-treated animals are dosed with D5W.

To conduct the Evans Blue dye assay, tumor-bearing animals are dosed with vehicle or test article at 0 hr, and then i.v. injected with 100 µL of a 1% (w/v) Evan's Blue dye (Sigma #E-2129; St. Louis, Mo., USA) solution in 0.9% NaCl at +1 hr. Tumors are excised at +4 hr, weighed and the tissue disassociated by incubation in 50 µL 1 N KOH at 60° C. for 16 hr. To extract the dye, 125 µL of a 0.6 N phosphoric acid and 325 µL acetone are added, and the samples vigorously vortexed and then microcentrifuged at 3000 RPM for 15 min to pellet cell debris. The optical absorbance of 200 µL of supernatant is then measured at 620 nM in a Triad spectrophotometer (Dynex Technologies, Chantilly, Va., USA). Background OD$_{620}$ values from similarly sized groups of vehicle or test article-treated animals that have not been injected with dye are subtracted as background. OD$_{620}$ values are then normalized for tumor weight and dye uptake is calculated relative to vehicle-treated tumors.

To examine the vascular disrupting activity of a compound of the invention, the Evans Blue dye assay is employed as a measurement of tumor blood volume. Graff et al., *Eur. J. Cancer* 36:1433-1440 (2000). Evans Blue dye makes a complex with serum albumin by electrostatic interaction between the sulphonic acid group of the dye and the terminal cationic nitrogens of the lysine residues in albumin. The dye leaves the circulation very slowly, principally by diffusion into extravascular tissues while still bound to albumin. Albumin-dye complex taken up by tumors is located in the extracellular space of non-necrotic tissue, and intracellular uptake and uptake in necrotic regions is negligible. The amount of dye present in a tumor is a measurement of the tumor blood volume and microvessel permeability. Compounds of the invention are expected to result in substantially decreased tumor dye uptake relative to vehicle-treated animals. Such a decrease in dye penetration into the tumor is consistent with there being a loss of blood flow to tumors due to blockage of tumor vasculature, consistent with a vascular disrupting mechanism of action.

Example 18

Inhibition of the Production of Inflammatory Cytokines in Human PBMCs

Human PBMC are isolated using Ficoll 400 and diatrizoate sodium (density 1.077 g/ml) solution and purified with RosetteSep (StemCell Technologies). The PBMCs are primed with human IFN-7 (800 U/ml, Pierce Biotechnology #R-IFNG-50), seeded at $0.5 \times 10^6/100$ µL/well in 96-well U-bottom plate with culture medium (RPMI 1640, 10% FBS, 1% Pen/Strep), and incubated in 37° C. for overnight. The cells are then stimulated with 1 µg/ml of LPS (Lipopolysaccharide, Sigma#L2654-1MG) or 0.025% of SAC (*Staphylococcus Aureus* Cowan, Calbiochem-Novabiochem Corp. #507858), and treated with a test compound at different concentrations with final DMSO concentration less than 0.5% for 16-18 hrs. About 180 µl/well of supernatant is collected and measured using ELISA kit or Bio-plex (Bio-Rad) to determine the levels of cytokine production. The cell survival is determined using Cell Counting Kit-8 (Dojindo Molecular Technologies, Inc.). Compounds of the invention are expected to broadly inhibit the production of proinflammatory cytokines.

Example 19

Suppression of Glucocorticoid Receptor Levels in Rat and Human PBMCs

Cell Preparation:
Whole blood samples from healthy human volunteers and male SD rats are collected and the PBMCs are isolated immediately as follows. 5 ml of whole blood is diluted with an equal volume of sterile 1×PBS. The diluted blood is overlayed carefully into a sterile centrifuge tube without disturbing the bottom layer that containing 5 ml of Ficoll-paque plus density gradient solution. The layered blood is centrifuged at 1500×g for 30 minutes at room temperature. The middle thin layer containing PBMCs is carefully removed, transferred to another sterile centrifuge tube, and washed twice with PBS to remove Percoll. Isolated rat and human PBMCs are cultured in 10% fetal bovine serum/DMEM.

Treatment:
The rat and human PBMCs are treated with DMSO (control), compounds of the invention, or 17-DMAG at concentrations of 0, 1, 5, 25, or 100 nM (in DMSO) for 16 hours. The cells are then collected and rinsed in ice-cold PBS and stored in liquid nitrogen until further analysis.

Immunoblot
PBMC are prepared in Western lysis buffer (10 mmol/L HEPES, 42 mmol/L KCl, 5 mmol/L $MgCl_2$, 0.1 mmol/L EDTA, 0.1 mmol/L EGTA, 1 mmol/L DTT, 1% Triton X-100, freshly supplemented with 1× protease inhibitor cocktail from Pierce, Rockford, Ill.). Lysate protein concentrations are quantified by bicinchoninic acid assay (Pierce) and normalized. Equal amounts of protein are loaded onto 10% NuPAGE Bis-Tris Gels (Invitrogen) and subsequently transferred onto polyvinylidene difluoride membranes. The membranes are blocked in 5% milk in TBST. Primary antibody of glucocorticod receptor from Santa Cruz Biotechnology, Inc. is added and incubated at room temperature for 1 hour with shaking. The blots are washed extensively in TBST before secondary antibodies are added for overnight incubation at 4° C. with gentle shaking. The blots are again washed extensively and developed with SuperSignal West Femto substrate (Pierce). The immunoblot analysis is performed to measure the level of total GRs by Quantity One software from Bio-Rad.

Example 20

Suppression of Glucocorticoid Receptor Levels in Human PBMCs and Renal Cells, as Well as in Several Human Cancer Cell Lines Cell Preparation:
Normal human renal proximal tubule epithelial cells and tumor cell lines of MV-4-11, Kasumi-1, and Hela are obtained from Cambrex Bioproducts and American Type Culture Collection, respectively. Cells are cultured with 10% fetal bovine serum/DMEM.

The whole blood samples from healthy human volunteers are collected and the PBMCs are isolated immediately as described in Example 15. Isolated human PBMCs are cultured in 10% fetal bovine serum/DMEM.

Treatment:
Human PBMCs, kasumi-1, My-4-11, Hela, and human renal proximal tubule epithelial cells are treated with DMSO (control), compounds of the invention, 17-DMAG at concentrations of 0, 5, 25, or 100 nM (in DMSO) for 16 hours. The cells are then collected and rinsed in ice-cold PBS and stored in liquid nitrogen until further analysis.

Immunoblot
PBMC, renal and tumor cell pellets are prepared in Western lysis buffer (10 mmol/L HEPES, 42 mmol/L KCl, 5 mmol/L $MgCl_2$, 0.1 mmol/L EDTA, 0.1 mmol/L EGTA, 1 mmol/L DTT, 1% Triton X-100, freshly supplemented with 1× protease inhibitor cocktail from Pierce, Rockford, Ill.). Lysate protein concentrations are quantified by bicinchoninic acid assay (Pierce) and normalized. Equal amounts of protein are loaded onto 10% NuPAGE Bis-Tris Gels (Invitrogen) and subsequently transferred onto polyvinylidene difluoride membranes. The membranes are blocked in 5% milk in TBST. Primary antibody of glucocorticod receptor from Santa Cruz Biotechnology, Inc. is added and incubated at room temperature for 1 hour with shaking. The blots are washed extensively in TBST before secondary antibodies are added for overnight incubation at 4° C. with gentle shaking. The blots are again washed extensively and developed with SuperSignal West Femto substrate (Pierce). Compounds of the invention are expected to suppress the expression of glucocorticoid receptors in cancer cells as well as in normal PBMCs and renal cells.

Example 21

Suppression of Glucocorticoid Receptor Levels In Vivo

Male adult Sprague-Dawley (SD) rats, five per group, are randomly assigned into five testing groups which received treatments as shown in Table 5:

TABLE 5

| Treatment group | Treatment received |
|---|---|
| G1 | 5 mL/kg of vehicle (5% DMSO/13.5% Cr-RH40/D5W) |
| G2 | 6 mg/kg of 17-DMAG |
| G3 | 5 mg/kg of Paclitaxel |
| G4 | 80 mg/kg of Compound of the invention |
| G5 | 50 mg/kg of Compound of the invention |

The test compounds are administered daily intravenously via tail vein for four days. All rats are sacrificed at the study day 5. About 1-2 mL of blood samples are collected per animal. The blood samples are then pulled together as a group for PBMC isolation. PBMCs are isolated and an immunoblot using an antibody that recognizes the glucocorticoid receptor is prepared, as described in Examples 19 and 20.

All publications, patent applications, patents, and other documents cited herein are incorporated by reference in their entirety. In case of conflict, the present specification, including definitions, will control. In addition, the materials, methods, and examples are illustrative only and not intended to be limiting.

What is claimed is:
1. A method of treating cancer in a subject in need thereof, wherein the cancer is selected the group consisting of myeloid leukemia, T cell leukemia, B cell leukemia, chronic myeloid leukemia, acute myelocytic leukemia, non-Hodgkin's lymphoma, multiple myeloma, non-small cell lung cancer, small cell lung cancer, melanoma, gastrointestinal stromal tumors, gastric cancer, breast cancer, renal cell carcinoma, prostate cancer, colon carcinoma, mesothelioma, pancreatic cancer and ovarian cancer, comprising administering to the subject an effective amount of a compound according to the structural formula:

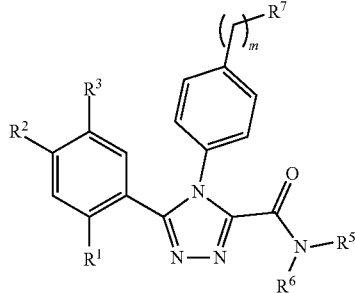

or a pharmaceutically acceptable salt thereof; wherein:
$R^1$ is H, $OR^{12}$ or $C_1$-$C_3$ alkyl;
$R^2$ is $OR^{12}$ or halo;
$R^3$ is H, $C_1$-$C_6$ alkyl or $C_3$-$C_6$ cycloalkyl;
m is 0 or 1;
$R^7$ is phenyl, $S(O)_pR^{10}$, $OR^{10}$, $N(R^{10})_2$ or $=NN(R^{10})_2$;
$R^5$ and $R^6$ are individually hydrogen, $C_1$-$C_6$ alkyl, $C_2$-$C_6$ alkenyl, $C_2$-$C_6$ alkynyl, $C_3$-$C_7$ cycloalkyl, 5-7 membered heterocyclyl, phenyl, benzyl, 5-7 membered heteroaryl, $-N(R^{12})_2$, $-C(O)R^{12}$, $-C(O)OR^{12}$, $-S(O)_pR^{12}$, or $-S(O)_pN(R^{12})_2$, wherein each $R^5$ and $R^6$ that is not hydrogen is optionally and independently substituted with one or more $R^{20}$; or $R^5$ and $R^6$, taken together with the nitrogen to which they are attached, form a 5-7 membered heterocyclyl which is optionally substituted with one or more $R^{20}$;
each $R^{10}$ is independently selected from H, $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, $-OR^{12}$, $-N(R^{12})_2$, $-C(O)R^{12}$, $-C(O)OR^{12}$, $-C(S)R^{12}$, $-C(O)SR^{12}$, $-C(O)N(R^{12})_2$, $-C(S)N(R^{12})_2$, $-C(NR^{12})OR^{12}$, $-C(NR^{12})R^{12}$, $-C(NR^{12})N(R^{12})_2$, $-C(NR^{12})SR^{12}$, $-S(O)_pR^{12}$, $-S(O)_pOR^{12}$ or $-S(O)_pN(R^{12})_2$, wherein the alkyl, alkenyl, alkynyl, cycloalkyl, heterocyclyl, aryl and heteroaryl represented by $R^{10}$ are independently and optionally substituted by one or more $R^{20}$; or two $R^{10}$ moieties attached to the same nitrogen atom are taken together to form a 5-14 membered heterocyclyl or a 5-14 membered heteroaryl, each of which are optionally and independently substituted with one or more $R^{20}$;
each $R^{12}$ is independently H, $C_1$-$C_3$ alkyl, $C_2$-$C_3$ alkenyl, $C_1$-$C_3$ haloalkyl, $C_1$-$C_3$ alkoxy, $C_1$-$C_3$ haloalkoxy, $C_3$-$C_7$ cycloalkyl, phenyl, or benzyl, wherein each $R^{12}$ with at least one hydrogen atom is optionally substituted with one or more $R^{20}$; or two $R^{12}$ substituents that are attached to the same atom or adjacent atoms, taken together with the atom(s) to which they are attached, form a 5-7 membered heterocyclyl or $C_3$-$C_7$ cycloalkyl which are each optionally and independently substituted with one or more $R^{20}$; and
each $R^{20}$ is independently selected from the group consisting of $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, $C_3$-$C_7$ cycloalkyl-($C_1$-$C_3$)alkyl, 5-14 membered heterocyclyl-($C_1$-$C_3$)alkyl, $C_6$-$C_{20}$ aryl-($C_1$-$C_3$)alkyl, 5-14 membered heteroaryl-($C_1$-$C_3$)alkyl, halo, cyano, nitro, azido, $-N(R^{12})_2$, $-OR^{12}$, $-C(O)R^{12}$, $-C(O)OR^{12}$, $-C(S)R^{12}$, $-C(O)SR^{12}$, $-C(S)SR^{12}$, $-C(S)OR^{12}$, $-C(O)N(R^{12})_2$, $-C(S)N(R^{12})_2$, $-C(NR^{12})OR^{12}$, $-C(NR^{12})R^{12}$, $-C(NR^{12})N(R^{12})_2$, $-C(NR^{12})SR^{12}$, $-OC(O)N(R^{12})_2$, $-OC(O)R^{12}$, $-OC(O)OR^{12}$, $-OC(S)OR^{12}$, $-OC(NR^{12})OR^{12}$, $-SC(O)R^{12}$, $-SC(O)OR^{12}$, $-SC(NR^{12})OR_{12}$, $-OC(S)R^{12}$, $-SC(S)R^{12}$, $-SC(S)OR^{12}$, $-OC(O)N(R^{12})_2$, $-OC(S)N(R^{12})_2$, $-OC(NR^{12})NR^{12})_2$, $-SC(O)N(R^{12})_2$, $-SC(NR^{12})N(R^{12})_2$, $-SC(S)N(R^{12})_2$, $-OC(NR^{12})R^{12}$, $-SC(NR^{12})R^{12}$, $-NR^{12}C(O)R^{12}$, $-NR^{12}C(S)R^{12}$, $-NR^{12}C(S)OR^{12}$, $-NR^{12}C(NR^{12})R^{12}$, $-NR^{12}C(O)OR^{12}$, $-NR^{12}C(NR^{12})OR^{12}$, $-NR^{12}C(O)N(R^{12})_2$, $-NR^{12}C(S)N(R^{12})_2$, $-NR^{12}C(NR^{12})N(R^{12})_2$, $-S(O)_pR^{12}$, $-OS(O)_pR^{12}$, $-OS(O)_pOR^{12}$, $-OS(O)_pN(R^{12})_2$, $-S(O)_pOR^{12}$, $-NR^{12}S(O)_pR^{12}$, $-NR^{12}S(O)_pN(R^{12})_2$, $-NR^{12}S(O)_pOR^{12}$, $-S(O)_pN(R^{12})_2$, $-SS(O)_pR^{12}$, $-SS(O)_pOR^{12}$, $-SS(O)_pN(R^{12})_2$, $-OP(O)(OR^{12})_2$, or $-SP(O)(OR^{12})_2$, wherein the alkyl, alkenyl, alkynyl, cycloalkyl, heterocyclyl, aryl, heteroaryl, aralkyl, and heteroaralkyl represented by $R^{20}$ are each optionally and independently substituted with one to three groups from halo, $C_1$-$C_3$ alkyl, phenyl, benzyl, $C_1$-$C_3$ haloalkyl, $C_1$-$C_3$ alkoxy, $C_1$-$C_3$ haloalkoxy, nitro, cyano, azido, amino and $C_1$-$C_5$ carbamoyl; or two $R^{20}$ moieties attached to the same atom form an oxo (=O), thioxo (=S) or imino (=$NR^{12}$);

provided that one of $R^1$ and $R^3$ is hydrogen.

2. A method of treating cancer in a subject in need thereof, wherein the cancer is selected the group consisting of myeloid leukemia, T cell leukemia, B cell leukemia, chronic myeloid leukemia, acute myelocytic leukemia, non-Hodgkin's lymphoma, multiple myeloma, non-small cell lung cancer, small cell lung cancer, melanoma, gastrointestinal stromal tumors, gastric cancer, breast cancer, renal cell carcinoma, prostate cancer, colon carcinoma, mesothelioma, pancreatic cancer and ovarian cancer, comprising administering to the subject an effective amount of a compound according to the structural formula:

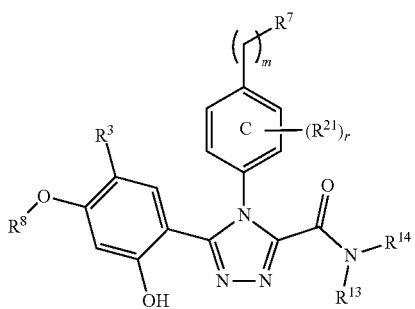

or a pharmaceutically acceptable salt thereof; wherein:
m is 0 or 1;
r is 0, 1 or 2;
$R^8$ is $C_1$-$C_3$ alkyl or $C_1$-$C_3$ haloalkyl;
$R^3$ is H, $C_1$-$C_4$ alkyl or $C_3$-$C_6$ cycloalkyl;
$R^7$ is phenyl, $S(O)_pR^{31}$, $OR^{31}$, $N(R^{31})_2$ or =$NN(R^{31})_2$;
$R^{13}$ and $R^{14}$ are individually hydrogen, $C_1$-$C_6$ alkyl, $C_2$-$C_6$ alkenyl, $C_2$-$C_6$ alkynyl, $C_3$-$C_7$ cycloalkyl, 5-7 membered heterocyclyl, phenyl, benzyl, 5-7 membered heteroaryl, —$N(R^{32})_2$, —$C(O)R^{32}$, —$C(O)OR^{32}$, —$S(O)_pR^{32}$, or —$S(O)_pN(R^{32})_2$, wherein each $R^{13}$ and $R^{14}$ that is not hydrogen is optionally and independently substituted with one or more $R^{21}$; or $R^{13}$ and $R^{14}$, taken together with the nitrogen to which they are attached, form a 5-7 membered heterocyclyl which is optionally substituted with one or more $R^{21}$;
each $R^{31}$ is independently selected from H, $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, —$OR^{32}$, —$C(O)R^{32}$, —$C(O)OR^{32}$, —$C(S)R^{32}$, —$C(O)SR^{32}$, —$C(O)N(R^{32})_2$, —$C(S)N(R^{32})_2$, —$C(NR^{32})OR^{32}$, —$C(NR^{32})R^{32}$, —$C(NR^{32})N(R^{32})_2$, —$C(NR^{32})SR^{32}$, —$S(O)_pR^{32}$, —$S(O)_pOR^{32}$ or —$S(O)_p N(R^{32})_2$, wherein the alkyl, alkenyl, alkynyl, cycloalkyl, heterocyclyl, aryl and heteroaryl represented by $R^{31}$ are independently and optionally substituted by one or more $R^{21}$; or two $R^{31}$ moieties attached to the same nitrogen atom are taken together to form a 5-14 membered heterocyclyl or a 5-14 membered heteroaryl, each of which are optionally and independently substituted with one or more $R^{21}$;
each $R^{32}$ is independently H, $C_1$-$C_3$ alkyl, $C_2$-$C_3$ alkenyl, $C_1$-$C_3$ haloalkyl, $C_1$-$C_3$ alkoxy, $C_1$-$C_3$ haloalkoxy, $C_3$-$C_7$ cycloalkyl, phenyl, or benzyl, wherein each $R^{32}$ with at least one hydrogen atom is optionally substituted with one or more $R^{21}$; or two $R^{32}$ substituents that are attached to the same atom or adjacent atoms, taken together with the atom(s) to which they are attached, form a 5-7 membered heterocyclyl or $C_3$-$C_7$ cycloalkyl which are each optionally and independently substituted with one or more $R^{21}$; and
each $R^{21}$ is independently selected from the group consisting of $C_1$-$C_6$ alkyl, $C_2$-$C_6$ alkenyl, $C_2$-$C_6$ alkynyl, $C_3$-$C_7$ cycloalkyl, 5-14 membered heterocyclyl, $C_6$-$C_{20}$ aryl, 5-14 membered heteroaryl, $C_3$-$C_7$ cycloalkyl-($C_1$-$C_3$)alkyl, 5-14 membered heterocyclyl-($C_1$-$C_3$)alkyl, $C_6$-$C_{20}$ aryl-($C_1$-$C_3$)alkyl, 5-14 membered heteroaryl-($C_1$-$C_3$)alkyl, halo, cyano, nitro, azido, —$N(R^{32})_2$, —$OR^{32}$, —$C(O)R^{32}$, —$C(O)OR^{32}$, —$C(S)R^{32}$, —$C(O)SR^{32}$, —$C(S)SR^{32}$, —$C(S)OR^{32}$, —$C(O)N(R^{32})_2$, —$C(S)N(R^{32})_2$, —$C(NR^{32})OR^{32}$, —$C(NR^{32})R^{32}$, —$C(NR^{32})N(R^{32})_2$, —$C(NR^{32})SR^{32}$, —$OC(O)N(R^{32})_2$, —$OC(O)R^{32}$, —$OC(O)OR^{32}$, —$OC(S)OR^{32}$, —$OC(NR^{12})OR^{32}$, —$SC(O)R^{32}$, —$SC(O)OR^{32}$, —$SC(NR^{32})OR^{32}$, —$OC(S)R^{32}$, —$SC(S)R^{32}$, —$SC(S)OR^{32}$, —$OC(O)N(R^{32})_2$, —$OC(S)N(R^{32})_2$, —$OC(NR^{32})N(R^{32})_2$, —$SC(O)N(R^{32})_2$, —$SC(NR^{32})N(R^{32})_2$, —$SC(S)N(R^{32})_2$, —$OC(NR^{32})R^{32}$, —$SC(NR^{32})R^{32}$, —$NR^{32}C(O)R^{32}$, —$NR^{32}C(S)R^{32}$, —$NR^{32}C(S)OR^{32}$, —$NR^{32}C(NR^{32})R^{32}$, —$NR^{32}C(O)OR^{32}$, —$NR^{32}C(NR^{32})OR^{32}$, —$NR^{32}C(O)N(R^{32})_2$, —$NR^{32}C(S)N(R^{32})_2$, —$NR^{32}C(NR^{32})N(R^{32})_2$, —$S(O)_pR^{32}$, —$OS(O)_pR^{32}$, —$OS(O)_pOR^{32}$, —$OS(O)_pN(R^{32})_2$, —$S(O)_pOR^{32}$, —$NR^{32}S(O)_pR^{32}$, —$NR^{32}S(O)_pN(R^{32})_2$, —$NR^{32}S(O)_pOR^{32}$, —$S(O)_pN(R^{32})_2$, —$SS(O)_pR^{32}$, —$SS(O)_pOR^{32}$, —$SS(O)_pN(R^{32})_2$, —$OP(O)(OR^{32})_2$, or —$SP(O)(OR^{32})_2$, wherein the alkyl, alkenyl, alkynyl, cycloalkyl, heterocyclyl, aryl, heteroaryl, aralkyl, and heteroaralkyl represented by $R^{21}$ are each optionally and independently substituted with one to three groups from halo, $C_1$-$C_3$ alkyl, phenyl, benzyl, $C_1$-$C_3$ haloalkyl, $C_1$-$C_3$ alkoxy, $C_1$-$C_3$ haloalkoxy, nitro, cyano, azido, amino and $C_1$—$O_5$ carbamoyl; or two $R^{21}$ moieties attached to the same atom form an oxo (=O), thioxo (=S) or imino (=$NR^{32}$).

3. A method of treating cancer in a subject in need thereof, wherein the cancer is selected the group consisting of myeloid leukemia, T cell leukemia, B cell leukemia, chronic myeloid leukemia, acute myelocytic leukemia, non-Hodgkin's lymphoma, multiple myeloma, non-small cell lung cancer, small cell lung cancer, melanoma, gastrointestinal stromal tumors, gastric cancer, breast cancer, renal cell carcinoma, prostate cancer, colon carcinoma, mesothelioma, pancreatic cancer and ovarian cancer, comprising administering to the subject an effective amount of a compound according to the structural formula:

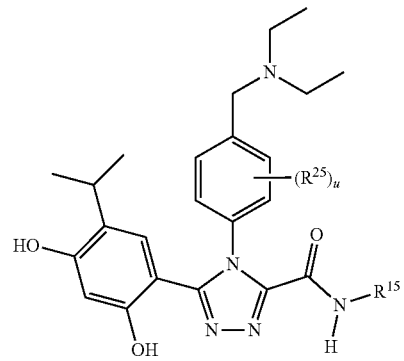

or a pharmaceutically acceptable salt thereof; wherein:

$R^{15}$ is $C_1$-$C_6$ alkyl, $C_2$-$C_6$ alkenyl, $C_3$-$C_7$ cycloalkyl, phenyl, benzyl, —C(O)$R^{42}$, —N($R^{42}$)$_2$, —C($NR^{42}$)$R^{42}$, C($NR^{42}$)N($R^{42}$)$_2$, —S(O)$_p R^{42}$ or —S(O)$_p$N($R^{42}$)$_2$, wherein each alkyl, alkenyl, cycloalkyl, phenyl and benzyl, represented by $R^{15}$ is optionally substituted with one or more $R^{22}$;

each $R^{42}$ is independently H or $C_1$-$C_4$ alkyl; or two $R^{42}$ moieties attached to the same nitrogen atom are taken together to form a 5-7 membered heterocyclyl; and each $R^{22}$ is independently halo, $C_1$-$C_3$ alkyl, $C_1$-$C_3$ haloalkyl, $C_1$-$C_3$ alkoxy, $C_1$-$C_3$ haloalkoxyl, $C_3$-$C_6$ cycloalkyl, 5-7 membered heterocycle, —C(O)$R^{42}$, —C(O)O$R^{42}$, —C(O)N($R^{42}$)$_2$, —N($R^{42}$)$_2$, or —N$R^{42}$C(O)$R^{42}$; or two $R^{21}$ moieties attached to the same atom, taken together, form an oxo (=O), thiooxo (=S), or imino (=N);

each $R^{25}$ is independently halo, $C_1$-$C_3$ alkyl, $C_1$-$C_3$ haloalkyl, $C_1$-$C_3$ alkoxy, $C_1$-$C_3$ haloalkoxyl, $C_3$-$C_6$ cycloalkyl, 5-7 membered heterocycle, —C(O)$R^{42}$, —C(O)O$R^{42}$, —C(O)N($R^{42}$)$_2$, —N($R^{42}$)$_2$, or —N$R^{42}$C(O)$R^{42}$; or two $R^{25}$ moieties attached to the same atom, taken together, form an oxo (=O), thiooxo (=S), or imino (=N); and u is 0, 1 or 2;

provided that $R^{15}$ is other than isopropyl or —(CH$_2$)$_2$N(CH$_3$)$_2$.

4. A method of treating cancer in a subject in need thereof, wherein the cancer is selected the group consisting of myeloid leukemia, T cell leukemia, B cell leukemia, chronic myeloid leukemia, acute myelocytic leukemia, non-Hodgkin's lymphoma, multiple myeloma, non-small cell lung cancer, small cell lung cancer, melanoma, gastrointestinal stromal tumors, gastric cancer, breast cancer, renal cell carcinoma, prostate cancer, colon carcinoma, mesothelioma, pancreatic cancer and ovarian cancer, comprising administering to the subject an effective amount of a compound according to the structural formula:

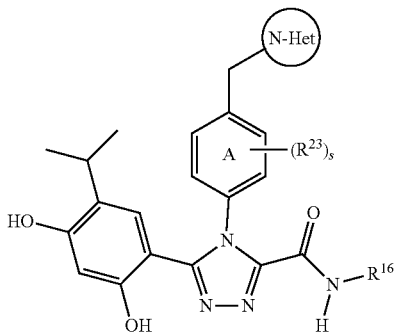

or a pharmaceutically acceptable salt thereof; wherein:

N-Het is piperidine, piperazine, morpholine, pyrrolidine, imidazolidine, hexahydropyrimidine or pyrazolidine, each optionally and independently substituted with one or two $R^{23}$;

$R^{16}$ is H, $C_1$-$C_6$ alkyl, $C_2$-$C_6$ alkenyl, $C_3$-$C_7$ cycloalkyl, phenyl, benzyl, —C(O)$R^{52}$, —N($R^{52}$)$_2$, —C($NR^{52}$)$R^{52}$, —C($NR^{52}$)N($R^{52}$)$_2$, —S(O)$_p R^{52}$ or —S(O)$_p$N($R^{52}$)$_2$, wherein each alkyl, alkenyl, cycloalkyl, phenyl and benzyl, represented by $R^{16}$ is optionally substituted with one or more $R^{23}$;

each $R^{52}$ is independently H or $C_1$-$C_4$ alkyl; or two $R^{52}$ moieties attached to the same nitrogen atom are taken together to form a 5-7 membered heterocyclyl; and each $R^{23}$ is independently halo, $C_1$-$C_3$ alkyl, $C_1$-$C_3$ haloalkyl, $C_1$-$C_3$ alkoxy, $C_1$-$C_3$ haloalkoxyl, $C_3$-$C_6$ cycloalkyl, 5-7 membered heterocycle, —C(O)$R^{52}$, —C(O)O$R^{52}$, —C(O)N($R^{52}$)$_2$, —N($R^{52}$)$_2$, or —N$R^{52}$C(O)$R^{52}$; or two $R^{23}$ moieties attached to the same atom, taken together, form an oxo (=O), thiooxo (=S), or imino (=N);

s is 0, 1 or 2;

provided that when N-Het is morpholine and s is 0, then $R^{16}$ is other than H, ethyl, isopropyl, isobutyl, propyl, cyclohexyl, or an ethylene substituted with hydroxyl, methoxy, dimethylamine, diethylamine, pyrrolidine, 4-methylpiperazine or morpholine;

when N-Het is 4-methylpiperidinyl and s is 0, then $R^{16}$ is other than H;

when N-Het is pyrrolidinyl and s is 0, then $R^{16}$ is other than an ethylene substituted with a pyrrolidine, morpholine, or 4-methyl-piperazine; and when N-Het is 4-methylpiperazinyl or 4-ethylpiperazinyl and s is 0, then $R^{16}$ is other than isopropyl.

5. The method of any one of claims 1-4, wherein the cancer is a B-cell non-Hodgkin's lymphoma selected from the group consisting of Burkitt's lymphoma, follicular lymphoma, diffuse large B-cell lymphoma, nodal marginal zone B-cell lymphoma, plasma cell neoplasms, small lymphocytic lymphoma/chronic lymphocytic leukemia, mantle cell lymphoma, and lymphoplamacytic lymphoma/Waldenstrom macroglobulinemia.

6. The method of any one of claims 1-4, wherein the cancer is a T-cell non-Hodgkin's lymphoma selected from the group consisting of anaplastic large-cell lymphoma, precursor-T-cell lymphoblastic leukemia/lymphoma, unspecified peripheral T-cell lymphoma, and angioimmunoblastic T-cell lymphoma.

7. The method of any one of claims 1-4, wherein the cancer is breast cancer or non-small cell lung cancer.

* * * * *